US012534450B2

(12) United States Patent
Wu et al.

(10) Patent No.: US 12,534,450 B2
(45) Date of Patent: *Jan. 27, 2026

(54) METHODS AND COMPOSITIONS FOR TARGETING PD-L1

(71) Applicant: Aligos Therapeutics, Inc., South San Francisco, CA (US)

(72) Inventors: Tongfei Wu, Boortmeerbeek (BE); Pierre Jean-Marie Bernard Raboisson, Wavre (BE); Francois Gonzalvez, Antwerp (BE); Antitsa Dimitrova Stoycheva, Half Moon Bay, CA (US); Cheng Liu, Burlingame, CA (US); Jerome Deval, Pacifica, CA (US); David McGowan, Brussels (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/658,848

(22) Filed: May 8, 2024

(65) Prior Publication Data

US 2024/0376078 A1 Nov. 14, 2024

Related U.S. Application Data

(63) Continuation of application No. 17/807,083, filed on Jun. 15, 2022, now Pat. No. 12,018,015.

(60) Provisional application No. 63/363,777, filed on Apr. 28, 2022, provisional application No. 63/263,427, filed on Nov. 2, 2021, provisional application No. 63/212,388, filed on Jun. 18, 2021.

(51) Int. Cl.

| | |
|---|---|
| ***C07D 401/14*** | (2006.01) |
| ***C07D 401/12*** | (2006.01) |
| ***C07D 403/12*** | (2006.01) |
| ***C07D 405/14*** | (2006.01) |
| ***C07D 413/14*** | (2006.01) |
| ***C07D 471/04*** | (2006.01) |
| ***C07D 487/10*** | (2006.01) |
| ***C07D 491/048*** | (2006.01) |
| ***C07D 498/10*** | (2006.01) |
| ***C07D 519/00*** | (2006.01) |

(52) U.S. Cl.

CPC ......... *C07D 401/14* (2013.01); *C07D 401/12* (2013.01); *C07D 403/12* (2013.01); *C07D 405/14* (2013.01); *C07D 413/14* (2013.01); *C07D 471/04* (2013.01); *C07D 487/10* (2013.01); *C07D 491/048* (2013.01); *C07D 498/10* (2013.01); *C07D 519/00* (2013.01)

(58) Field of Classification Search

None

See application file for complete search history.

(56) References Cited

U.S. PATENT DOCUMENTS

| | | | |
|---|---|---|---|
| 11,760,761 | B2 | 9/2023 | Wu et al. |
| 11,760,764 | B2 | 9/2023 | Wu et al. |
| 12,018,015 | B2 | 6/2024 | Wu et al. |
| 2003/0199516 | A1 | 10/2003 | Moser et al. |
| 2004/0167224 | A1 | 8/2004 | Ozaki et al. |
| 2004/0180906 | A1 | 9/2004 | Flynn et al. |
| 2005/0288286 | A1 | 12/2005 | Flynn et al. |
| 2006/0223759 | A1 | 10/2006 | Eickmeier et al. |
| 2006/0281750 | A1 | 12/2006 | Li et al. |
| 2008/0293936 | A1 | 11/2008 | Burchhardt |
| 2009/0012091 | A1 | 1/2009 | Yu |
| 2014/0117329 | A1 | 5/2014 | Lee et al. |
| 2014/0225072 | A1 | 8/2014 | Kim et al. |
| 2014/0353624 | A1 | 12/2014 | Kim et al. |
| 2015/0014645 | A1 | 1/2015 | Park et al. |
| 2015/0034919 | A1 | 2/2015 | Kim et al. |
| 2015/0090962 | A1 | 4/2015 | Kim et al. |
| 2015/0236264 | A1 | 8/2015 | Kim et al. |
| 2016/0276595 | A1 | 9/2016 | Kim et al. |
| 2016/0308129 | A1 | 10/2016 | Stoessel et al. |
| 2017/0057957 | A1 | 3/2017 | Lan et al. |
| 2018/0273519 | A1 | 9/2018 | Wu et al. |
| 2021/0177828 | A1 | 6/2021 | Wu et al. |
| 2023/0002413 | A1 | 1/2023 | Wu et al. |

(Continued)

FOREIGN PATENT DOCUMENTS

| | | |
|---|---|---|
| CA | 3163389 | 7/2021 |
| CA | 3182595 | 12/2021 |

(Continued)

OTHER PUBLICATIONS

Le Grazie M, Biagini MR, Tarocchi M, Polvani S, Galli A. Chemotherapy for hepatocellular carcinoma: The present and the future. World J Hepatol. Jul. 28, 2017;9(21):907-920. (Year: 2017).*

"IUPAC-IUB Commission on Biochemical Nomenclature Abbreviated Nomenclature of Synthetic Polypeptides (Polymerized Amino Acids)* Revised Recommendations (1971)" *Biochemistry*. (1972) 11(5):942-944.

International Search Report and Written Opinion mailed Aug. 30, 2022 for PCT Application No. PCT/US2022/033653, filed Jun. 15, 2022.

International Preliminary Report on Patentability issued Dec. 14, 2023 for PCT Application No. PCT/US2022/033653, filed Jun. 15, 2022.

Office Action dated Jun. 14, 2023 for U.S. Appl. No. 17/807,083, filed Jun. 15, 2022.

(Continued)

*Primary Examiner* — James H Alstrum-Acevedo

*Assistant Examiner* — Lauren Wells

(74) *Attorney, Agent, or Firm* — Knobbe, Martens, Olson & Bear, LLP

(57) ABSTRACT

Provided herein are compounds that can be useful as inhibitors of PD-1, PD-L1 or the PD-1/PD-L1 interaction. Also provided herein are pharmaceutical compositions of a compound of Formula (I), or a pharmaceutically acceptable salt thereof, and methods of using a compound of Formula (I), or a pharmaceutically acceptable salt thereof, for the treatment of PD-L1 related diseases including but not limited to liver diseases, cancer, hepatocellular carcinoma, viral diseases, or hepatitis B.

19 Claims, 1 Drawing Sheet

(56) References Cited

U.S. PATENT DOCUMENTS

| | | | |
|---|---|---|---|
| 2023/0010258 A1 | 1/2023 | Kim et al. | |
| 2023/0031213 A1 | 2/2023 | Wu et al. | |
| 2023/0065527 A1 | 3/2023 | Wu et al. | |
| 2023/0145793 A1 | 5/2023 | Liu et al. | |
| 2023/0192713 A1 | 6/2023 | Wu et al. | |
| 2024/0277706 A1 | 8/2024 | Wu et al. | |

FOREIGN PATENT DOCUMENTS

| | | |
|---|---|---|
| DE | 102004056226 | 5/2006 |
| EP | 3540803 | 9/2019 |
| JP | 2019203026 | 11/2019 |
| KR | 10-2015-0144590 | 12/2015 |
| KR | 10-2018-0053121 | 5/2018 |
| KR | 10-2019-0007789 | 1/2019 |
| KR | 10-2020-0069184 | 6/2020 |
| WO | WO 2003/084948 | 10/2003 |
| WO | WO 2004/039795 | 5/2004 |
| WO | WO 2004/060305 | 7/2004 |
| WO | WO 2004/060306 | 7/2004 |
| WO | WO 2006/116713 | 2/2006 |
| WO | WO 2008/086014 | 7/2008 |
| WO | WO 2009/007753 | 1/2009 |
| WO | WO 2009/027746 | 3/2009 |
| WO | WO 2009/030952 | 3/2009 |
| WO | WO 2009/036066 | 3/2009 |
| WO | WO 2010/007114 | 1/2010 |
| WO | WO 2010/027746 | 3/2010 |
| WO | WO 2011/143129 | 11/2011 |
| WO | WO 2011/143365 | 11/2011 |
| WO | WO 2011/143366 | 11/2011 |
| WO | WO 2011/143495 | 11/2011 |
| WO | WO 2011/153553 | 12/2011 |
| WO | WO 2012/053186 | 4/2012 |
| WO | WO 2012/094328 | 10/2012 |
| WO | WO 2013/019621 | 2/2013 |
| WO | WO 2013/019635 | 2/2013 |
| WO | WO 2013/074633 | 5/2013 |
| WO | WO 2013/118071 | 8/2013 |
| WO | WO 2014/026079 | 2/2014 |
| WO | WO 2014/028968 | 2/2014 |
| WO | WO 2015/034820 | 3/2015 |
| WO | WO 2015/049651 | 4/2015 |
| WO | WO 2015/063046 | 5/2015 |
| WO | WO 2015/086108 | 6/2015 |
| WO | WO 2015/104677 | 7/2015 |
| WO | WO 2015/110999 | 7/2015 |
| WO | WO 2015/158233 | 10/2015 |
| WO | WO 2017/048197 | 3/2017 |
| WO | WO 2017/122209 | 7/2017 |
| WO | WO 2018/013789 | 1/2018 |
| WO | WO 2018/119224 | 6/2018 |
| WO | WO 2018/138359 | 8/2018 |
| WO | WO 2018/178010 | 10/2018 |
| WO | WO 2018/214980 | 11/2018 |
| WO | WO 2019/141202 | 7/2019 |
| WO | WO 2019/175897 | 9/2019 |
| WO | WO 2019/183587 | 9/2019 |
| WO | WO 2019/246570 | 12/2019 |
| WO | WO 2020/086739 | 4/2020 |
| WO | WO 2020/143385 | 7/2020 |
| WO | WO 2020/198026 | 10/2020 |
| WO | WO 2020/232256 | 11/2020 |
| WO | WO 2021/076691 | 4/2021 |
| WO | WO 2021/086076 | 5/2021 |
| WO | WO 2021/158481 | 8/2021 |
| WO | WO 2021/174046 | 9/2021 |
| WO | WO 2021/174048 | 9/2021 |
| WO | WO 2021/185256 | 9/2021 |
| WO | WO 2021/236771 | 11/2021 |
| WO | WO 2021/254005 | 12/2021 |
| WO | WO 2022/040002 | 2/2022 |
| WO | WO 2022/266236 | 12/2022 |
| WO | WO 2023/011629 | 2/2023 |
| WO | WO 2023/114365 | 6/2023 |
| WO | WO 2024/155717 | 7/2024 |
| WO | WO 2025/015063 A1 | 1/2025 |

OTHER PUBLICATIONS

Office Action dated Nov. 26, 2024 for Eurasian Application No. 202393246, filed Dec. 14, 2023.

Extended European Search Report issued in European Patent Application No. 22825757.2, dated Feb. 27, 2025 in 11 pages.

* cited by examiner

1A
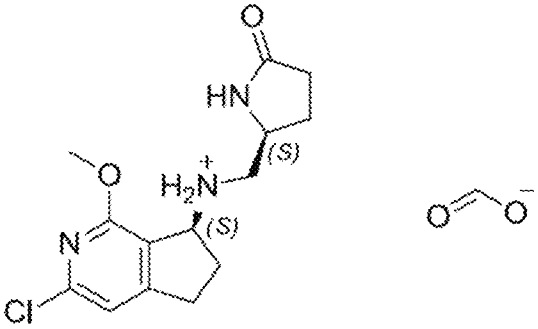
Absolute configuration structure
1B
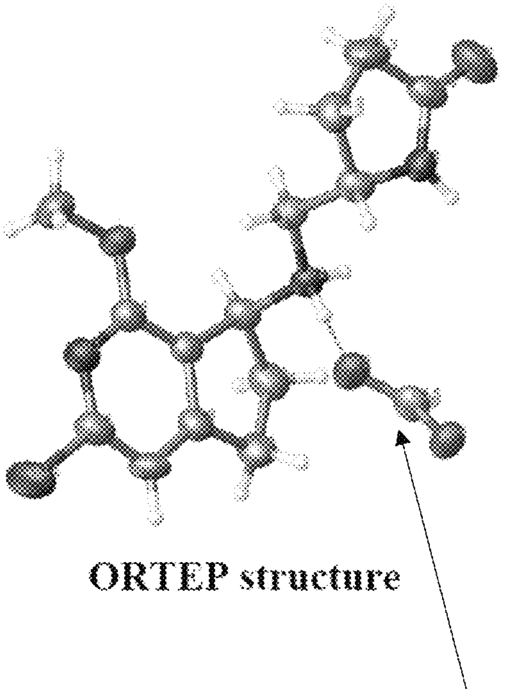
ORTEP structure
Formate

METHODS AND COMPOSITIONS FOR TARGETING PD-L1

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6. This application is a continuation of U.S. application Ser. No. 17/807,083, filed Jun. 15, 2022, which claims priority to U.S. Provisional Application Nos. 63/212,388, filed Jun. 18, 2021, 63/263,427, filed Nov. 2, 2021 and 63/363,777, filed Apr. 28, 2022, each of which is hereby incorporated by reference in their entireties including any drawings.

FIELD

The present application relates to the fields of chemistry, biochemistry, molecular biology and medicine. The present disclosure related to compounds that can be useful as inhibitors of PD-1, PD-L1 or the PD-1/PD-L1 interaction. Also disclosed herein are pharmaceutical compositions of compounds described herein and uses of or methods of using the compounds for the treatment of PD-L1 related diseases including but not limited to liver diseases, cancer, hepatocellular carcinoma, viral diseases, or hepatitis B.

BACKGROUND

The programmed cell death 1 (PD-1) immune checkpoint expressed on the surface of activated $CD4^+$ and $CD8^+$ T cells controls an inhibitory mechanism to prevent autoimmunity. Engagement of PD-1 by programmed death-ligand 1 (PD-L1) expressed on the multitude of cell types, including macrophages, dendritic cells, mast cells as well as cancer cells induces T cell exhaustion resulting in reduction or loss of effector cytokine production (e.g. IL-2, TNF-$\alpha$, IFN-$\gamma$) and upregulation of other inhibitory receptors and immune checkpoints (e.g. CTLA-4, LAG-3, and BTLA), or T cell apoptosis. High expression of PD-L1 is exhibited by many types of cancers to escape tumor immune surveillance and has been associated with poorer prognosis. PD-1-mediated immunosuppression is also linked to some viral infections, such as hepatitis B. There is an ongoing need for PD-1/PD-L1 therapies and improvements thereof for the treatment of disease.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

BRIEF DESCRIPTION OF THE DRAWINGS

FIGS. 1A and 1B show the absolute configuration structure and ORTEP crystal structure of the formate salt of Intermediate 5-1b.

DETAILED DESCRIPTION

Hepatocellular carcinoma (HCC) is the most common form of liver cancer. HCC can be caused by a variety of conditions, such as alcohol consumption, cirrhosis, and viral infections that cause hepatitis, such as hepatitis B virus, hepatitis C virus, and hepatitis D virus. The inflammation, fibrosis, and cirrhosis linked with these conditions can induce malignancies in affected liver cells. HCC has relatively poor prognosis, with a five-year survival rate of about 30%, depending on if full surgical resection of the tumor is possible.

For early disease, surgical resection is used. However, most HCC are identified at later stages because of difficulties in diagnosing. Upon late stage diagnosis, the tumors are unresectable and most patients are given systemic therapies. The current standard of care in front line are multi-kinase inhibitors (including, for example, sorafenib and/or lenvatinib). Most patients are refractory or relapse from these treatments, and undergo second line therapies that have anti-angiogenic agents (including, for example, Regorafinib, Cabozantinib, and/or Ramicirumab) or immune checkpoint inhibitors (including, for example, nivolumab and/or pembrolizumab). However, most patients do not respond to first and second therapies, and the clinical benefit is poor, with overall survival not exceeding one year. In addition, biomarker driven therapies are lacking. Thus, there is a need to develop more tolerable and efficacious therapies for the treatment of HCC and related liver disorders.

HBV is a partially double-stranded circular DNA of about 3.2 kilobase (kb) pairs, and is classified into eight genotypes, A to H. The HBV replication pathway has been studied in great detail. One part of replication includes the formation of the covalently closed circular DNA (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of an HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Programmed cell death 1, or programmed death 1 (PD-1) is a 268 amino acid long type I transmembrane protein found as a surface marker on T cells and other immune cells. As an immune checkpoint, PD-1 serves to negatively regulate immune responses to prevent autoimmune disorder. PD-1 protein (NCBI accession number NP_005009.2) is expressed from the cluster of differentiation 279 (CD279) gene (NCBI accession number NG_012110.1) or mRNA transcript (NCBI accession number NM_005018.3). In some preferred embodiments, PD-1 is the human PD-1 protein, and CD279 is the human CD279 transcript or gene on chromosome 2. It should be understood that a person with ordinary skill in the art would view the terms PD-1 and CD279 as often nominally interchangeable when considering the nucleic acid (DNA or RNA) or corresponding translated protein, or the sequences thereof.

Programmed cell death-ligand 1, or programmed death-ligand 1 (PD-L1), also known as B7 homolog 1 (B7-H1) is 272 amino acid long type I transmembrane protein found as a surface marker on many different cell types. PD-L1 is a major ligand of PD-1 and results in inhibition of T cell cytotoxicity and cytokine production. Cancer cells such as HCC cells take advantage of this immune checkpoint by upregulating PD-L1 expression, resulting in dysfunctional anti-tumor immunity by proximal T cells. Viruses also have been observed to modulate the PD-1/PD-L1 pathway to inhibit immune host response. Hepatitis B virus has been shown to upregulate PD-L1 in infected hepatocytes, and PD-1 in associated T cells. PD-L1 protein (NCBI accession number NP_054862.1) is expressed from the cluster of differentiation 274 (CD274) transcript (NCBI accession number NM_014143.4). In some preferred embodiments, PD-L1 is the human PD-L1 protein, and CD274 is the human CD274 transcript or gene on chromosome 9. It should be understood that a person with ordinary skill in the art would view the terms PD-L1 and CD274 as often nominally interchangeable when considering the nucleic acid (DNA or RNA) or corresponding translated protein, or the sequences thereof.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. To the extent publications and patents or patent applications incorporated by reference contradict the disclosure contained in the specification, the specification is intended to supersede and/or take precedence over any such contradictory material. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3 groups) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated).

The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained $—CH_2—$ tethering groups, forming bonds to connect molecular fragments via their terminal carbon atoms. In some embodiments, a lower alkylene can include 1, 2, 3, 4, 5 or 6 carbons. Examples include but are not limited to methylene ($—CH_2—$), ethylene ($—CH_2CH_2—$), propylene ($—CH_2CH_2CH_2—$) and butylene ($—CH_2CH_2CH_2CH_2—$). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. In some instances, a haloalkoxy can be —OR, wherein R is a $C_{1-4}$ alkyl substituted by 1, 2 or 3 halogens. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(═O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(═O)OR" group in which R can be the same as defined with respect to O-carboxy. An ester and C-carboxy may be substituted or unsubstituted.

A "thiocarbonyl" group refers to a "—C(═S)R" group in which R can be the same as defined with respect to O-carboxy. A thiocarbonyl may be substituted or unsubstituted.

A "trihalomethanesulfonyl" group refers to an "$X_3CSO_2—$" group wherein each X is a halogen.

A "trihalomethanesulfonamido" group refers to an "$X_3CS(O)_2N(R_A)—$" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a $—NH_2$ group.

As used herein, the term "hydroxy" refers to a —OH group.

A "cyano" group refers to a "—CN" group.

The term "azido" as used herein refers to a $—N_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(═O)— group.

An "S-sulfonamido" group refers to a "$—SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)—$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "$—OC(═O)N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "$ROC(═O)N(R_A)—$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "$—OC(═S)—N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "$ROC(═S)N(R_A)—$" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—$NHR_A$" in which $R_A$ can be independently alkyl, alkenyl, alkynyl, cycloalkyl, cycloalkenyl, aryl, heteroaryl, heterocyclyl, aryl (alkyl), heteroaryl(alkyl) or heterocyclyl(alkyl). A mono-substituted amine may be substituted or unsubstituted. In some instances, a mono-substituted amine can be —$NHR_A$, wherein $R_A$ can be an unsubstituted $C_{1-6}$ alkyl or an unsubstituted or a substituted benzyl.

A "di-substituted amine" refers to a "—$NR_AR_B$" in which $R_A$ and $R_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl (alkyl). A mono-substituted amine may be substituted or unsubstituted. In some instances, a mono-substituted amine can be —$NR_AR_B$, wherein $R_A$ and $R_B$ can be independently an unsubstituted $C_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11: 942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt (for example, ammonium or triethylammonium salt), an alkali metal salt, such as a lithium, a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

COMPOUNDS

Examples of embodiments of the present application include the following:

Embodiment 1

A compound of Formula (I), or a pharmaceutically acceptable salt thereof, having the structure:

(I)

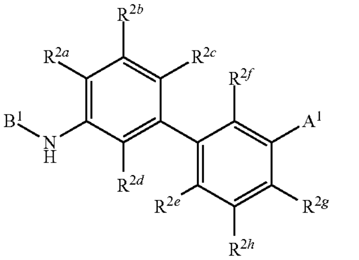

wherein: $A^1$ can be

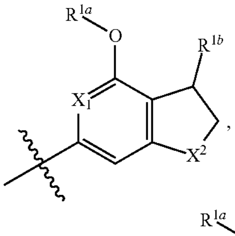
,
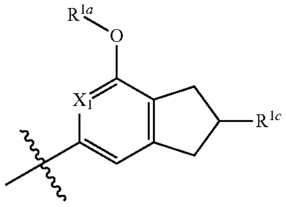
or
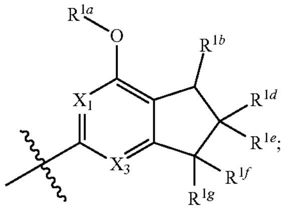

$B^1$ can be

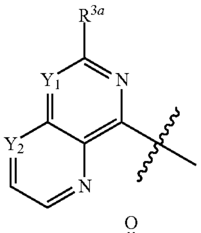
,
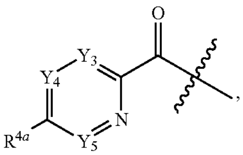
,
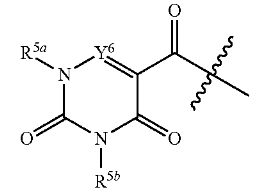
or
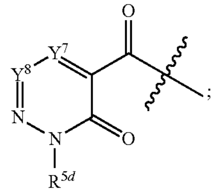
;

each $X^1$ can be selected from CH and N (nitrogen); $X^2$ can be O (oxygen); $X^3$ can be selected from CH, C-halo and N; $Y^1$ can be selected from N (nitrogen) and CH; $Y^2$ can be selected from N (nitrogen) and CH; $Y^3$ can be selected from N (nitrogen) and CH; $Y^4$ can be selected from N (nitrogen) and CH; $Y^5$ can be selected from N (nitrogen), CH and C—$OCH_3$; $Y^6$ can be selected from N and $CR^{5c}$; $Y^7$ can be $CR^{5e}$; $Y^8$ can be $CR^{5f}$; each $R^{1a}$ can be selected from —$C_{1-4}$ alkyl, —$C_{1-4}$ haloalkyl, —$CH_2$($C_{3-6}$ monocyclic cycloalkyl), —$C_{2-4}$ alkyl($C_{1-4}$ alkoxy), —$C_{2-4}$ alkyl ($C_{1-4}$ haloalkoxy), —$CH_2$(4-6 membered monocyclic heterocyclyl) and —$CH_2$(5-6 membered monocyclic heteroaryl); each $R^{1b}$ can be selected from —$N(R^{m1})R^{n1}$ and —$R^{x1}$; $R^{1c}$ can be selected from —$N(R^{m1})R^{n1}$ and —$R^{x1}$; $R^{1d}$ can be selected from hydrogen, —$CH_3$, —$CH_2CH_3$, —OH, —$OCH_3$ and —F; $R^{1e}$ can be selected from hydrogen, —$CH_3$, —$CH_2CH_3$ and —F; $R^{1f}$ can be selected from hydrogen, —$CH_3$, —$CH_2CH_3$, —OH, —$OCH_3$ and —F; $R^{1g}$ can be selected from hydrogen, —$CH_3$, —$CH_2CH_3$ and —F; $R^{2a}$, $R^{2b}$, $R^{2c}$, $R^{2e}$, $R^{2g}$, $R^{2h}$ can be independently selected from hydrogen and halogen; $R^{2d}$ and $R^{2f}$ can be independently selected from hydrogen, halogen, cyano, —$CH_3$, —$CH_2CH_3$, —$CH_2OH$, —$OCH_3$ and —$SCH_3$; $R^{3a}$ can be selected from H (hydrogen), —$CH_3$, —$CF_3$ and —$CHF_2$; $R^{4a}$ can be selected from H (hydrogen), halogen, —$C_{1-4}$ alkyl, —$C_{1-4}$ haloalkyl, —$CH_2R^{4b}$ and —$C(CH_3)R^{4b}$; $R^{4b}$ can be selected from —$N(R^{m2})R^{n2}$ and —$R^{y1}$; $R^{5a}$ can be selected from hydrogen, —$CH_3$, —$C_{2-4}$ alkyl and —$C_{2-4}$ haloalkyl; $R^{5b}$ can be selected from hydrogen, —$CH_3$, —$C_{2-4}$ alkyl and —$C_{2-4}$ haloalkyl; $R^{5c}$ can be selected from hydrogen, —$CH_3$, —$C_{2-4}$ alkyl and —$C_{2-4}$ haloalkyl; $R^{5d}$ can be selected from hydrogen, —$CH_3$, —$C_{2-4}$ alkyl and —$C_{2-4}$ haloalkyl; $R^{5e}$ can be selected from hydrogen, halogen and —$CH_3$; $R^{5f}$ can be selected from hydrogen, halogen, —OH, —CN and —$CH_3$; $R^{m1}$ can be selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and —$R^{x2}$; wherein the monocyclic heteroaryl, the bicyclic heteroaryl the monocyclic heterocyclyl and the bicyclic heterocyclyl can contain at least one atom or group of atoms independently selected from the group consisting of O (oxygen), S (sulfur), C(═O), S(═O), $S(═O)_2$ and N (nitrogen); wherein the —$C_4$ alkyl can be optionally substituted with one or two or three substituents independently selected from halogen, cyano, hydroxy, —$C_{1-4}$ alkoxy, —$C_{1-4}$ haloalkyl, —$C_{1-4}$ haloalkoxy, —$C(═O)OR^{Z1}$, —$C(═O)NHS(═O)_2R^{Z3}$, —$C(═O)N(R^{Z1})R^{Z2}$, —$S(═O)_2R^{Z3}$, —$S(═O)_2N(R^{Z1})R^{Z2}$, —$N(R^{Z1})C(═O)R^{Z3}$, —$N(R^{Z1})S(═O)R^{Z3}$, —$N(R^{Z1})C(═O)N(R^{Z2})R^{Z3}$ and —$N(R^{Z1})S(═O)N(R^{Z2})R^{Z3}$; wherein the $C_{3-6}$ monocyclic cycloalkyl, the $C_{5-12}$ bicyclic cycloalkyl, the 5- or 6-membered monocyclic heteroaryl, the 4-7 membered monocyclic heterocyclyl, the 8-11 membered fused-heteroaryl and the 8-11 membered fused-heterocyclyl can be optionally substituted with one, two, three or four substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —$C(═O)R^{Z1}$, —$C(═O)OR^{Z1}$, —$C(═O)NHS(═O)_2R^{Z3}$, —$C(═O)N(R^{Z1})R^{Z2}$, —$S(═O)_2R^{Z3}$, —$S(═O)_2N(R^{Z1})R^{Z2}$, —$N(R^{Z1})C(═O)R^{Z3}$, —$N(R^{Z1})S(═O)R^{Z3}$, —$N(R^{Z1})C(═O)N$ $(R^{Z2})R^{Z3}$ and —$N(R^{Z1})S(═O)N(R^{Z2})R^{Z3}$; and $R^{n1}$ can be hydrogen, —$C_{1-4}$ alkyl, —$C_{1-4}$ haloalkyl, $C_{3-6}$ monocyclic cycloalkyl($CH_2$)— or —$C(═O)OR^{Z4}$; $R^{m2}$ can be selected from —$CH_3$, —$C_{2-4}$ alkyl, —$C_{1-4}$ haloalkyl and —$R^{y2}$, wherein the —$C_{2-4}$ alkyl is optionally substituted with hydroxy; $R^{n2}$ can be selected from H (hydrogen), —$C_{1-4}$ alkyl and —$C_{1-4}$ haloalkyl; $R^{x1}$ can be selected from:

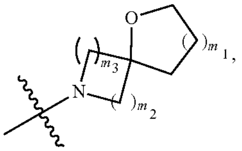
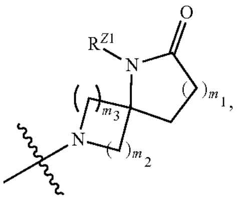
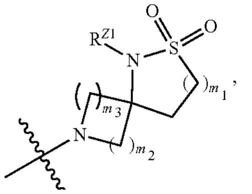
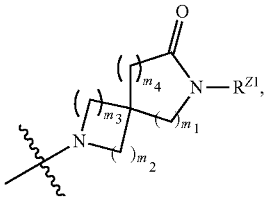
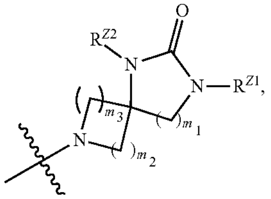
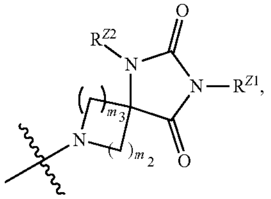
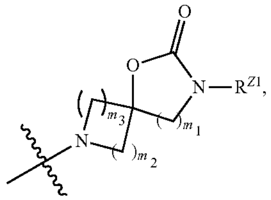
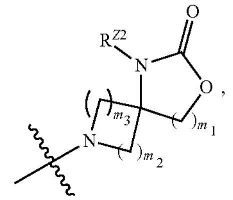
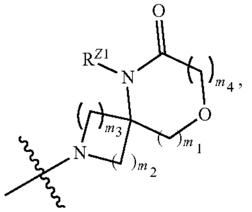
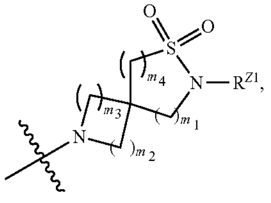
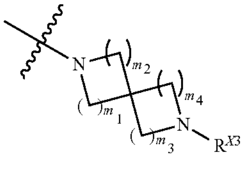
,
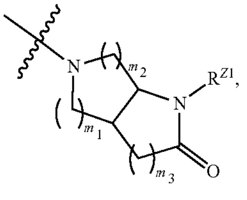
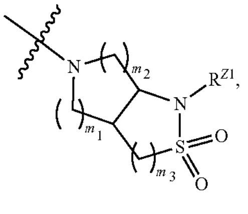
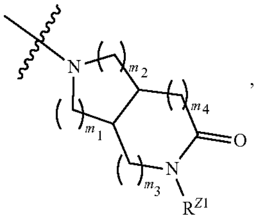
, -continued

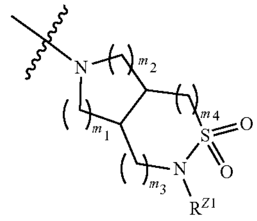
,
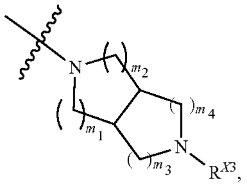
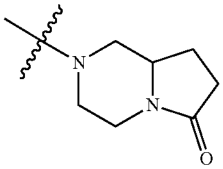
,
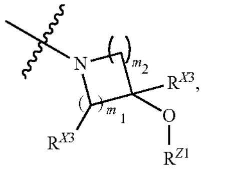
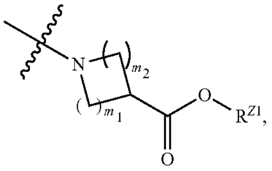
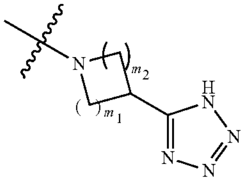
,
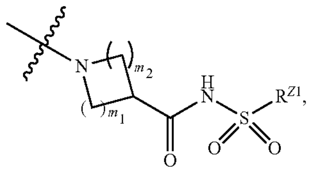
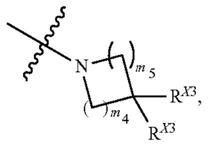
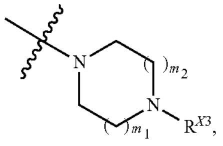
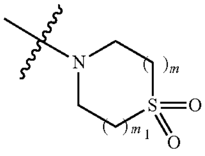
,
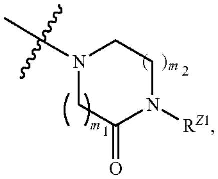
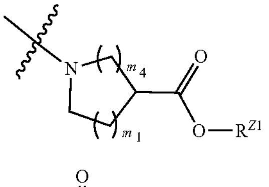
and
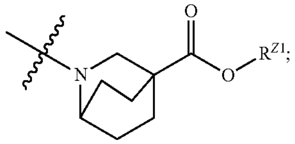

wherein $R^{x1}$ can be optionally substituted with one or two substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —$C(═O)OR^{Z1}$, —$C(═O)NHS(═O)_2R^{Z3}$, —$C(═O)N(R^{Z1})R^{Z2}$, —$S(═O)_2R^{Z3}$, —$S(═O)_2N(R^{Z1})R^{Z2}$, —$N(R^{Z1})C(═O)R^{Z3}$, —$N(R^{Z1})S(═O)R^{Z3}$, —$N(R^{Z1})C(═O)N(R^{Z1})R^{Z3}$ and —$N(R^{Z1})S(═O)_2N(R^{Z2})R^{Z3}$; $R^{x2}$ can be selected from:

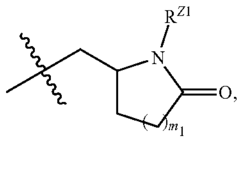
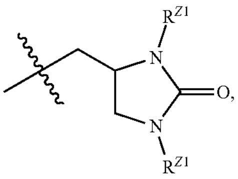

-continued
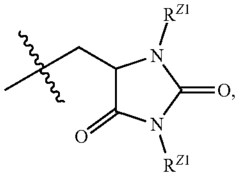
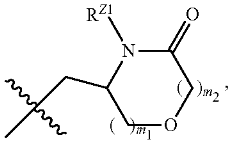
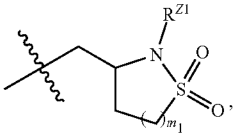
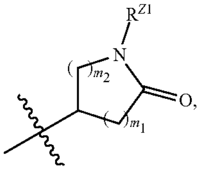
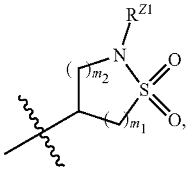
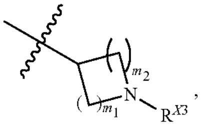
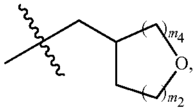
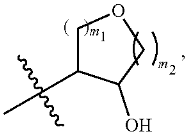
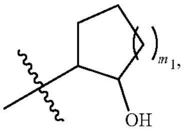
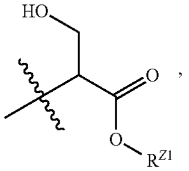
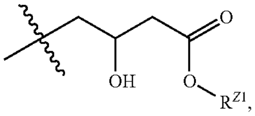
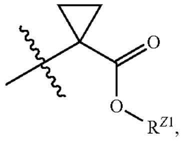
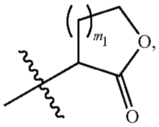
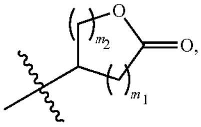
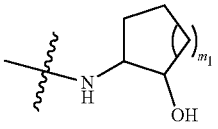
and
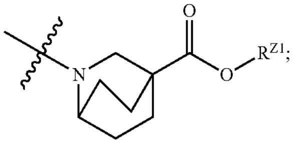
$R^{y1}$ can be selected from:
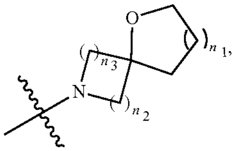
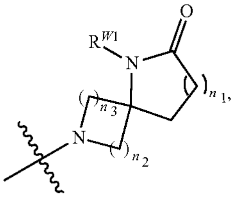
-continued
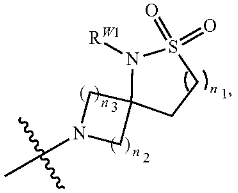
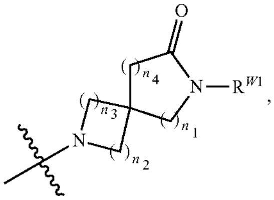
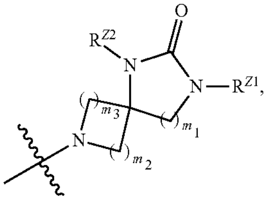
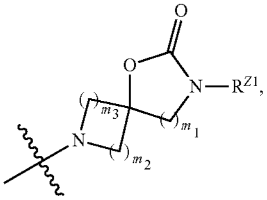
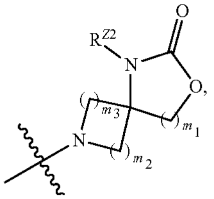
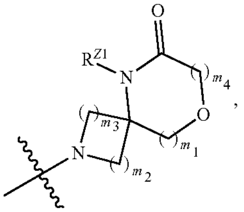
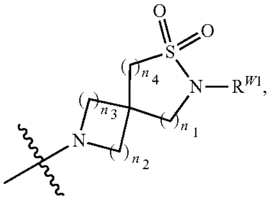
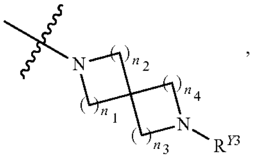
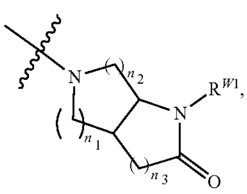
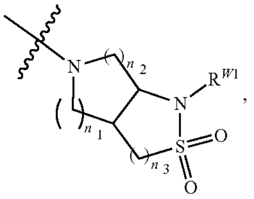
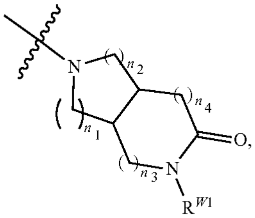
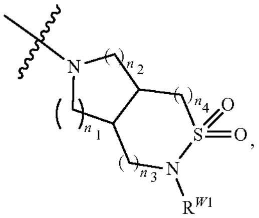
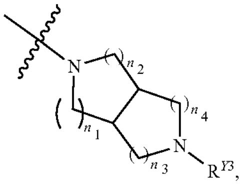
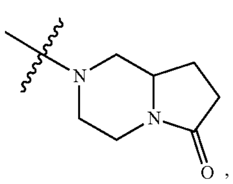
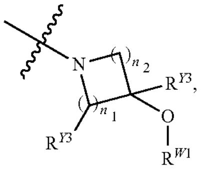
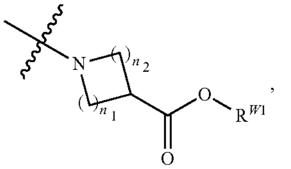

-continued

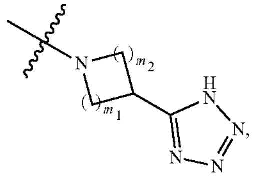
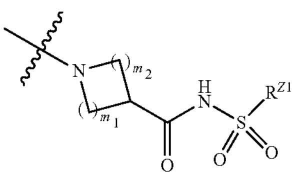
,
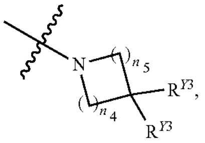
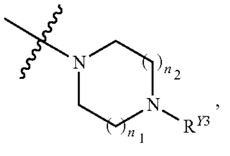
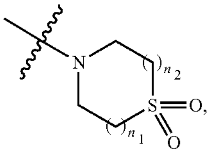
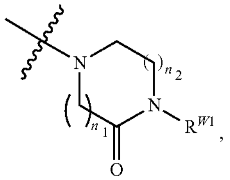
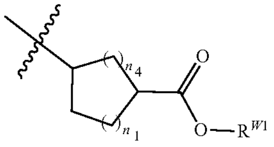
and
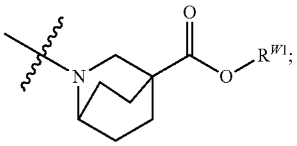

wherein $R^{y1}$ can be optionally substituted with one or two substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —C(═O)O$R^{W1}$, —C(═O)NHS(═O)$_2$ $R^{W3}$, —C(═O)N($R^{W1}$)$R^{W2}$, —S(═O)$_2$$R^{W3}$, —S(═O)N ($R^{W1}$)$R^{W2}$, —N($R^{W1}$)C(═O)$R^{W3}$, —N($R^{W1}$)S(═O)$R^{W3}$, —N($R^{W1}$)C(═O)N($R^{W2}$)$R^{W3}$ and —N($R^{W1}$)S(═O)N($R^{W2}$) $R^{W3}$; $R^{y2}$ can be selected from:

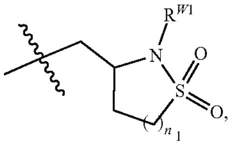
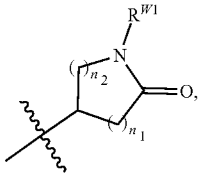
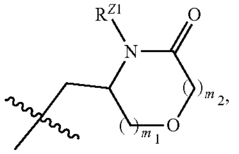
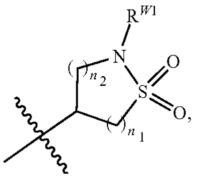
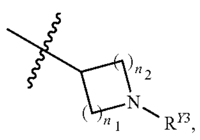
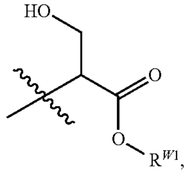

-continued

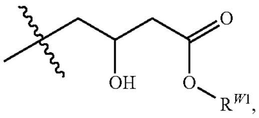
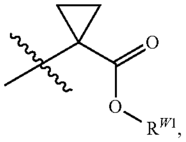
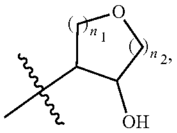
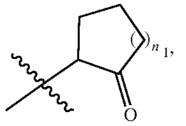
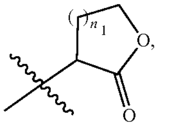
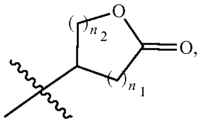
and
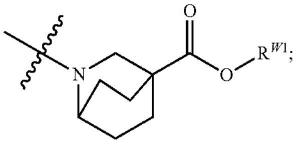

$m_1$, $m_2$, $m_3$, $n_1$, $n_2$ and $n_3$ can be independently 1 or 2; $m_4$ and $n_4$ can be independently 0, 1 or 2; $m_5$ and $n_5$ can be independently 1, 2, 3 or 4; each $R^{X3}$ can be independently selected from hydrogen, halogen, —$C_{1-4}$ alkyl, —$C_{1-4}$ haloalkyl, —C(═O)$R^{Z3}$, —C(═O)O$R^{Z1}$, —S(═O)$_2$$R^{Z1}$, —C(═O)N($R^{Z1}$)$R^{Z2}$ and —S(═O)N($R^{Z1}$)$R^{Z2}$; each $R^{Y3}$ can be independently selected from hydrogen, halogen, —$C_{1-4}$ alkyl, —$C_{1-4}$ haloalkyl, —C(═O)$R^{W3}$, —C(═O) O$R^{W3}$, —S(═O)$_2$$R^{W3}$, —C(═O)N($R^{W1}$)$R^{W2}$ and —S(═O) N($R^{W1}$)$R^{W2}$; $R^{Z1}$ and $R^{Z2}$ can be independently selected from hydrogen, —$C_{1-4}$ alkyl, and —$C_{1-4}$ haloalkyl; or $R^{Z1}$ and $R^{Z2}$ can be taken together to form a monocyclic heterocyclyl when attached to the same nitrogen; $R^{W1}$ and $R^{W2}$ can be independently selected from hydrogen, —$C_{1-4}$ alkyl and —$C_{1-4}$ haloalkyl; $R^{Z3}$ and $R^{W3}$ can be independently selected from hydrogen, —$C_{1-4}$ alkyl and —$C_{1-4}$ haloalkyl; and $R^{Z4}$ can be selected from hydrogen, —$C_{1-4}$ alkyl and 5- to 6-membered monocyclic heterocyclyl($CH_2$)— optionally substituted with —$C_{1-4}$ alkyl. In some embodiments, a compound of Formula (I), or a pharmaceutically acceptable salt thereof, can be where $A^1$ can be

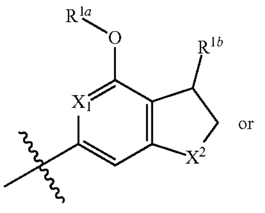
or
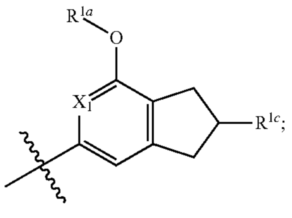

$B^1$ can be

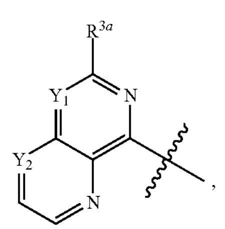
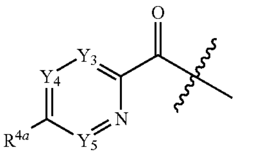
or

-continued

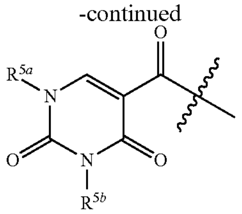
;

$X^1$ can be selected from CH and N (nitrogen); $X^2$ can be selected from O (oxygen) and $CH_2$; $Y^1$ can be selected from N (nitrogen) and CH; $Y^2$ can be selected from N (nitrogen) and CH; $Y^3$ can be selected from N (nitrogen) and CH; $Y^4$ can be selected from N (nitrogen) and CH; $Y^5$ can be selected from N (nitrogen), CH and C—$OCH_3$; $R^{1a}$ can be selected from —$C_{1-4}$ alkyl, —$C_{1-4}$ haloalkyl, —$CH_2$($C_{3-6}$ monocyclic cycloalkyl) and —$CH_2$(4-6 membered monocyclic heterocyclyl) and —$CH_2$(5-6 membered monocyclic heteroaryl); $R^{1b}$ can be selected from —N($R^{m1}$)$R^{n1}$ and —$R^{x1}$; $R^{1c}$ can be selected from —N($R^{m1}$)$R^{n1}$ and —$R^{x1}$; $R^{2a}$, $R^{2b}$, $R^{2c}$, $R^{2e}$, $R^{2g}$, $R^{2h}$ can be independently selected from hydrogen and halogen; $R^{2d}$ and $R^{2f}$ can be independently selected from hydrogen, halogen, cyano, —$CH_3$, —$CH_2CH_3$, —$CH_2OH$, —$OCH_3$ and —$SCH_3$; $R^{3a}$ can be selected from H (hydrogen), —$CH_3$, —$CF_3$ and —$CHF_2$; $R^{4a}$ can be selected from H (hydrogen), halogen, —$C_{1-4}$ alkyl, —$C_{1-4}$ haloalkyl, —$CH_2R^{4b}$ and —C($CH_3$)$R^{4b}$; $R^{4b}$ can be selected from —N($R^{m2}$)$R^{n2}$ and —$R^{y1}$; $R^{5a}$ can be selected from —$CH_3$, —$C_{2-4}$ alkyl and —$C_{2-4}$ haloalkyl; $R^{5b}$ can be selected from —$CH_3$, —$C_{2-4}$ alkyl and —$C_{2-4}$ haloalkyl; $R^{m1}$ can be selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and —$R^{x2}$; wherein the monocyclic heteroaryl, the bicyclic heteroaryl the monocyclic heterocyclyl and the bicyclic heterocyclyl can contain at least one atom or group of atoms independently selected from the group consisting of O (oxygen), S (sulfur), C(═O), S(═O), S(═O)$_2$ and N (nitrogen); wherein the —$C_{1-4}$ alkyl can be optionally substituted with one or two or three substituents independently selected from halogen, cyano, hydroxy, —$C_{1-4}$ alkoxy, —$C_{1-4}$ haloalkyl, —$C_{1-4}$ haloalkoxy, —C(═O)$OR^{Z1}$, —C(═O)NHS(═O)$_2R^{Z3}$, —C(═O)N($R^{Z1}$)$R^{Z2}$, —S(═O)$_2R^{Z3}$, —S(═O)$_2$N($R^{Z1}$)$R^{Z2}$, —N($R^{Z1}$)C(═O)$R^{Z3}$, —N($R^{Z1}$)S(═O)$R^{Z3}$, —N($R^{Z1}$)C(═O)N($R^{Z2}$)$R^{Z3}$ and —N($R^{Z1}$)S(═O)N($R^{Z2}$)$R^{Z3}$; wherein the $C_{3-6}$ monocyclic cycloalkyl, the $C_{5-12}$ bicyclic cycloalkyl, the 5- or 6-membered monocyclic heteroaryl, the 4-7 membered monocyclic heterocyclyl, the 8-11 membered fused-heteroaryl and the 8-11 membered fused-heterocyclyl can be optionally substituted with one or two or three substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —C(═O)$OR^{Z1}$, —C(═O)NHS(═O)$_2$ $R^{Z3}$, —C(═O)N($R^{Z1}$)$R^{Z2}$, —S(═O)$_2R^{Z3}$, —S(═O)$_2$N ($R^{Z1}$)$R^{Z2}$, —N($R^{Z1}$)C(═O)$R^{Z3}$, —N($R^{Z1}$)S(═O)$R^{Z3}$, —N($R^{Z1}$)C(═O)N($R^{Z2}$)$R^{Z3}$ and —N($R^{Z1}$)S(═O)N($R^{Z2}$) $R^{Z3}$; and $R^{n1}$ can be hydrogen, —$C_{1-4}$ alkyl, —$C_{1-4}$halolkyl or $C_{3-6}$ monocyclic cycloalkyl($CH_2$); $R^{m2}$ can be selected from —$CH_3$, —$C_{2-4}$ alkyl, —$C_{1-4}$ haloalkyl and —$R^{y2}$, wherein the —$C_{2-4}$ alkyl is optionally substituted with hydroxy; $R^{n2}$ can be selected from H (hydrogen), —$C_{1-4}$ alkyl and —$C_{1-4}$ haloalkyl; $R^{x1}$ can be selected from:

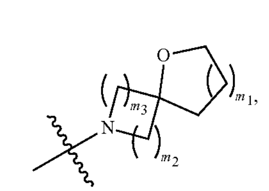
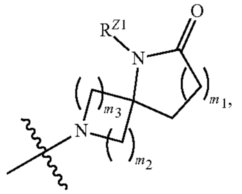
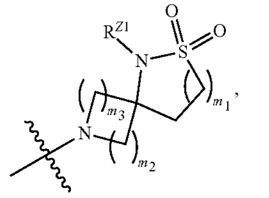
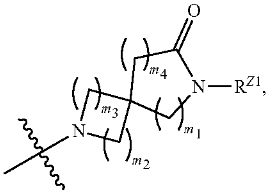
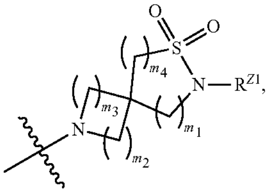
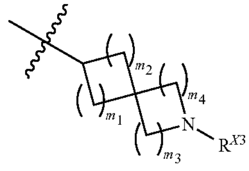
,
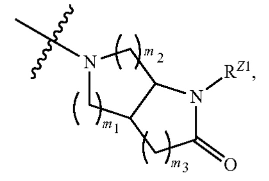
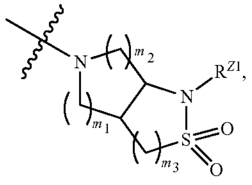
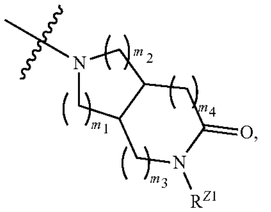
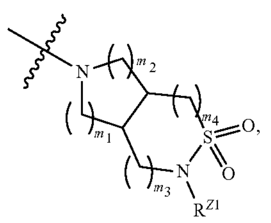
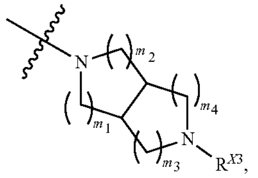
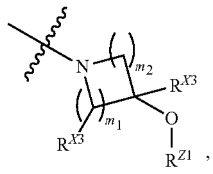
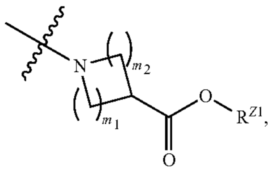
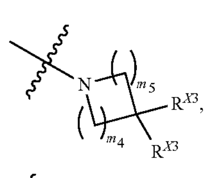
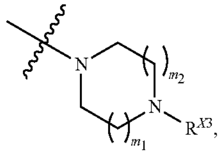
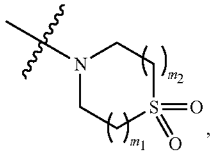
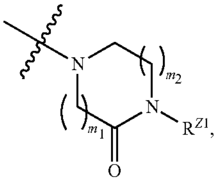
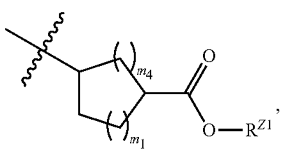
and -continued

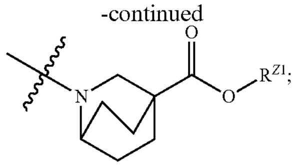

wherein $R^{x1}$ can be optionally substituted with one or two substituents independently selected from halogen, cyano, $—C_{1-4}$ alkyl, hydroxy, $—C_{1-4}$ alkoxy, $—C_{1-4}$ haloalkyl, $—C_{1-4}$ haloalkoxy, $—C(=O)OR^{Z1}$, $—C(=O)NHS(=O)_2R^{Z3}$, $—C(=O)N(R^{Z1})R^{Z2}$, $—S(=O)_2R^{Z3}$, $—S(=O)_2N(R^{Z1})R^{Z2}$, $—N(R^{Z1})C(=O)R^{Z3}$, $—N(R^{Z1})S(=O)R^{Z3}$, $—N(R^{Z1})C(=O)N(R^{Z1})R^{Z3}$ and $—N(R)S(=O)_2N(R^{Z2})R^{Z3}$; $R^{x2}$ can be selected from:

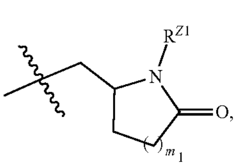
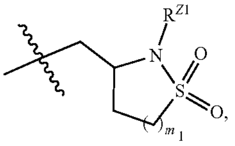
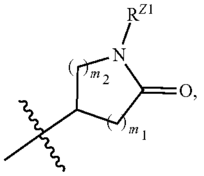
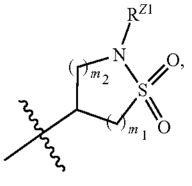
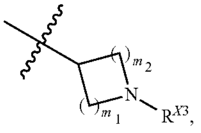
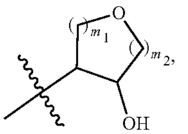
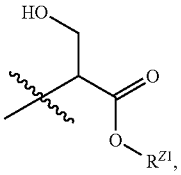
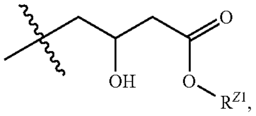
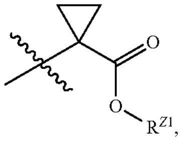
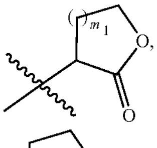
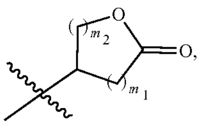
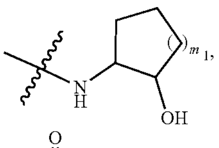 and
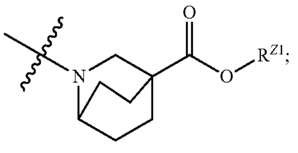

$R^{y1}$ can be selected from:

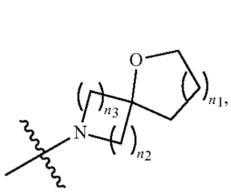
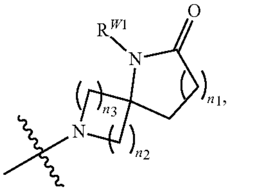
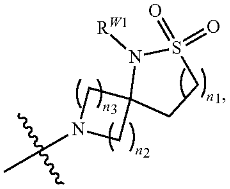
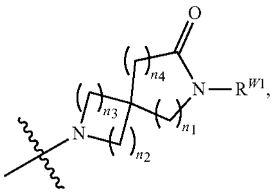
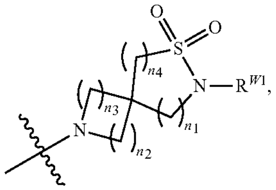
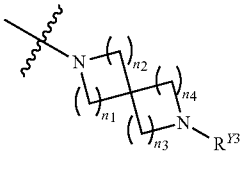,
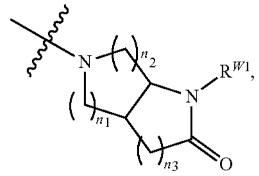
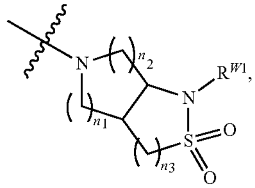
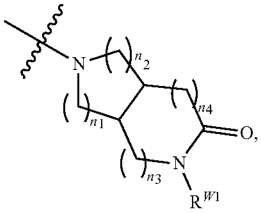
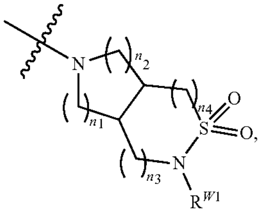
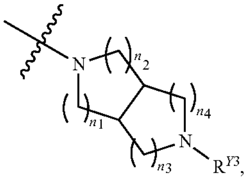
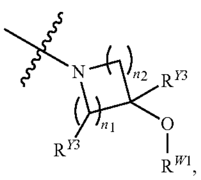
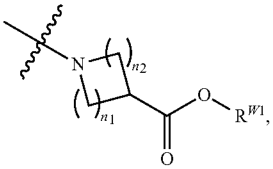
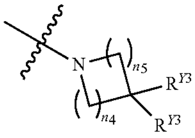,
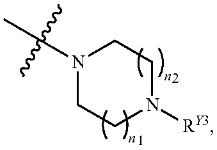
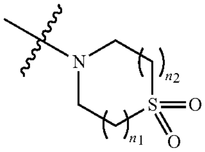,
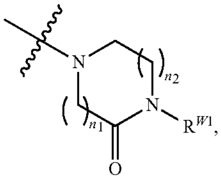
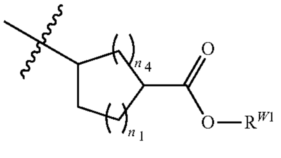 and -continued

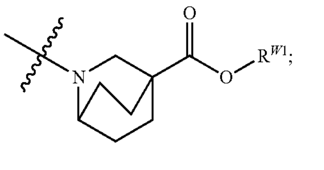

wherein $R^{y1}$ can be optionally substituted with one or two substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —C(═O)$OR^{W1}$, —C(═O)NHS(═O)$_2$$R^{W3}$, —C(═O)N($R^{W1}$)$R^{W2}$, —S(═O)$_2$$R^{W3}$, —S(═O)N($R^{W1}$)$R^{W2}$, —N($R^{W1}$)C(═O)$R^{W3}$, —N($R^{W1}$)S(═O)$R^{W3}$, —N($R^{W1}$)C(═O)N($R^{W2}$)$R^{W3}$ and —N($R^{W1}$)S(═O)N($R^{W2}$)$R^{W3}$; $R^{y2}$ can be selected from:

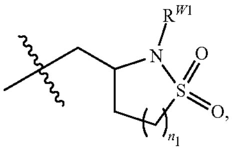

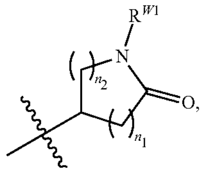

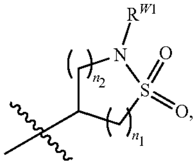

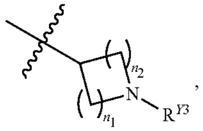

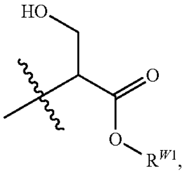

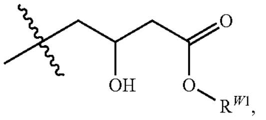

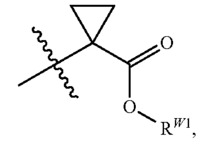

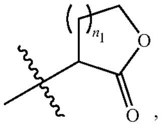

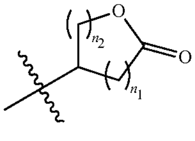

and

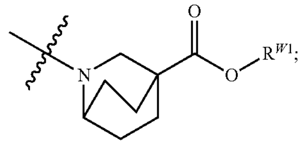

$m_1$, $m_2$, $m_3$, $n_1$, $n_2$ and $n_3$ can be independently 1 or 2; $m_4$ and $n_4$ can be independently 0, 1 or 2; $m_5$ and $n_5$ can be independently 1, 2, 3 or 4; each $R^{X3}$ can be independently selected from hydrogen, halogen, —$C_{1-4}$ alkyl, —$C_{1-4}$ haloalkyl, —C(═O)$R^{Z3}$, —C(═O)$OR^{Z1}$, —S(═O)$_2$$R^{Z1}$, —C(═O)N($R^{Z1}$)$R^{Z2}$ and —S(═O)N($R^{Z1}$)$R^{Z2}$; each $R^{Y3}$ can be independently selected from hydrogen, halogen, —$C_{1-4}$ alkyl, —$C_{1-4}$ haloalkyl, —C(═O)$R^{W3}$, —C(═O)$OR^{W3}$, —S(═O)$_2$$R^{W3}$, —C(═O)N($R^{W1}$)$R^{W2}$ and —S(═O)N($R^{W1}$)$R^{W2}$; $R^{Z1}$, $R^{Z2}$, $R^{W1}$ and $R^{W2}$ can be independently selected from hydrogen, —$C_{1-4}$ alkyl, and —$C_{1-4}$ haloalkyl; and $R^{Z3}$ and $R^{W3}$ can be independently selected from hydrogen, —$C_{1-4}$ alkyl and —$C_{1-4}$ haloalkyl. In some embodiments, a compound of Formula (I), or a pharmaceutically acceptable salt thereof, can be where $A^1$ can be

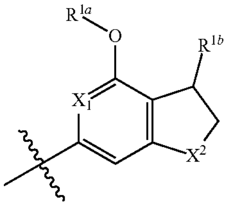

or

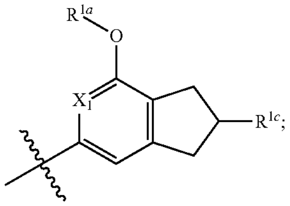

$B^1$ can be

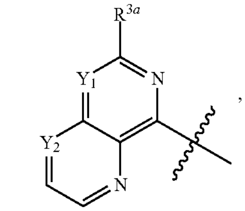

,

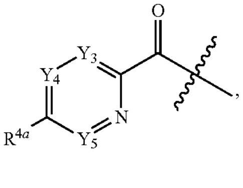

,

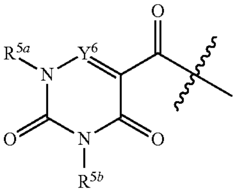

or

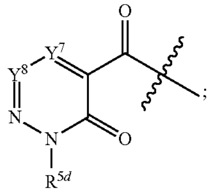

;

$X^1$ can be selected from CH and N (nitrogen); $X^2$ can be selected from O (oxygen) and $CH_2$; $Y^1$ can be selected from N (nitrogen) and CH; $Y^2$ can be selected from N (nitrogen) and CH; $Y^3$ can be selected from N (nitrogen) and CH; $Y^4$ can be selected from N (nitrogen) and CH; $Y^5$ can be selected from N (nitrogen), CH and C—$OCH_3$; $Y^6$ can be selected from N and $CR^{5c}$; $Y^7$ can be $CR^{5e}$; $Y^8$ can be $CR^{5f}$; $R^{1a}$ can be selected from —$C_{1-4}$ alkyl, —$C_{1-4}$ haloalkyl, —$CH_2$($C_{3-6}$ monocyclic cycloalkyl), —$CH_2$(4-6 membered monocyclic heterocyclyl) and —$CH_2$(5-6 membered monocyclic heteroaryl); $R^{1b}$ can be selected from —N($R^{m1}$)$R^{n1}$ and —$R^{x1}$; $R^{1c}$ can be selected from —N($R^{m1}$)$R^{n1}$ and —$R^{x1}$; $R^{2a}$, $R^{2b}$, $R^{2c}$, $R^{2e}$, $R^{2g}$, $R^{2h}$ can be independently selected from hydrogen and halogen; $R^{2d}$ and $R^{2f}$ can be independently selected from hydrogen, halogen, cyano, —$CH_3$, —$CH_2CH_3$, —$CH_2OH$, —$OCH_3$ and —$SCH_3$; $R^{3a}$ can be selected from H (hydrogen), —$CH_3$, —$CF_3$ and —$CHF_2$; $R^{4a}$ can be selected from H (hydrogen), halogen, —$C_{1-4}$ alkyl, —$C_{1-4}$ haloalkyl, —$CH_2R^{4b}$ and —C($CH_3$)$R^{4b}$; $R^{4b}$ can be selected from —N($R^{m2}$)$R^{n2}$ and —$R^{y1}$; $R^{5a}$ can be selected from hydrogen, —$CH_3$, —$C_{2-4}$ alkyl and —$C_{2-4}$ haloalkyl; $R^{5b}$ can be selected from hydrogen, —$CH_3$, —$C_{2-4}$ alkyl and —$C_{2-4}$ haloalkyl; $R^{5c}$ can be selected from hydrogen, —$CH_3$, —$C_{2-4}$ alkyl and —$C_{2-4}$ haloalkyl; $R^{5d}$ can be selected from hydrogen, —$CH_3$, —$C_{2-4}$ alkyl and —$C_{2-4}$ haloalkyl; $R^{5e}$ can be selected from hydrogen, halogen and —$CH_3$; $R^{5f}$ can be selected from hydrogen, halogen, —OH, CN and —$CH_3$; $R^{m1}$ can be selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and —$R^{x2}$; wherein the monocyclic heteroaryl, the bicyclic heteroaryl the monocyclic heterocyclyl and the bicyclic heterocyclyl can contain at least one atom or group of atoms independently selected from the group consisting of O (oxygen), S (sulfur), C(═O), S(═O), $S(=O)_2$ and N (nitrogen); wherein the $-C_4$ alkyl can be optionally substituted with one or two or three substituents independently selected from halogen, cyano, hydroxy, $-C_{1-4}$ alkoxy, $-C_{1-4}$haloalkyl, $-C_{1-4}$ haloalkoxy, $-C(=O)OR^{Z1}$, $-C(=O)NHS(=O)_2R^{Z3}$, $-C(=O)N(R^{Z1})R^{Z2}$, $-S(=O)_2R^{Z3}$, $-S(=O)_2N(R^{Z1})R^{Z2}$, $-N(R^{Z1})C(=O)R^{Z3}$, $-N(R^{Z1})S(=O)R^{Z3}$, $-N(R^{Z1})C(=O)N(R^{Z2})R^{Z3}$ and $-N(R^{Z1})S(=O)N(R^{Z2})R^{Z3}$; wherein the $C_{3-6}$ monocyclic cycloalkyl, the $C_{5-12}$ bicyclic cycloalkyl, the 5- or 6-membered monocyclic heteroaryl, the 4-7 membered monocyclic heterocyclyl, the 8-11 membered fused-heteroaryl and the 8-11 membered fused-heterocyclyl can be optionally substituted with one or two or three substituents independently selected from halogen, cyano, $-C_{1-4}$ alkyl, hydroxy, $-C_{1-4}$ alkoxy, $-C_{1-4}$ haloalkyl, $-C_{1-4}$ haloalkoxy, $-C(=O)OR^{Z1}$, $-C(=O)NHS(=O)_2R^{Z3}$, $-C(=O)N(R^{Z1})R^{Z2}$, $-S(=O)_2R^{Z3}$, $-S(=O)_2N(R^{Z1})R^{Z2}$, $-N(R^{Z1})C(=O)R^{Z3}$, $-N(R^{Z1})S(=O)R^{Z3}$, $-N(R^{Z1})C(=O)N(R^{Z2})R^{Z3}$ and $-N(R^{Z1})S(=O)N(R^{Z2})R^{Z3}$; and $R^{n1}$ can be hydrogen, $-C_{1-4}$ alkyl, $-C_{1-4}$ haloalkyl, $C_{3-6}$ monocyclic cycloalkyl$(CH_2)-$ or $-C(=O)OR^{Z4}$; $R^{m2}$ can be selected from $-CH_3$, $-C_{2-4}$ alkyl, $-C_{1-4}$ haloalkyl and $-R^{y2}$, wherein the $-C_{2-4}$ alkyl is optionally substituted with hydroxy; $R^{n2}$ can be selected from H (hydrogen), $-C_{1-4}$ alkyl and $-C_{1-4}$ haloalkyl; $R^{x1}$ can be selected from:

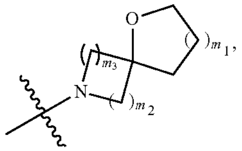
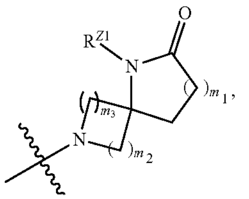
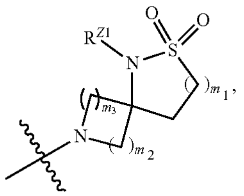
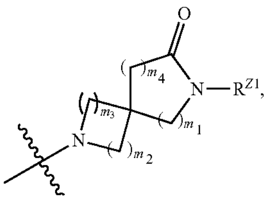
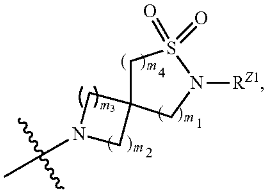
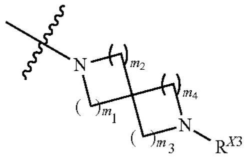
,
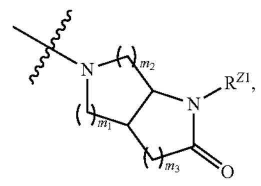
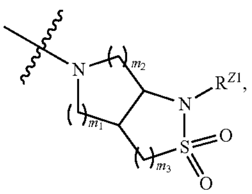
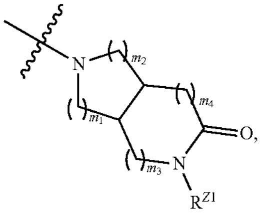
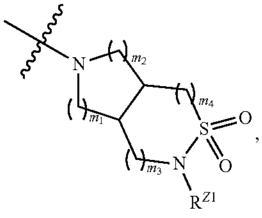
, -continued

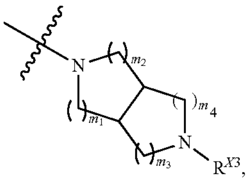
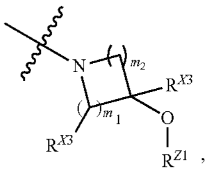
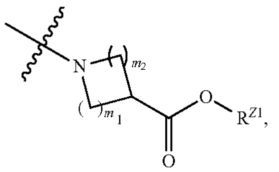
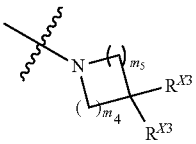
,
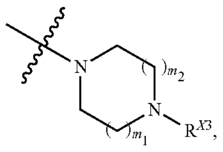
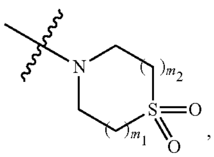
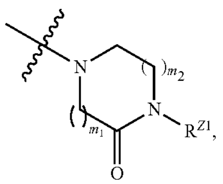
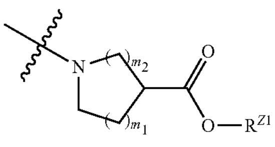
and
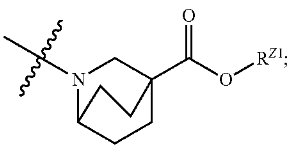

wherein $R^{x1}$ can be optionally substituted with one or two substituents independently selected from halogen, cyano, $-C_{1-4}$ alkyl, hydroxy, $-C_{1-4}$ alkoxy, $-C_{1-4}$ haloalkyl, $-C_{1-4}$ haloalkoxy, $-C(=O)OR^{Z1}$, $-C(=O)NHS(=O)_2R^{Z3}$, $-C(=O)N(R^{Z1})R^{Z2}$, $-S(=O)_2R^{Z3}$, $-S(=O)_2N(R^{Z1})R^{Z2}$, $-N(R^{Z1})C(=O)R^{Z3}$, $-N(R^{Z1})S(=O)R^{Z3}$, $-N(R^{Z1})C(=O)N(R^{Z1})R^{Z3}$ and $-N(R^{z1})S(=O)_2N(R^{Z2})R^{Z3}$; $R^{x2}$ can be selected from:

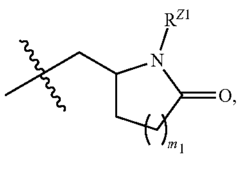
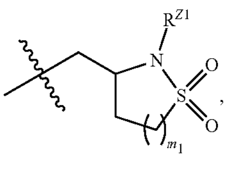
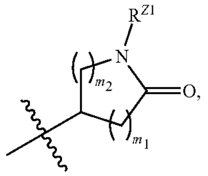
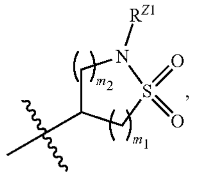
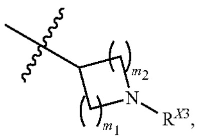
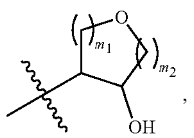

-continued

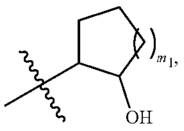

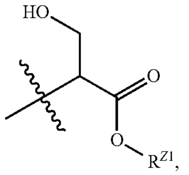

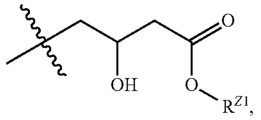

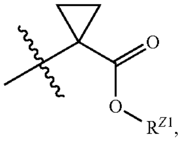

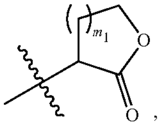

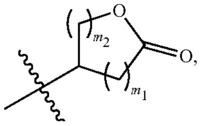

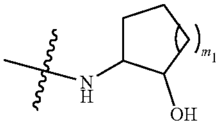

and

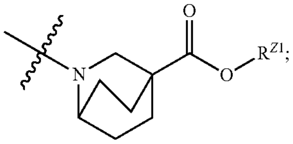

$R^{y1}$ can be selected from:

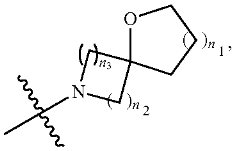

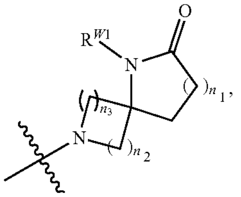

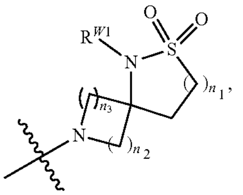

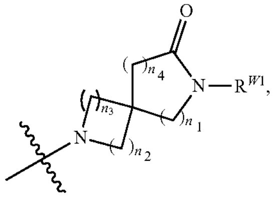

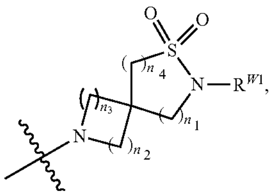

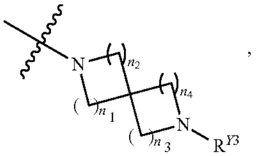

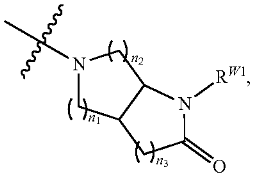

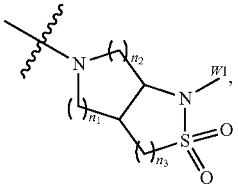

-continued

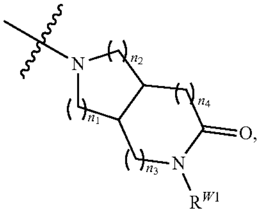

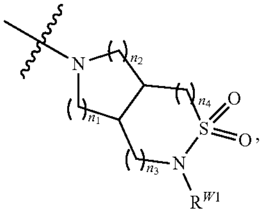

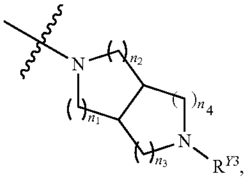

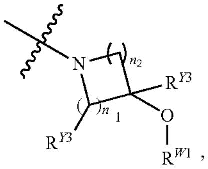

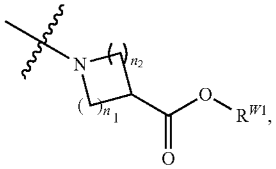

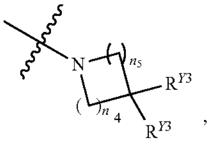

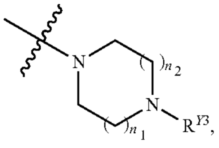

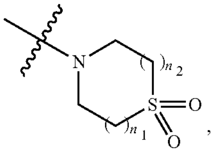

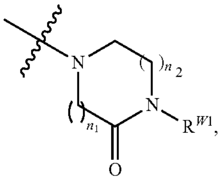

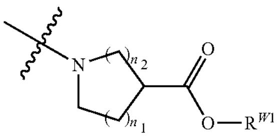

and

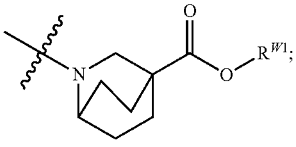

wherein $R^{y1}$ can be optionally substituted with one or two substituents independently selected from halogen, cyano, $—C_{1-4}$ alkyl, hydroxy, $—C_{1-4}$ alkoxy, $—C_{1-4}$haloalkyl, $—C_{1-4}$ haloalkoxy, $—C(=O)OR^{W1}$, $—C(=O)NHS(=O)_2R^{W3}$, $—C(=O)N(R^{W1})R^{W2}$, $—S(=O)_2R^{W3}$, $—S(=O)N(R^{W1})R^{W2}$, $—N(R^{W1})C(=O)R^{W3}$, $—N(R^{W1})S(=O)R^{W3}$, $—N(R^{W1})C(=O)N(R^{W2})R^{W3}$ and $—N(R^{W1})S(=O)N(R^{W2})R^{W3}$; $R^{y2}$ can be selected from:

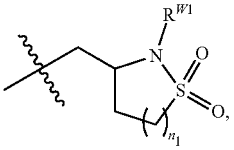

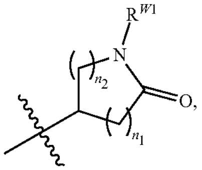

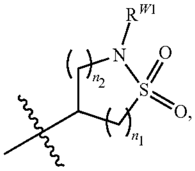

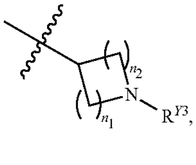

-continued

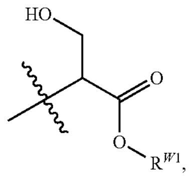
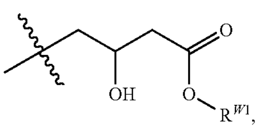
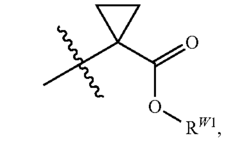
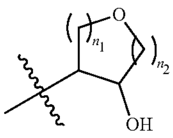
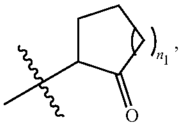
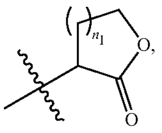
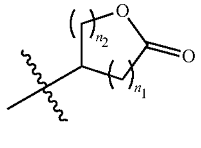
and
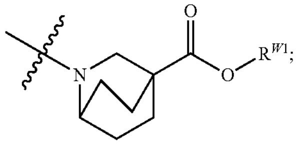

$m_1$, $m_2$, $m_3$, $n_1$, $n_2$ and $n_3$ can be independently 1 or 2; $m_4$ and $n_4$ can be independently 0, 1 or 2; $m_5$ and $n_5$ can be independently 1, 2, 3 or 4; each $R^{X3}$ can be independently selected from hydrogen, halogen, —$C_{1-4}$ alkyl, —$C_{1-4}$ haloalkyl, —C(═O)$R^{Z3}$, —C(═O)O$R^{Z1}$, —S(═O)$_2R^{Z1}$, —C(═O)N($R^{Z1}$)$R^{Z2}$ and —S(═O)N($R^{Z1}$)$R^{Z2}$; each $R^{Y3}$ can be independently selected from hydrogen, halogen, —$C_{1-4}$ alkyl, —$C_{1-4}$ haloalkyl, —C(═O)$R^{W3}$, —C(═O)O$R^{W3}$, —S(═O)$_2R^{W3}$, —C(═O)N($R^{W1}$)$R^{W2}$ and —S(═O)N($R^{W1}$)$R^{W2}$; $R^{Z1}$ and $R^{Z2}$ can be independently selected from hydrogen, —$C_{1-4}$ alkyl, and —$C_{1-4}$ haloalkyl; or $R^{Z1}$ and $R^{Z2}$ can be taken together to form a monocyclic heterocyclyl when attached to the same nitrogen; $R^{W1}$ and $R^{W2}$ can be independently selected from hydrogen, —$C_{1-4}$ alkyl and —$C_{1-4}$ haloalkyl; $R^{Z3}$ and $R^{W3}$ can be independently selected from hydrogen, —$C_{1-4}$ alkyl and —$C_{1-4}$ haloalkyl; and $R^{Z4}$ can be selected from hydrogen, —$C_{1-4}$ alkyl and 5- to 6-membered monocyclic heterocyclyl($CH_2$)— optionally substituted with —$C_{1-4}$ alkyl. In some embodiments, a compound of Formula (I), or a pharmaceutically acceptable salt thereof, can be where $A^1$ can be

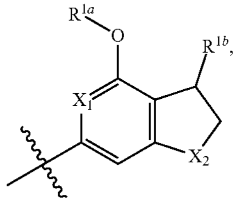
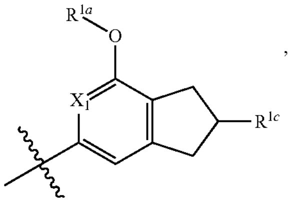
, or
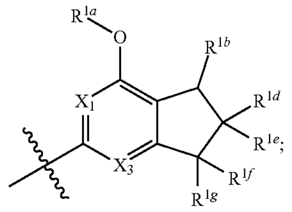

B can be

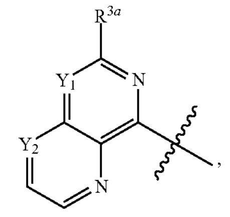
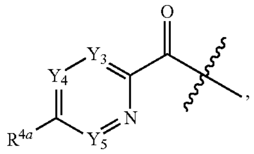
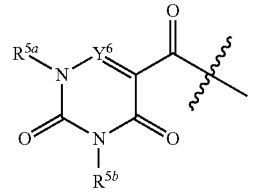
or
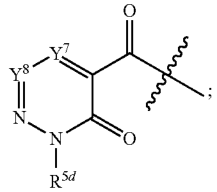

each $X^1$ can be selected from CH and N (nitrogen); $X^2$ can be O (oxygen); $X^3$ can be selected from CH, C-halo and N; $Y^1$ can be selected from N (nitrogen) and CH; $Y^2$ can be selected from N (nitrogen) and CH; $Y^3$ can be selected from N (nitrogen) and CH; $Y^4$ can be selected from N (nitrogen) and CH; $Y^5$ can be selected from N (nitrogen), CH and C—$OCH_3$; $Y^6$ can be selected from N and $CR^{5c}$; $Y^7$ can be $CR^{5e}$; $Y^8$ can be $CR^{5f}$; each $R^{1a}$ can be selected from —$C_{1-4}$ alkyl, —$C_{1-4}$ haloalkyl, —$CH_2$($C_{3-6}$ monocyclic cycloalkyl), —$C_{2-4}$ alkyl($C_{1-4}$ alkoxy), —$C_{2-4}$ alkyl ($C_{1-4}$ haloalkoxy), —$CH_2$(4-6 membered monocyclic heterocyclyl) and —$CH_2$(5-6 membered monocyclic heteroaryl); each $R^{1b}$ can be selected from —N($R^{m1}$)$R^{n1}$ and —$R^{x1}$; $R^{1c}$ can be selected from —N($R^{m1}$)$R^{n1}$ and —$R^{x1}$; $R^{1d}$ can be selected from hydrogen, —$CH_3$, —$CH_2CH_3$, —OH, —$OCH_3$ and —F; $R^{1e}$ can be selected from hydrogen, —$CH_3$, —$CH_2CH_3$ and —F; $R^{1f}$ can be selected from hydrogen, —$CH_3$, —$CH_2CH_3$, —OH, —$OCH_3$ and —F; $R^{1g}$ can be selected from hydrogen, —$CH_3$, —$CH_2CH_3$ and —F; $R^{2a}$, $R^{2b}$, $R^{2c}$, $R^{2e}$, $R^{2g}$, $R^{2h}$ can be independently selected from hydrogen and halogen; $R^{2d}$ and $R^{2f}$ can be independently selected from hydrogen, halogen, cyano, —$CH_3$, —$CH_2CH_3$, —$CH_2OH$, —$OCH_3$ and —$SCH_3$; $R^{3a}$ can be selected from H (hydrogen), —$CH_3$, —$CF_3$ and —$CHF_2$; $R^{4a}$ can be selected from H (hydrogen), halogen, —$C_{1-4}$ alkyl, —$C_{1-4}$ haloalkyl, —$CH_2R^{4b}$ and —C($CH_3$)$R^{4b}$; $R^{4b}$ can be selected from —N($R^{12}$)$R^{n2}$ and —$R^{y1}$; $R^{5a}$ can be selected from hydrogen, —$CH_3$, —$C_{2-4}$ alkyl and —$C_{2-4}$ haloalkyl; $R^{5b}$ can be selected from hydrogen, —$CH_3$, —$C_{2-4}$ alkyl and —$C_{2-4}$ haloalkyl; $R^{5c}$ can be selected from hydrogen, —$CH_3$, —$C_{2-4}$ alkyl and —$C_{2-4}$ haloalkyl; $R^{5d}$ can be selected from hydrogen, —$CH_3$, —$C_{2-4}$ alkyl and —$C_{2-4}$ haloalkyl; $R^{5e}$ can be selected from hydrogen, halogen and —$CH_3$; $R^5$ can be selected from hydrogen, halogen, —OH, —CN and —$CH_3$; $R^{m1}$ can be selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and —$R^{x2}$; wherein the monocyclic heteroaryl, the bicyclic heteroaryl the monocyclic heterocyclyl and the bicyclic heterocyclyl can contain at least one atom or group of atoms independently selected from the group consisting of O (oxygen), S (sulfur), C(═O), S(═O), S(═O)$_2$ and N (nitrogen); wherein the —$C_{1-4}$ alkyl can be optionally substituted with one or two or three substituents independently selected from halogen, cyano, hydroxy, —$C_{1-4}$ alkoxy, —$C_{1-4}$ haloalkyl, —$C_{1-4}$ haloalkoxy, —C(═O)O$R^{Z1}$, —C(═O)NHS(═O)$_2R^{Z3}$, —C(═O)N $(R^{Z1})R^{Z2}$, $—S(═O)_2R^{Z3}$, $—S(═O)_2N(R^{Z1})R^{Z2}$, $—N(R^{Z1})C(═O)R^{Z3}$, $—N(R^{Z1})S(═O)R^{Z3}$, $—N(R^{Z1})C(═O)N(R^{Z2})R^{Z3}$ and $—N(R^{Z1})S(═O)N(R^{Z2})R^{Z3}$; wherein the $C_{3-6}$ monocyclic cycloalkyl, the $C_{5-12}$ bicyclic cycloalkyl, the 5- or 6-membered monocyclic heteroaryl, the 4-7 membered monocyclic heterocyclyl, the 8-11 membered fused-heteroaryl and the 8-11 membered fused-heterocyclyl can be optionally substituted with one or two or three substituents independently selected from halogen, cyano, $—C_{1-4}$ alkyl, hydroxy, $—C_{1-4}$ alkoxy, $—C_{1-4}$ haloalkyl, $—C_{1-4}$ haloalkoxy, $—C(═O)OR^{Z1}$, $—C(═O)NHS(═O)_2R^{Z3}$, $—C(═O)N(R^{Z1})R^{Z2}$, $—S(═O)_2R^{Z3}$, $—S(═O)_2N(R^{Z1})R^{Z2}$, $—N(R^{Z1})C(═O)R^{Z3}$, $—N(R^{Z1})S(═O)R^{Z3}$, $—N(R^{Z1})C(═O)N(R^{Z2})R^{Z3}$ and $—N(R^{Z1})S(═O)N(R^{Z2})R^{Z3}$; and $R^{n1}$ can be hydrogen, $—C_{1-4}$ alkyl, $—C_{1-4}$ haloalkyl, $C_{3-6}$ monocyclic cycloalkyl$(CH_2)$— or $—C(═O)OR^{Z4}$; $R^{m2}$ can be selected from $—CH_3$, $—C_{2-4}$ alkyl, $—C_{1-4}$ haloalkyl and $—R^{y2}$, wherein the $—C_{2-4}$ alkyl is optionally substituted with hydroxy; $R^{n2}$ can be selected from H (hydrogen), $—C_{1-4}$ alkyl and $—C_{1-4}$ haloalkyl; $R^{x1}$ can be selected from:

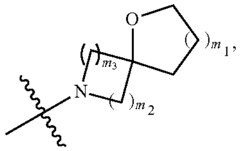
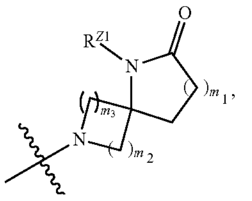
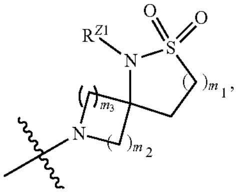
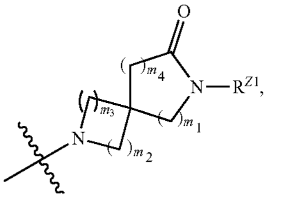
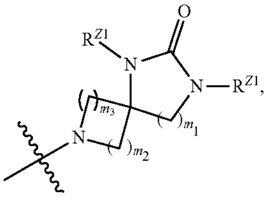
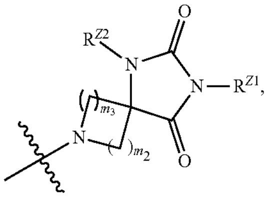
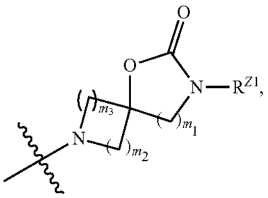
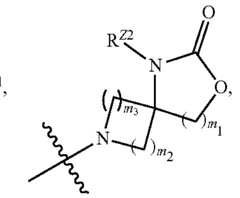
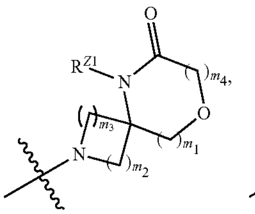
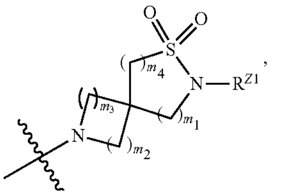
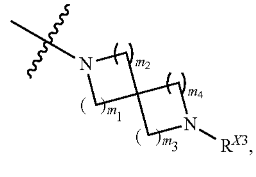
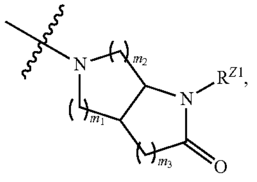

-continued

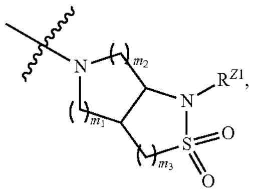
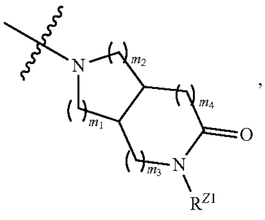
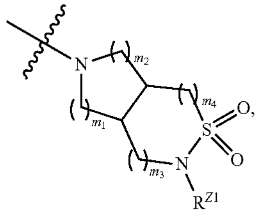
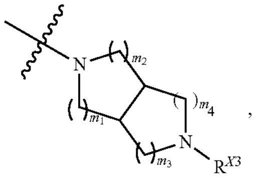
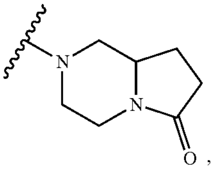
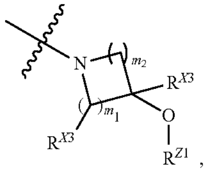
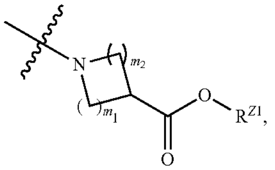
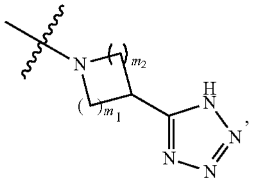
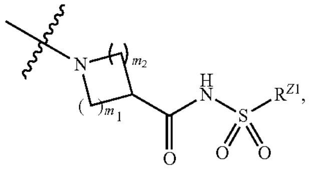
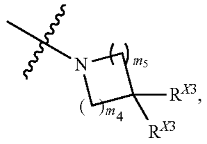
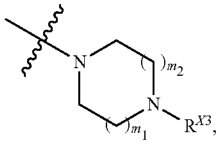
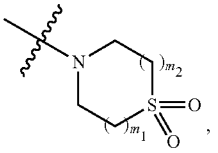
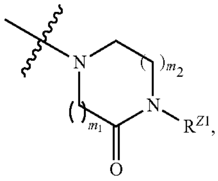
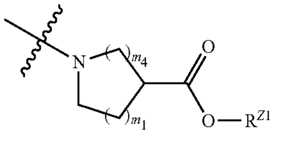
and
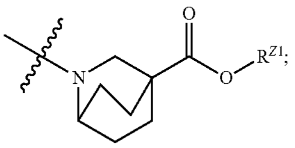

wherein $R^{x1}$ can be optionally substituted with one or two substituents independently selected from halogen, cyano, $—C_{1-4}$ alkyl, hydroxy, $—C_{1-4}$ alkoxy, $—C_{1-4}$ haloalkyl, $—C_{1-4}$ haloalkoxy, $—C(═O)OR^{Z1}$, $—C(═O)NHS(═O)_2R^{Z3}$, $—C(═O)N(R^{Z1})R^{Z2}$, $—S(═O)_2R^{Z3}$, $—S(═O)_2N(R^{Z1})R^{Z2}$, $—N(R^{Z1})C(═O)R^{Z3}$, $—N(R^{Z1})S(═O)R^{Z3}$, $—N(R^{Z1})C(═O)N(R^{Z1})R^{Z3}$ and $—N(R^{z1})S(═O)_2N(R^{Z2})R^{Z3}$; $R^{x2}$ can be selected from:

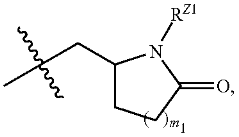
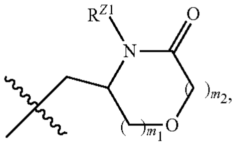
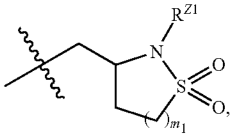
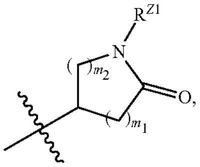
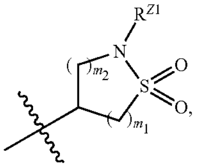
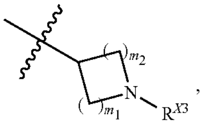
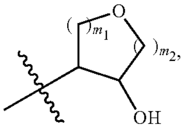
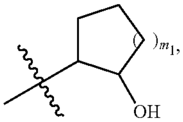
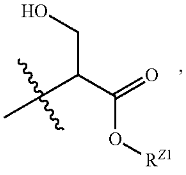
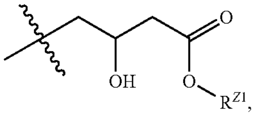
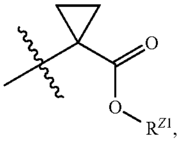
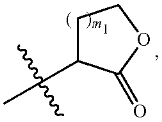
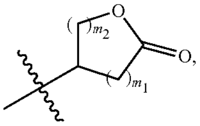
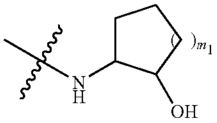
and
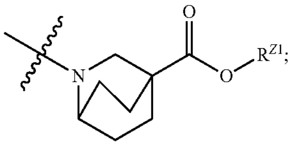
$R^{y1}$ can be selected from:
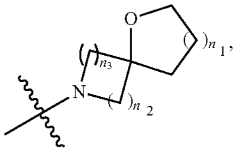
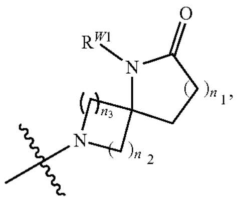
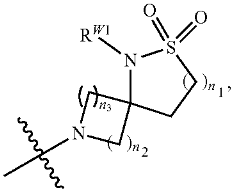
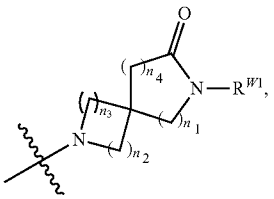
-continued
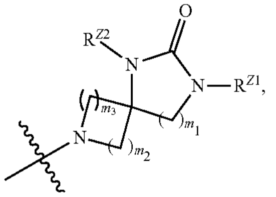
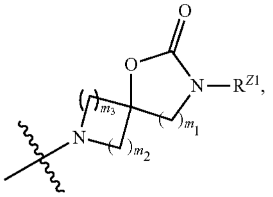
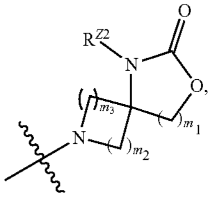
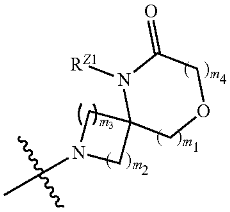
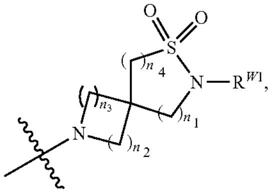
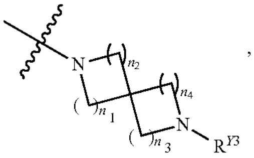
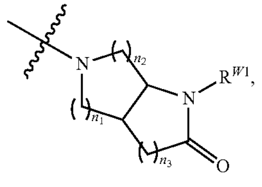
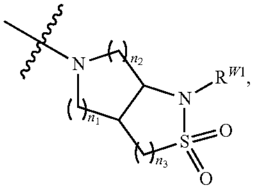
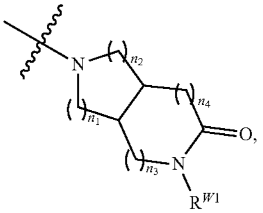
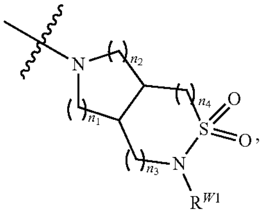
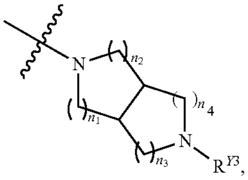
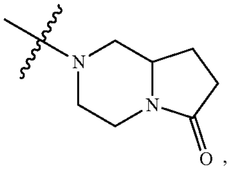
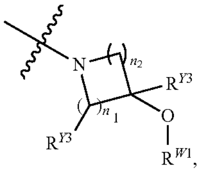
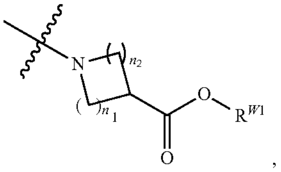
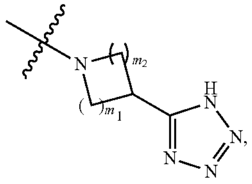
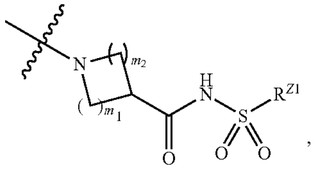
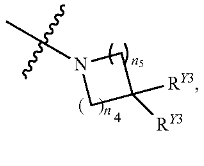
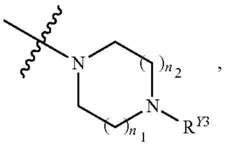

-continued

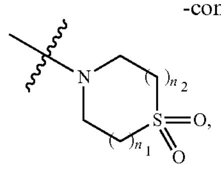
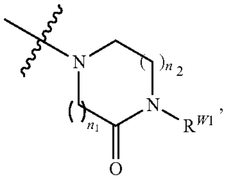
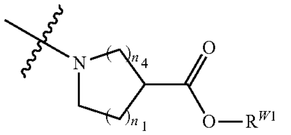
and
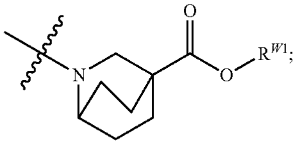

wherein $R^{y1}$ can be optionally substituted with one or two substituents independently selected from halogen, cyano, $—C_{1-4}$ alkyl, hydroxy, $—C_{1-4}$ alkoxy, $—C_{1-4}$ haloalkyl, $—C_{1-4}$ haloalkoxy, $—C(=O)OR^{W1}$, $—C(=O)NHS(=O)_2R^{W3}$, $—C(=O)N(R^{W1})R^{W2}$, $—S(=O)_2R^{W3}$, $—S(=O)N(R^{W1})R^{W2}$, $—N(R^{W1})C(=O)R^{W3}$, $—N(R^{W1})S(=O)R^{W3}$, $—N(R^{W1})C(=O)N(R^{W2})R^{W3}$ and $—N(R^{W1})S(=O)N(R^{W2})R^{W3}$; $R^{y2}$ can be selected from:

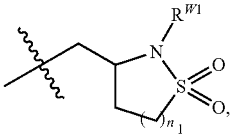
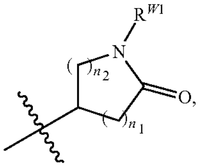
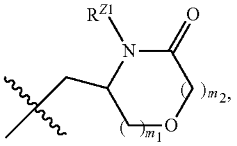
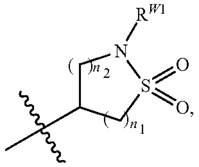
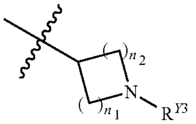
,
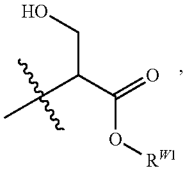
,
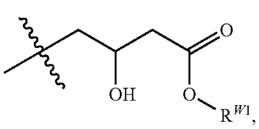
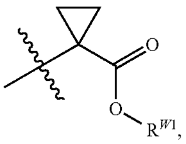
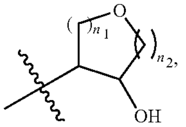
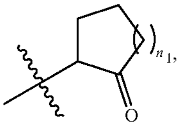
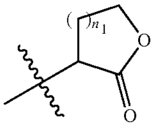
,
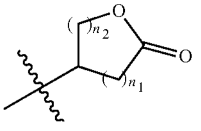
and -continued

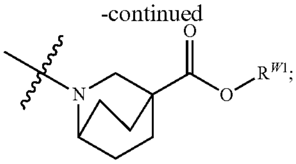

$m_1$, $m_2$, $m_3$, $n_1$, $n_2$ and $n_3$ can be independently 1 or 2; $m_4$ and $n_4$ can be independently 0, 1 or 2; $m_5$ and $n_5$ can be independently 1, 2, 3 or 4; each $R^{X3}$ can be independently selected from hydrogen, halogen, $—C_{1-4}$ alkyl, $—C_{1-4}$ haloalkyl, $—C(=O)R^{Z3}$, $—C(=O)OR^{Z1}$, $—S(=O)_2R^{Z1}$, $—C(=O)N(R^{Z1})R^{Z2}$ and $—S(=O)N(R^{Z1})R^{Z2}$; each $R^{Y3}$ can be independently selected from hydrogen, halogen, $—C_{1-4}$ alkyl, $—C_{1-4}$ haloalkyl, $—C(=O)R^{W3}$, $—C(=O)OR^{W3}$, $—S(=O)_2R^{W3}$, $—C(=O)N(R^{W1})R^{W2}$ and $—S(=O)N(R^{W1})R^{W2}$; $R^{Z1}$ and $R^{Z2}$ can be independently selected from hydrogen, $—C_{1-4}$ alkyl, and $—C_{1-4}$ haloalkyl; or $R^{Z1}$ and $R^{Z2}$ can be taken together to form a monocyclic heterocyclyl when attached to the same nitrogen; $R^{W1}$ and $R^{W2}$ can be independently selected from hydrogen, $—C_{1-4}$ alkyl and $—C_{1-4}$ haloalkyl; $R^{Z3}$ and $R^{W3}$ can be independently selected from hydrogen, $—C_{1-4}$ alkyl and $—C_{1-4}$ haloalkyl; and $R^{Z4}$ can be selected from hydrogen, $—C_{1-4}$ alkyl and 5- to 6-membered monocyclic heterocyclyl$(CH_2)$— optionally substituted with $—C_{1-4}$ alkyl.

Embodiment 2

The compound of Embodiment 1, wherein $A^1$ can be

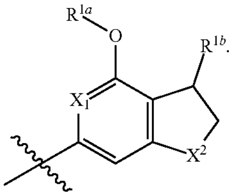

Embodiment 3

The compound of Embodiment 2, wherein $X^1$ can be CH.

Embodiment 4

The compound of Embodiment 2, wherein $X^1$ can be N (nitrogen).

Embodiment 5

The compound of any one of Embodiments 2-4, wherein $R^{1a}$ can be $—C_{1-4}$ alkyl. Examples of $C_{1-4}$ alkyls include methyl, ethyl, n-propyl, iso-propyl, n-butyl, iso-butyl, sec-butyl and tert-butyl.

Embodiment 6

The compound of any one of Embodiments 2-4, wherein $R^{1a}$ can be $—C_{1-4}$ haloalkyl, such as $—CF_3$, $—CHF_2$, $—CH_2F$, $—CCl_3$, $—CHCl_2$, $—CH_2Cl$, $—CH_2CF_3$ and $—CH_2CHF_2$.

Embodiment 7

The compound of any one of Embodiments 2-4, wherein $R^{1a}$ can be —$C_{2-4}$ alkyl($C_{1-4}$ alkoxy) or —$C_{2-4}$ alkyl ($C_{1-4}$ haloalkoxy).

Embodiment 8

The compound of any one of Embodiments 2-4, wherein $R^{1a}$ can be selected from —$CH_2$($C_{3-6}$ monocyclic cycloalkyl), —$CH_2$(4-6 membered monocyclic heterocyclyl) and —$CH_2$(5-6 membered monocyclic heteroaryl). Exemplary monocyclic cycloalkyls include cyclopropyl, cyclobutyl, cyclopentyl and cyclohexyl. In some embodiments, the 4-6 membered monocyclic heterocyclyl of the —$CH_2$(4-6 membered monocyclic heterocyclyl) and/or the 5-6 membered monocyclic heteroaryl of the —$CH_2$(5-6 membered monocyclic heteroaryl) can include one or more ring atoms (such as 1, 2 or 3) selected from N (nitrogen), O (oxygen) and S (sulfur).

Embodiment 9

The compound of any one of Embodiments 2-8, wherein $R^{1b}$ can be —N($R^{m1}$)$R^{n1}$.

Embodiment 10

The compound of Embodiment 9, wherein $R^{n1}$ can be hydrogen, such that Rib can be —NH($R^{m1}$).

Embodiment 11

The compound of any one of Embodiments 2-8, wherein $R^{m1}$ can be —C(═O)O$R^{Z4}$. In some embodiments, $R^{Z4}$ can be a $C_{1-4}$ alkyl. In other embodiments, $R^{Z4}$ can be 5- to 6-membered monocyclic heterocyclyl($CH_2$)— optionally substituted with —$C_{1-4}$ alkyl.

Embodiment 12

The compound of any one of Embodiments 9-11, wherein $R^{m1}$ can be —$C_{1-4}$ alkyl optionally substituted with —C(═O)O$R^{Z1}$ or 4-7 membered monocyclic heterocyclyl optionally substituted with hydroxy. Examples of $C_{1-4}$ alkyls include methyl, ethyl, n-propyl, iso-propyl, n-butyl, iso-butyl, sec-butyl and tert-butyl. In some embodiments, the 4-7 membered monocyclic heterocyclyl optionally substituted with hydroxy can include one or more ring atoms (such as 1, 2 or 3) selected from N (nitrogen), O (oxygen) and S (sulfur).

Embodiment 13

The compound of Embodiment 12, wherein $R^{m1}$ can be

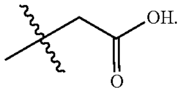 [SMILES: *CC(=O)O]

Embodiment 14

The compound of Embodiment 12, wherein $R^{m1}$ can be tetrahydrofuran or tetrahydro-2H-pyran, each optionally substituted with hydroxy.

Embodiment 15

The compound of Embodiment 14, wherein $R^{m1}$ can be

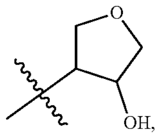
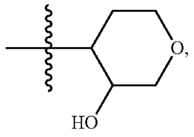
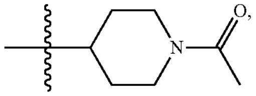
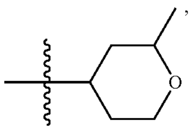
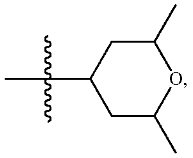
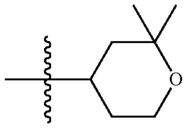
or
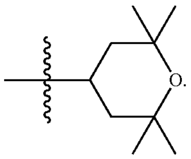

In some embodiments, $R^{m1}$ can be

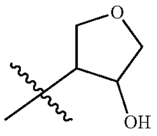
or
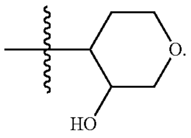

In other embodiments, $R^{m1}$ can be

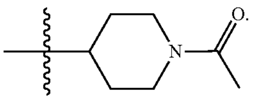

Embodiment 16

The compound of any one of Embodiments 9-11, wherein $R^{m1}$ can be —$R^{x2}$.

Embodiment 17
The compound of Embodiment 16, wherein —$R^{x2}$ can be
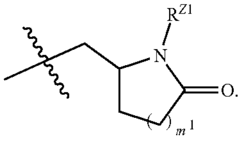
In some embodiments, —$R^{x2}$ can be
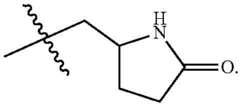 [SMILES: *CC1CCC(=O)N1]
Embodiment 18
The compound of any one of Embodiments 2-8, wherein $R^{1b}$ can be —$R^{x1}$.
Embodiment 19
The compound of Embodiment 18, wherein —$R^{x1}$ can be selected from:
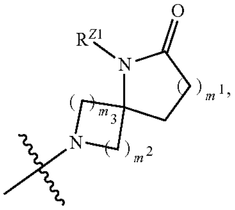
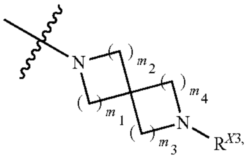
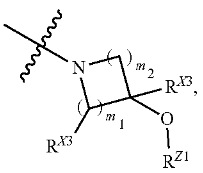
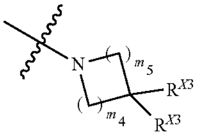
and
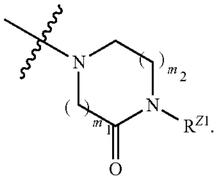
Embodiment 20
The compound of Embodiment 19, wherein —$R^{x1}$ can be selected from:
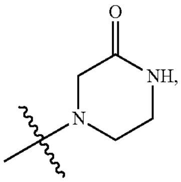
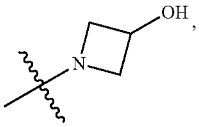
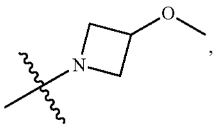
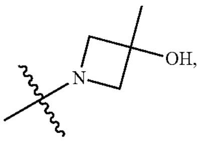
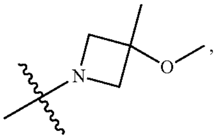
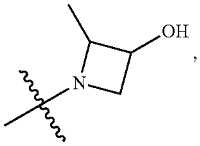
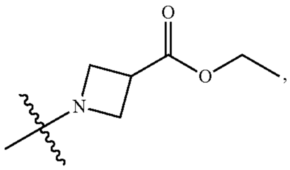
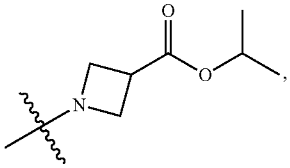
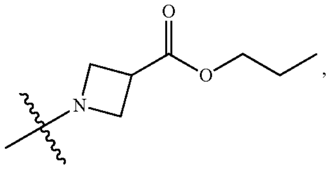
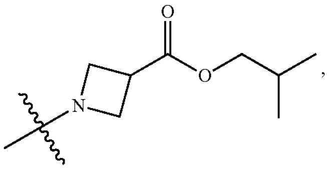
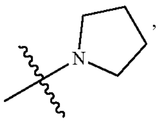
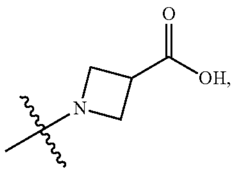
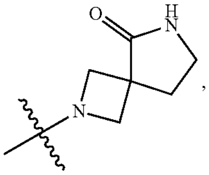
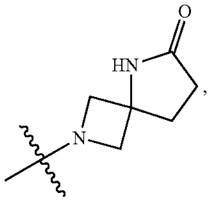
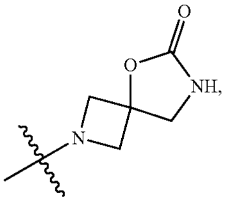

-continued

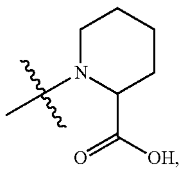,

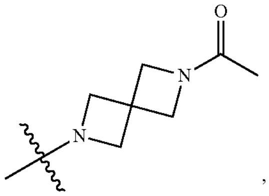,

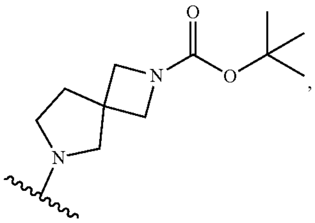,

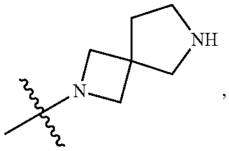,

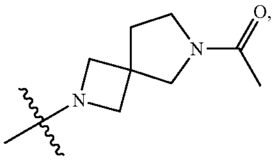

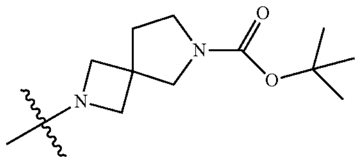

and

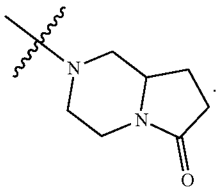.

In some embodiments, —$R^{x1}$ can be selected from:

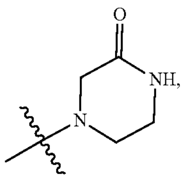

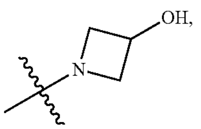

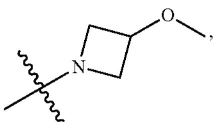,

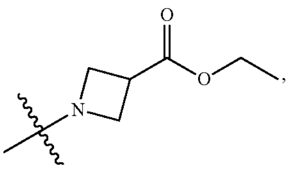,

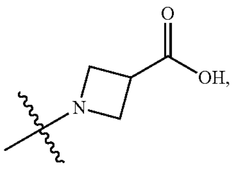

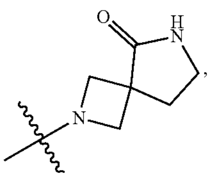,

-continued

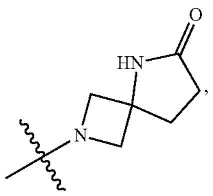,

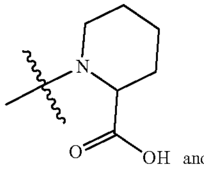

and

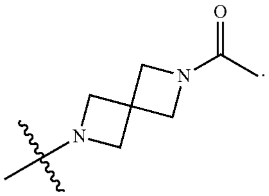.

Embodiment 21

The compound of Embodiment 21, wherein $A^1$ can be

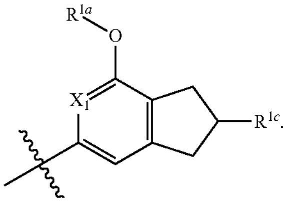.

Embodiment 22

The compound of Embodiment 21, wherein $X^1$ can be CH.

Embodiment 23

The compound of Embodiment 21, wherein $X^1$ can be N (nitrogen).

Embodiment 24

The compound of any one of Embodiments 21-23, wherein $R^{1a}$ can be —$C_{1-4}$ alkyl, such as methyl, ethyl, n-propyl, iso-propyl, n-butyl, iso-butyl, sec-butyl and tert-butyl.

Embodiment 25

The compound of any one of Embodiments 21-23, wherein $R^{1a}$ can be —$C_{1-4}$ haloalkyl. Examples of suitable $C_{1-4}$ haloalkyls include, but are not limited to, —$CF_3$, —$CHF_2$, —$CH_2F$, —$CCl_3$, —$CHCl_2$, —$CH_2Cl$, —$CH_2CF_3$ and —$CH_2CHF_2$.

Embodiment 26

The compound of any one of Embodiments 21-23, wherein $R^{1a}$ can be selected from —$CH_2$($C_{3-6}$ monocyclic cycloalkyl), —$CH_2$(4-6 membered monocyclic heterocyclyl) and —$CH_2$(5-6 membered monocyclic heteroaryl).

Examples of monocyclic cycloalkyls include cyclopropyl, cyclobutyl, cyclopentyl and cyclohexyl. In some embodiments, the 4-6 membered monocyclic heterocyclyl of the —$CH_2$(4-6 membered monocyclic heterocyclyl) and/or the 5-6 membered monocyclic heteroaryl of the —$CH_2$(5-6 membered monocyclic heteroaryl) can include one or more ring atoms (such as 1, 2 or 3) selected from N (nitrogen), O (oxygen) and S (sulfur).

Embodiment 27

The compound of any one of Embodiments 21-26, wherein $R^{1c}$ can be —N($R^{m1}$)$R^{n1}$.

Embodiment 28

The compound of Embodiment 27, wherein $R^{n1}$ can be hydrogen.

Embodiment 29

The compound of Embodiment 27, wherein $R^{n1}$ can be —C(═O)$OR^{Z4}$. In some embodiments, $R^{Z4}$ can be a $C_{1-4}$ alkyl. In other embodiments, $R^{Z4}$ can be 5- to 6-membered monocyclic heterocyclyl($CH_2$)— optionally substituted with —$C_{1-4}$ alkyl.

Embodiment 30

The compound of any one of Embodiments 27-29, wherein $R^{m1}$ can be $C_{3-6}$ monocyclic cycloalkyl, —$C_{1-4}$ alkyl optionally substituted with —C(═O)$OR^{Z1}$ or 4-7 membered monocyclic heterocyclyl optionally substituted with hydroxy. Exemplary $C_{1-4}$ alkyls include methyl, ethyl, n-propyl, iso-propyl, n-butyl, iso-butyl, sec-butyl and tert-butyl. In some embodiments, the 4-7 membered monocyclic heterocyclyl optionally substituted with hydroxy can include one or more ring atoms (such as 1, 2 or 3) selected from N (nitrogen), O (oxygen) and S (sulfur).

Embodiment 31

The compound of Embodiment 30, wherein $R^{m1}$ can be

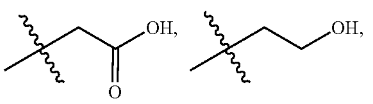

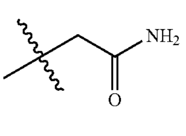

or

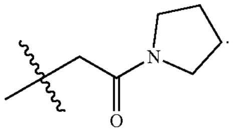

Embodiment 32

The compound of Embodiment 30, wherein $R^{m1}$ can be oxetane, tetrahydrofuran or tetrahydro-2H-pyran, each optionally substituted with hydroxy.

Embodiment 33

The compound of Embodiment 32, wherein $R^{m1}$ can be

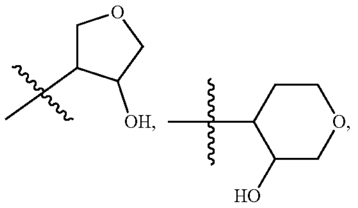

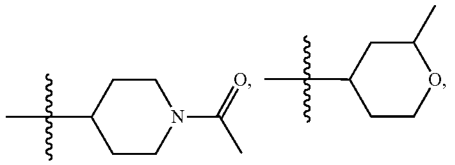

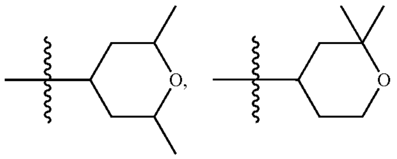

or

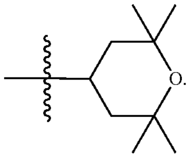

In some embodiments, $R^{m1}$ can be

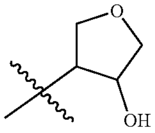

or

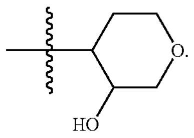

In other embodiments, $R^{m1}$ can be

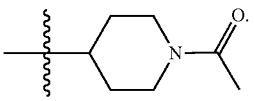 [SMILES: *C1CCN(C(C)=O)CC1]

Embodiment 34

The compound of any one of Embodiments 27-29, wherein $R^{m1}$ can be —$R^{x2}$.

Embodiment 35
The compound of Embodiment 34, wherein —$R^{x2}$ can be
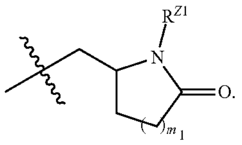
In some embodiments, —$R^{x2}$ can be
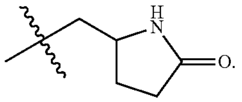 [SMILES: *CC1CCC(=O)N1]
Embodiment 36
The compound of any one of Embodiments 21-26, wherein $R^{1c}$ can be —$R^{x1}$.
Embodiment 37
The compound of Embodiment 36, wherein —$R^{x1}$ can be selected from:
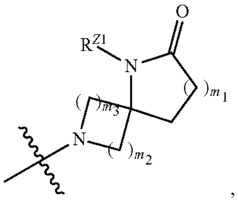
,
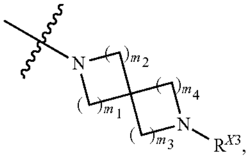
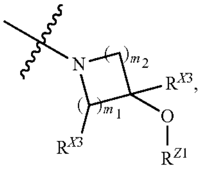
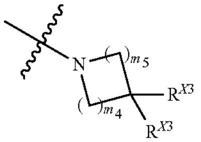
and
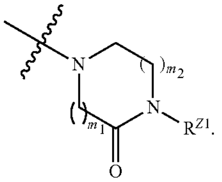
Embodiment 38
The compound of Embodiment 37, wherein —$R^{x1}$ can be selected from:
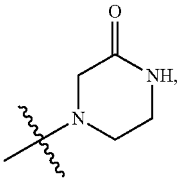
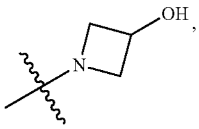
,
-continued
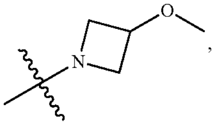
,
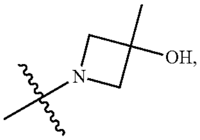
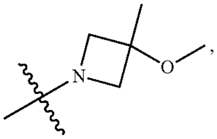
,
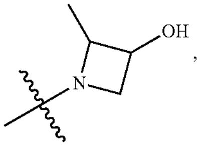
,
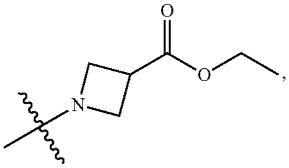
,
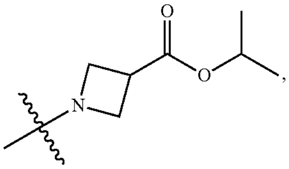
,
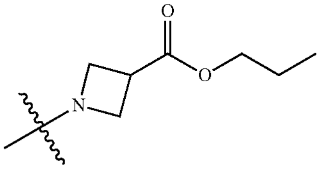
,
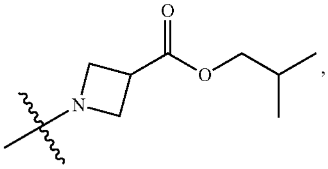
,
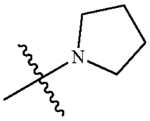
,
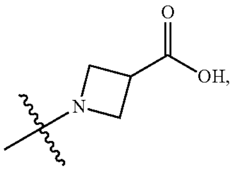
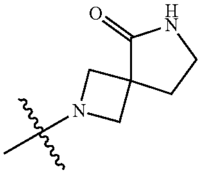
,
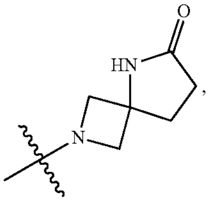
,
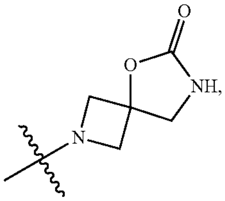
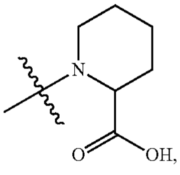
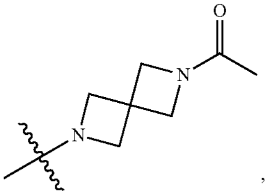
, -continued

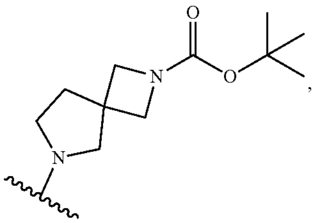
,
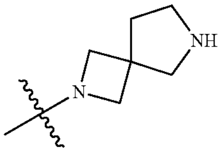
,
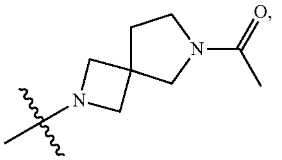
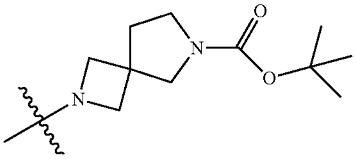
and
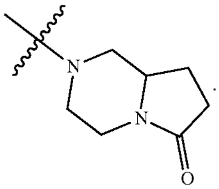

In some embodiments, —$R^{x1}$ can be selected from:

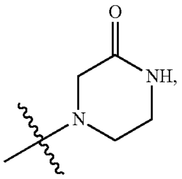
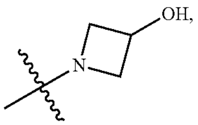
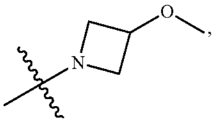
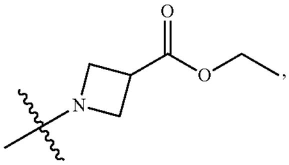
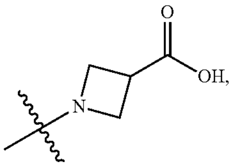
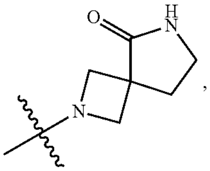
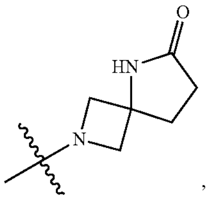
,
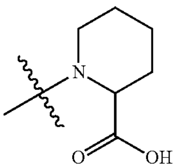
and -continued

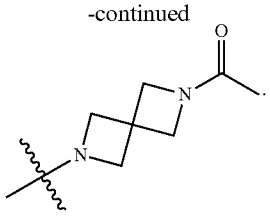

Embodiment 39

The compound of Claim 1, wherein $A^1$ is

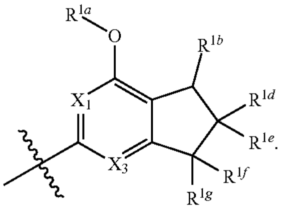

Embodiment 40

The compound of Embodiment 39, wherein $X^1$ is CH.

Embodiment 41

The compound of Embodiment 39, wherein $X^1$ is N.

Embodiment 42

The compound of any one of Embodiments 39-41, wherein $X^3$ is CH.

Embodiment 43

The compound of any one of Embodiments 39-41, wherein $X^3$ is C-halo.

Embodiment 44

The compound of any one of Embodiments 39-41, wherein $X^3$ is N.

Embodiment 45

The compound of any one of Embodiments 39-44, wherein $R^{1a}$ is —$C_{1-4}$ alkyl. As an example, $R^{1a}$ can be —$CH_3$.

Embodiment 46

The compound of any one of Embodiments 39-44, wherein $R^{1a}$ is —$C_{1-4}$ haloalkyl.

Embodiment 47

The compound of any one of Embodiments 39-44, wherein $R^{1a}$ is selected from the group consisting of —$CH_2$($C_{3-6}$ monocyclic cycloalkyl), —$CH_2$(4-6 membered monocyclic heterocyclyl) and —$CH_2$(5-6 membered monocyclic heteroaryl).

Embodiment 48

The compound of any one of Embodiments 39-47, wherein $R^{1b}$ is —N($R^{m1}$)$R^{n1}$.

Embodiment 49

The compound of any one of Embodiments 39-47, wherein $R^{n1}$ is hydrogen.

Embodiment 50

The compound of any one of Embodiments 39-47, wherein $R^{n1}$ is —C(═O)O$R^{Z4}$.

Embodiment 51

The compound of any one of Embodiments 39-50, wherein $R^{m1}$ is hydrogen.

Embodiment 52

The compound of any one of Embodiments 39-50, wherein $R^{m1}$ is —$C_{1-4}$ alkyl optionally substituted with —C(═O)O$R^{Z1}$ or 4-7 membered monocyclic heterocyclyl optionally substituted with hydroxy.

Embodiment 53

The compound of any one of Embodiments 39-50, wherein $R^{m1}$ is $C_5$ monocyclic cycloalkyl or $C_6$ monocyclic cycloalkyl.

Embodiment 54

The compound of Embodiment 52, wherein $R^{m1}$ is

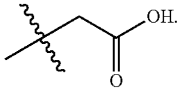 [SMILES: *CC(=O)O]

Embodiment 55

The compound of Embodiment 52, wherein $R^{m1}$ is tetrahydrofuran or tetrahydro-2H-pyran, each optionally substituted with hydroxy, or piperidine optionally substituted with —C(═O)$R^{Z1}$.

Embodiment 56

The compound of Embodiment 55, wherein $R^{m1}$ is wherein $R^{m1}$ can be

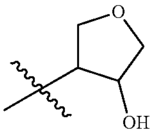
,
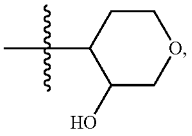

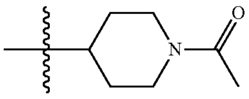
,
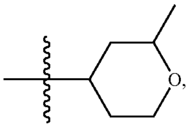

-continued

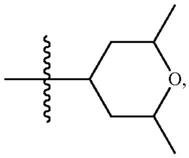

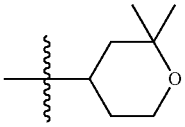
or

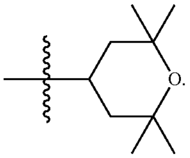

In some embodiments, $R^{m1}$ can

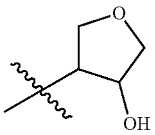
or
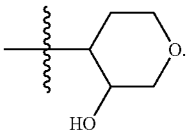

In other embodiments, $R^{m1}$ can be

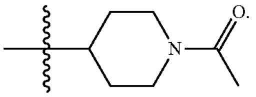

Embodiment 57

The compound of any one of Embodiments 39-50, wherein $R^{m1}$ is —$R^{x2}$.

Embodiment 58

The compound of Embodiment 57, wherein —$R^{x2}$ is

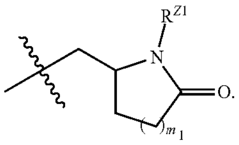

In some embodiments, —$R^{x2}$ is

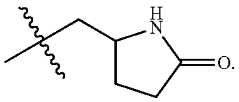 [SMILES: *CC1CCC(=O)N1]

Embodiment 59

The compound of Embodiment 57, wherein —$R^{x2}$ is

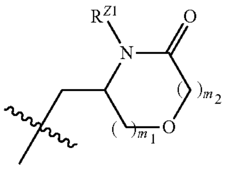
or
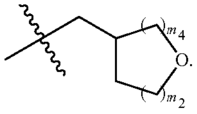

Embodiment 60

The compound of any one of Embodiments 39-47, wherein $R^{1b}$ is —$R^{x1}$.

Embodiment 61

The compound of Embodiment 60, wherein —$R^{x1}$ is selected from the group consisting of:

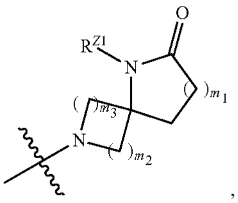
,
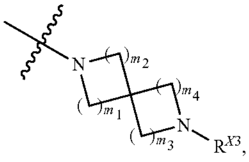
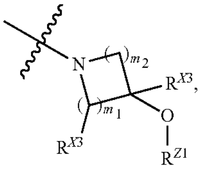
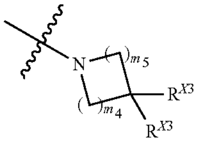
and
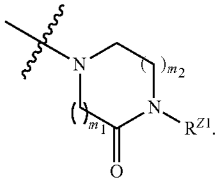

In some embodiments, $R^{x1}$ can be

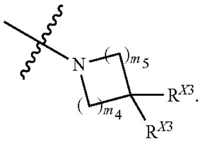

For example, $R^{x1}$ can be

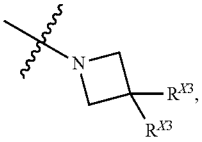

wherein one $R^{X3}$ can be hydrogen; and the other $R^{X3}$ can be —C(═O)$OR^{Z1}$, wherein $R^{Z1}$ can be —$C_{1-4}$ alkyl.

Embodiment 62

The compound of Embodiment 61, wherein —$R^{x1}$ is selected from the group consisting of:

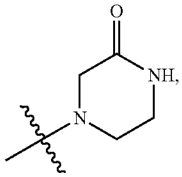
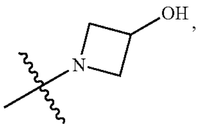
,
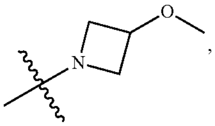
,
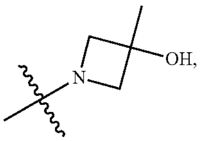
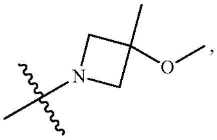
,
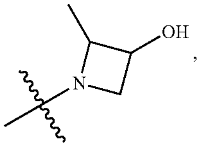
,
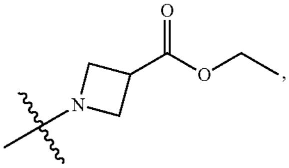
,
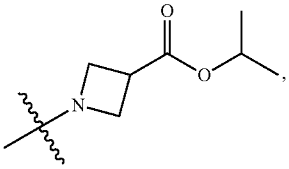
,
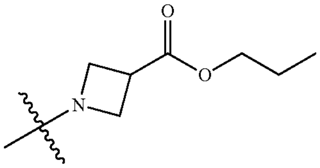
,
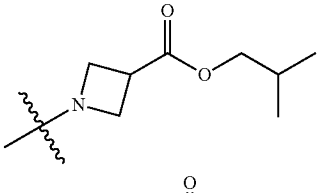
,
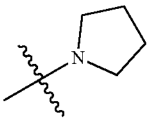
,
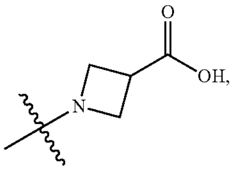
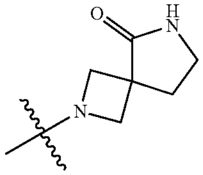
,
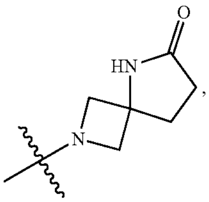
,
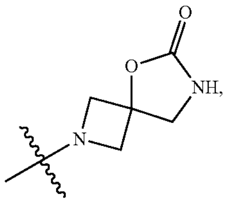

-continued

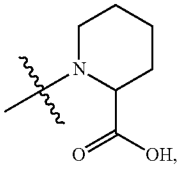

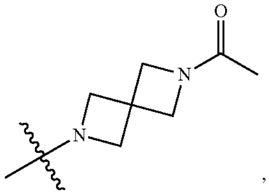
,

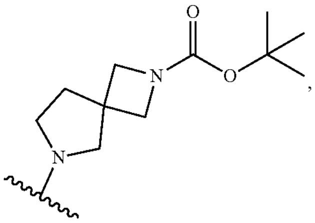
,

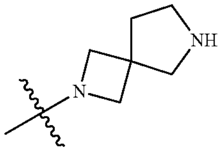
,

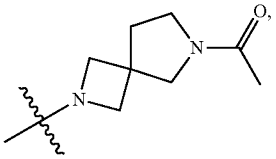

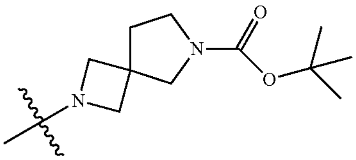
and

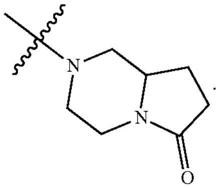

In some embodiments, —$R^{x1}$ can be selected from:

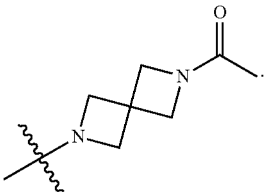 [SMILES: *N1CC2(C1)CN(C(C)=O)C2]

Embodiment 63

The compound of any one of Embodiments 39-62, wherein $R^{1d}$ is hydrogen.

Embodiment 64

The compound of any one of Embodiments 39-62, wherein $R^{1d}$ is —OH.

Embodiment 65

The compound of any one of Embodiments 39-62, wherein $R^{1d}$ is —$CH_3$.

Embodiment 66

The compound of any one of Embodiments 39-62, wherein $R^{1d}$ is —F.

Embodiment 67

The compound of any one of Embodiments 63-66, wherein $R^{1e}$ is hydrogen.

Embodiment 68

The compound of any one of Embodiments 63-66, wherein $R^{1e}$ is —$CH_3$.

Embodiment 69

The compound of any one of Embodiments 63-68, wherein $R^{1f}$ is hydrogen.

Embodiment 70

The compound of any one of Embodiments 63-68, wherein $R^{1f}$ is —$CH_3$.

Embodiment 71

The compound of any one of Embodiments 63-70, wherein $R^{1g}$ is hydrogen.

Embodiment 72

The compound of any one of Embodiments 1-71, wherein $B^1$ can be

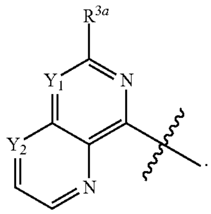

Embodiment 73

The compound of Embodiment 72, wherein $Y^1$ can be N (nitrogen).

Embodiment 74

The compound of Embodiment 72, wherein $Y^1$ can be CH.

Embodiment 75

The compound of any one of Embodiments 72-74, wherein $Y^2$ can be N (nitrogen).

Embodiment 76

The compound of any one of Embodiments 72-74, wherein $Y^2$ is CH.

Embodiment 77

The compound of any one of Embodiments 72-76, wherein $R^{3a}$ can be H (hydrogen).

Embodiment 78

The compound of any one of Embodiments 72-76, wherein $R^{3a}$ can be $-CH_3$.

Embodiment 79

The compound of any one of Embodiments 72-76, wherein $R^{3a}$ can be $-CF_3$.

Embodiment 80

The compound of any one of Embodiments 72-76, wherein $R^{3a}$ can be $-CHF_2$.

Embodiment 81

The compound of any one of Embodiments 1-71, wherein $B^1$ can be

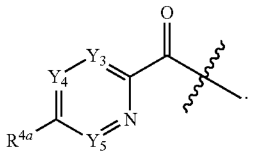

Embodiment 82

The compound of Embodiment 81, wherein $Y^3$ can be N (nitrogen).

Embodiment 83

The compound of Embodiment 81, wherein $Y^3$ can be CH.

Embodiment 84

The compound of any one of Embodiments 81-83, wherein $Y^4$ can be N (nitrogen).

Embodiment 84

The compound of any one of Embodiments 81-83, wherein $Y^4$ can be CH.

Embodiment 86

The compound of any one of Embodiments 81-85, wherein $Y^5$ can be N (nitrogen).

Embodiment 87

The compound of any one of Embodiments 81-85, wherein $Y^5$ can be CH.

Embodiment 88

The compound of any one of Embodiments 81-85, wherein $Y^5$ can be $C-OCH_3$.

Embodiment 89

The compound of any one of Embodiments 81-88, wherein $R^{4a}$ can be H (hydrogen).

Embodiment 90

The compound of any one of Embodiments 81-88, wherein $R^{4a}$ can be halogen. In some embodiments, $R^{4a}$ can be fluoro. In other embodiments, $R^{4a}$ can be chloro.

Embodiment 91

The compound of any one of Embodiments 81-88, wherein $R^{4a}$ can be $-C_{1-4}$ alkyl, such as methyl, ethyl, n-propyl, iso-propyl, n-butyl, iso-butyl, sec-butyl and tert-butyl.

Embodiment 92

The compound of any one of Embodiments 81-88, wherein $R^{4a}$ can be $-C_{1-4}$ haloalkyl. For example, $R^{4a}$ can be selected from $-CF_3$, $-CHF_2$, $-CH_2F$, $-CCl_3$, $-CHCl_2$, $-CH_2Cl$, $-CH_2CF_3$ or $-CH_2CHF_2$.

Embodiment 93

The compound of any one of Embodiments 81-88, wherein $R^{4a}$ can be $-CH_2R^{4b}$.

Embodiment 94

The compound of any one of Embodiments 81-88, wherein $R^{4a}$ can be $-C(CH_3)R^{4b}$.

Embodiment 95

The compound of Embodiment 93 or 94, wherein $R^{4b}$ can be $-N(R^{m2})R^{n2}$.

Embodiment 96

The compound of Embodiment 95, wherein $R^{12}$ can be $-CH_3$.

Embodiment 97

The compound of Embodiment 95, wherein $R^{m2}$ can be $-C_{2-4}$ alkyl, such as ethyl, n-propyl, iso-propyl, n-butyl, iso-butyl, sec-butyl and tert-butyl.

Embodiment 98

The compound of Embodiment 95, wherein $R^{m2}$ can be $-C_{1-4}$ haloalkyl. In some embodiments, $R^{12}$ can be selected from $-CF_3$, $-CHF_2$, $-CH_2F$, $-CCl_3$, $-CHCl_2$, $-CH_2Cl$, $-CH_2CF_3$ and $-CH_2CHF_2$.

Embodiment 99

The compound of Embodiment 95, wherein $R^{12}$ can be $-C_{2-4}$ alkyl substituted with hydroxy. Examples of suitable $C_{2-4}$ alkyls include ethyl, n-propyl, iso-propyl, n-butyl, iso-butyl, sec-butyl and tert-butyl.

Embodiment 100

The compound of any one of Embodiments 95-99, wherein $R^{n2}$ can be H (hydrogen).

Embodiment 101

The compound of any one of Embodiments 95-99, wherein $R^{n2}$ can be —$C_{1-4}$ alkyl. For example, $R^{n2}$ can be methyl, ethyl, n-propyl, iso-propyl, n-butyl, iso-butyl, sec-butyl or tert-butyl.

Embodiment 102

The compound of any one of Embodiments 95-99, wherein $R^{n2}$ can be —$C_{1-4}$ haloalkyl. For example, $R^{n2}$ can be —$CF_3$, —$CHF_2$, —$CH_2F$, —$CCl_3$, —$CHCl_2$, —$CH_2Cl$, —$CH_2CF_3$ or —$CH_2CHF_2$.

Embodiment 103

The compound of Embodiment 93 or 94, wherein $R^{4b}$ can be —$R^{y1}$.

Embodiment 104

The compound of any one of Embodiments 1-71, wherein $B^1$ can be

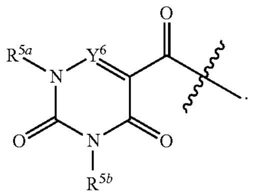

Embodiment 105

The compound of Embodiment 104, $R^{5a}$ can be hydrogen.

Embodiment 106

The compound of Embodiment 104, $R^{5a}$ can be —$CH_3$.

Embodiment 107

The compound of Embodiment 104, $R^{5a}$ can be —$C_{2-4}$ alkyl. Exemplary $C_{2-4}$ alkyls include ethyl, n-propyl, iso-propyl, n-butyl, iso-butyl, sec-butyl and tert-butyl.

Embodiment 108

The compound of Embodiment 104, $R^{5a}$ can be —$C_{2-4}$ haloalkyl. Suitable $C_{2-4}$ haloalkyls include, but are not limited to, —$CH_2CF_3$, —$CH_2CHF_2$, —$CH_2CH_2CF_3$, —$CH_2CH_2CHF_2$, —$CH_2CH_2CH_2CF_3$ and —$CH_2CH_2CH_2CHF_2$.

Embodiment 109

The compound of any one of Embodiments 104-108, wherein $R^{5b}$ is hydrogen.

Embodiment 110

The compound of any one of Embodiments 104-108, wherein $R^{5b}$ can be —$CH_3$.

Embodiment 111

The compound of any one of Embodiments 104-108, wherein $R^{5b}$ can be —$C_{2-4}$ alkyl, such as ethyl, n-propyl, iso-propyl, n-butyl, iso-butyl, sec-butyl and tert-butyl.

Embodiment 112

The compound of any one of Embodiments 104-108, wherein $R^{5b}$ can be —$C_{2-4}$ haloalkyl. Exemplary $C_{2-4}$ haloalkyls include, but are not limited to, —$CH_2CF_3$, —$CH_2CHF_2$, —$CH_2CH_2CF_3$, —$CH_2CH_2CHF_2$, —$CH_2CH_2CH_2CF_3$ and —$CH_2CH_2CH_2CHF_2$.

Embodiment 113

The compound of any one of Embodiments 104-112, wherein $Y^6$ can be N (nitrogen).

Embodiment 114

The compound of any one of Embodiments 104-112, wherein $Y^6$ can be $CR^{5c}$.

Embodiment 115

The compound of Embodiment 114, wherein $R^{5c}$ can be hydrogen.

Embodiment 116

The compound of Embodiment 114, wherein $R^{5c}$ can be —$CH_3$.

Embodiment 117

The compound of Embodiment 114, wherein $R^{5c}$ can be —$C_{2-4}$ alkyl, for example, ethyl, n-propyl, iso-propyl, n-butyl, iso-butyl, sec-butyl and tert-butyl.

Embodiment 118

The compound of Embodiment 114, wherein $R^{5c}$ can be —$C_{2-4}$ haloalkyl. A non-limiting list of $C_{2-4}$ haloalkyls include, but are not limited to, —$CH_2CF_3$, —$CH_2CHF_2$, —$CH_2CH_2CF_3$, —$CH_2CH_2CHF_2$, —$CH_2CH_2CH_2CF_3$ and —$CH_2CH_2CH_2CHF_2$.

Embodiment 119

The compound of any one of Embodiments 1-71, wherein $B^1$ can be

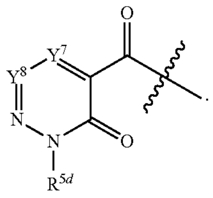

Embodiment 120

The compound of Embodiment 119, wherein $R^{5d}$ can be hydrogen.

Embodiment 121

The compound of Embodiment 119, wherein $R^{5d}$ can be $-CH_3$.

Embodiment 122

The compound of Embodiment 119, wherein $R^{5d}$ can be $-C_{2-4}$ alkyl.

Embodiment 123

The compound of Embodiment 119, wherein $R^{5d}$ can be $-C_{2-4}$ haloalkyl.

Embodiment 124

The compound of any one of Embodiments 119-123, wherein $Y^7$ can be $CR^{5e}$, wherein $R^{5e}$ is hydrogen.

Embodiment 125

The compound of any one of Embodiments 119-123, wherein $Y^7$ can be $CR^{5e}$, wherein $R^{5e}$ is halogen, such as fluoro or chloro.

Embodiment 126

The compound of any one of Embodiments 119-123, wherein $Y^7$ can be $CR^{5e}$, wherein $R^{5e}$ is $-CH_3$.

Embodiment 127

The compound of any one of Embodiments 119-126, wherein $Y^8$ can be $CR^{5f}$, wherein $R^{5f}$ can be hydrogen.

Embodiment 128

The compound of any one of Embodiments 119-126, wherein $Y^8$ can be $CR^{5f}$, wherein $R^{5f}$ can be halogen, such as F, Cl or Br.

Embodiment 129

The compound of any one of Embodiments 119-126, wherein $Y^8$ can be $CR^{5f}$, wherein $R^{5f}$ can be —OH.

Embodiment 130

The compound of any one of Embodiments 119-126, wherein $Y^8$ can be $CR^{5'}$, wherein $R^{5'}$ can be CN.

Embodiment 131

The compound of any one of Embodiments 119-126, wherein $Y^8$ can be $CR^{5f}$, wherein $R^{5f}$ can be $-CH_3$.

Embodiment 132

The compound of any one of Embodiments 1-131, wherein $R^{2a}$, $R^{2b}$, $R^{2c}$, $R^{2e}$, $R^{2g}$ and $R^{2g}$ can be each hydrogen.

Embodiment 133

The compound of any one of Embodiments 1-131, wherein $R^{2a}$, $R^{2c}$, $R^{2e}$, $R^{2g}$ and $R^{2h}$ are each hydrogen; and $R^{2b}$ is halogen.

Embodiment 134

The compound of any one of Embodiments 1-131, wherein $R^{2b}$, $R^{2c}$, $R^{2e}$, $R^{2g}$ and $R^{2h}$ are each hydrogen; and $R^{2a}$ is halogen.

Embodiment 135

The compound of any one of Embodiments 1-134, wherein $R^{2d}$ and $R^{2f}$ can be each halogen. In some embodiments, $R^{2d}$ and $R^{2f}$ can be each fluoro. In other embodiments, $R^{2d}$ and $R^{2f}$ can be each chloro.

Embodiment 136

The compound of any one of Embodiments 1-134, wherein $R^{2d}$ and $R^{2f}$ can be each $-CH_3$.

Embodiment 137

The compound of any one of Embodiments 1-134, wherein $R^{2d}$ can be halogen; and $R^{2f}$ can be $-CH_3$.

Embodiment 138

The compound of any one of Embodiments 1-134, wherein $R^{2d}$ is $-CH_3$; and $R^{2f}$ is halogen.

Embodiment 139

The compound of any one of Embodiments 1-134, wherein $R^{2d}$ is cyano; and $R^{2f}$ is halogen.

Embodiment 140

The compound of any one of Embodiments 1-134, wherein $R^{2d}$ is $-OCH_3$; and $R^{2f}$ is halogen.

Embodiment 141

The compound of any one of Embodiments 133-135 or 137-140, wherein the halogen can be chloro or fluoro.

Embodiment 142
The compound of Embodiment 1 selected from:
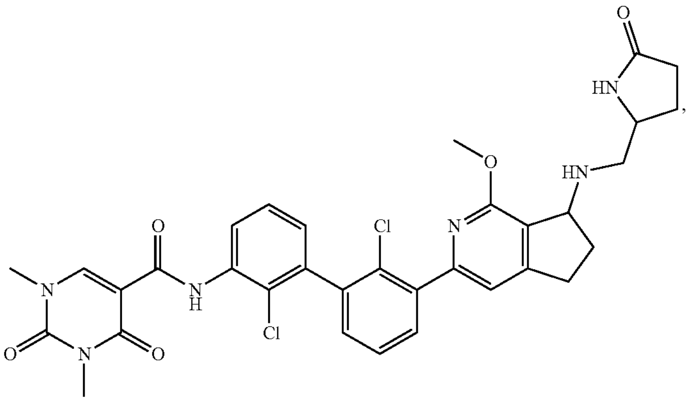
,
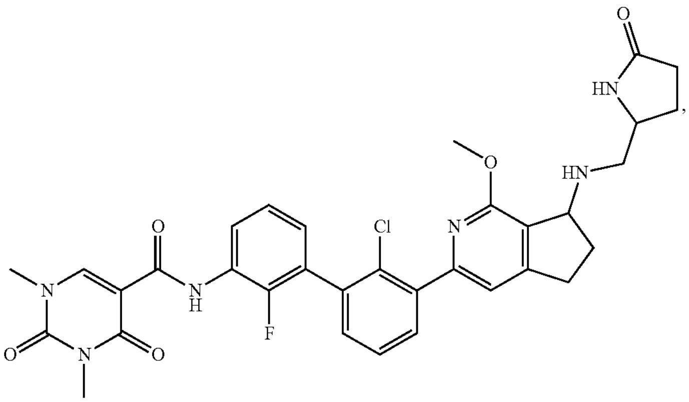
,
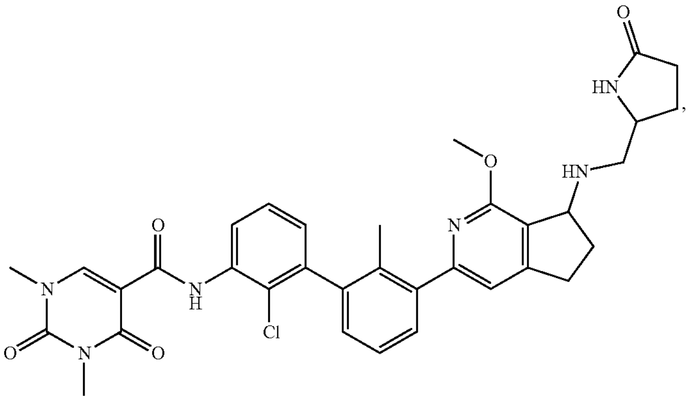
,
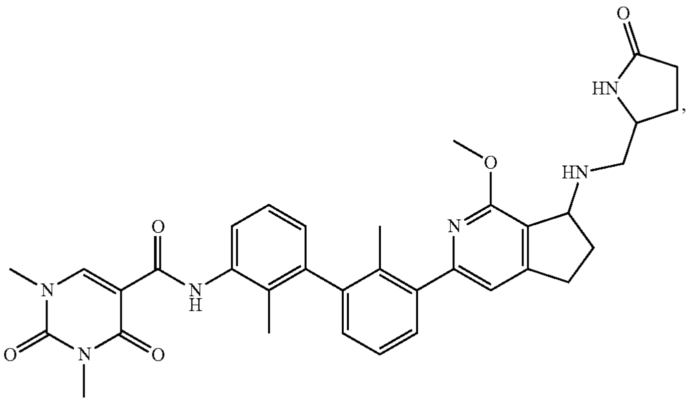
, -continued
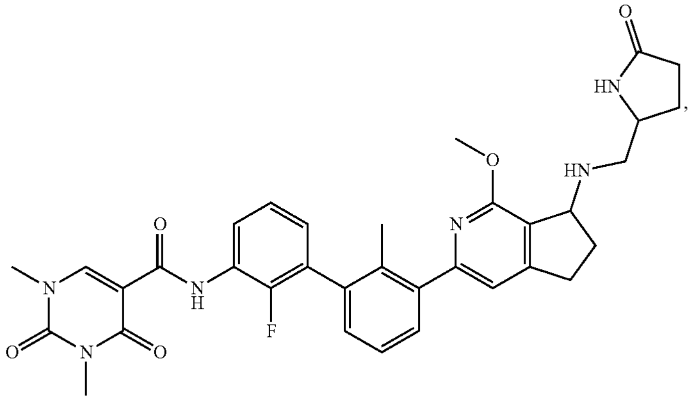
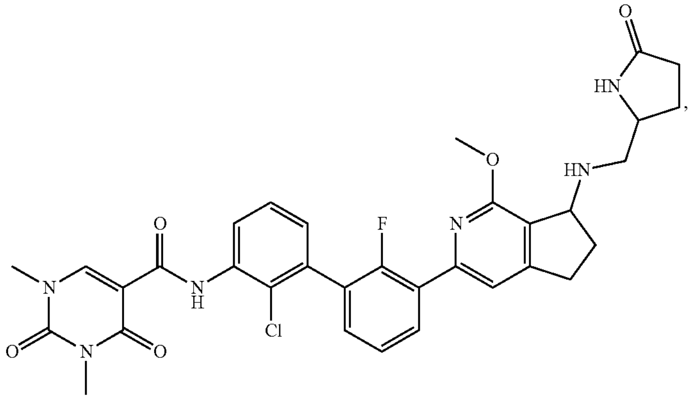
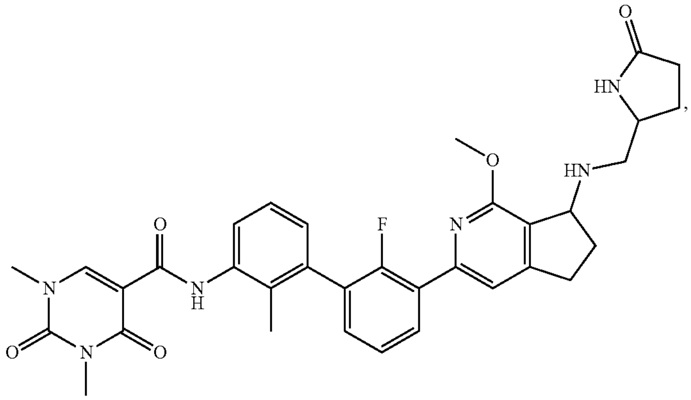
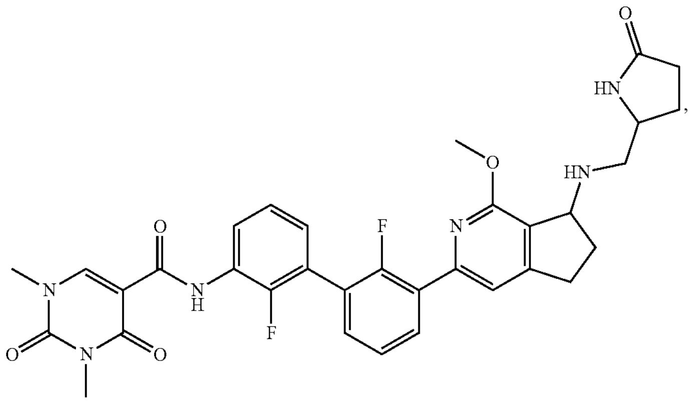

-continued
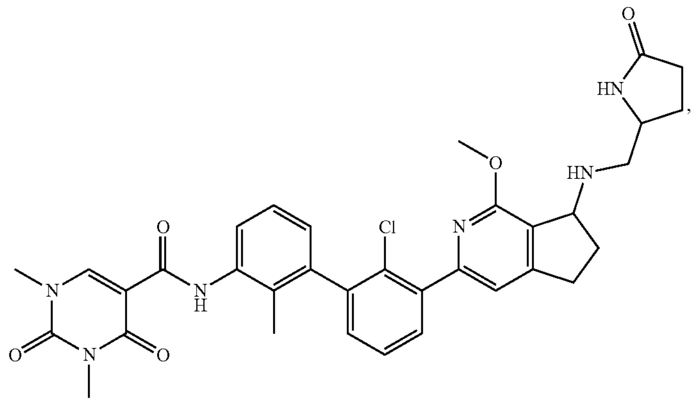
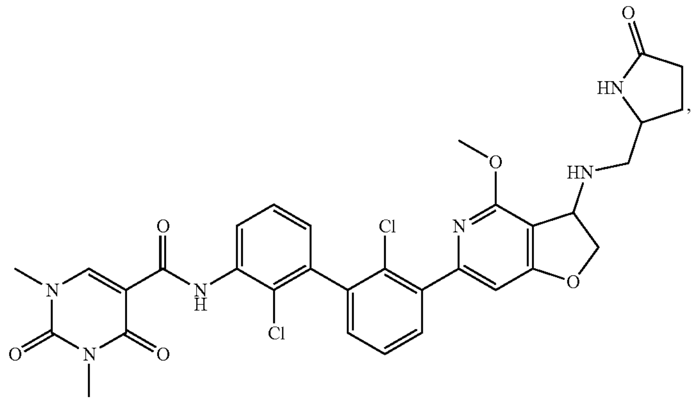
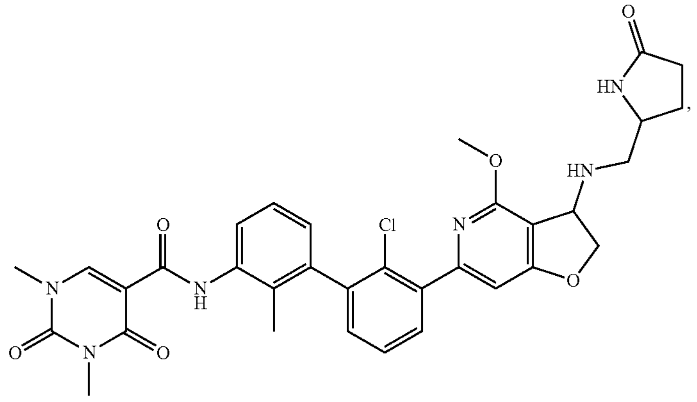
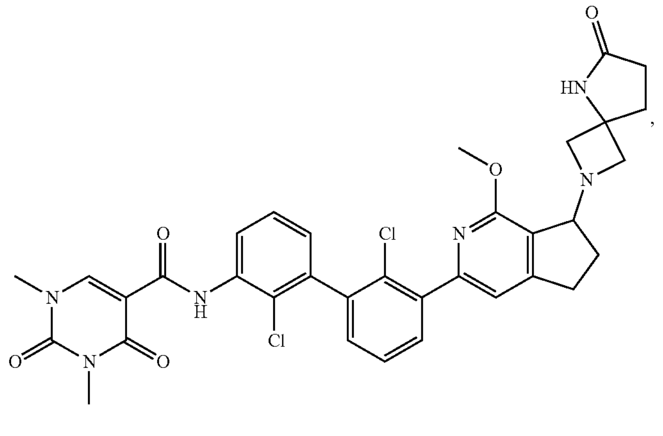

-continued
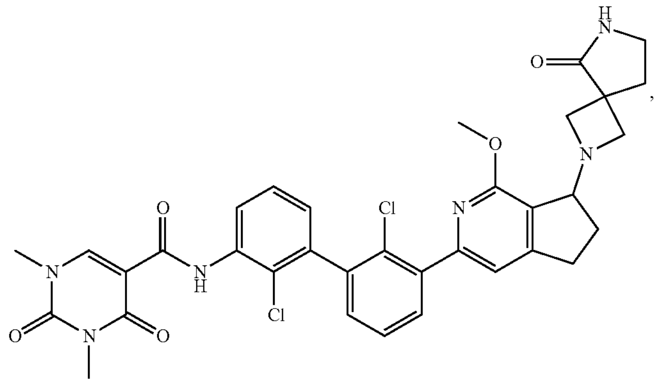
,
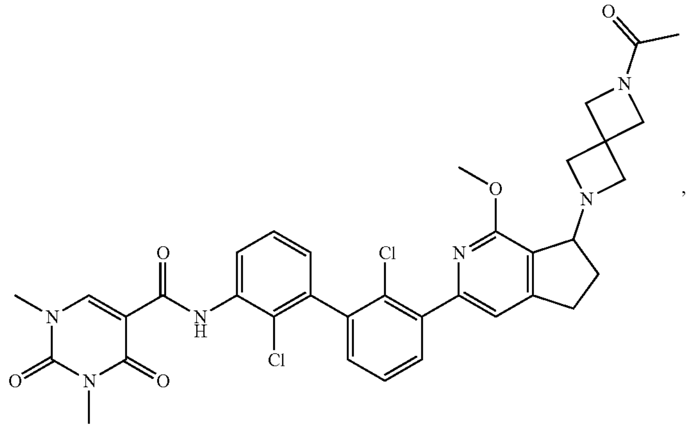
,
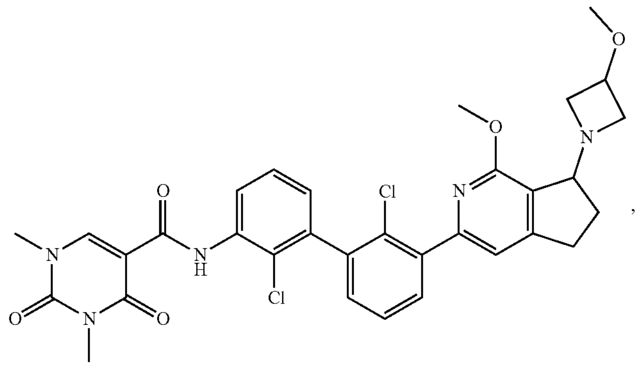
,
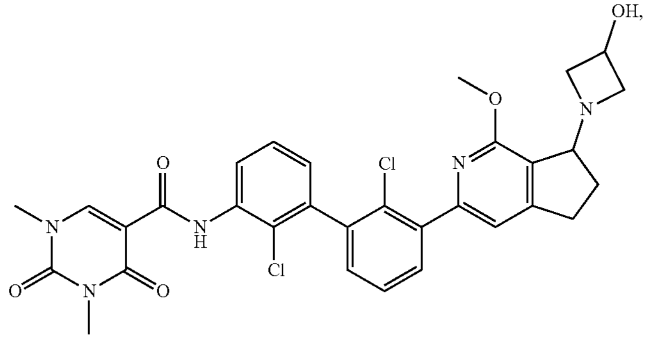

-continued
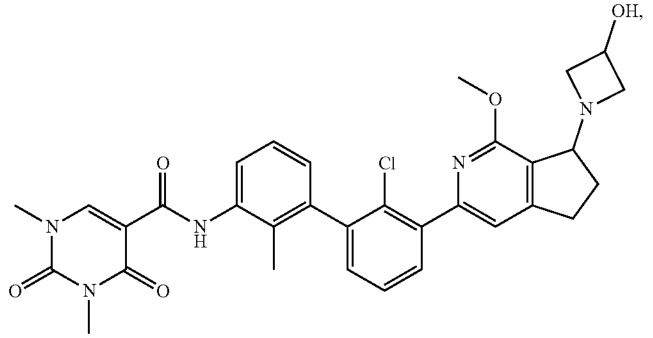
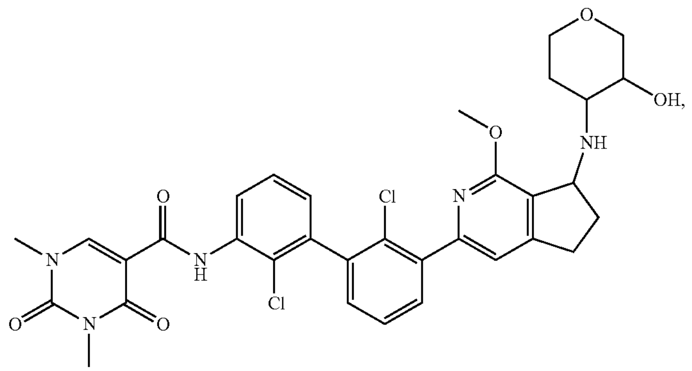
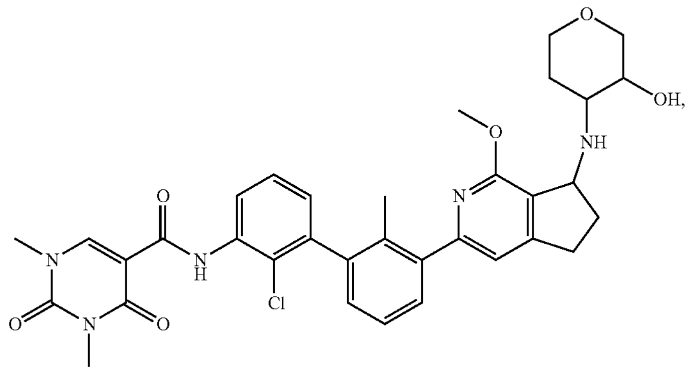
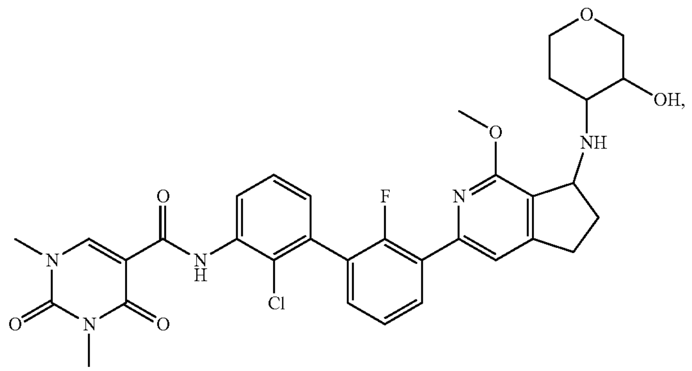

-continued
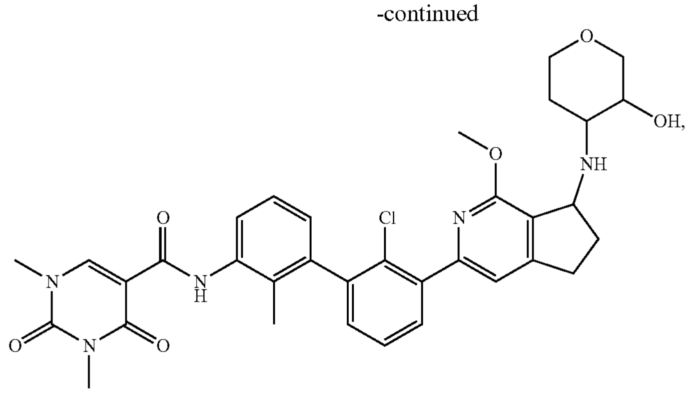
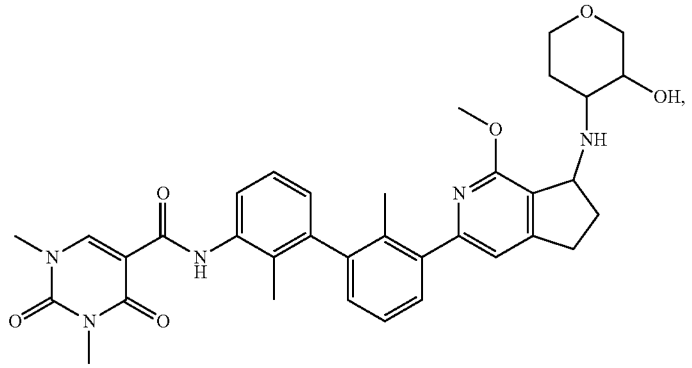
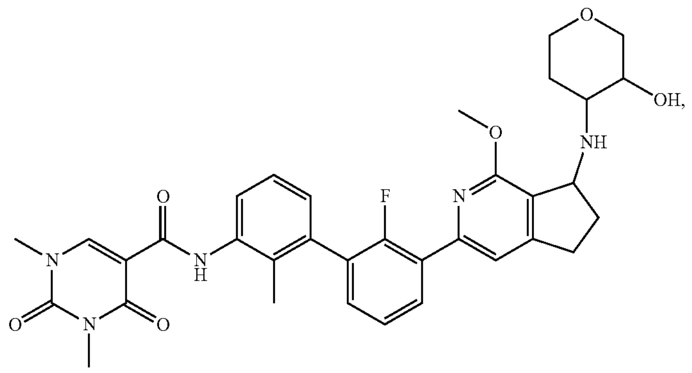
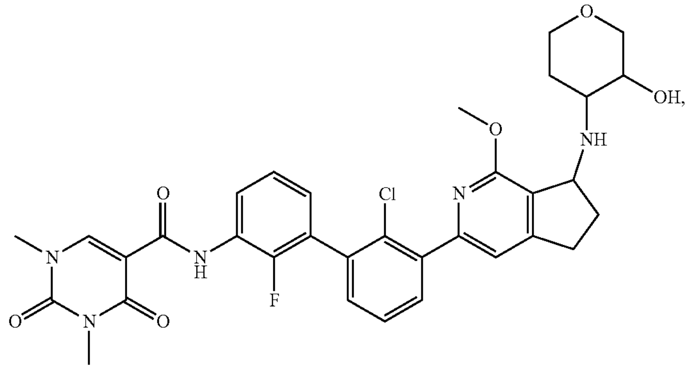

-continued
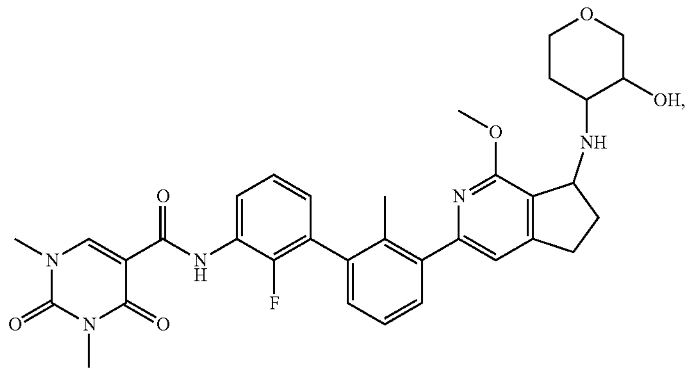
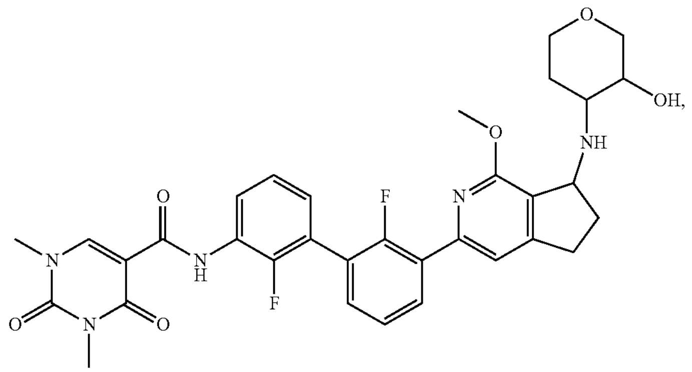
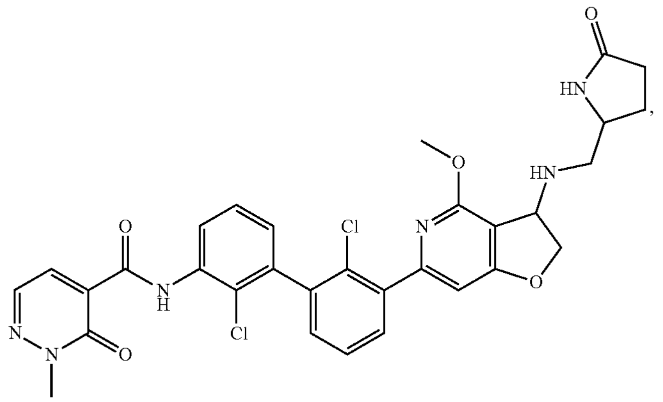
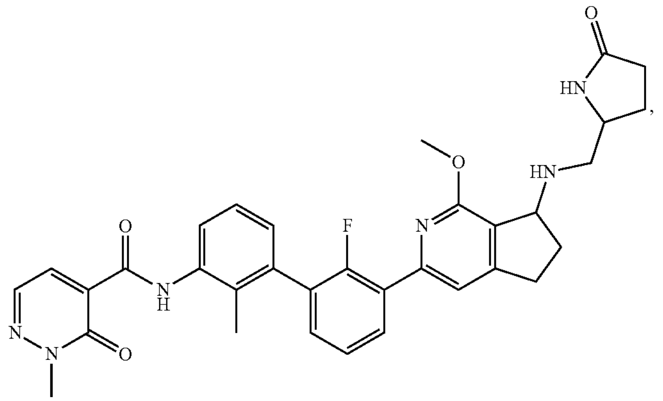

-continued
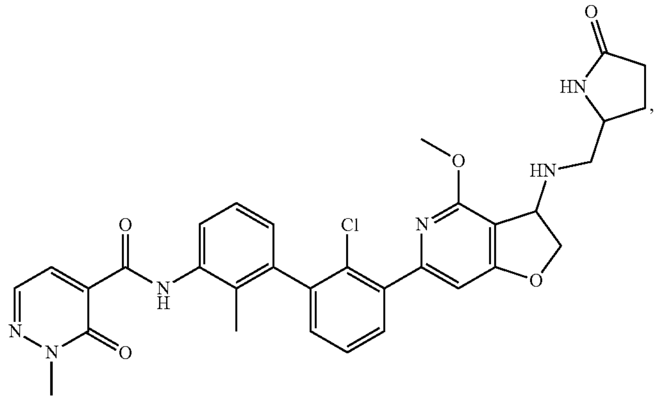
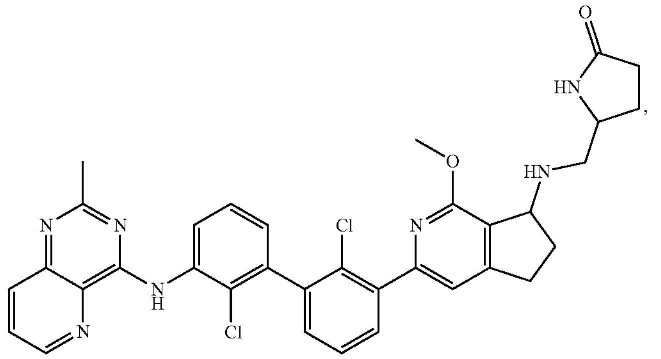
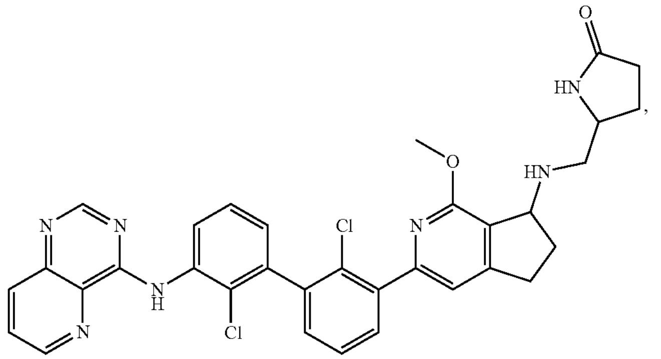
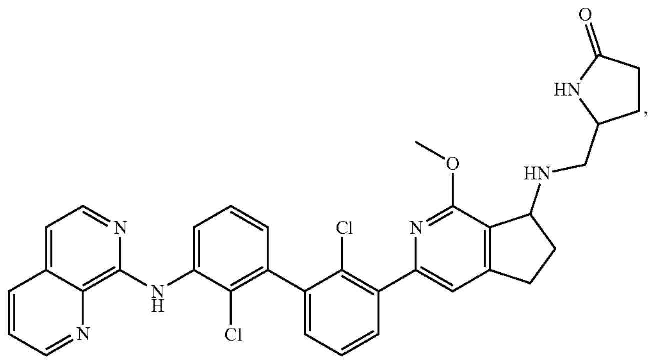

-continued
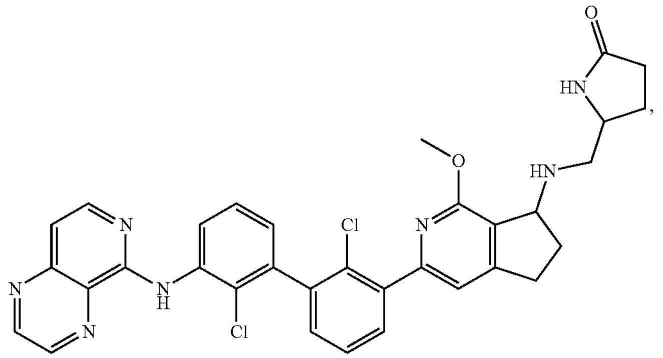
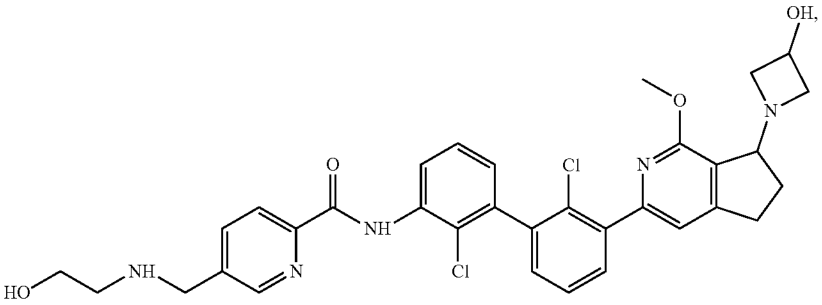
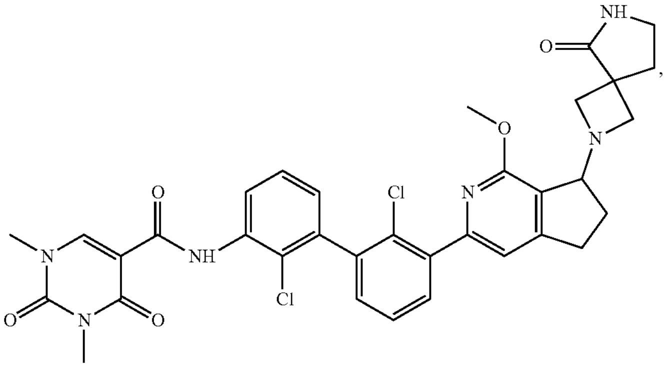
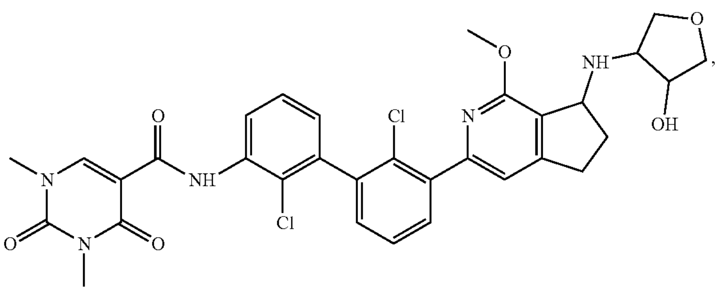
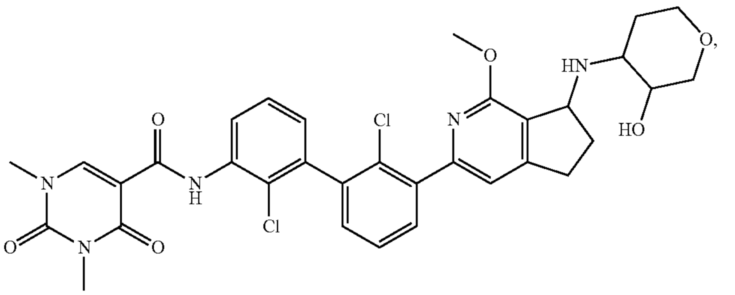

-continued
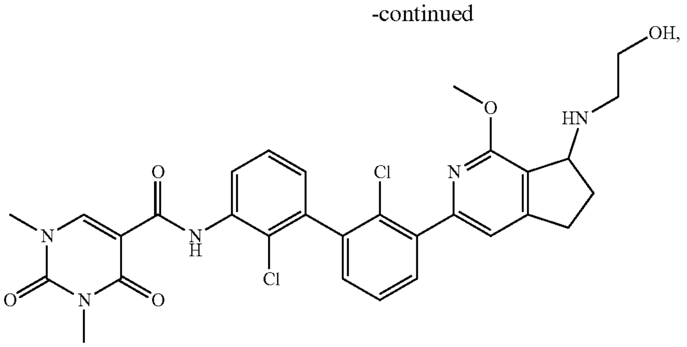
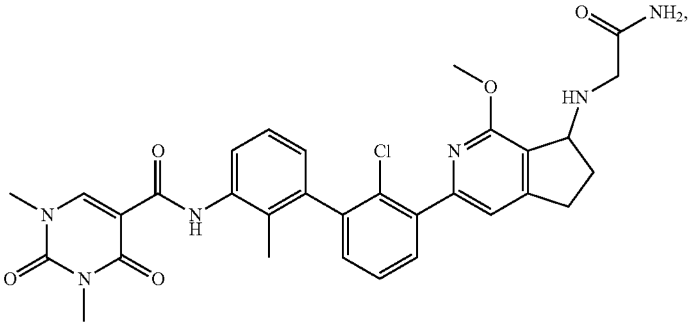
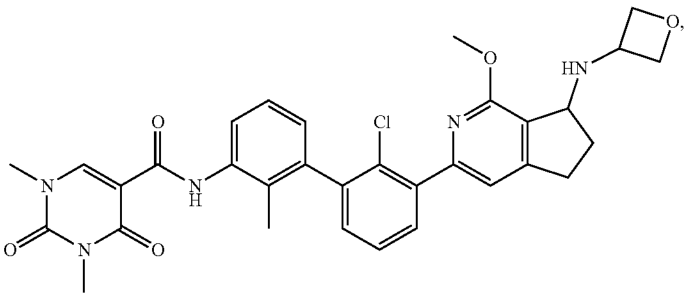
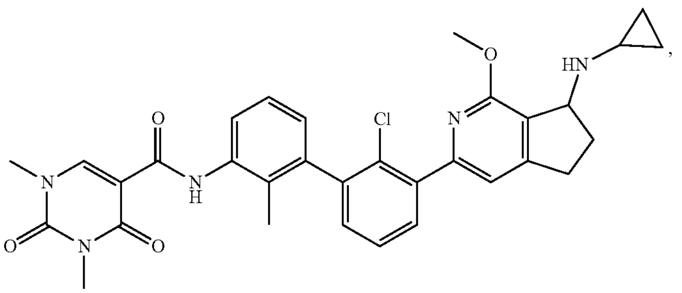
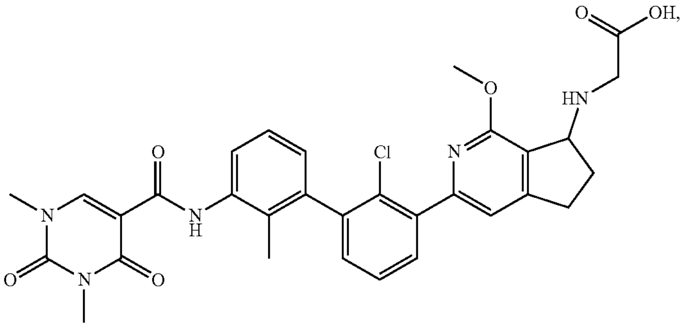

-continued
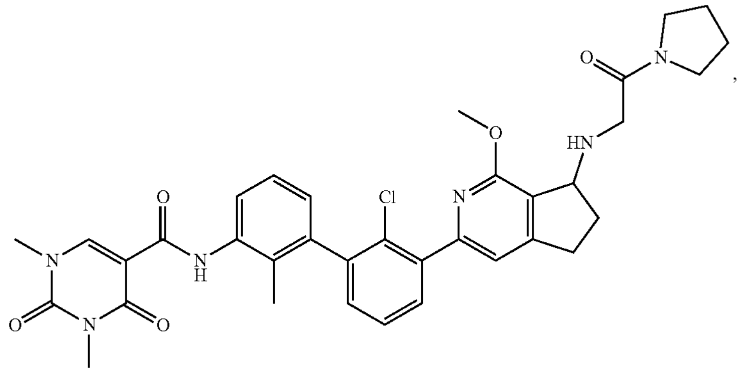
,
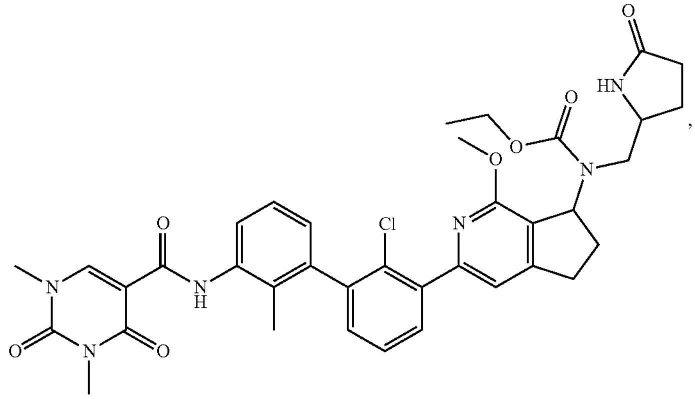
,
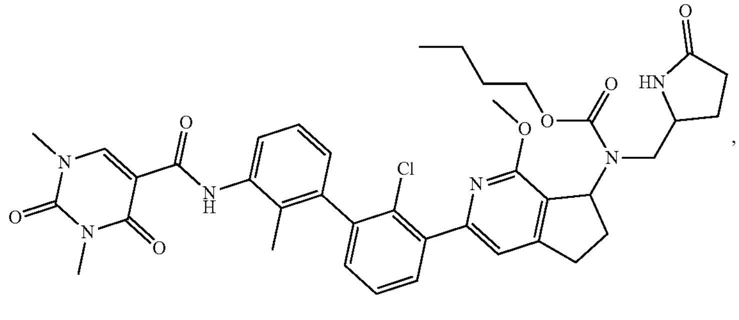
,
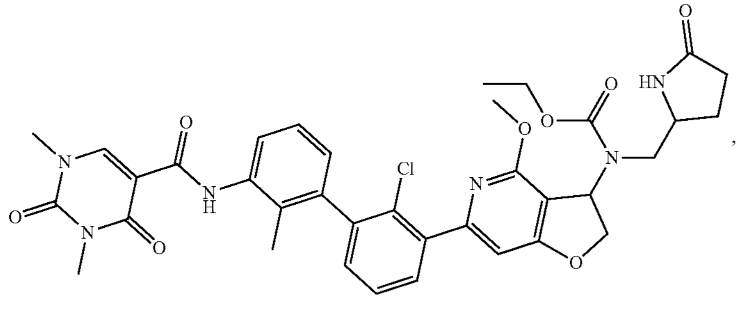
,

-continued
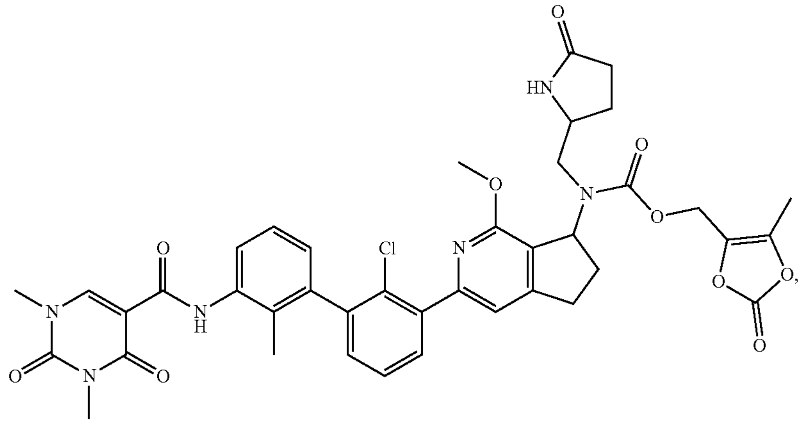
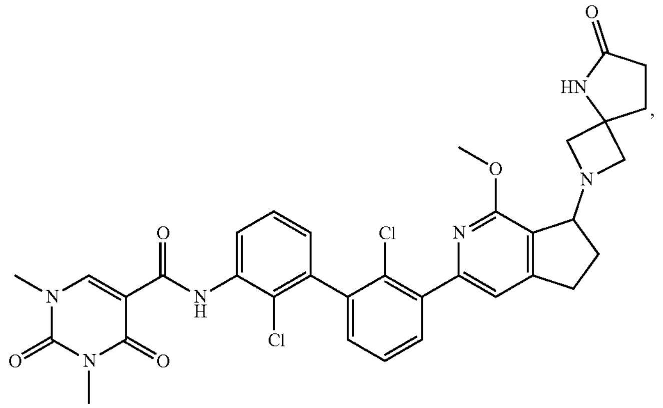
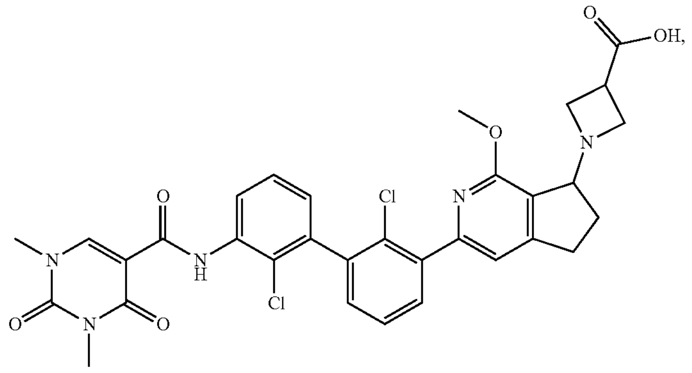
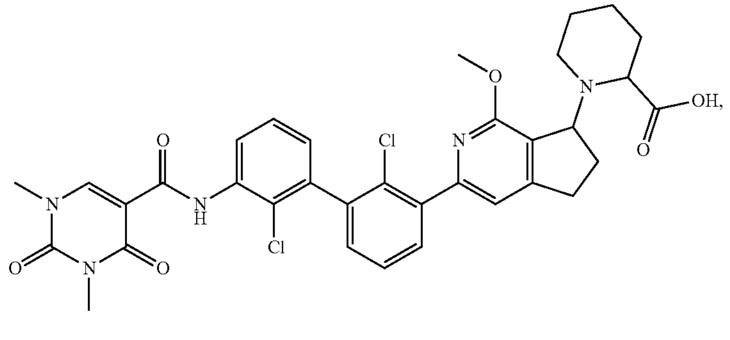

-continued
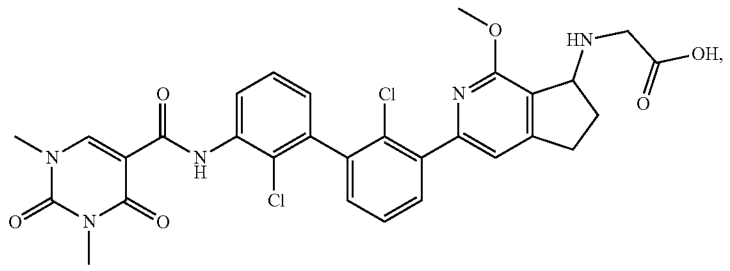
,
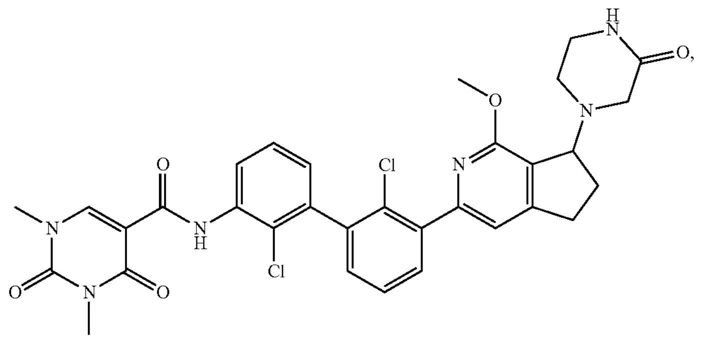
,
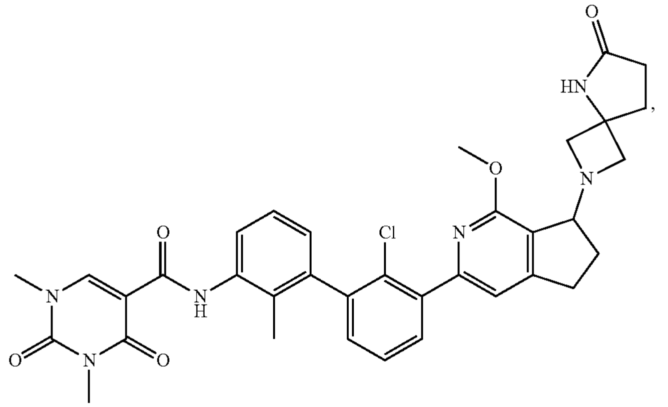
,
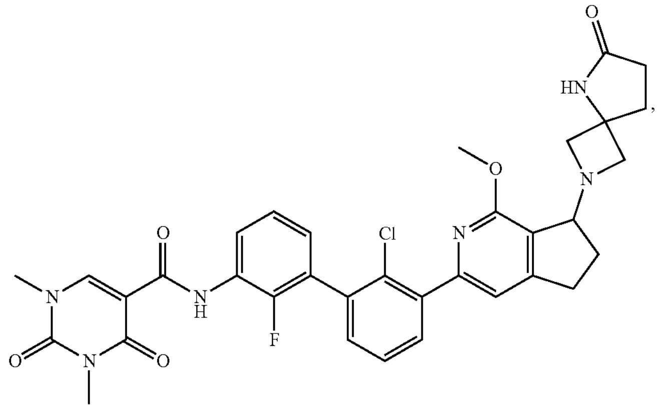
,

-continued
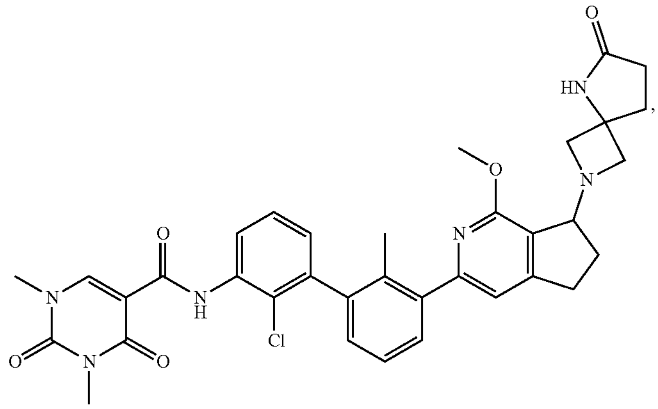
,
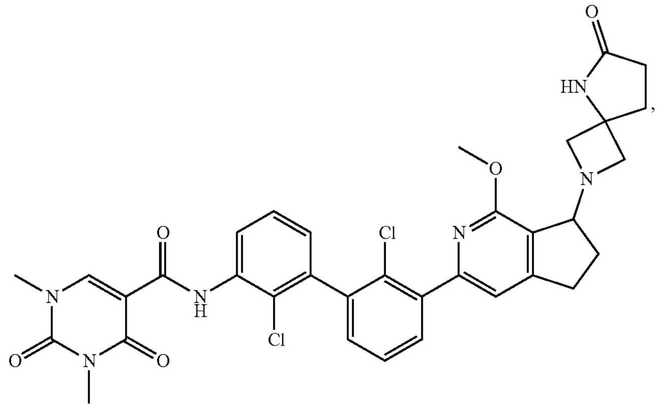
,
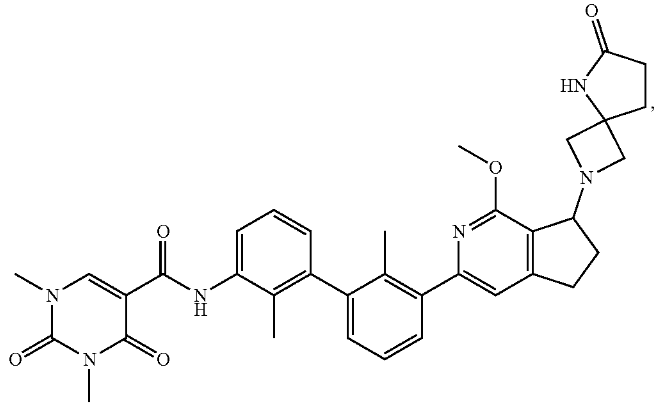
,
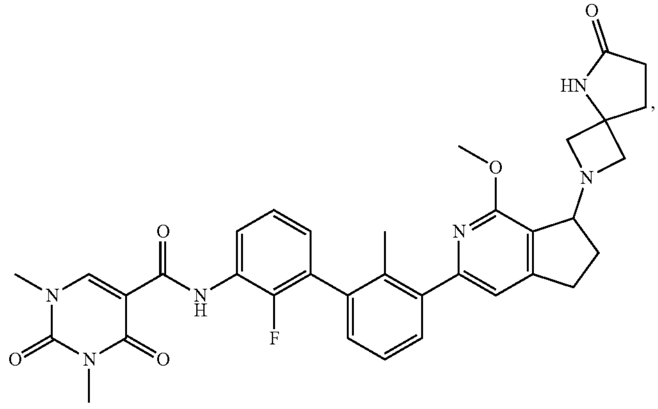
,

-continued
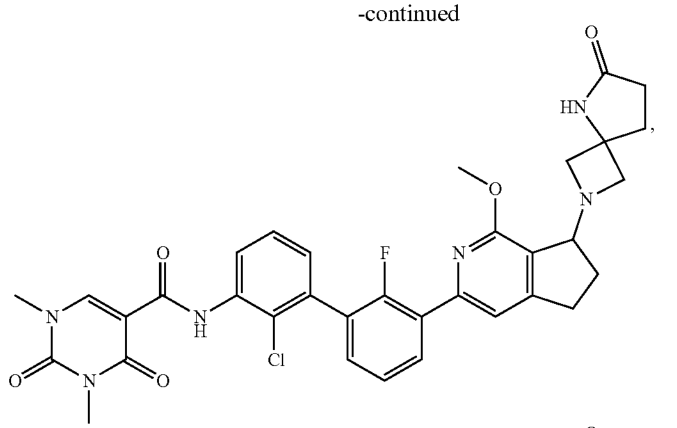
,
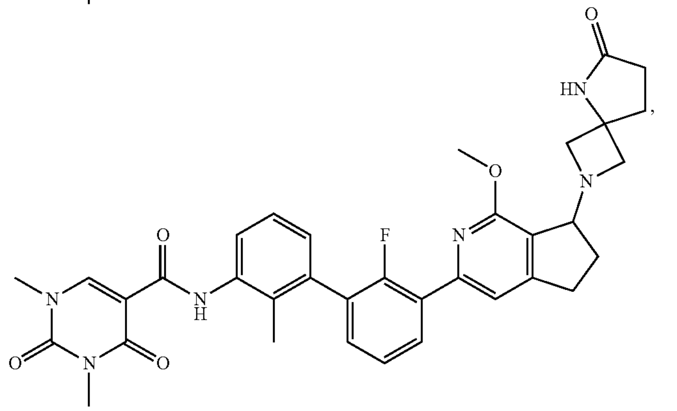
,
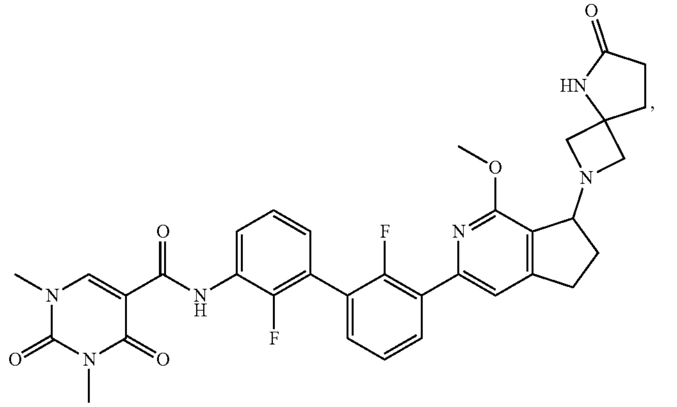
,
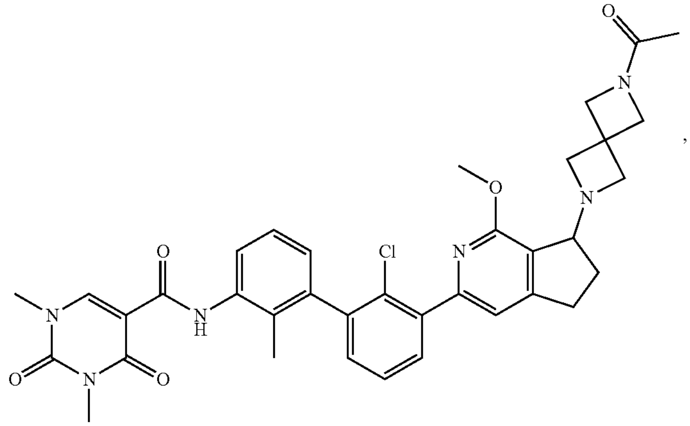
,

-continued
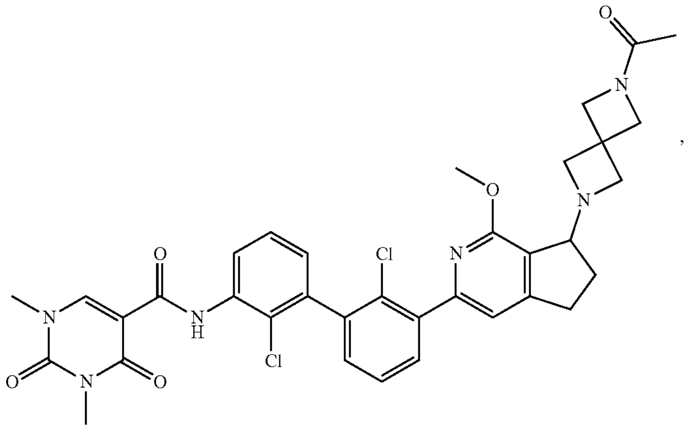
,
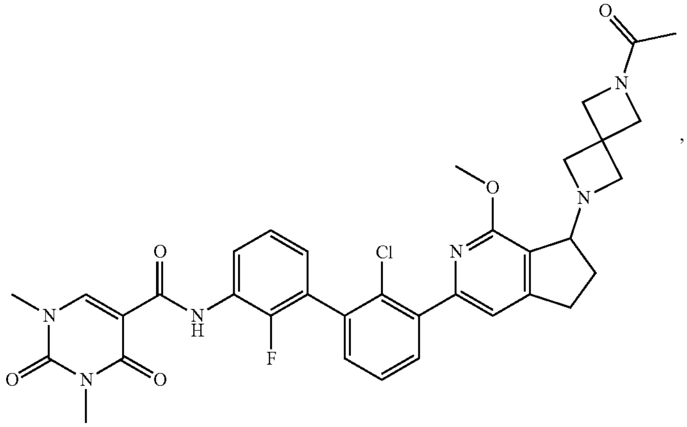
,
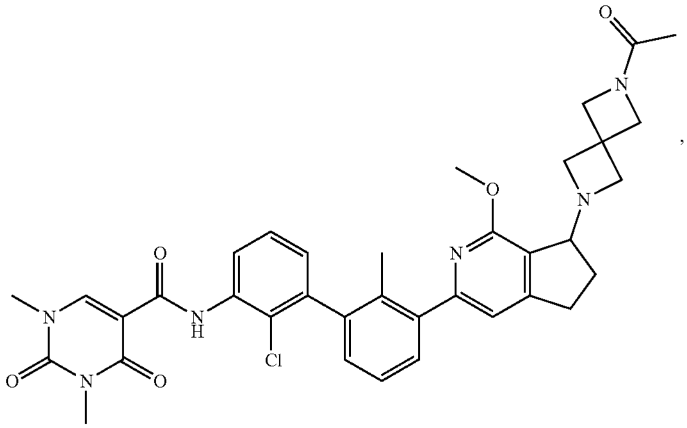
,
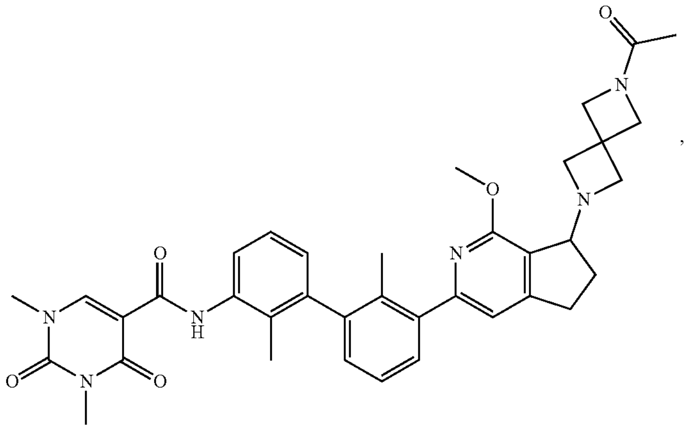
,

-continued
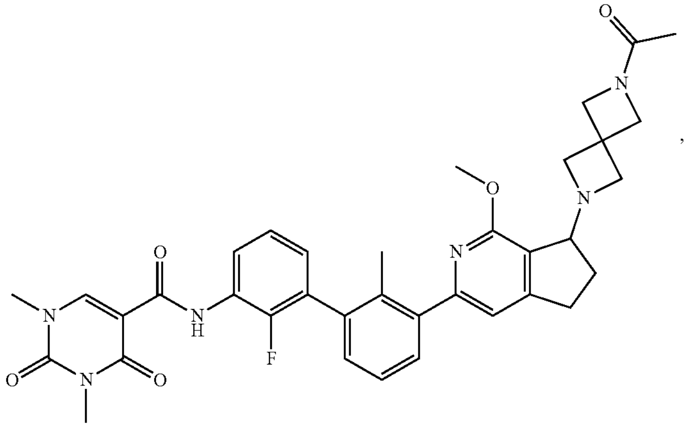
,
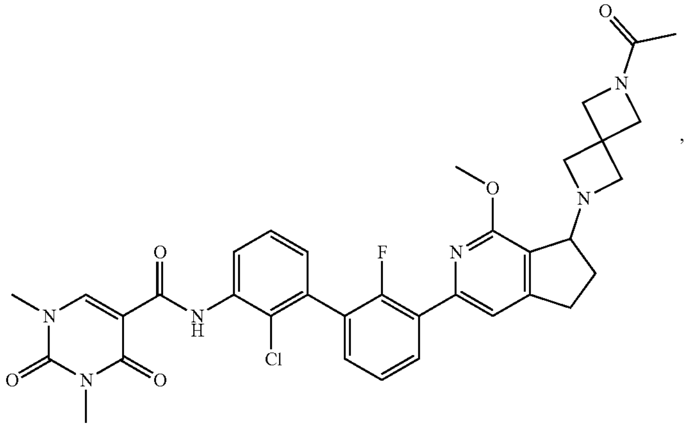
,
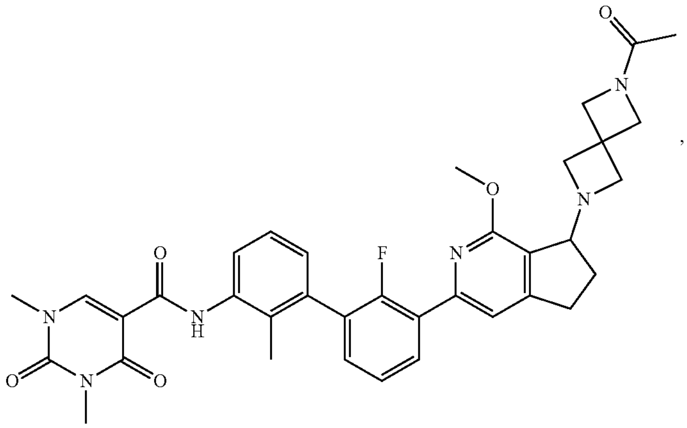
,
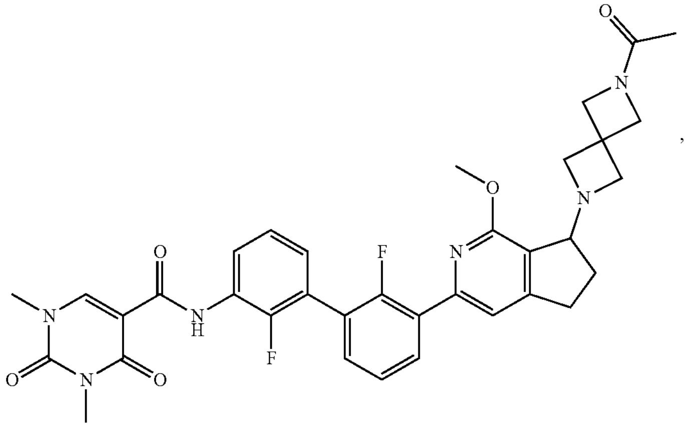
,

-continued
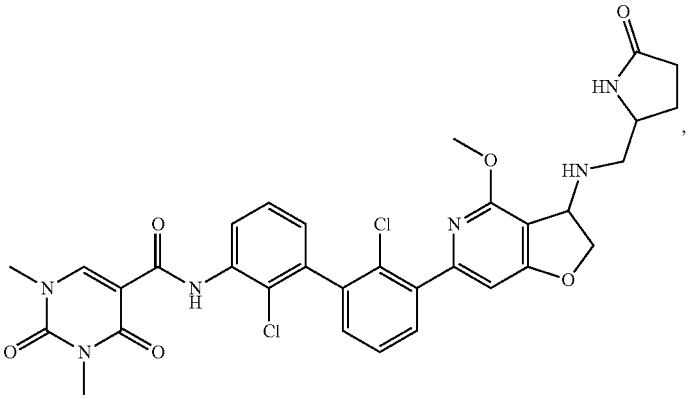
,
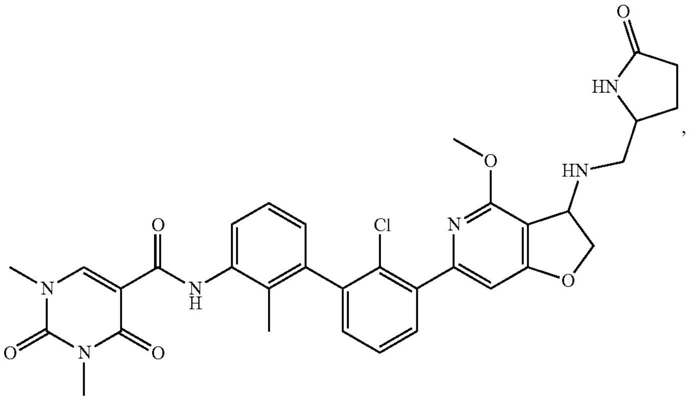
,
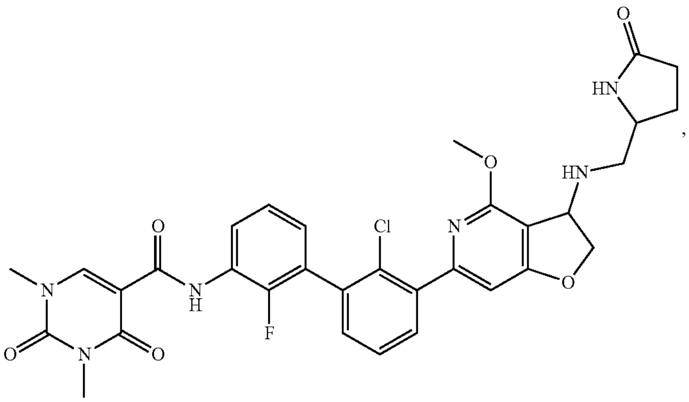
,
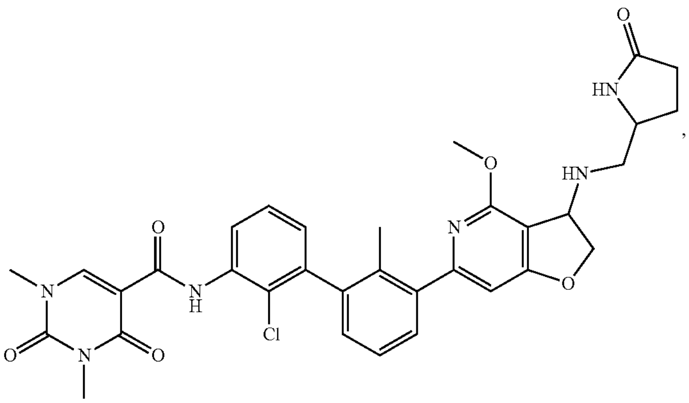
,

-continued
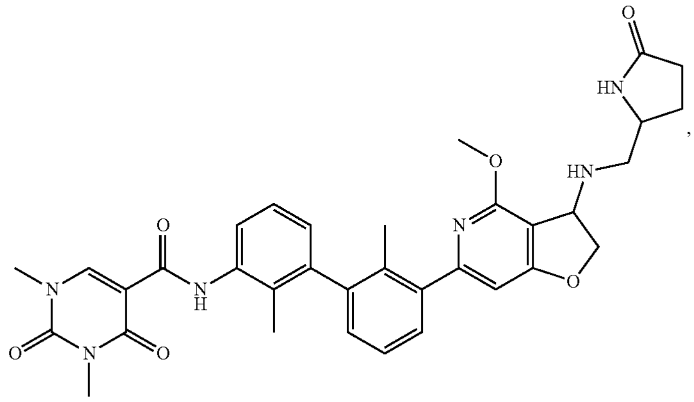,
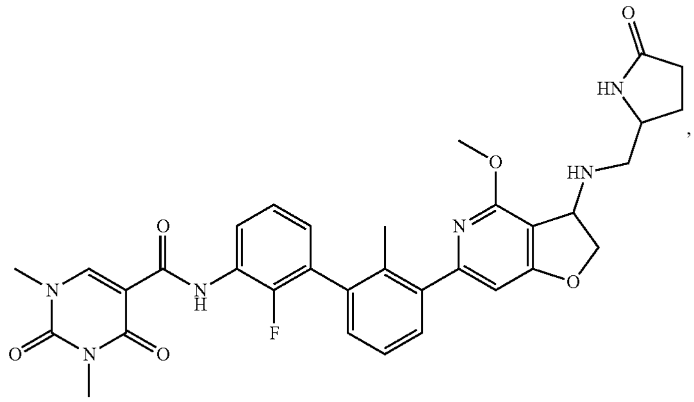,
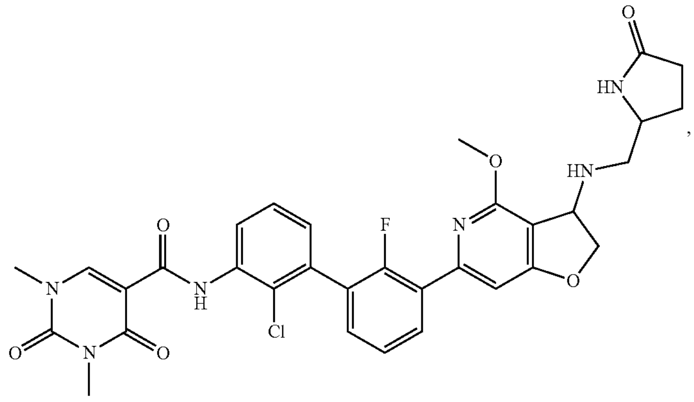,
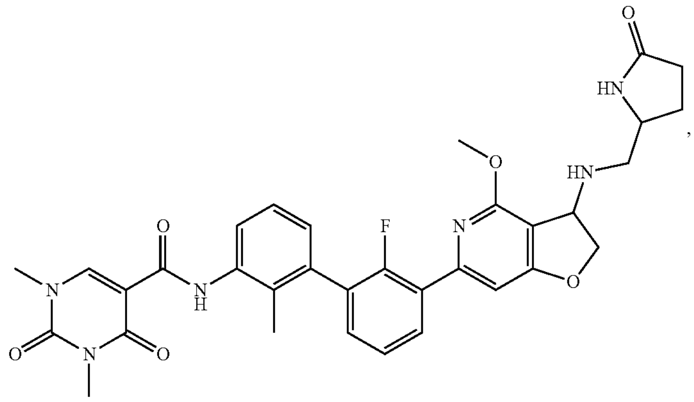,

-continued
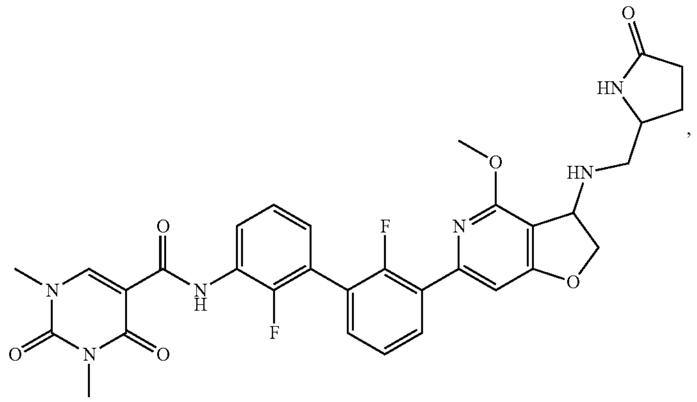
,
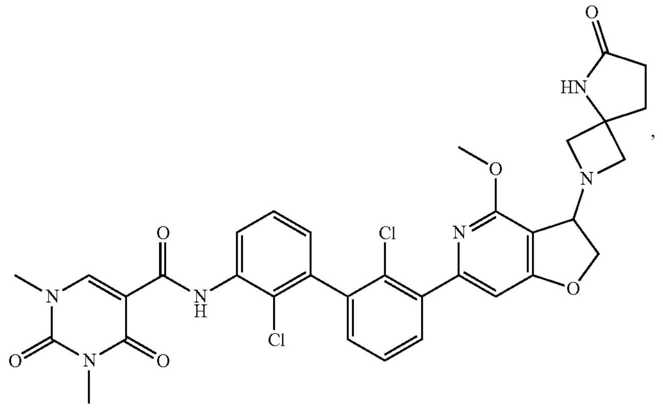
,
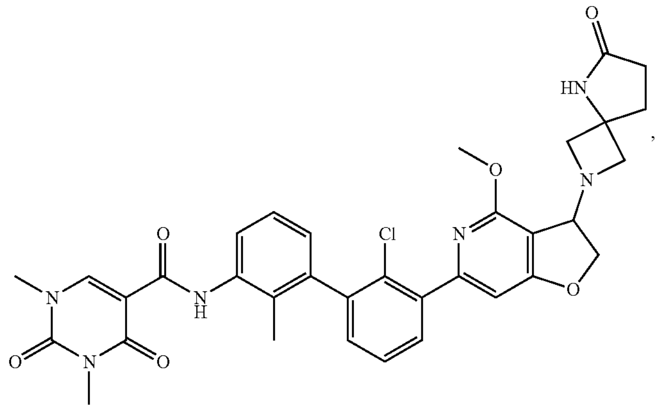
,
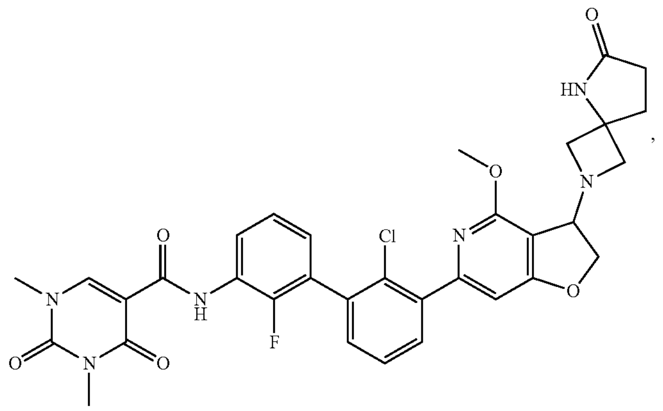
,

-continued
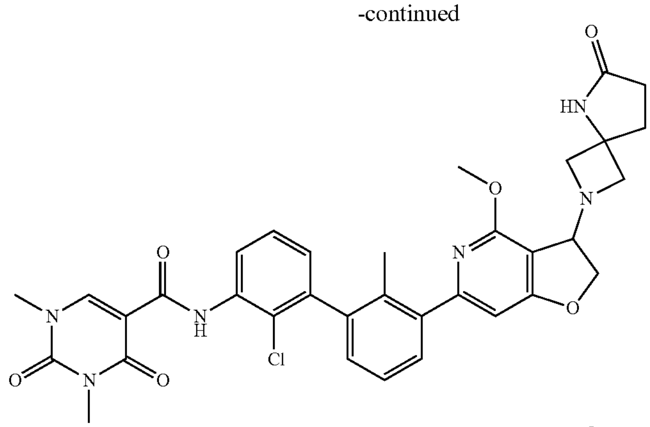
,
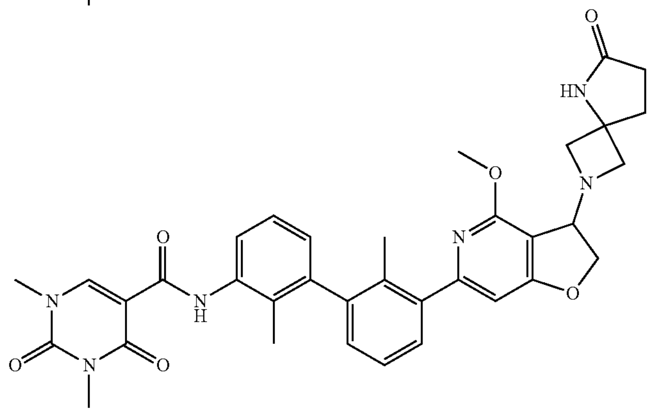
,
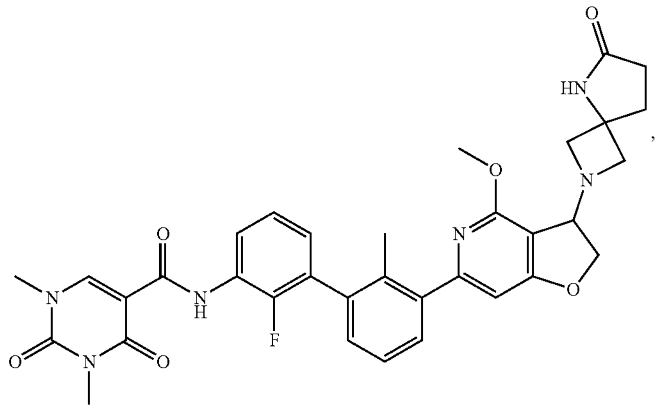
,
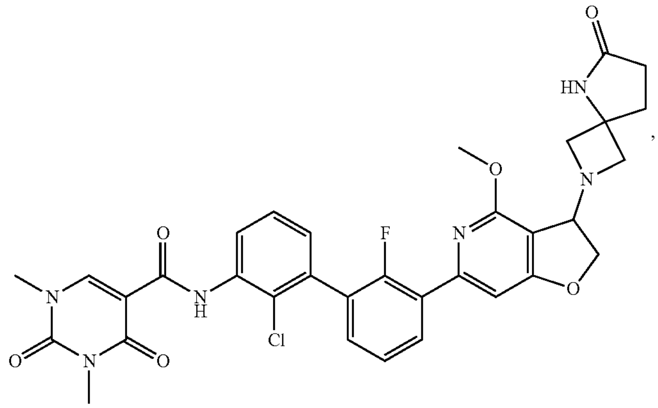
,

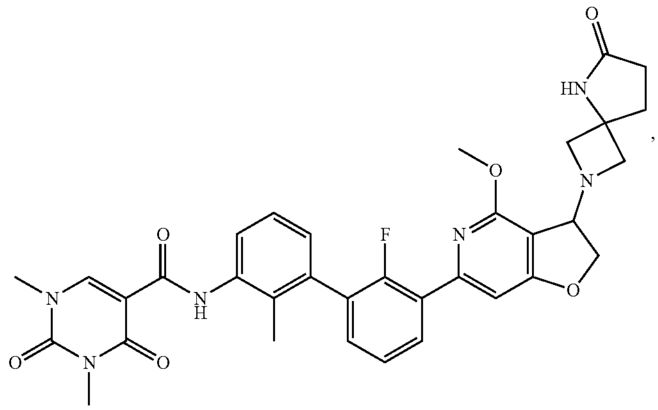
,
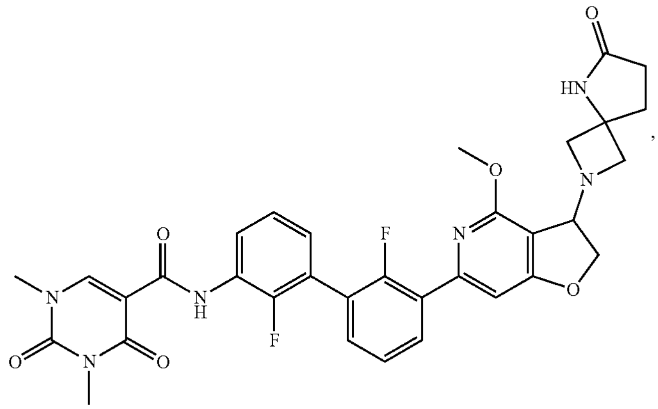
,
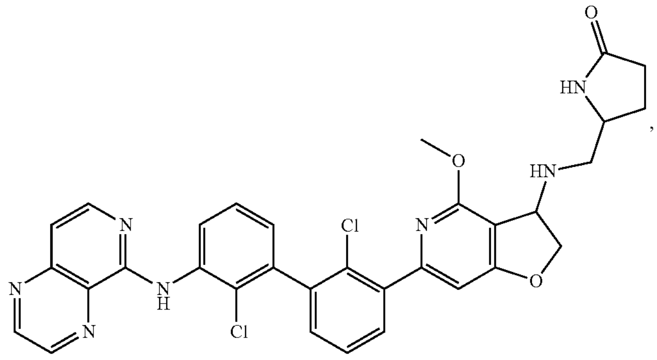
,
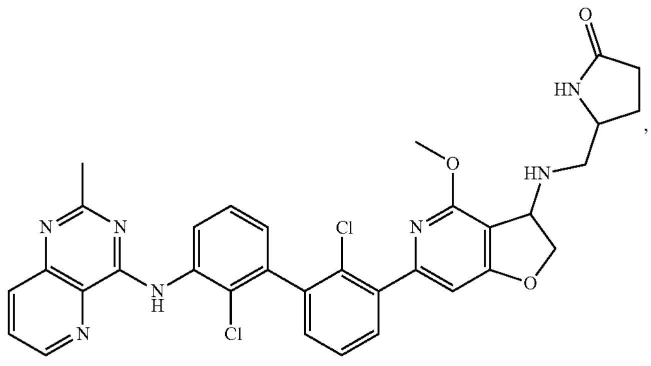
,

-continued
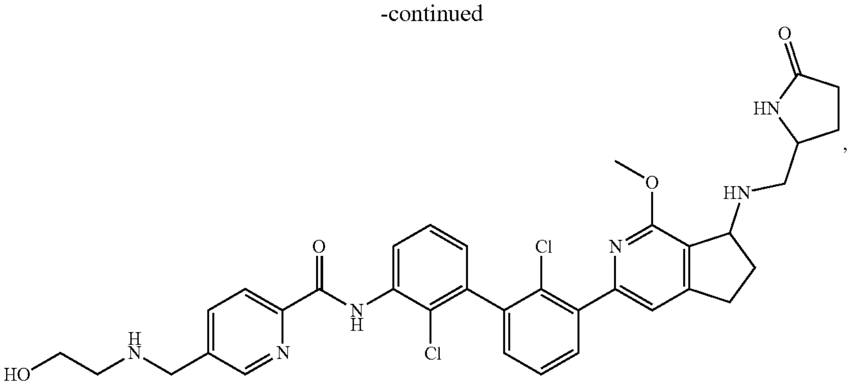
,
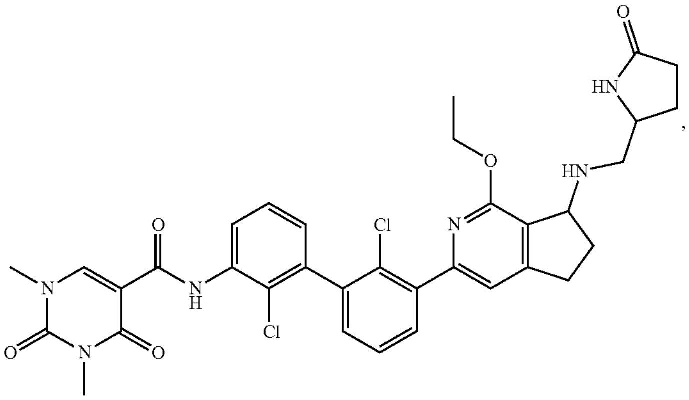
,
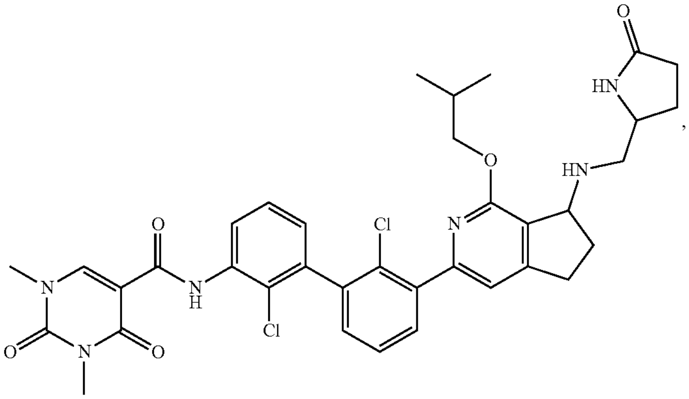
,
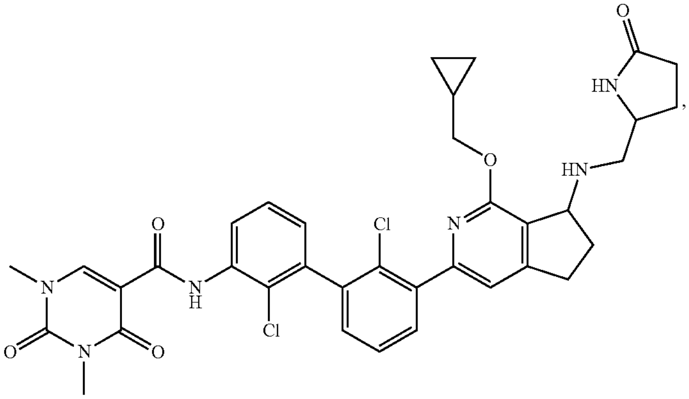
,

-continued
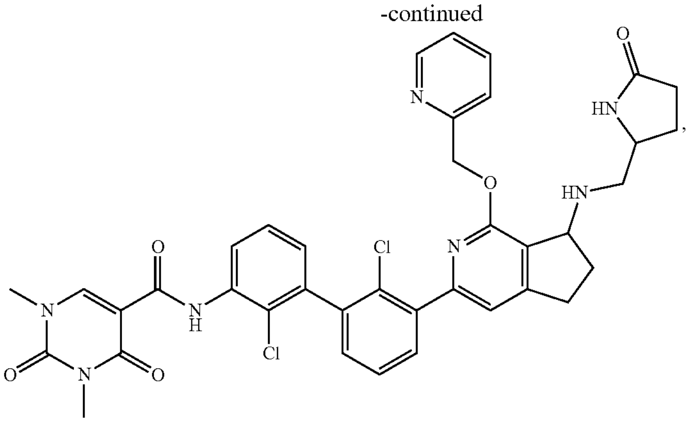
,
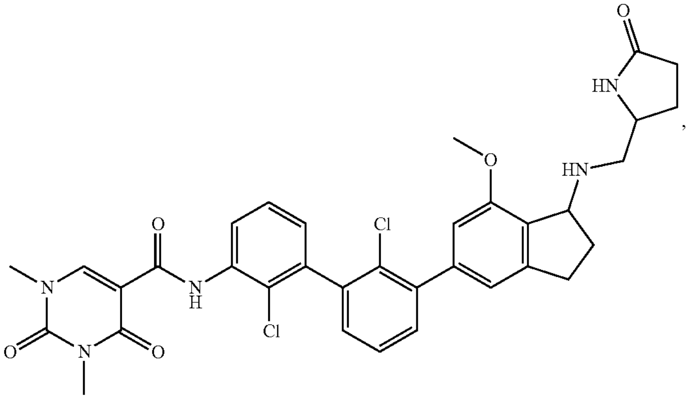
,
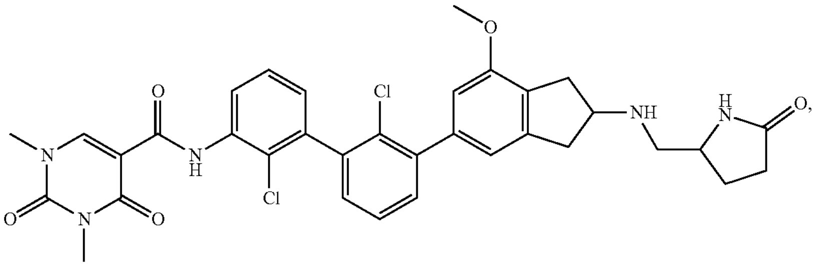
,
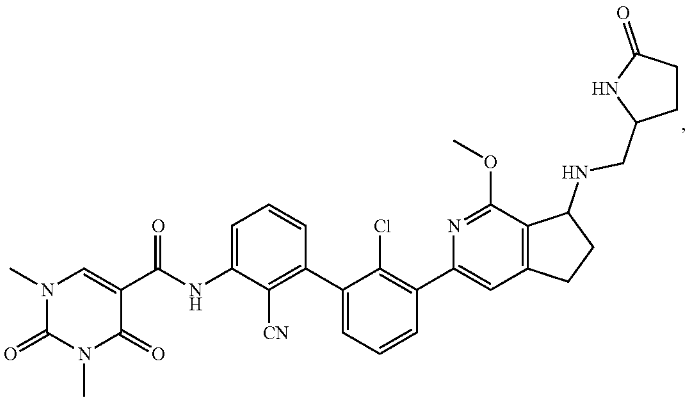
,

-continued
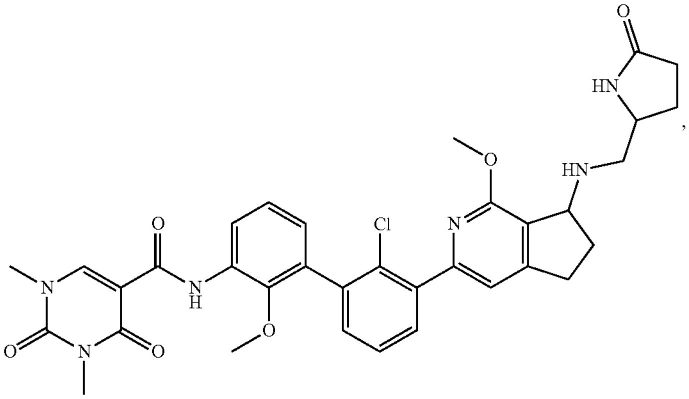
,
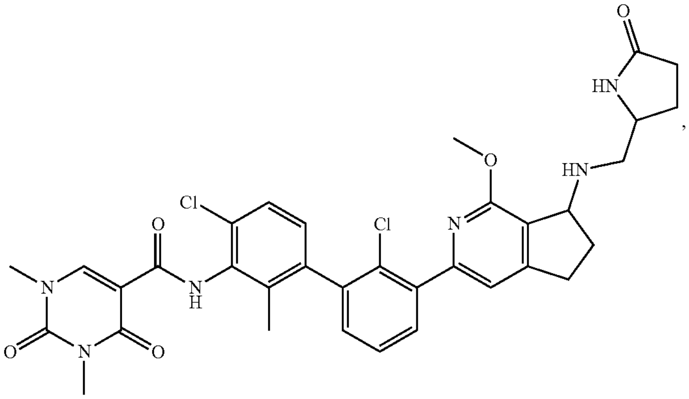
,
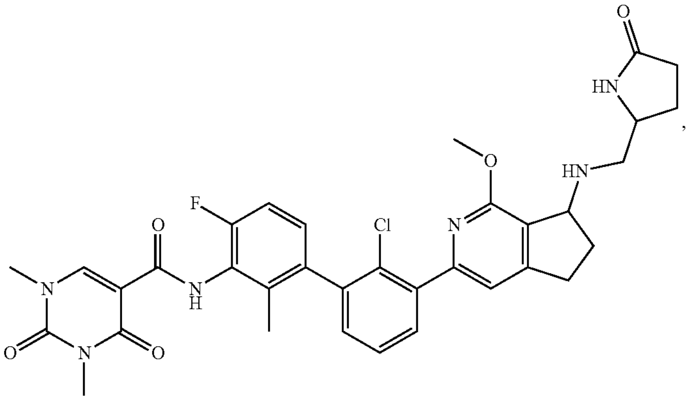
,
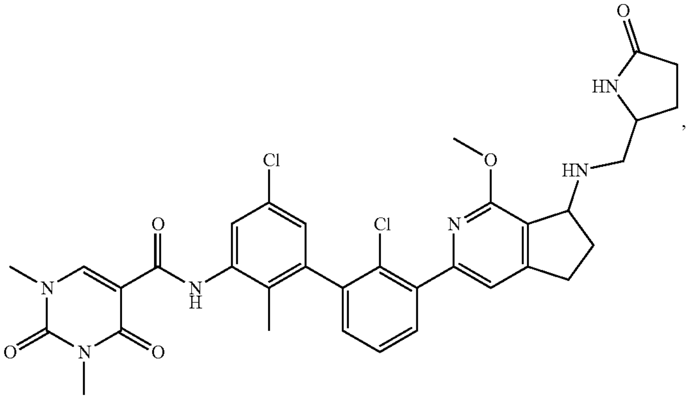
,

-continued
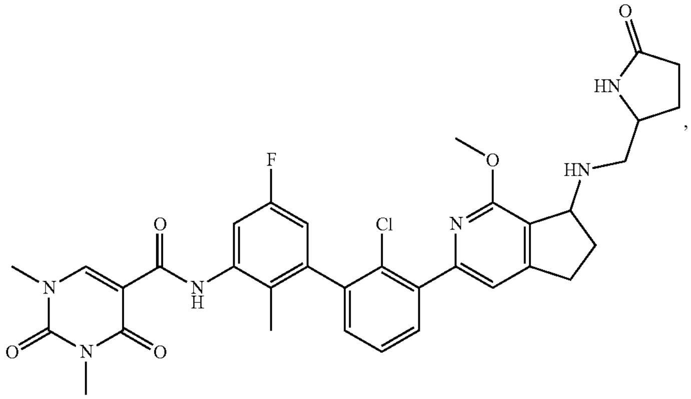
,
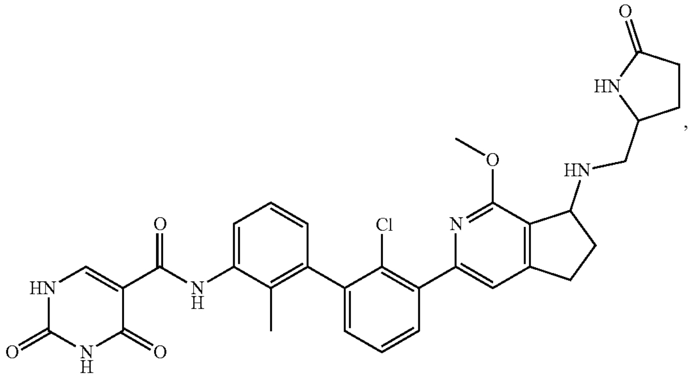
,
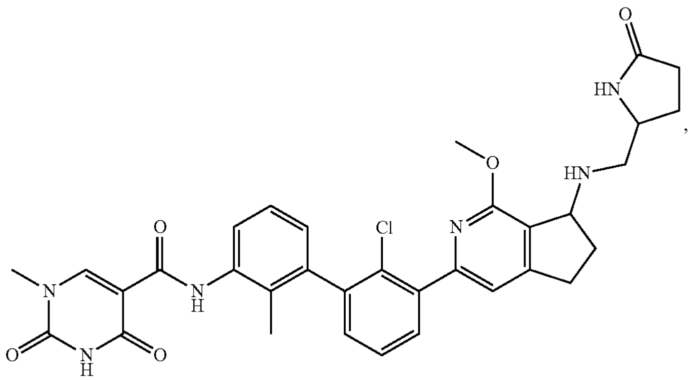
,
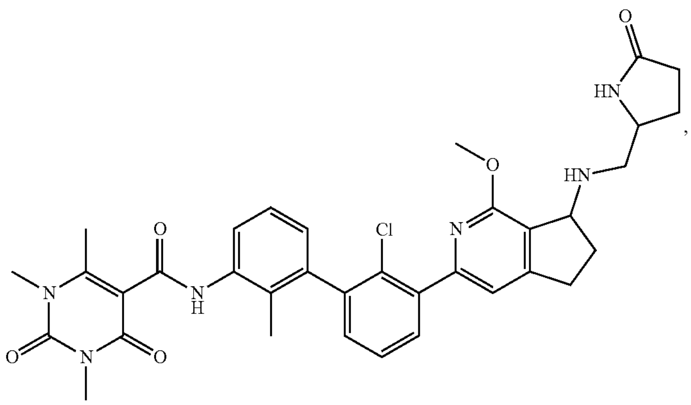
,

-continued
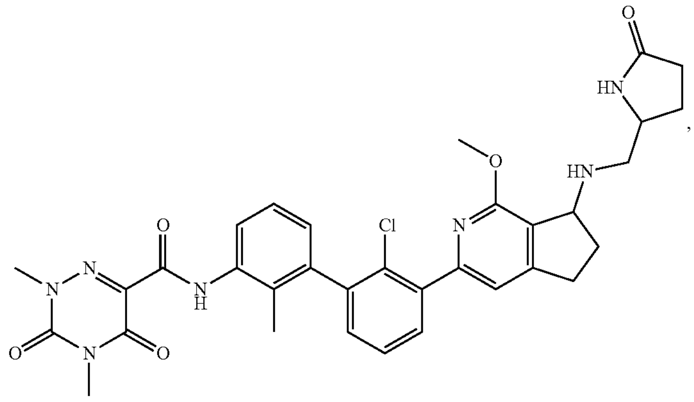
,
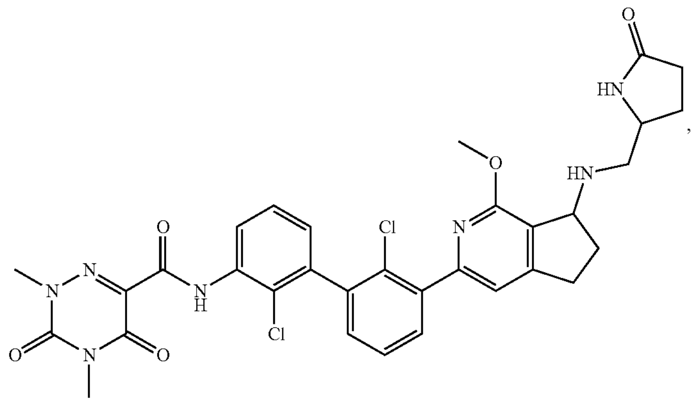
,
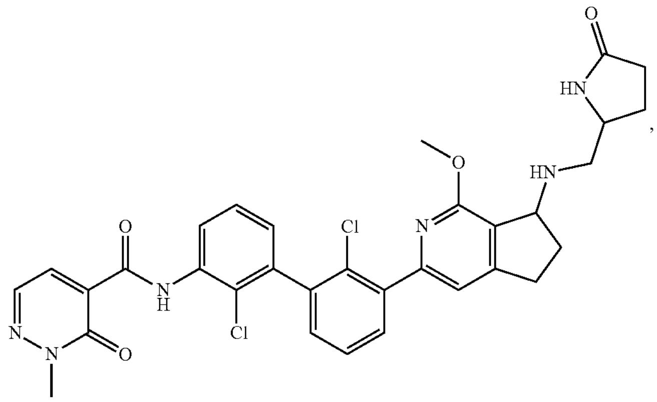
,
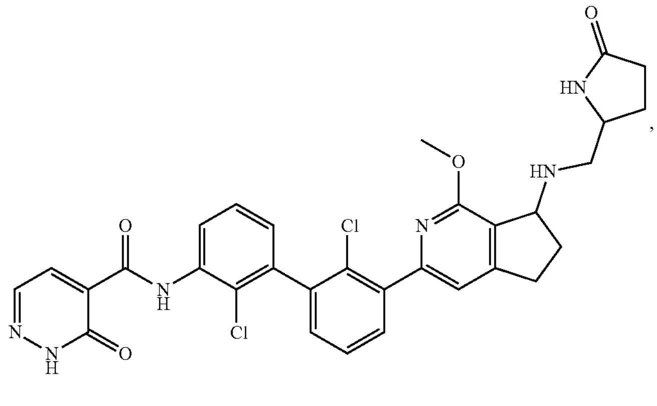
,

-continued
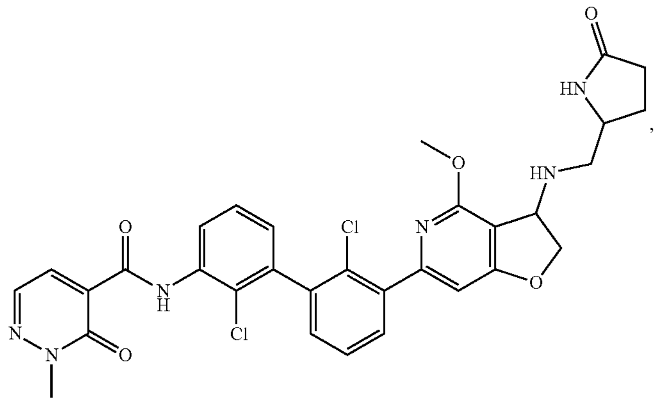
,
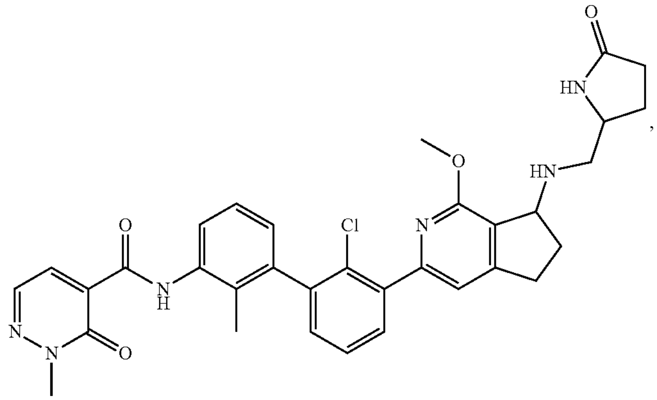
,
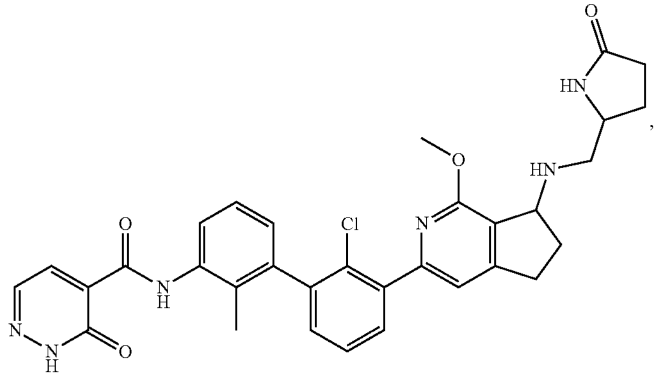
,
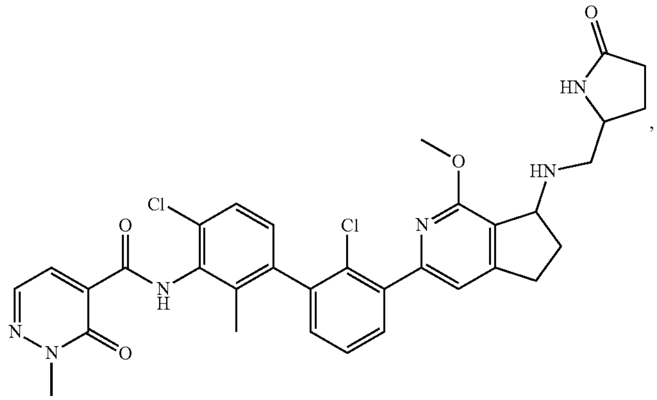
,

-continued
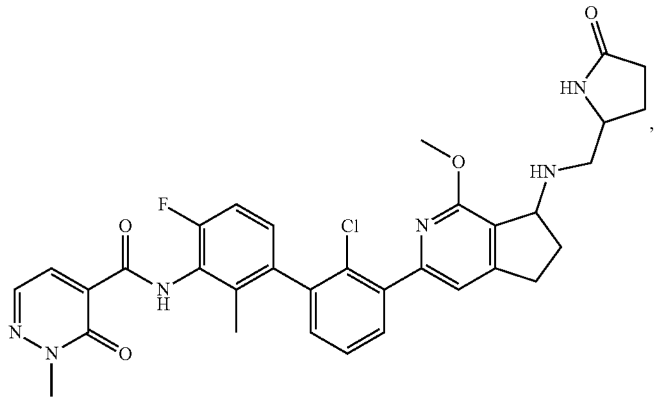
,
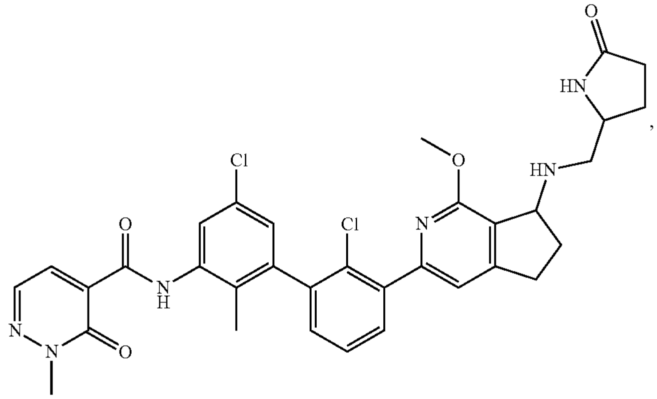
,
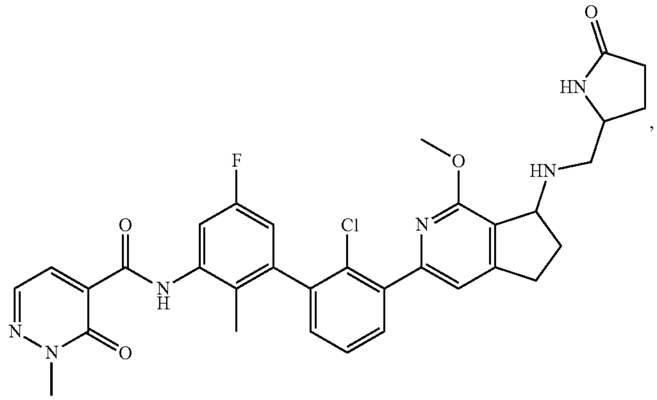
,
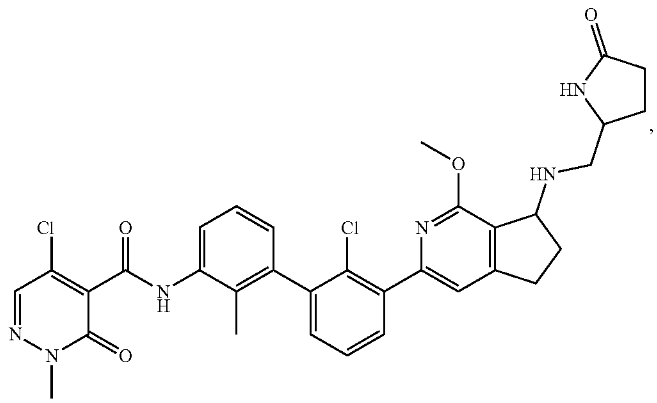
,

-continued
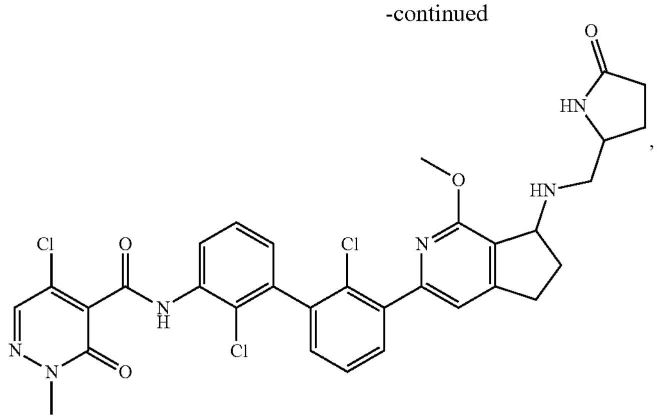
,
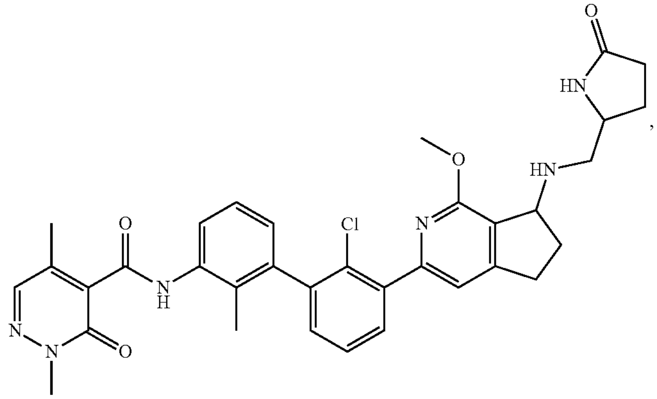
,
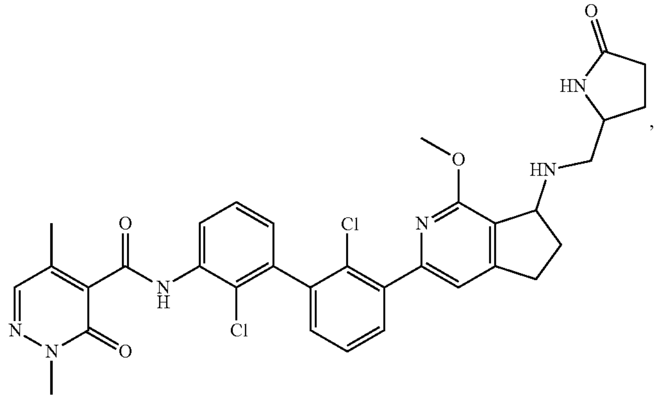
,
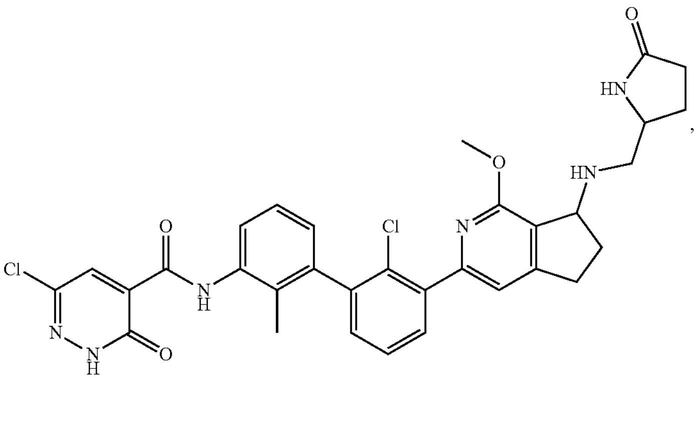
,

-continued
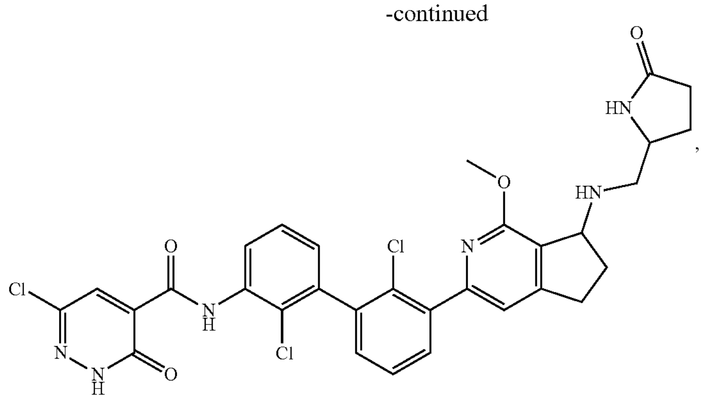
,
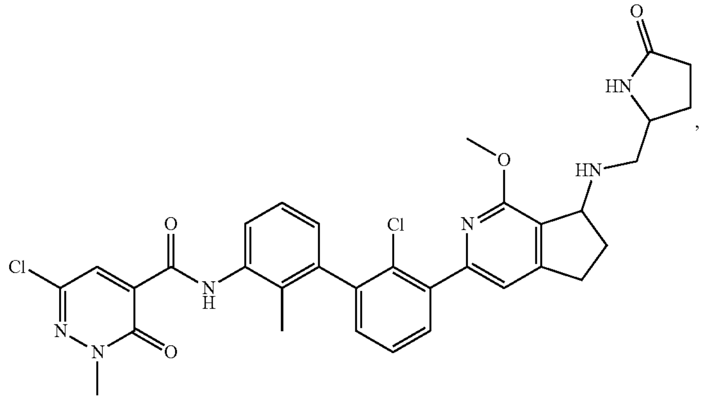
,
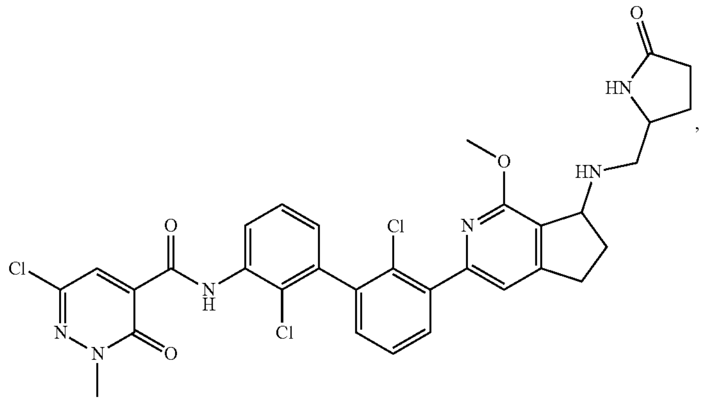
,
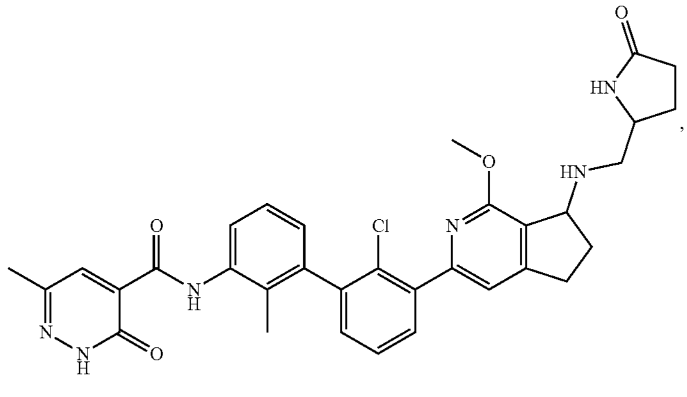
,

-continued
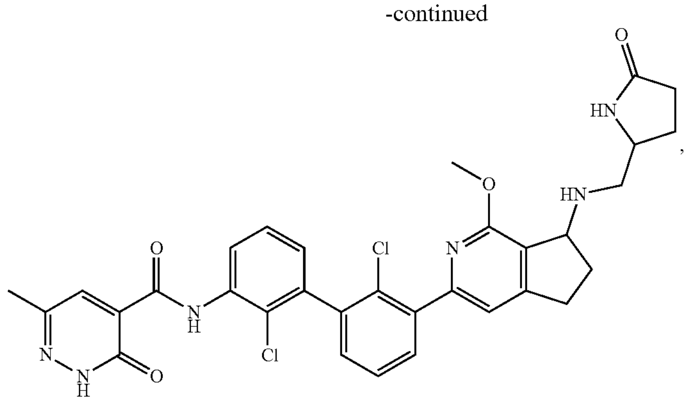
,
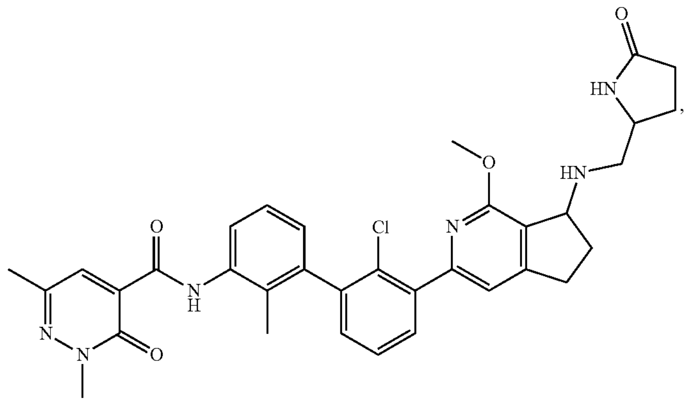
,
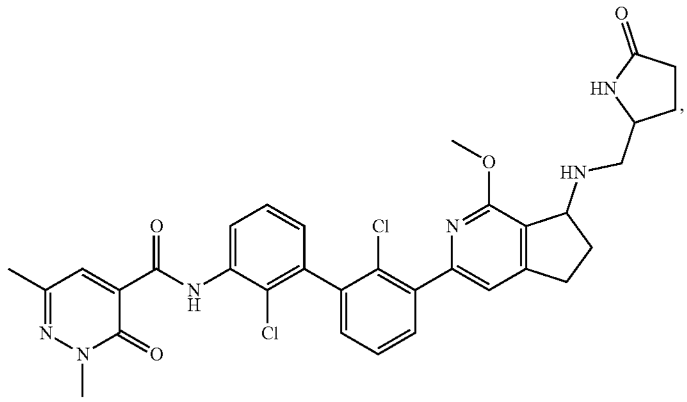
,
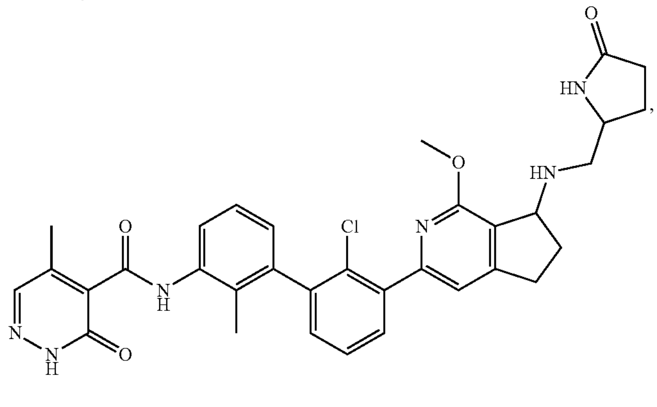
,

-continued
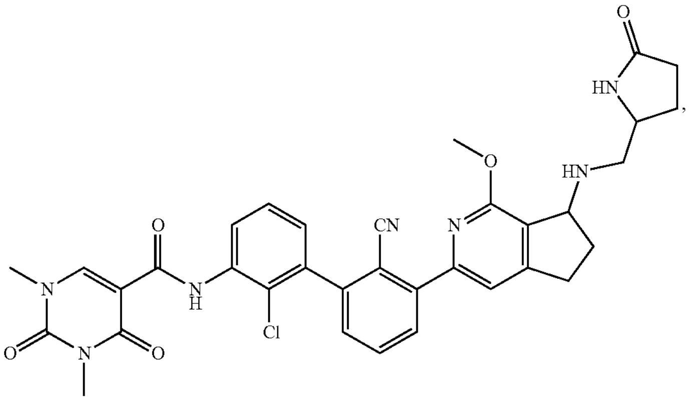
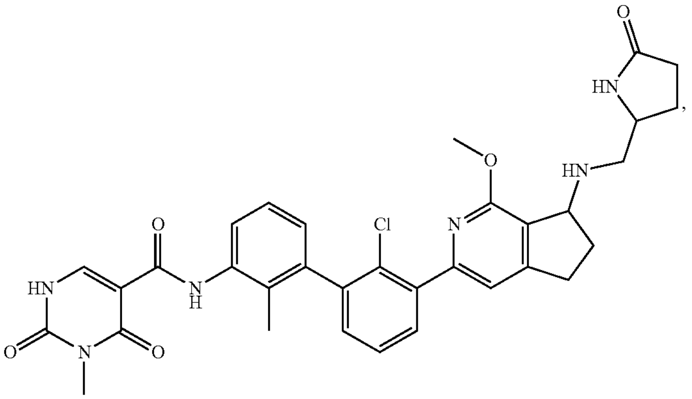
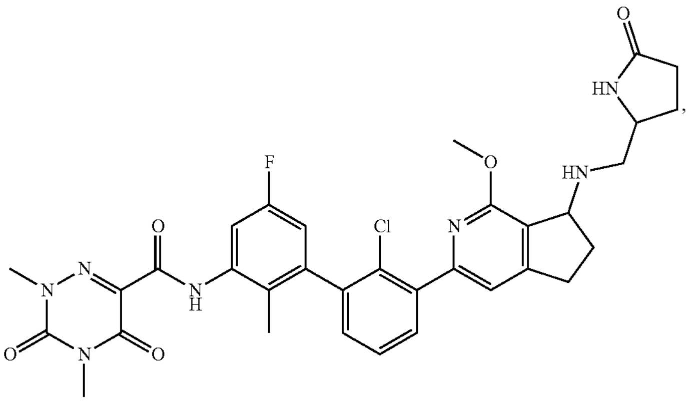
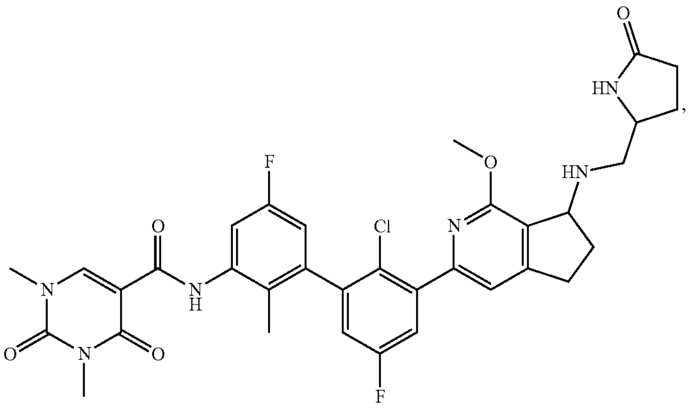

-continued
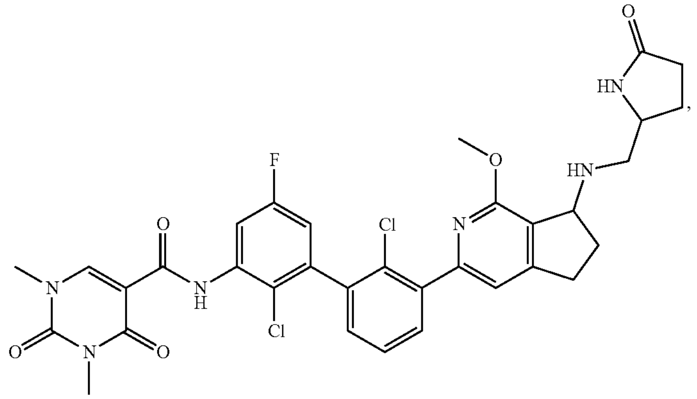
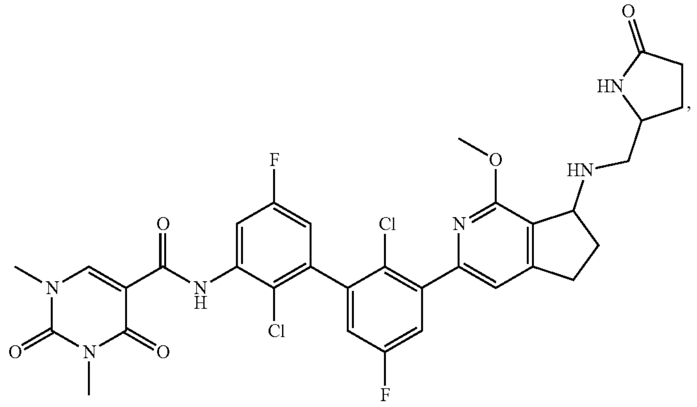
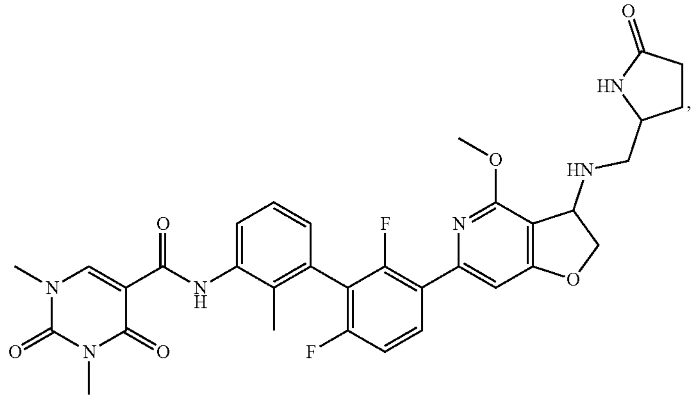
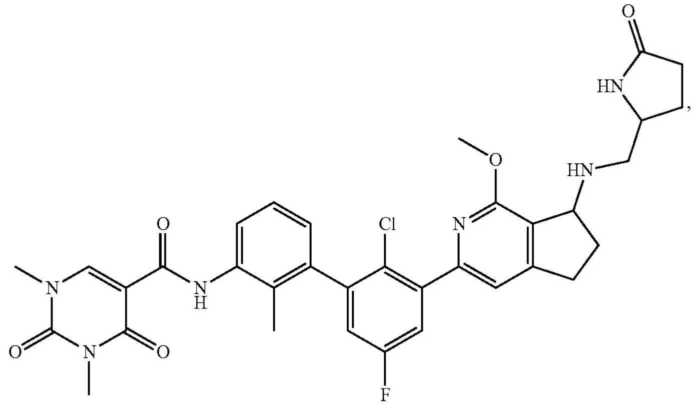

-continued
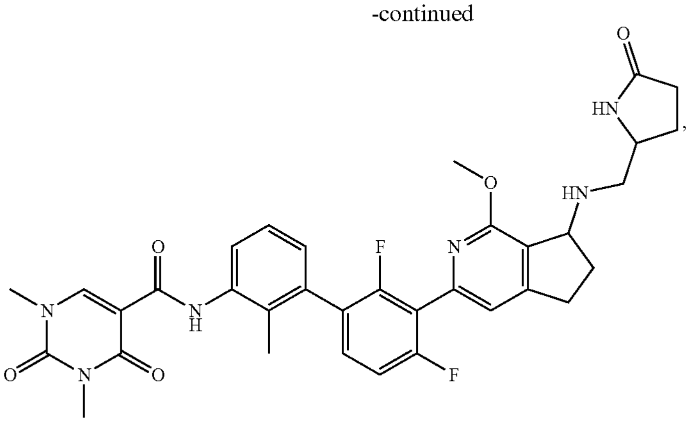
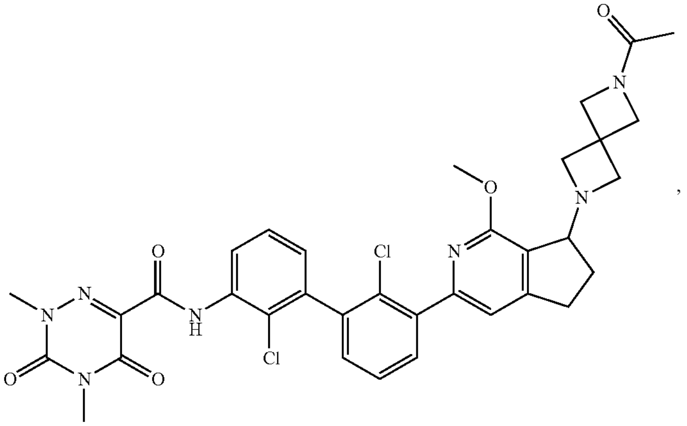
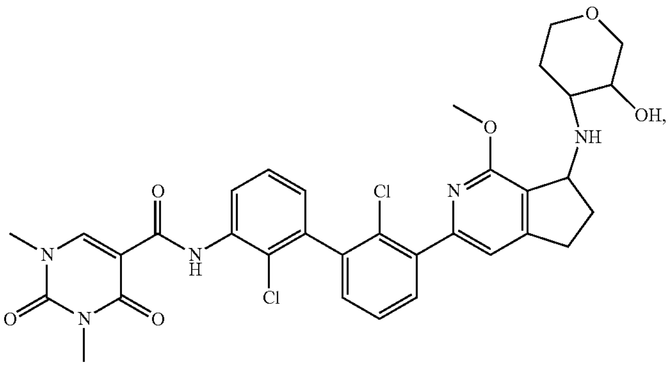
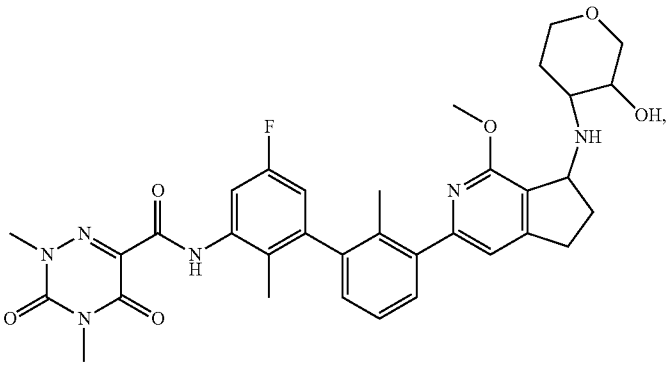

-continued
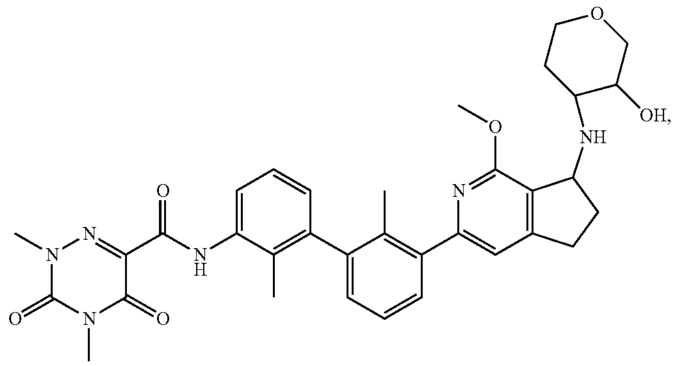
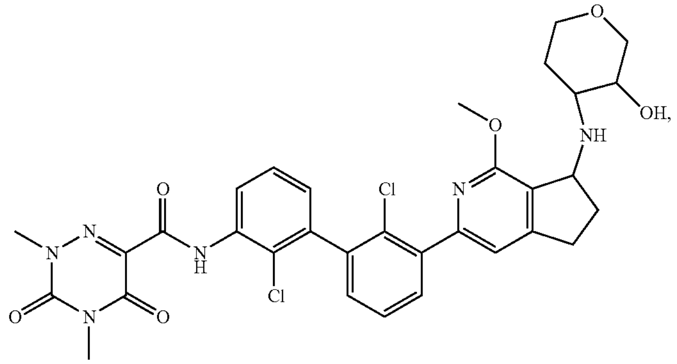
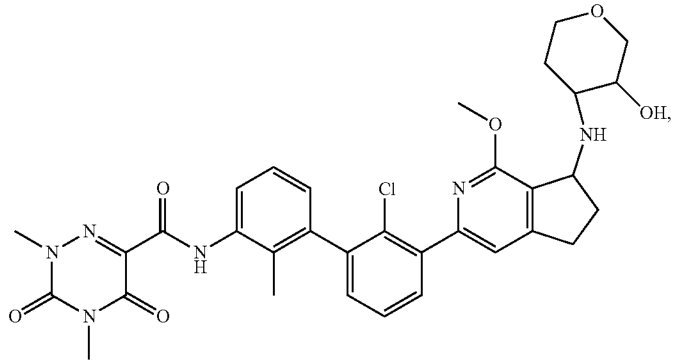
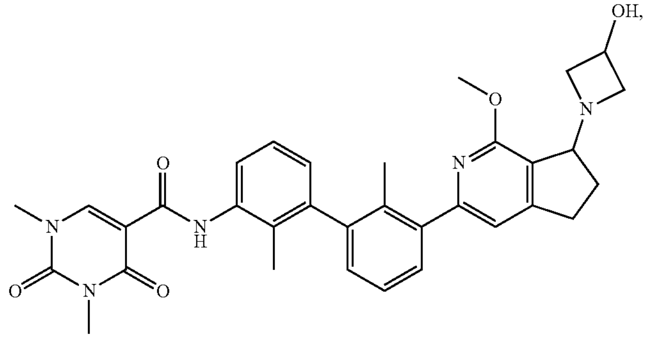

-continued
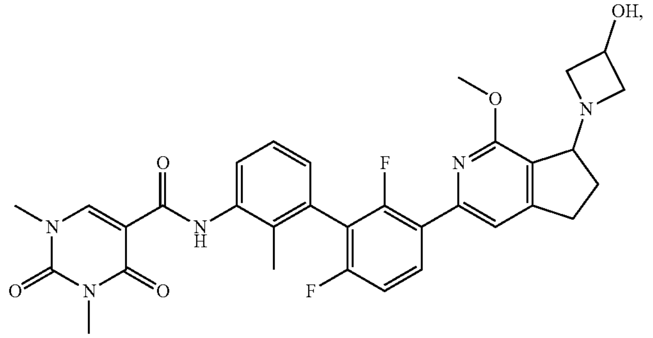
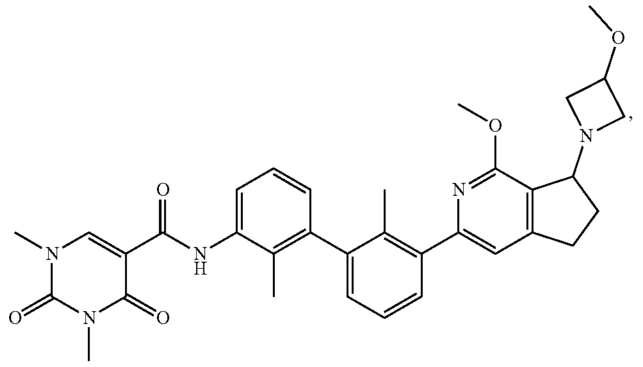
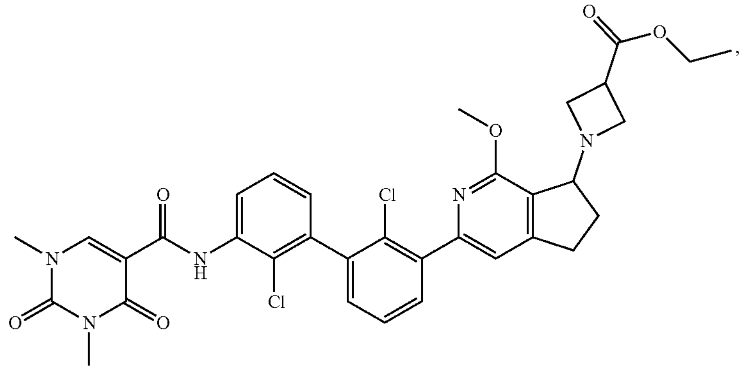
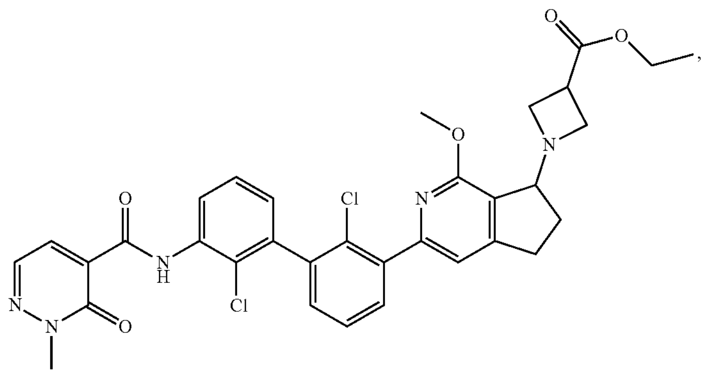

-continued
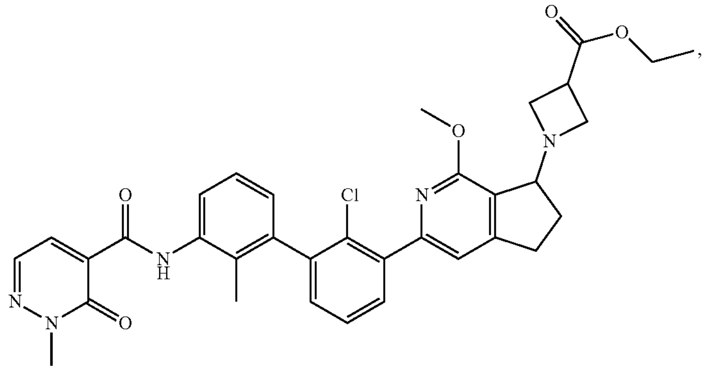
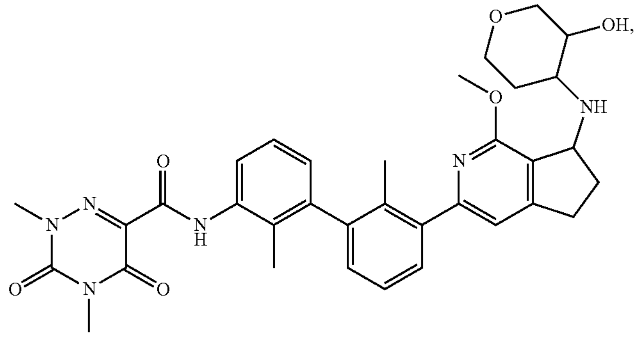
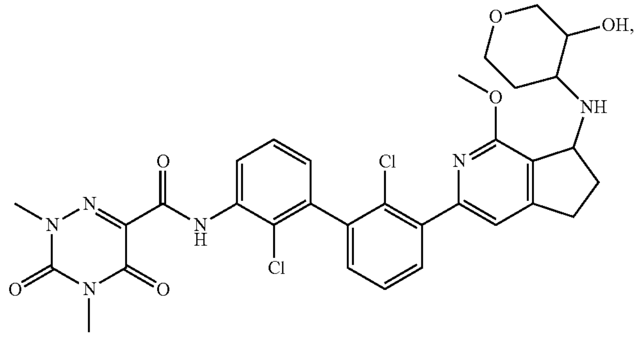
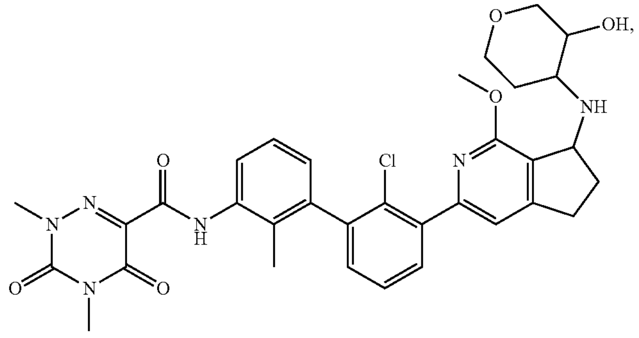
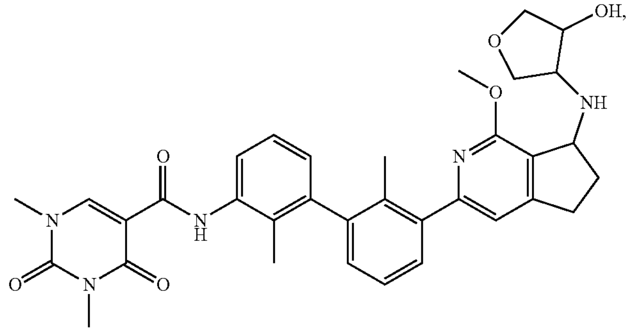

-continued
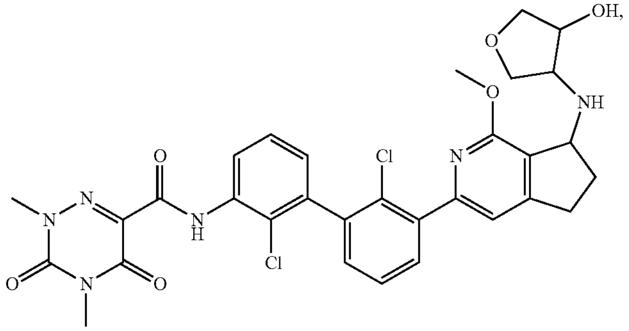
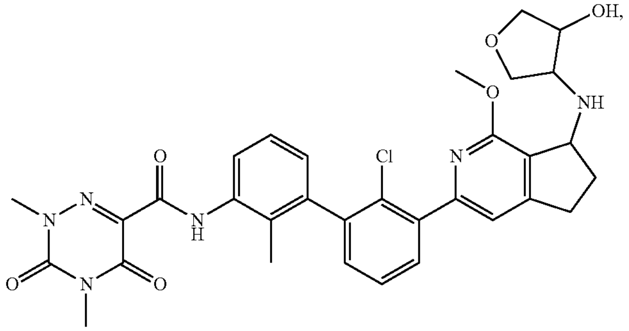
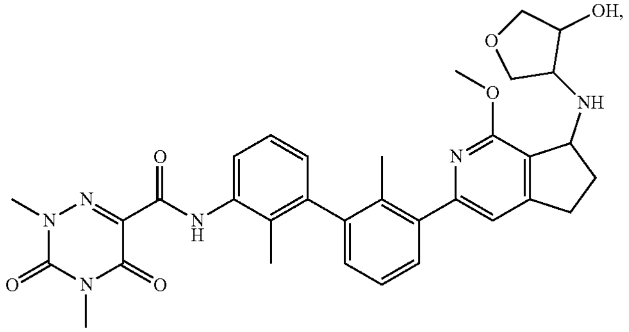
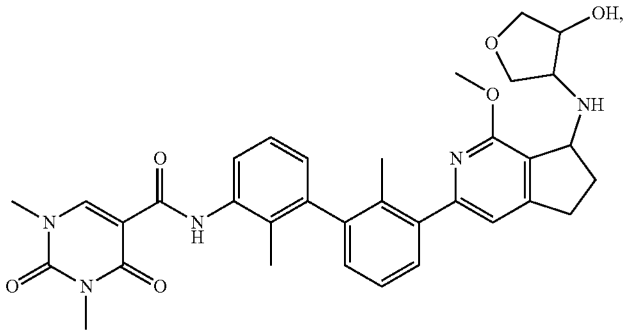
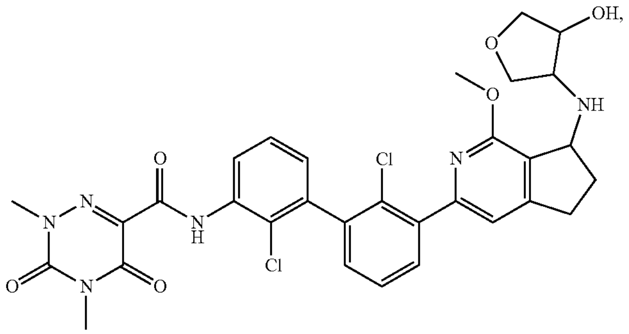

-continued
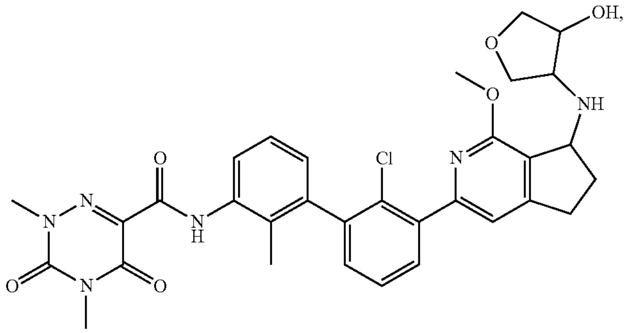
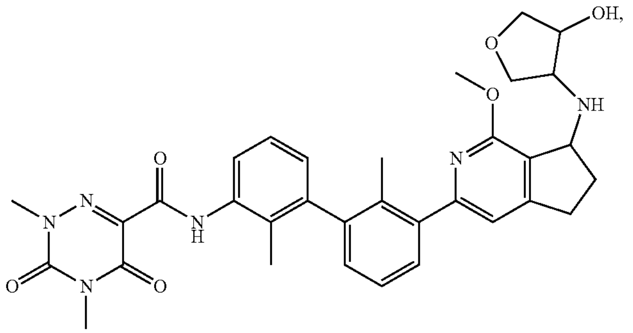
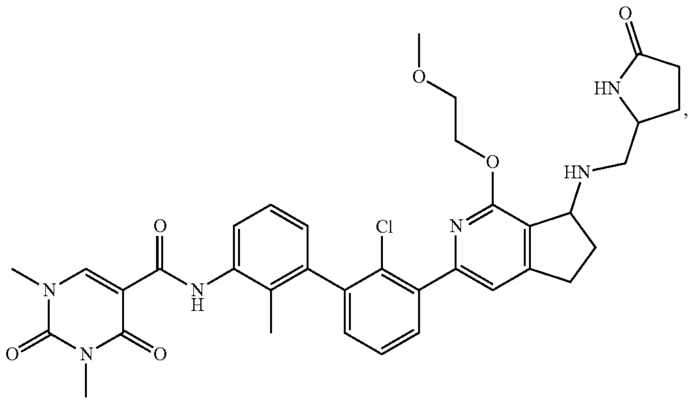
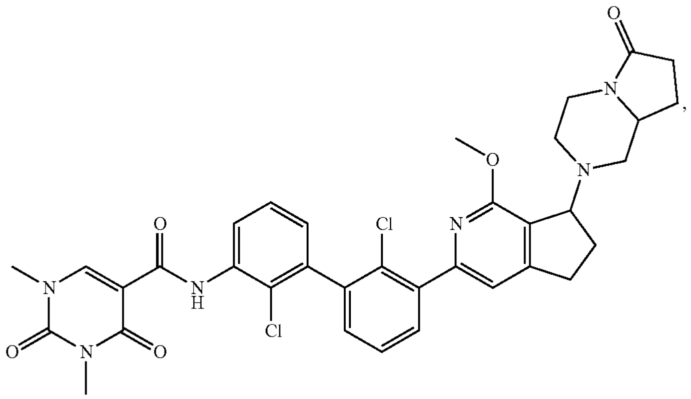

-continued
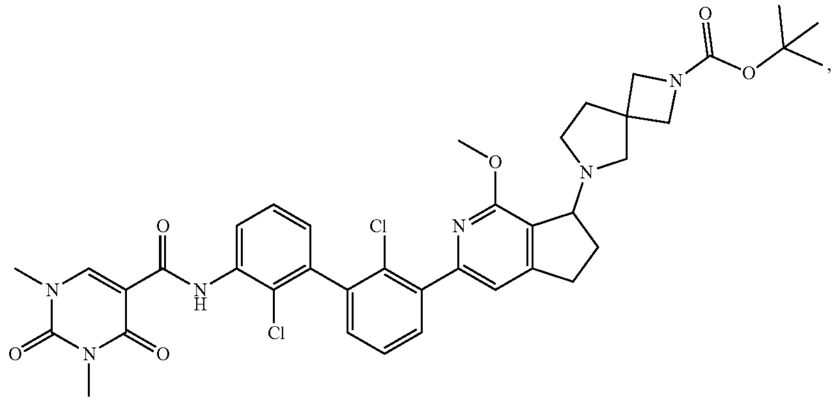
,
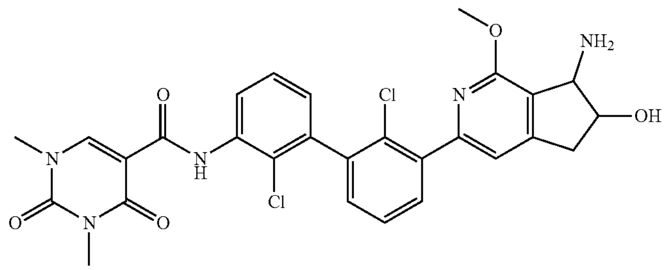
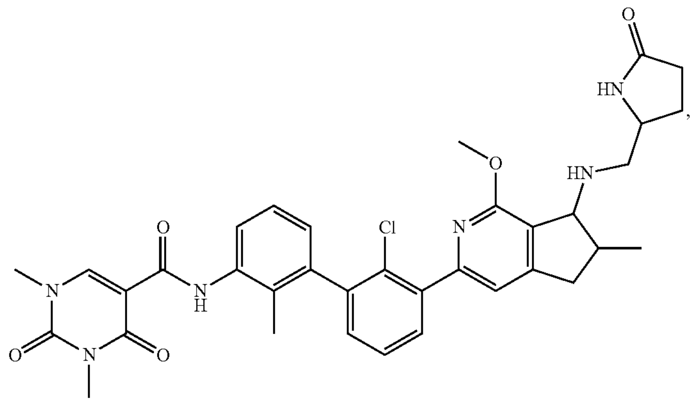
,
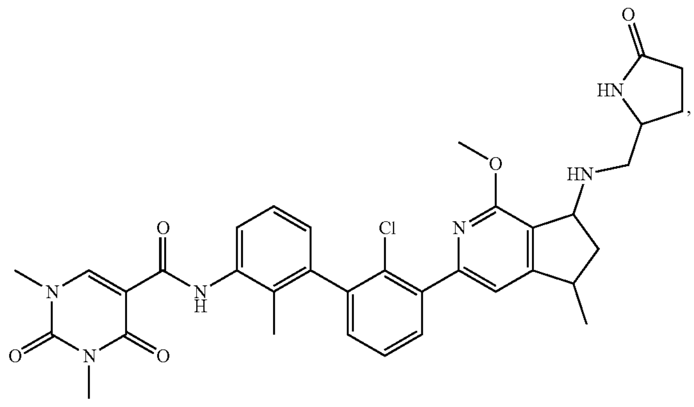
,

-continued
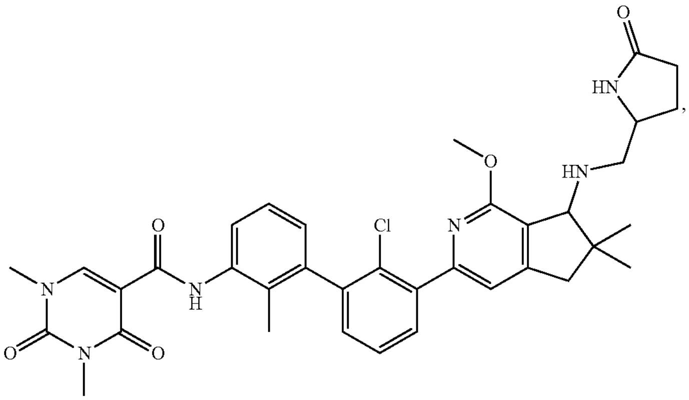
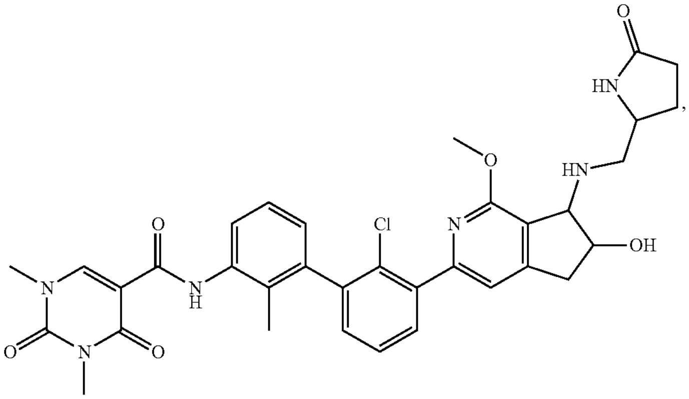
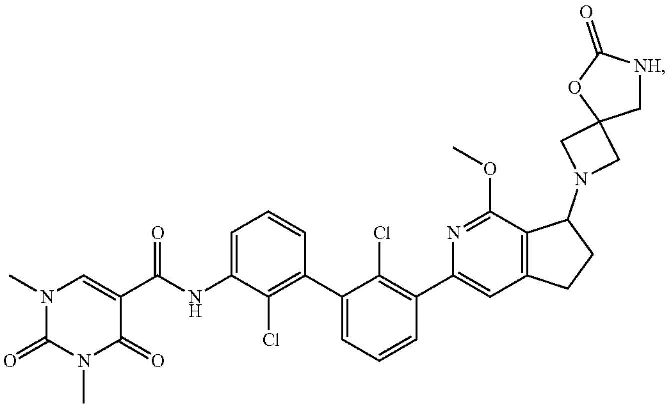
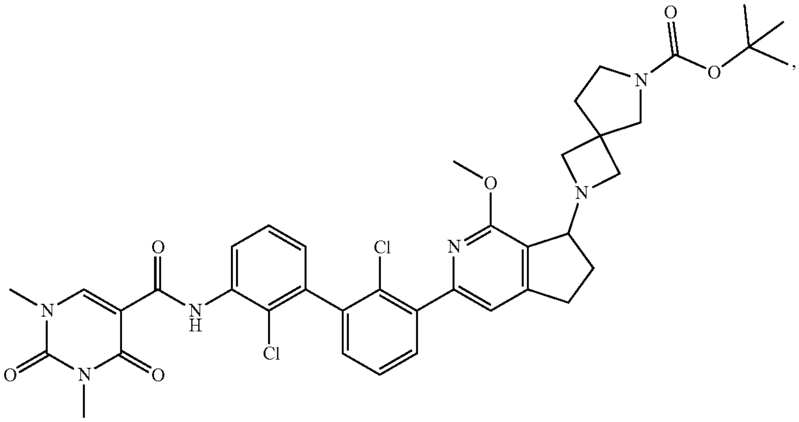

-continued
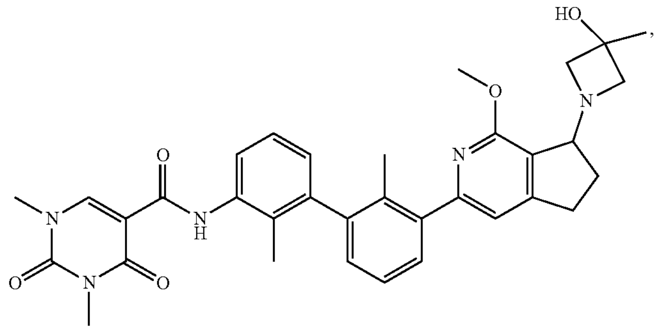
,
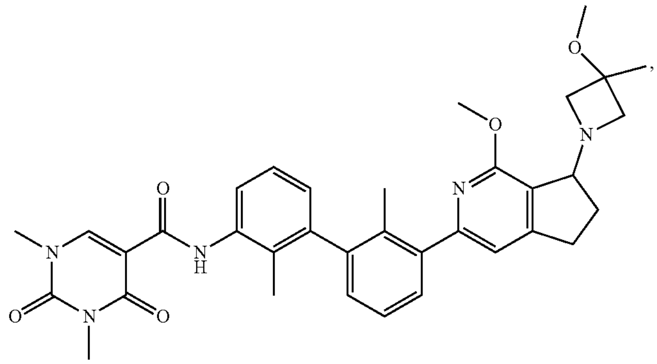
,
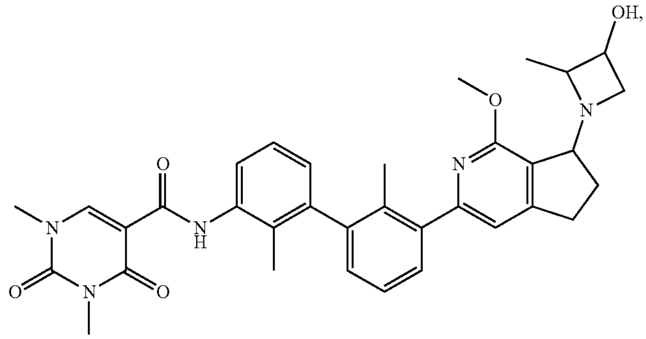
,
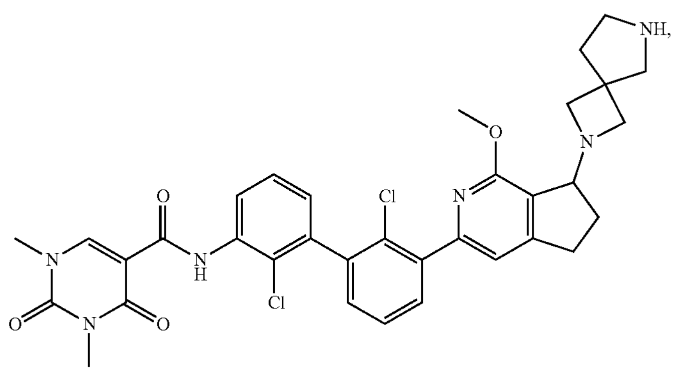
,

-continued
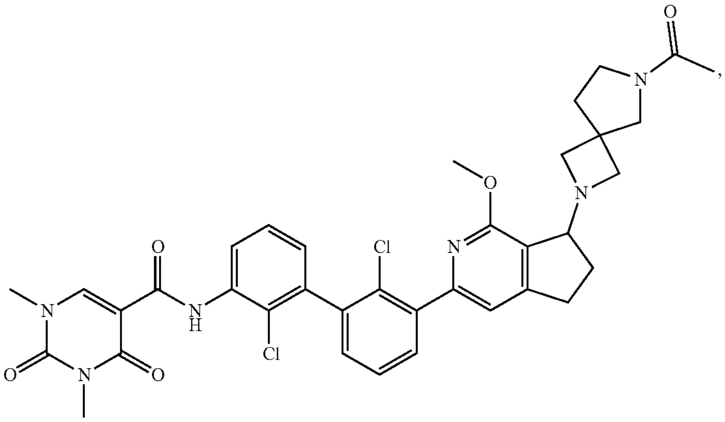
,
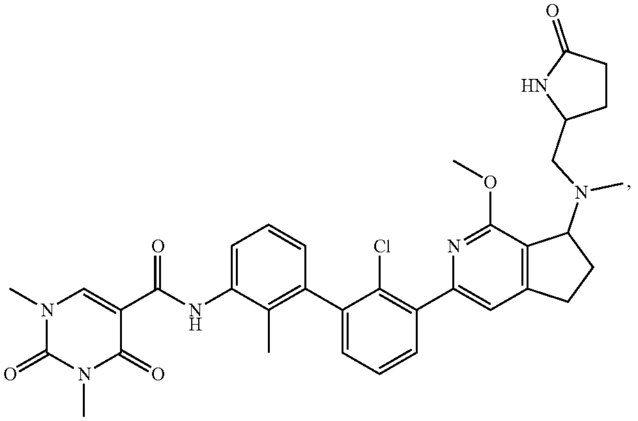
,
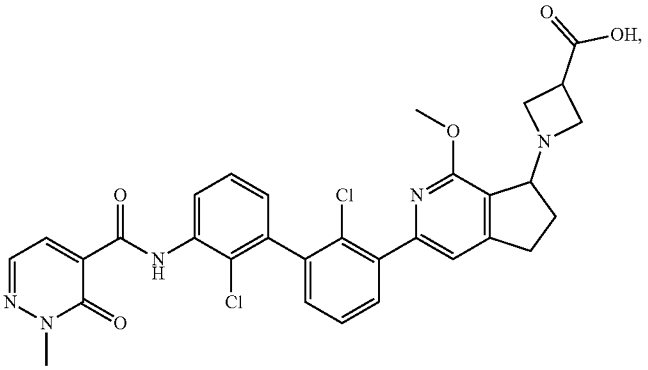
,
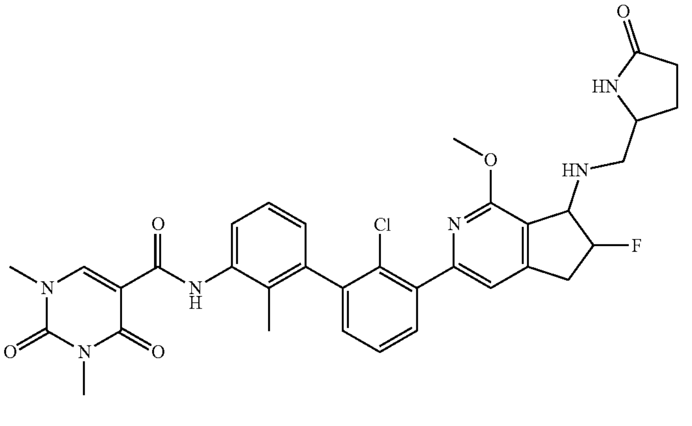
and

-continued
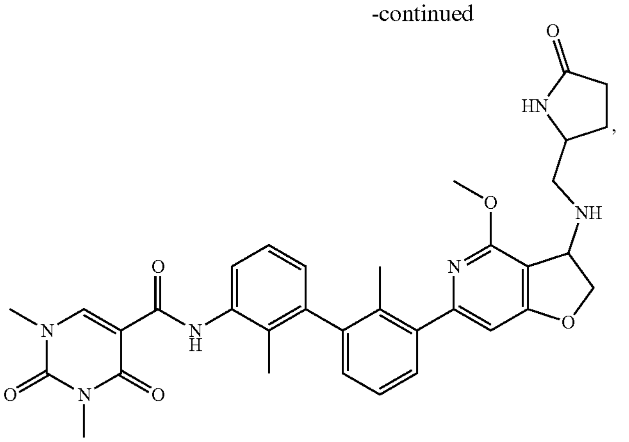
pharmaceutically acceptable salt of any of the foregoing.
Embodiment 143
The compound of Embodiment 1 selected from:
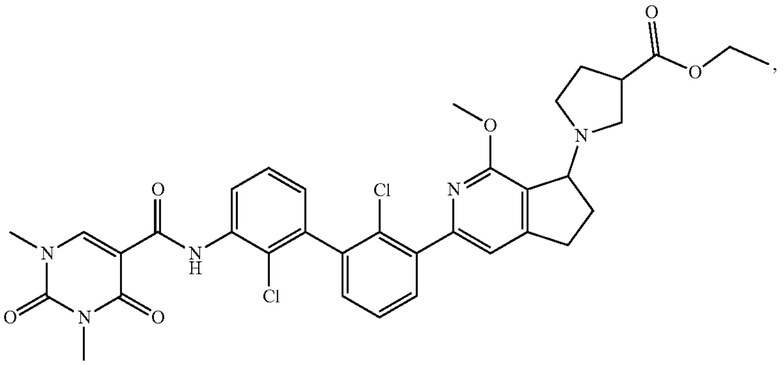
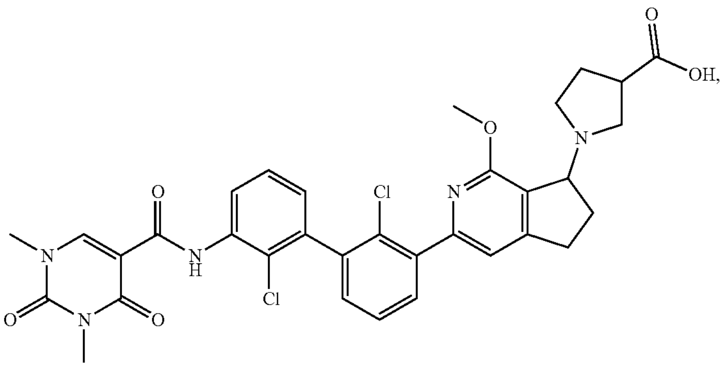

-continued
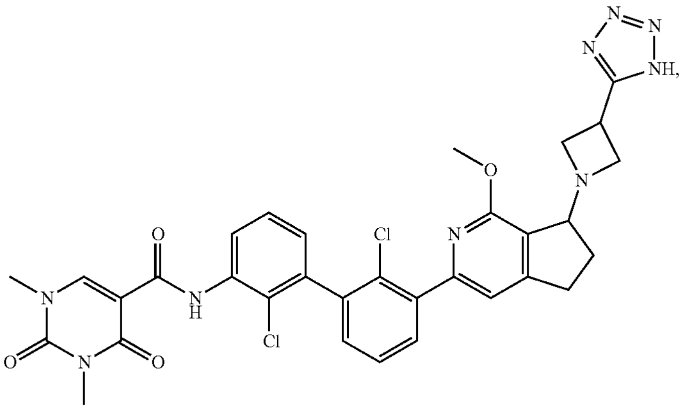
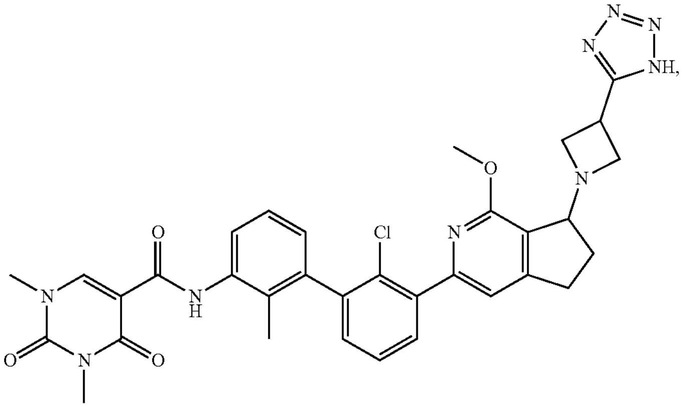
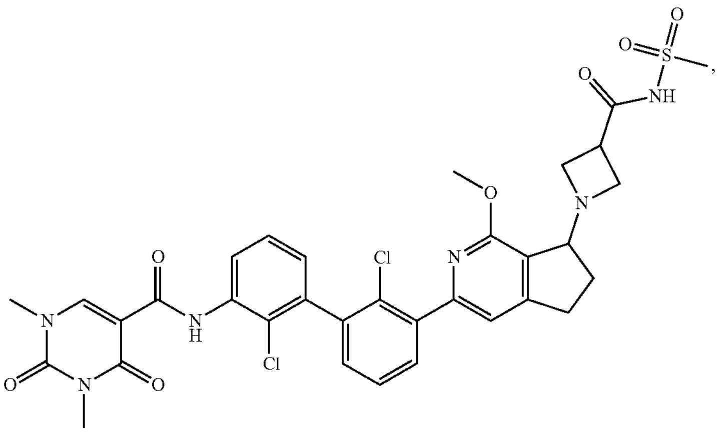
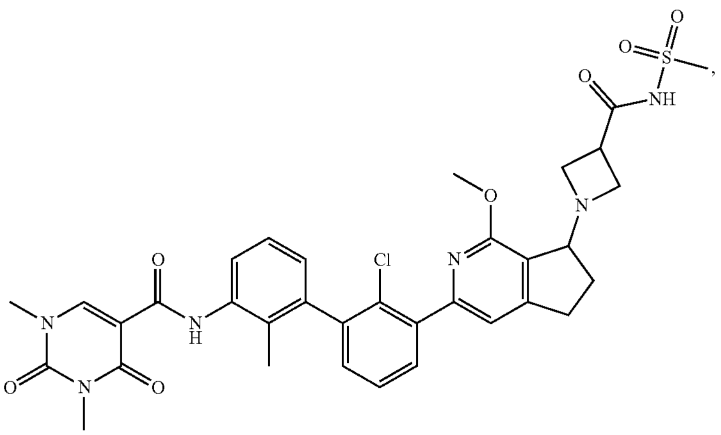

-continued
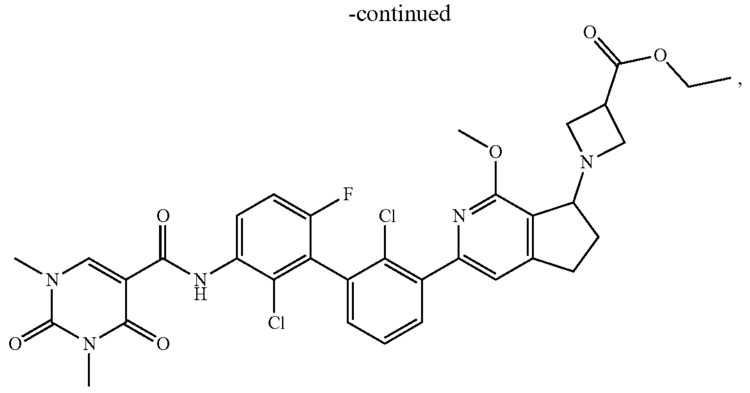
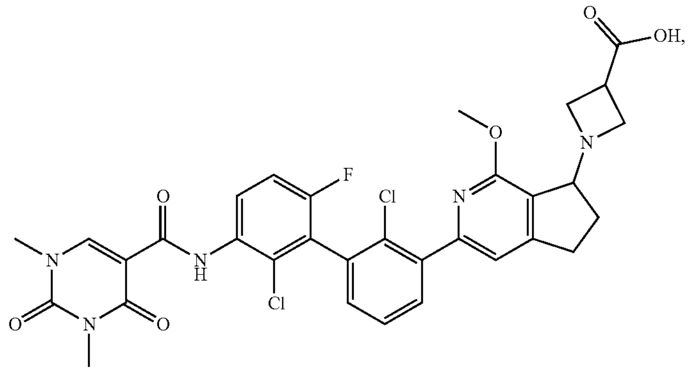
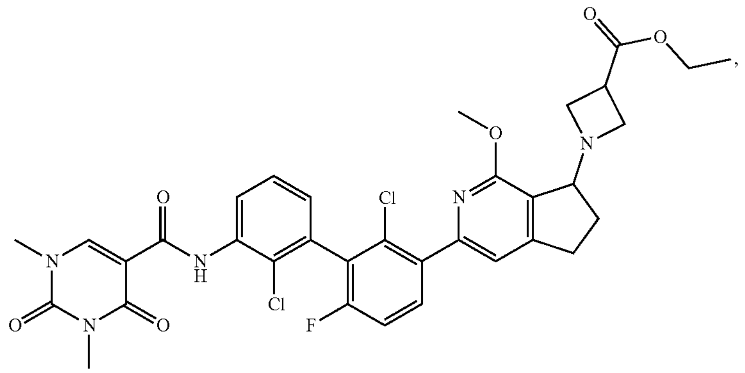
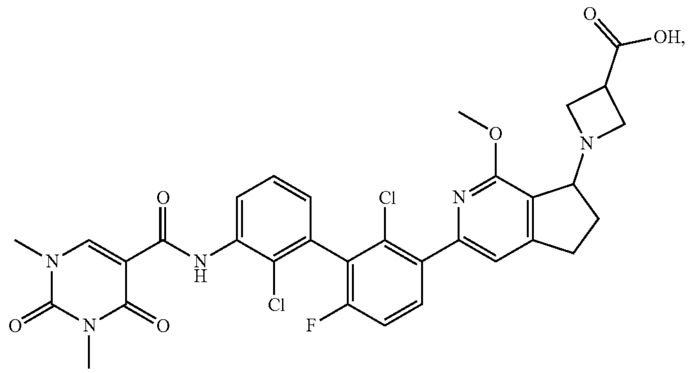

-continued
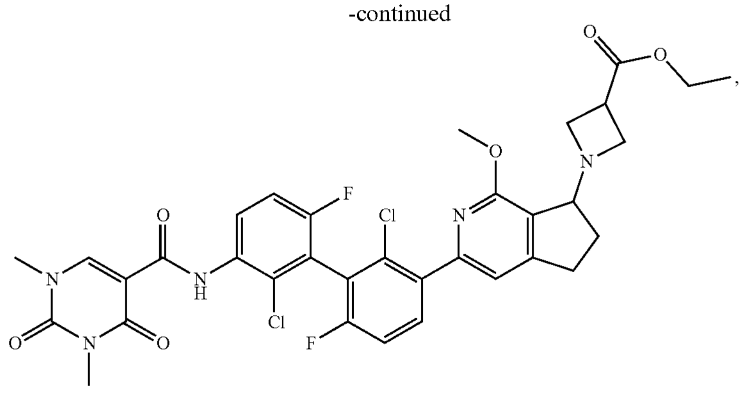
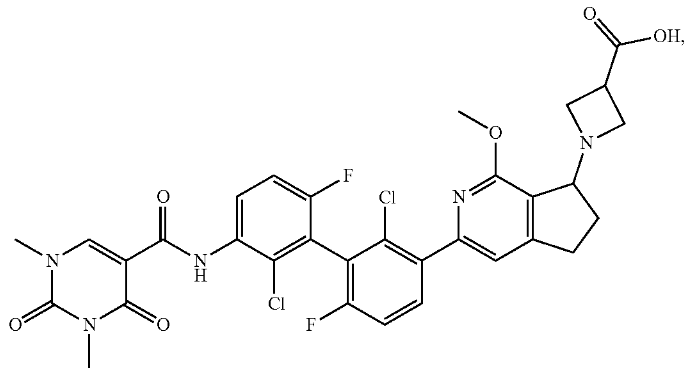
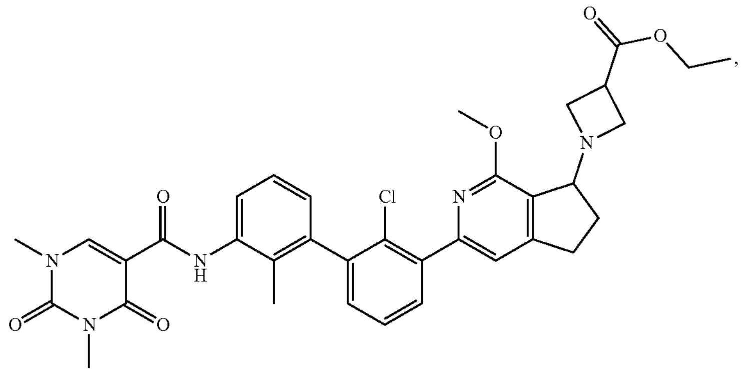
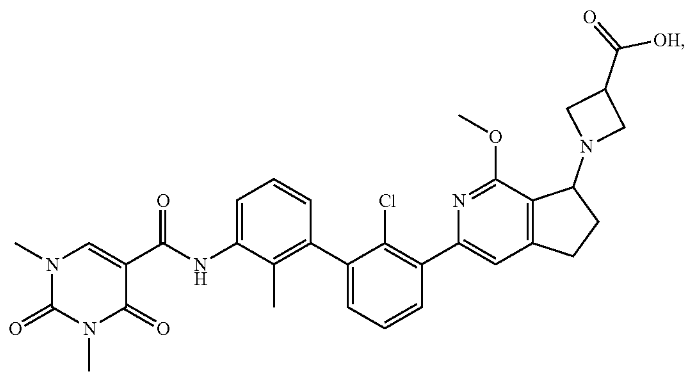

-continued
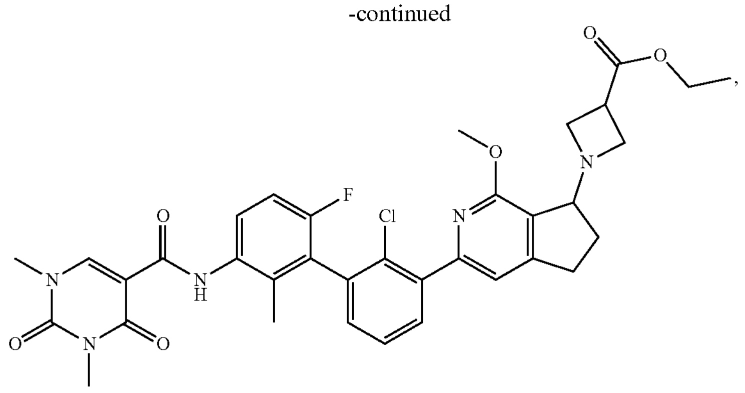
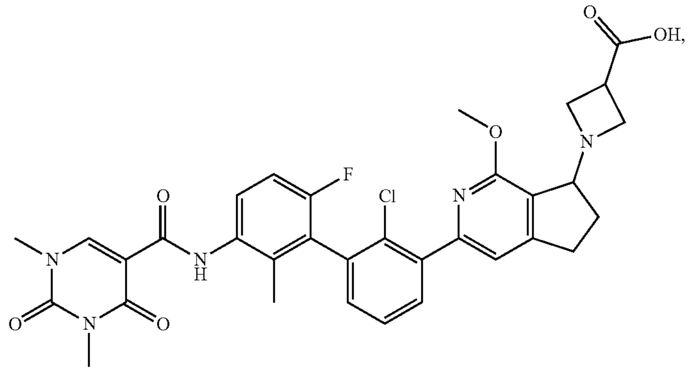
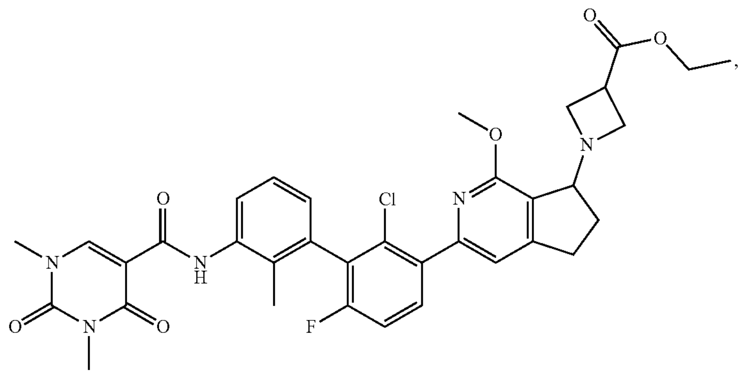
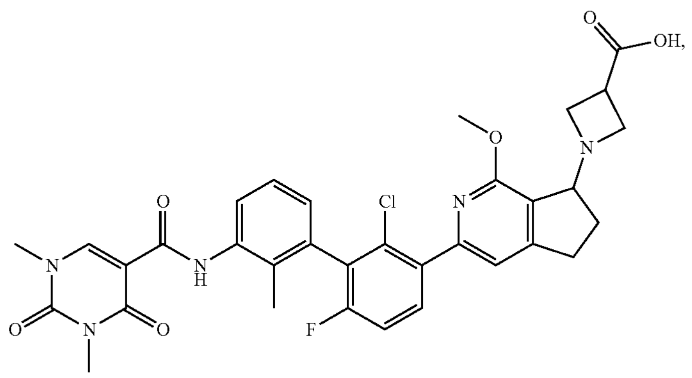

-continued
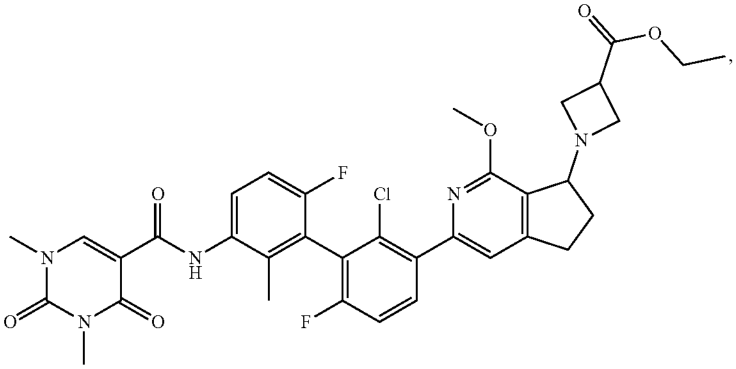
,
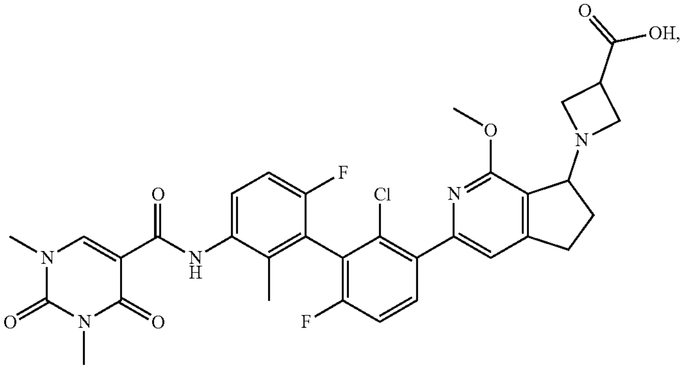
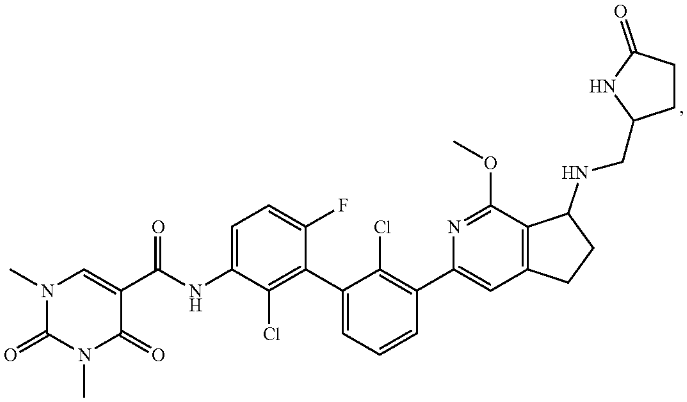
,
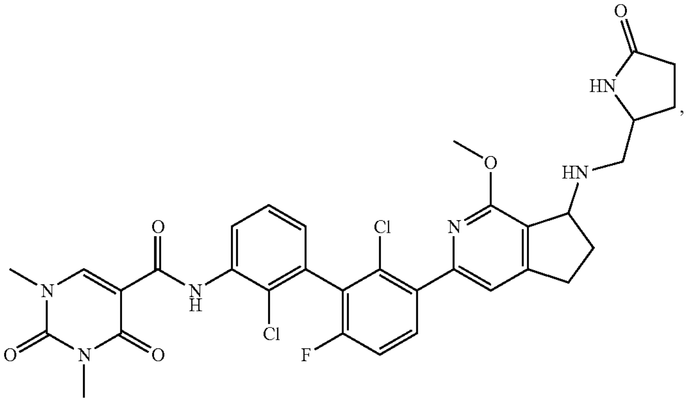
,

-continued
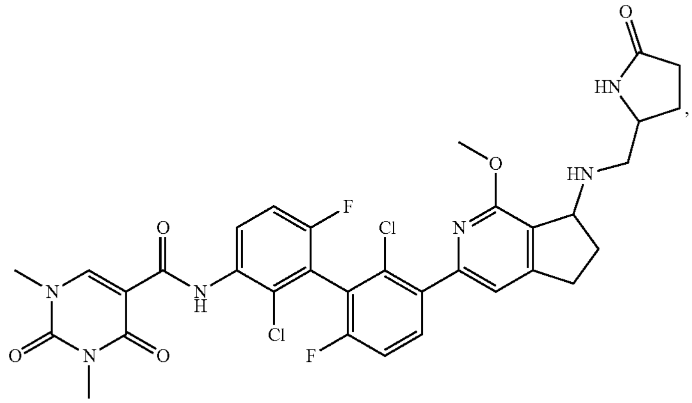
,
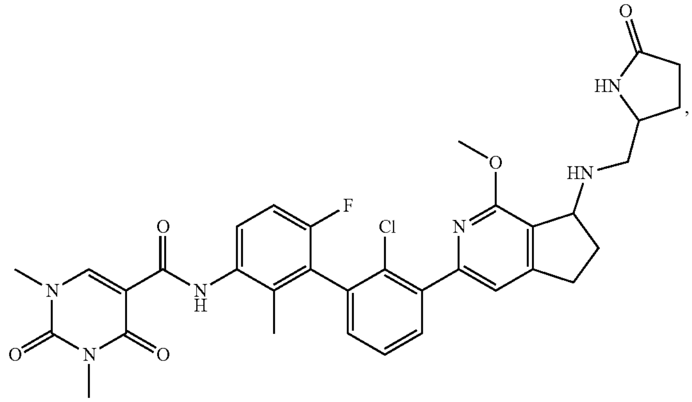
,
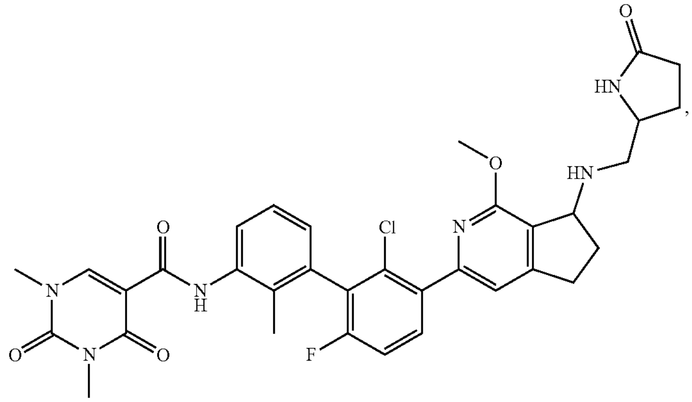
,
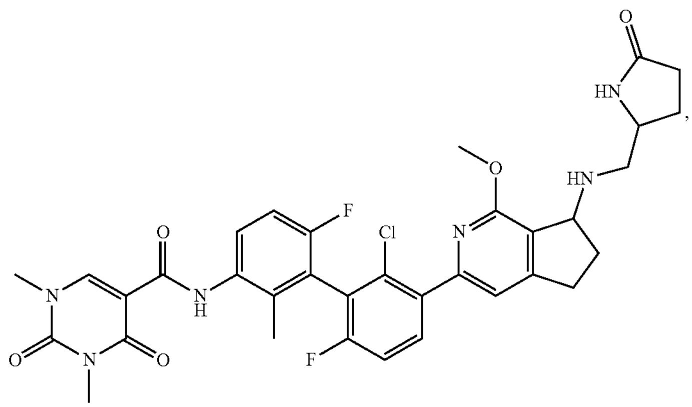
,

-continued
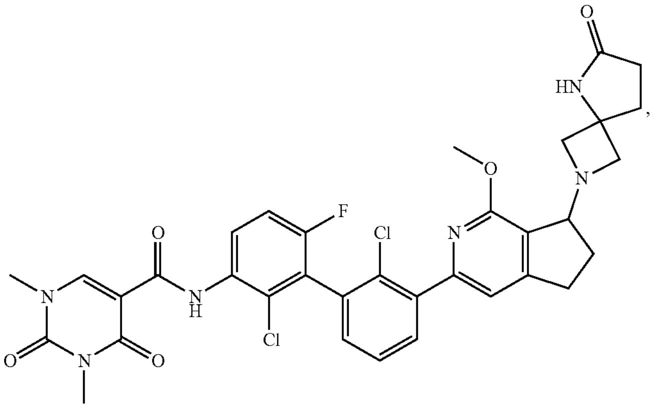
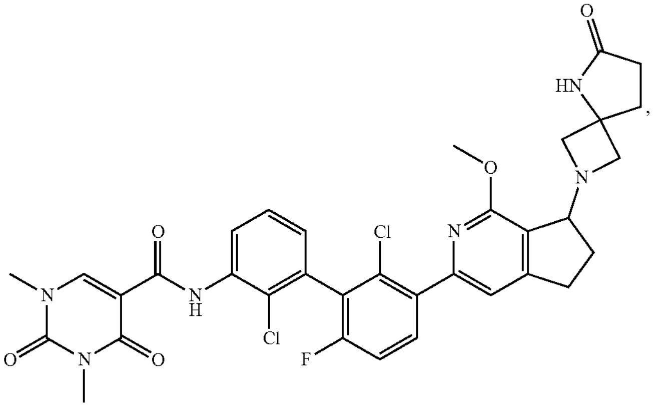
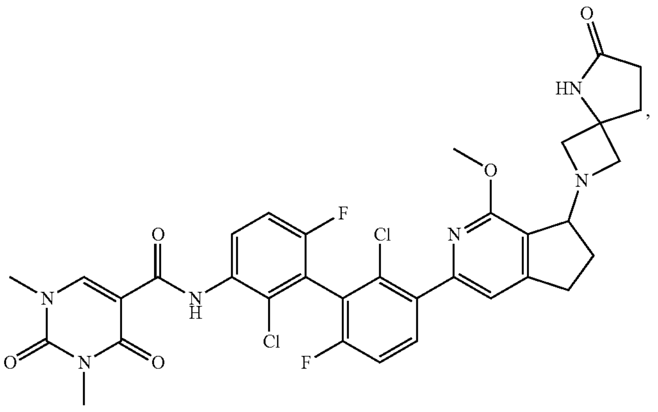
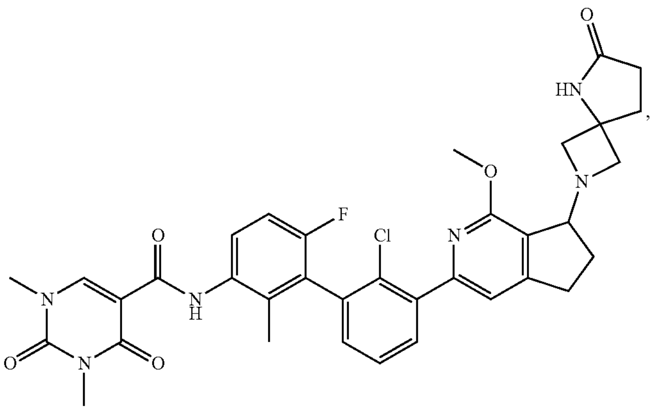

-continued
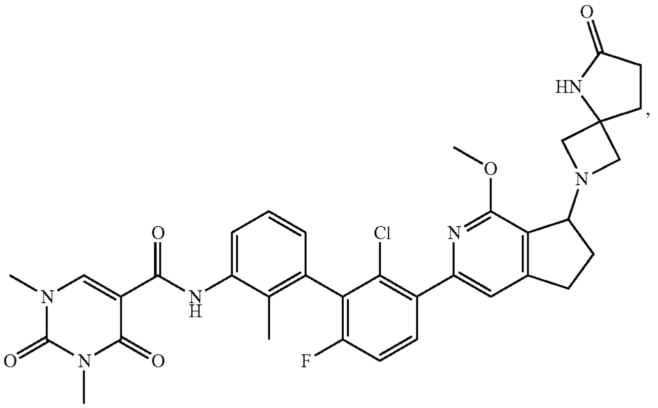
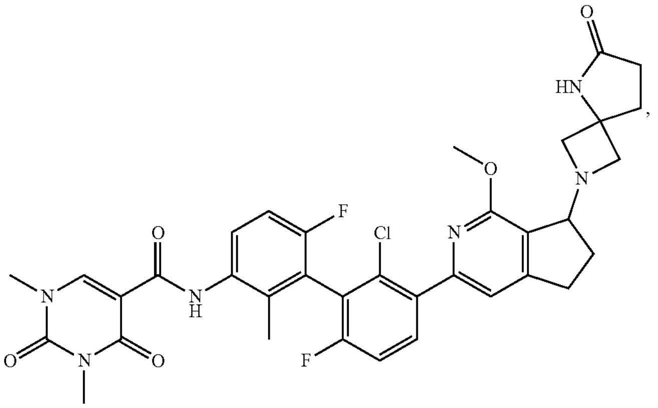
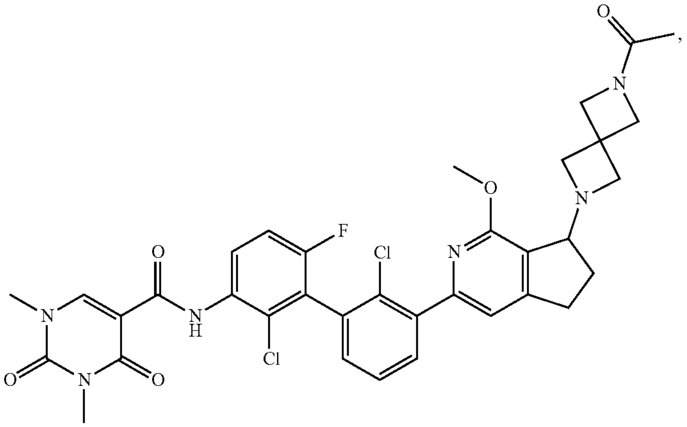
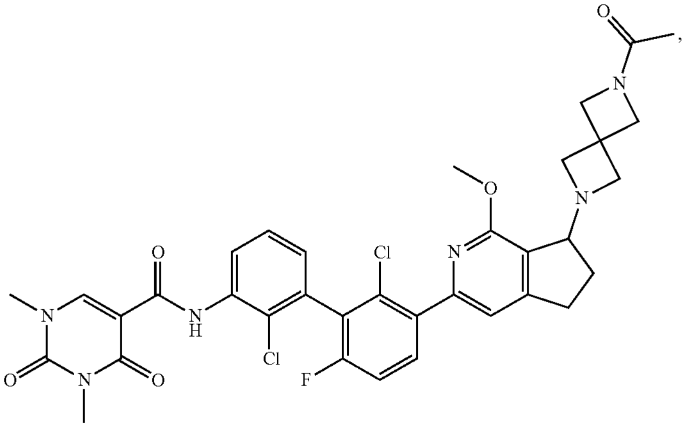

-continued
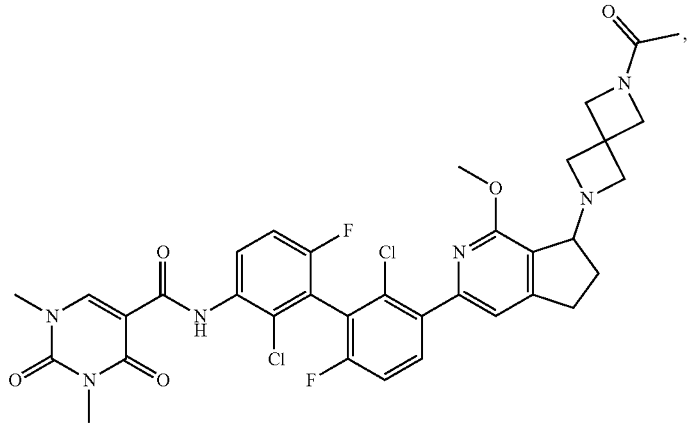
,
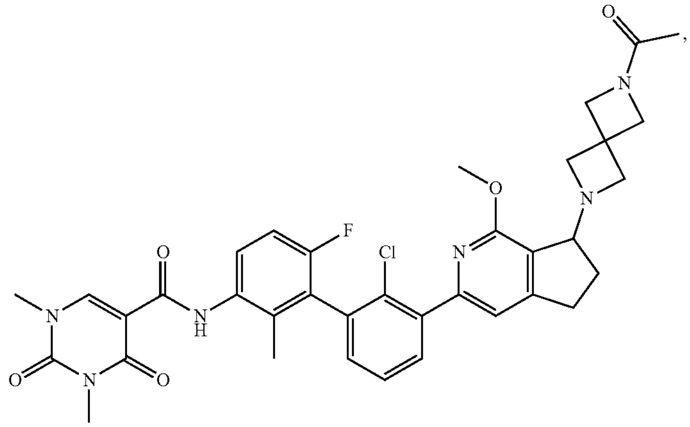
,
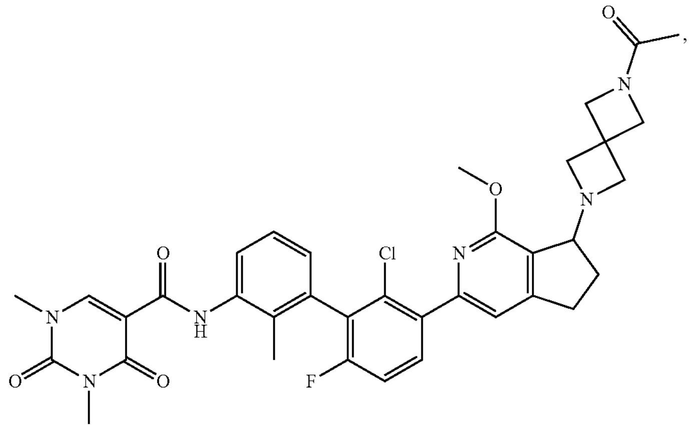
,
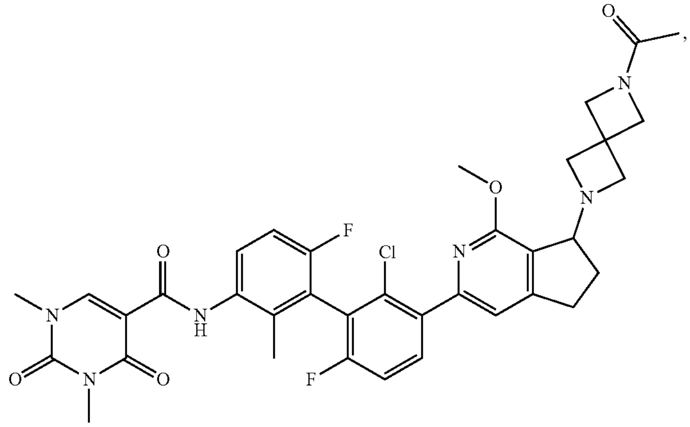
,

-continued
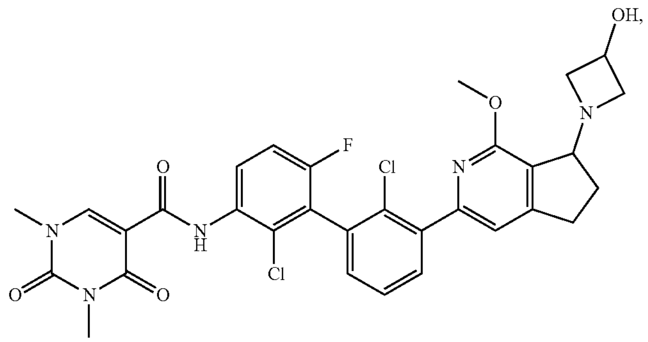
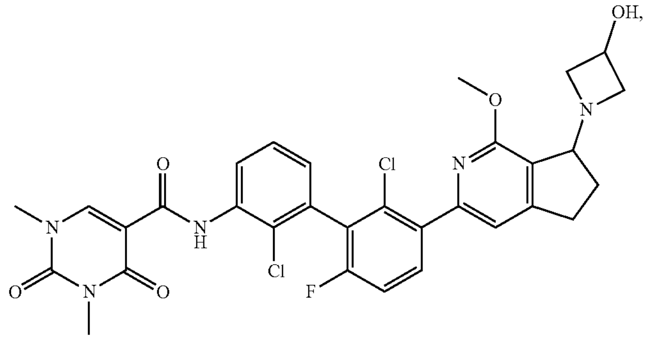
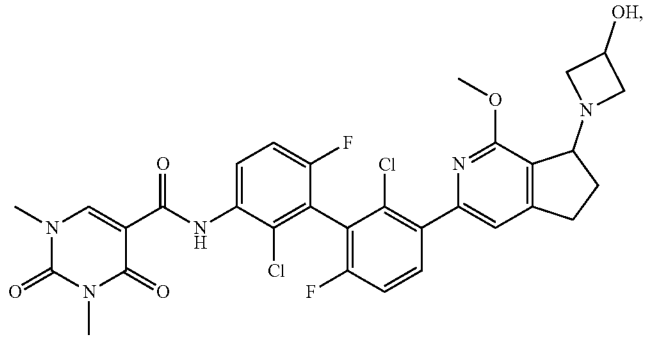
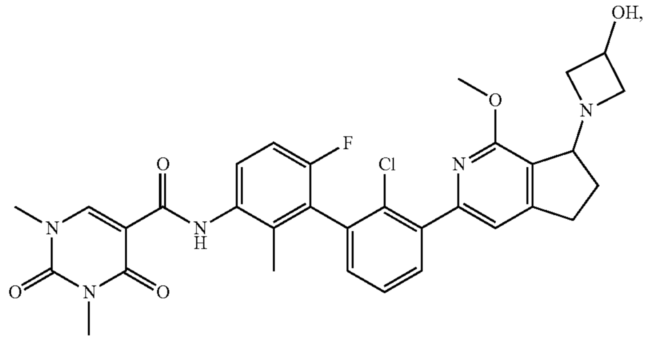
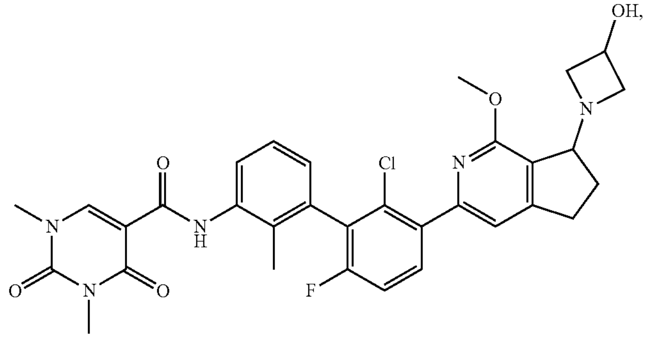

-continued
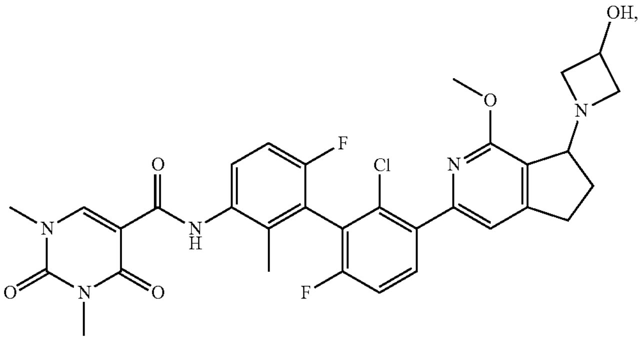
,
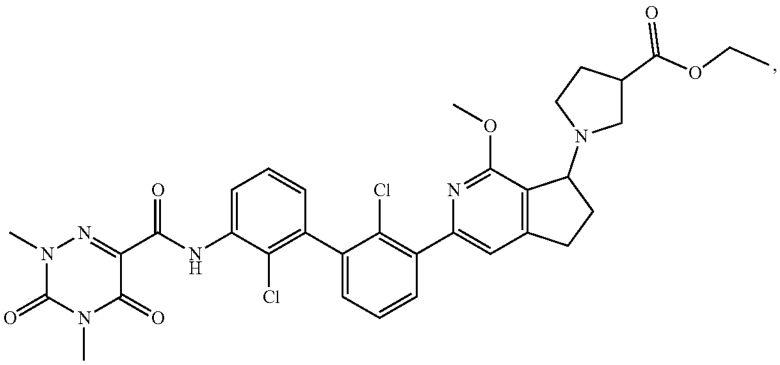
,
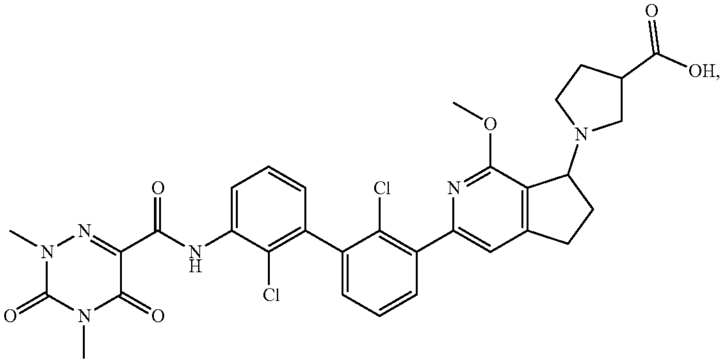
,
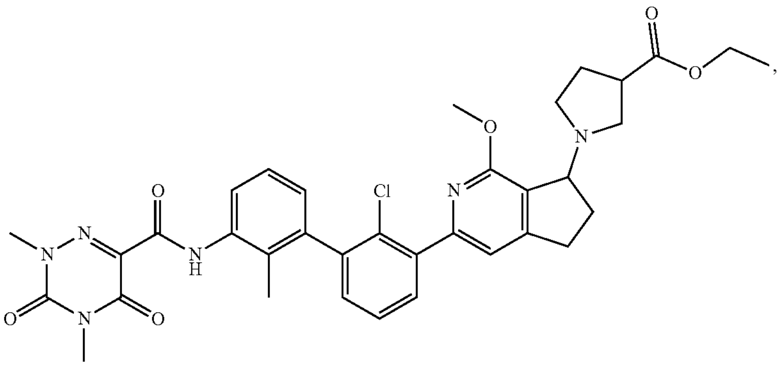
,

-continued
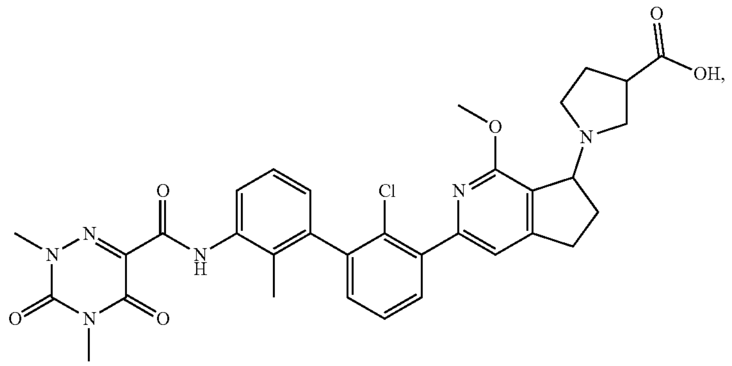
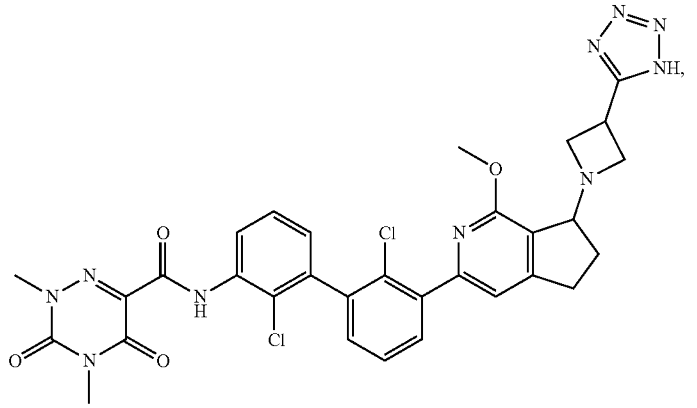
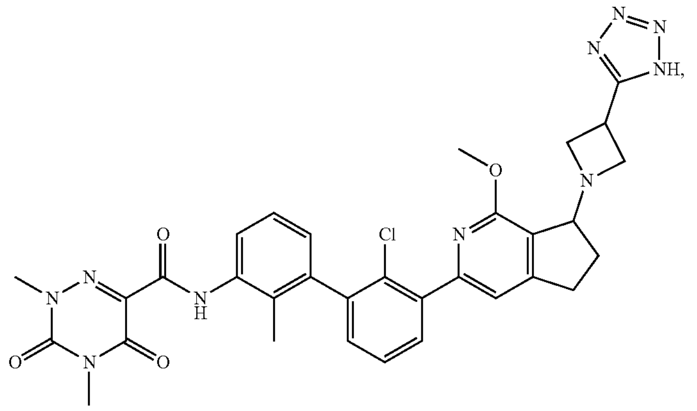
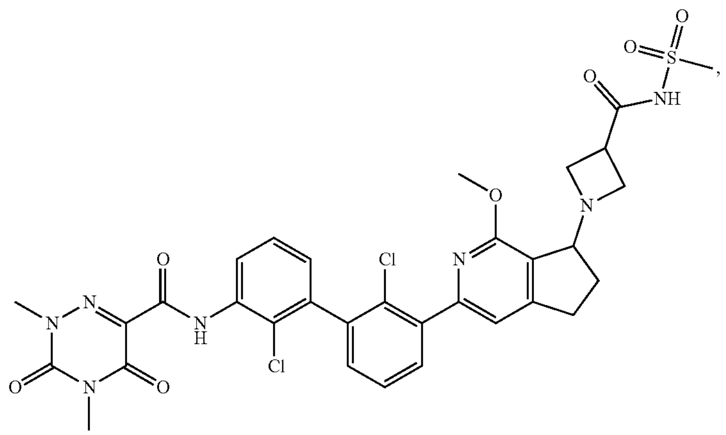

-continued
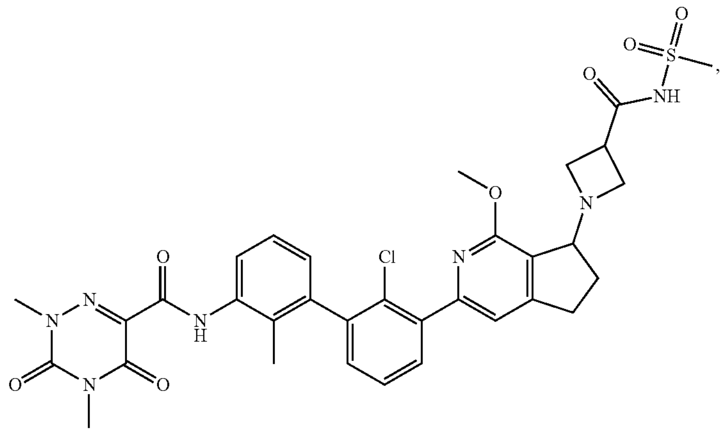
,
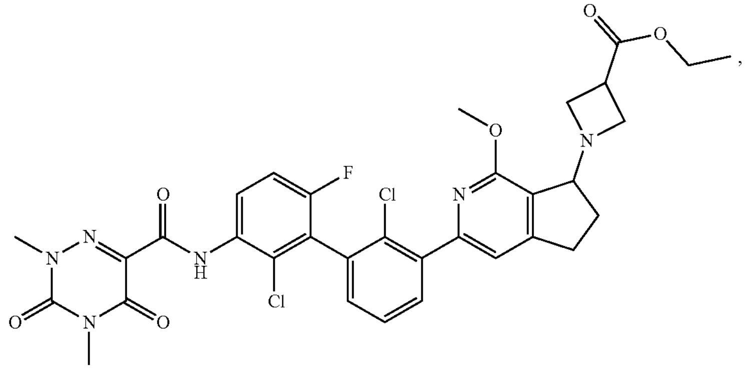
,
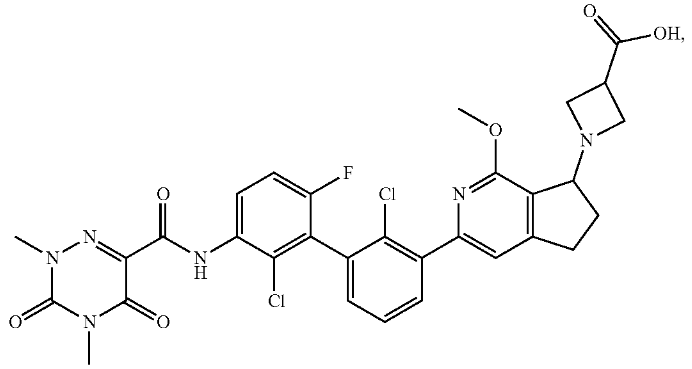
,
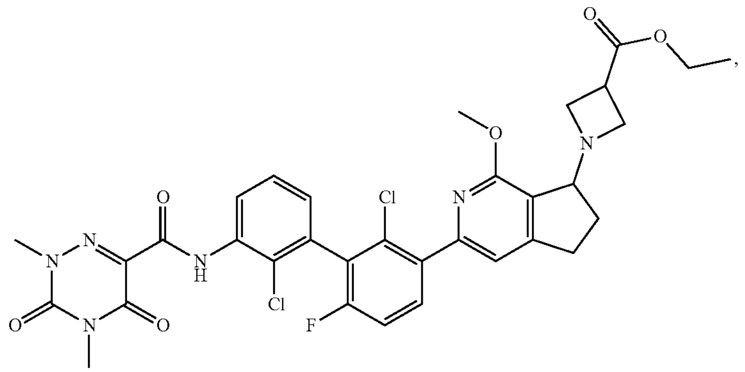
,

-continued
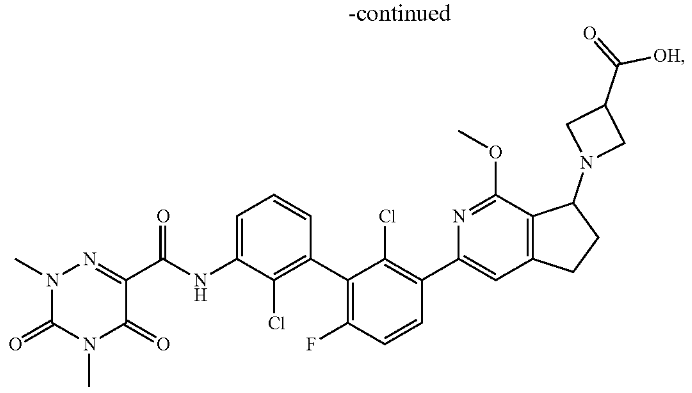
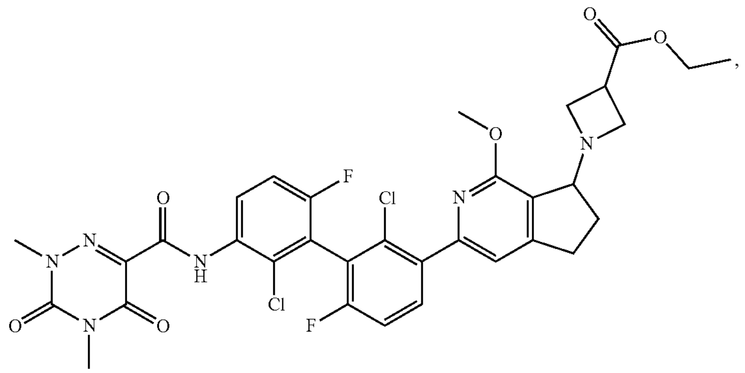
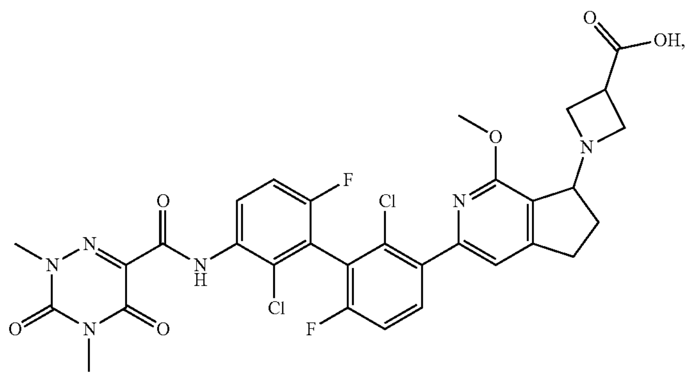
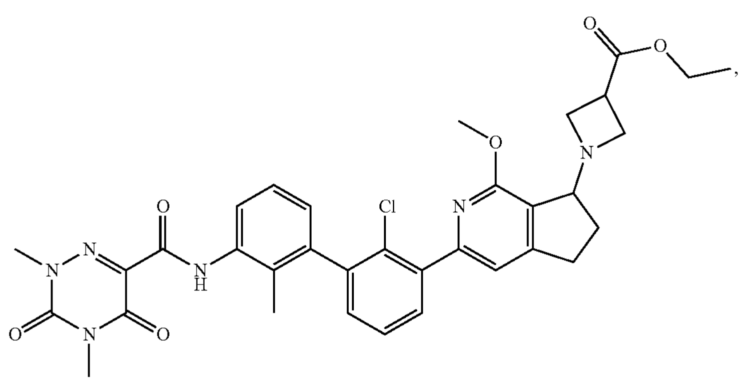

-continued
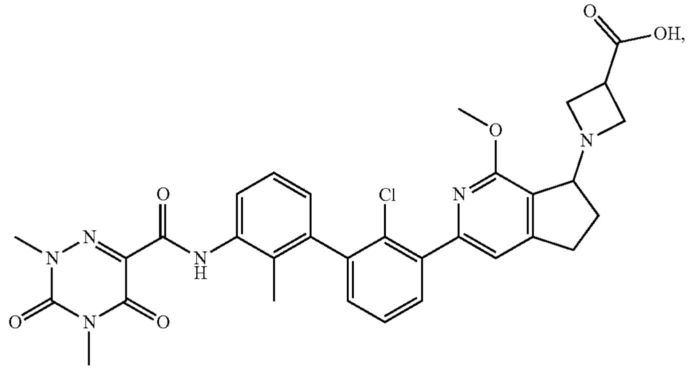
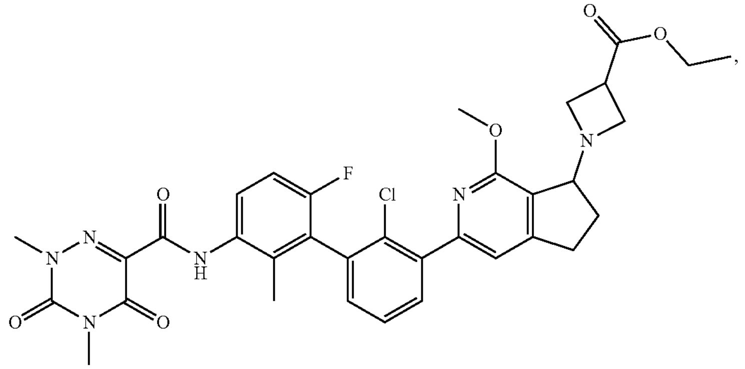
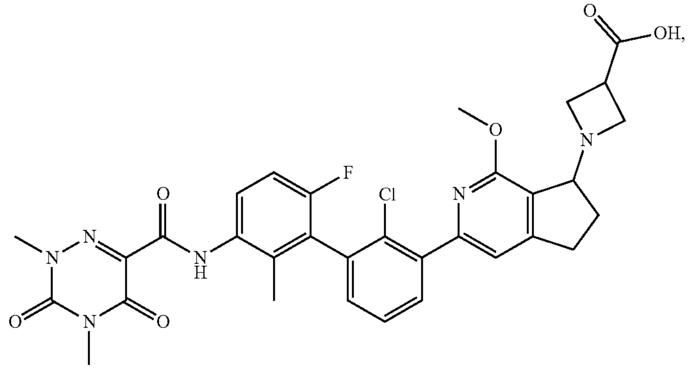
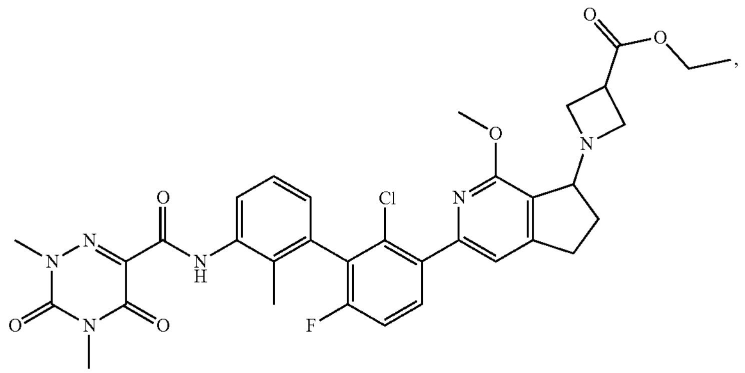

-continued
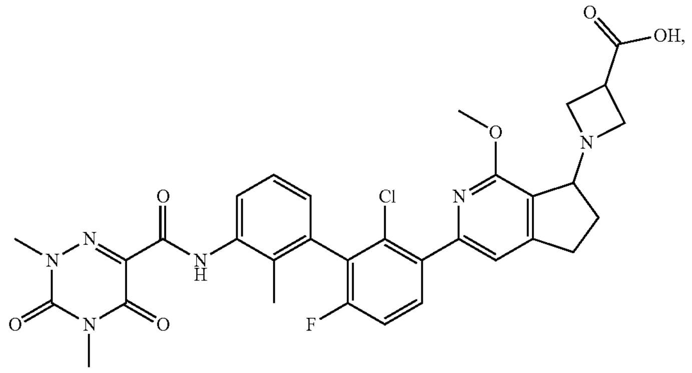
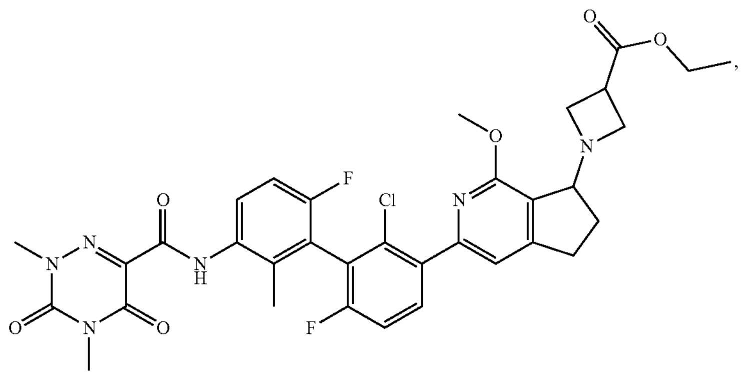
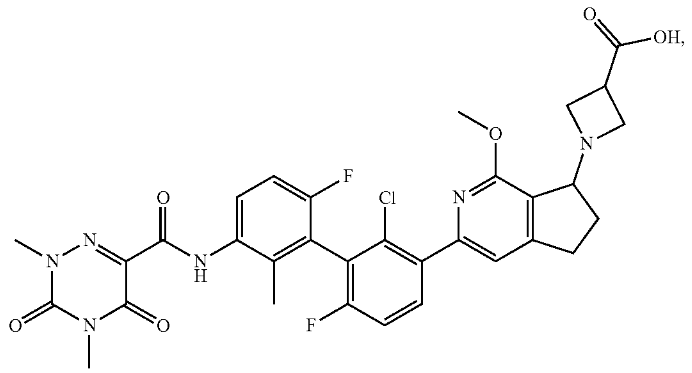
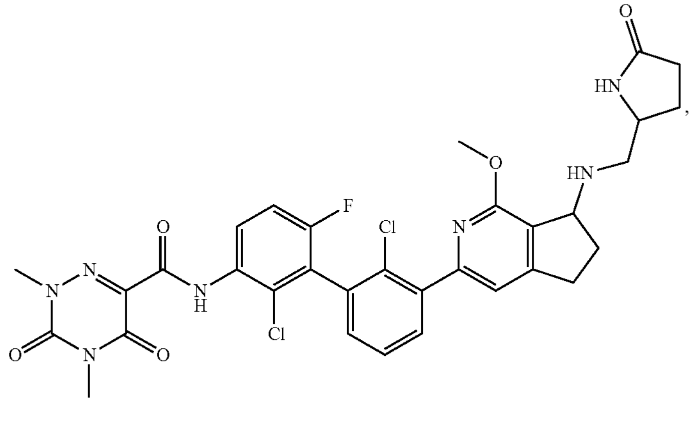

-continued
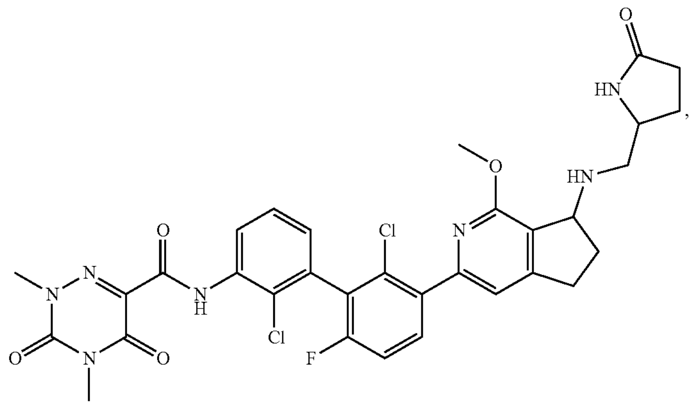
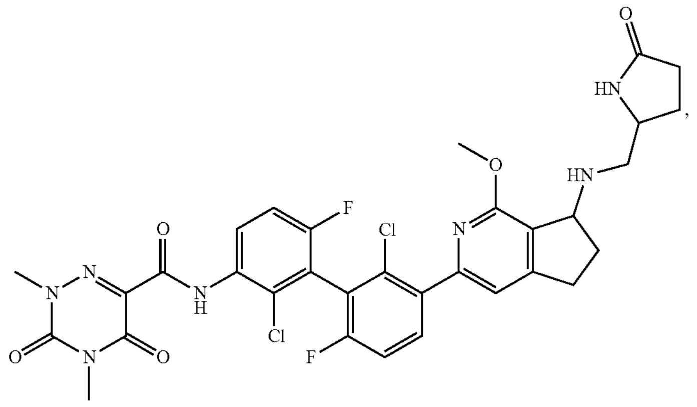
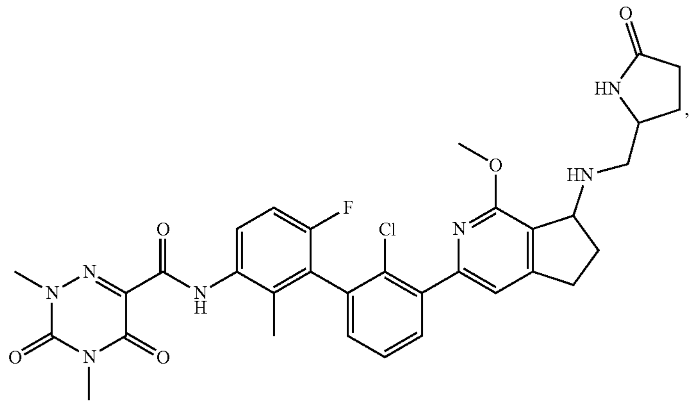
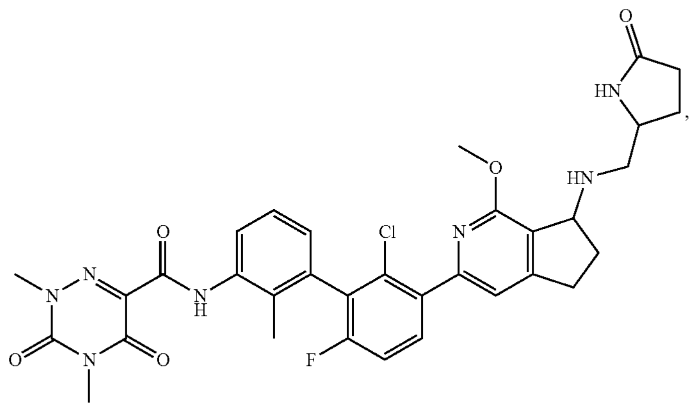

-continued
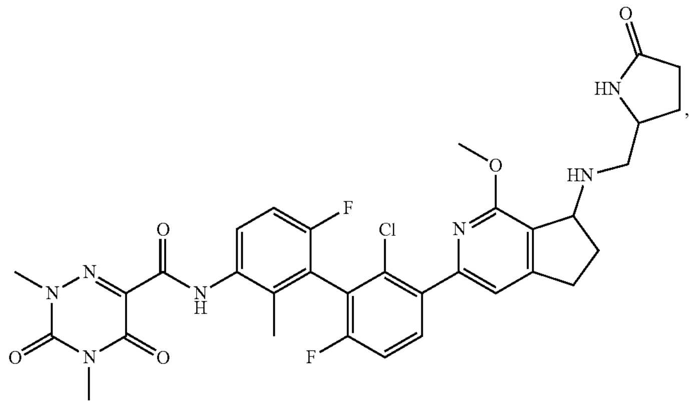
,
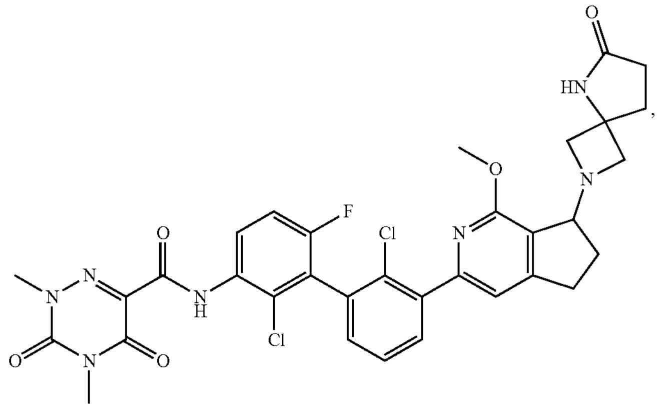
,
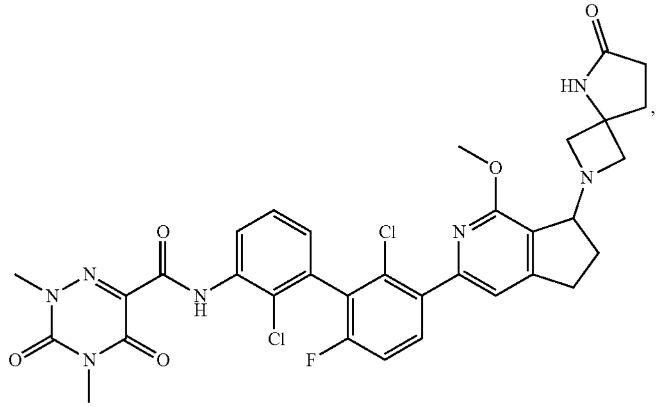
,
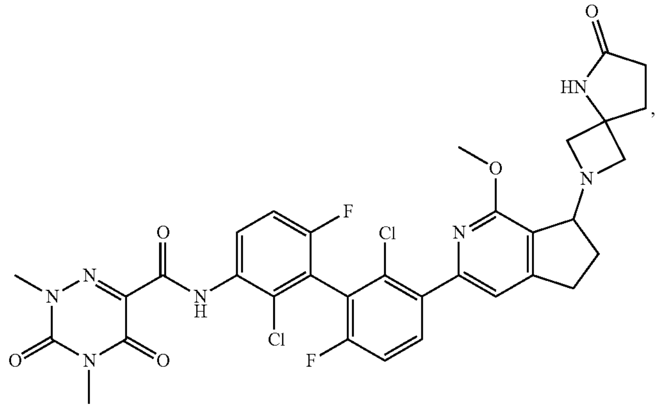
,

-continued
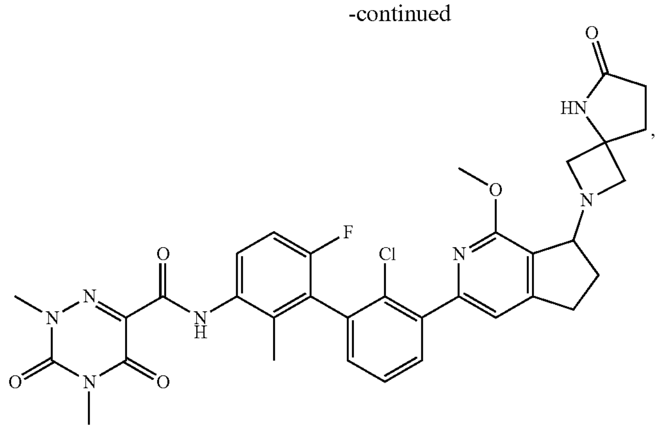
,
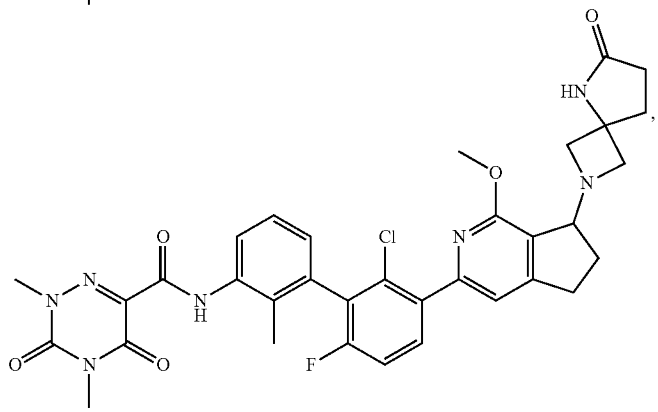
,
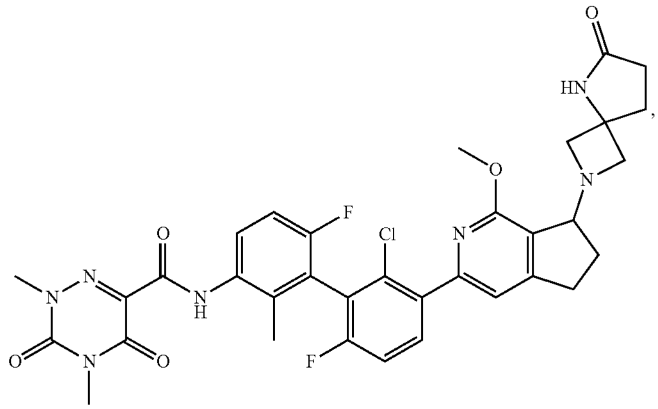
,
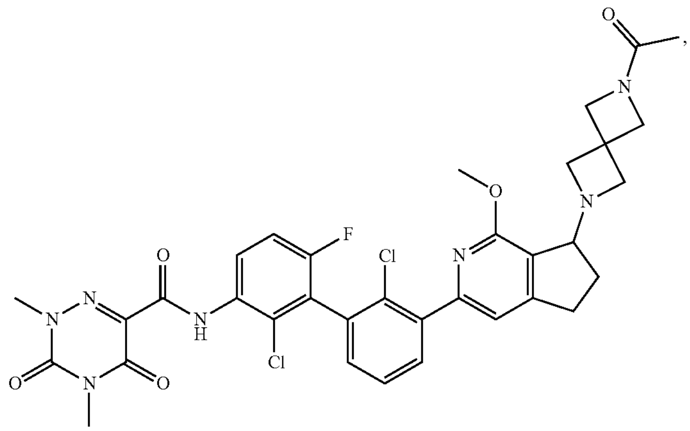
,

-continued
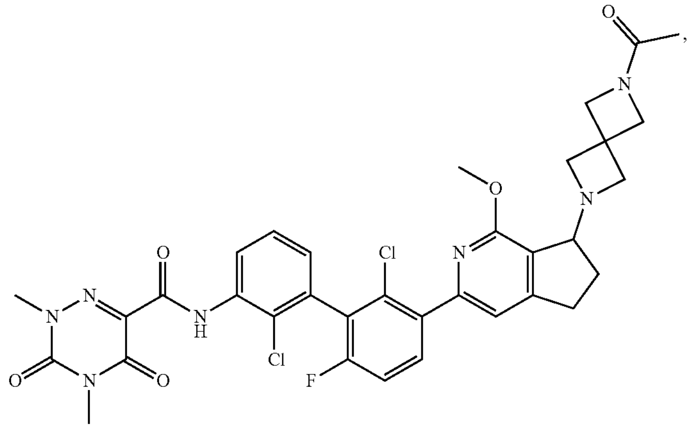
,
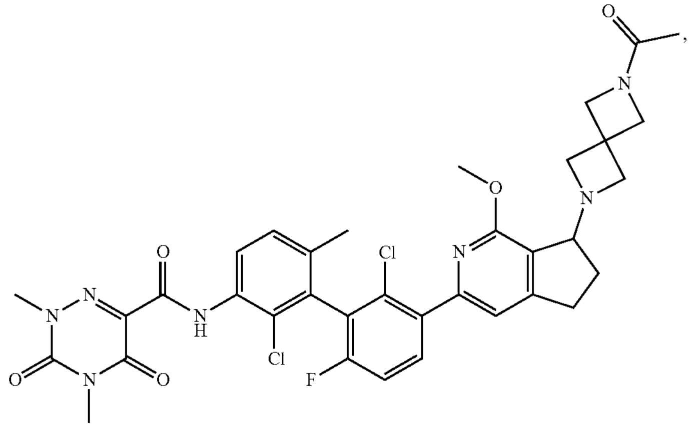
,
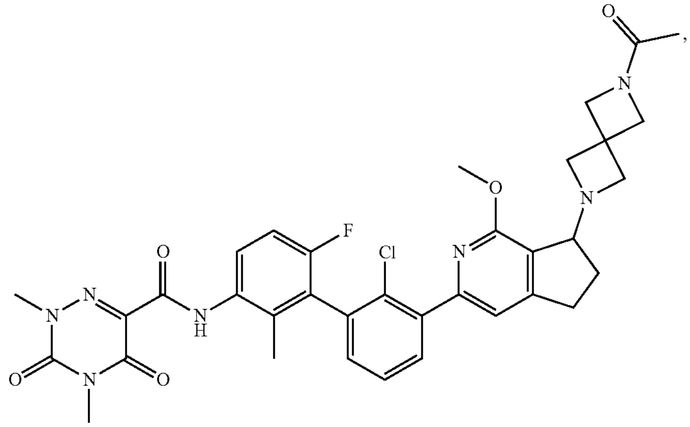
,
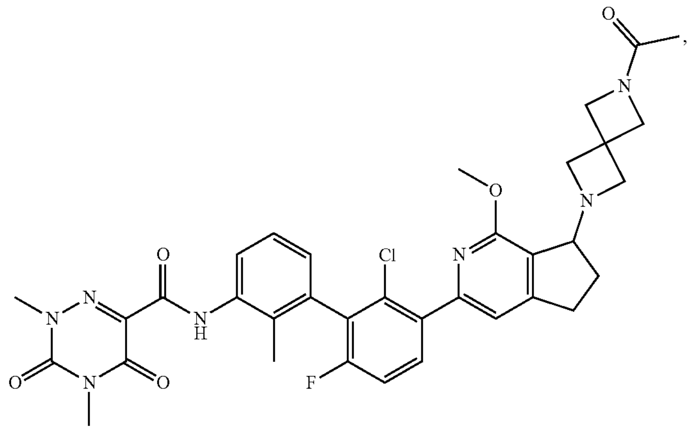
,

-continued
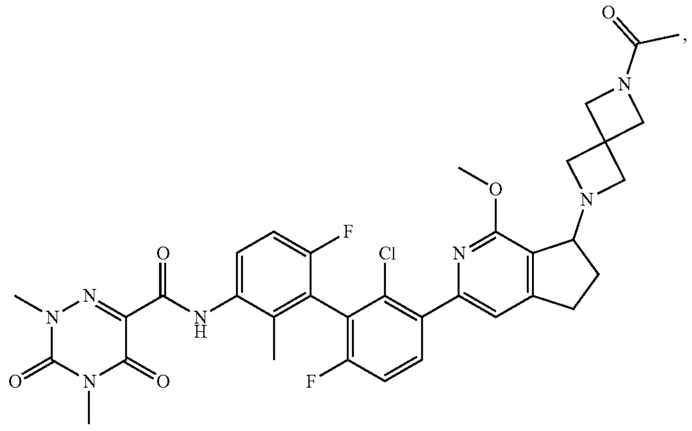
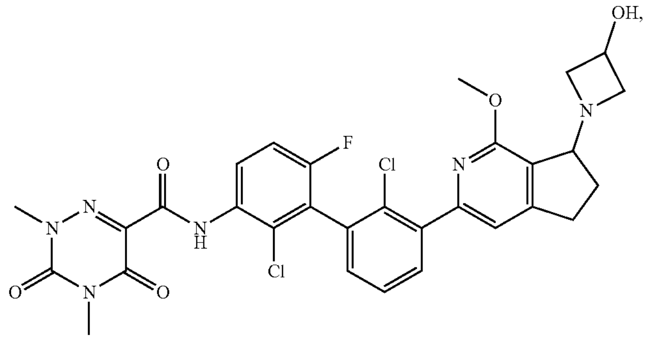
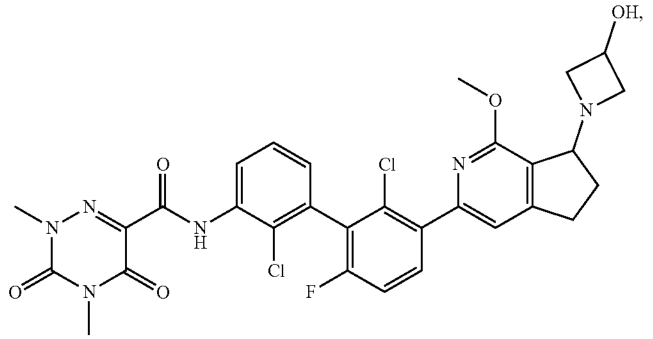
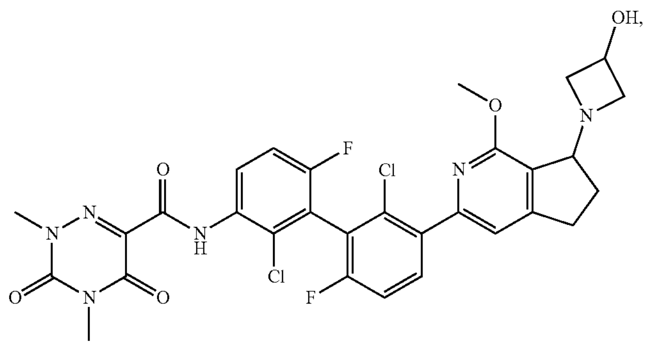

-continued
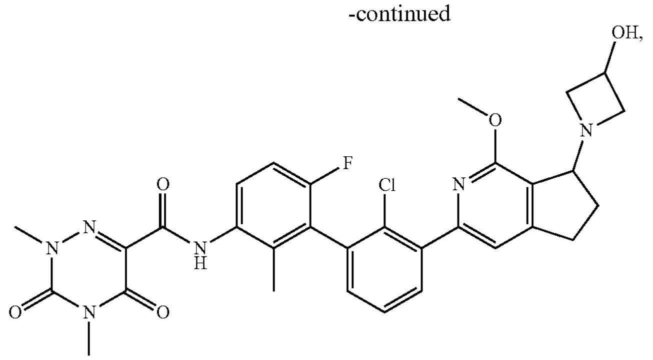
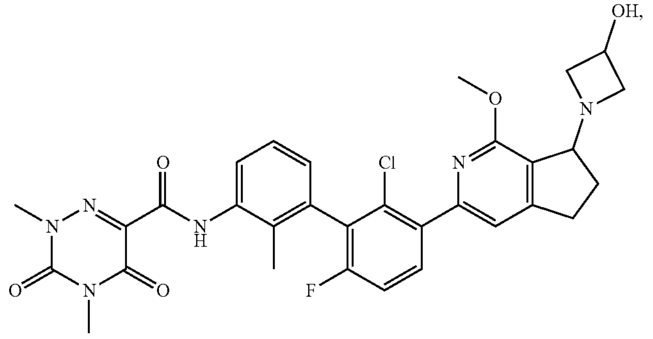
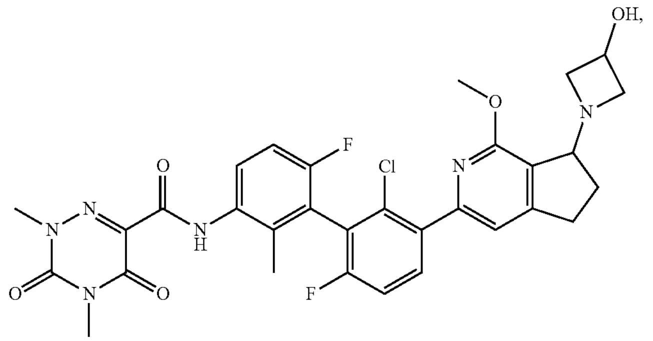
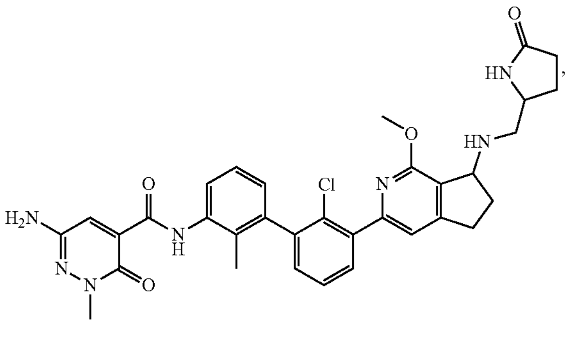
-continued
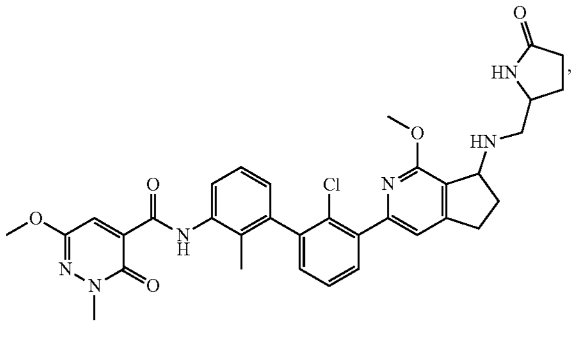

-continued
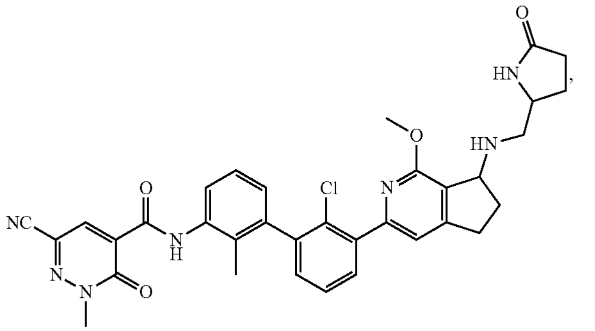
,
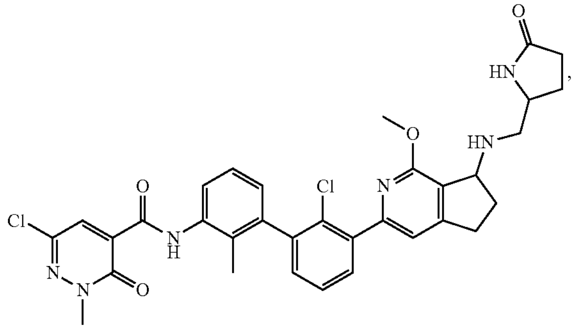
,
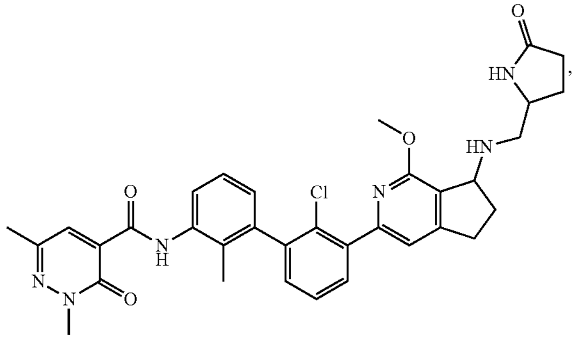
,
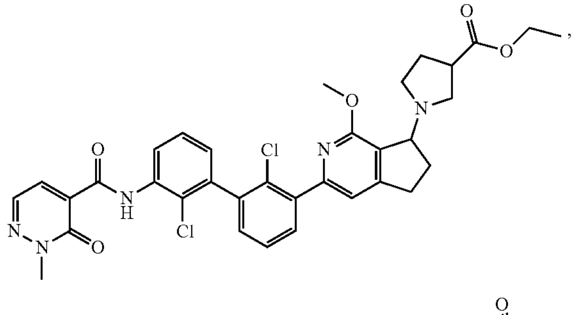
,
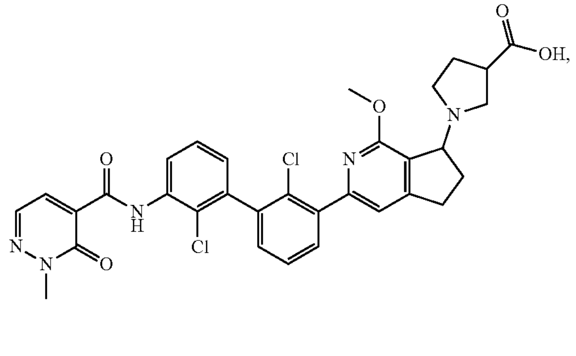
,
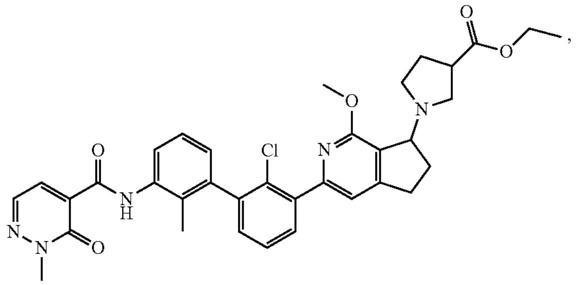
,
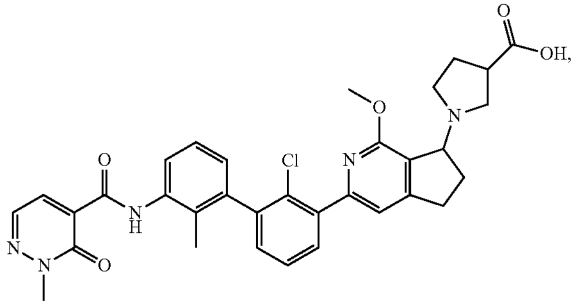
,
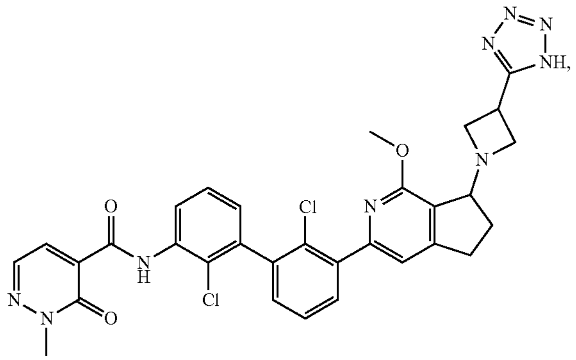
,
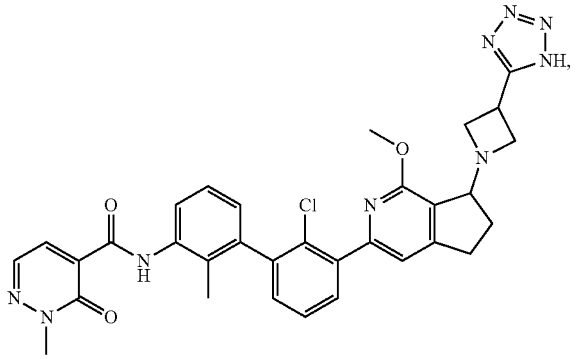
,
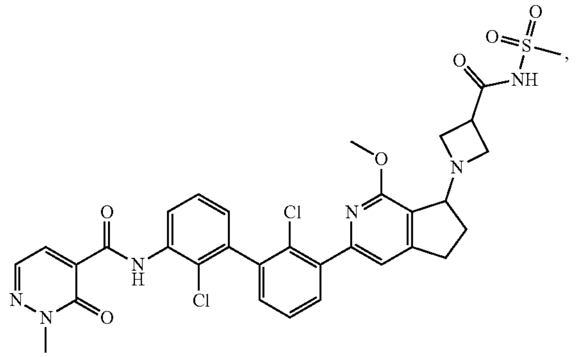
, -continued
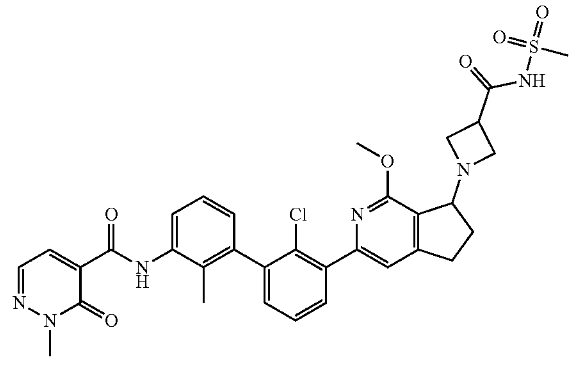
,
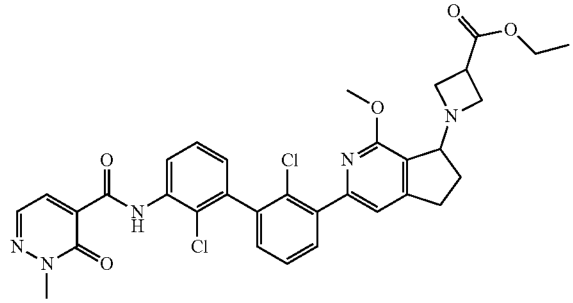
,
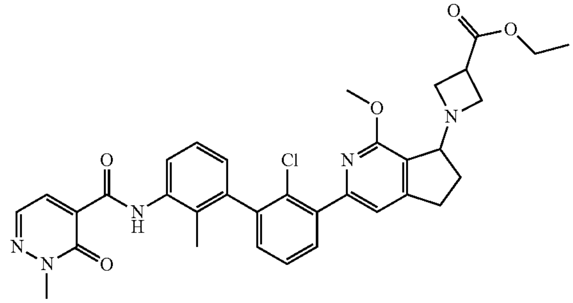
,
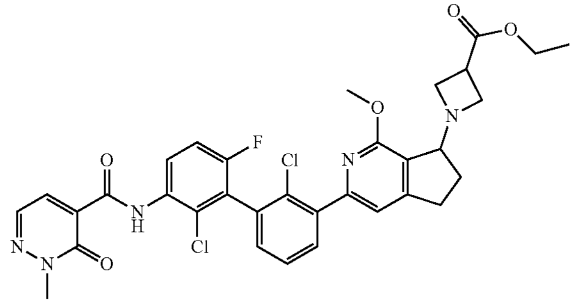
,
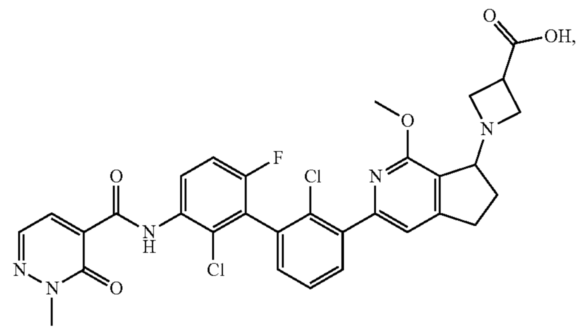
,
-continued
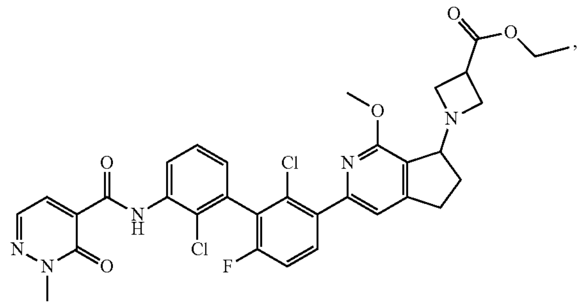
,
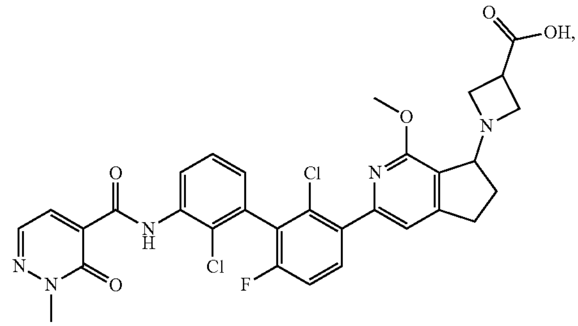
,
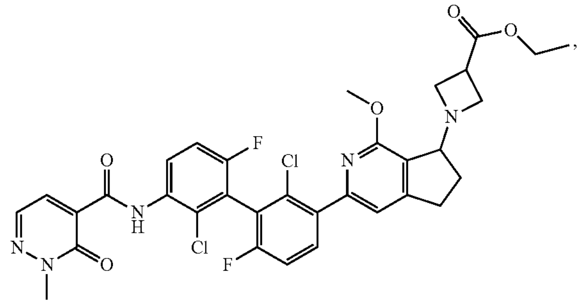
,
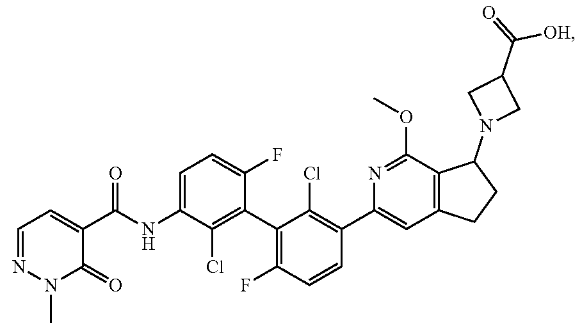
,
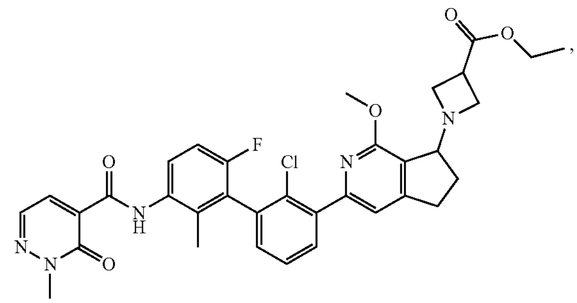
, -continued
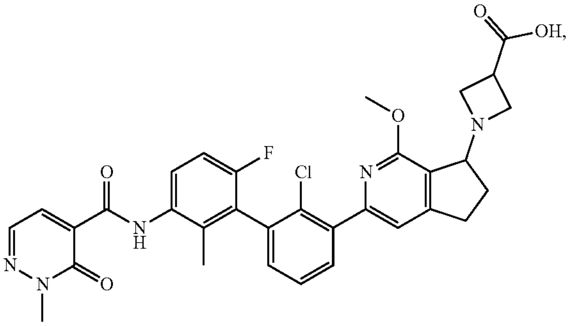
,
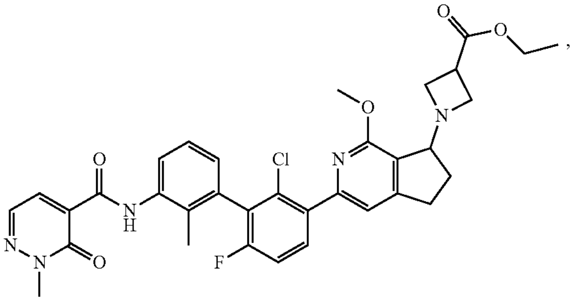
,
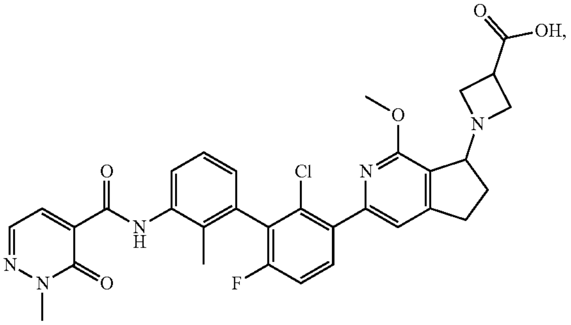
,
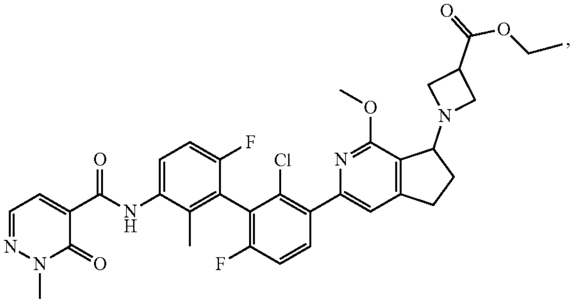
,
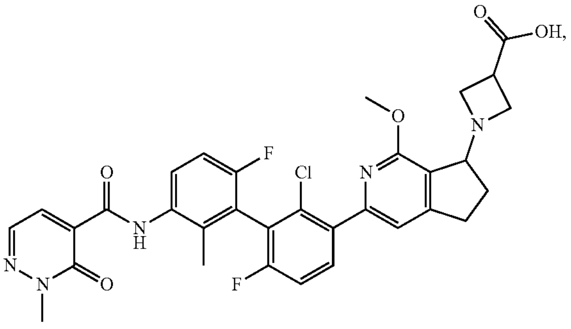
,
-continued
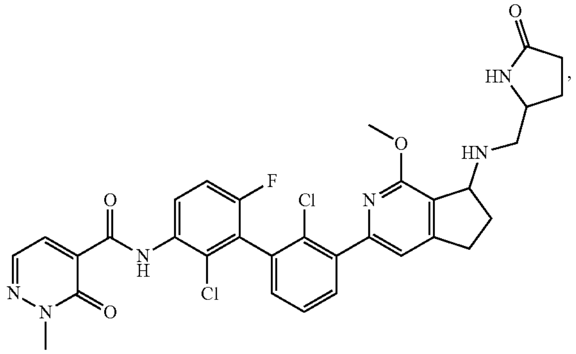
,
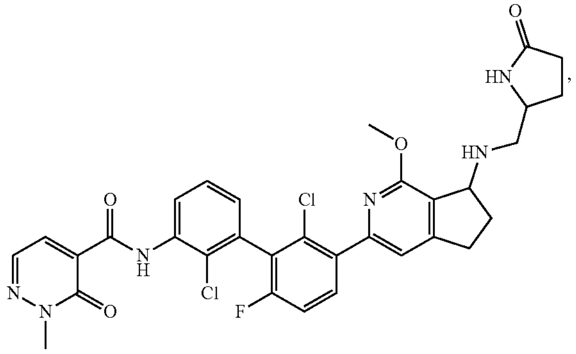
,
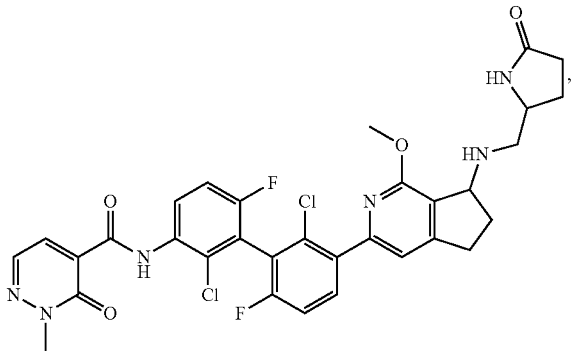
,
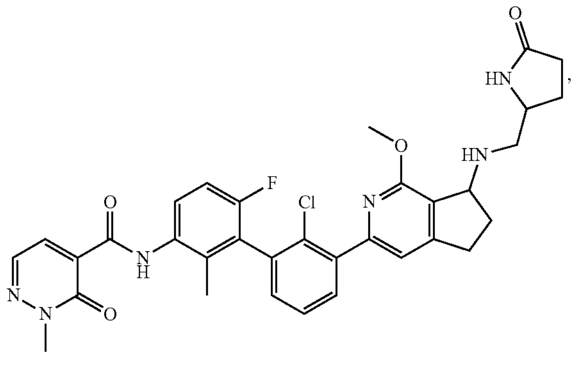
, -continued
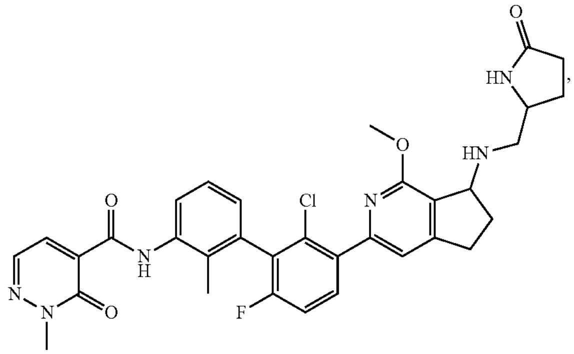
,
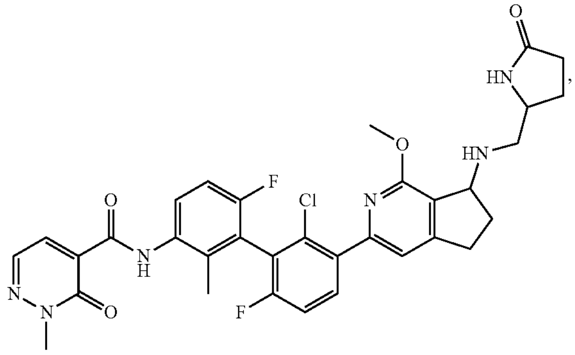
,
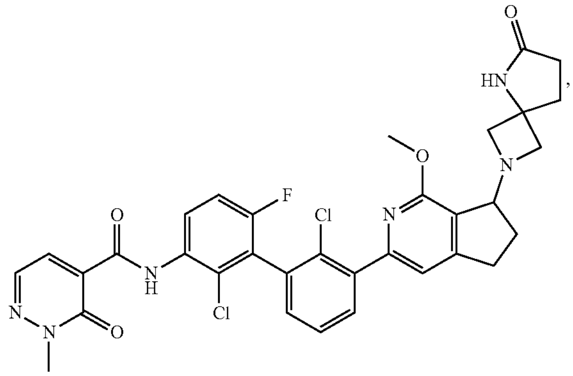
,
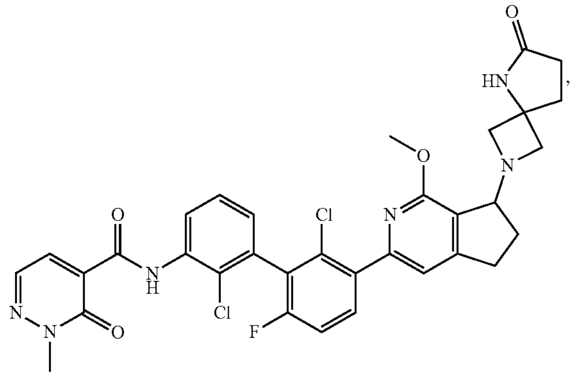
-continued
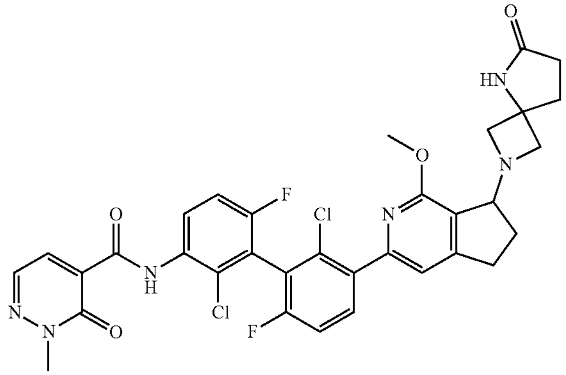
,
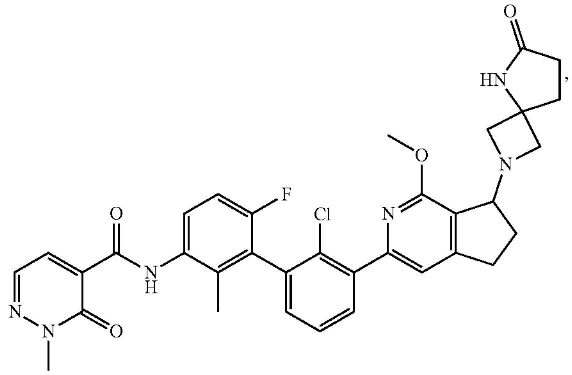
,
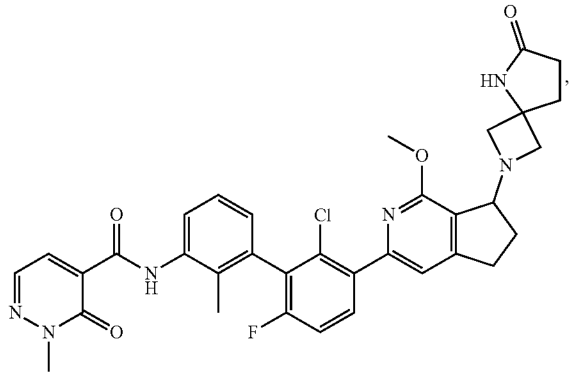
,
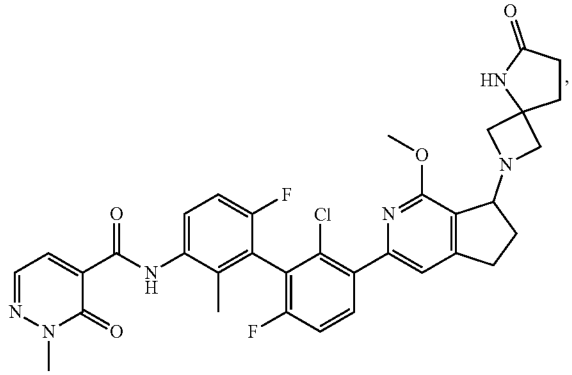
, -continued
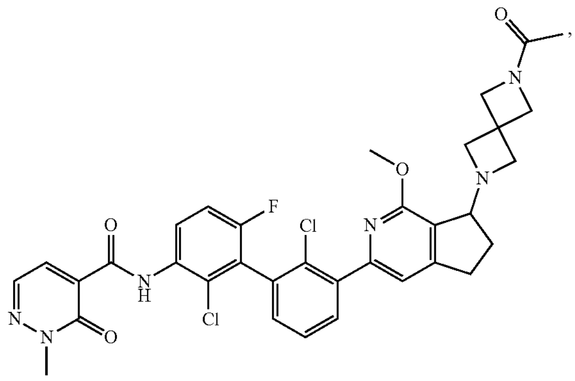
,
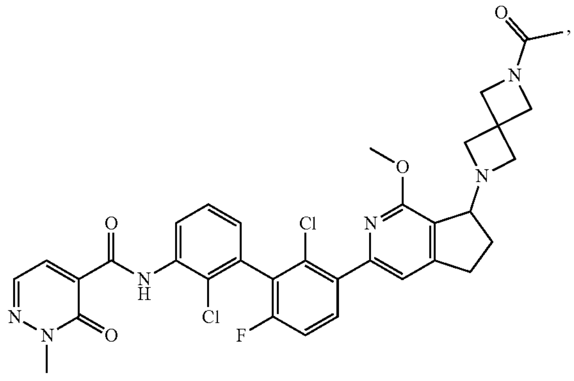
,
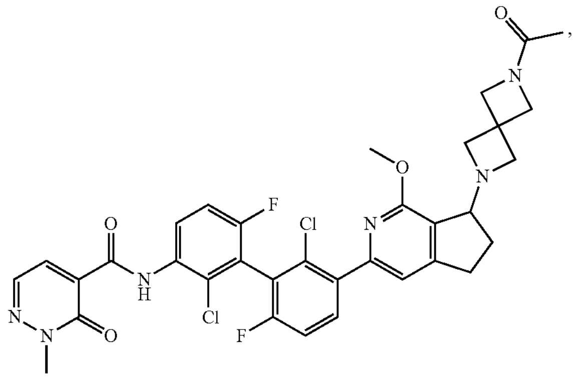
,
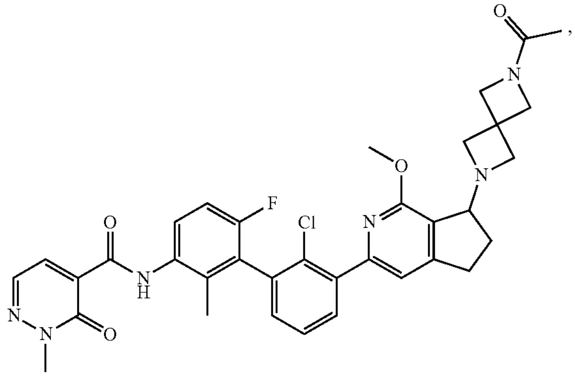
,
-continued
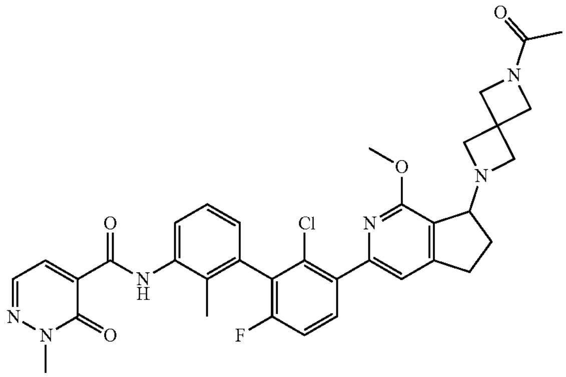
,
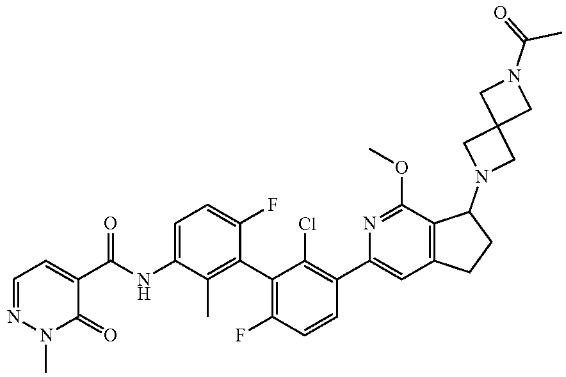
,
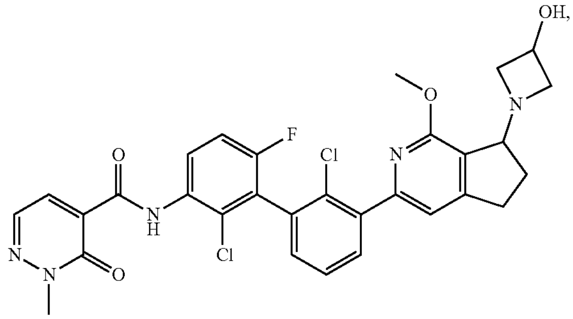
,
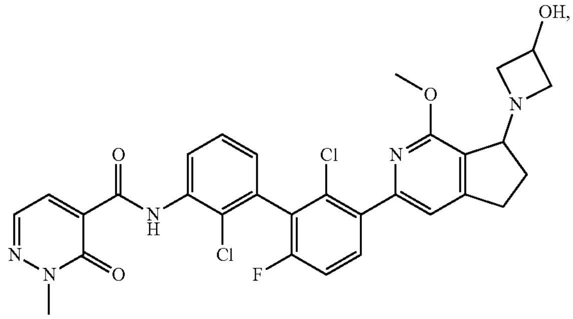
,
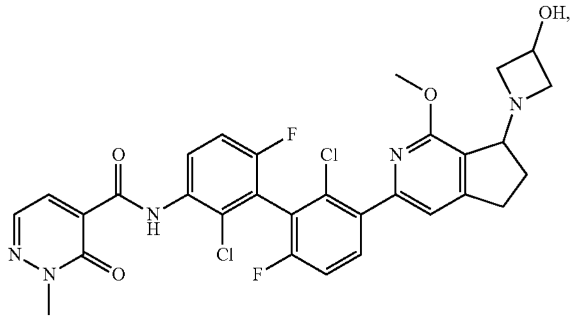
, -continued
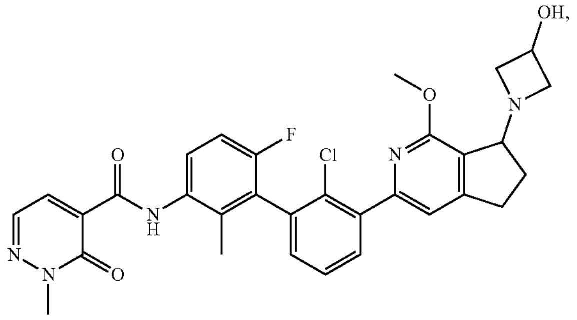
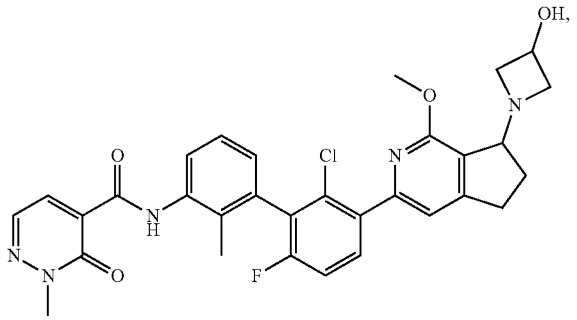
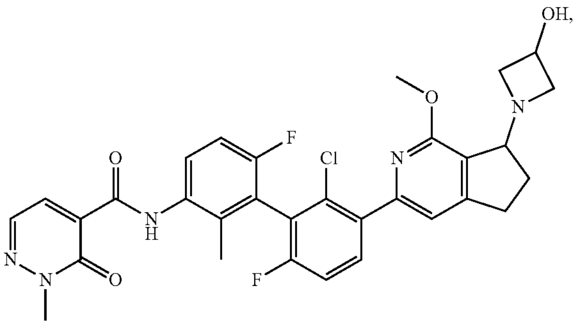
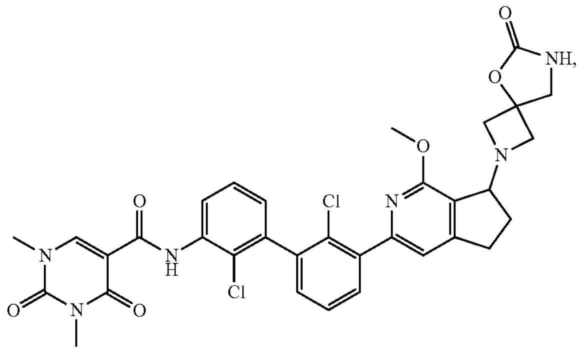
-continued
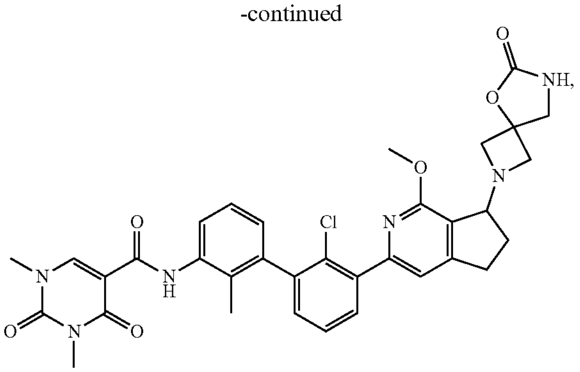
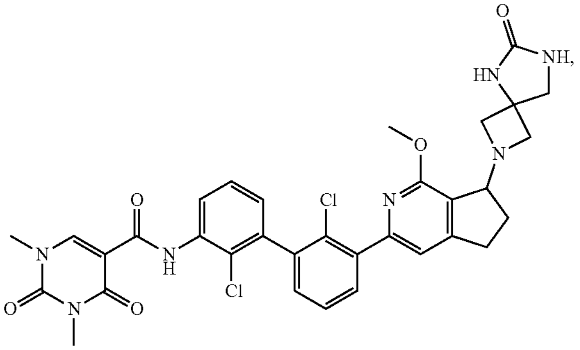
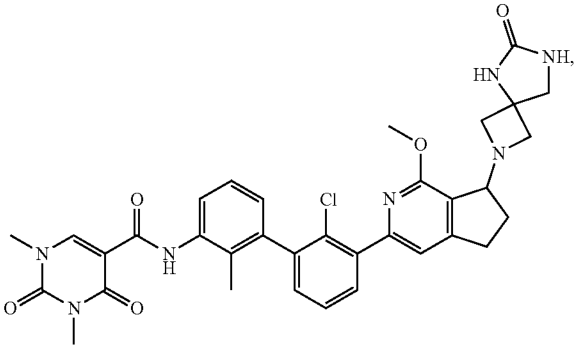
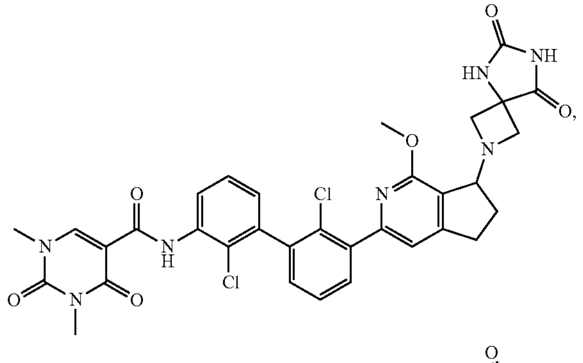
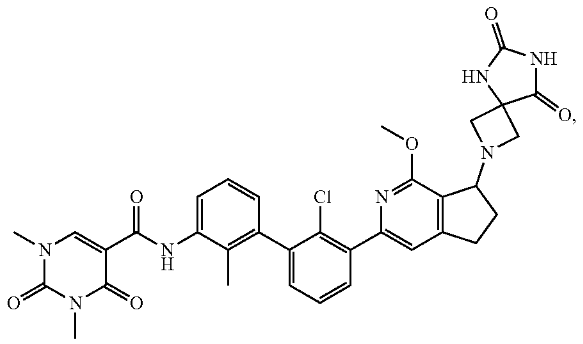

-continued
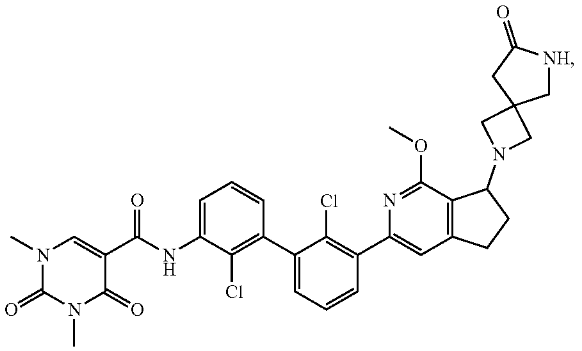
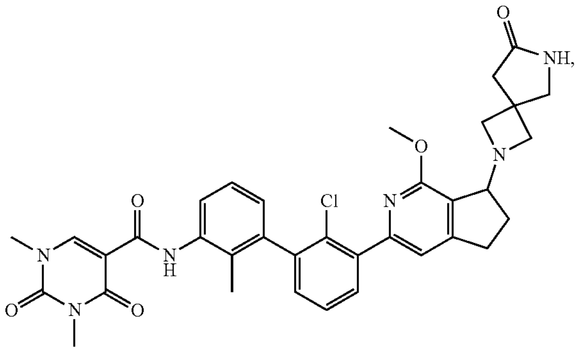
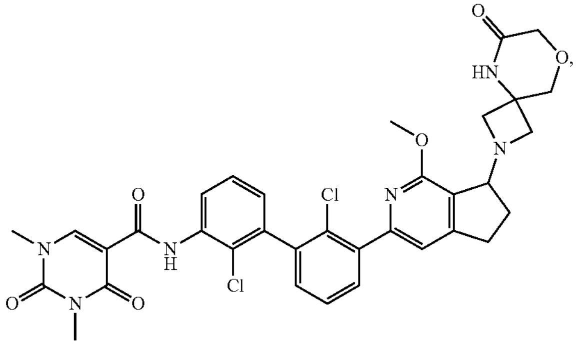
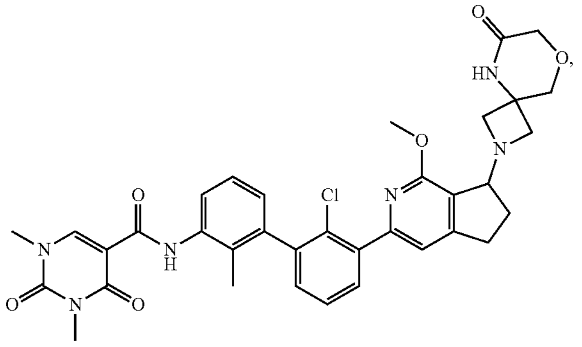
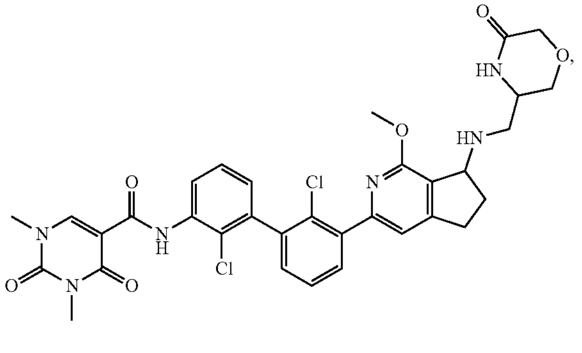
-continued
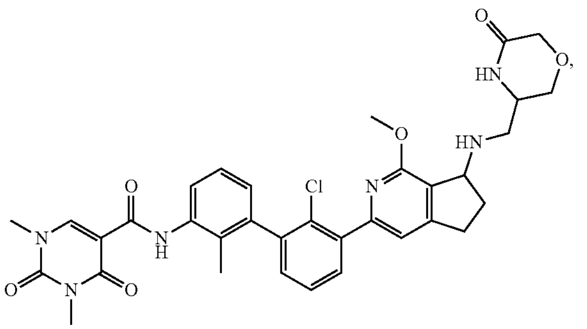
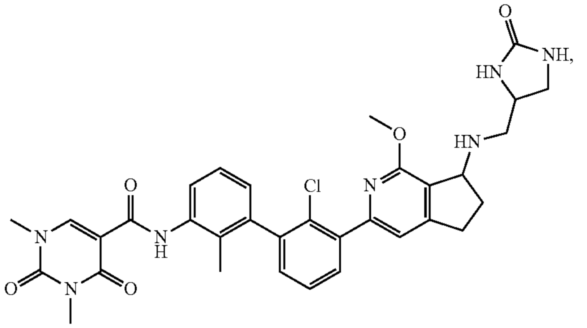
or a pharmaceutically acceptable salt of any of the foregoing.
Embodiment 144
The compound of Embodiment 1 selected from:
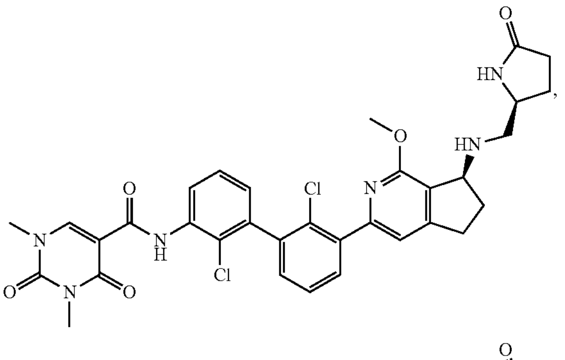
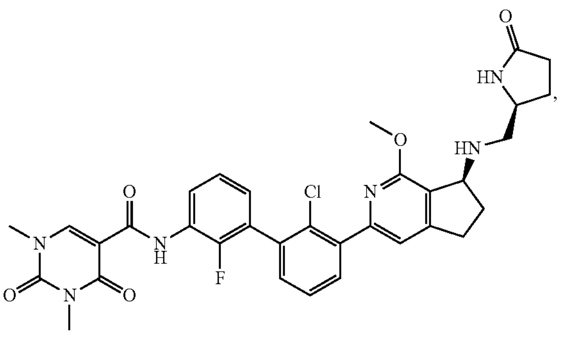

-continued
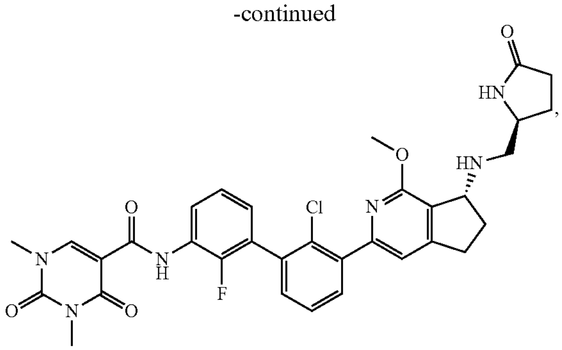
,
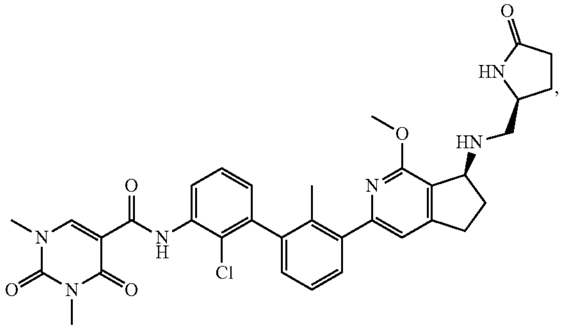
,
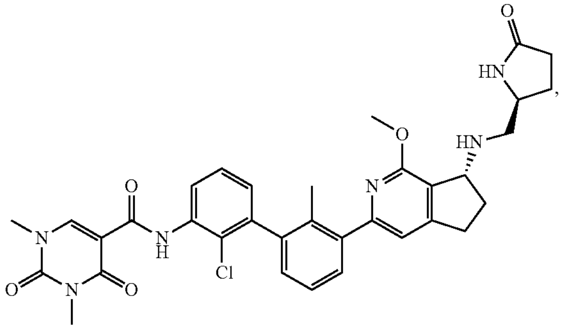
,
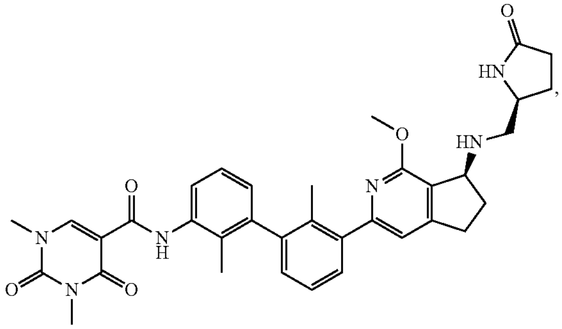
,
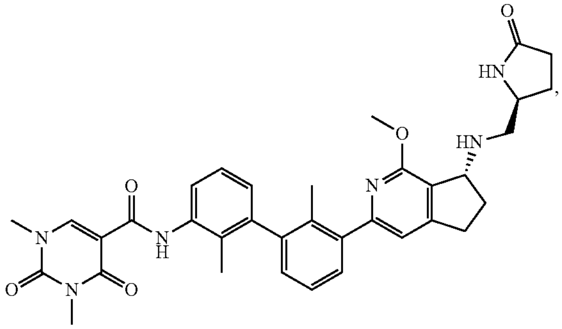
,
-continued
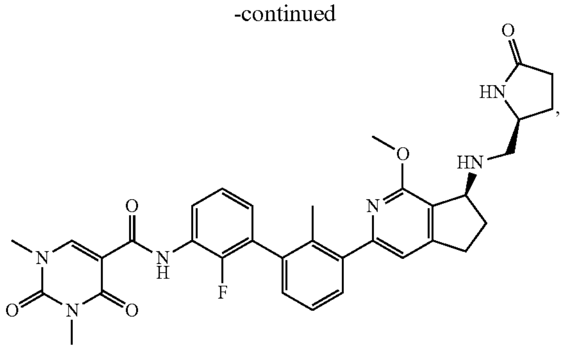
,
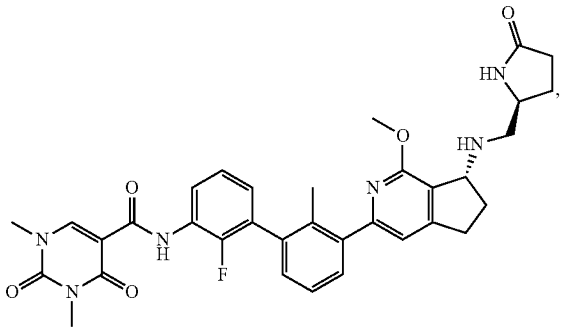
,
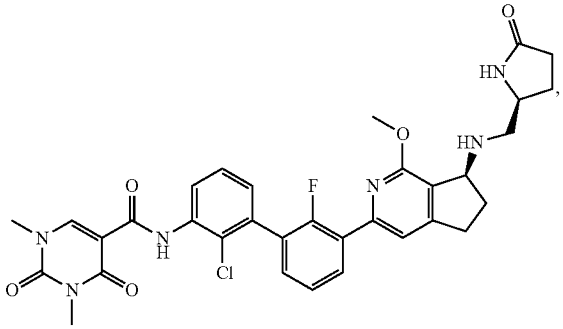
,
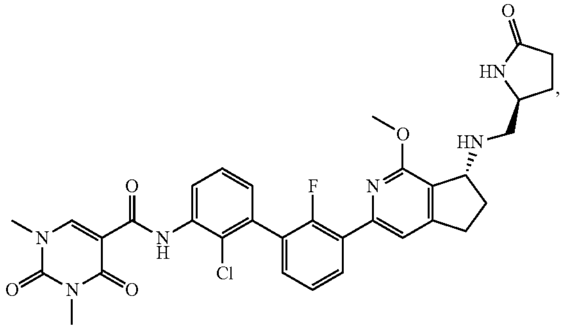
,
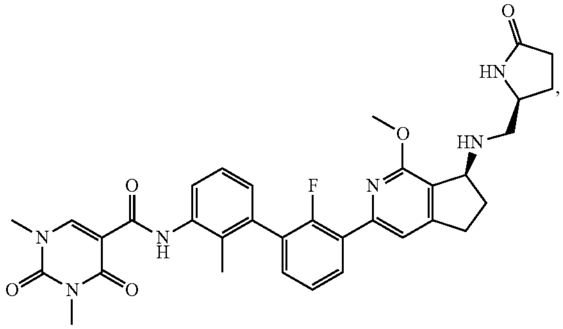
, -continued
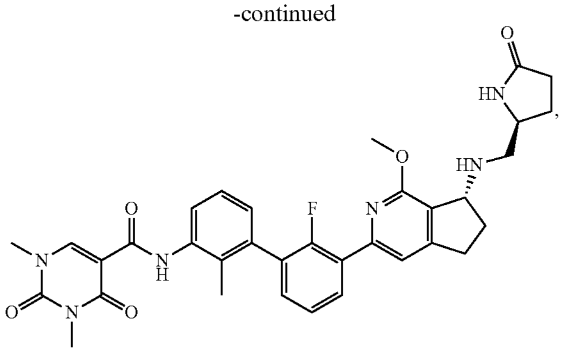
,
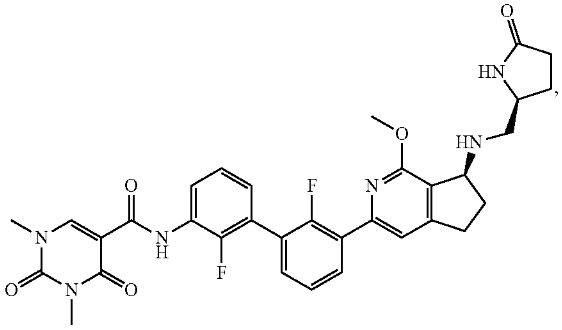
,
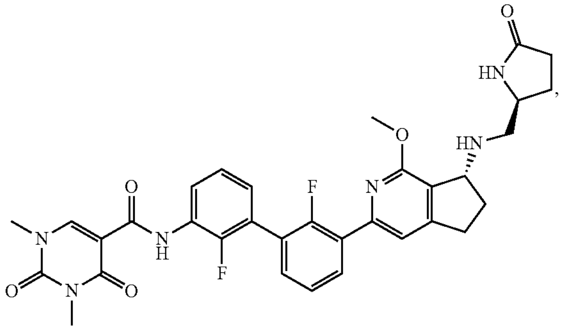
,
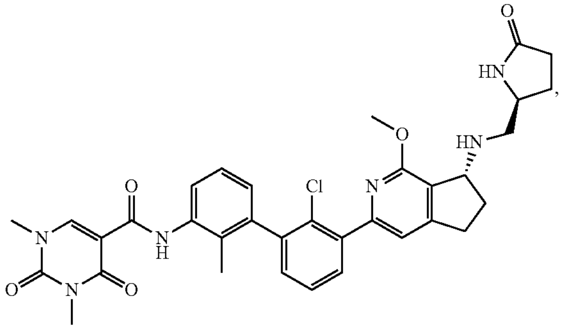
,
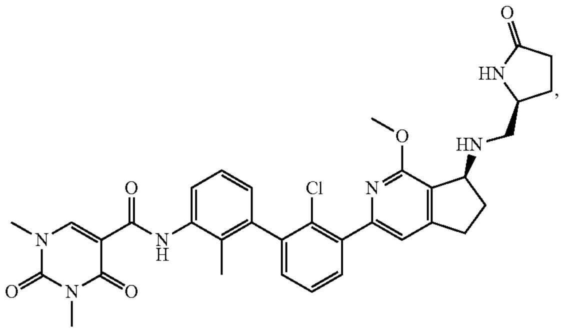
,
-continued
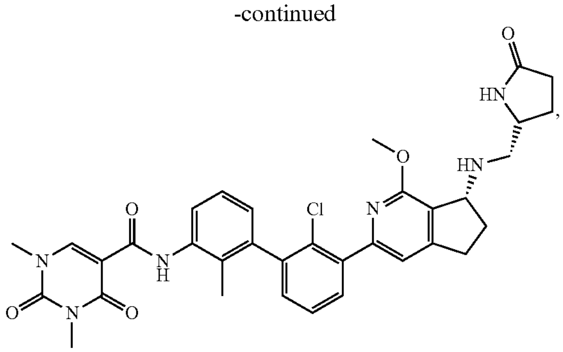
,
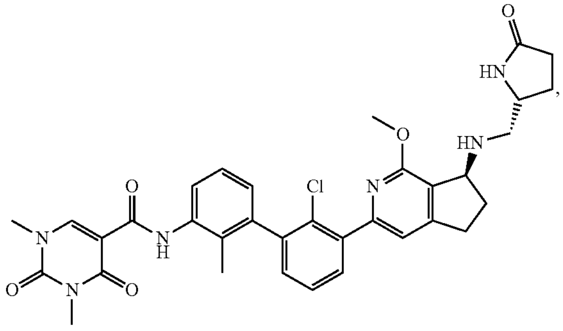
,
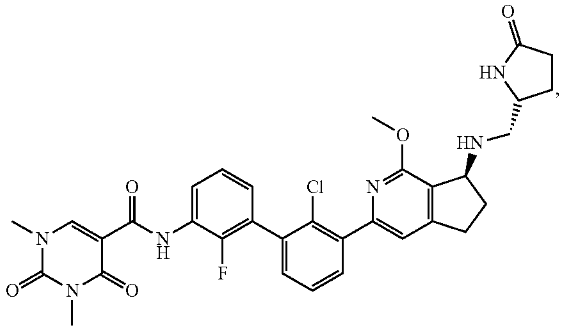
,
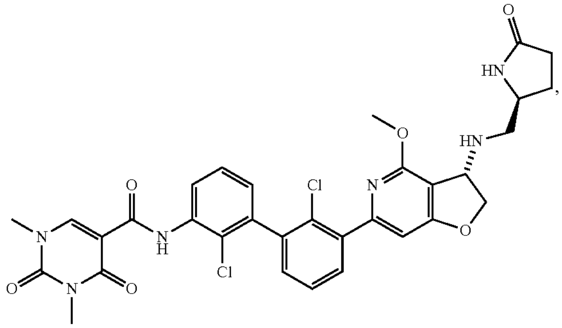
,
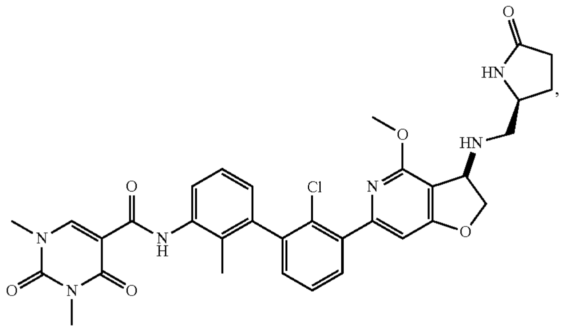
, -continued
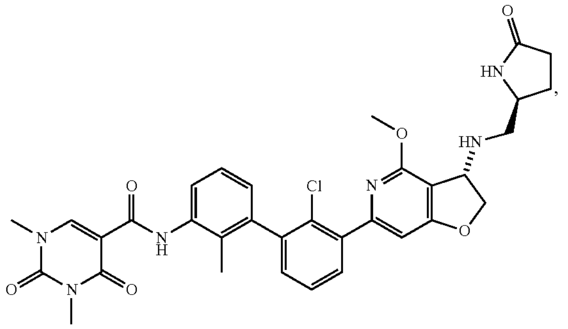
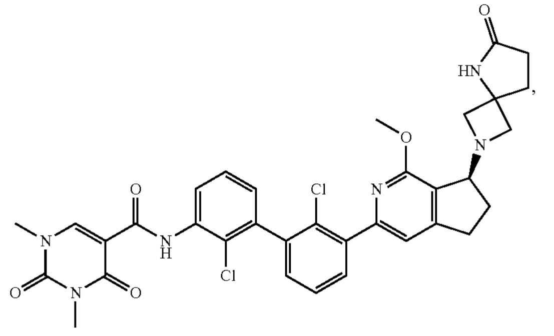
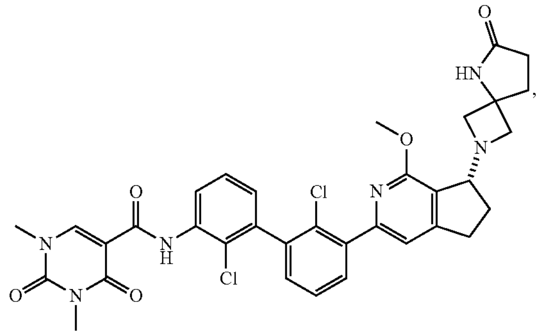
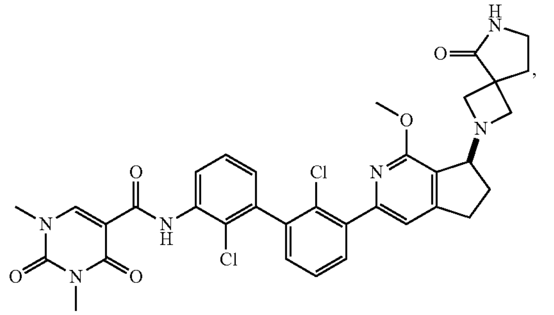
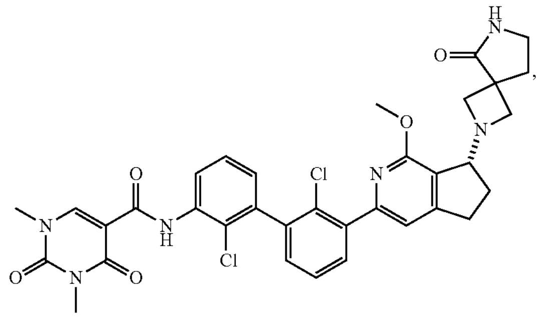
-continued
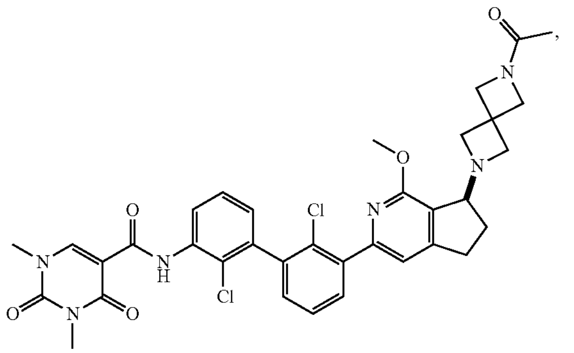
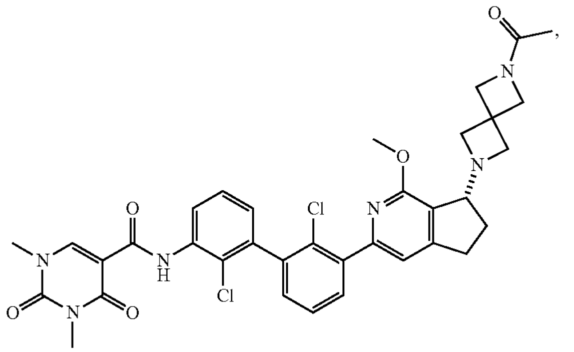
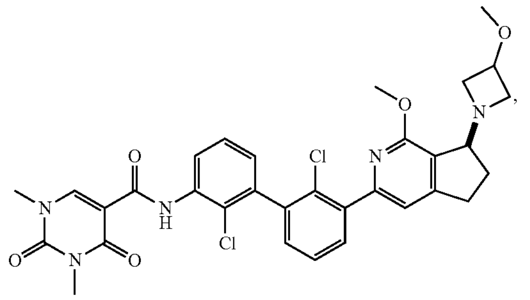
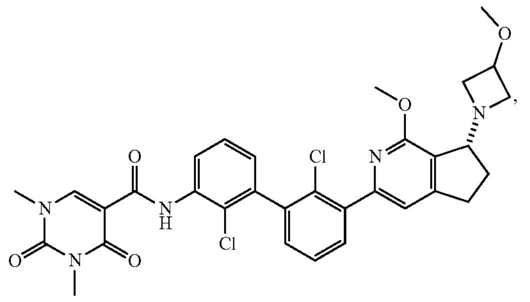
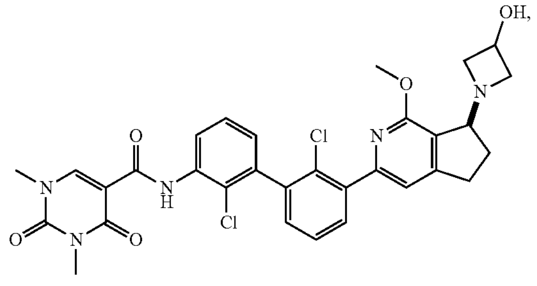

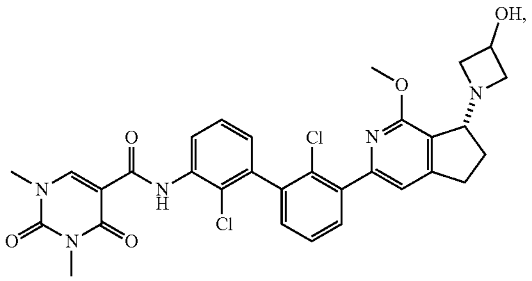
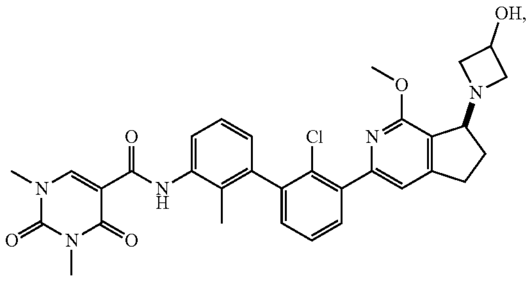
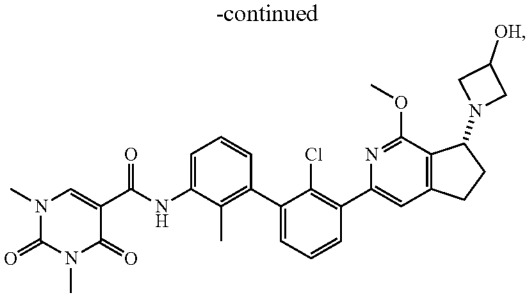
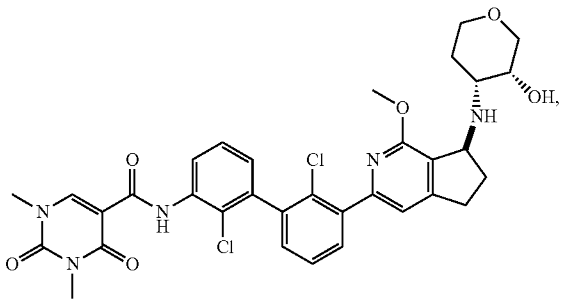
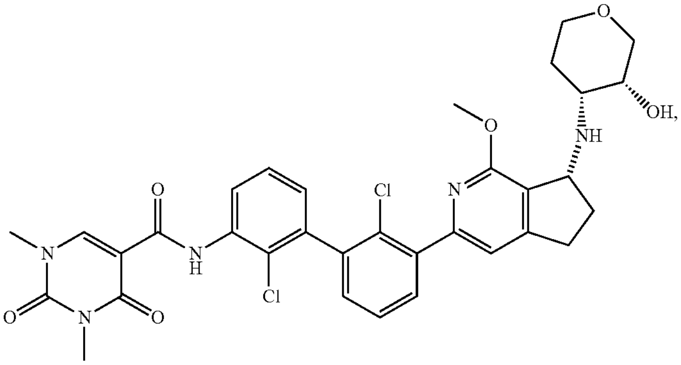
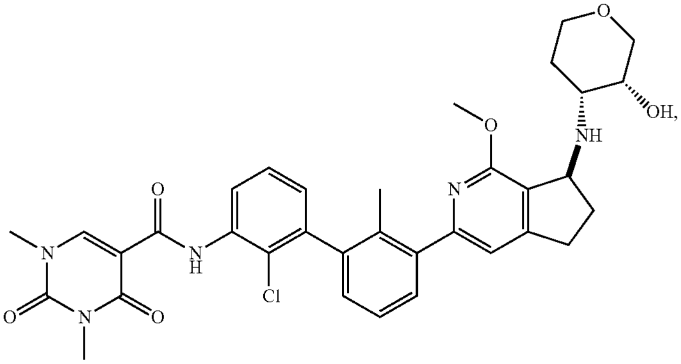

-continued
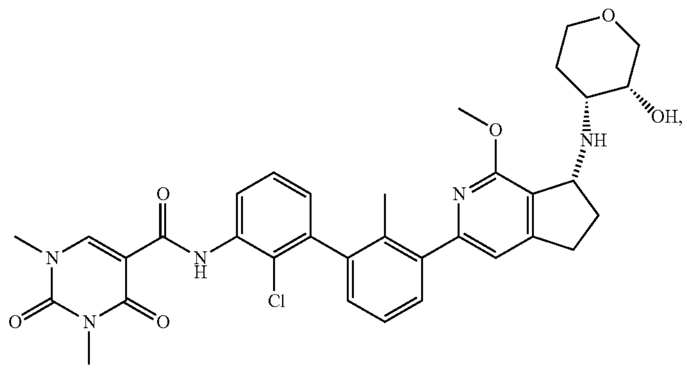
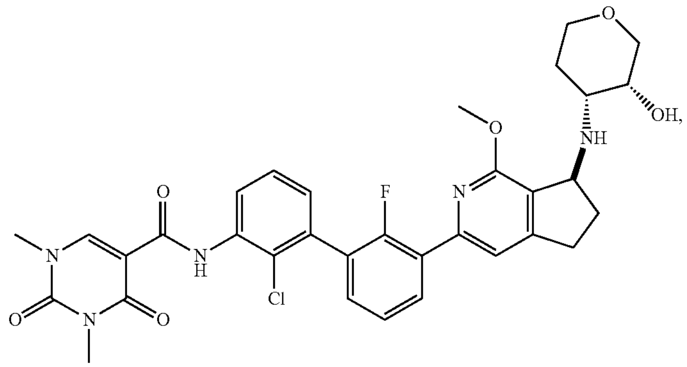
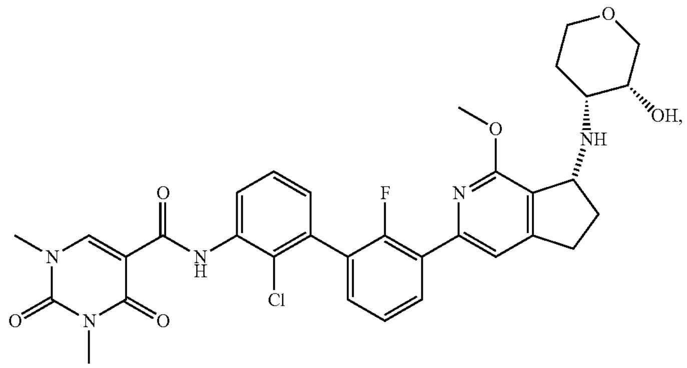
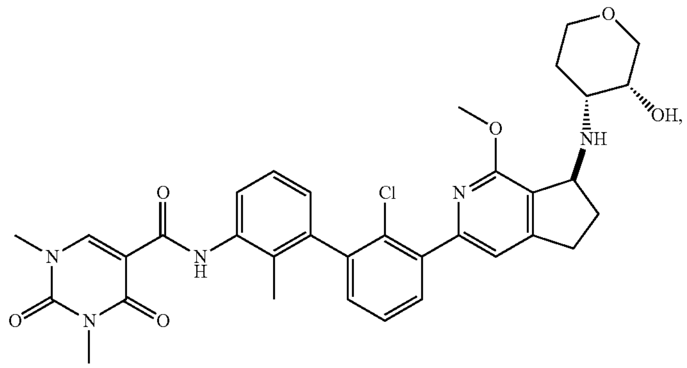

-continued
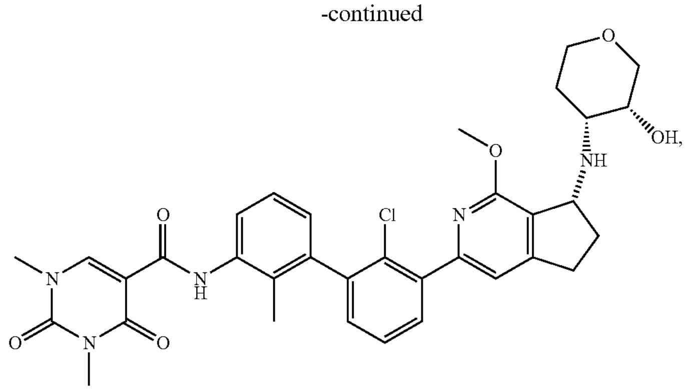
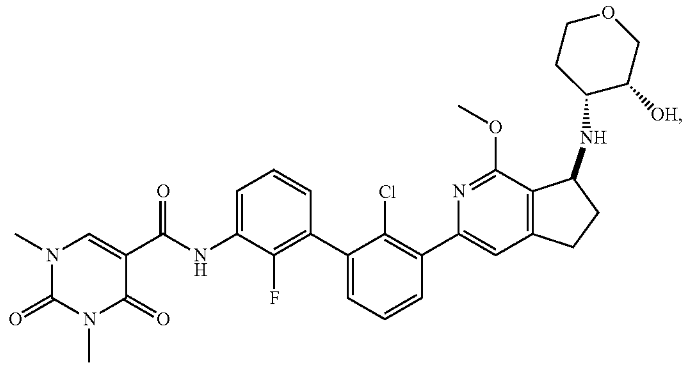
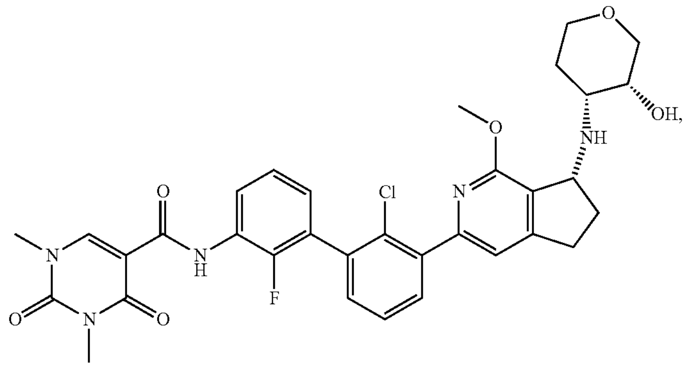
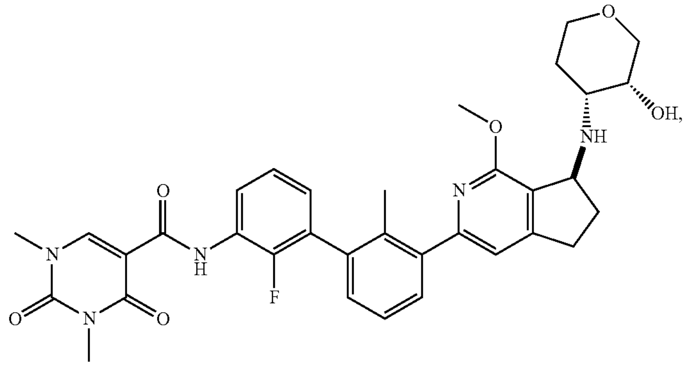

-continued
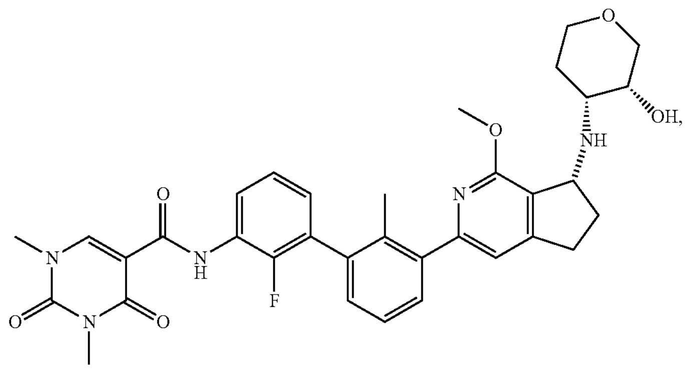
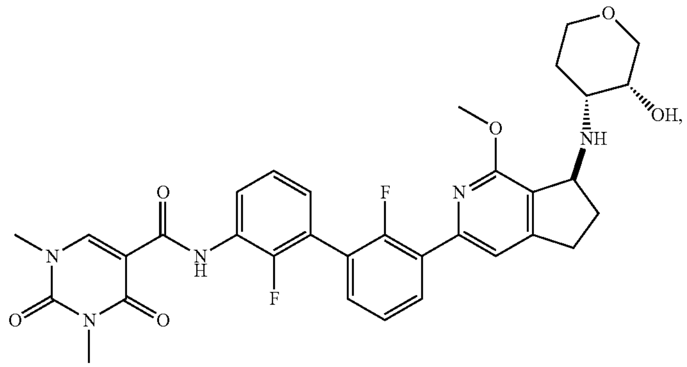
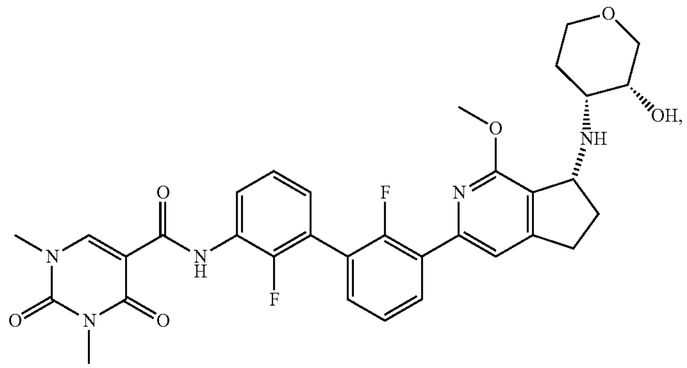
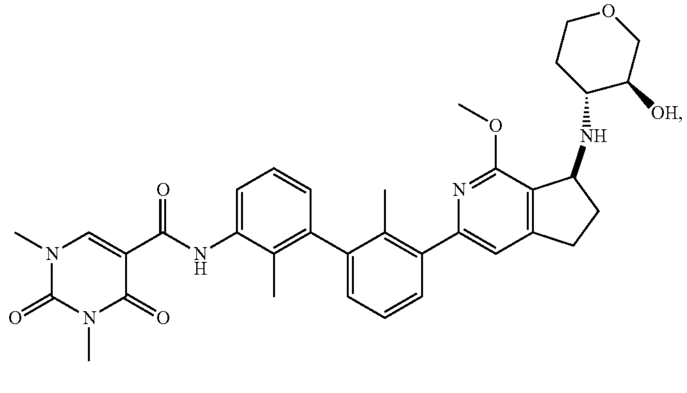

-continued
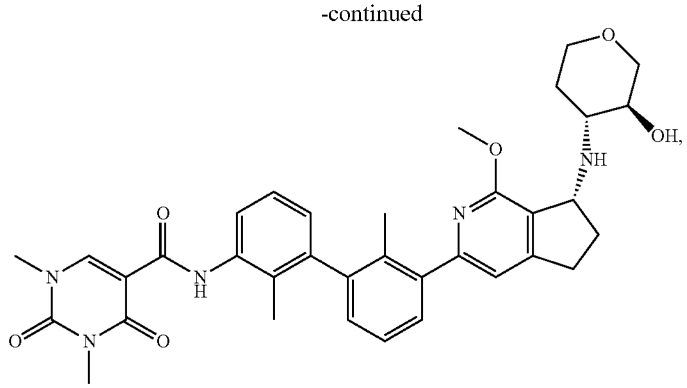
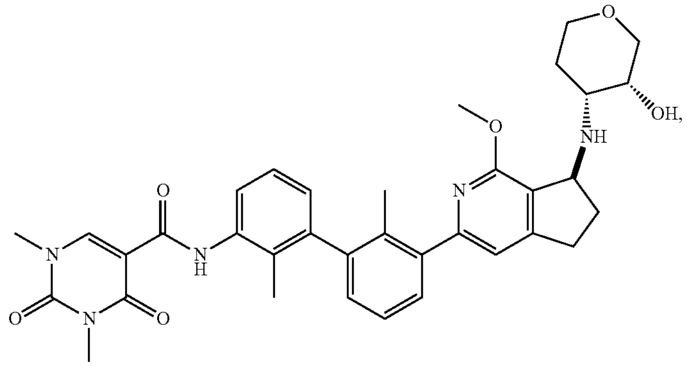
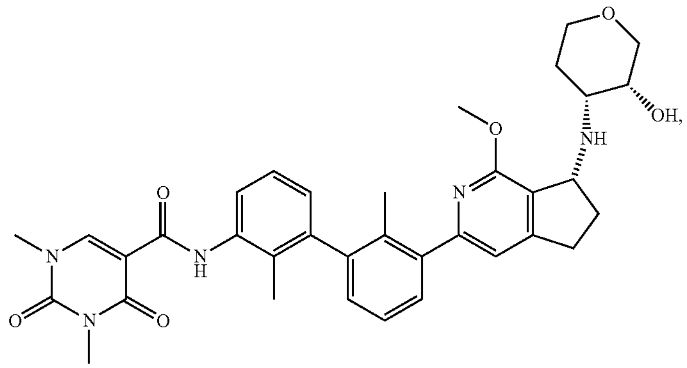
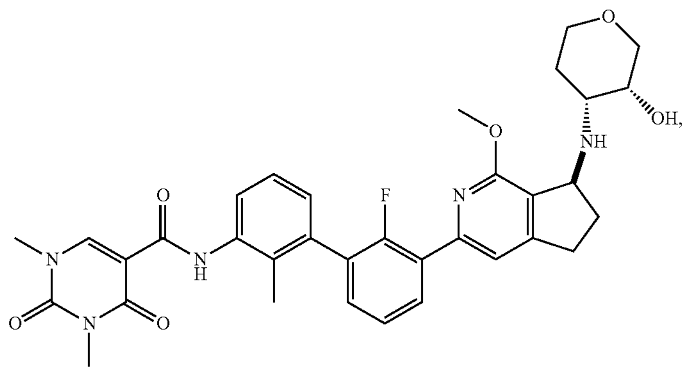

-continued
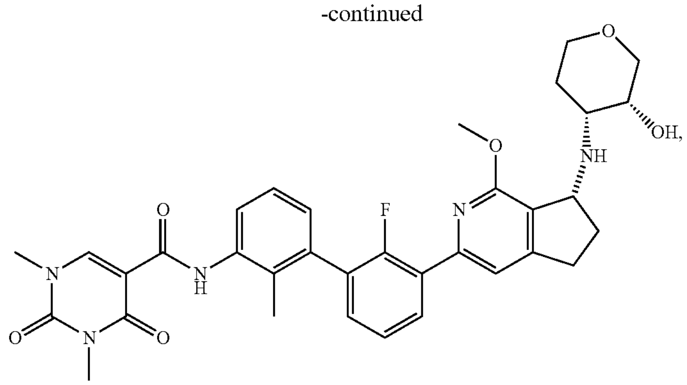
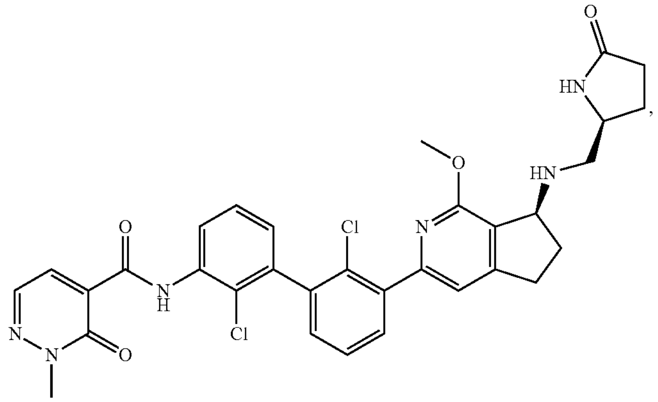
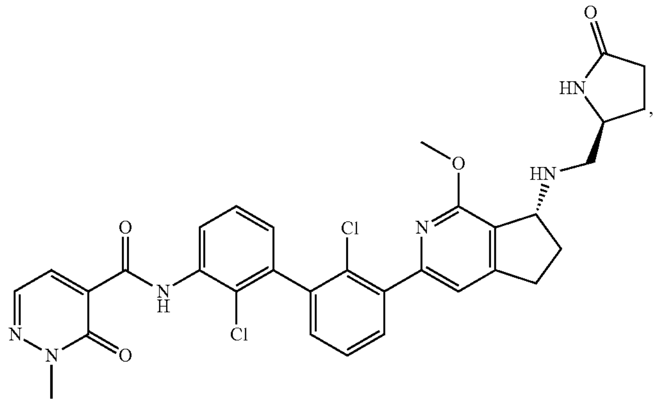
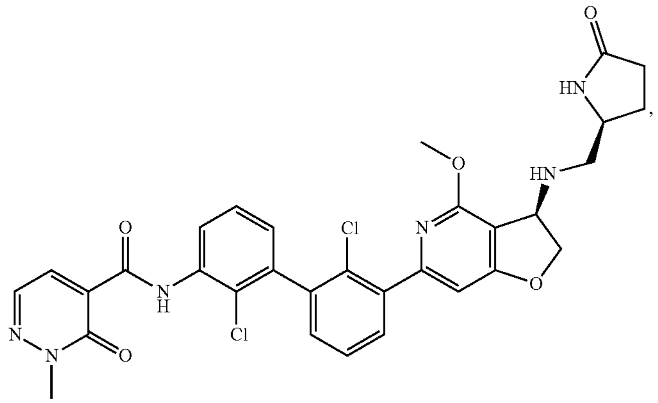

-continued
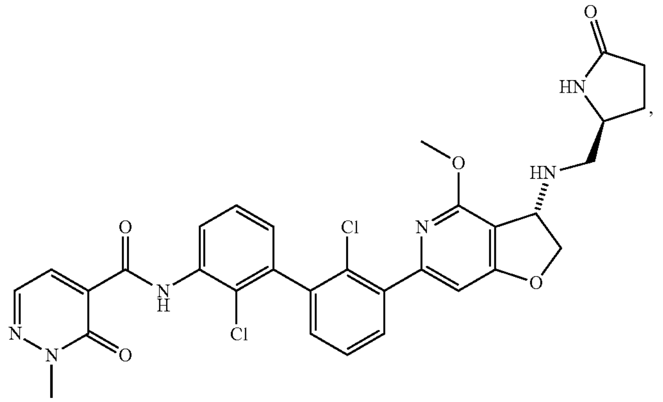
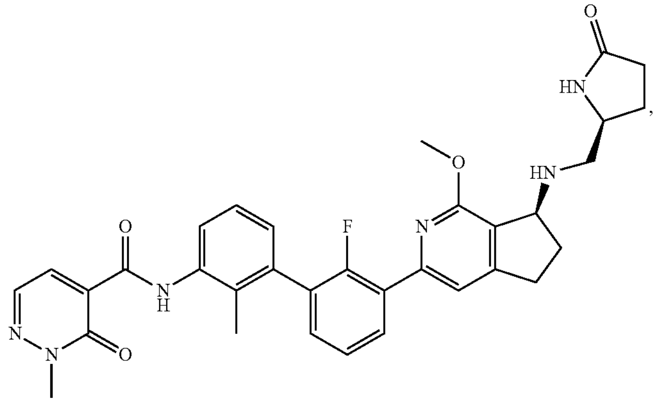
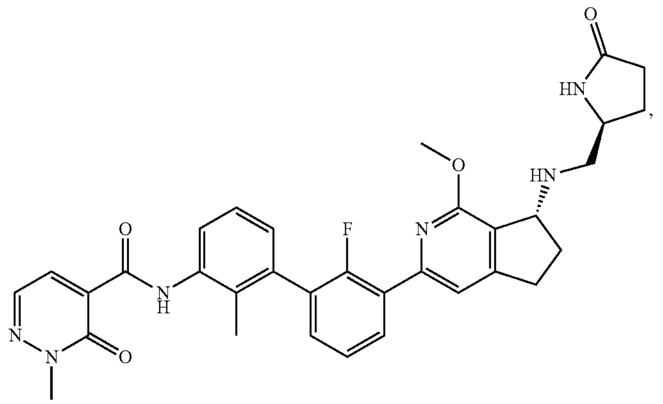
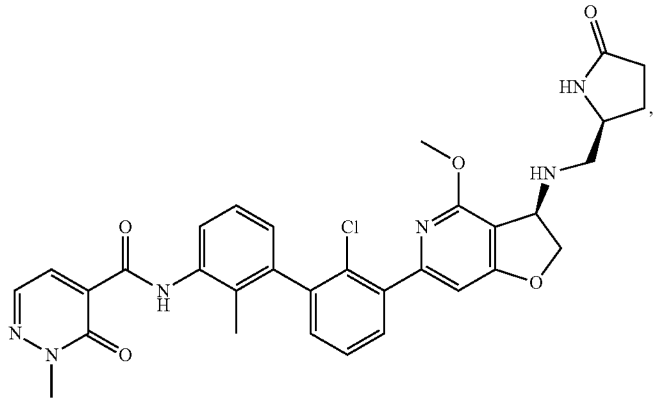

-continued
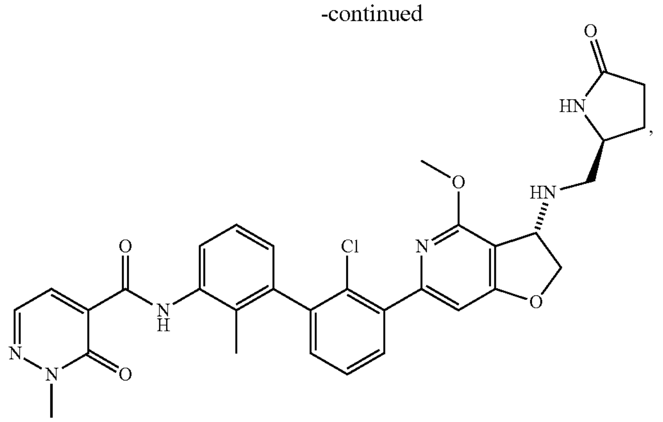
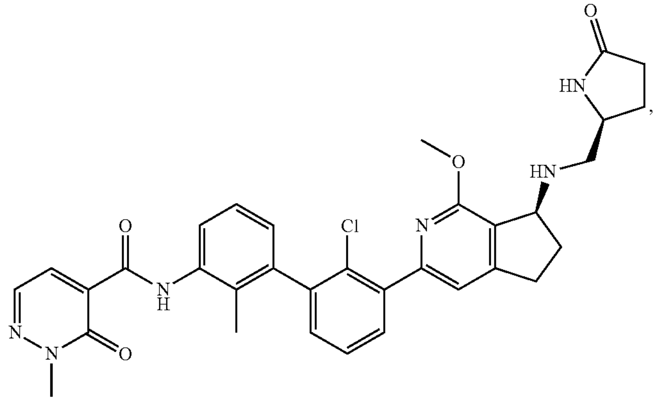
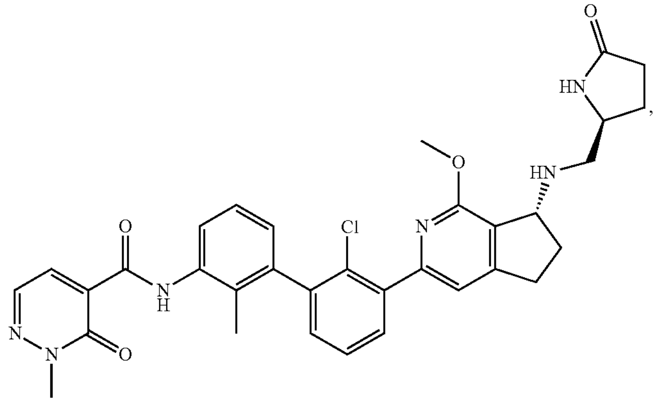
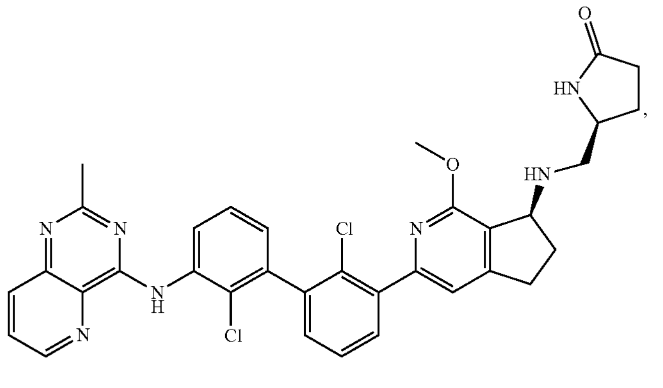

-continued
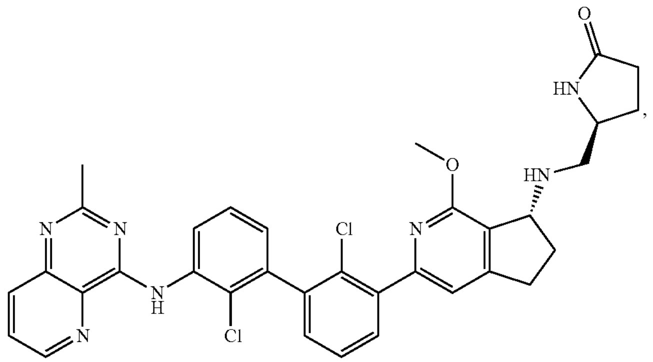
,
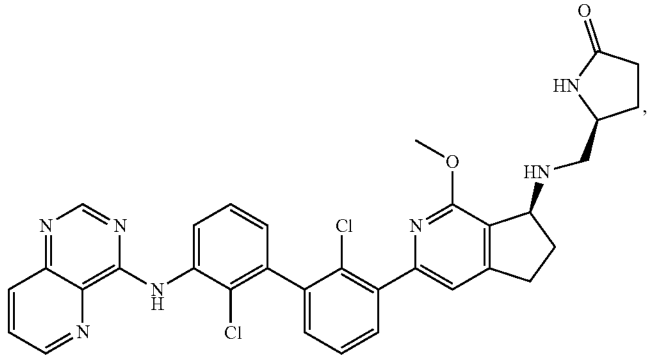
,
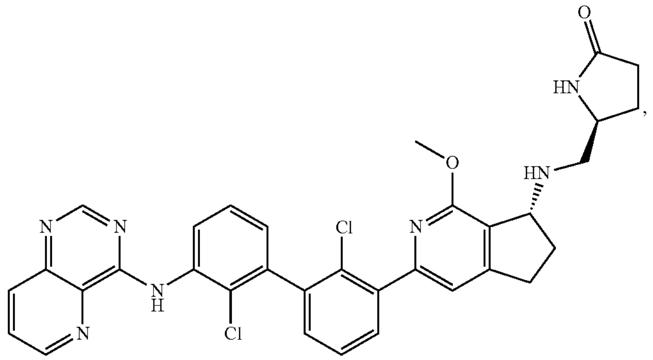
,
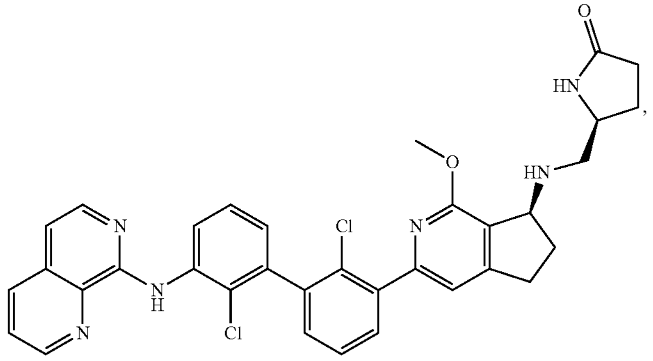
,

-continued
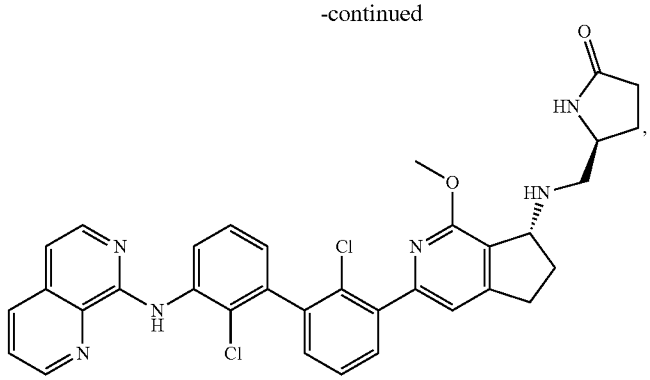
,
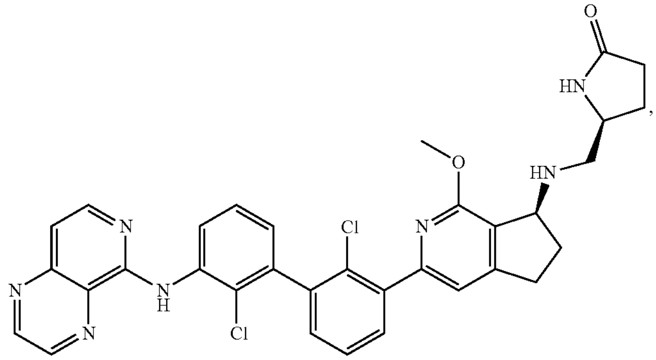
,
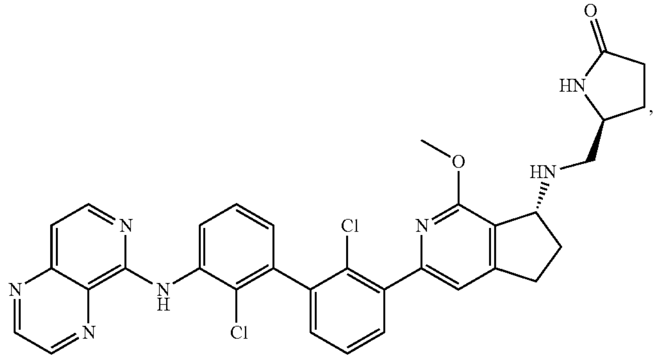
,
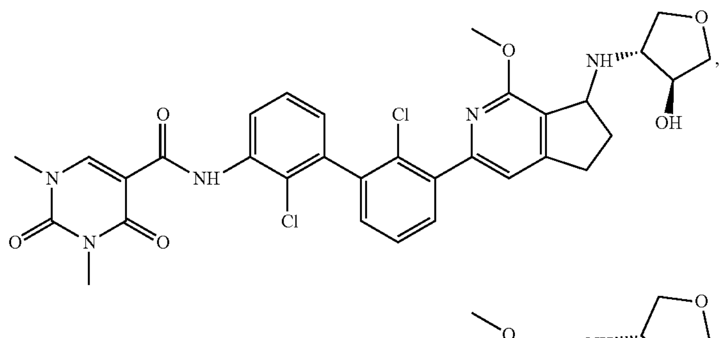
,
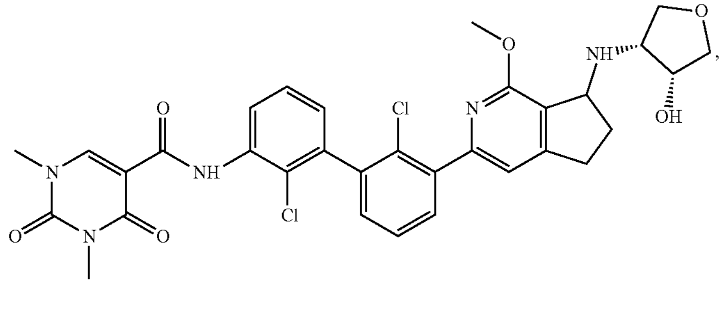
, -continued
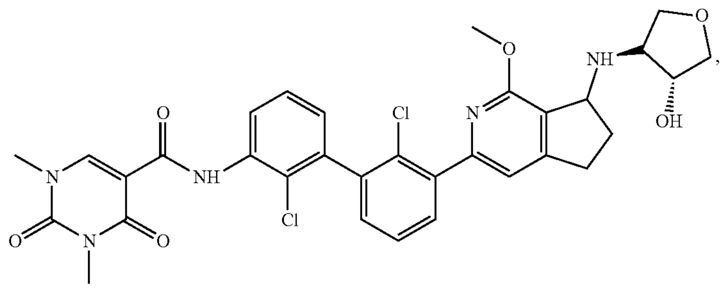
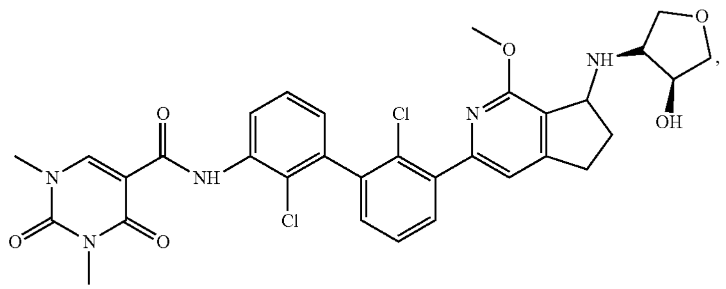
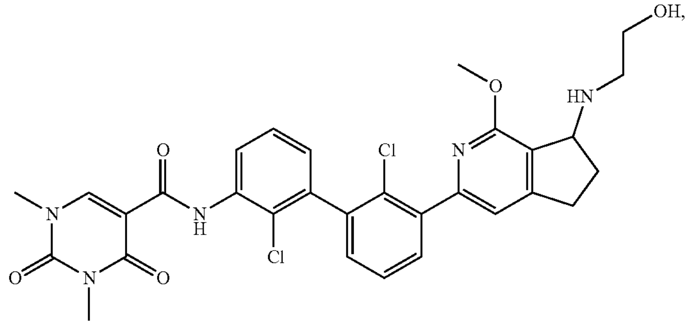
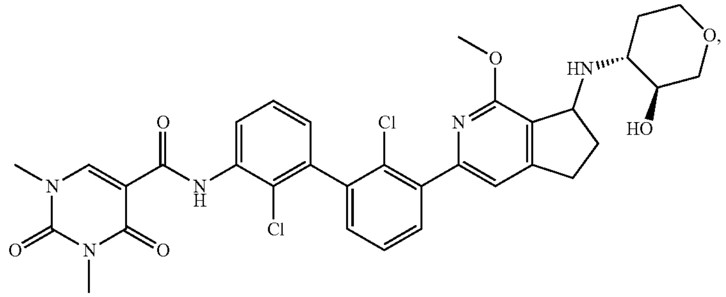
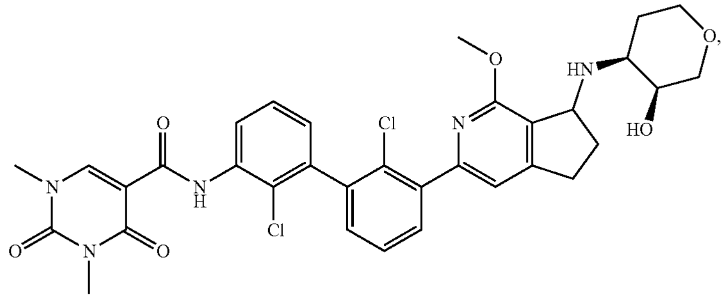

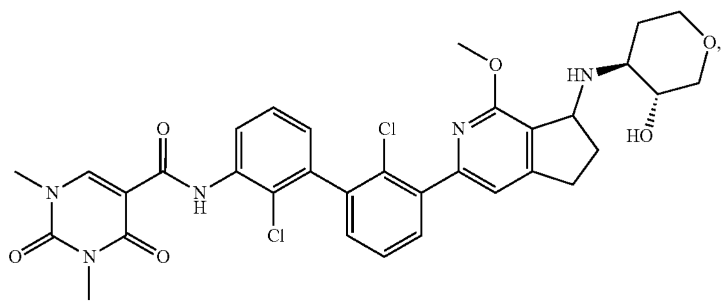
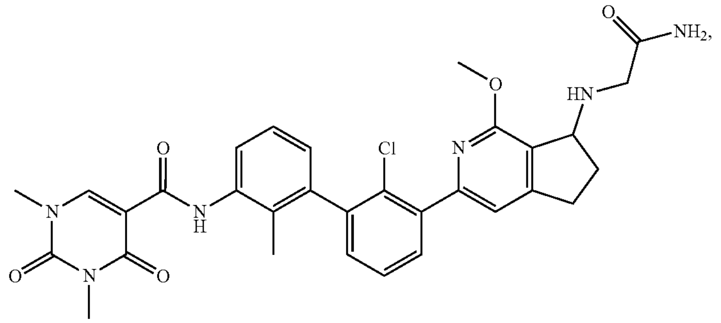
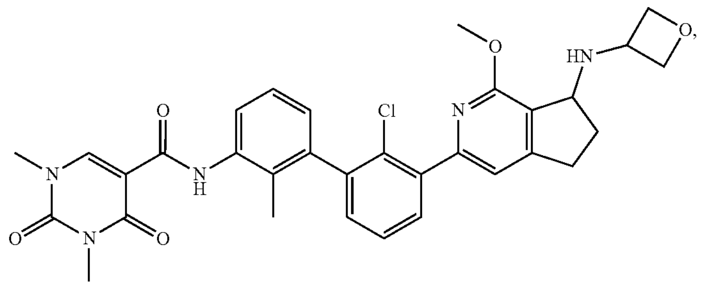
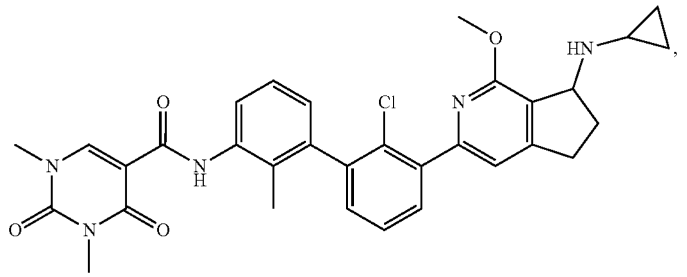
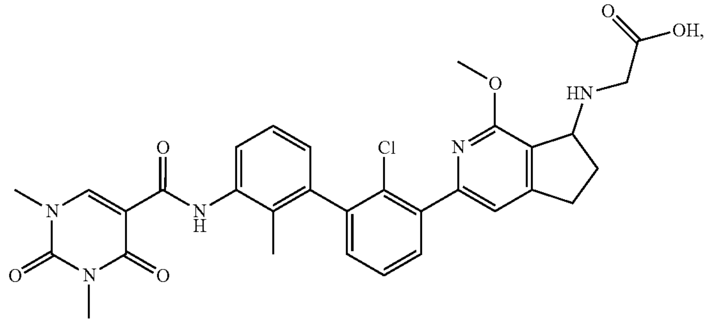

-continued
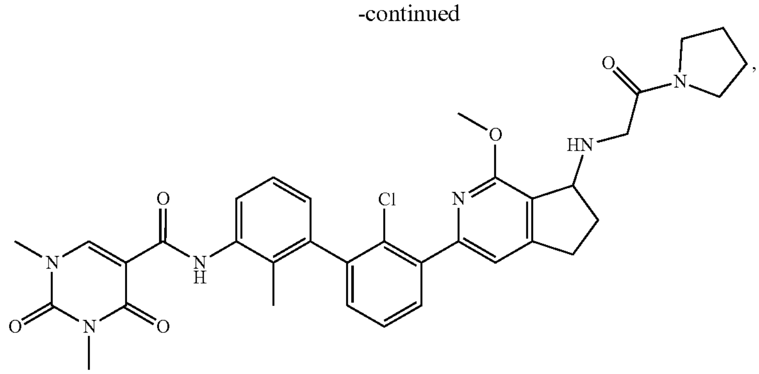
,
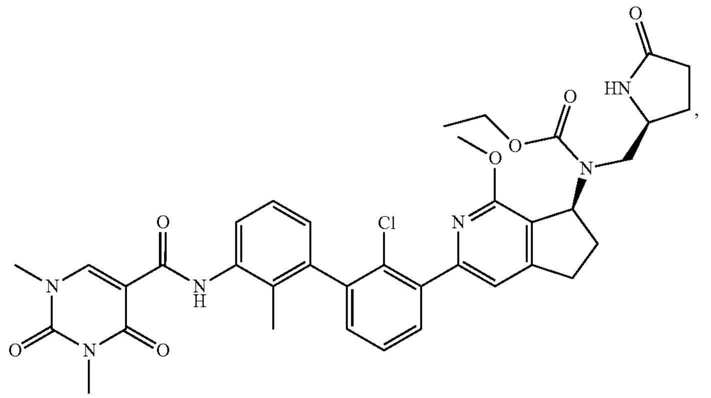
,
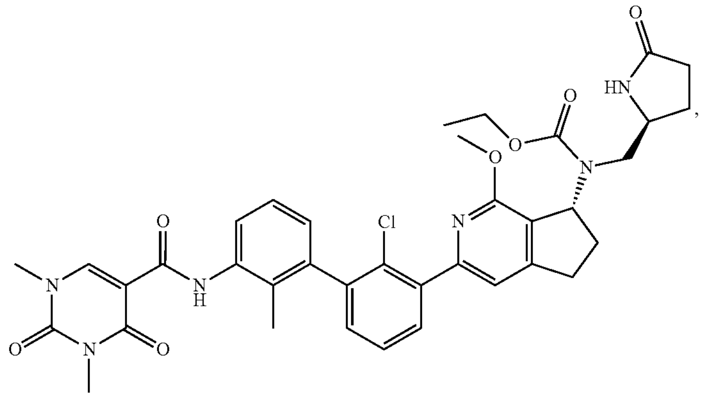
,
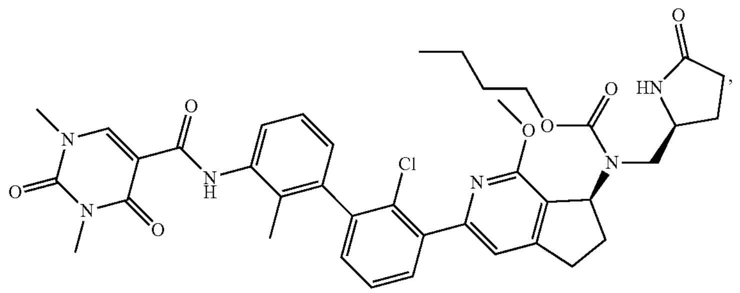
,
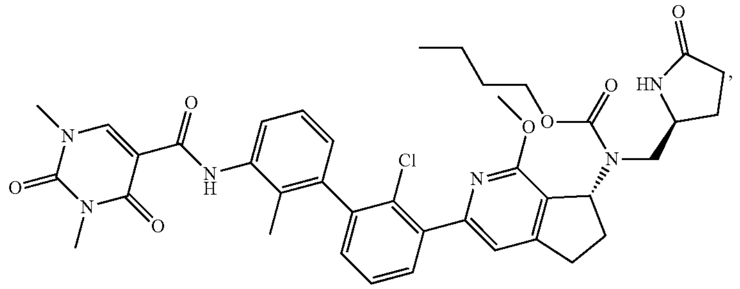
, -continued
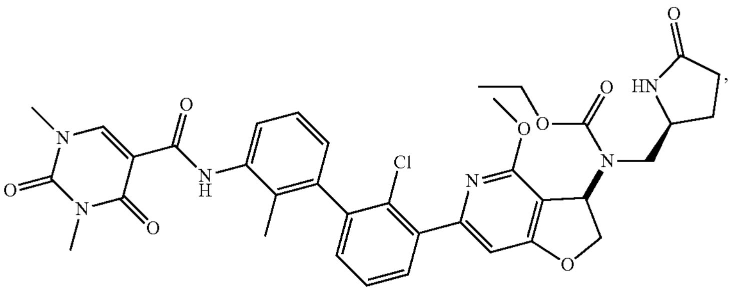
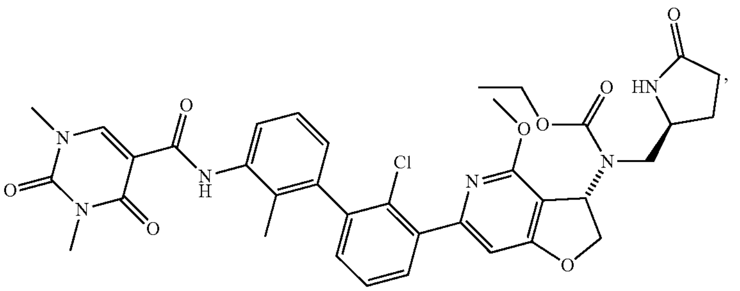
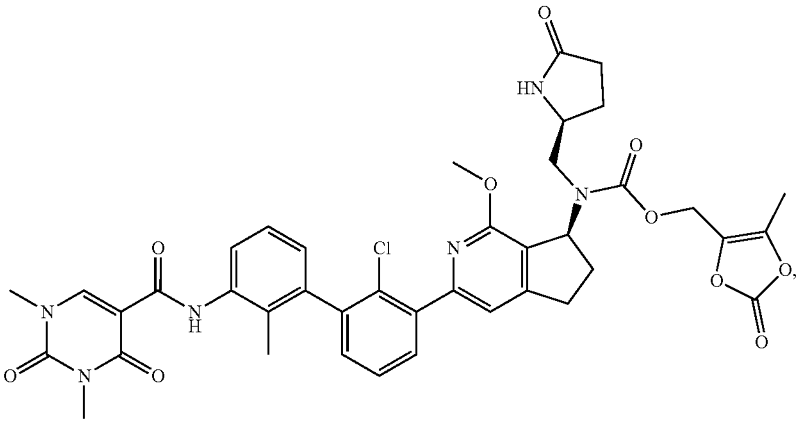
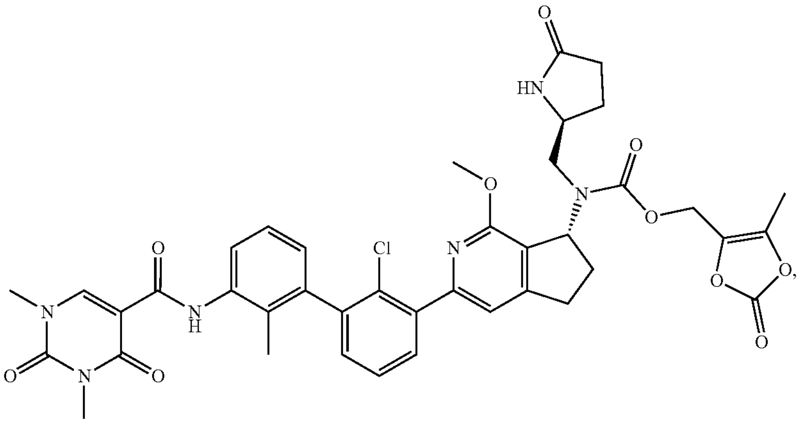

-continued
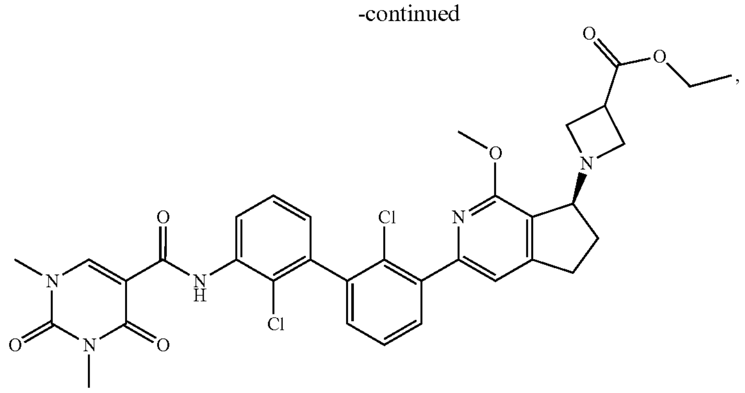
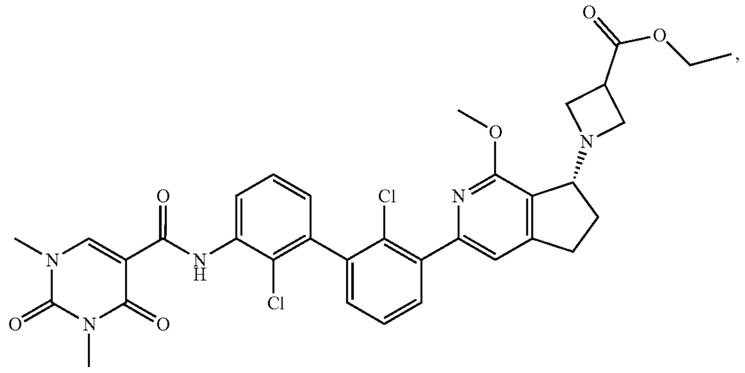
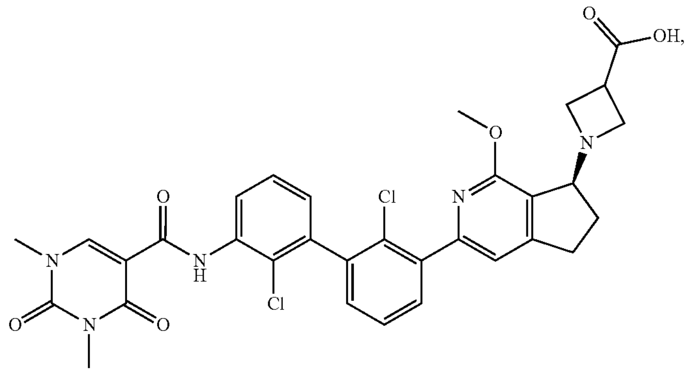
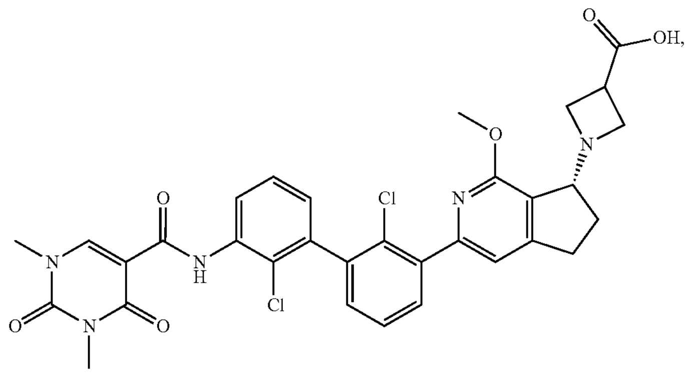

-continued
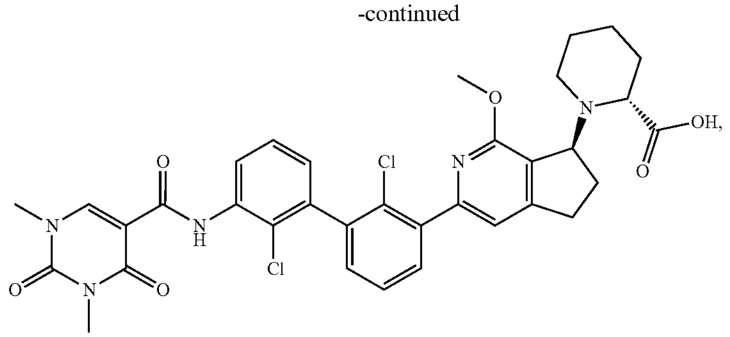
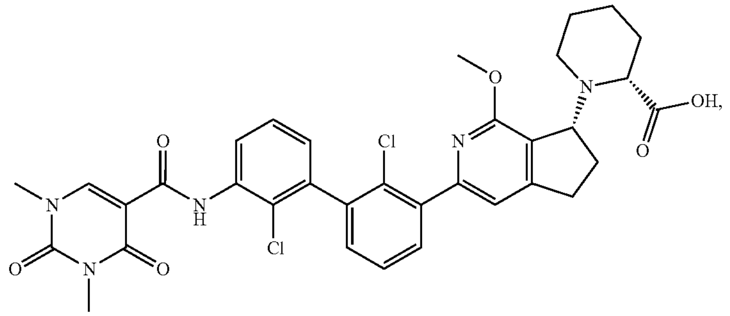
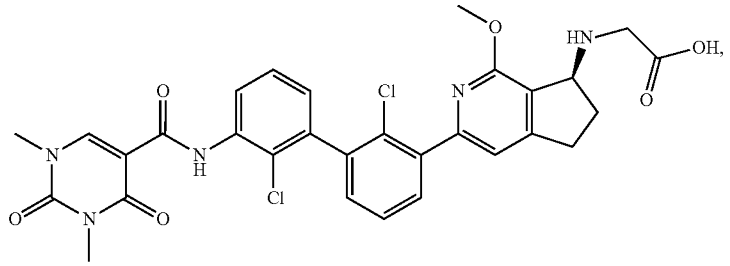
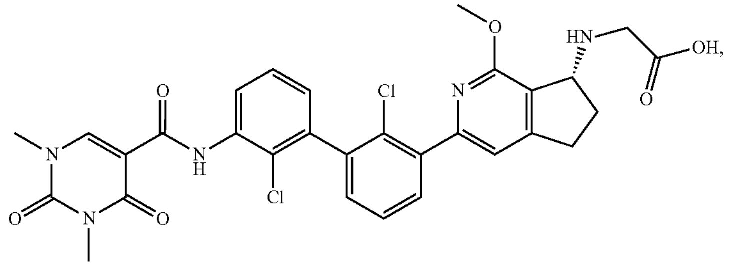
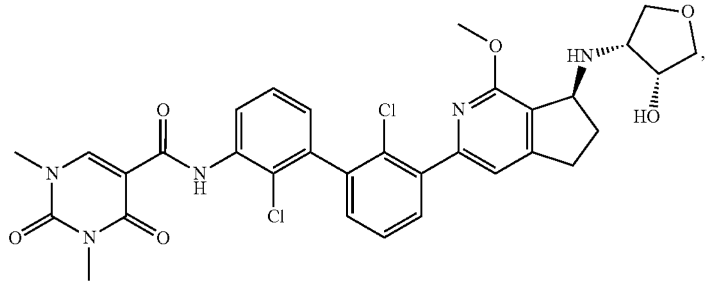
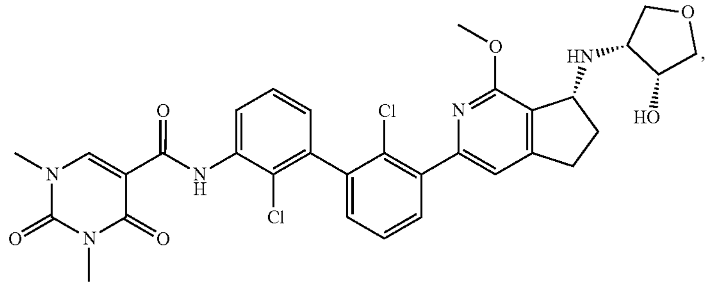

-continued
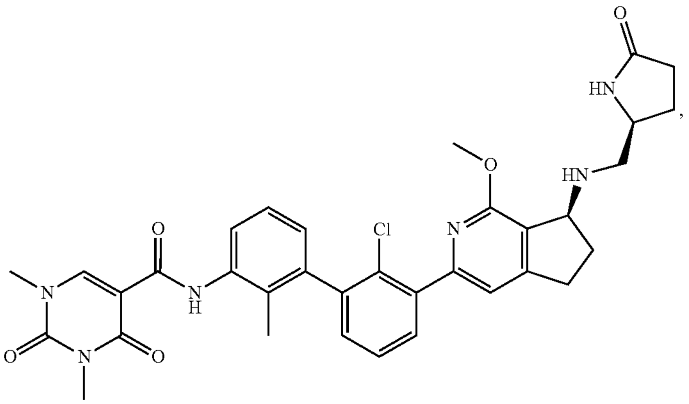
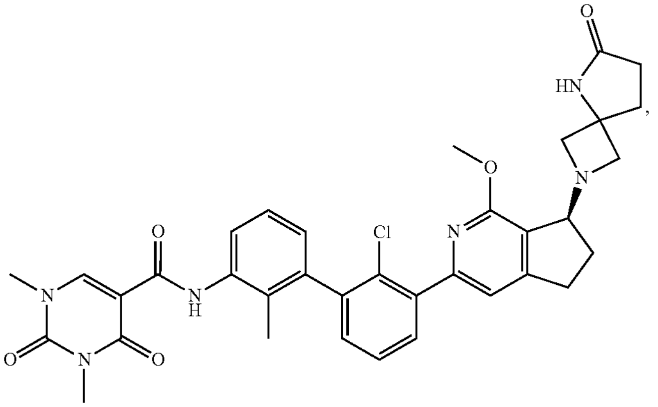
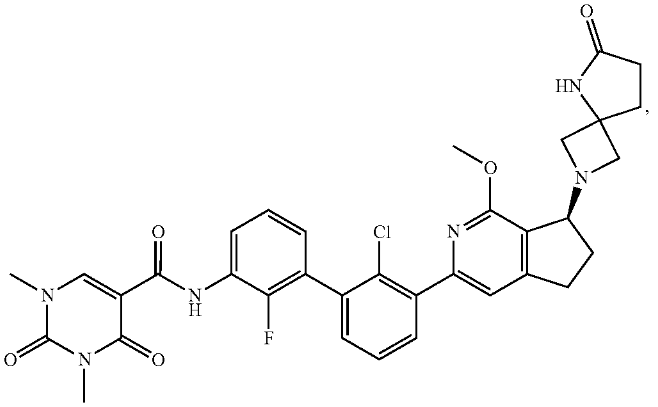
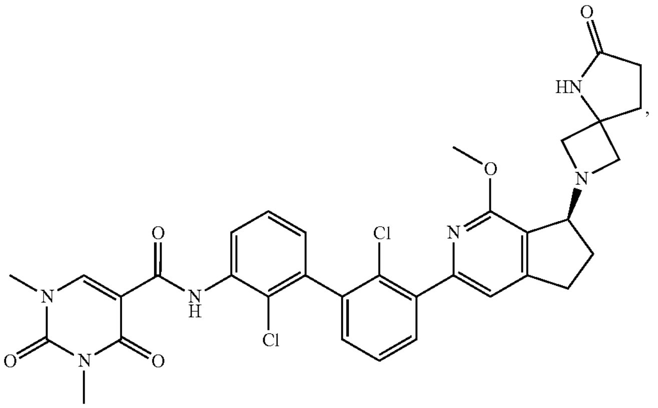

-continued
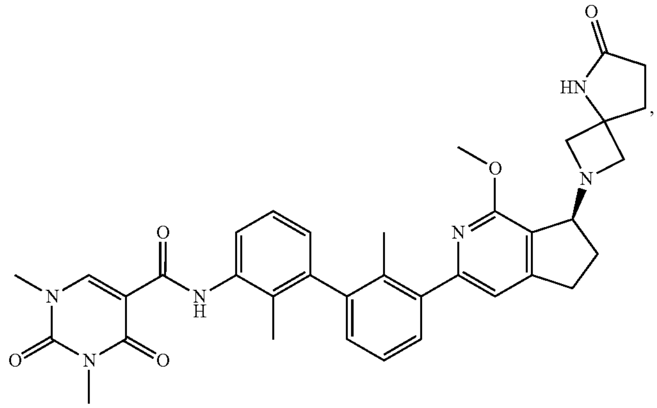
,
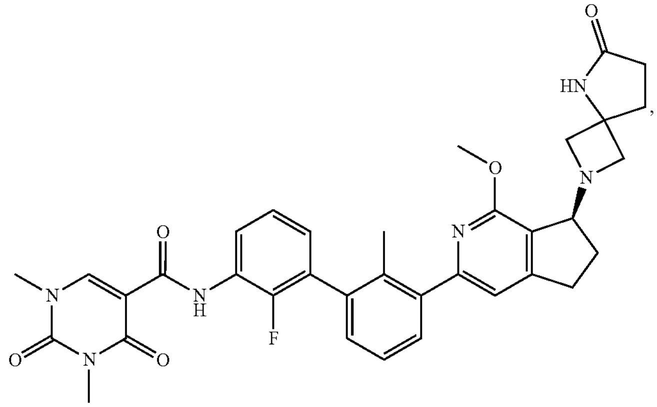
,
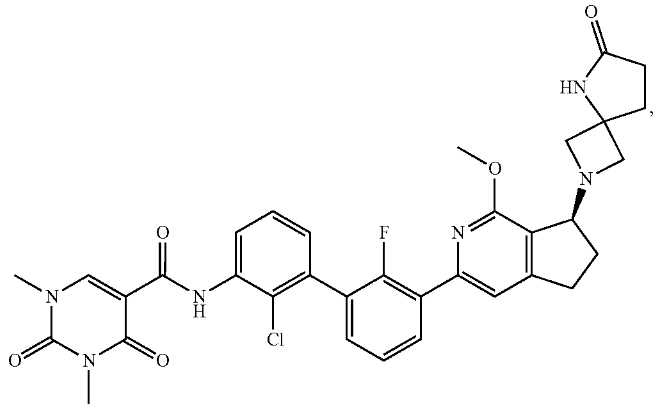
,
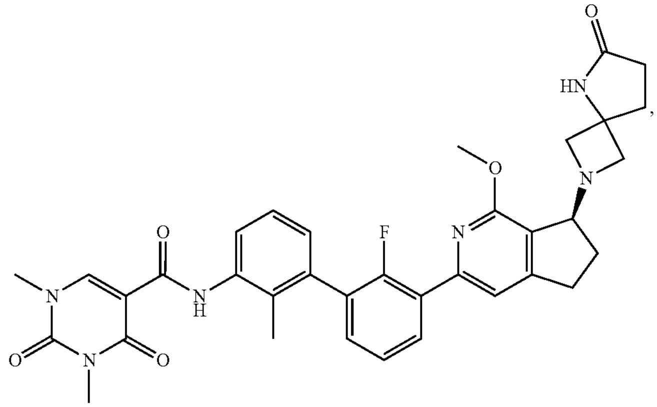
,

-continued
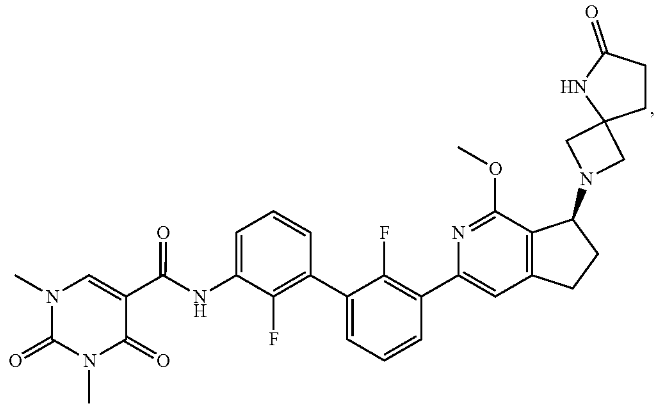
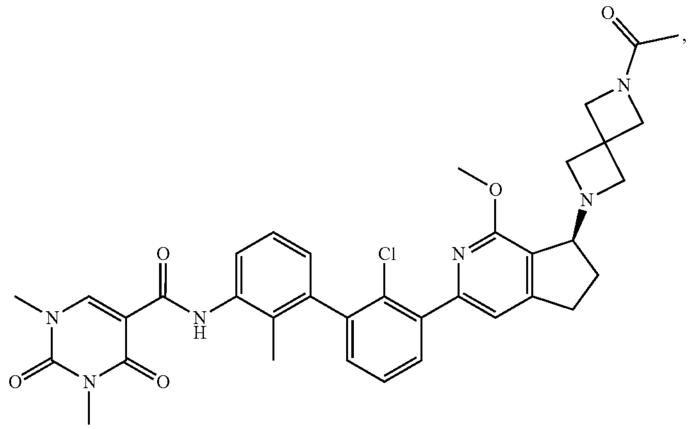
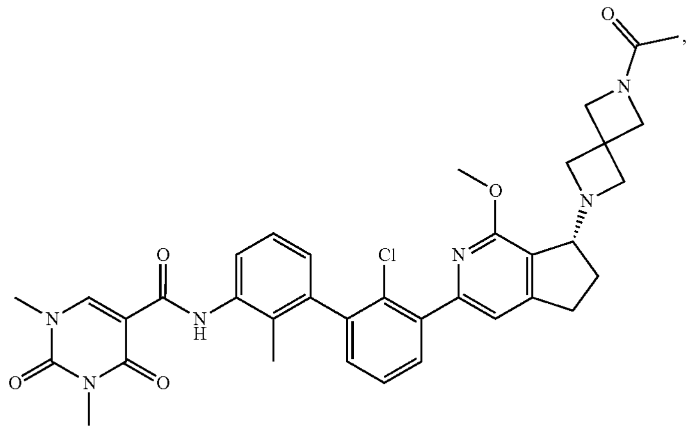
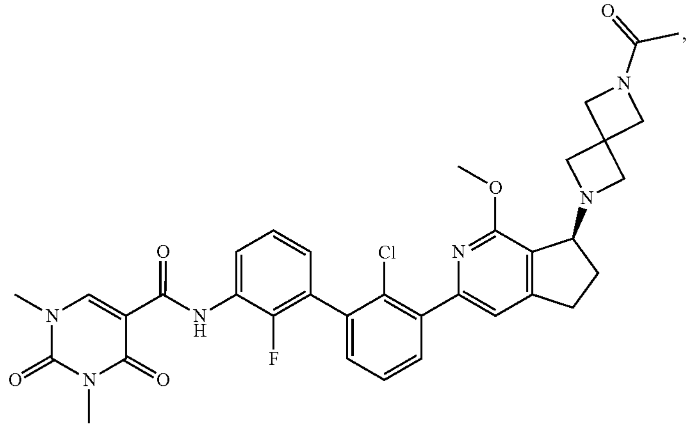

-continued
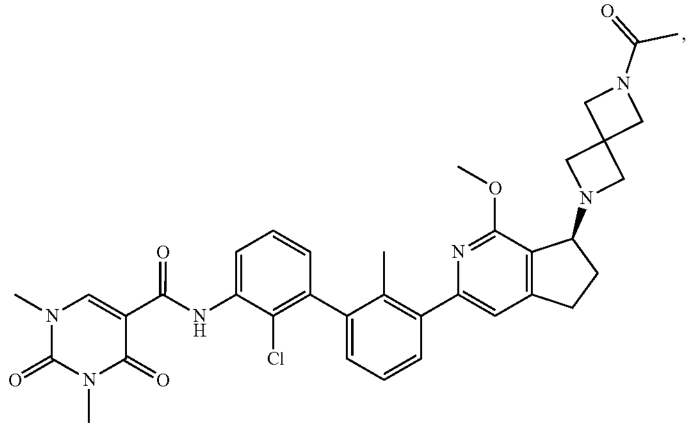
,
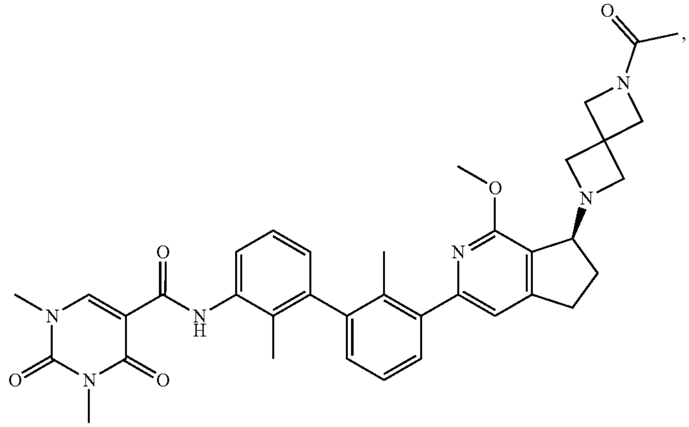
,
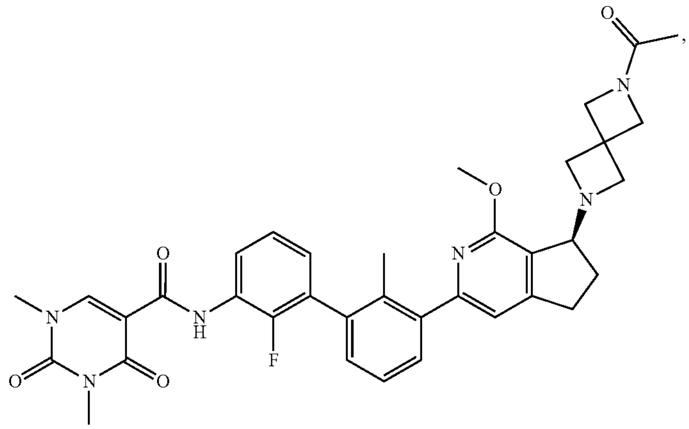
,
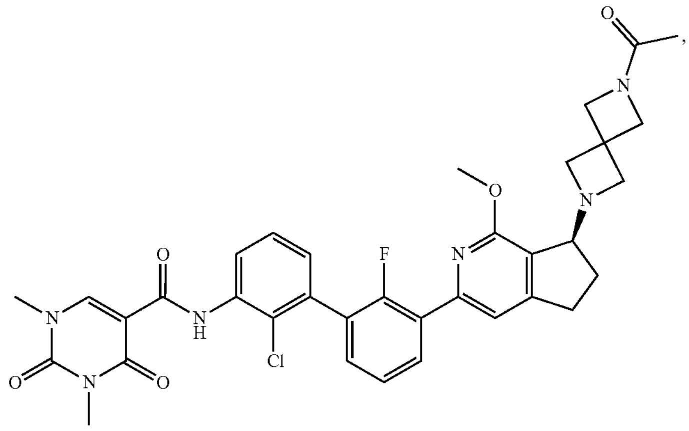
,

-continued
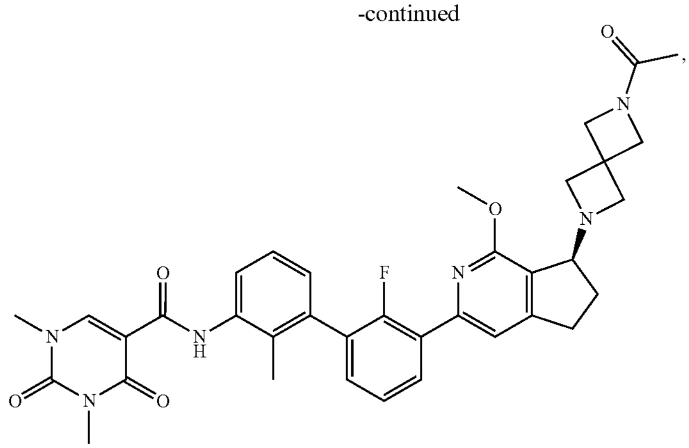
,
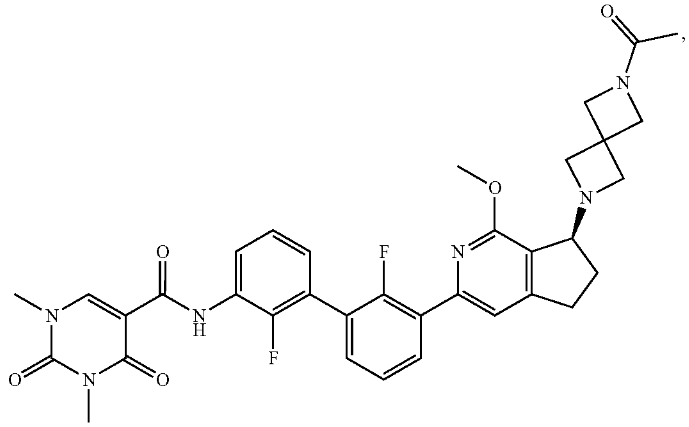
,
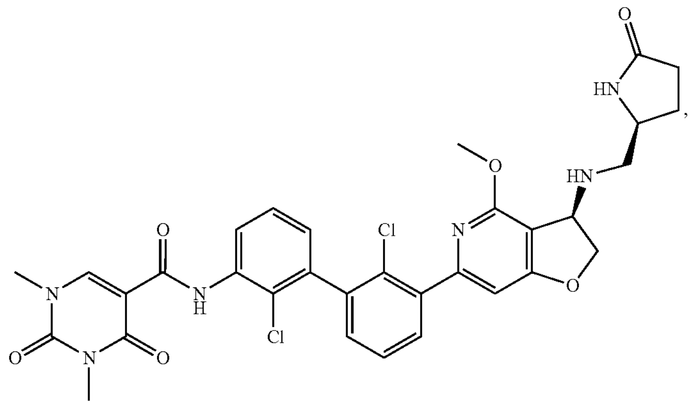
,
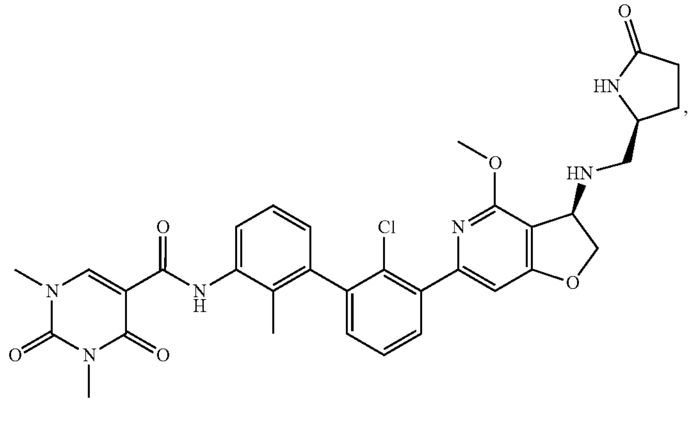
,

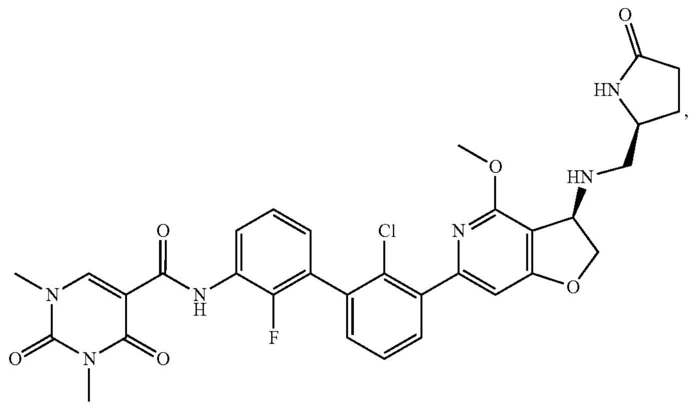
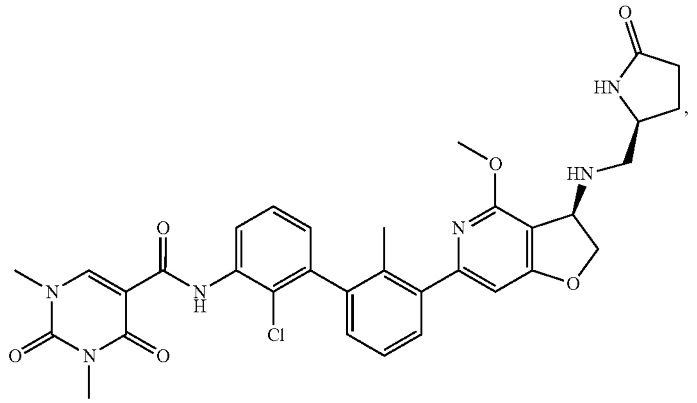
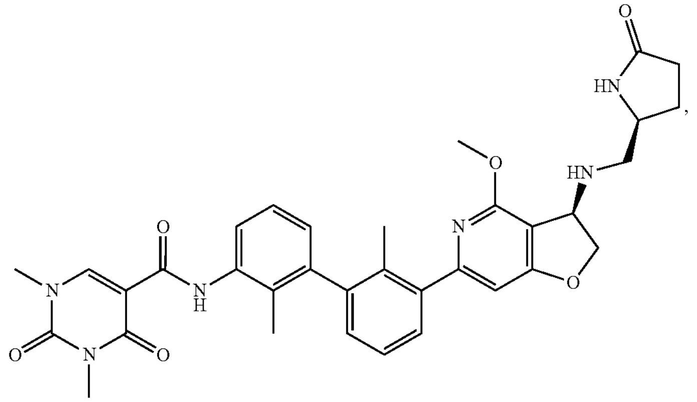
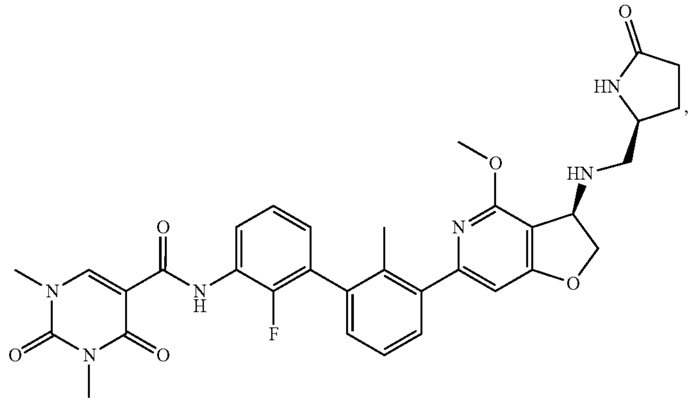

-continued
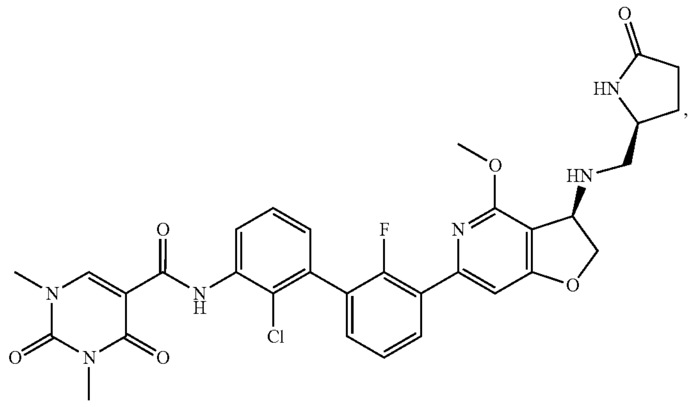
,
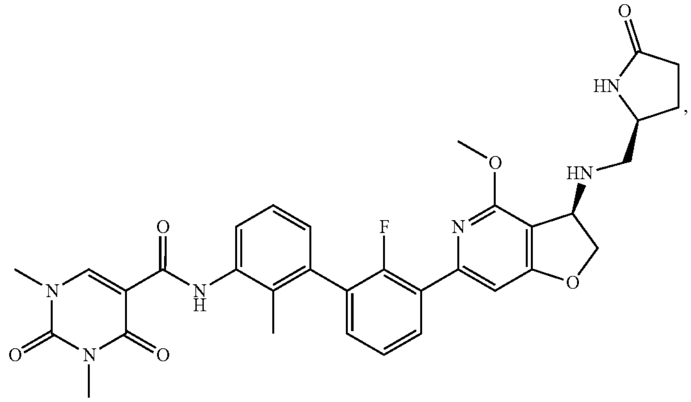
,
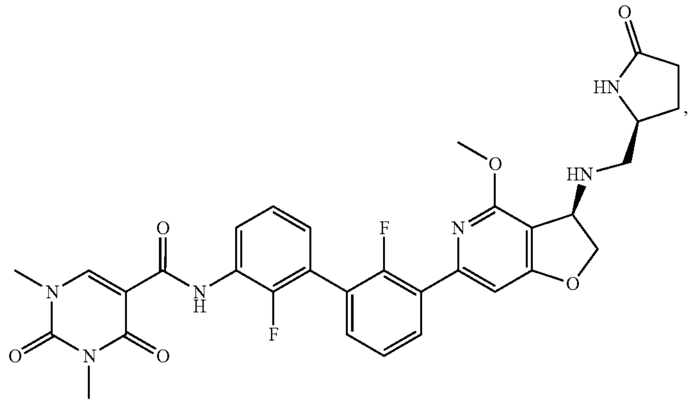
,
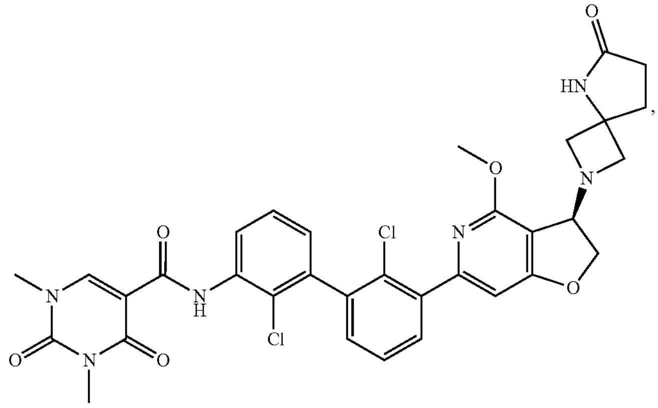
,

-continued
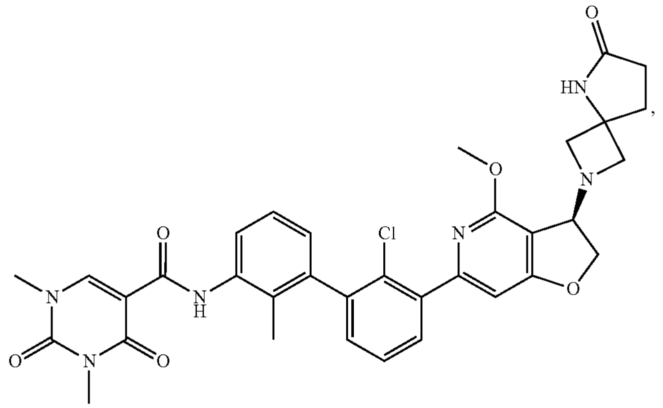
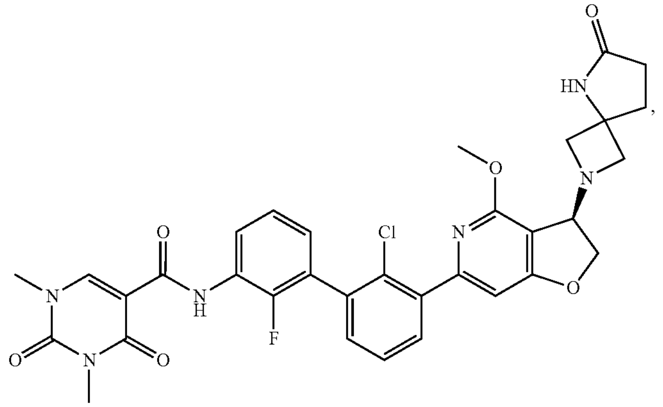
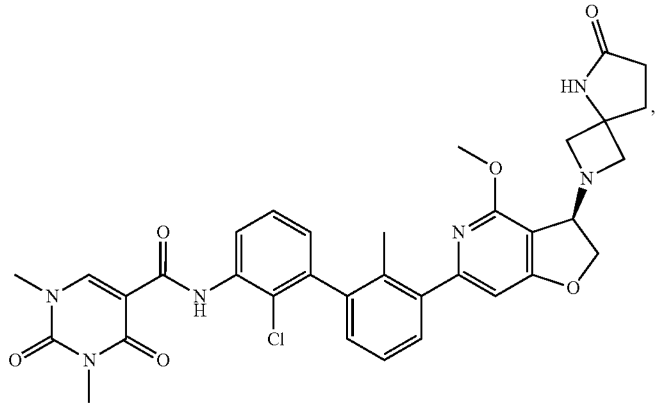
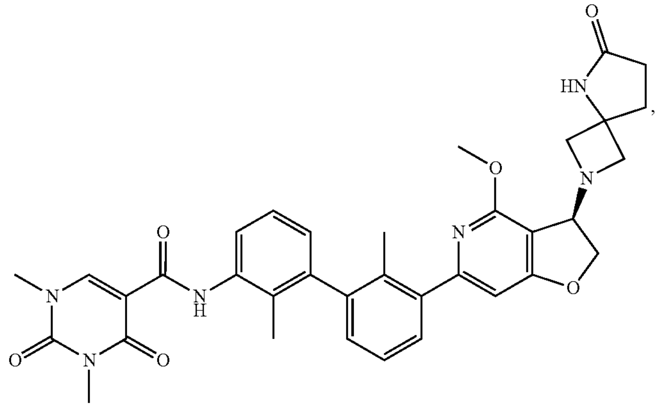

-continued
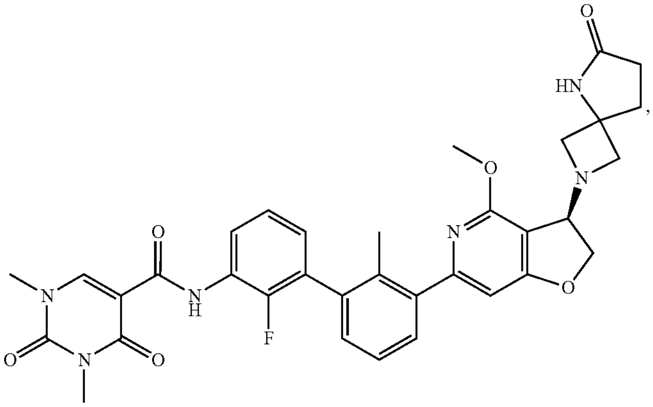
,
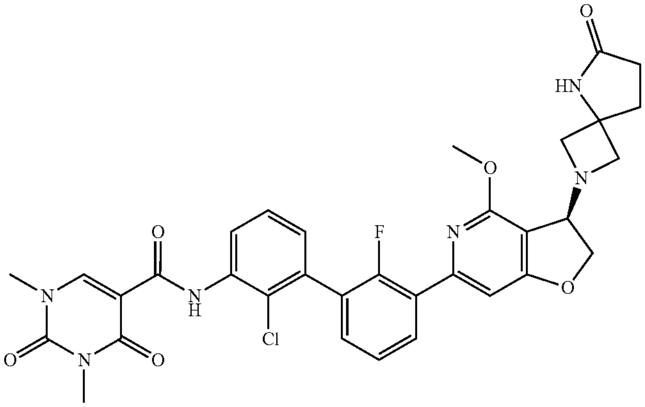
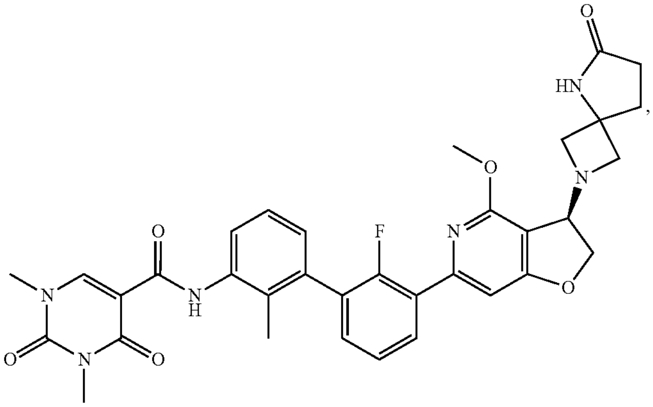
,
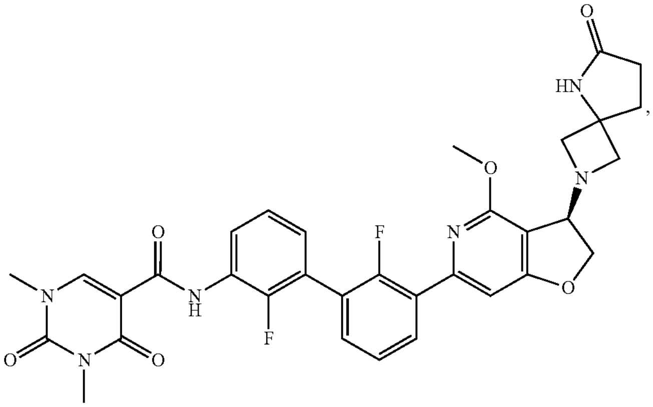
,

-continued
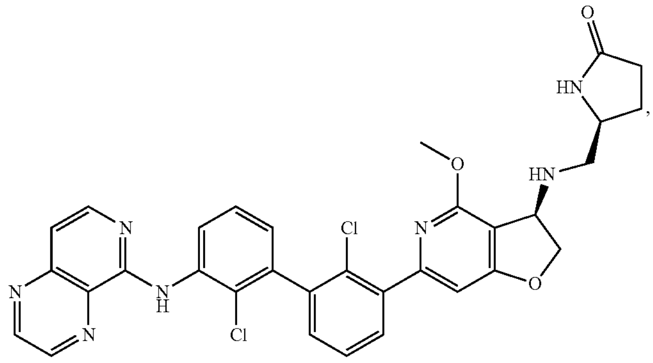
,
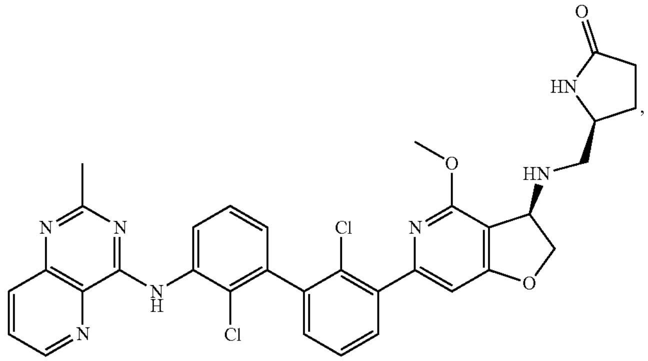
,
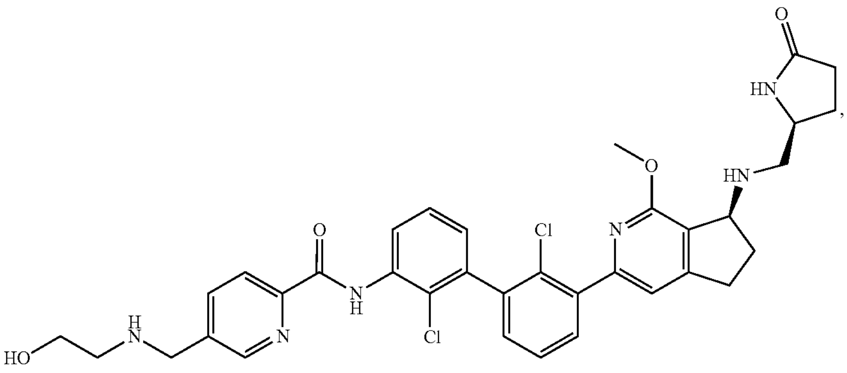
,
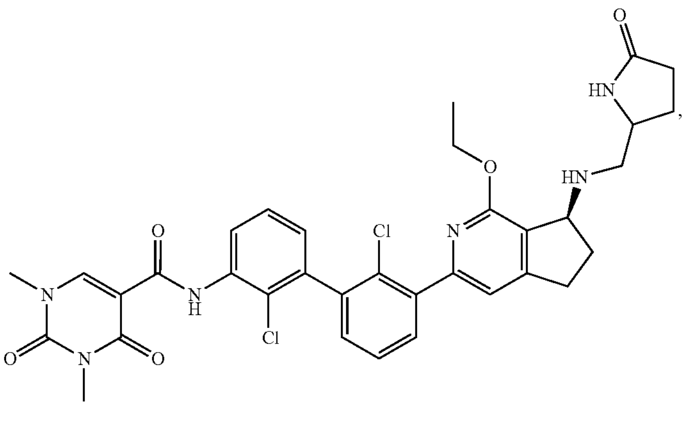
,

-continued
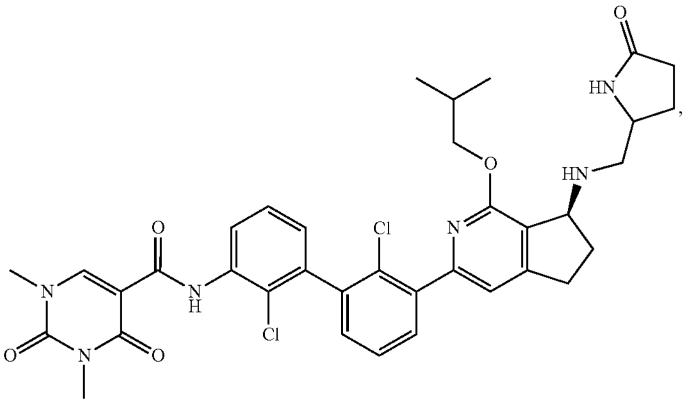
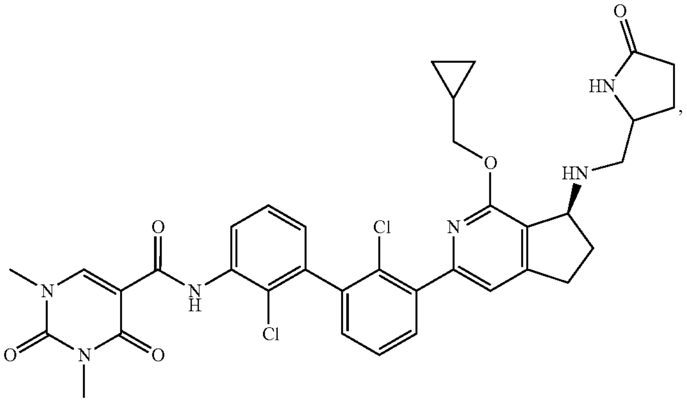
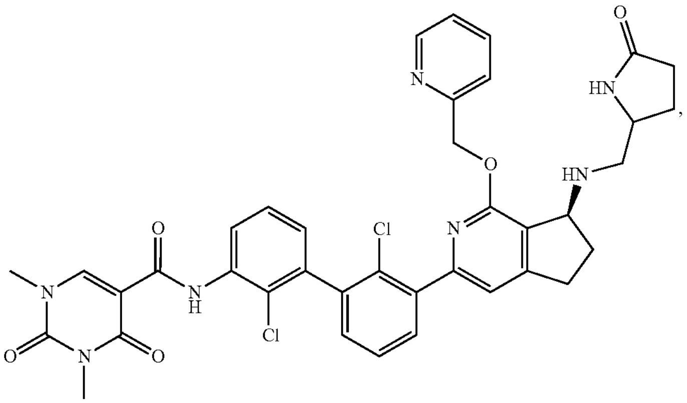
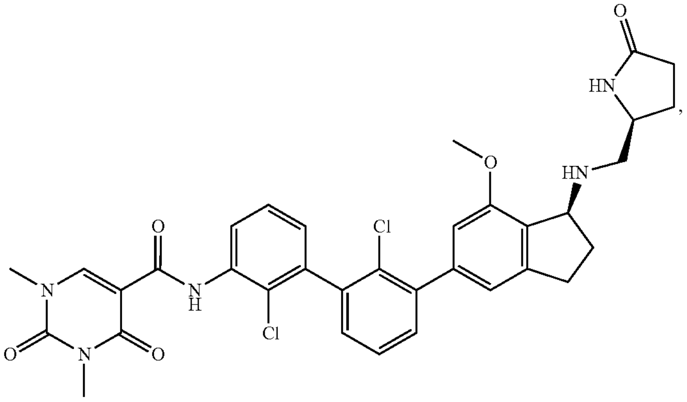

-continued
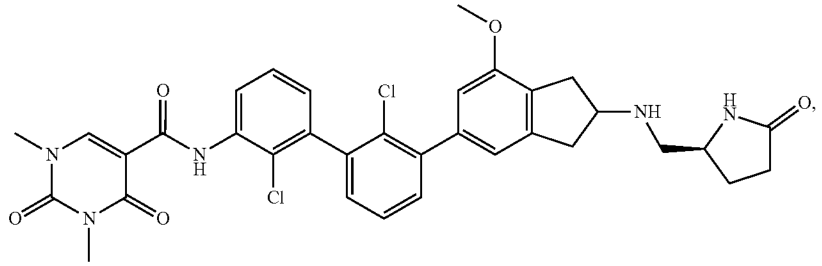
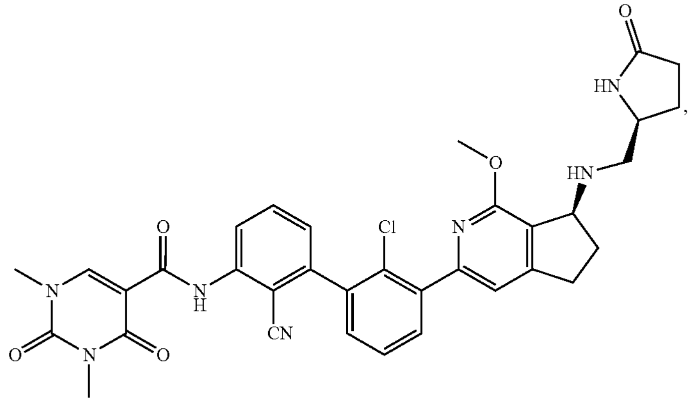
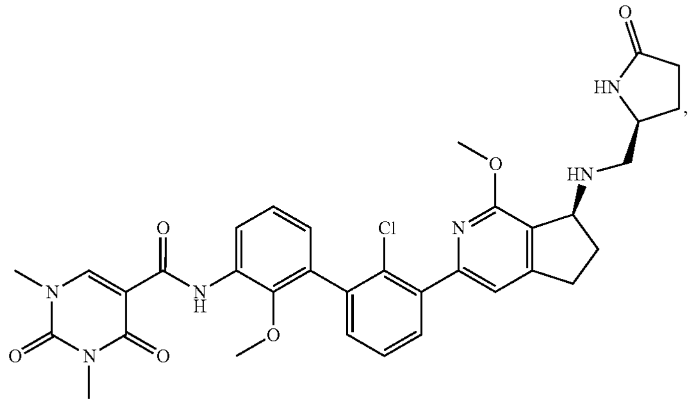
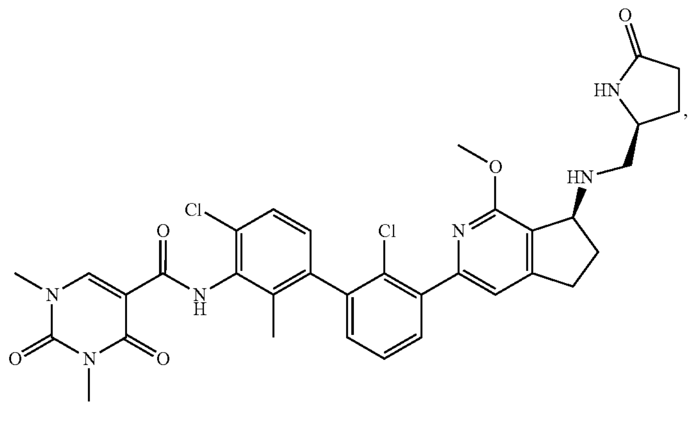

-continued
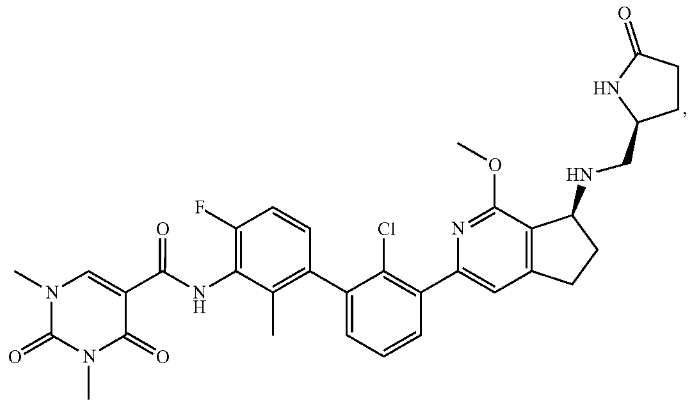
,
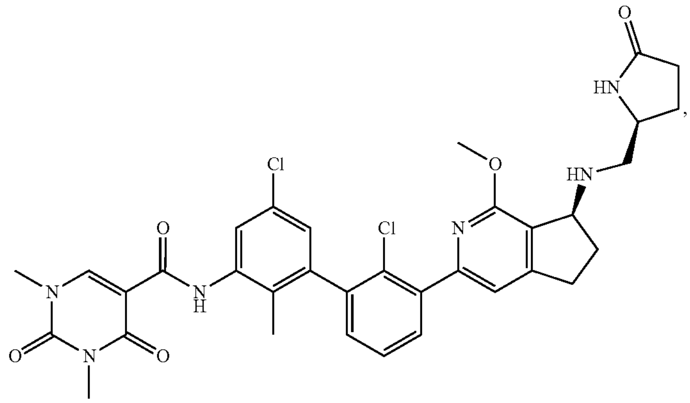
,
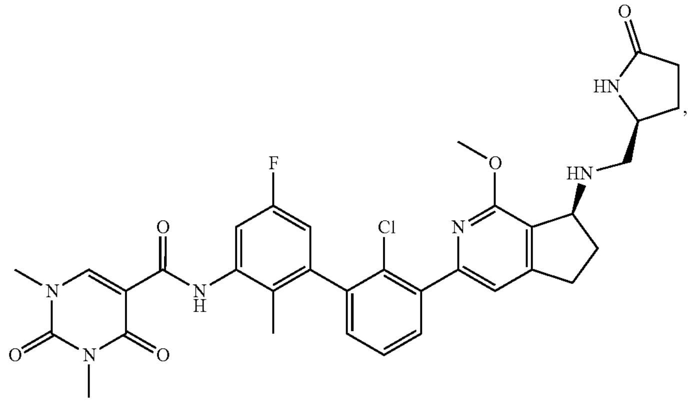
,
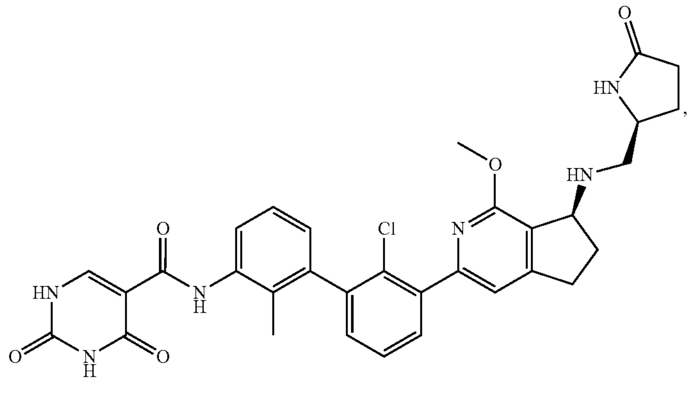
,

-continued
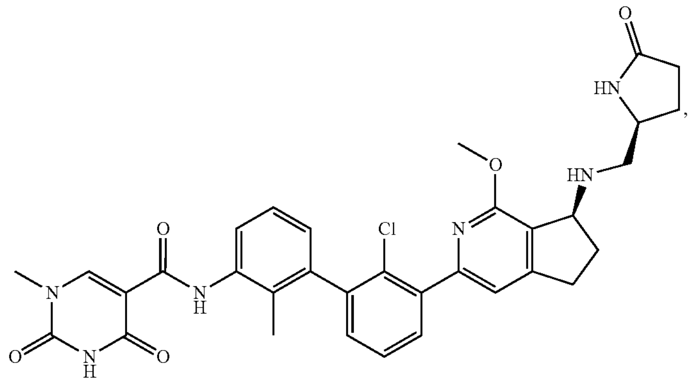
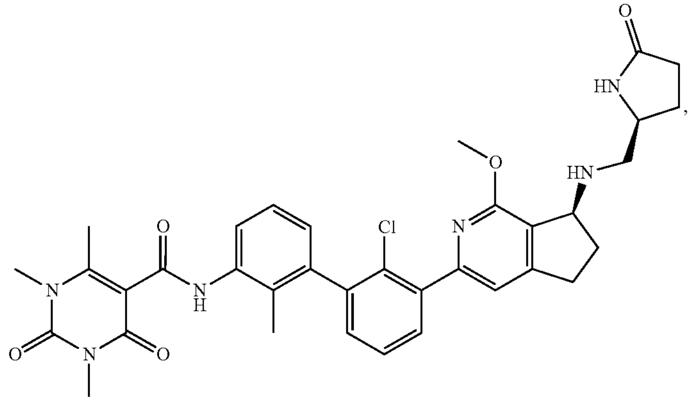
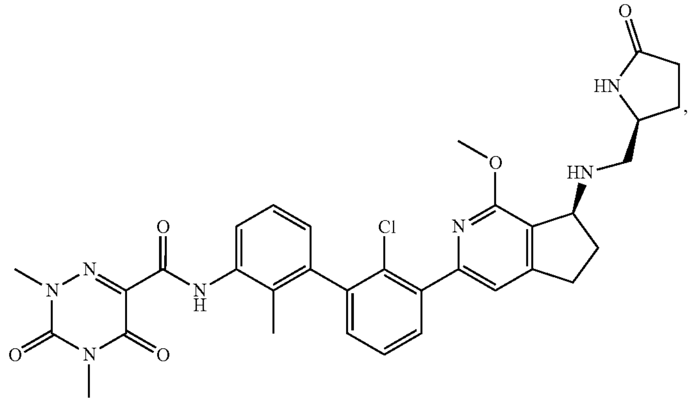
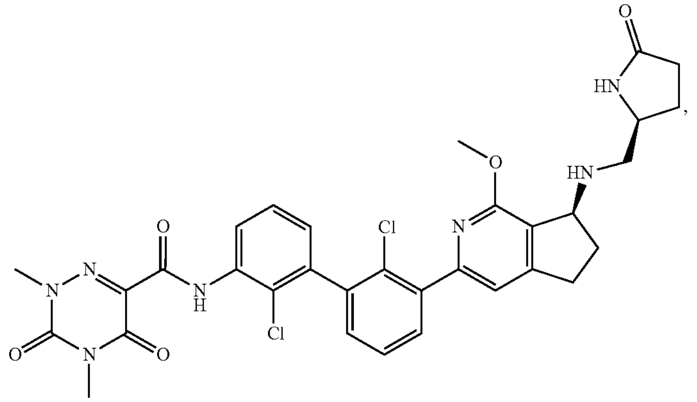

-continued
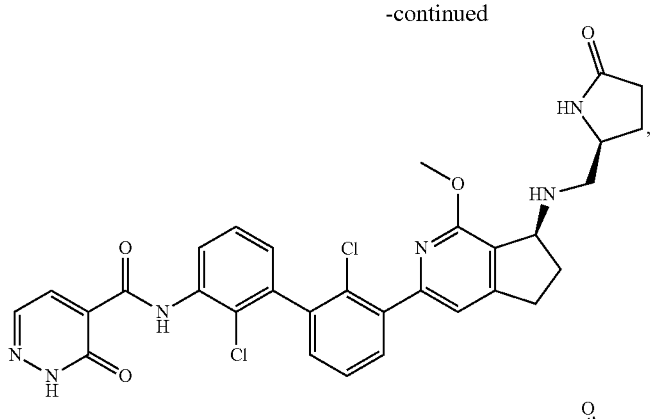
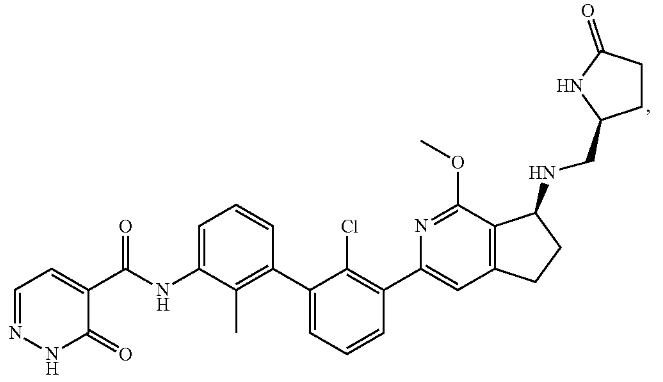
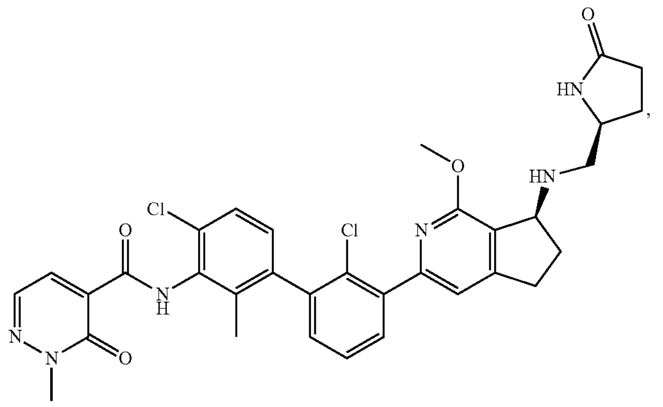
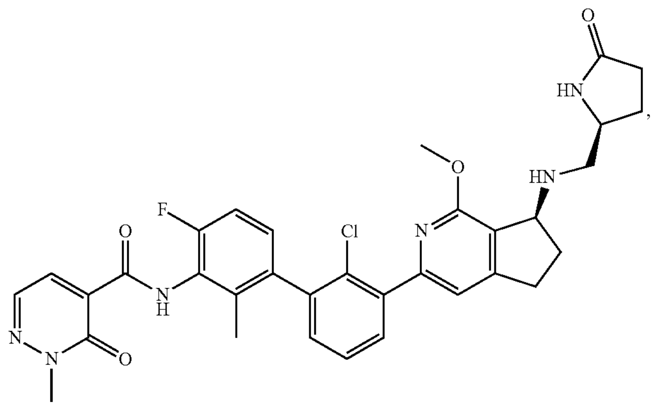

-continued
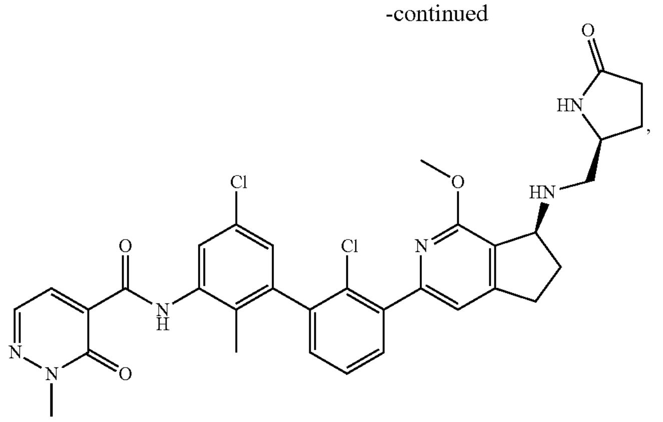
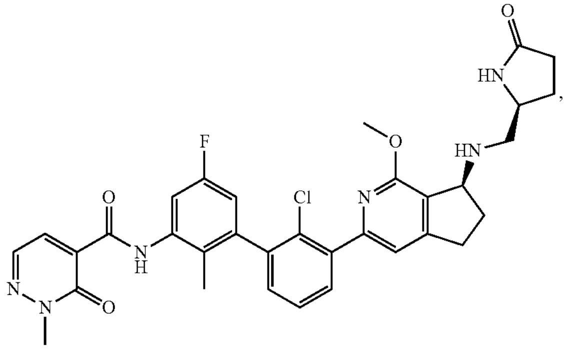 [SMILES: COc1nc(-c2cccc(-c3cc(F)cc(NC(=O)c4ccnn(C)c4=O)c3C)c2Cl)cc2c1[C@@H](NC[C@@H]1CCC(=O)N1)CC2]
-continued
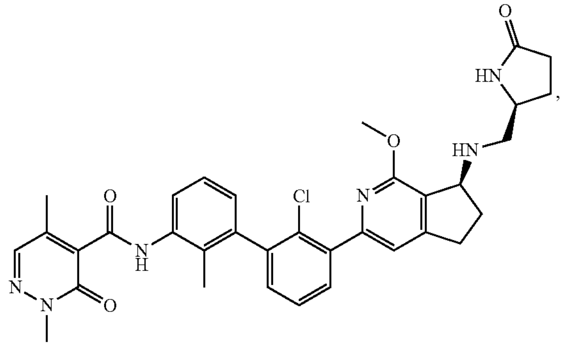
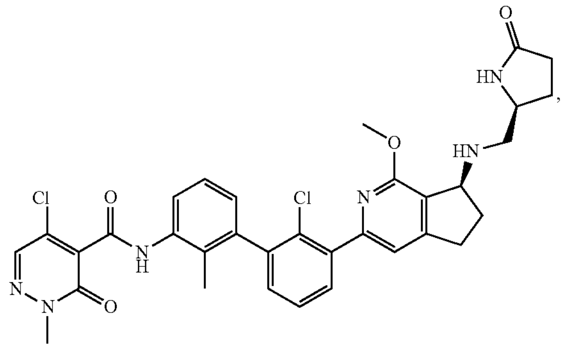
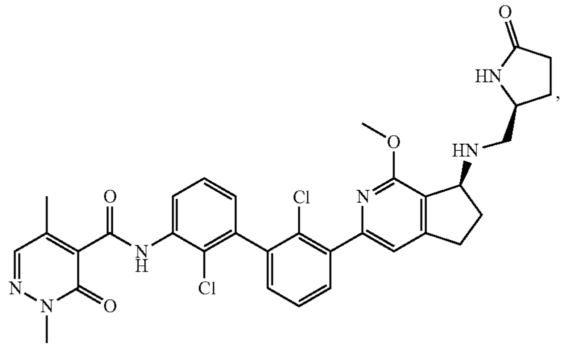
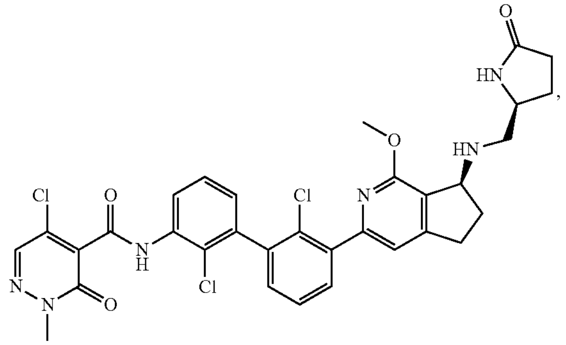
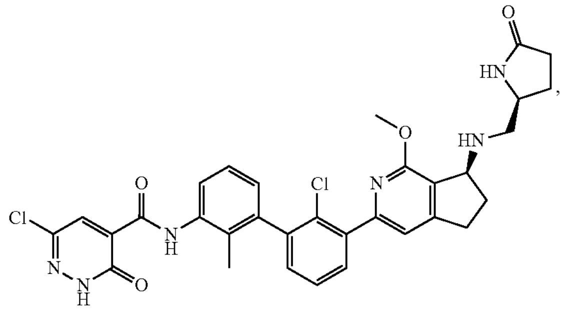

-continued
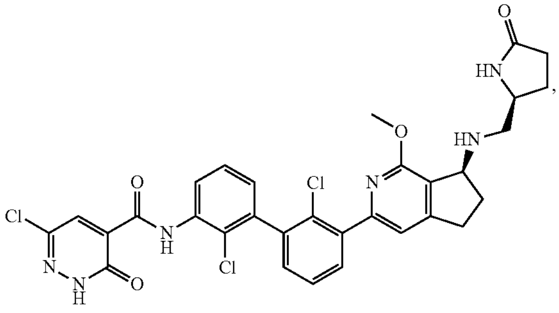
,
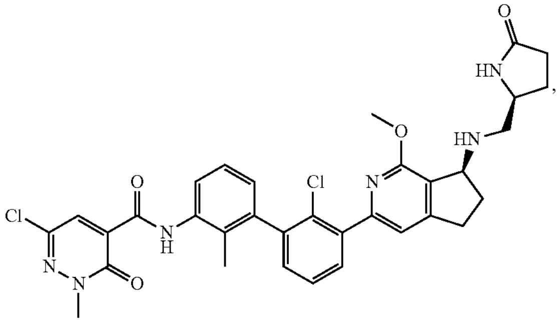
,
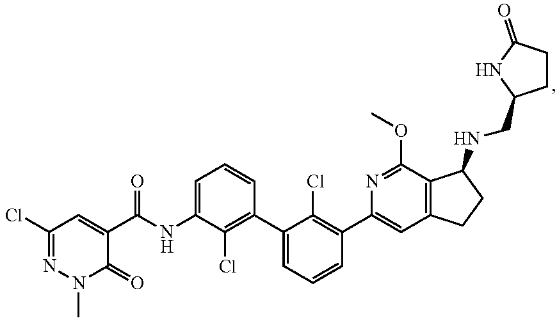
,
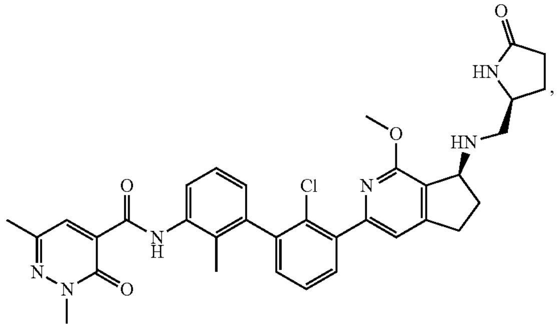
,
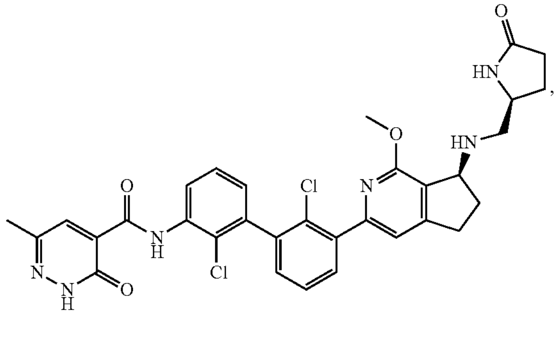
,
-continued
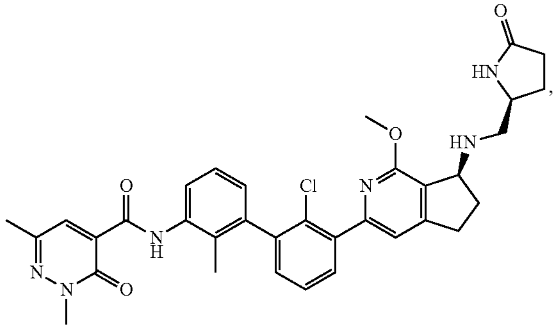
,
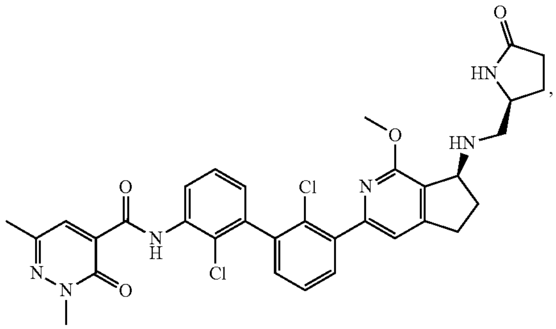
,
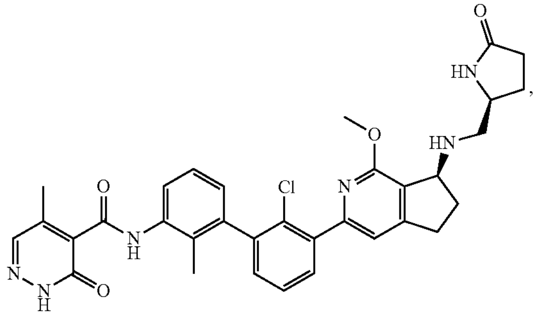
,
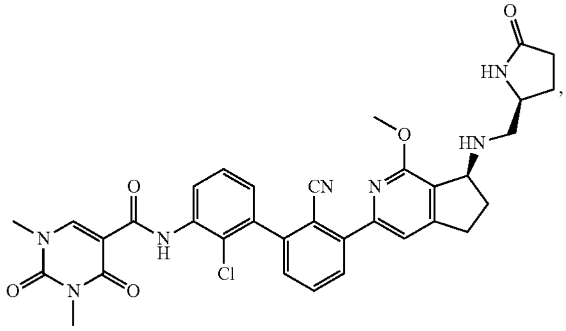
,
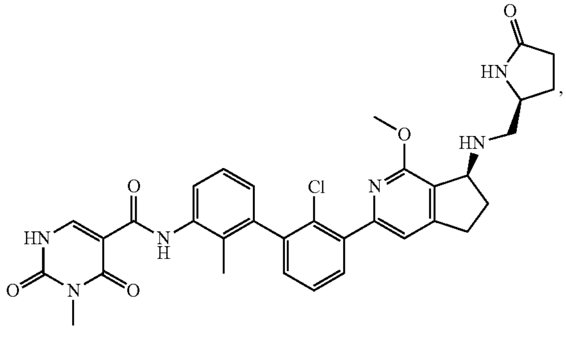
, -continued
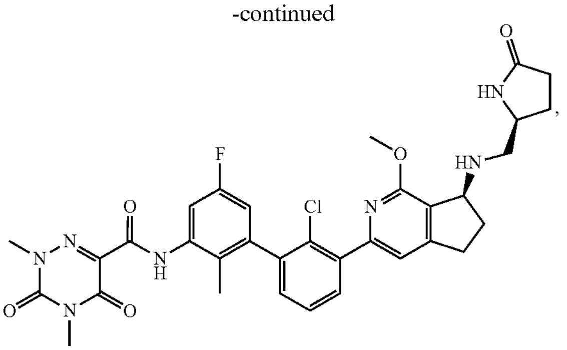
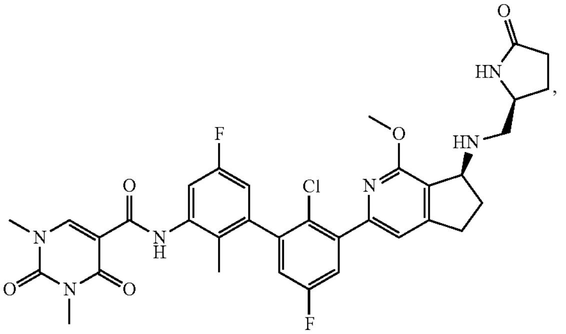
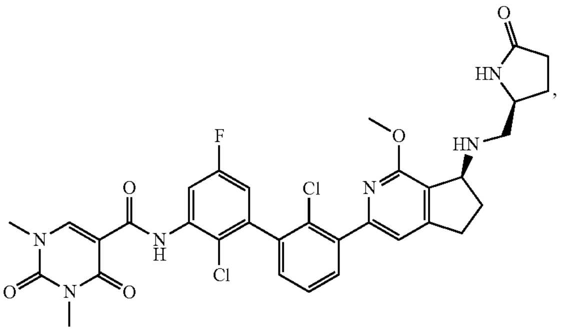
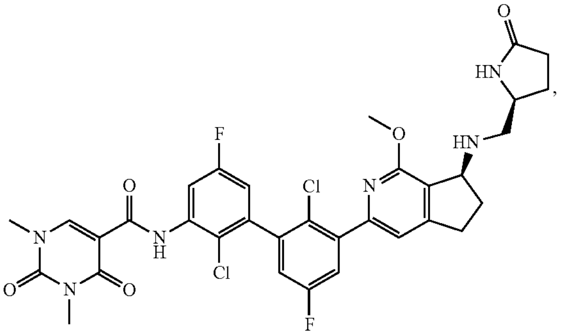
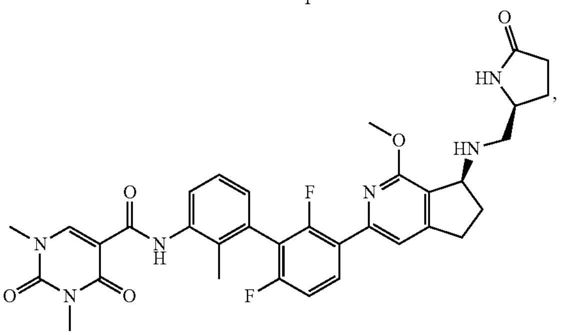
-continued
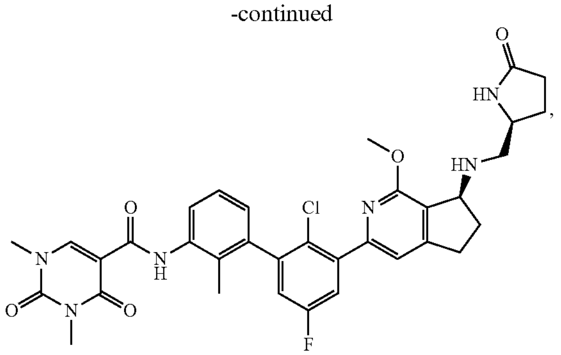
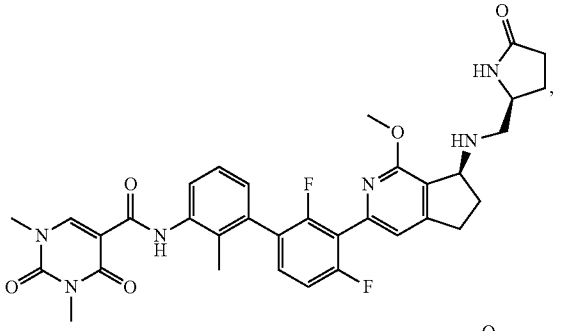
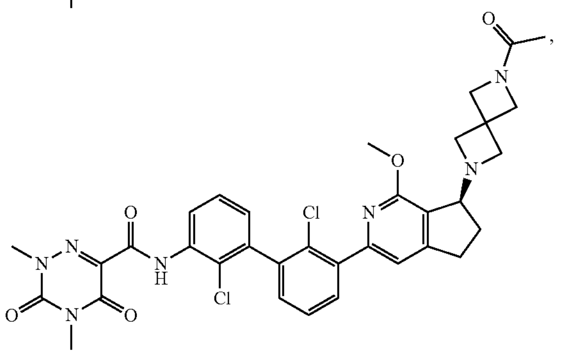
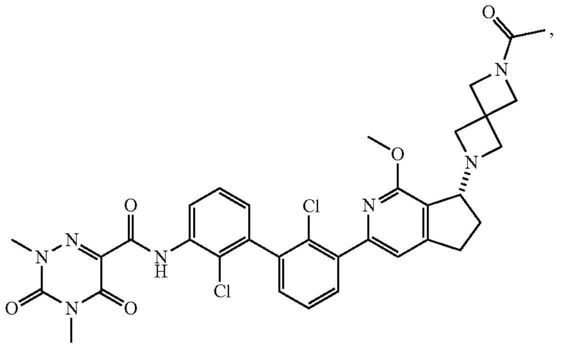
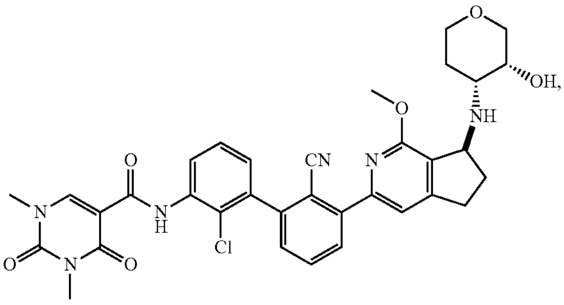

-continued
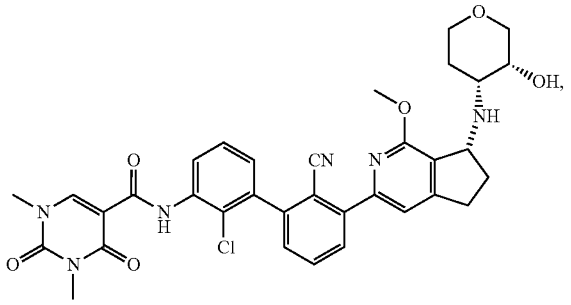
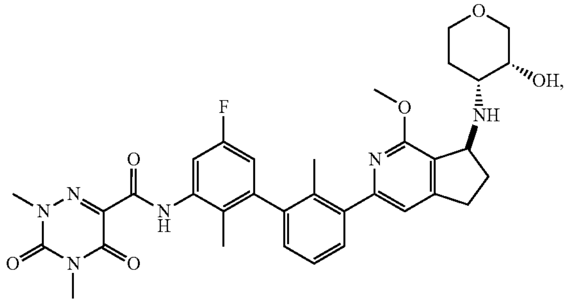
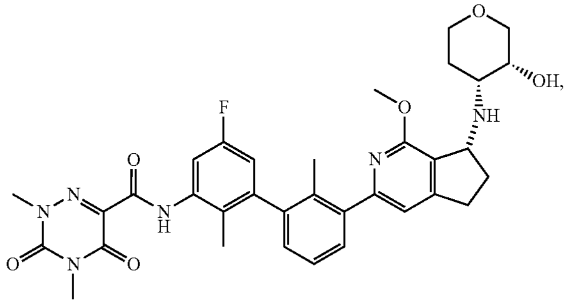
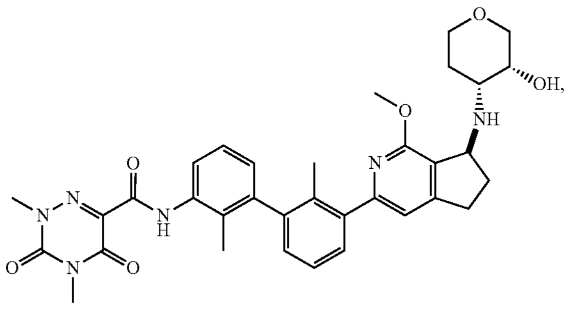
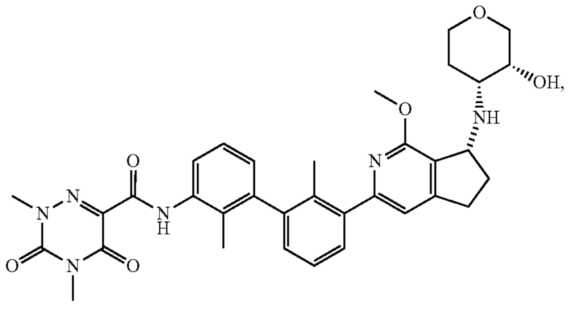
-continued
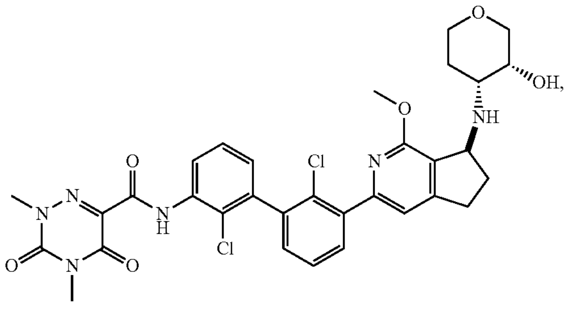
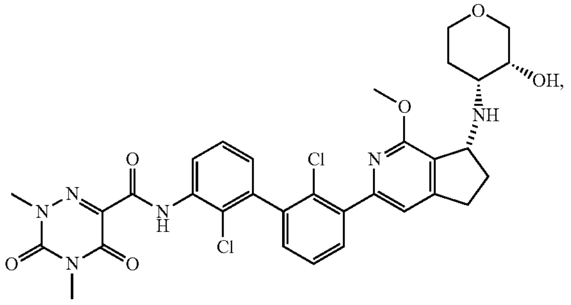
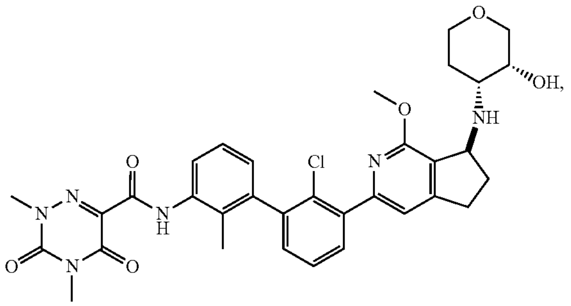
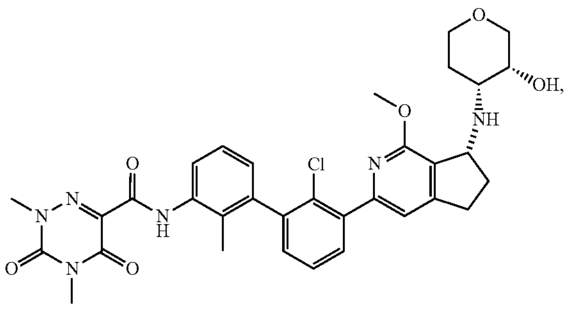
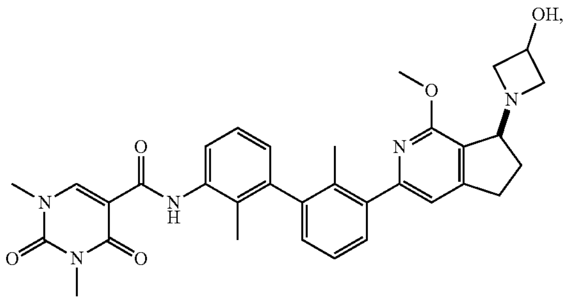

-continued
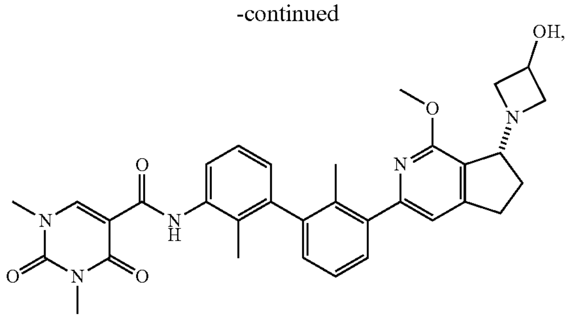
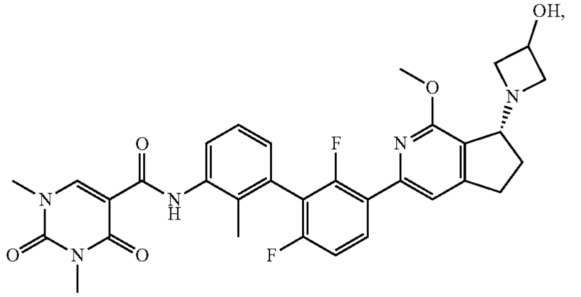
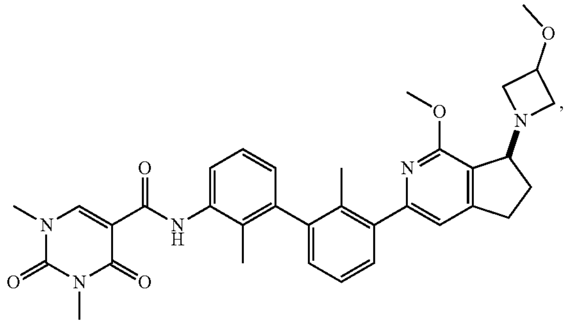
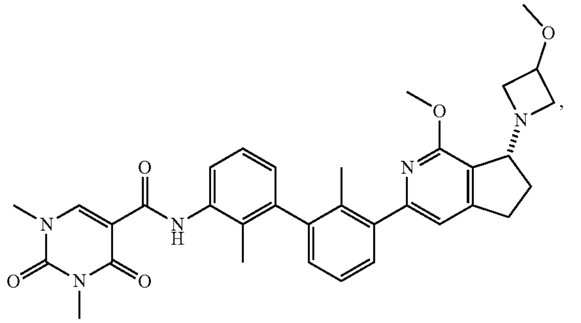
-continued
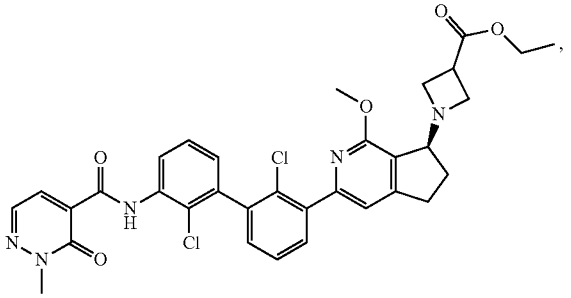
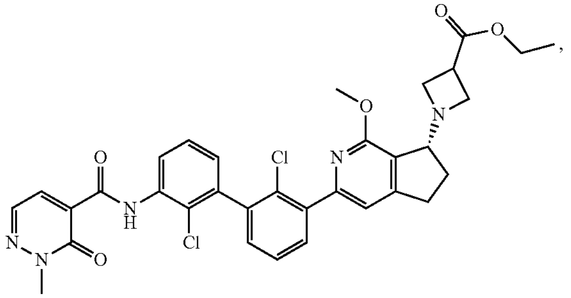
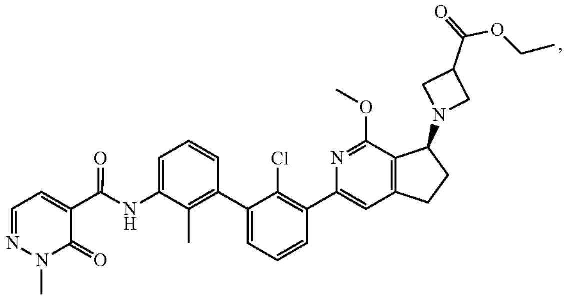
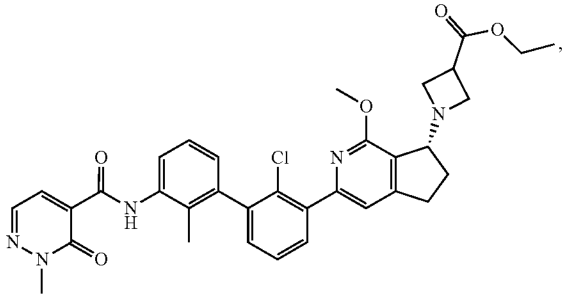 [SMILES: CCOC(=O)C1CN([C@@H]2CCc3cc(-c4cccc(-c5cccc(NC(=O)c6ccnn(C)c6=O)c5C)c4Cl)nc(OC)c32)C1]
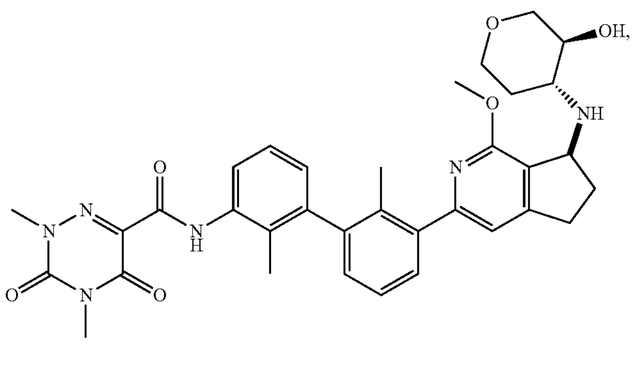

-continued
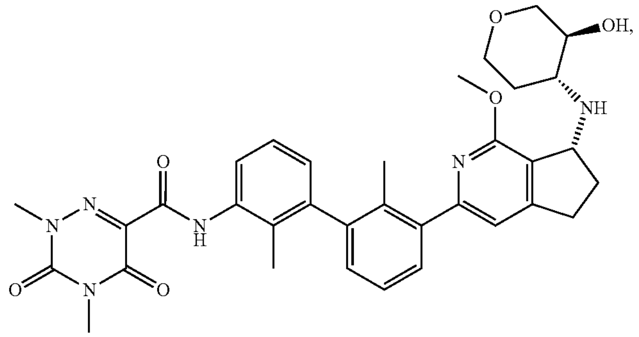
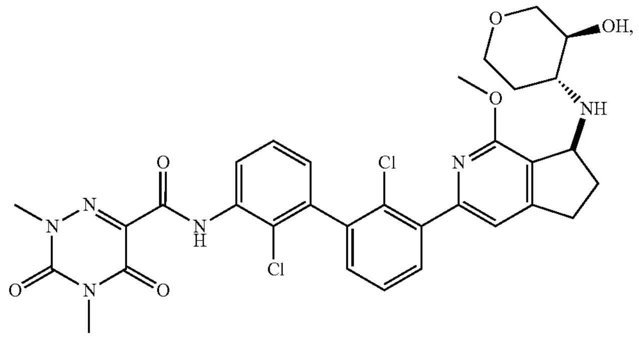
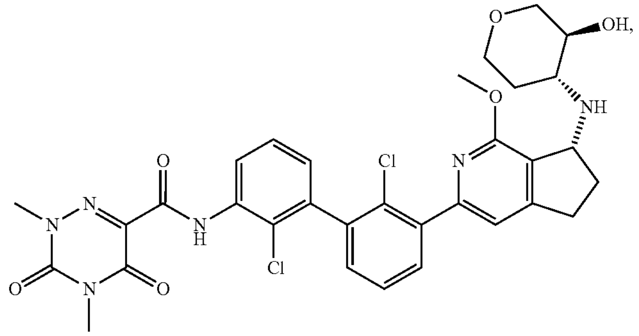
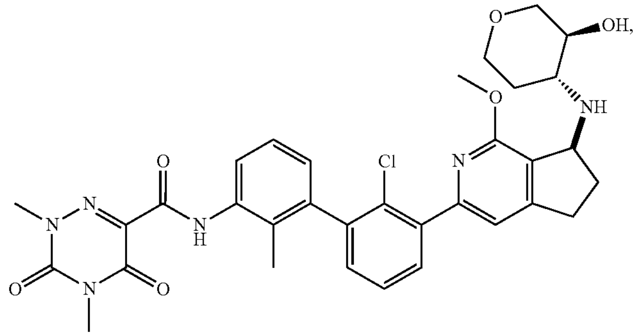
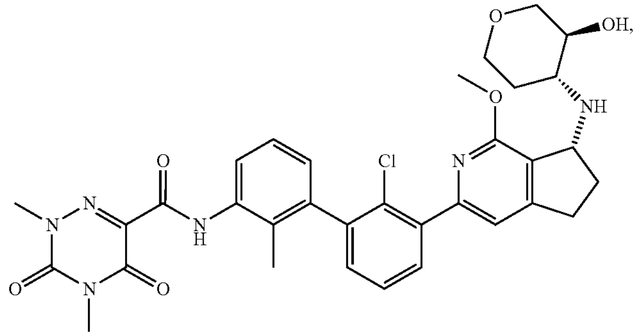

-continued
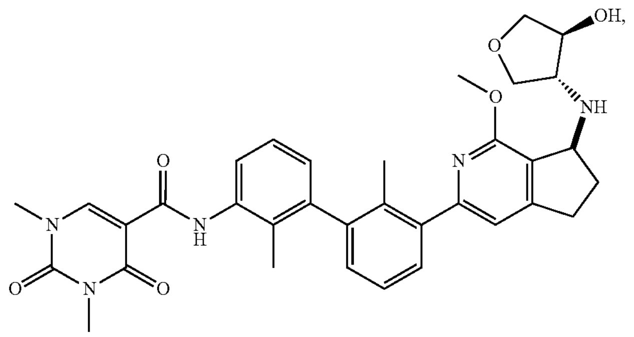
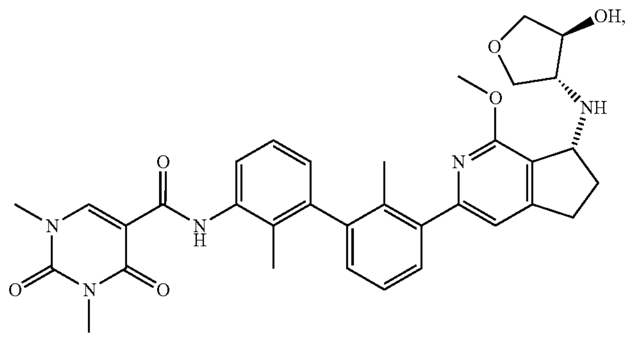
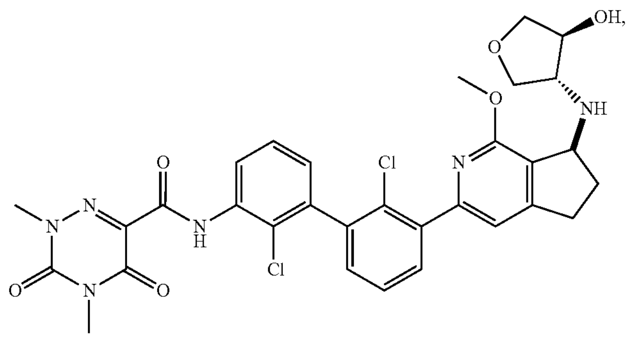
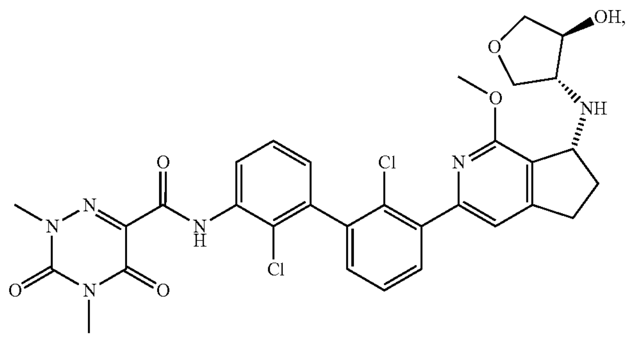
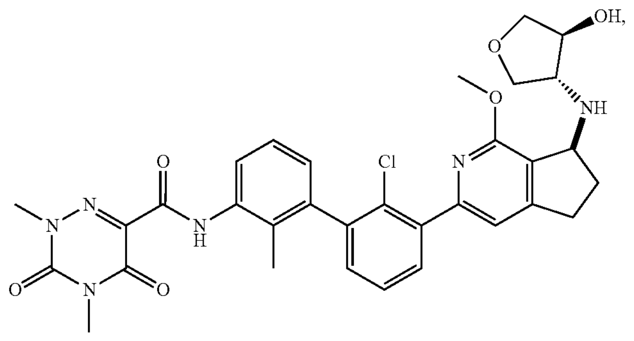

-continued
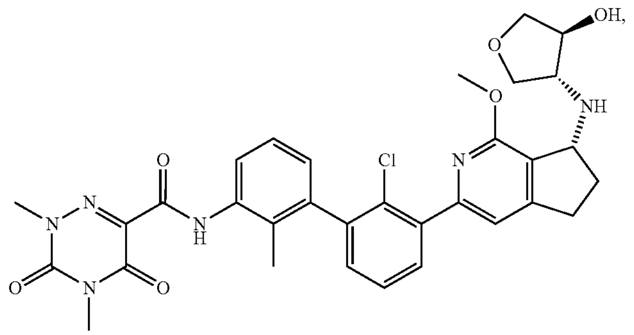
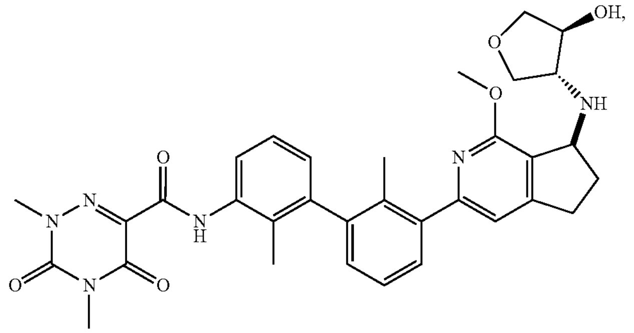
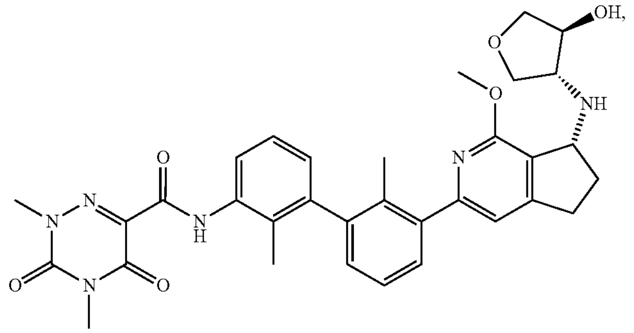
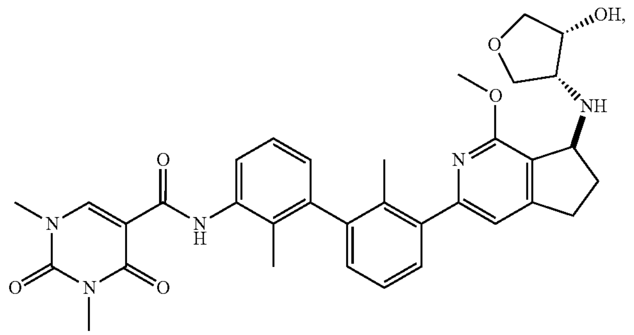
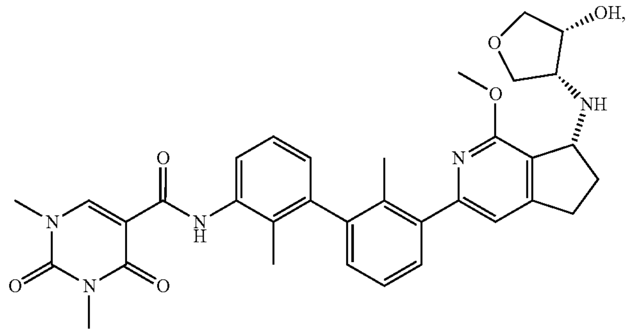

-continued
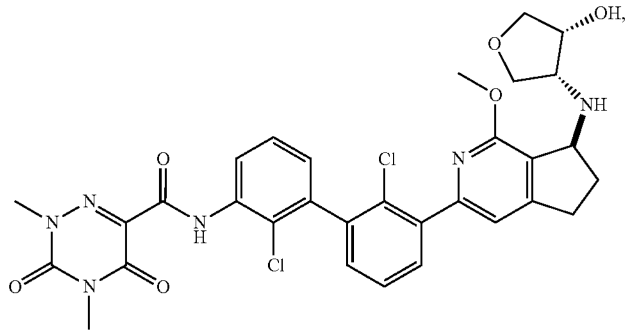
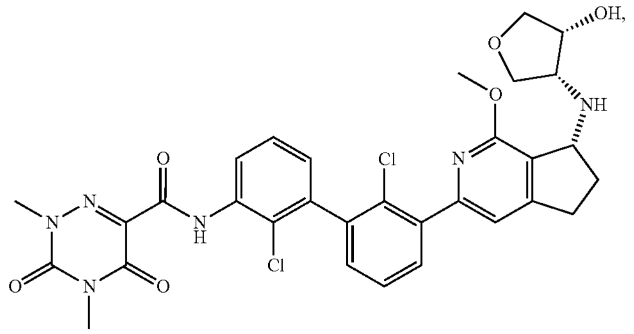
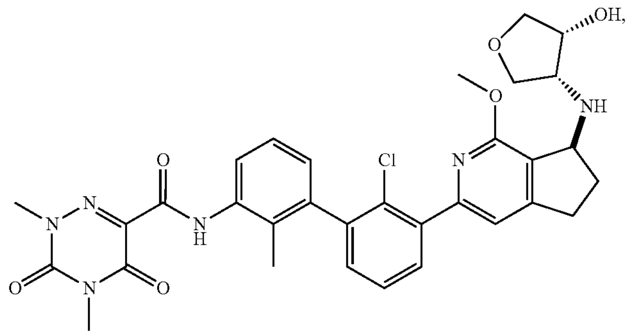
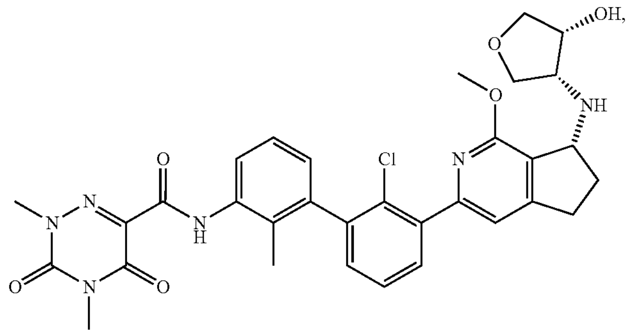
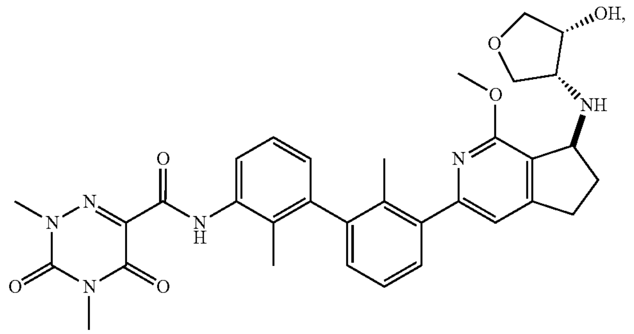

-continued
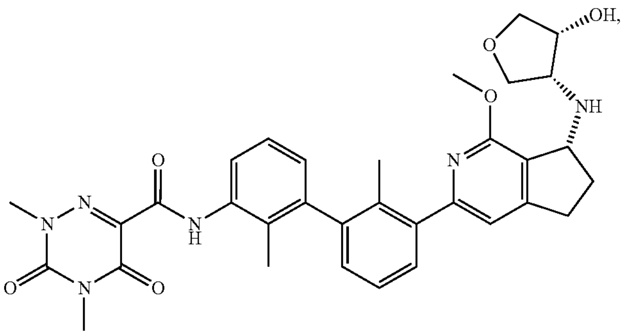
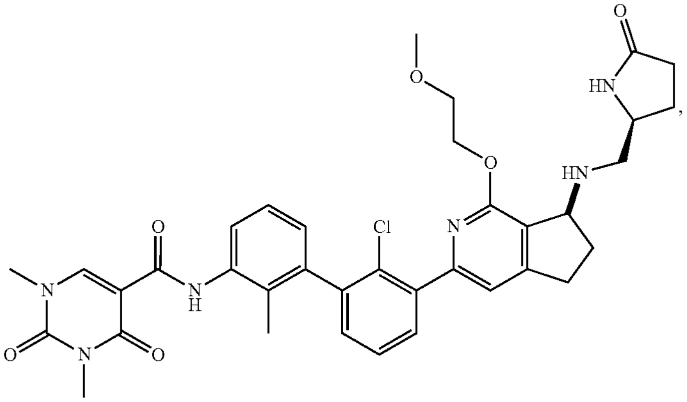
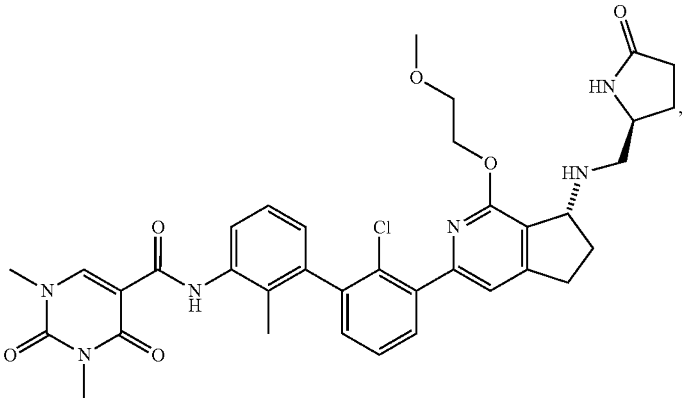
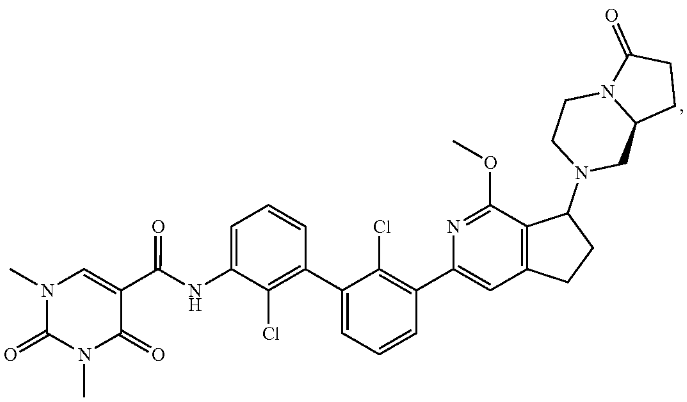

-continued
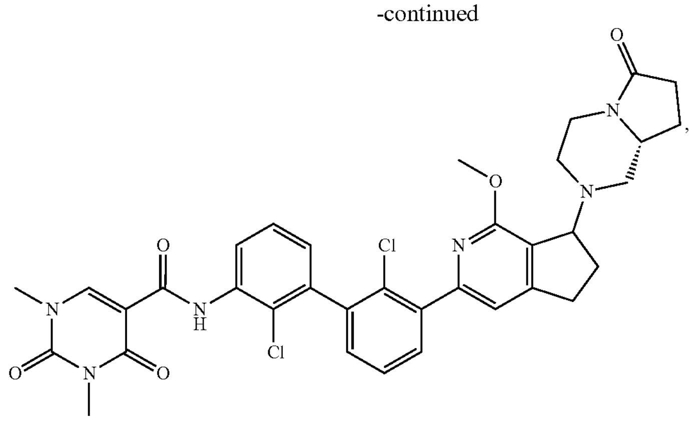
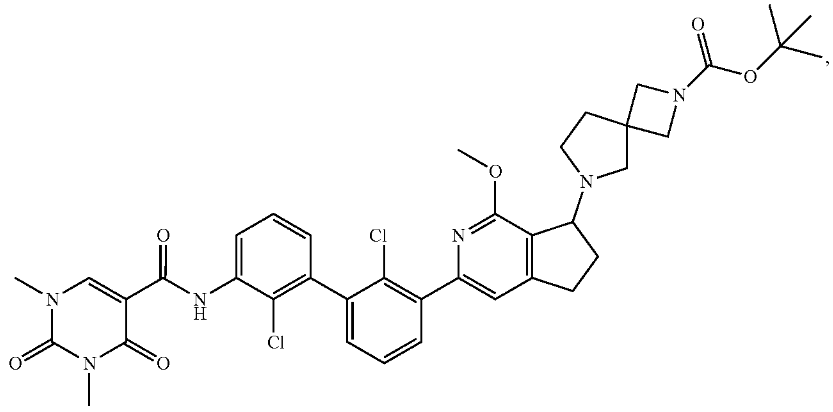
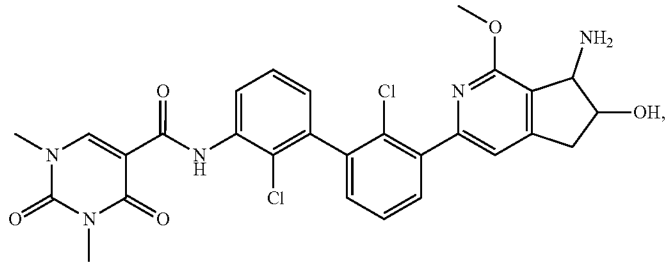
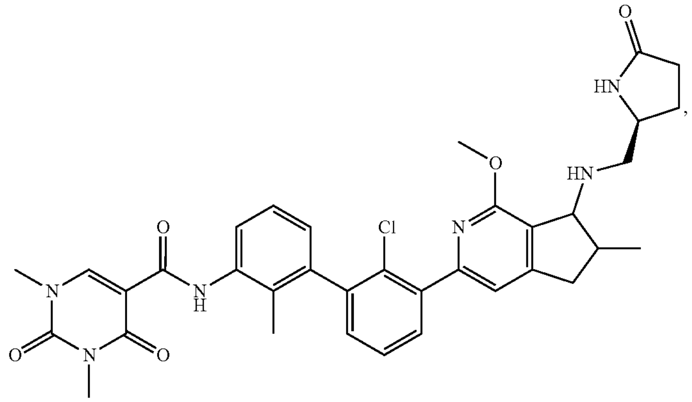

-continued
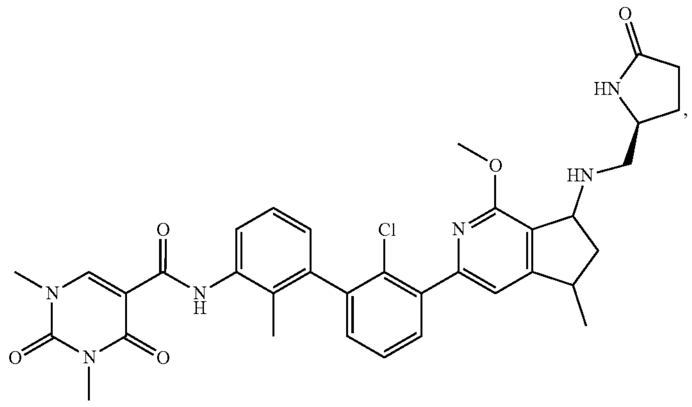
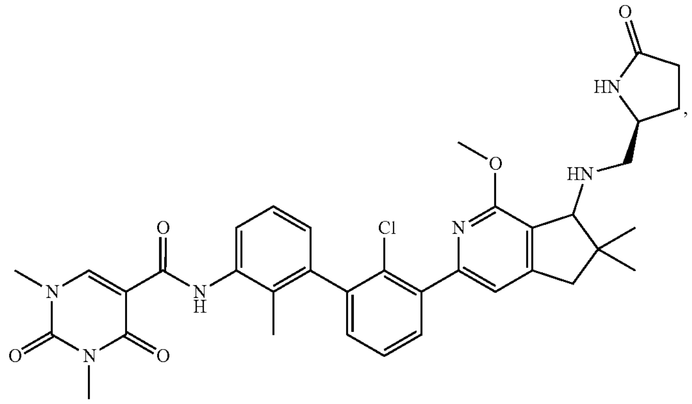
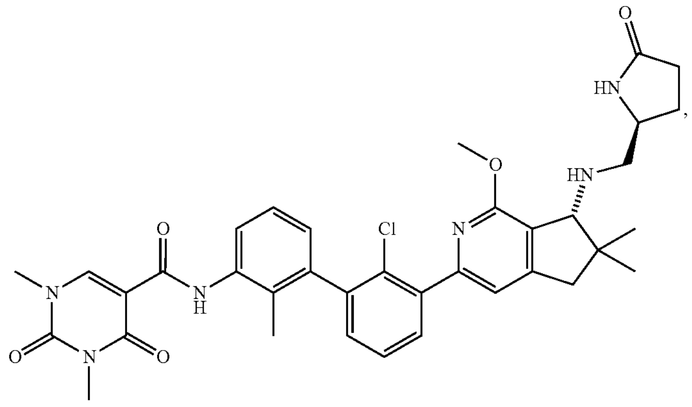
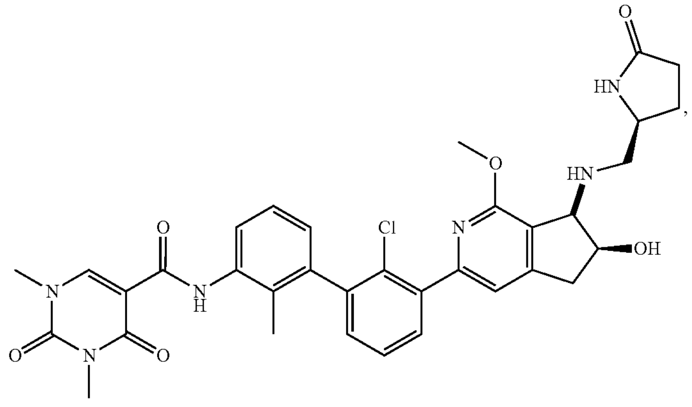

-continued
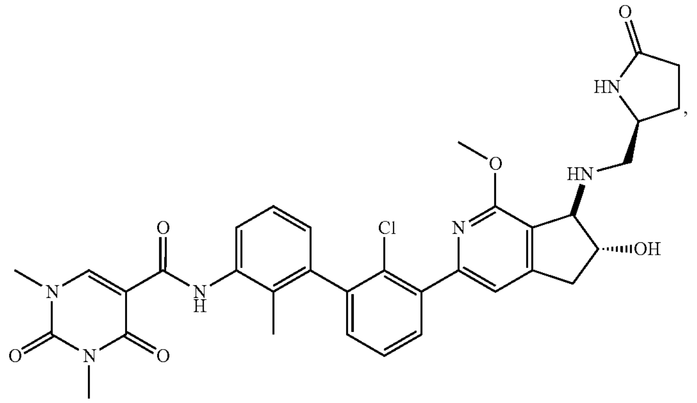
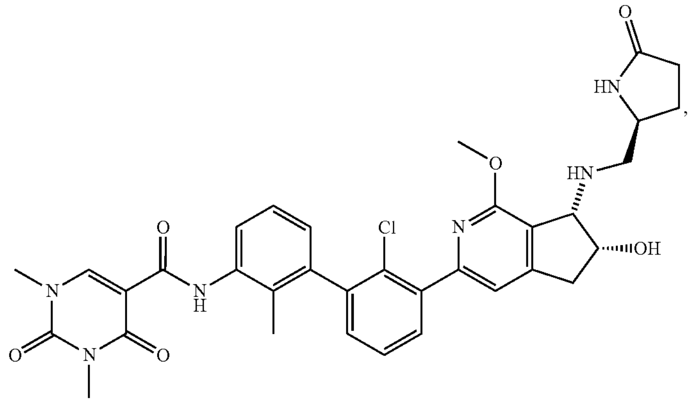
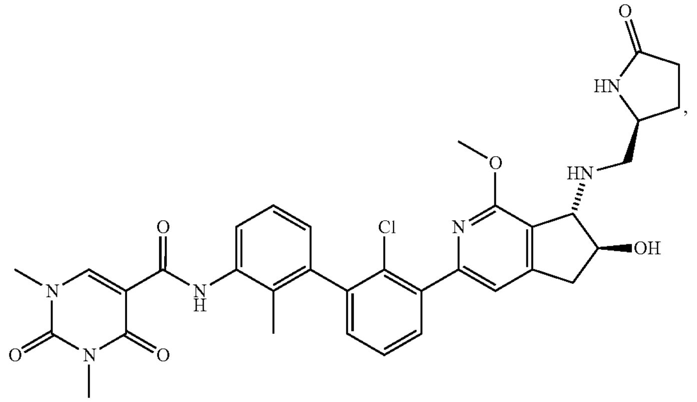
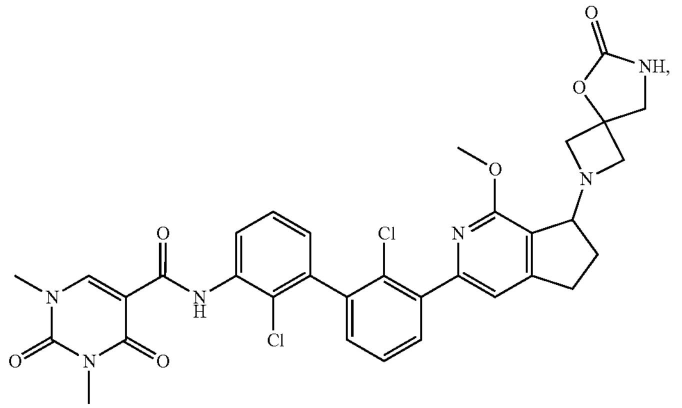

-continued
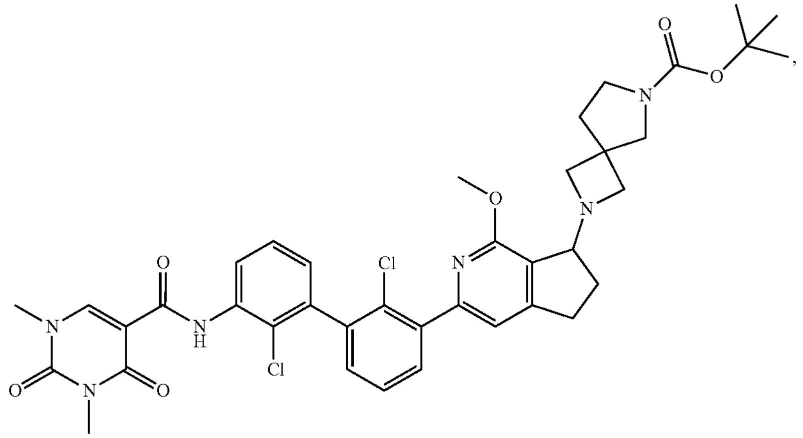
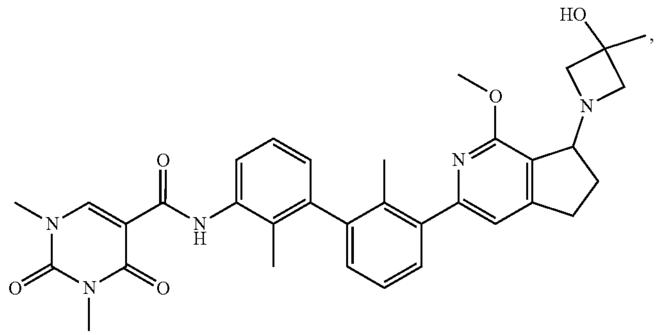
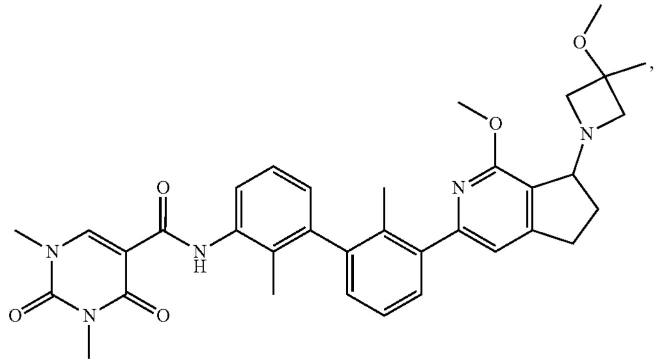
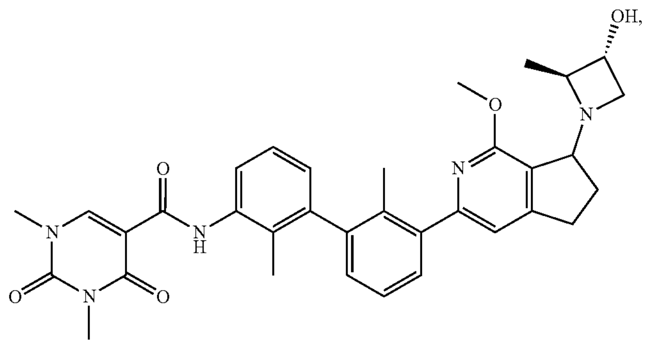

-continued
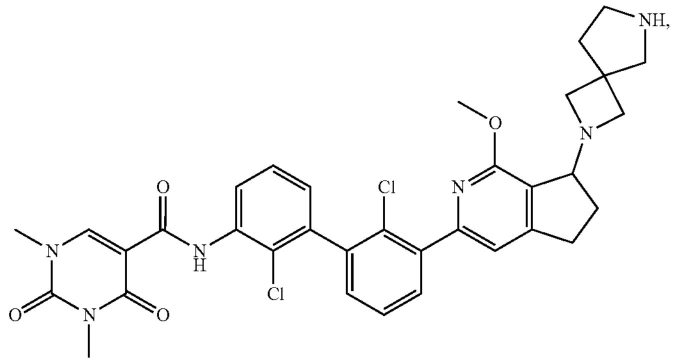
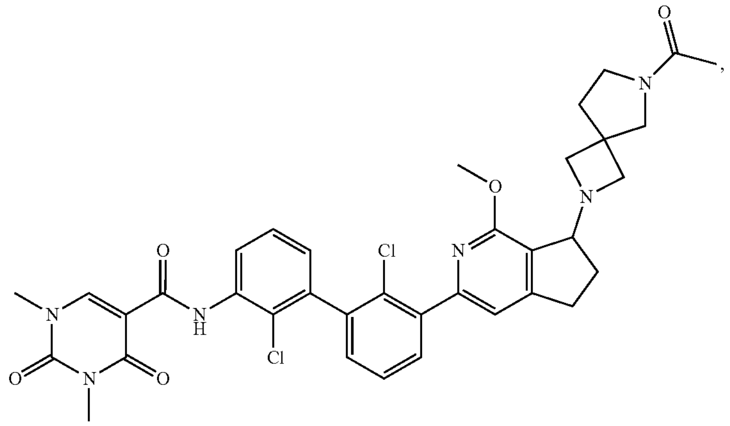
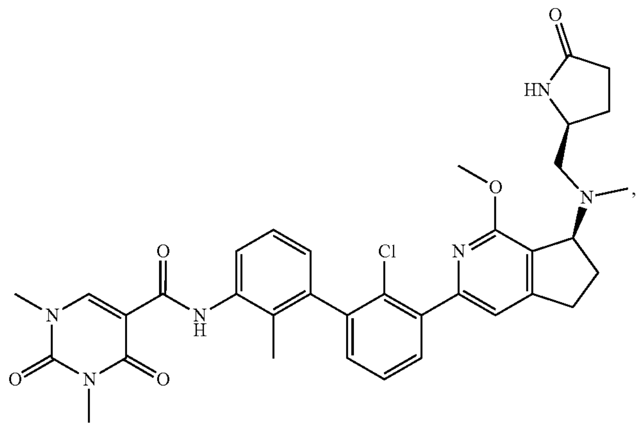
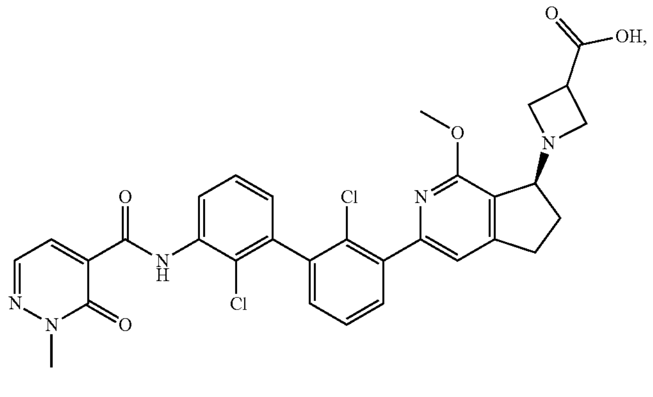

-continued
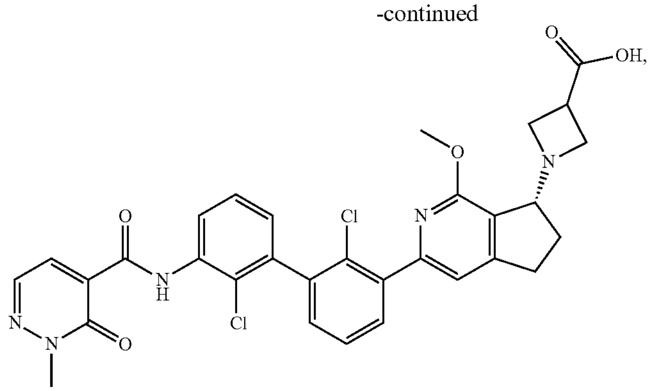
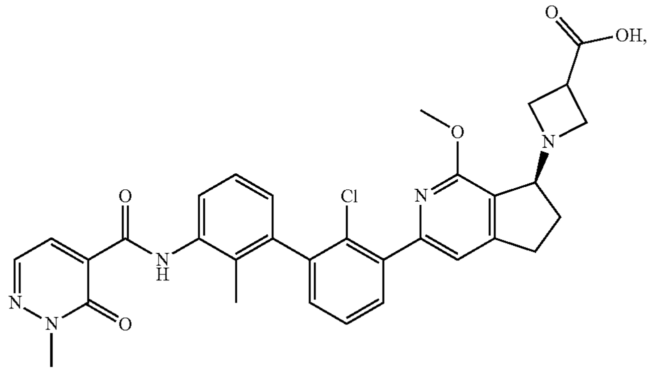
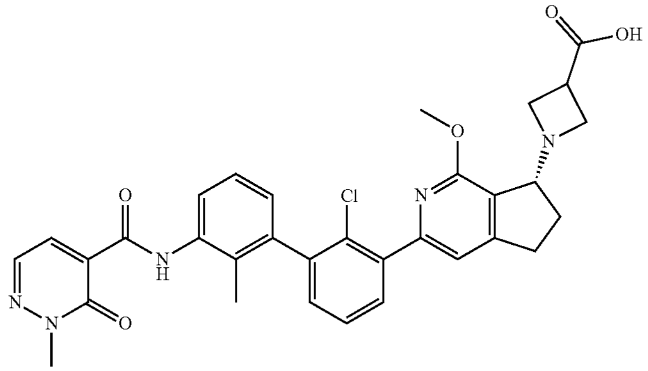
and
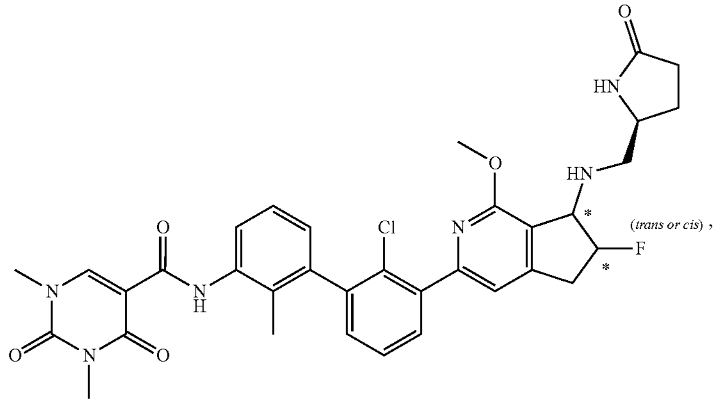 [SMILES: COc1nc(-c2cccc(-c3cccc(NC(=O)c4cn(C)c(=O)n(C)c4=O)c3C)c2Cl)cc2c1C(NC[C@@H]1CCC(=O)N1)C(F)C2]
or a pharmaceutically acceptable salt of any of the foregoing.

Embodiment 145
The compound of Embodiment 1 selected from:
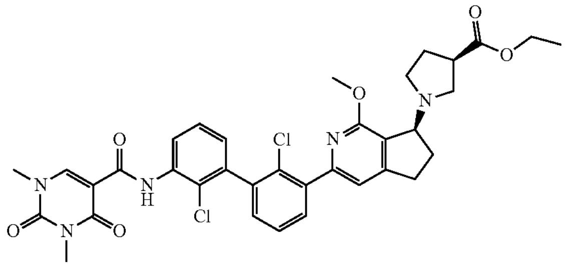
,
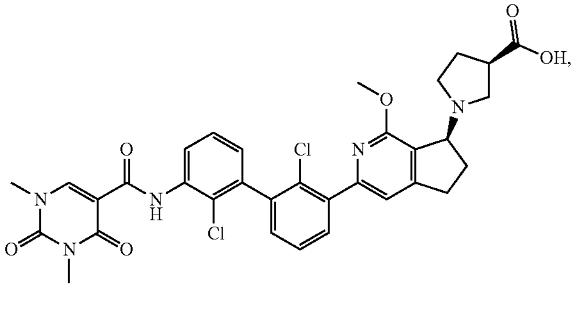
,
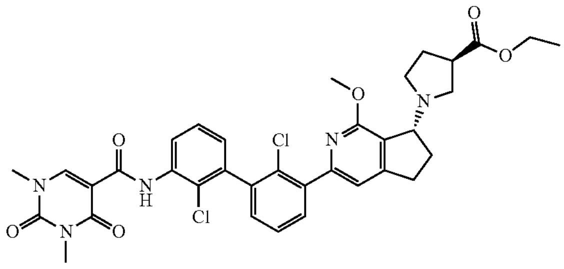
,
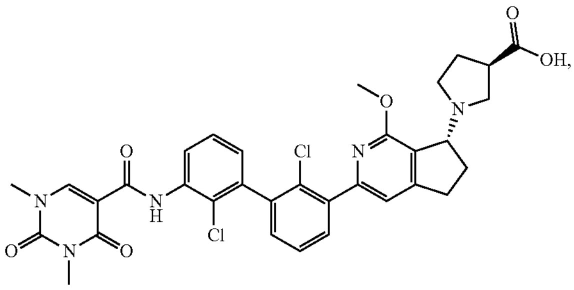
,
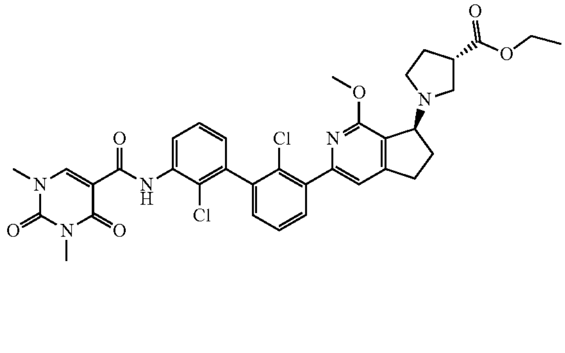
,
-continued
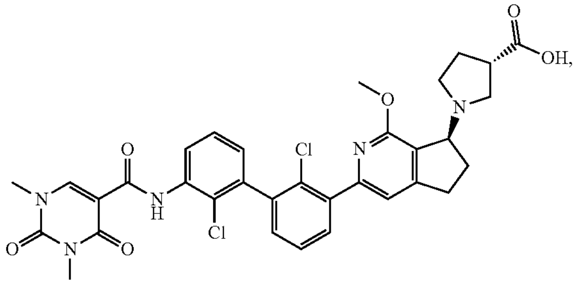
,
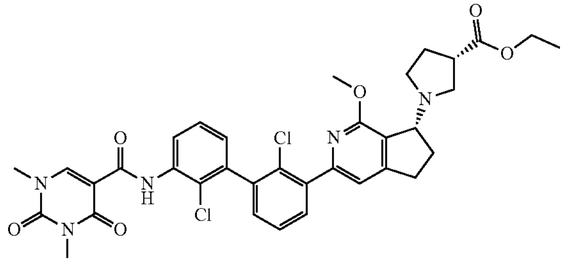
,
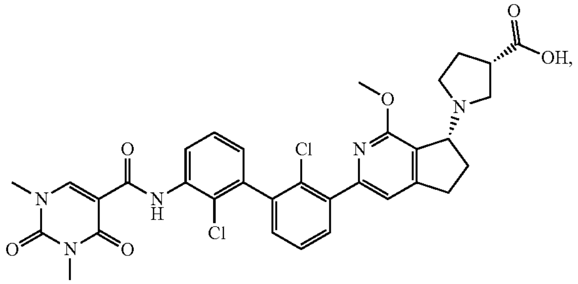
,
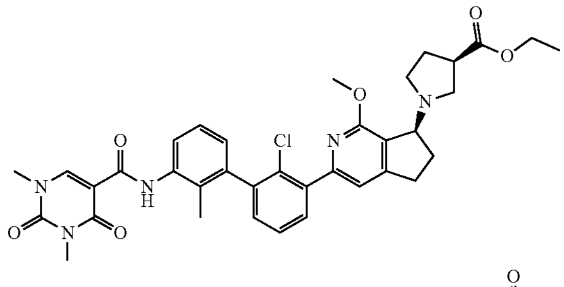
,
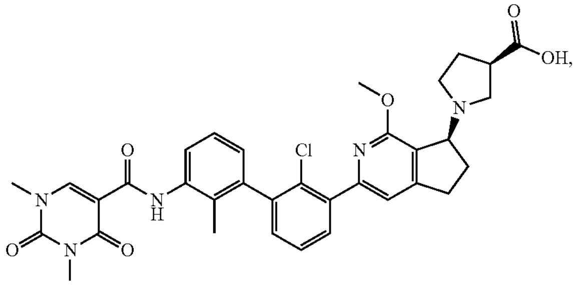
,
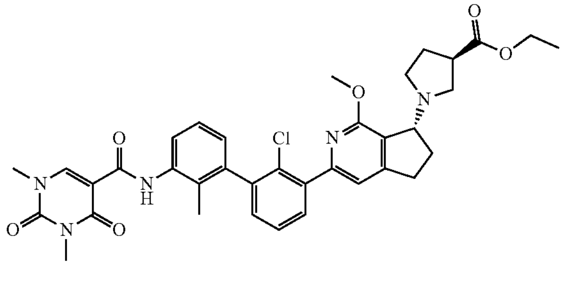
, -continued
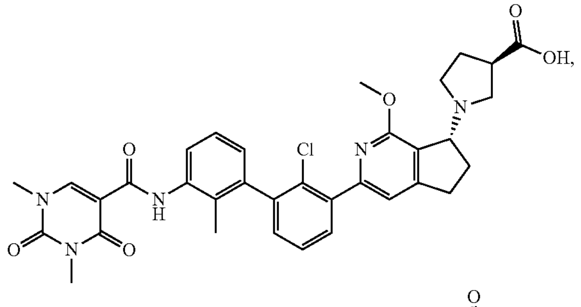
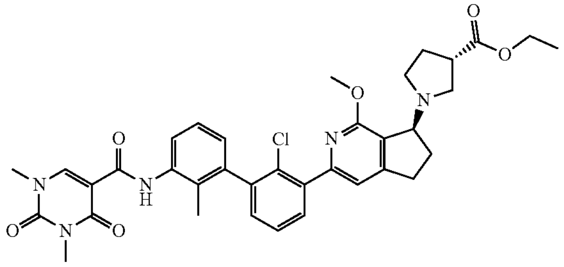
,
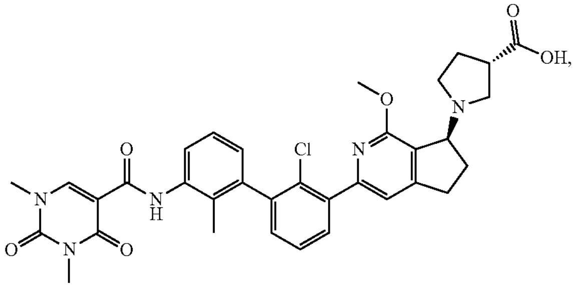
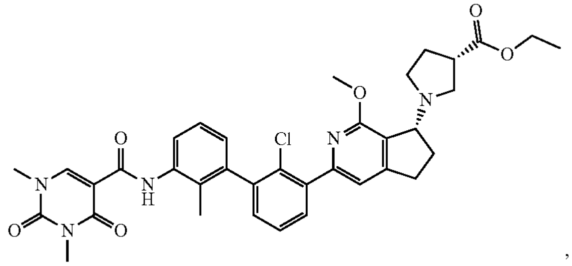
,
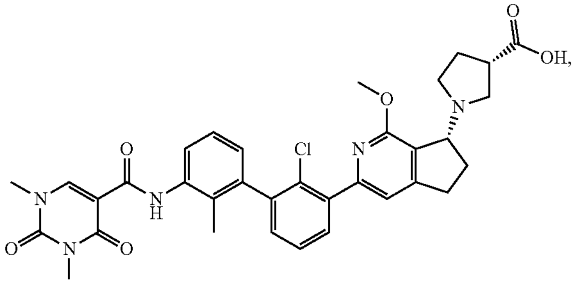
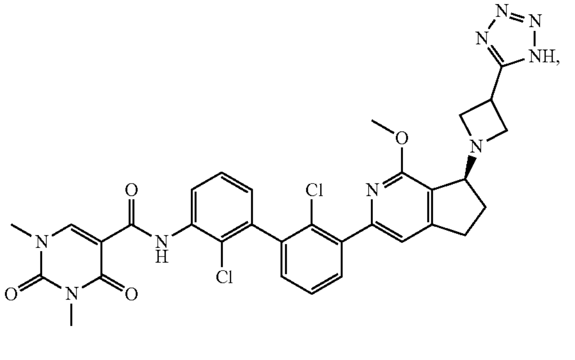
-continued
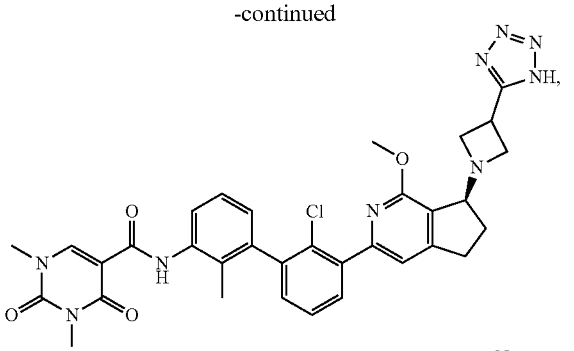
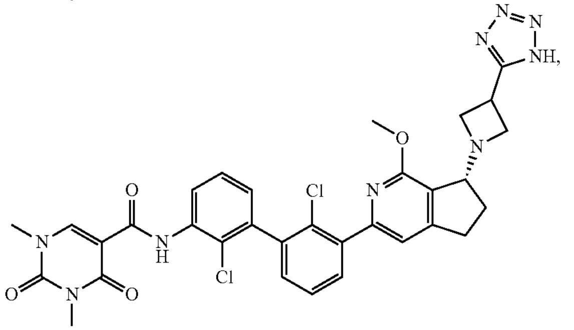
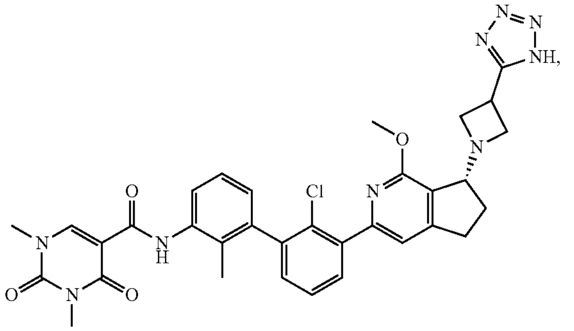
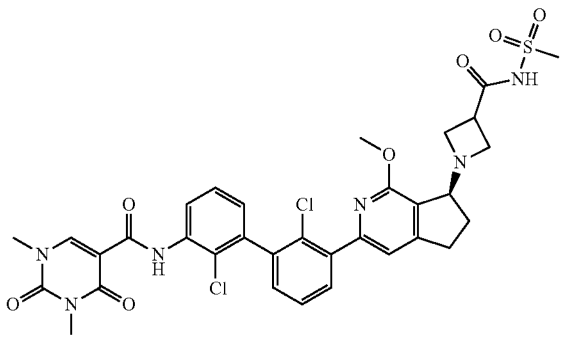
,
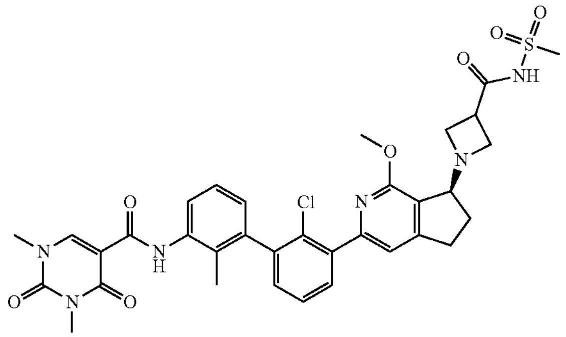
, -continued
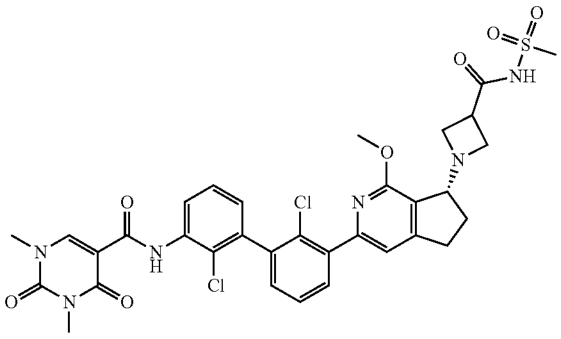
,
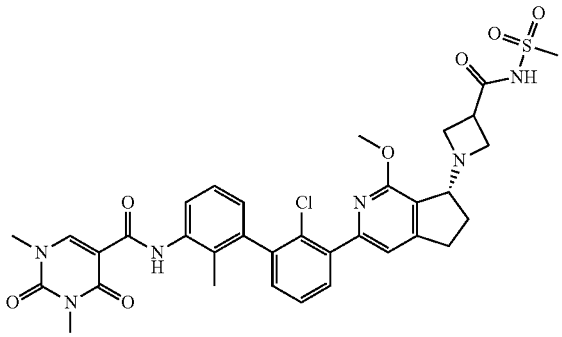
,
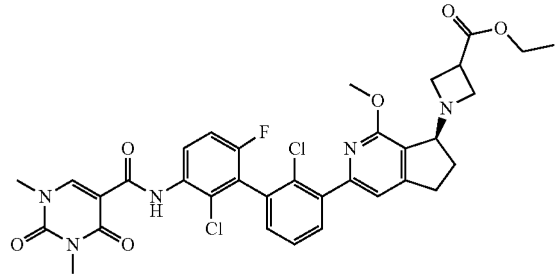
,
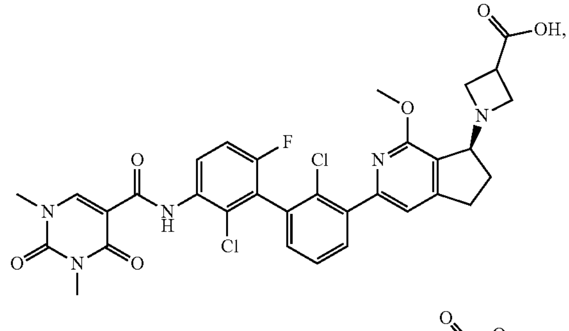
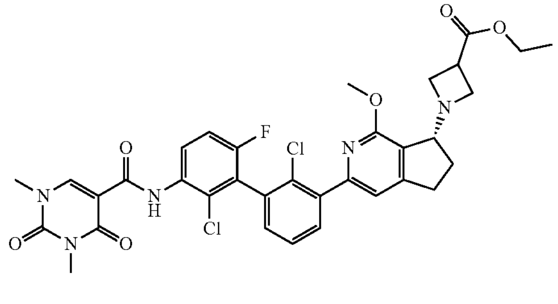
,
-continued
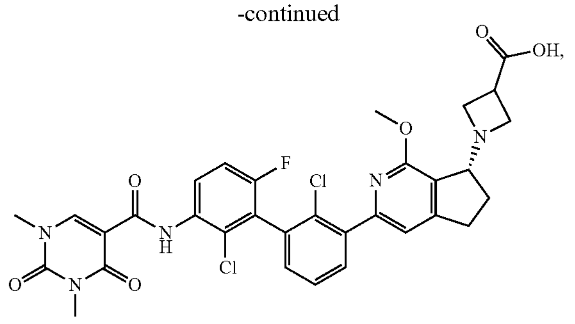
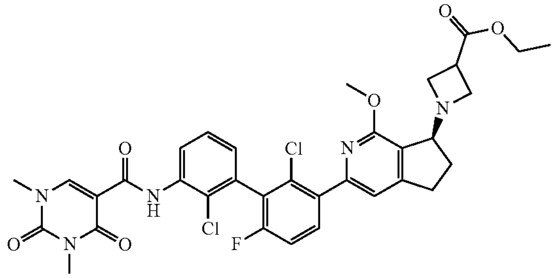
,
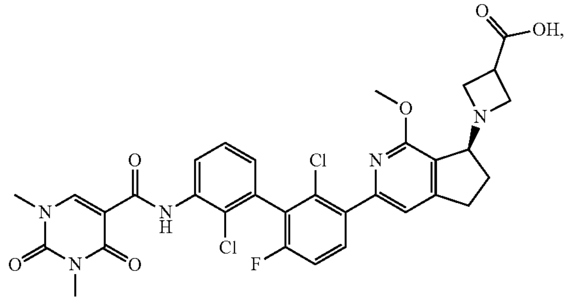
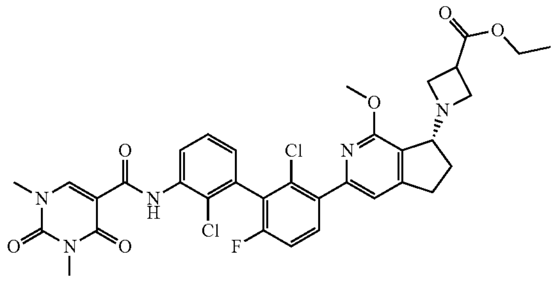
,
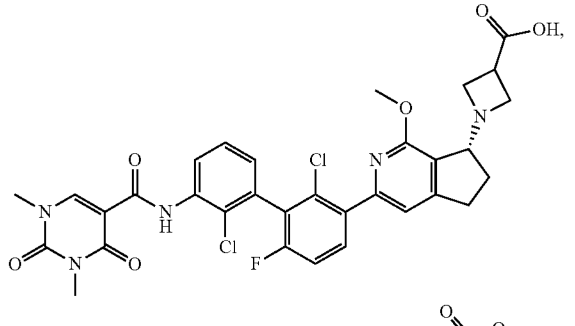
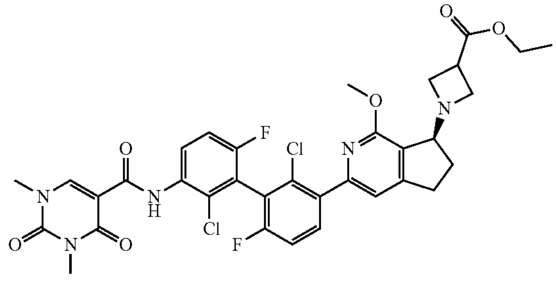
, -continued
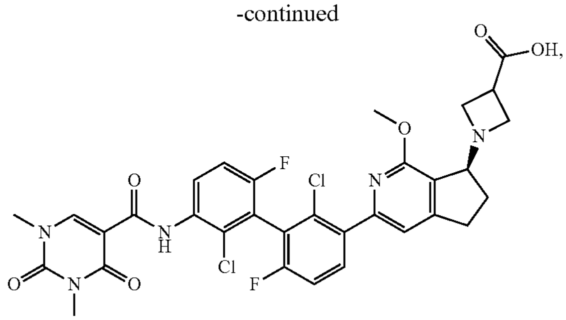
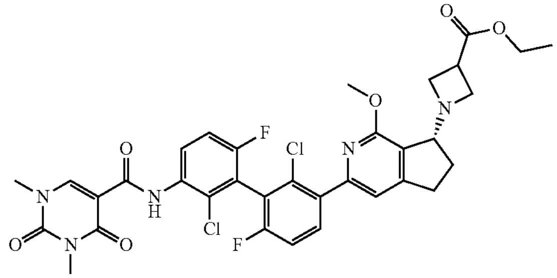
,
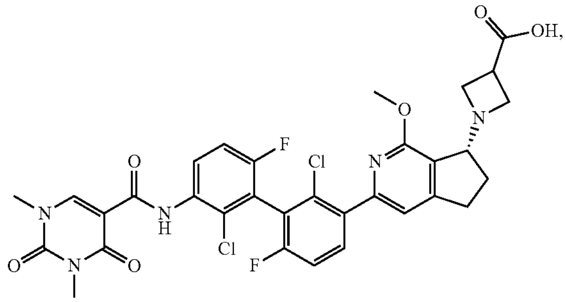
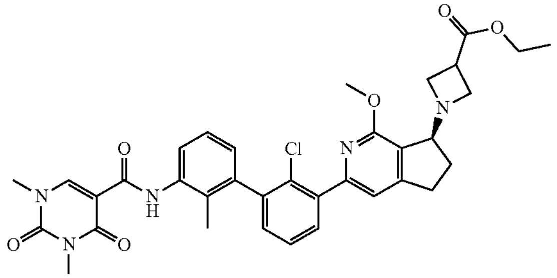
,
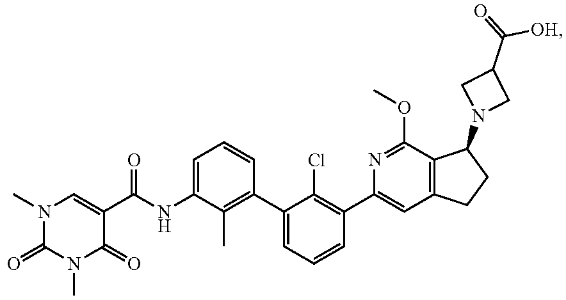
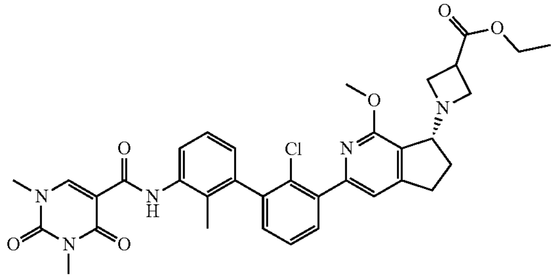
,
-continued
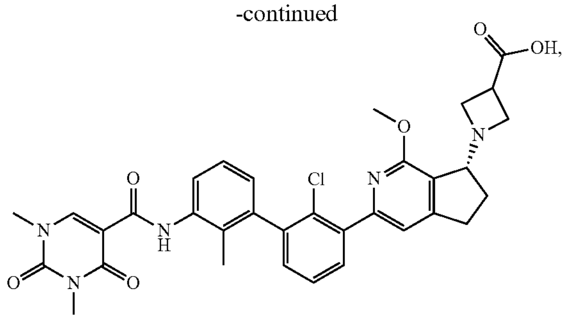
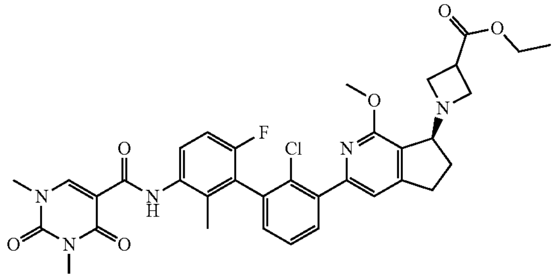
,
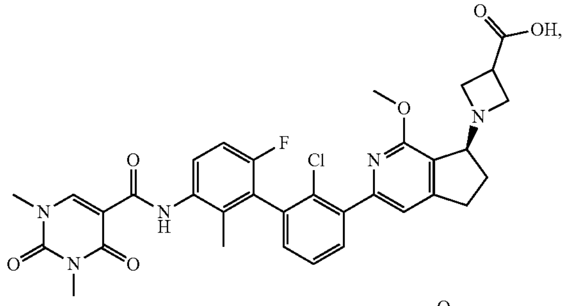
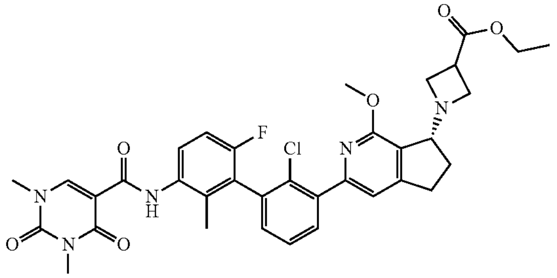
,
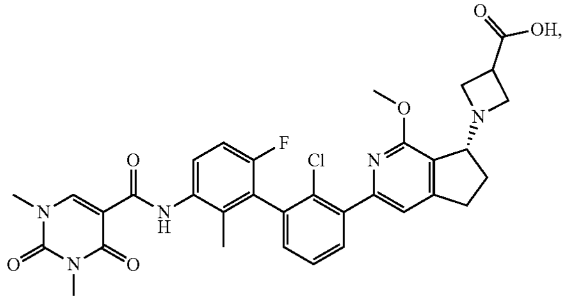
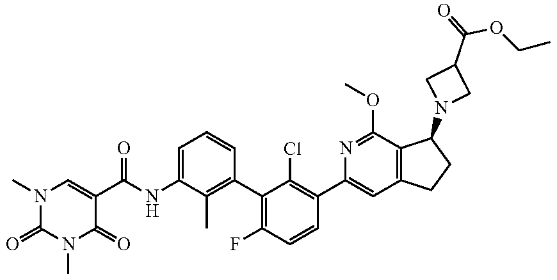
, -continued
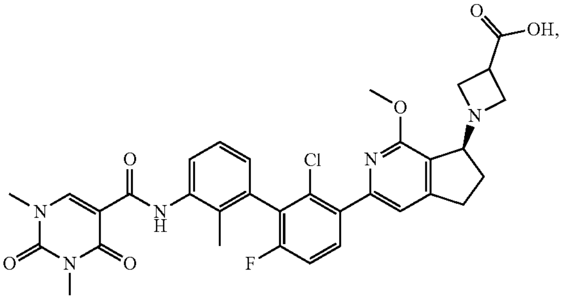
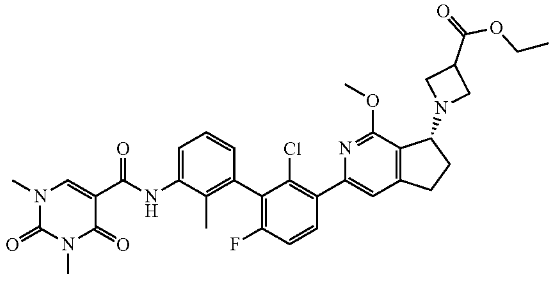
,
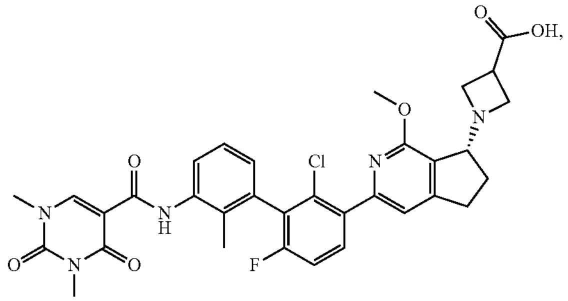
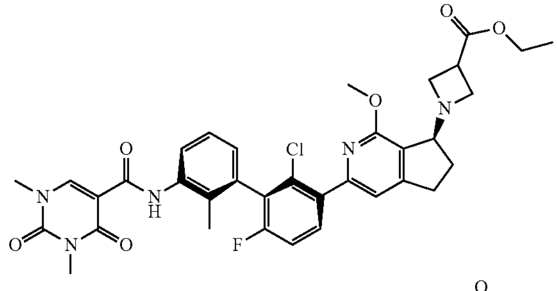
,
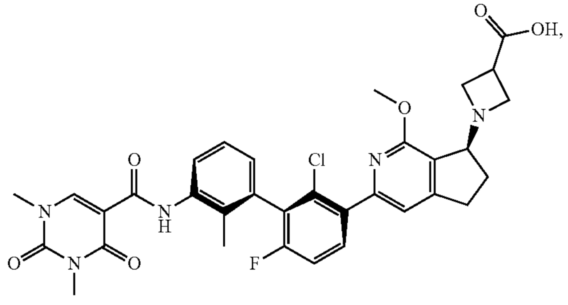
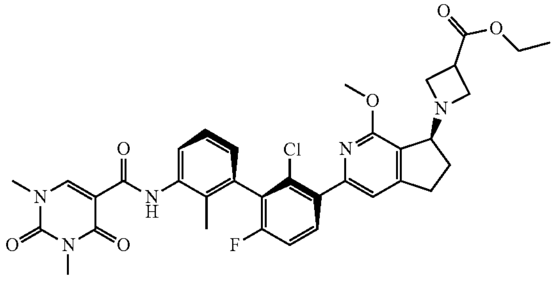
,
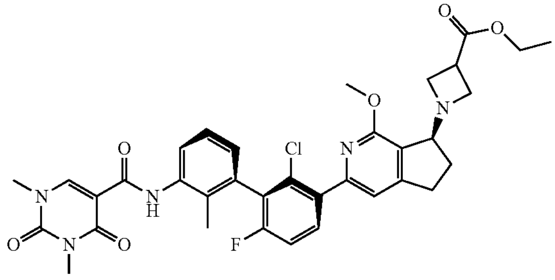
,
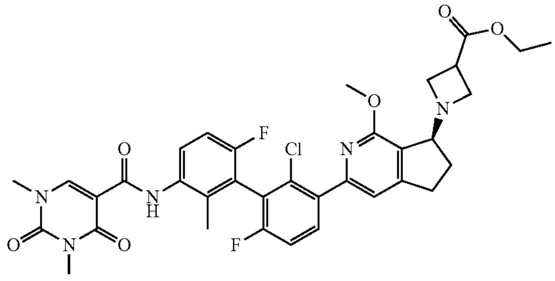
,
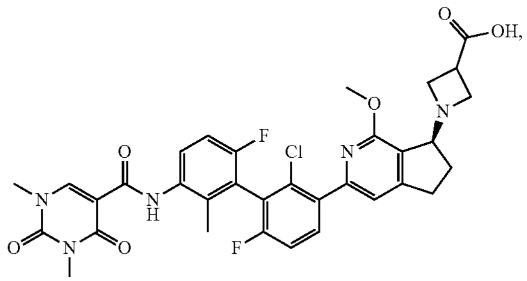
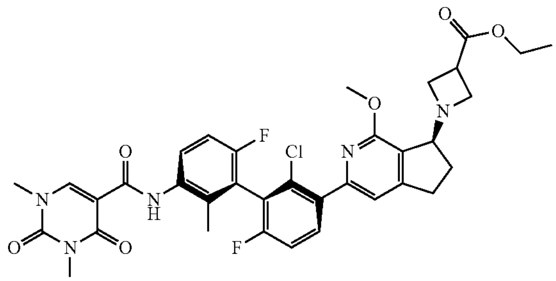
,
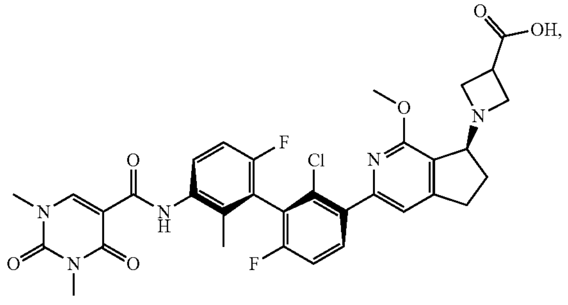

-continued
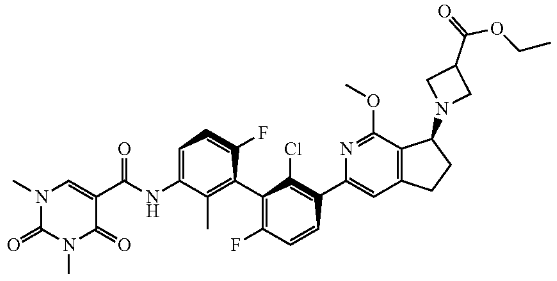
,
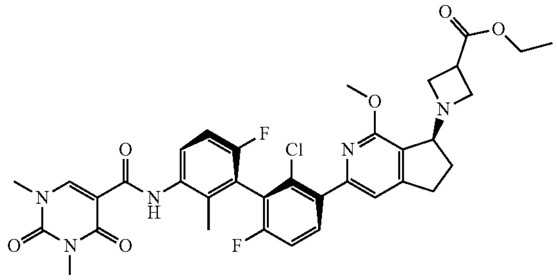
,
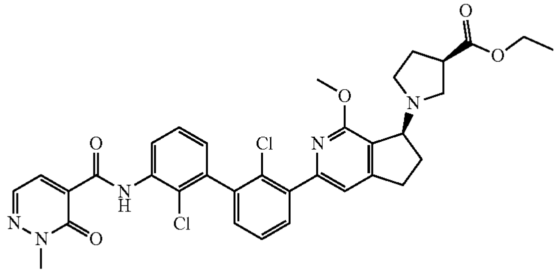
,
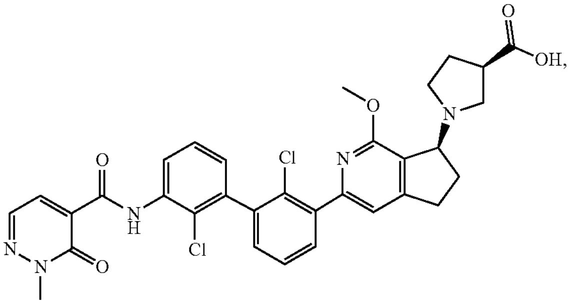
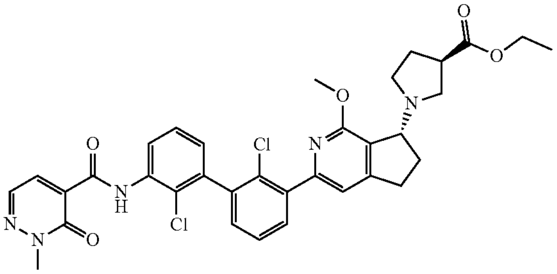
,
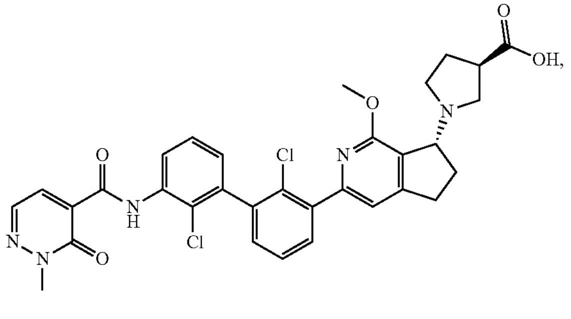
-continued
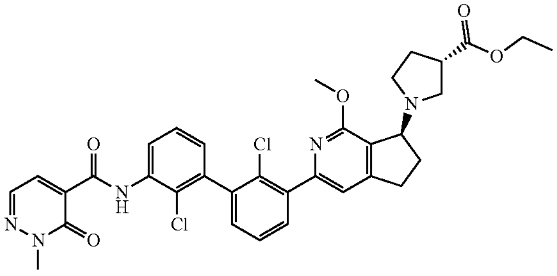
,
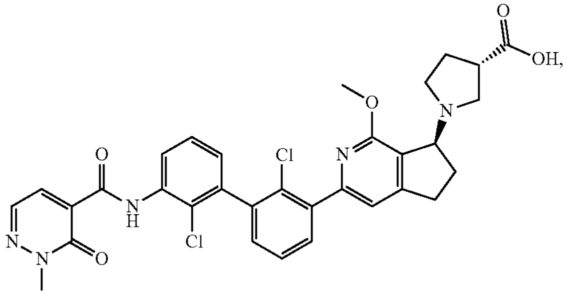
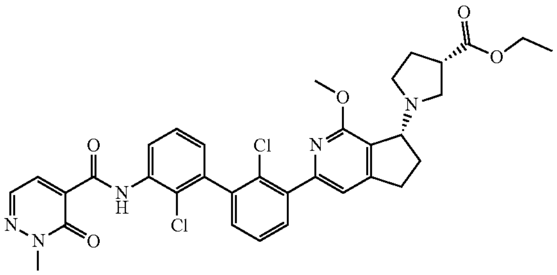
,
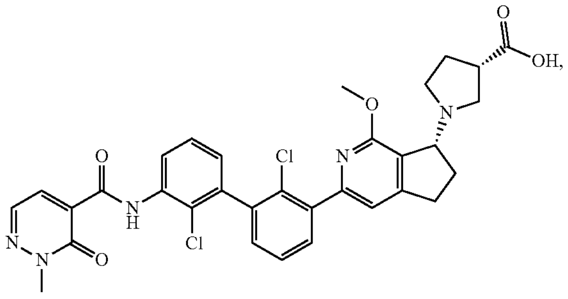
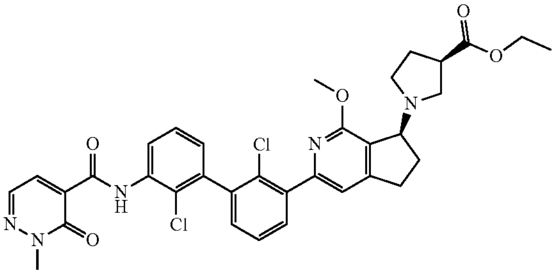
,
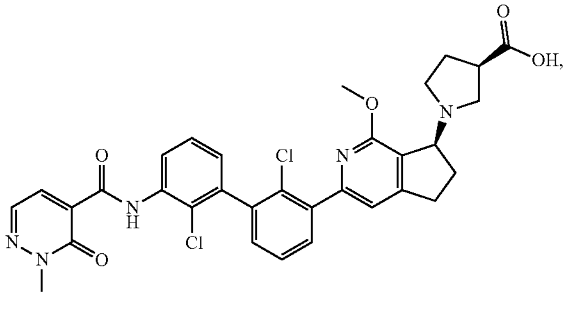

-continued
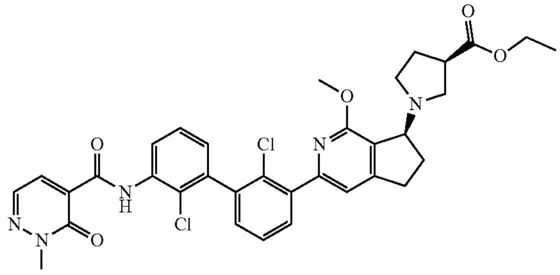
,
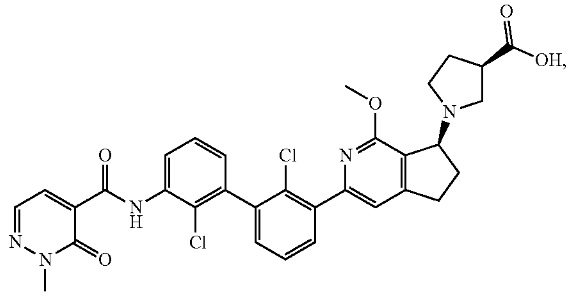
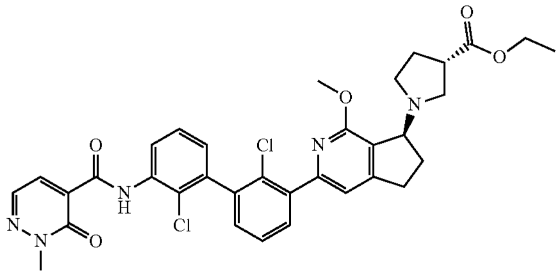
,
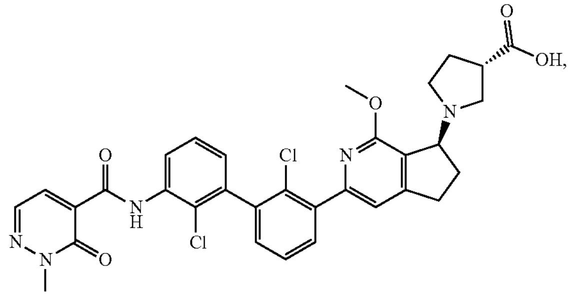
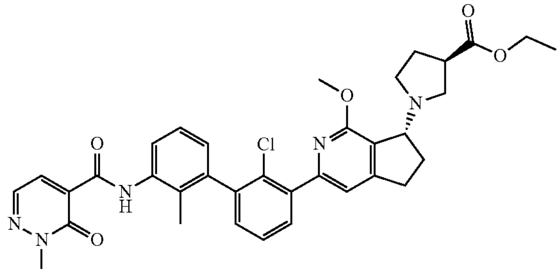
,
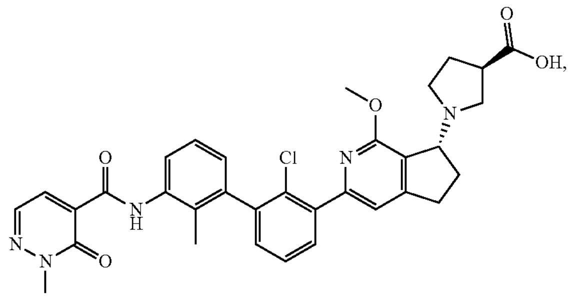
-continued
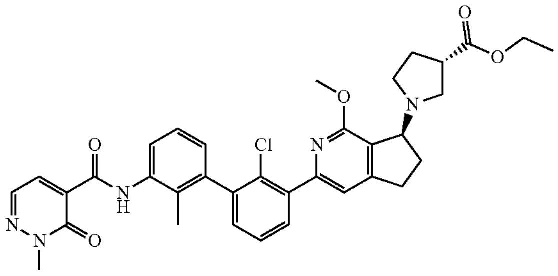
,
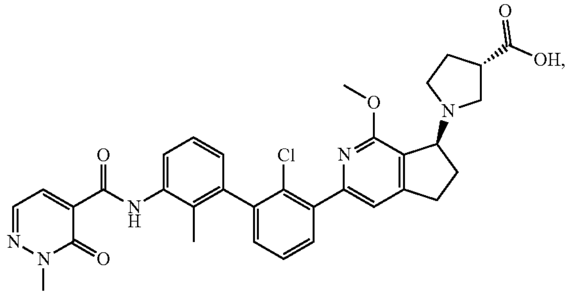
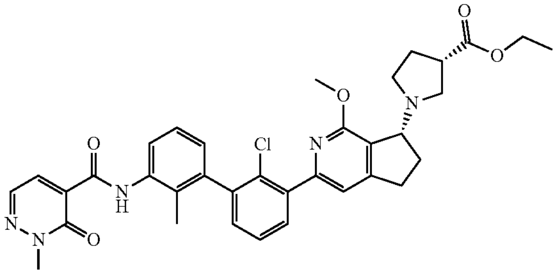
,
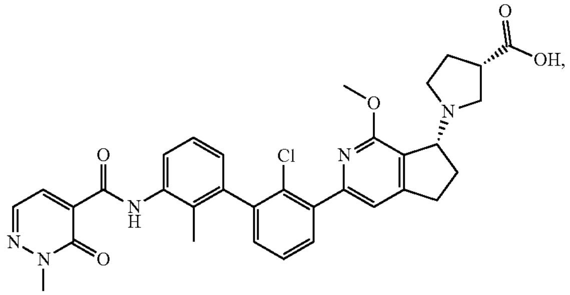
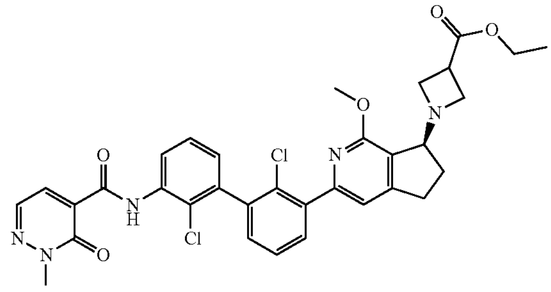
, -continued
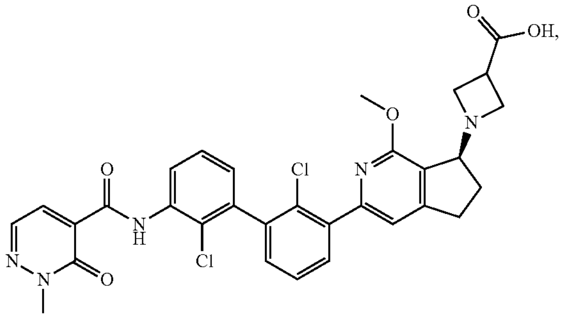
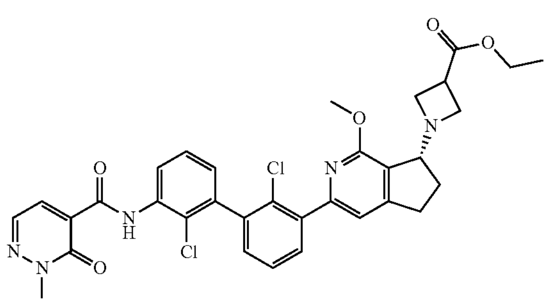
,
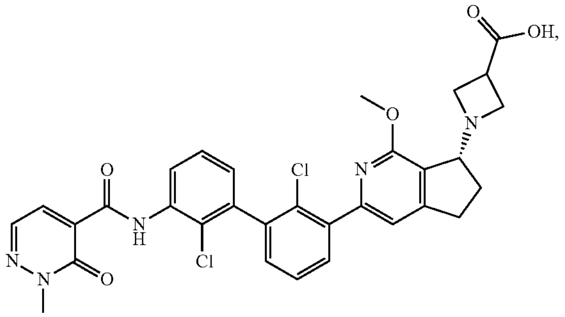
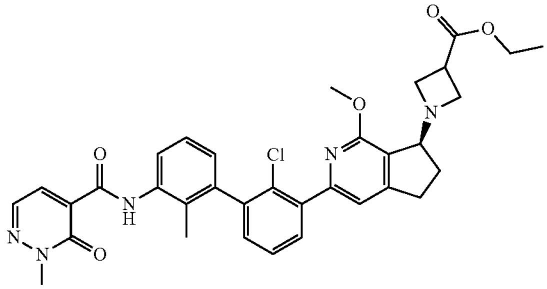
,
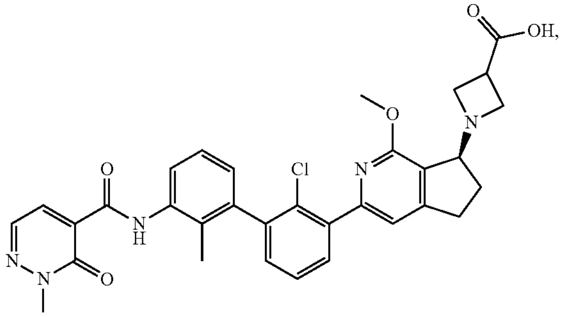
-continued
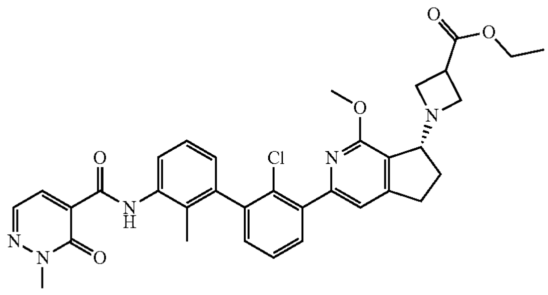
,
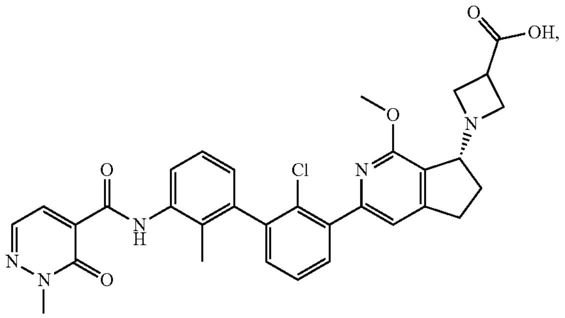
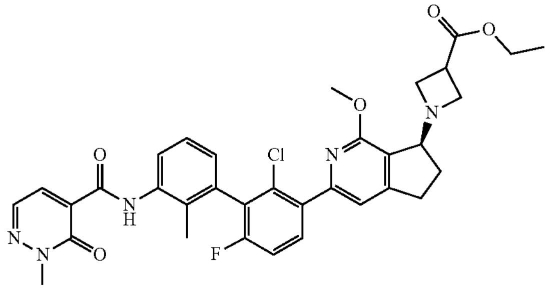
,
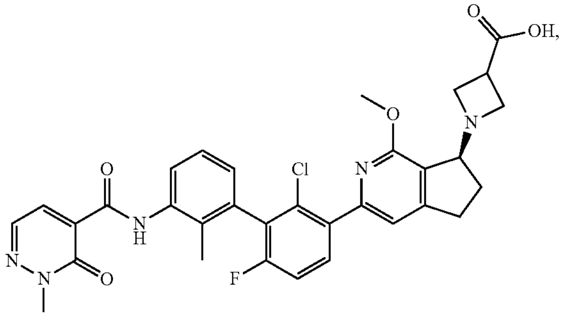
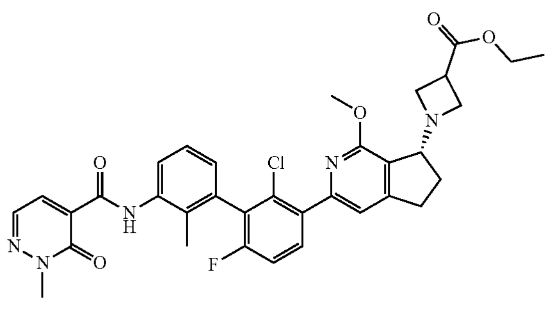
, -continued
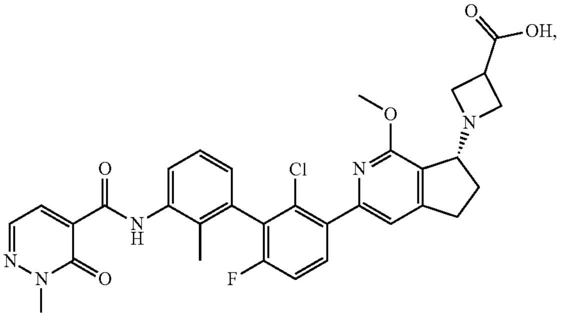
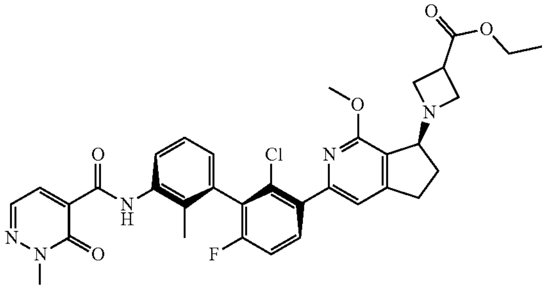
,
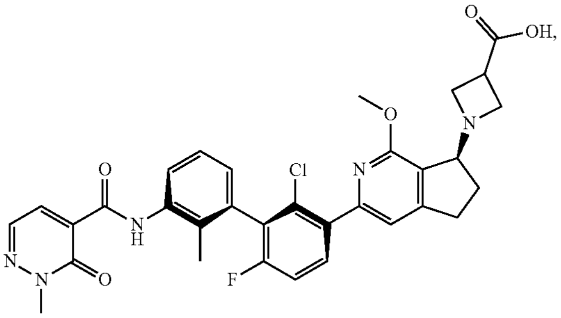
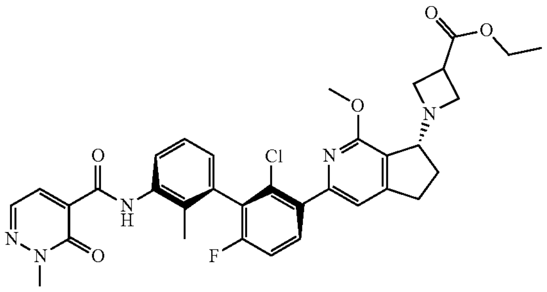
,
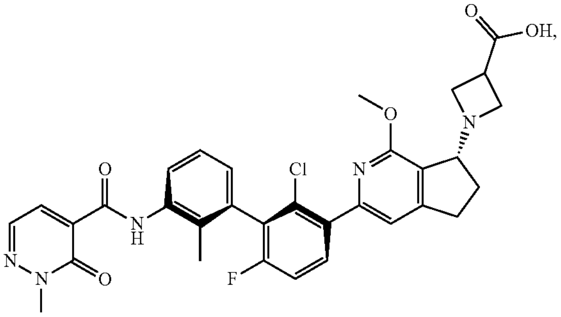
-continued
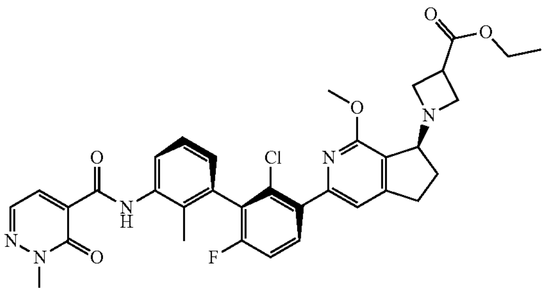
,
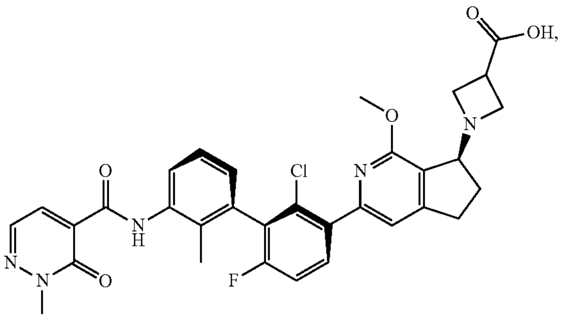
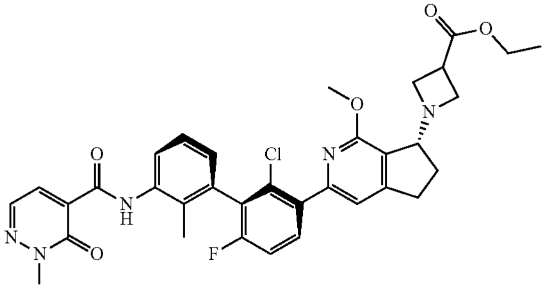
,
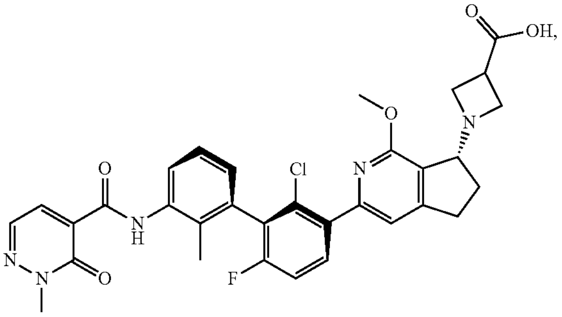
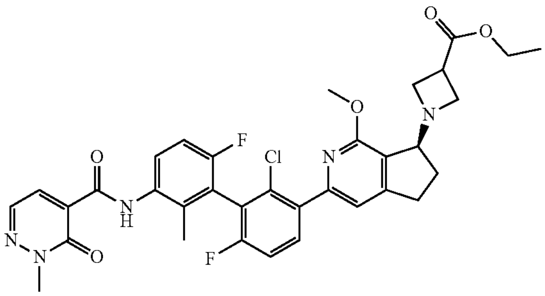
, -continued
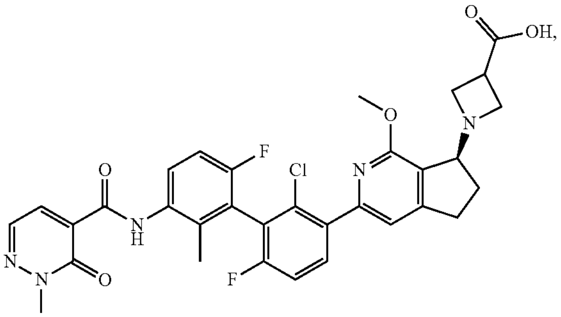
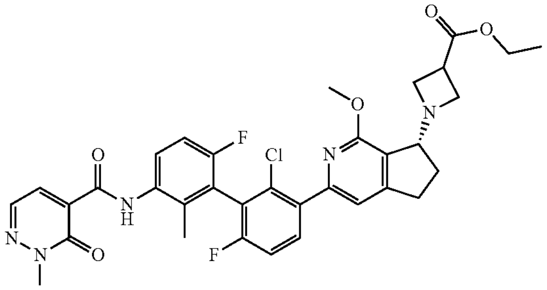
,
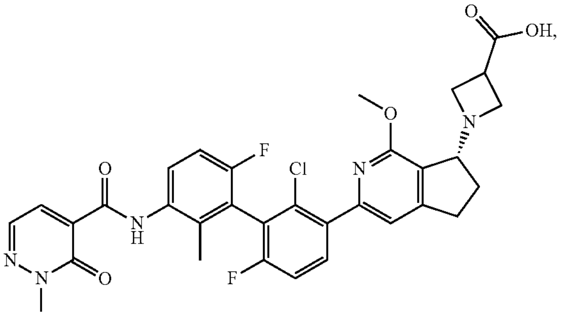
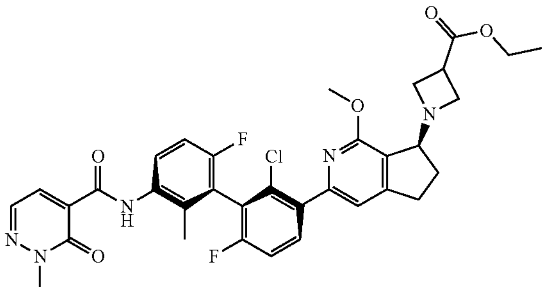
,
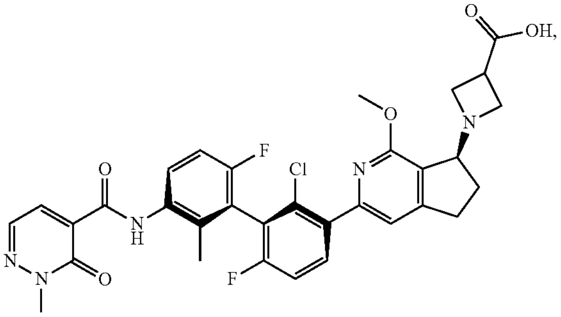
-continued
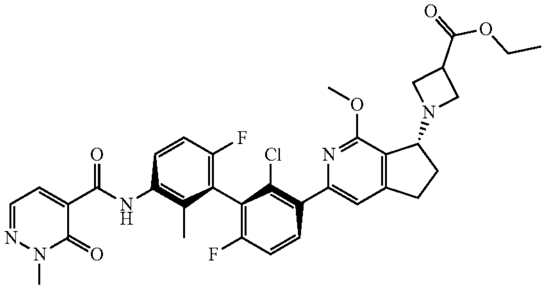
,
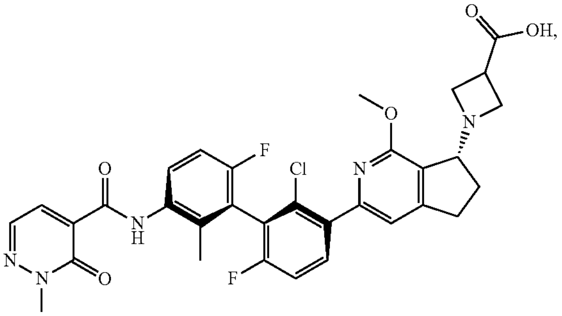
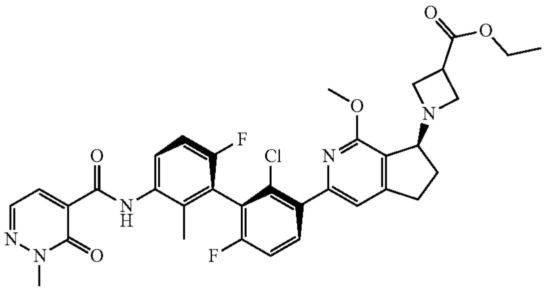
,
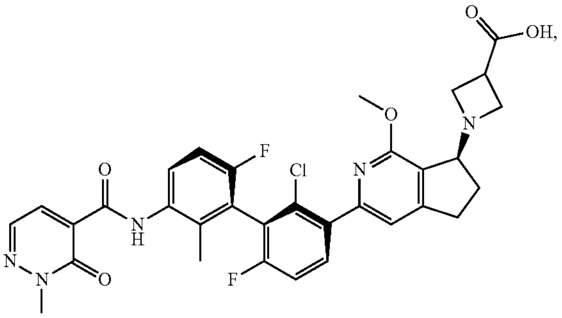
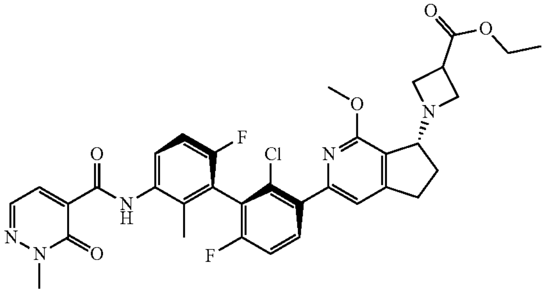
, -continued
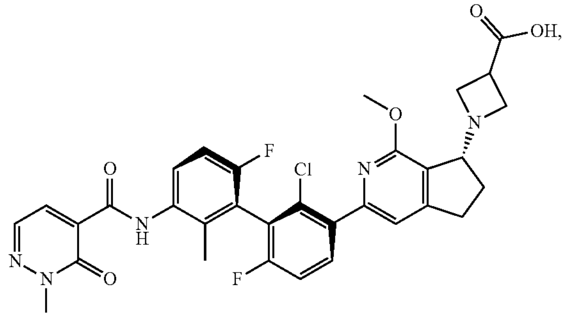
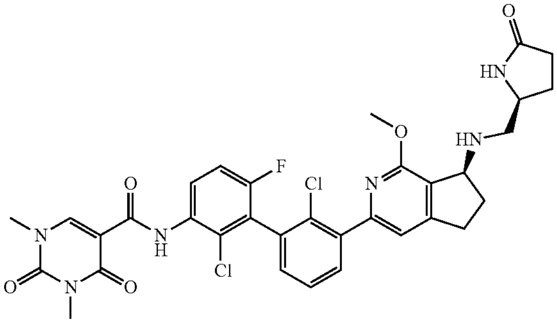
,
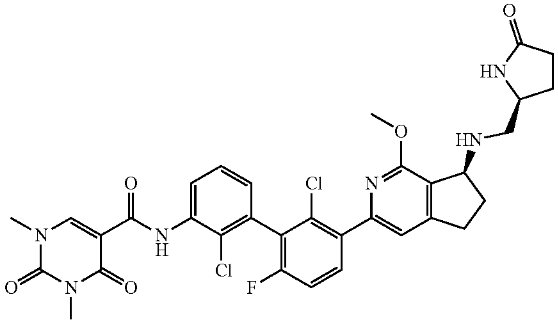
,
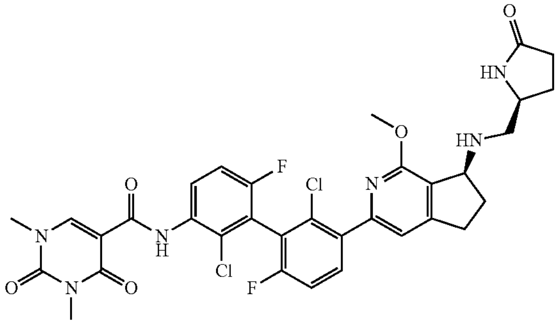
,
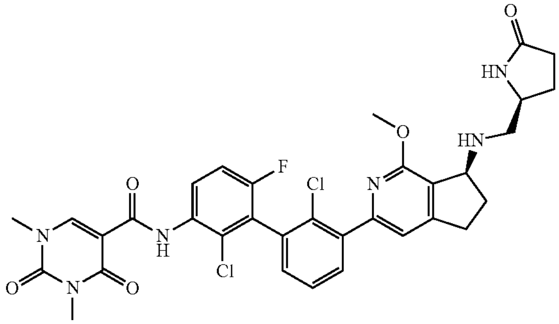
,
-continued
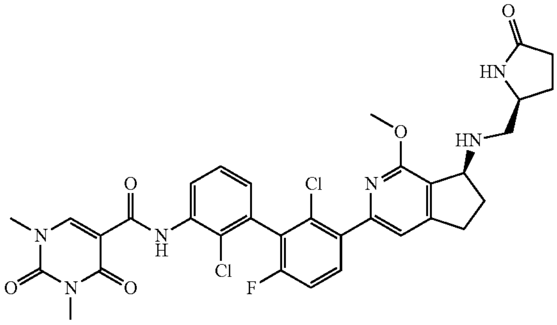
,
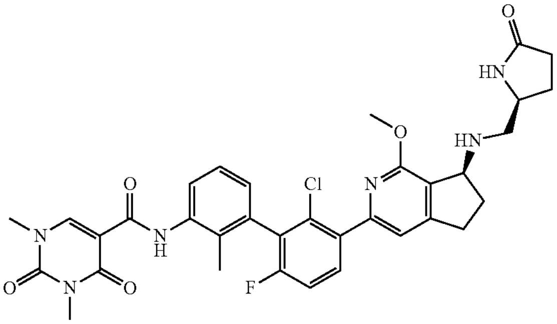
,
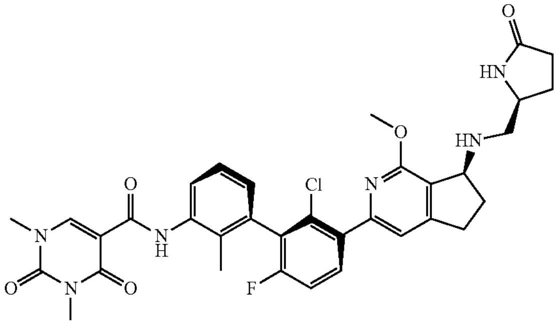
,
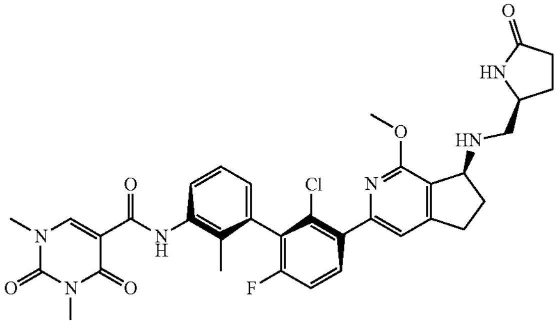
,
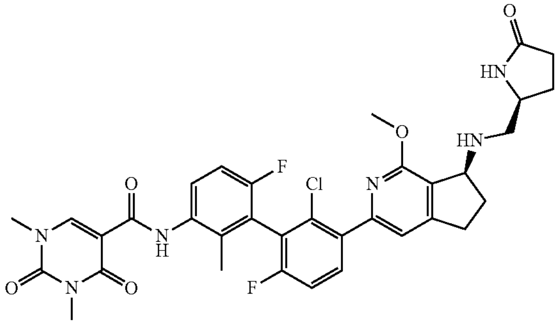
, -continued
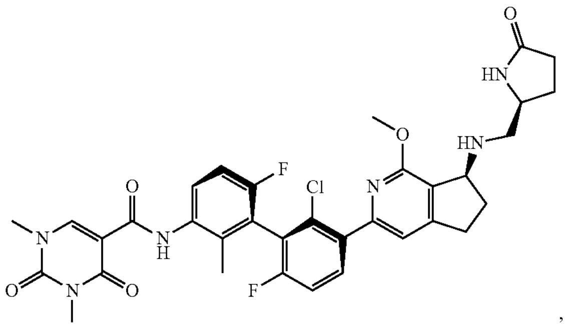
,
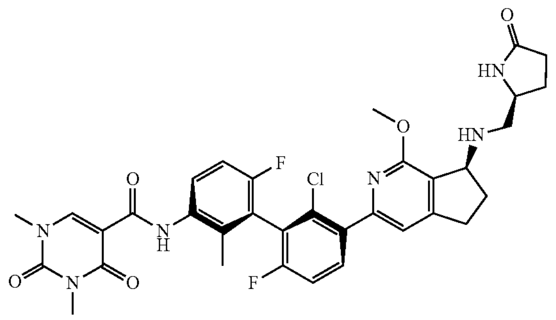
,
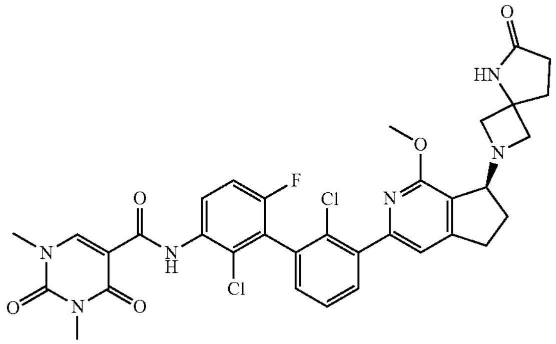
,
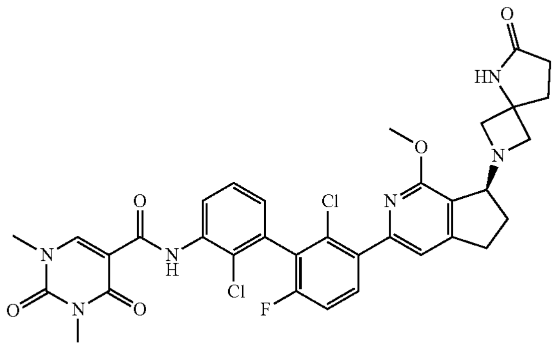
,
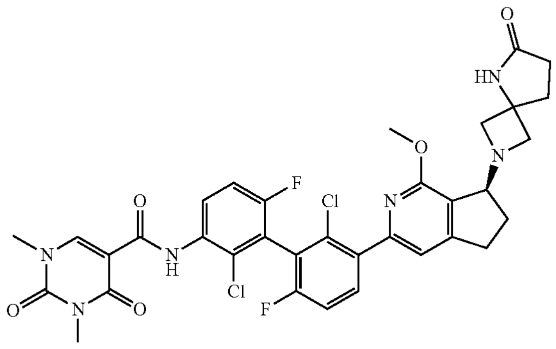
,
-continued
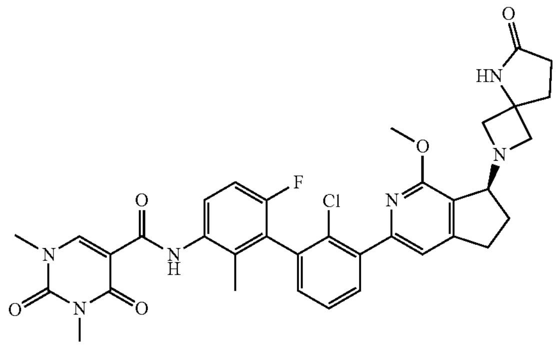
,
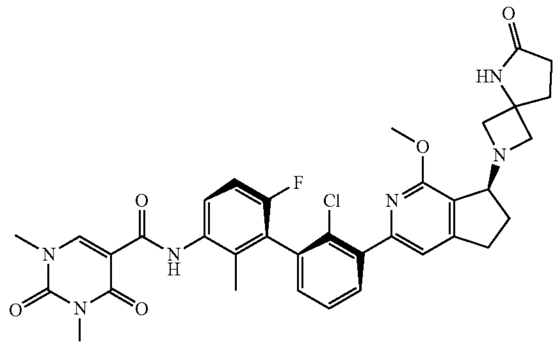
,
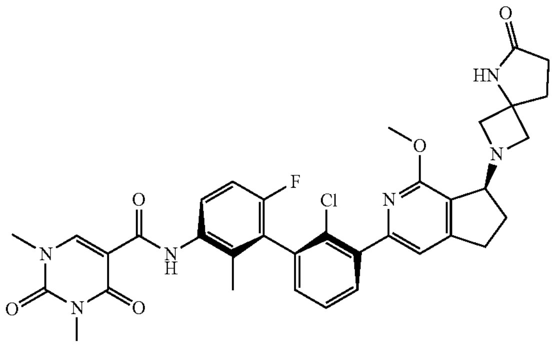
,
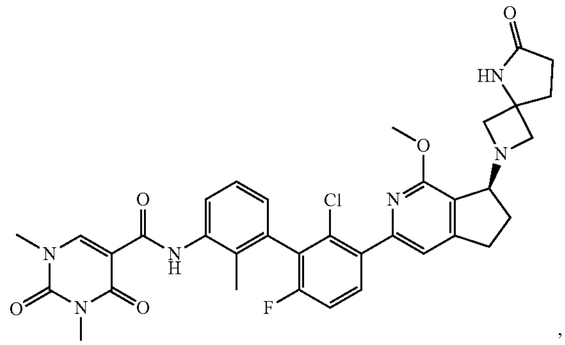
,
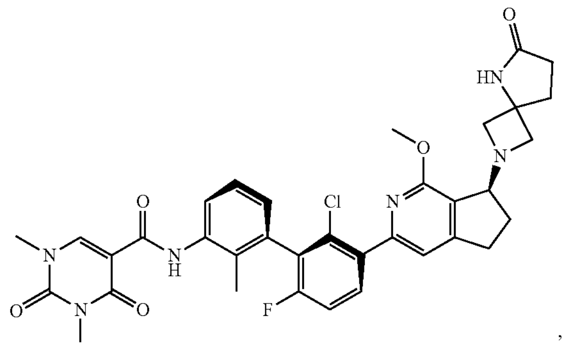
,

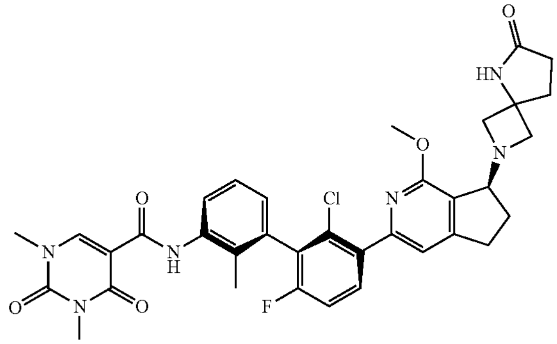,
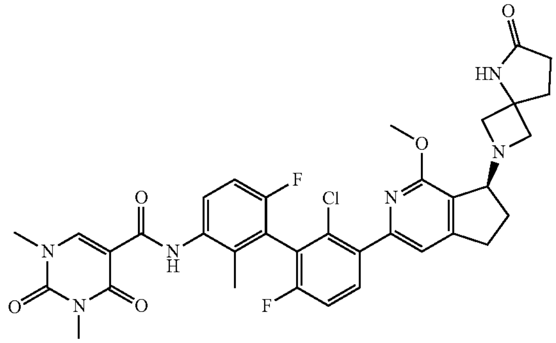,
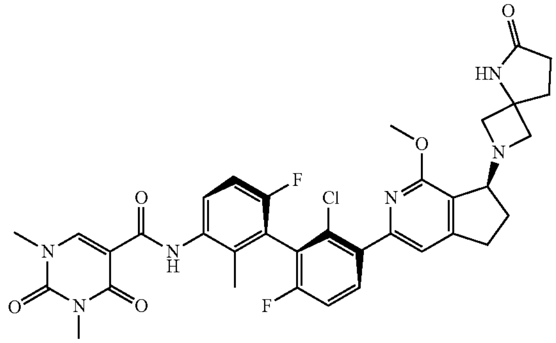,
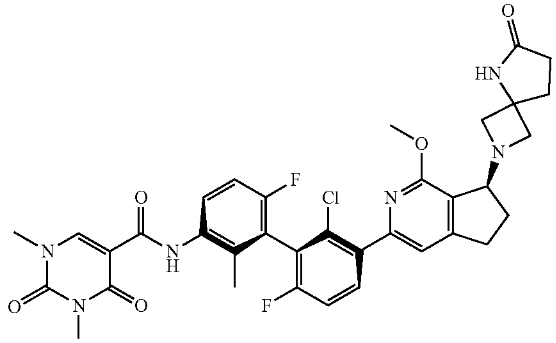,
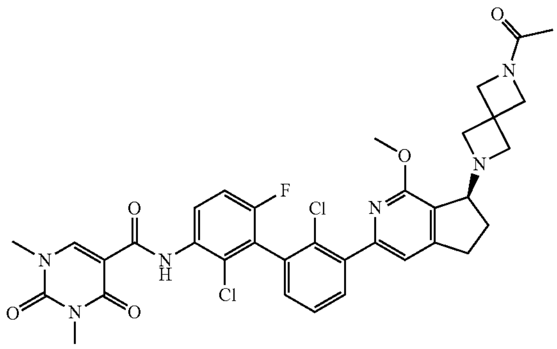,
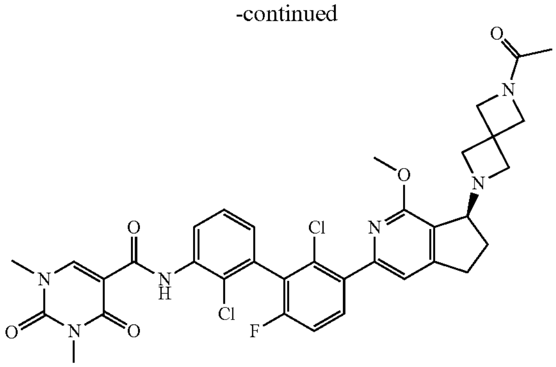,
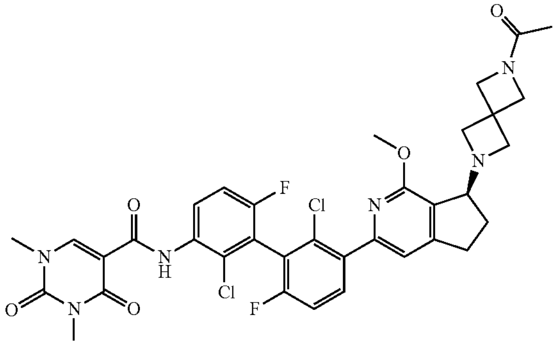,
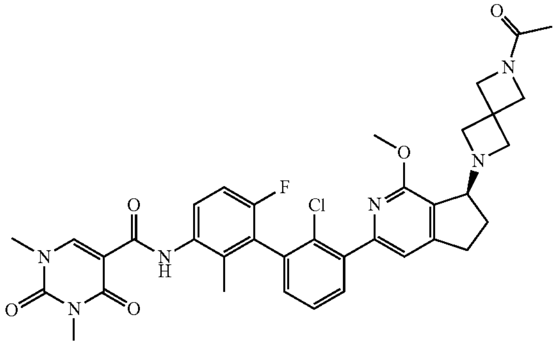,
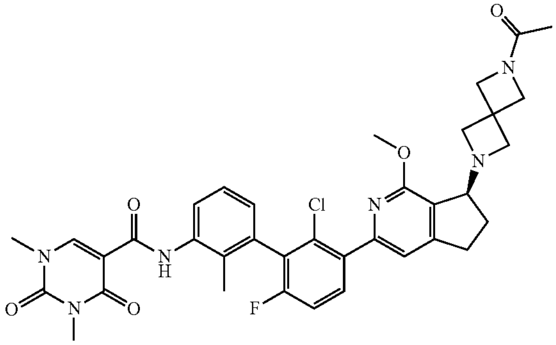,
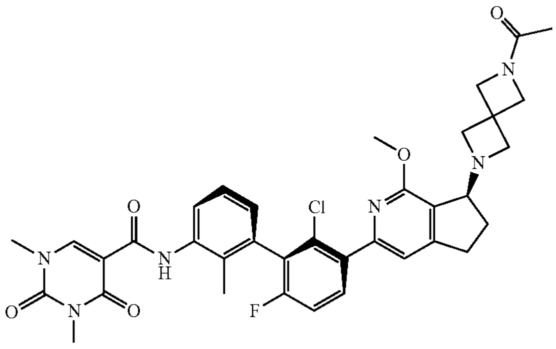, -continued
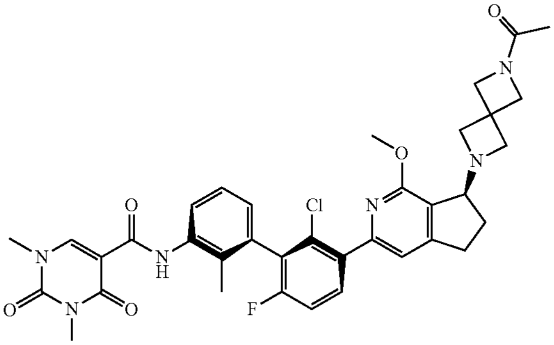
,
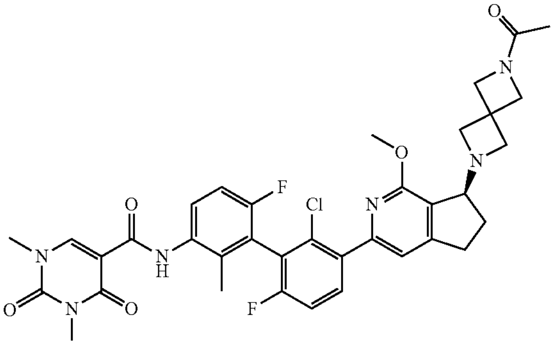
,
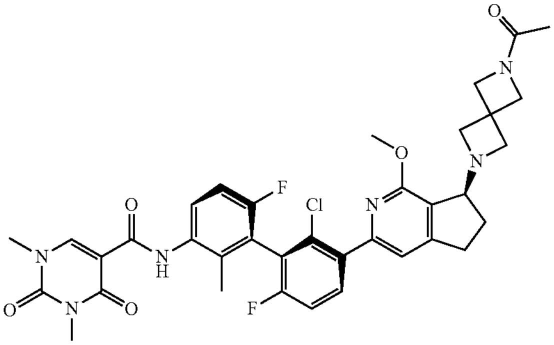
,
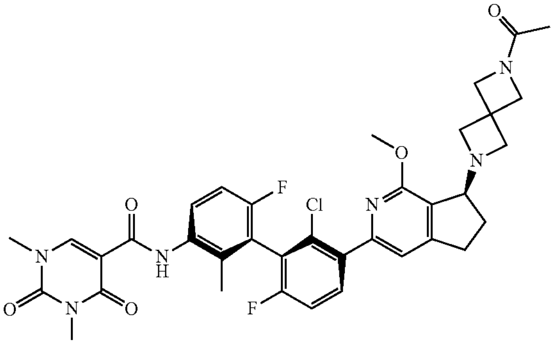
,
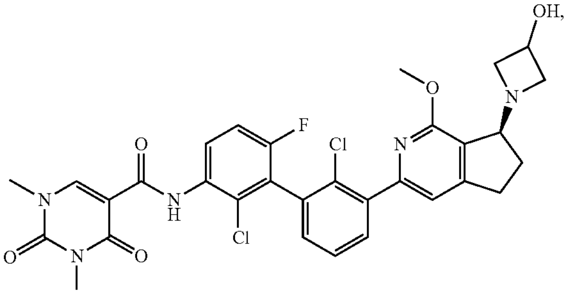
-continued
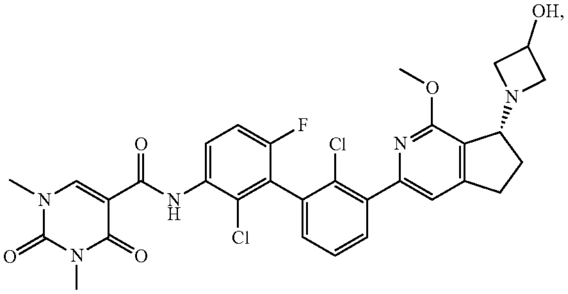
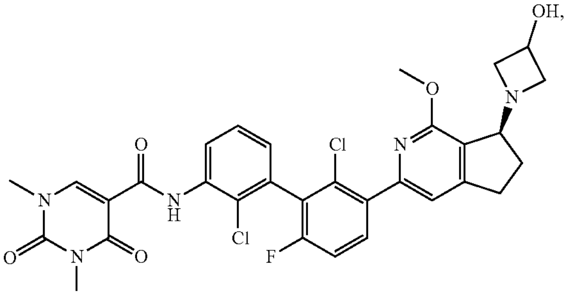
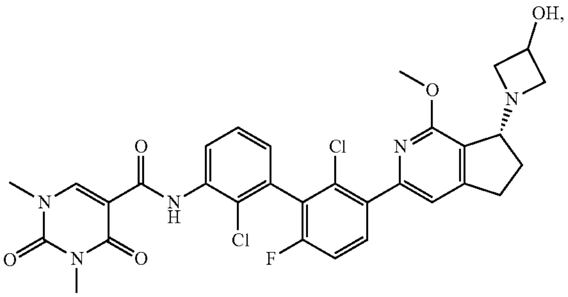
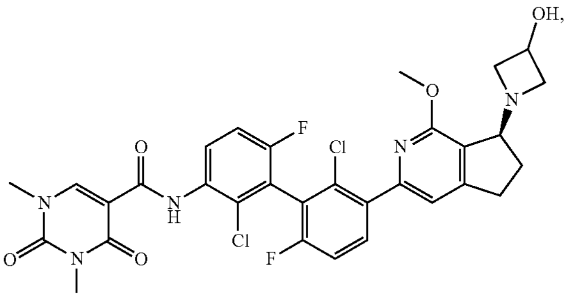
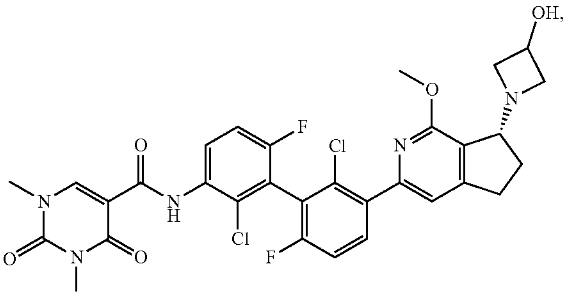

-continued
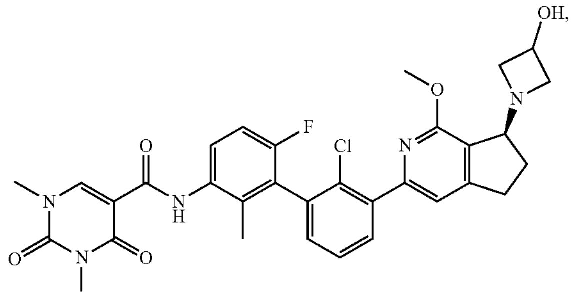
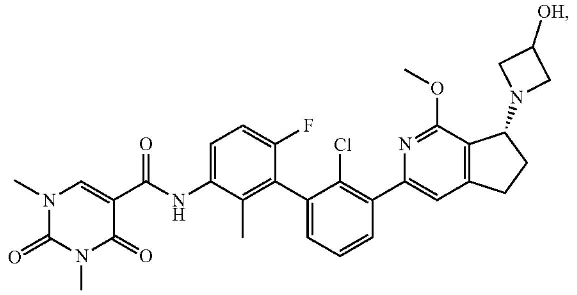
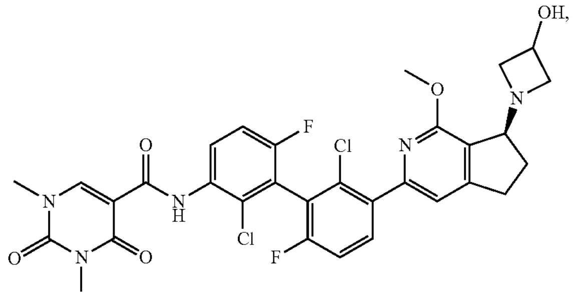
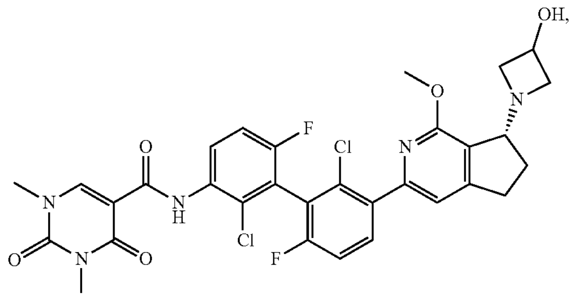
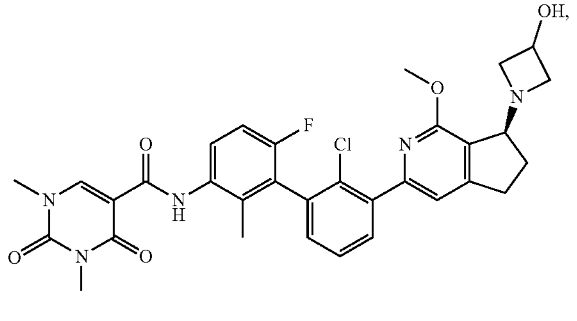
-continued
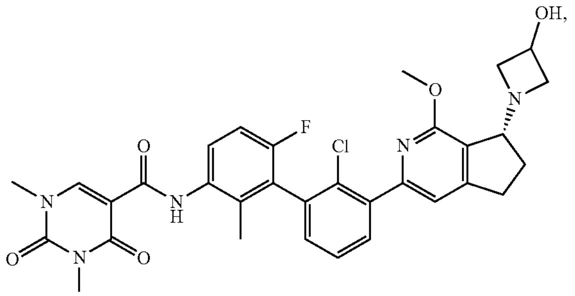
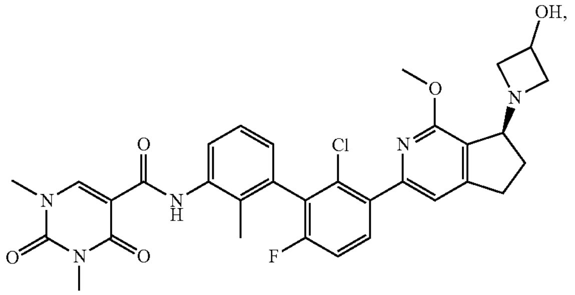
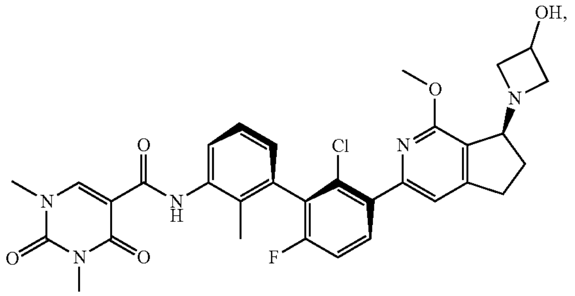
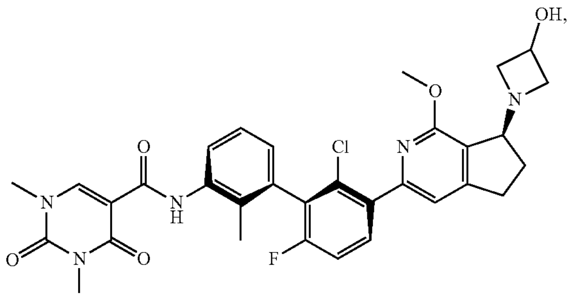
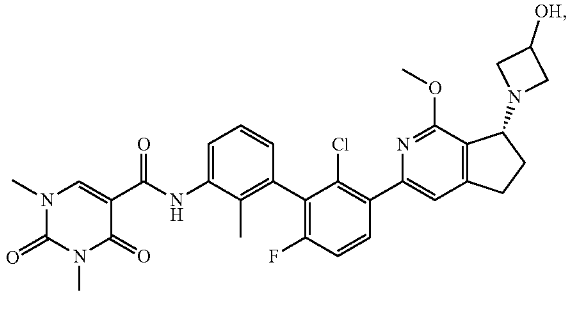

-continued
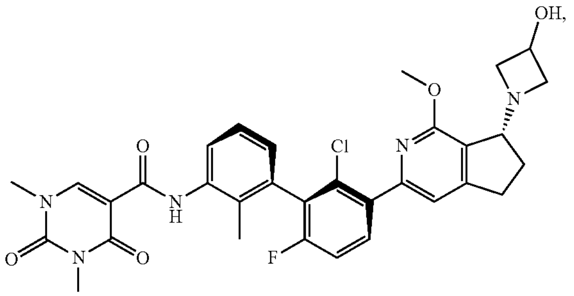
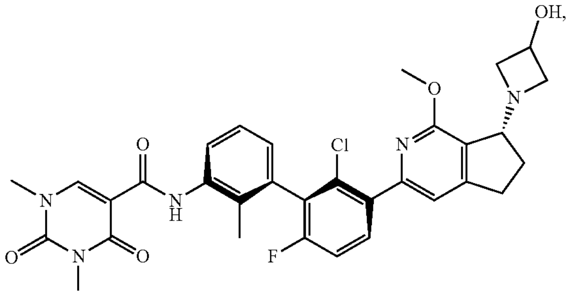
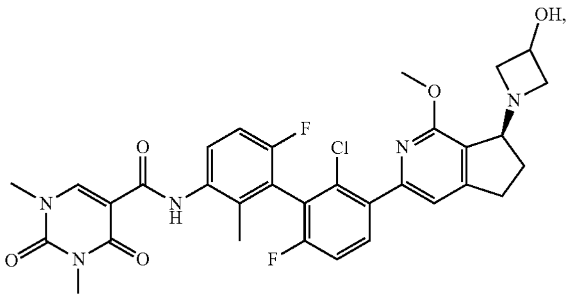
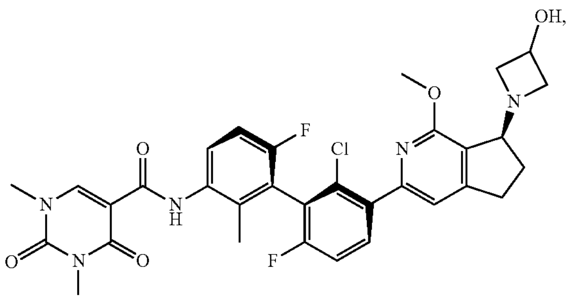
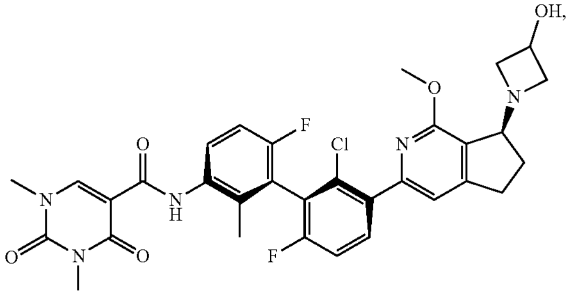
-continued
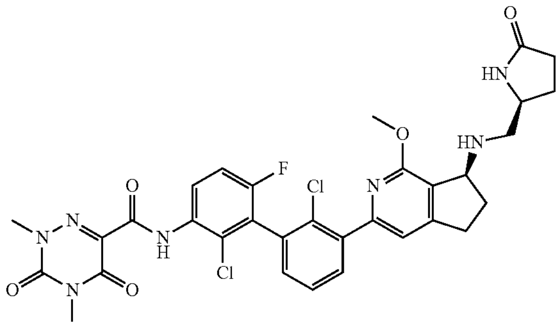
,
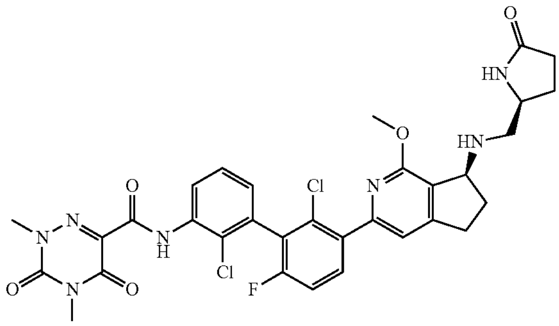
,
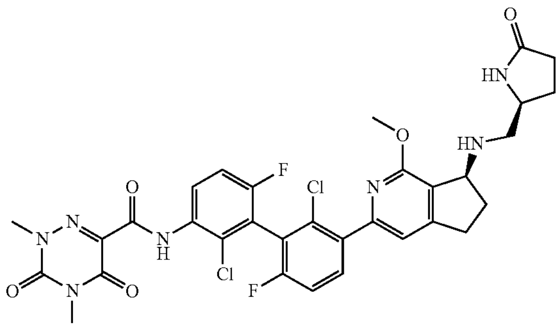
,
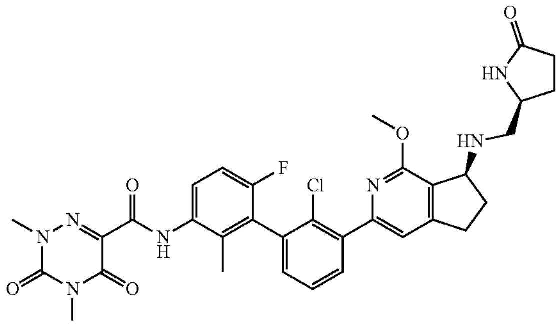
,
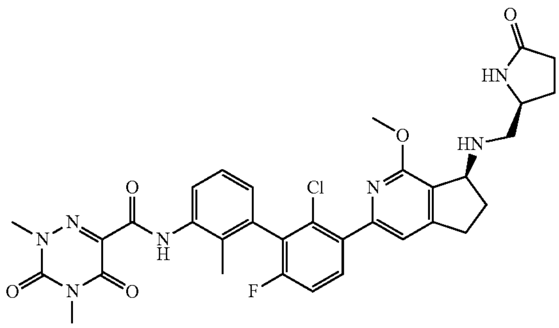
, -continued
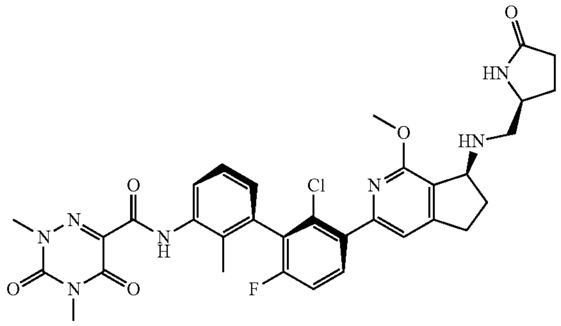
,
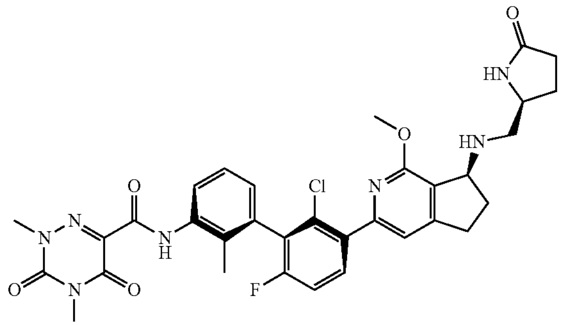
,
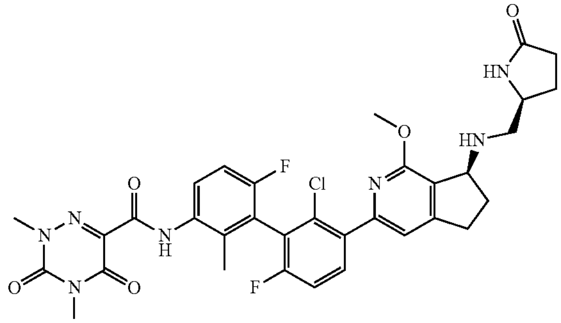
,
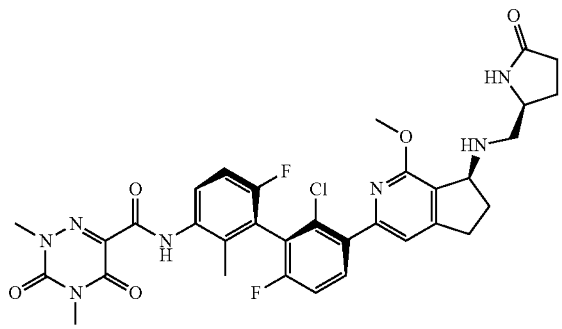
,
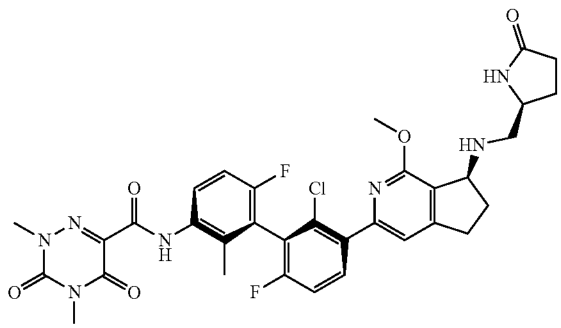
,
-continued
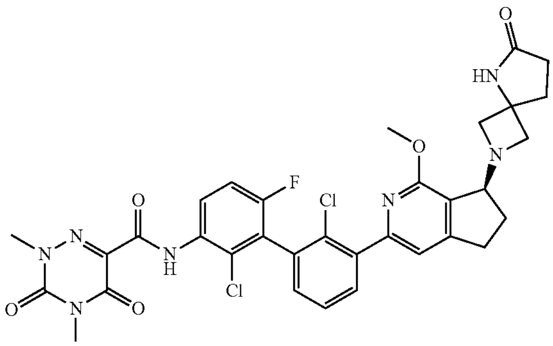
,
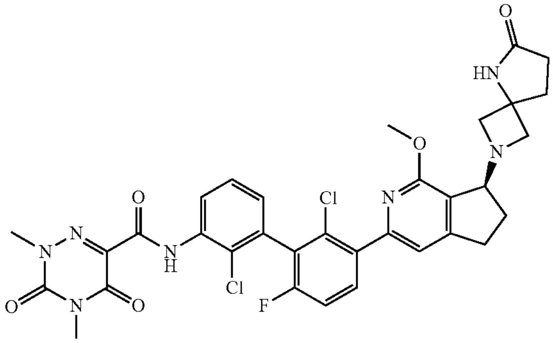
,
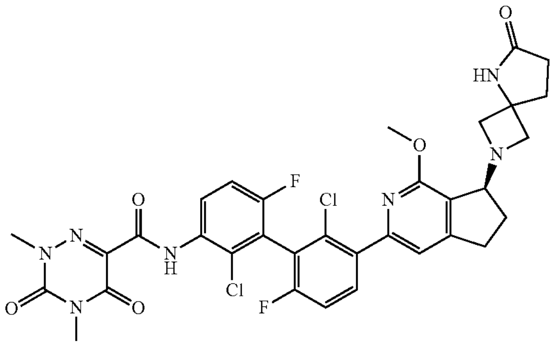
,
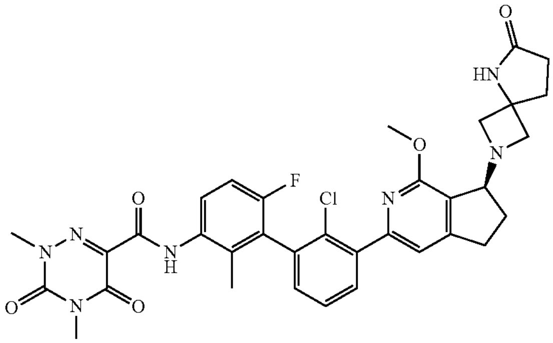
,
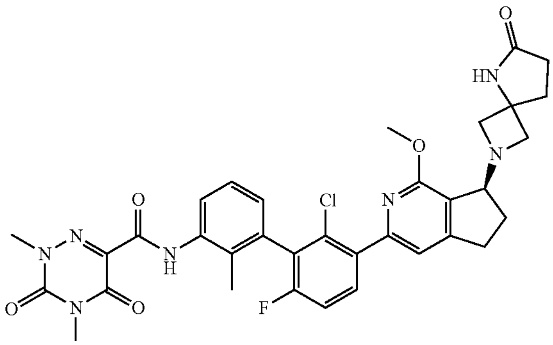
, -continued
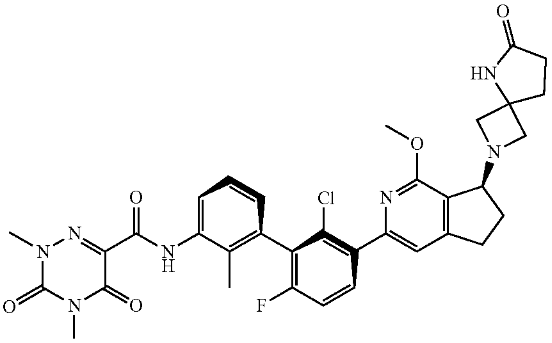
,
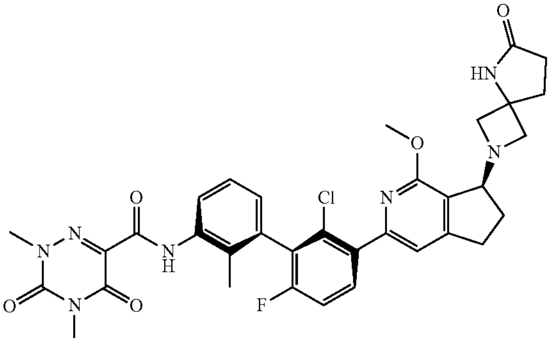
,
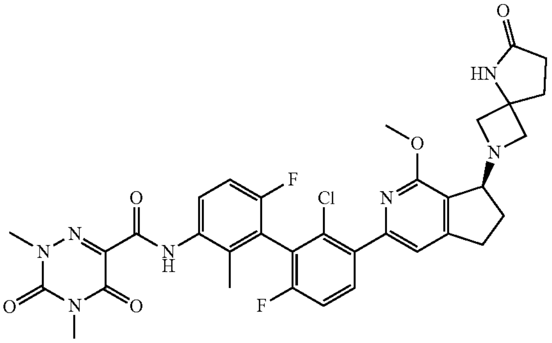
,
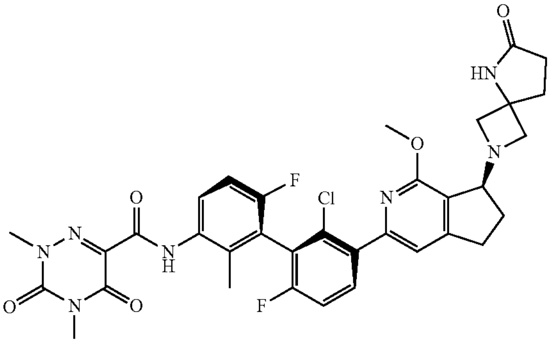
,
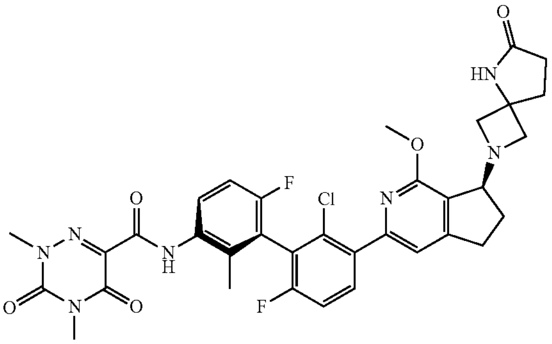
,
-continued
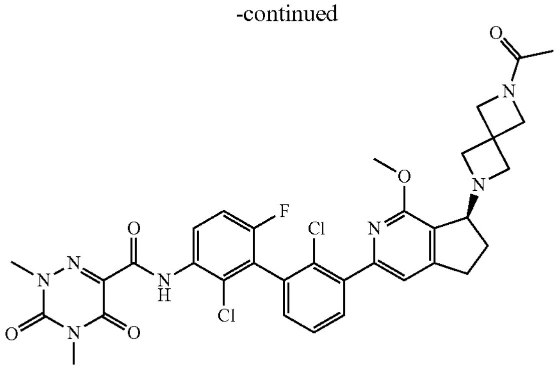
,
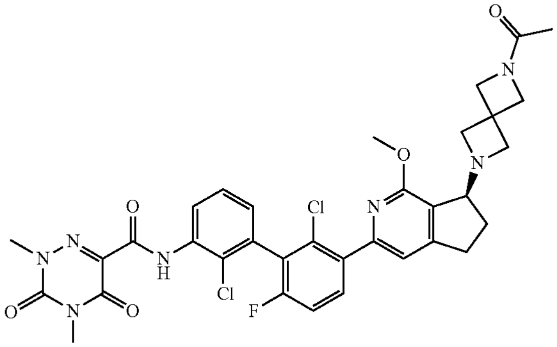
,
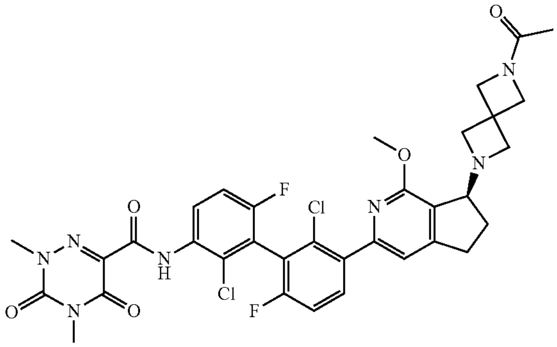
,
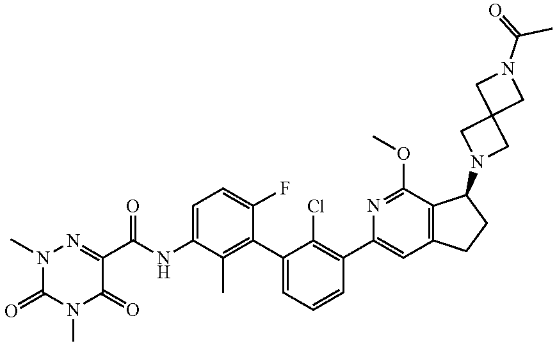
,
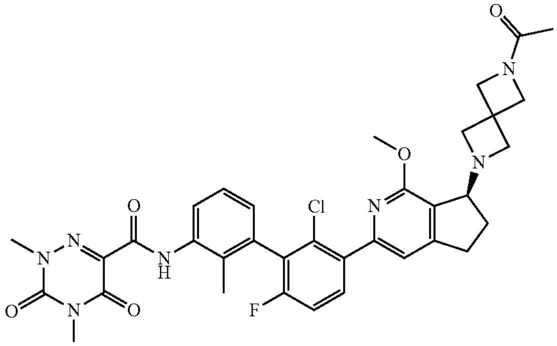
, -continued
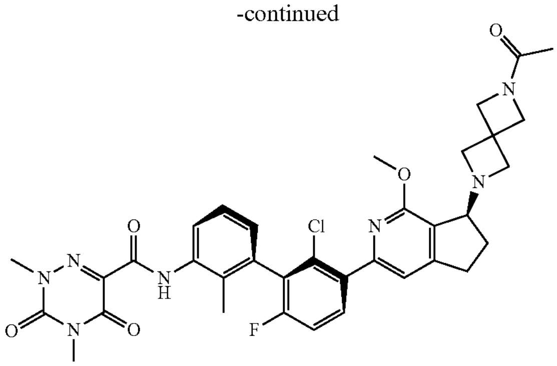
,
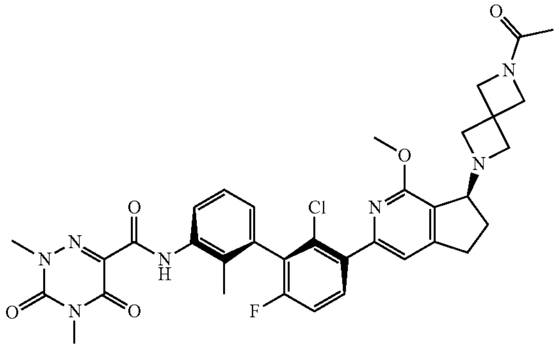
,
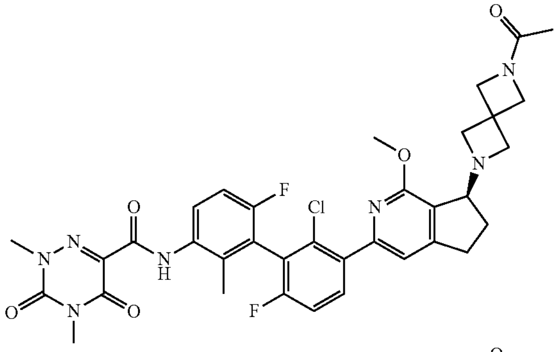
,
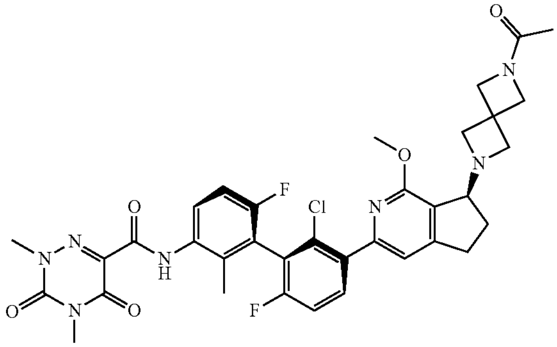
,
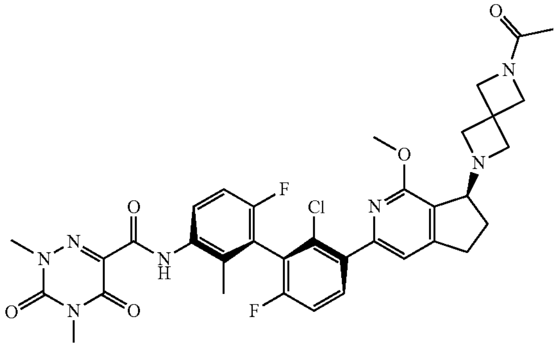
,
-continued
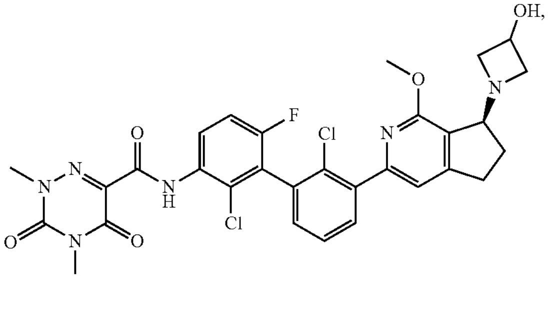
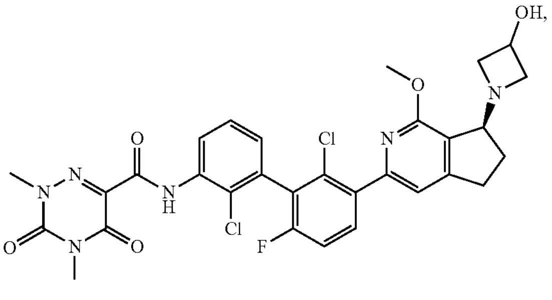
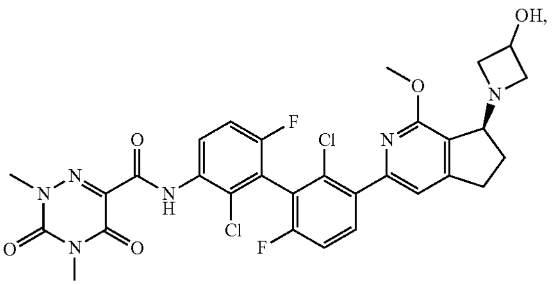
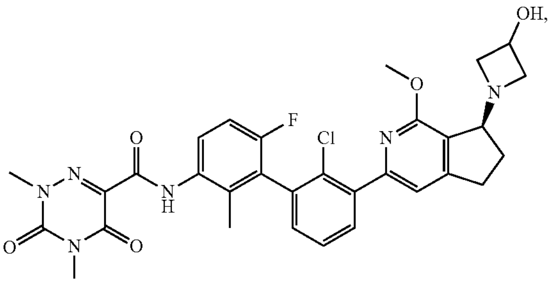
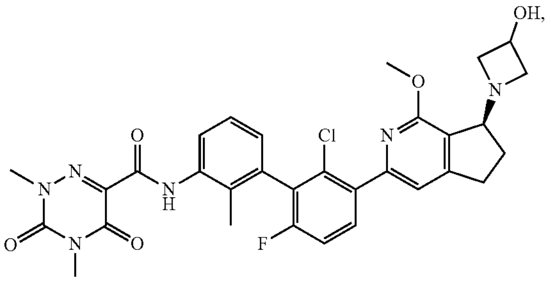

-continued
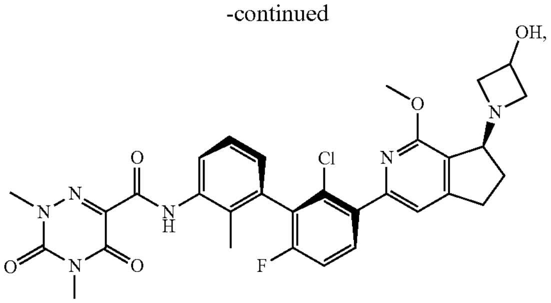
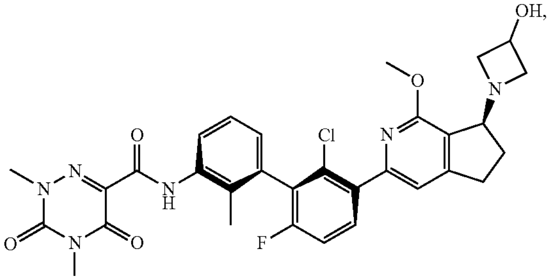
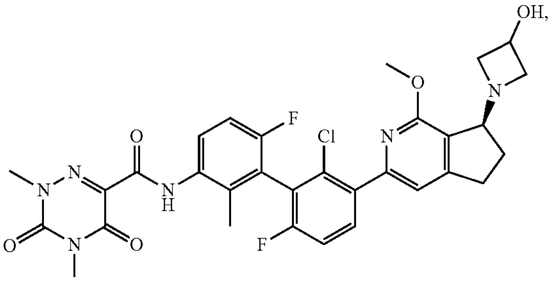
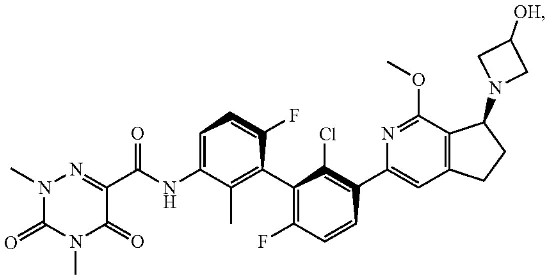
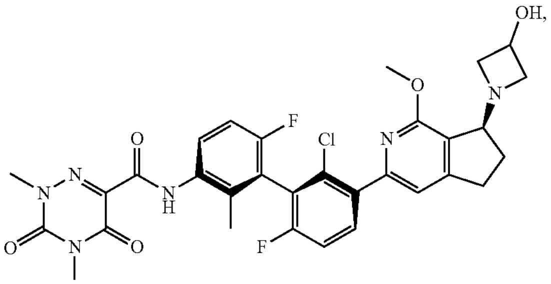
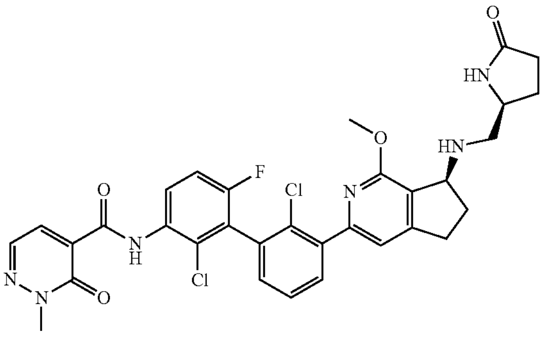
,
-continued
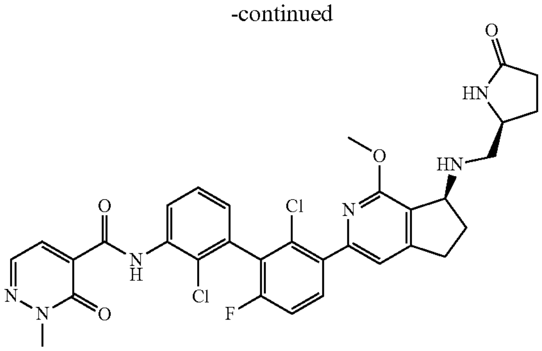
,
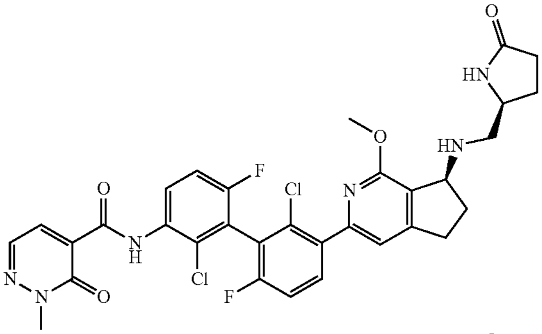
,
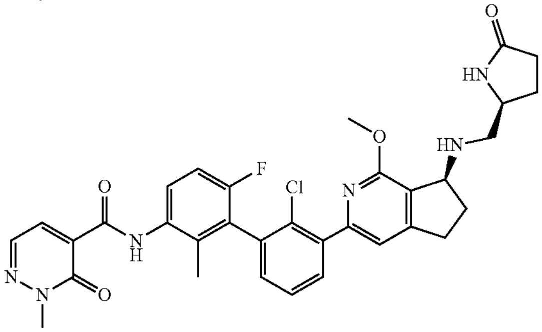
,
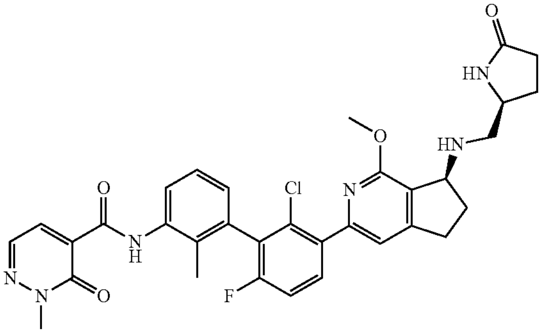
,
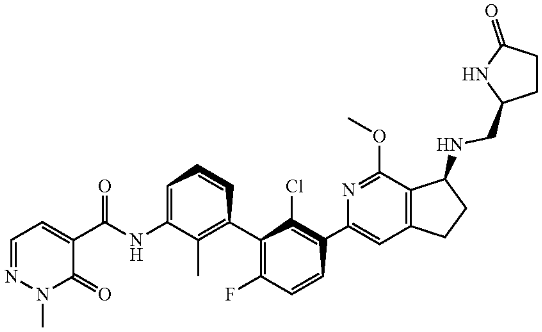
,

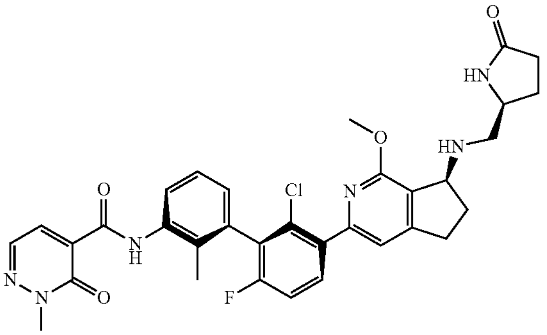
,
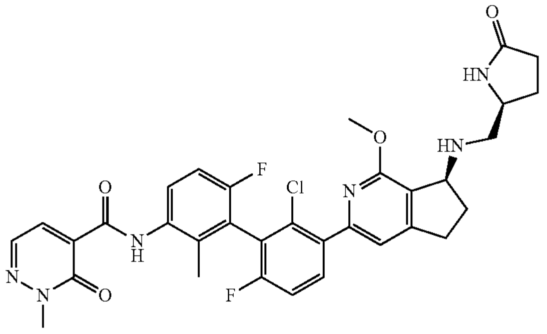
,
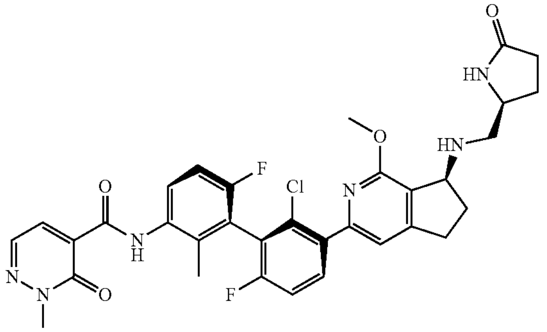
,
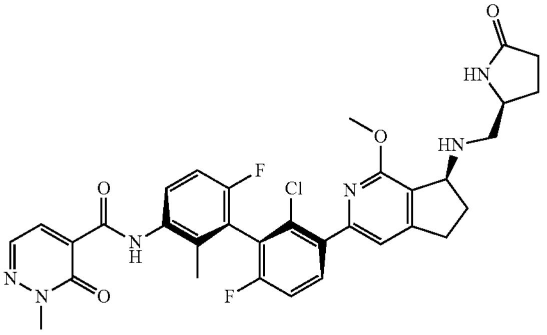
,
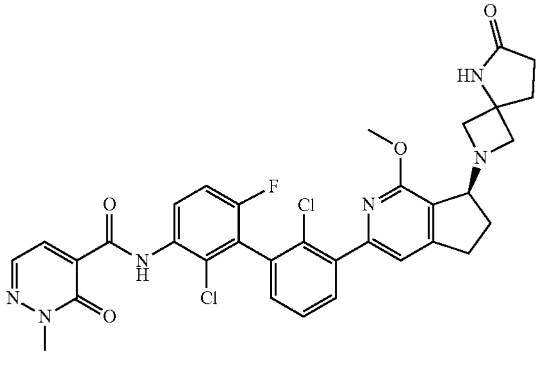
,
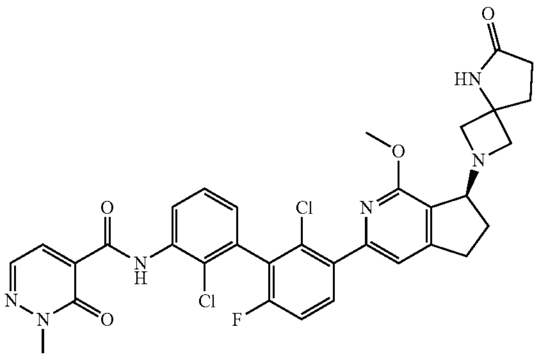
,
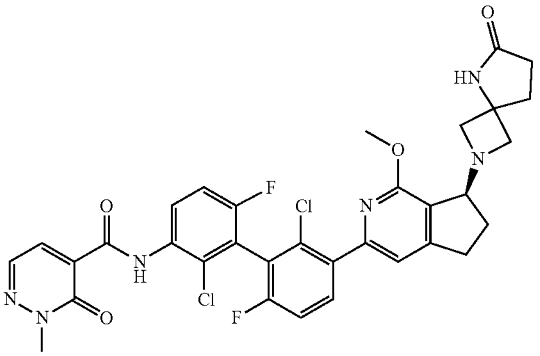
,
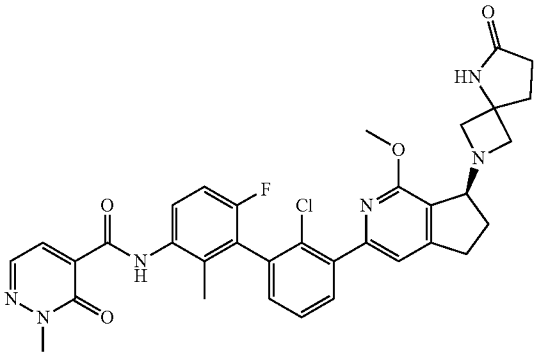
,
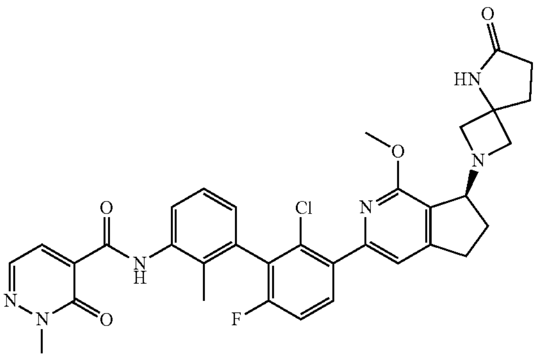
, -continued
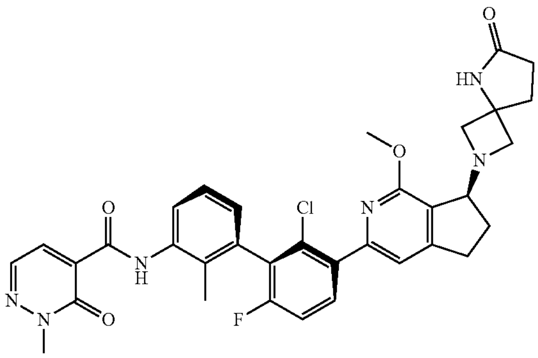
,
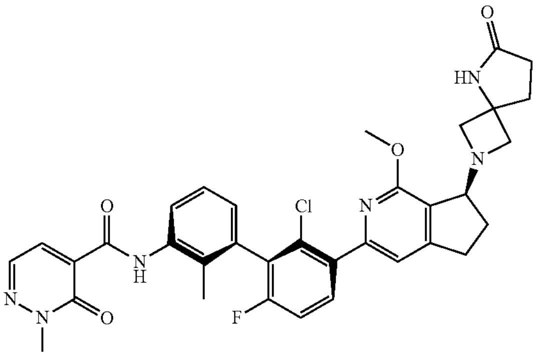
,
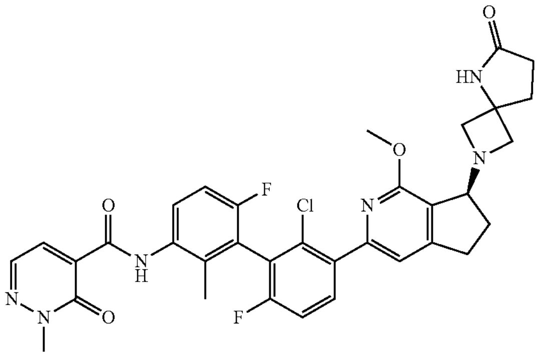
,
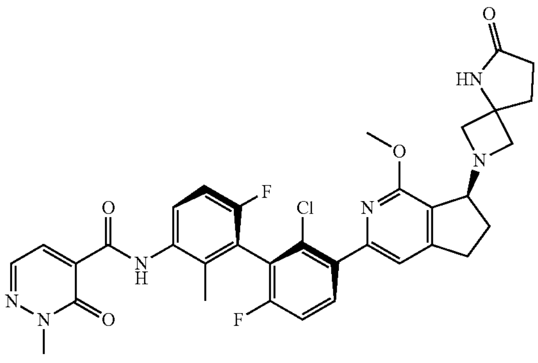
,
-continued
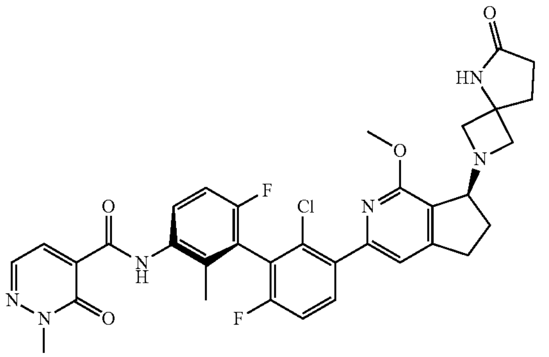
,
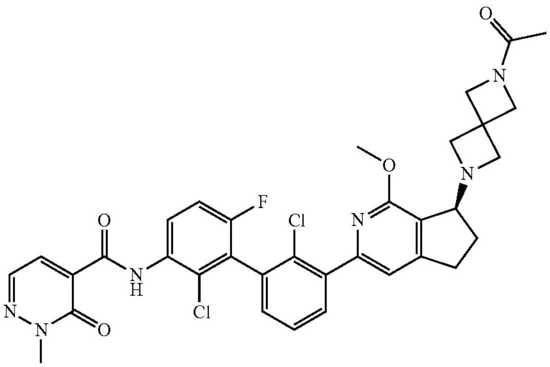
,
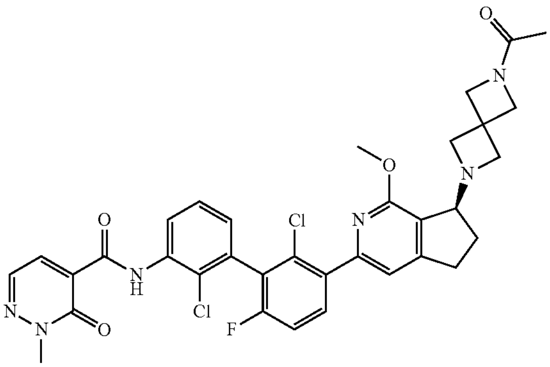
,
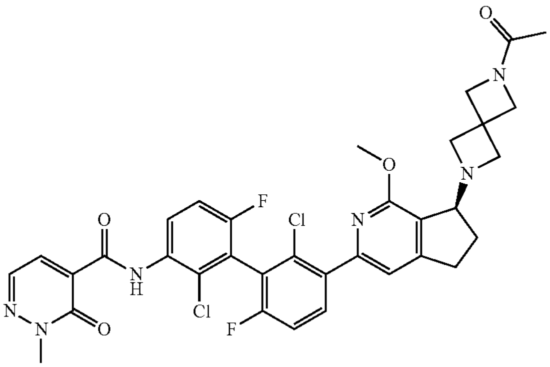
, -continued
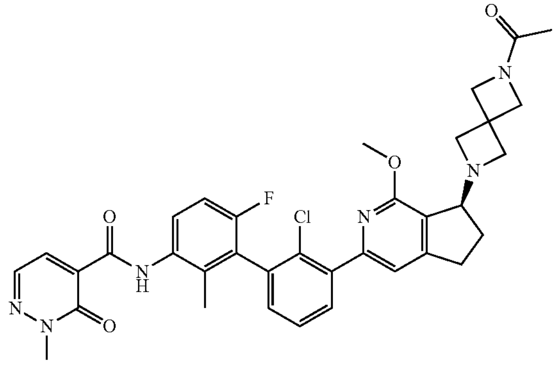
,
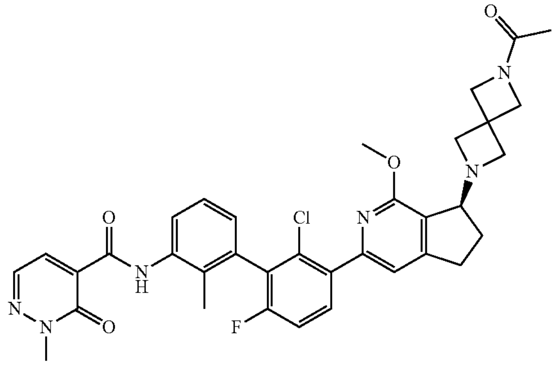
,
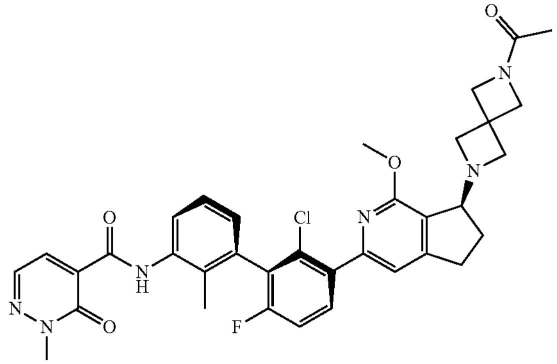
,
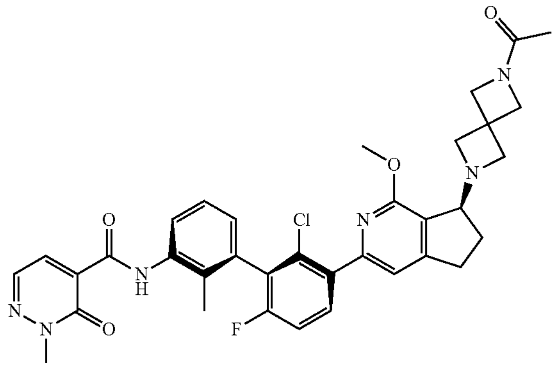
,
-continued
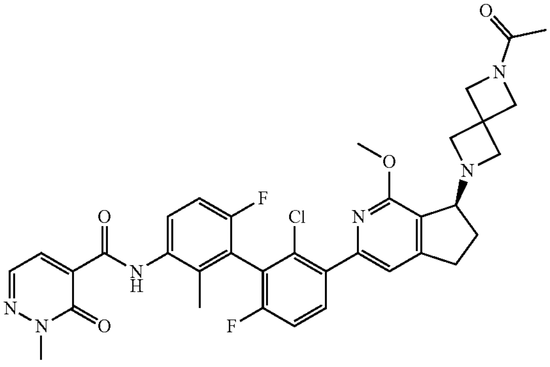
,
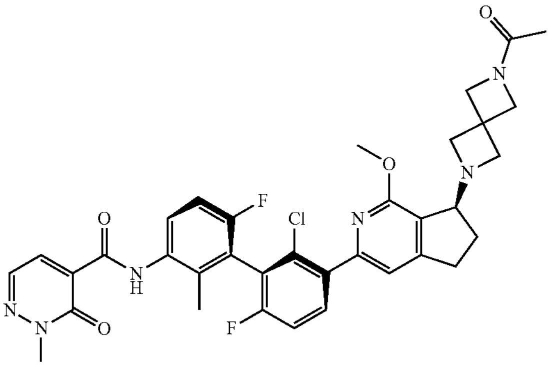
,
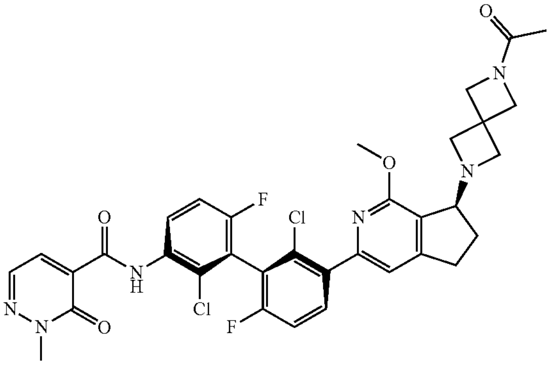
,
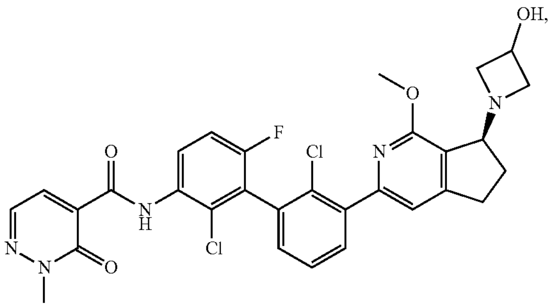
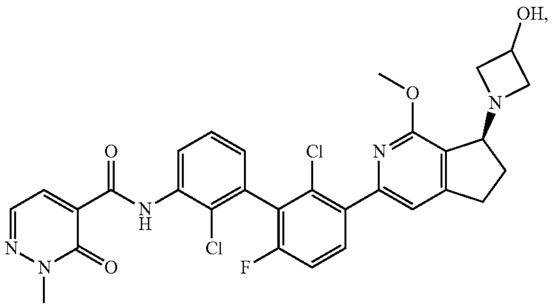

-continued
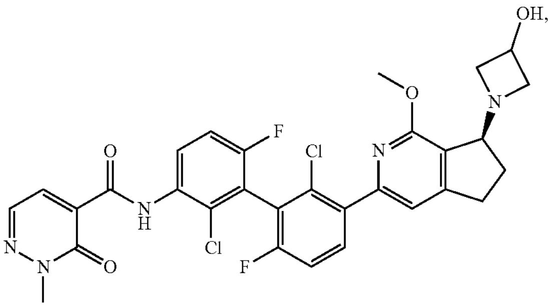
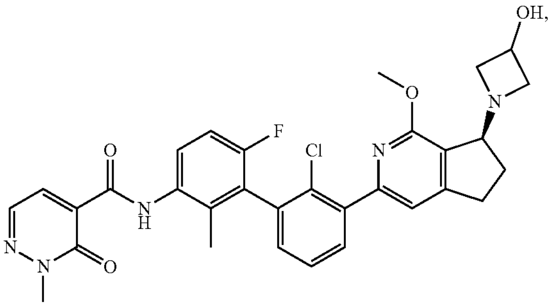
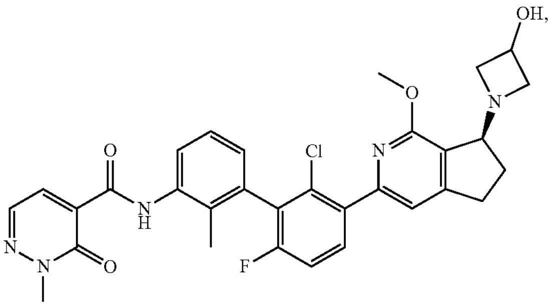
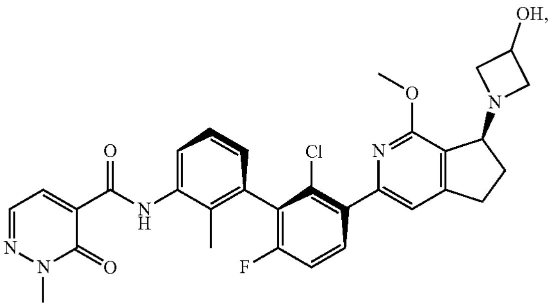
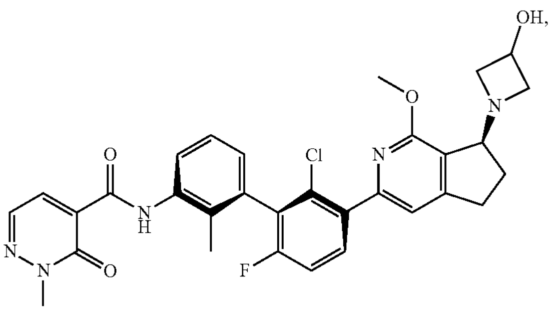
-continued
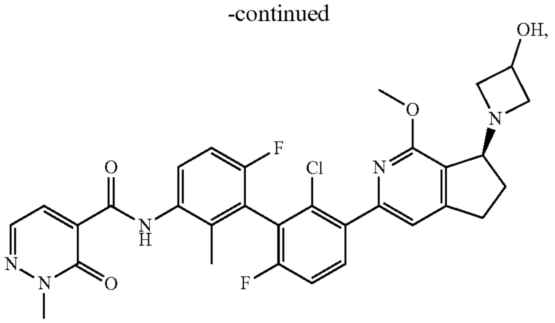
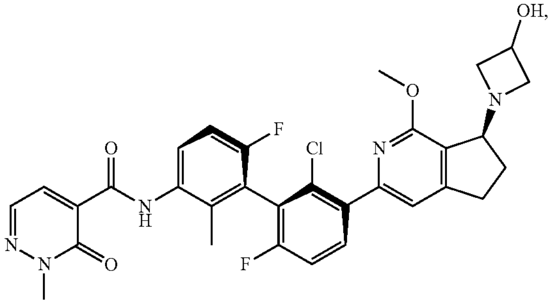
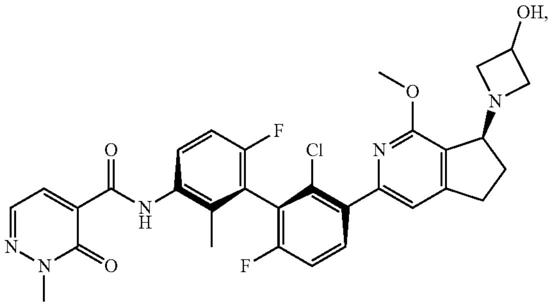
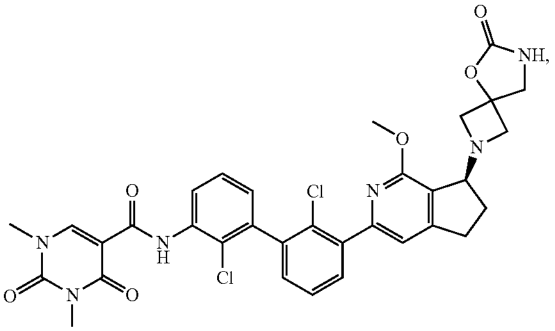
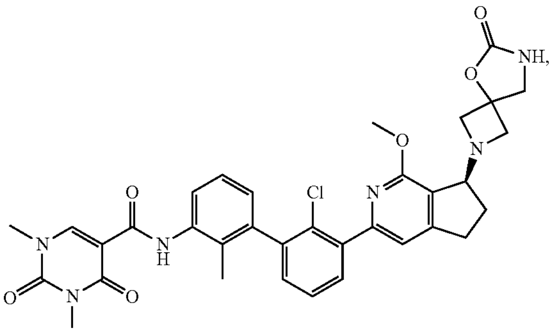

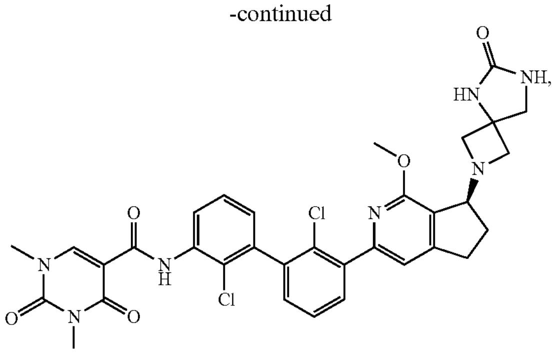
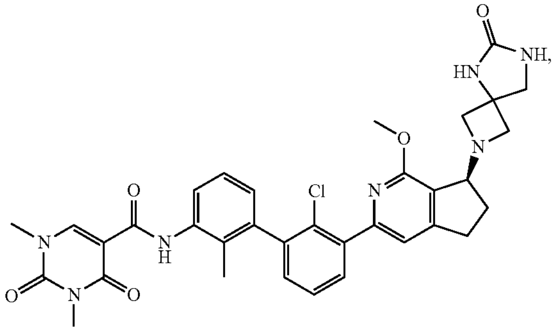
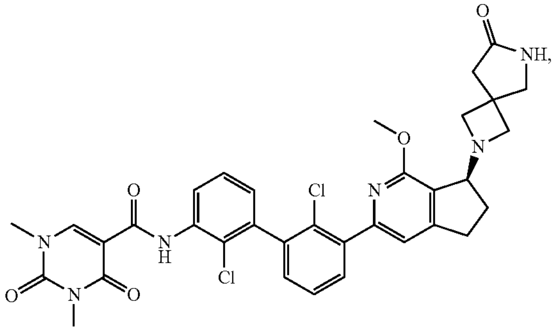
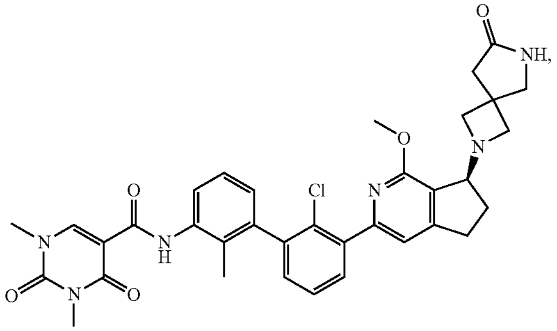
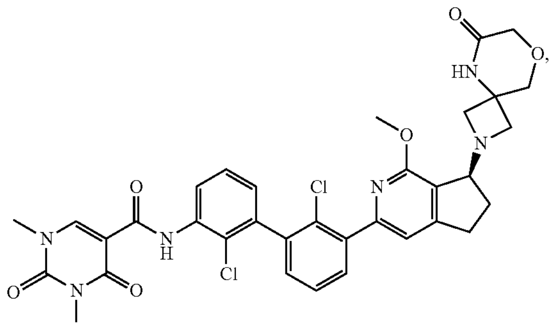
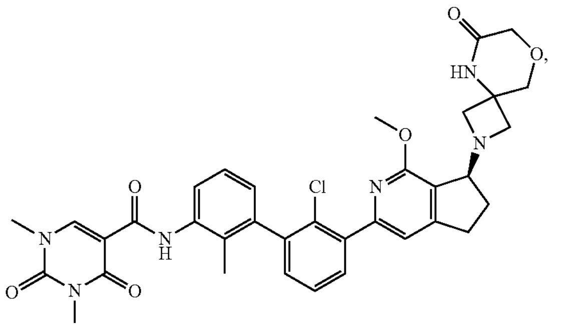
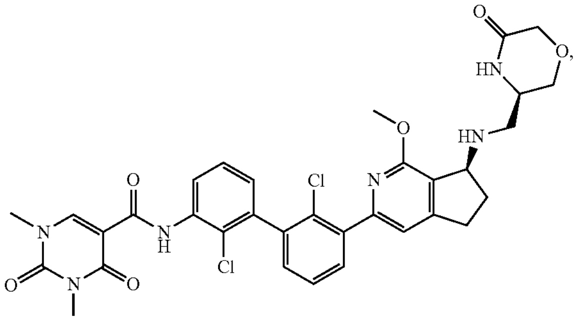
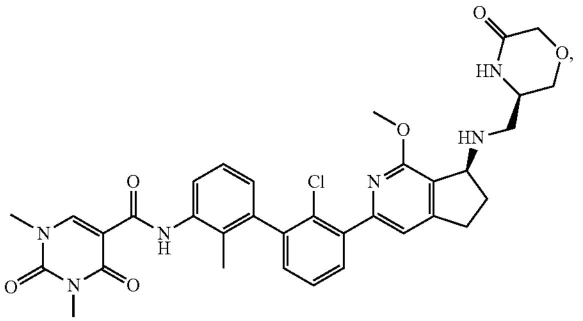
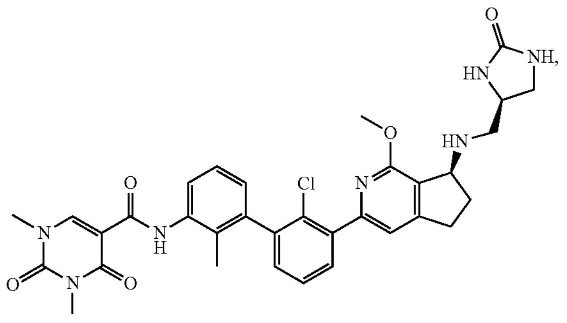
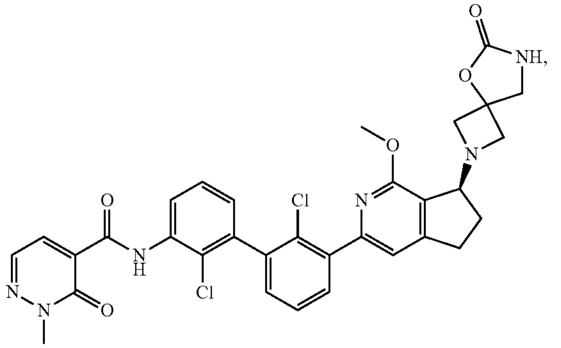

-continued
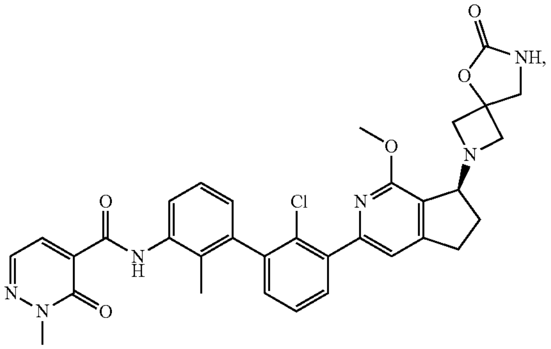
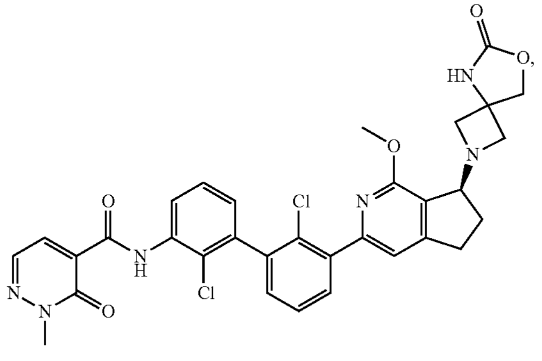
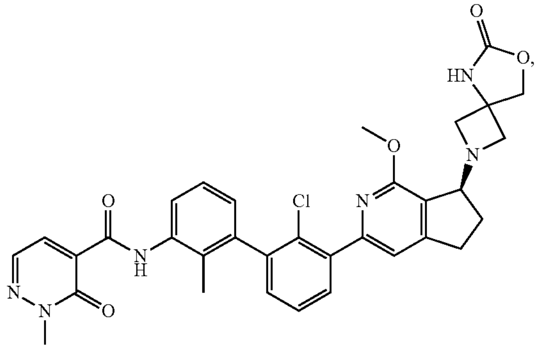
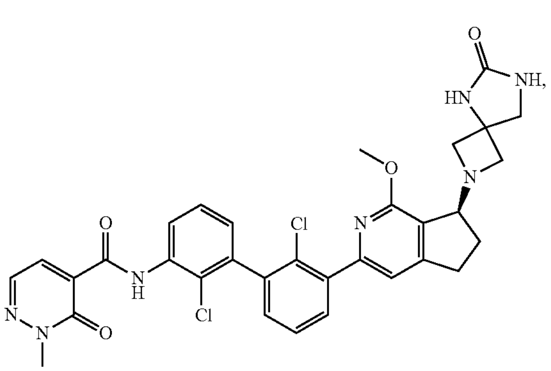
-continued
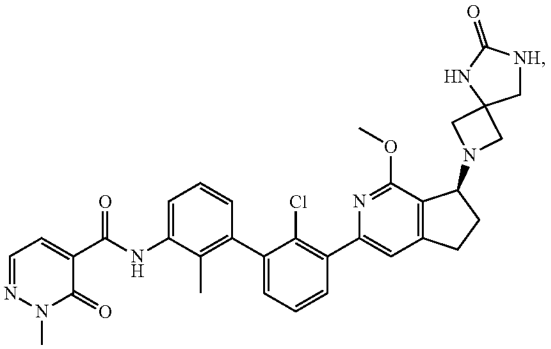
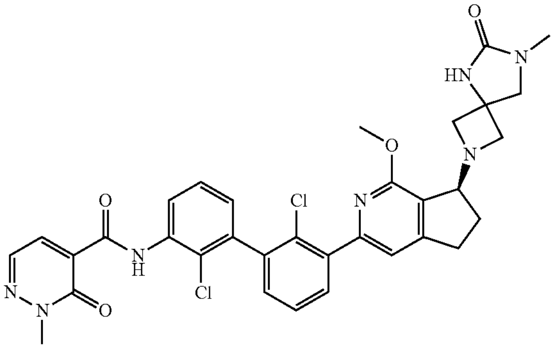
,
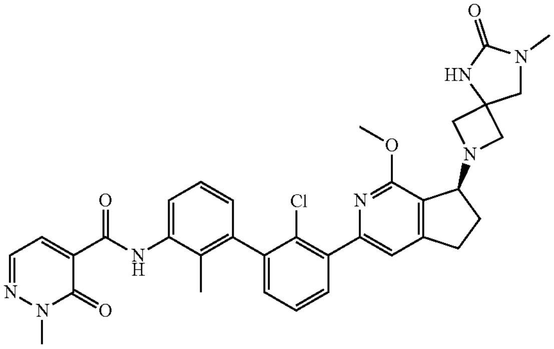
,
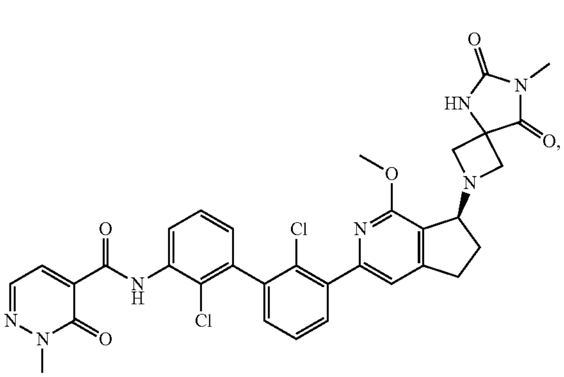

-continued
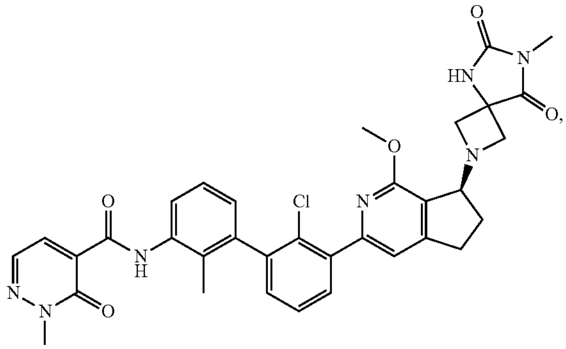
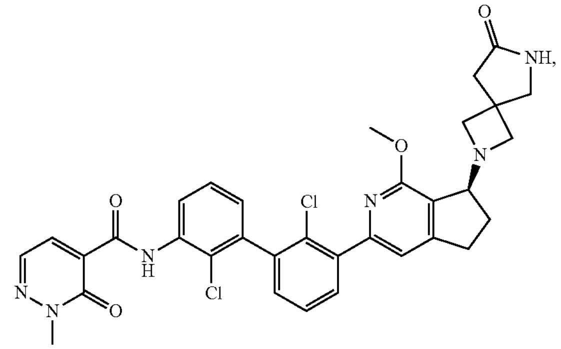
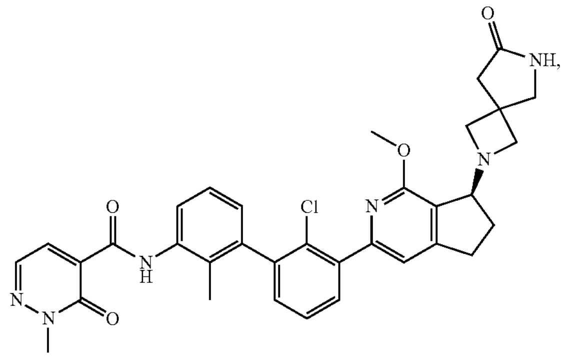
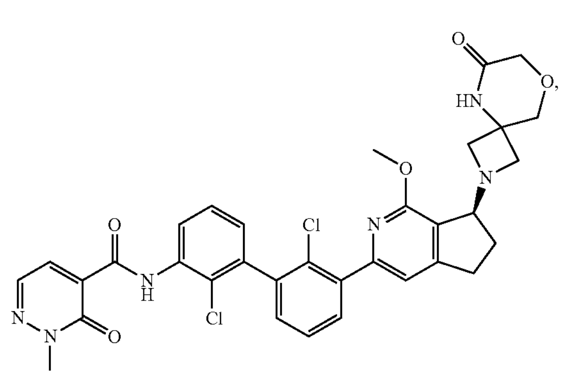
-continued
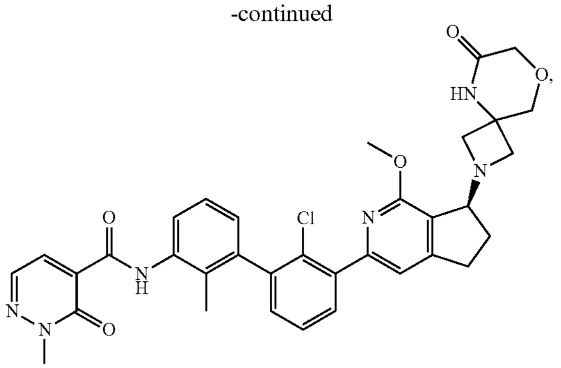
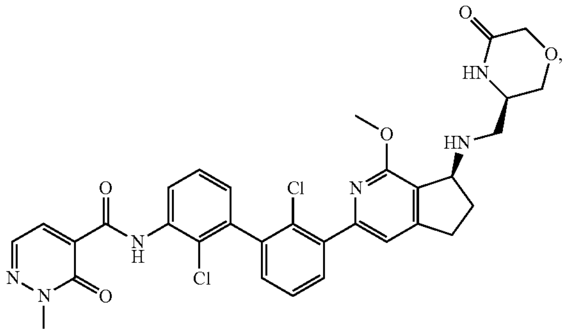
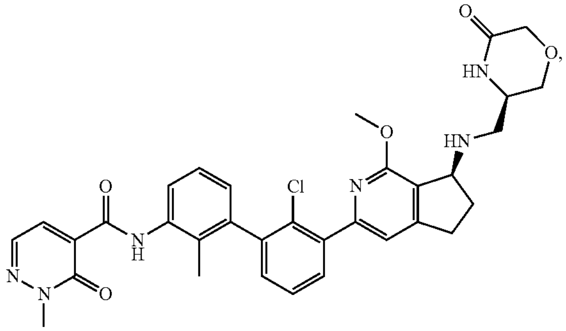
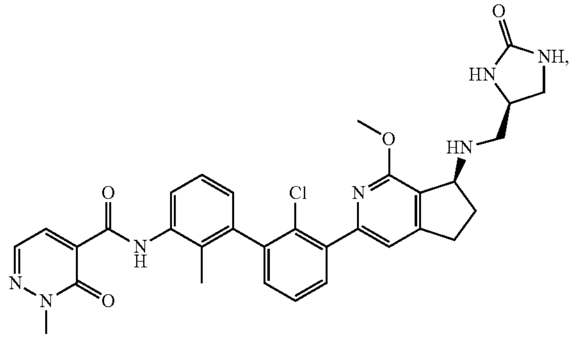
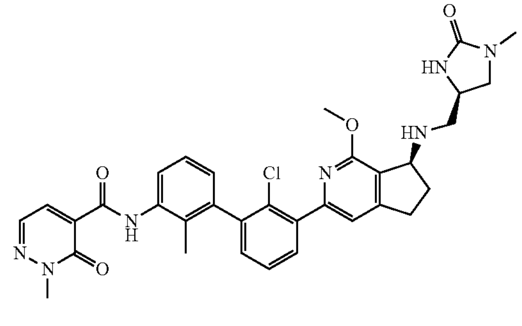
and -continued
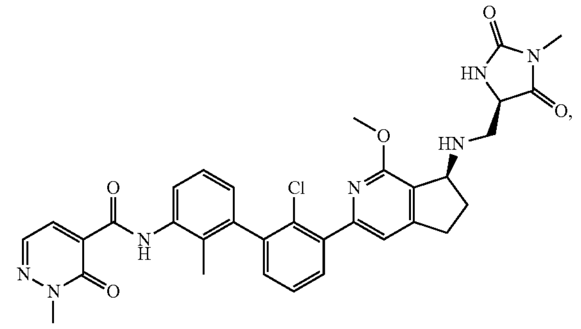
or a pharmaceutically acceptable salt of any of the foregoing.
Embodiment 146
The compound of Embodiment 1 selected from:
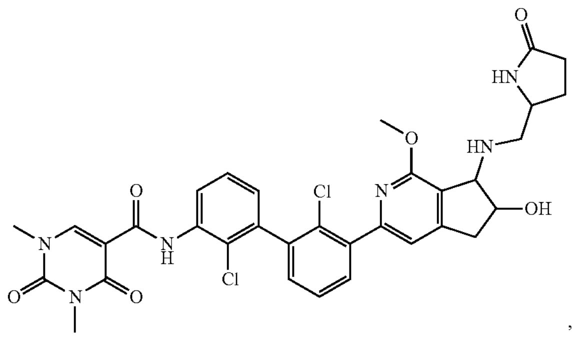
,
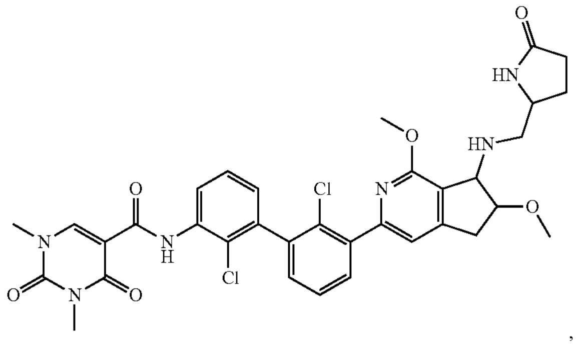
,
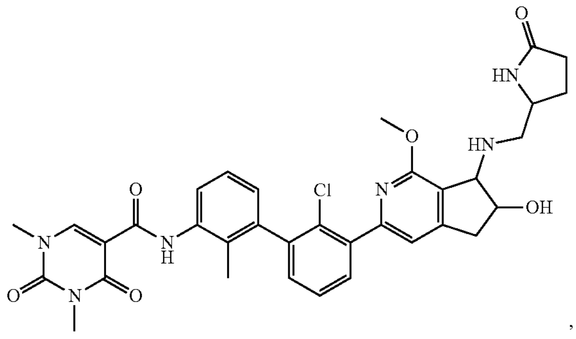
,
-continued
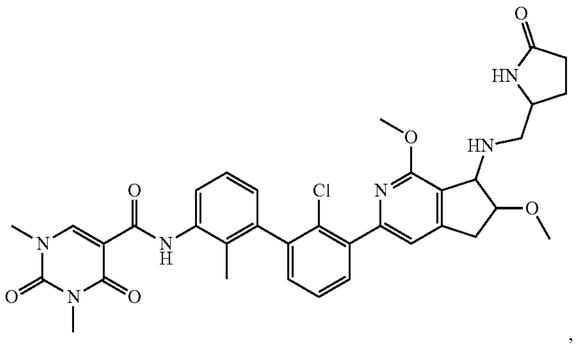
,
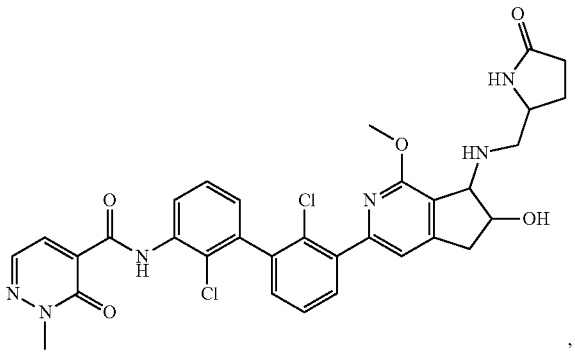
,
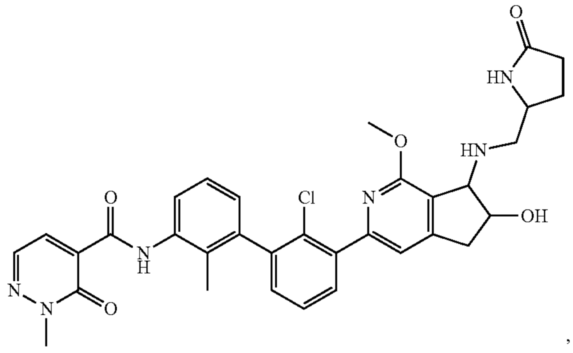
,
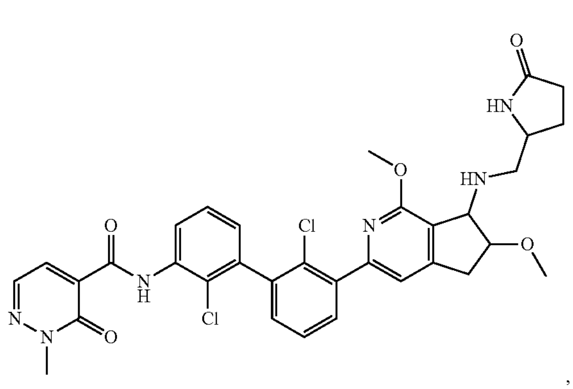
, -continued
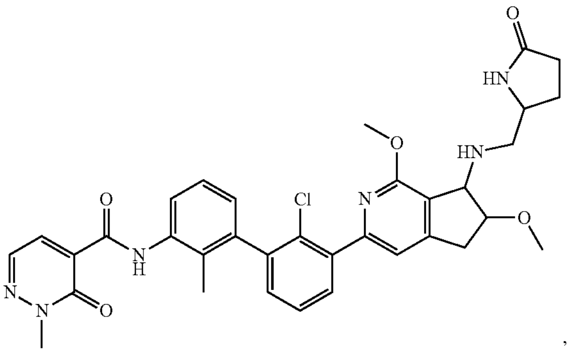
,
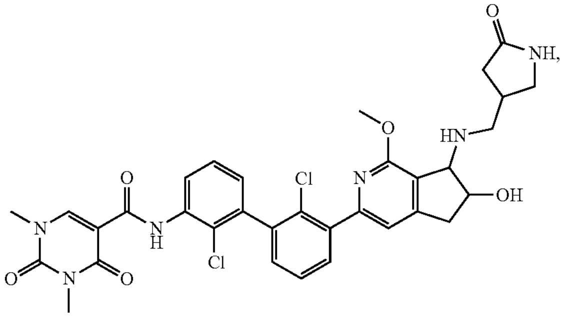
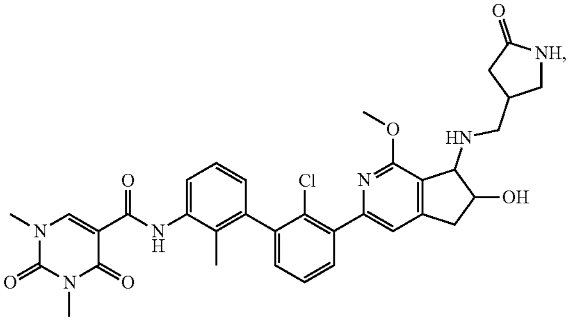
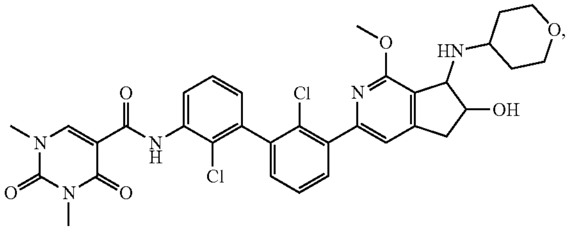
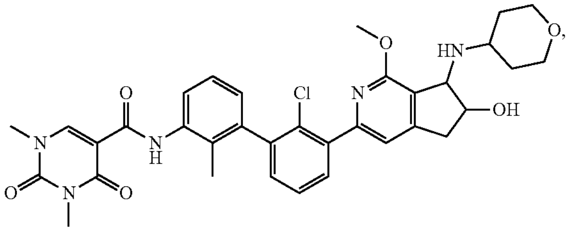
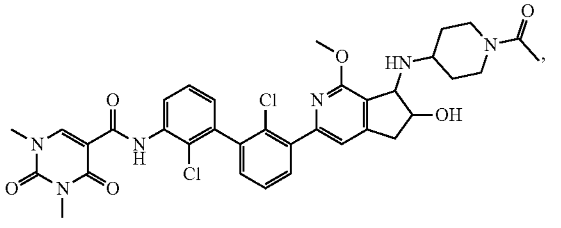
-continued
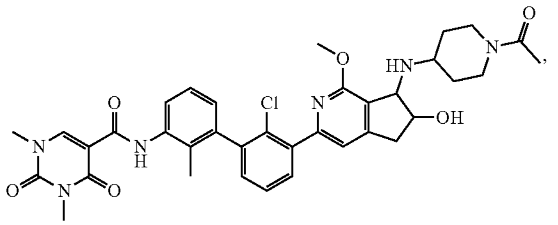
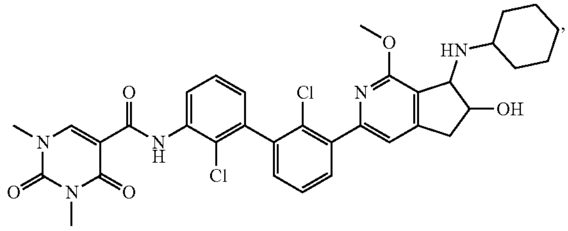
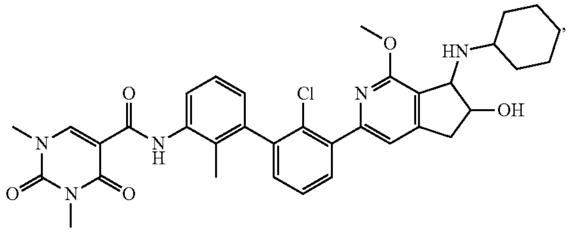
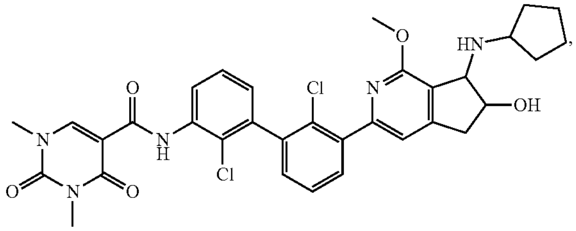
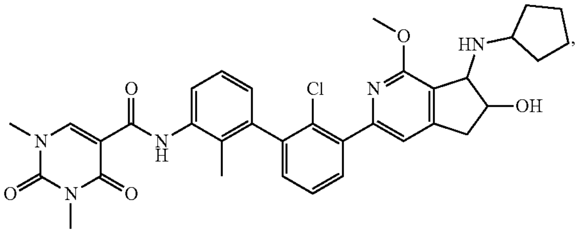
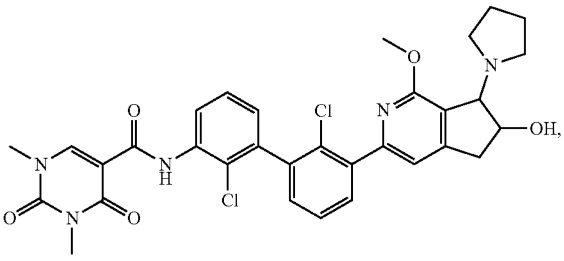
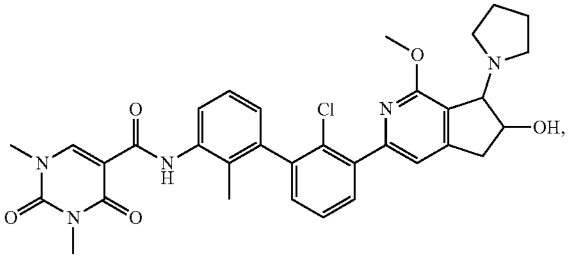

-continued
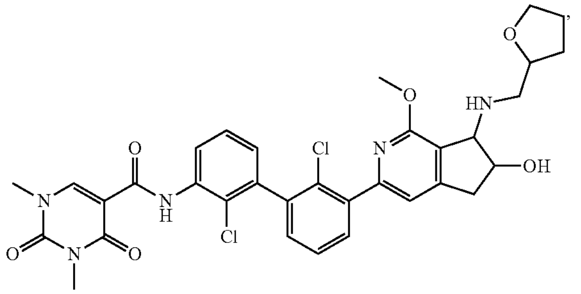
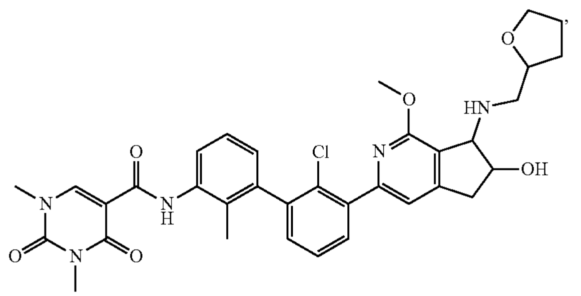
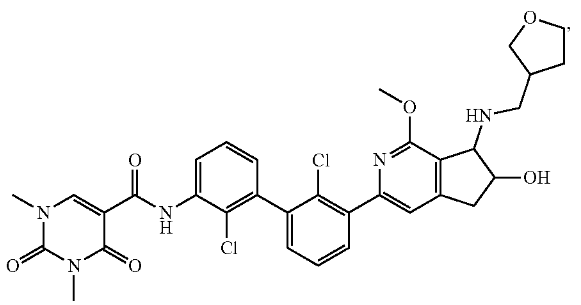
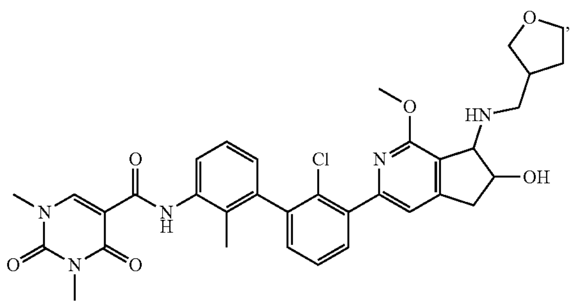
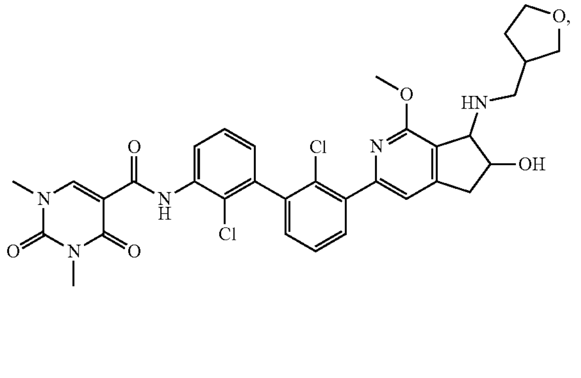
-continued
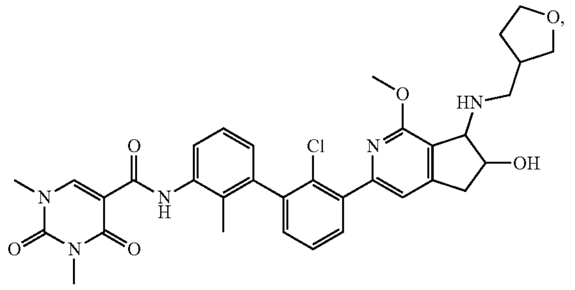
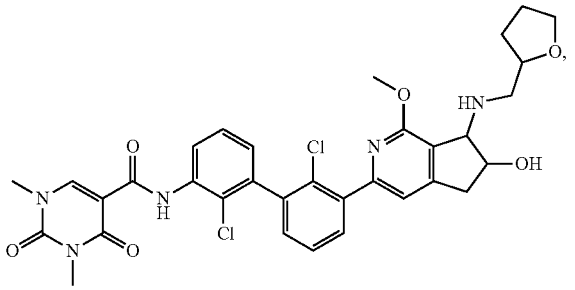
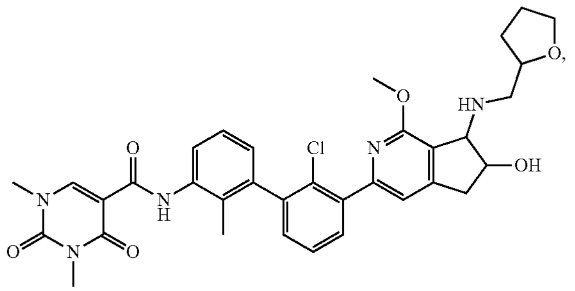
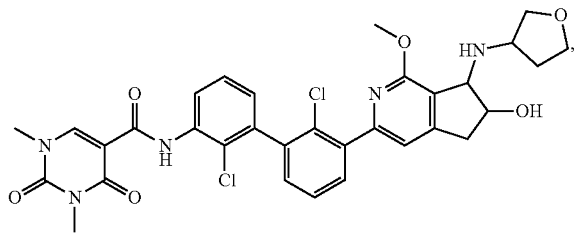
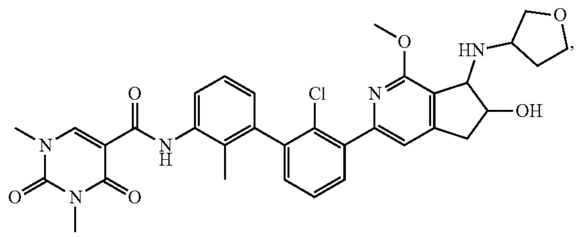
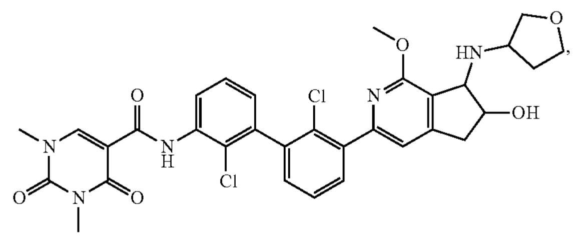

-continued
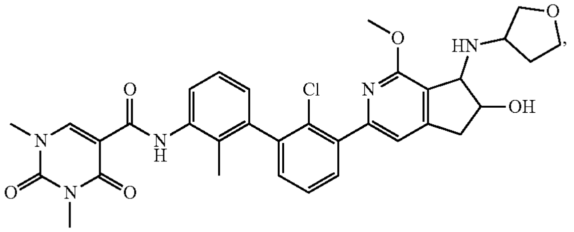
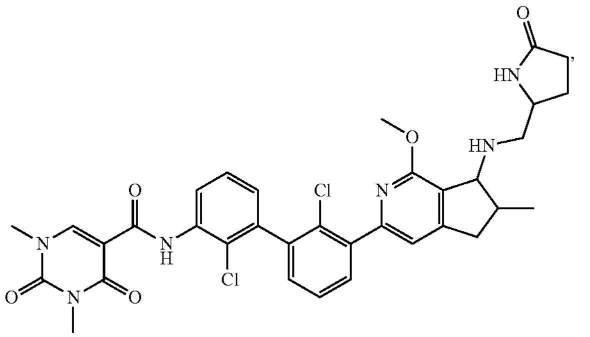
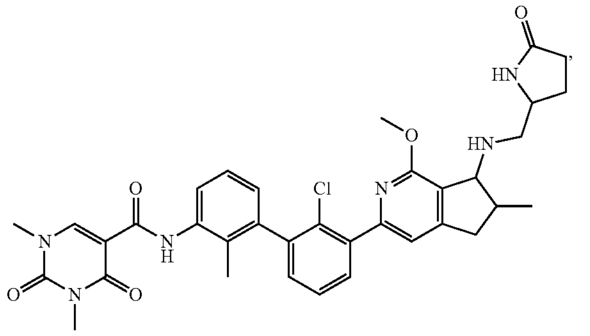
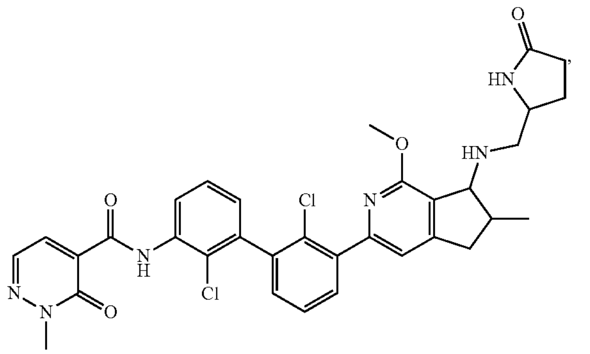
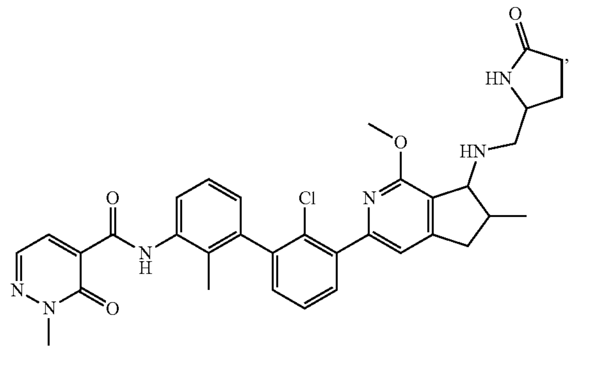
-continued
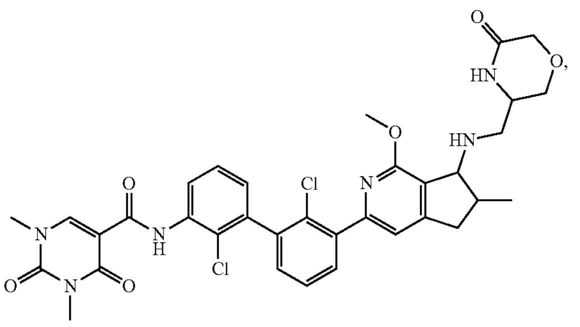
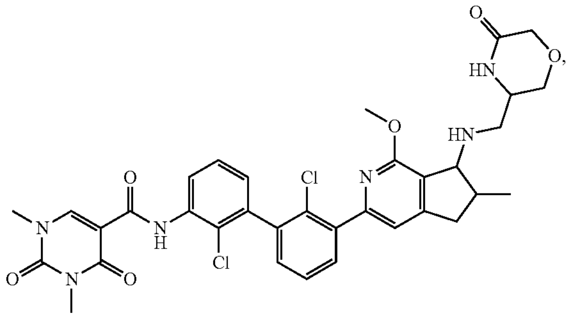
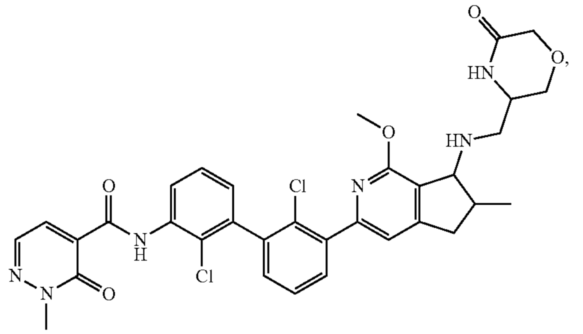
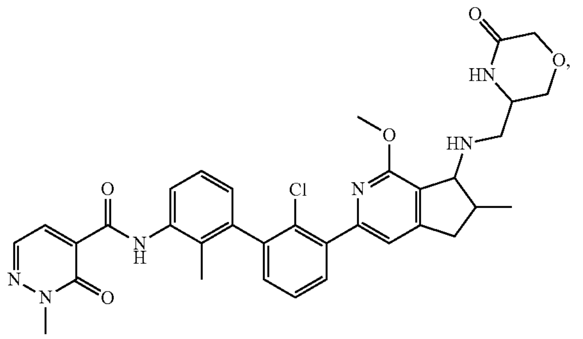
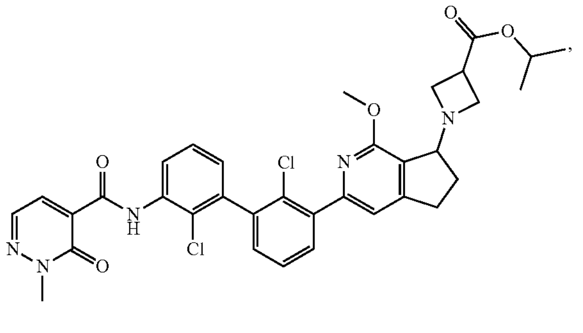

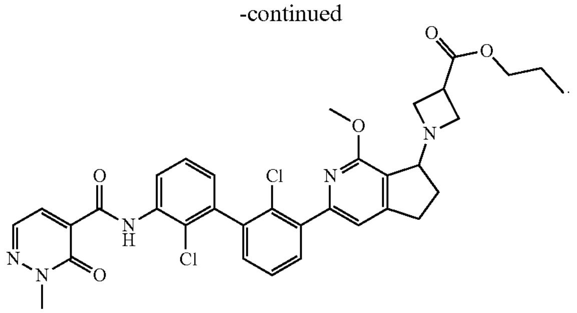
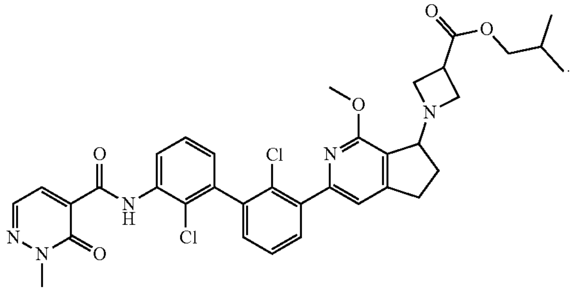
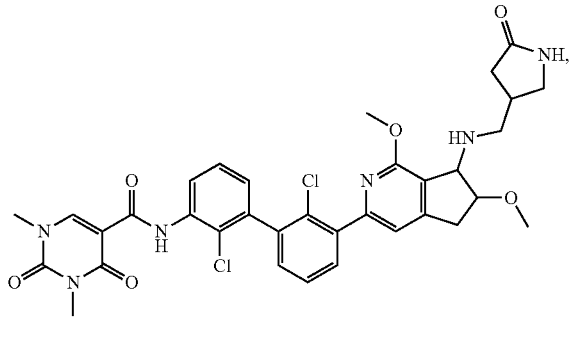
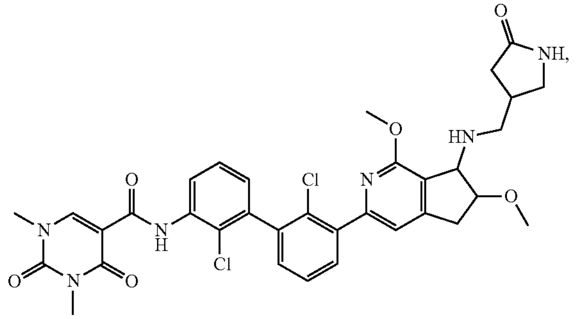
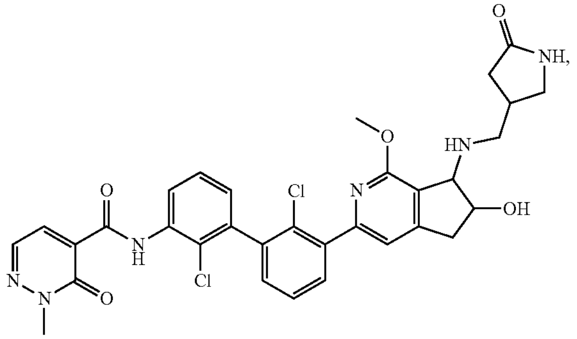
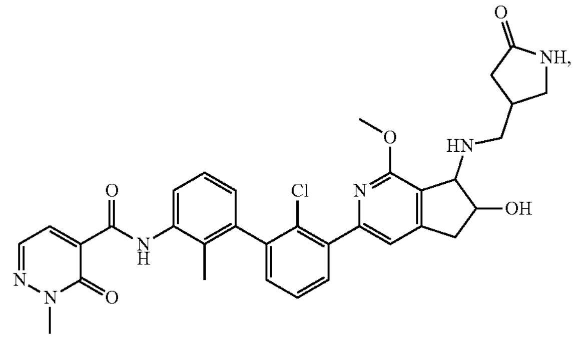
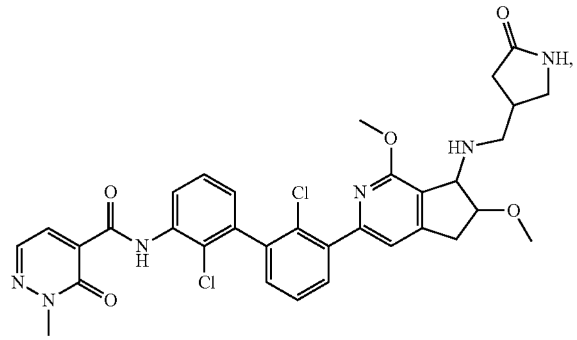
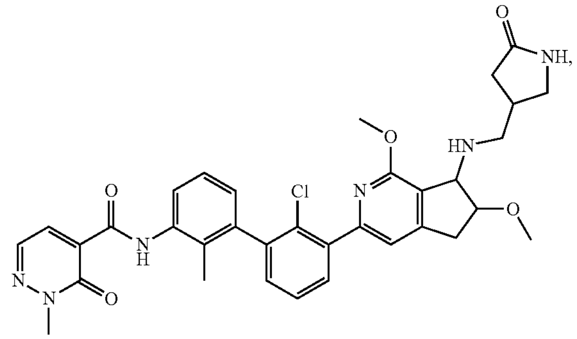
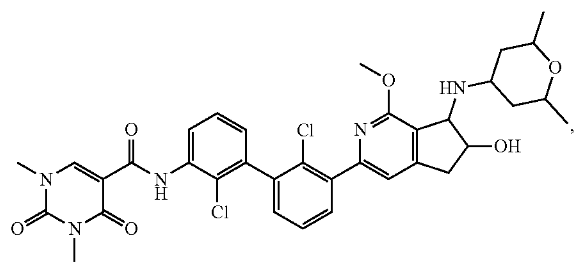
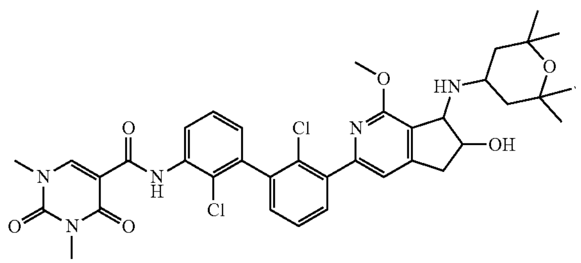

-continued
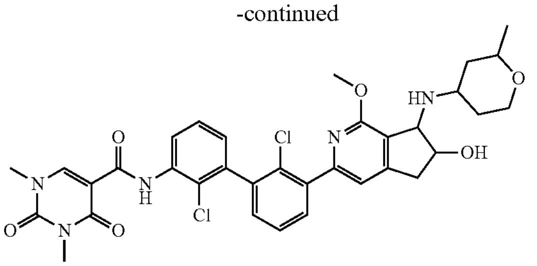
and
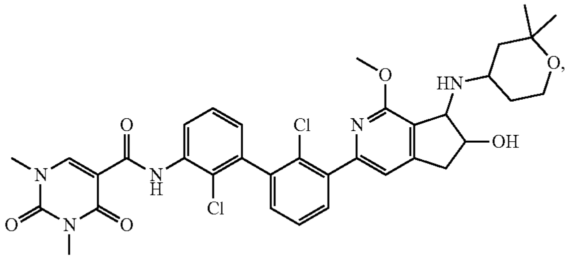
or a pharmaceutically acceptable salt of an of the foregoing.
Embodiment 147
The compound of Embodiment 1 selected from:
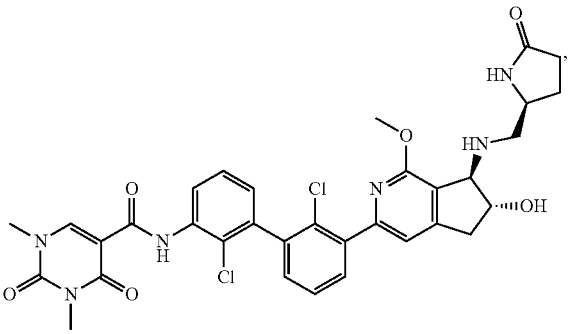
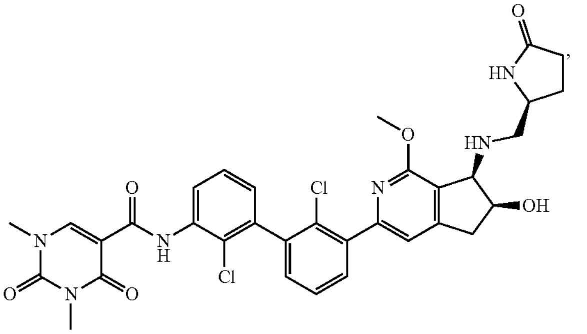
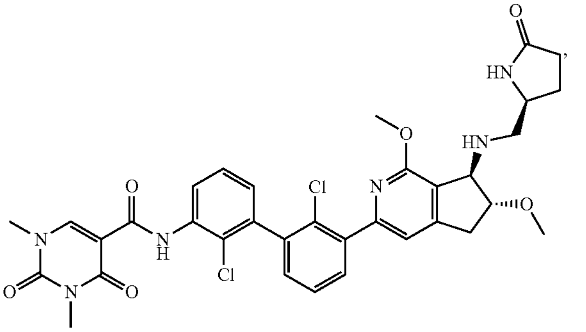
-continued
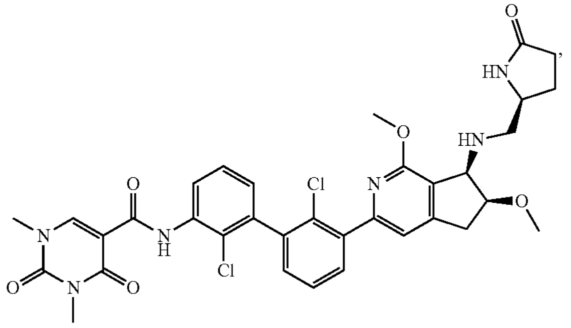
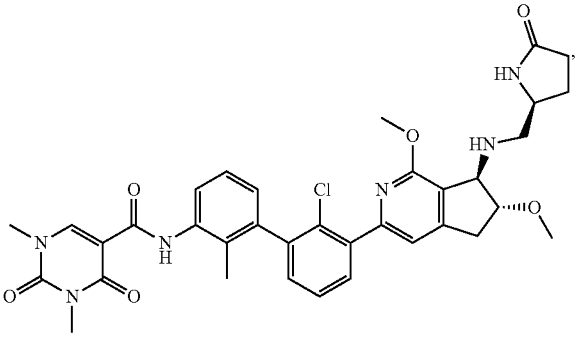
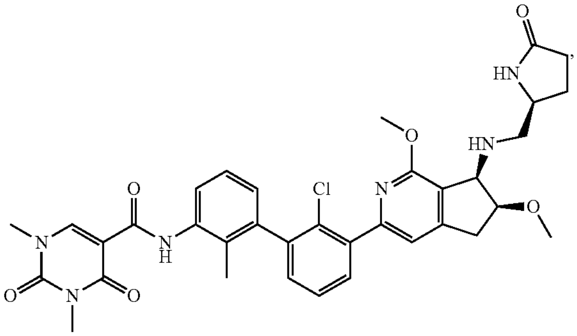
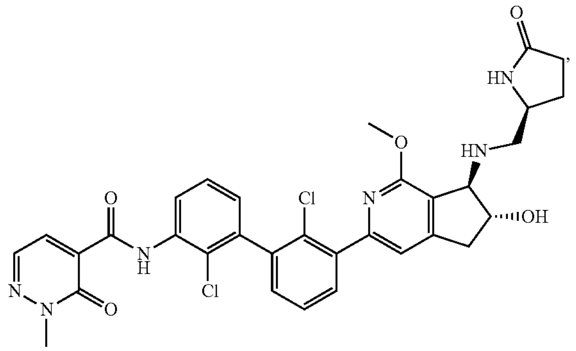
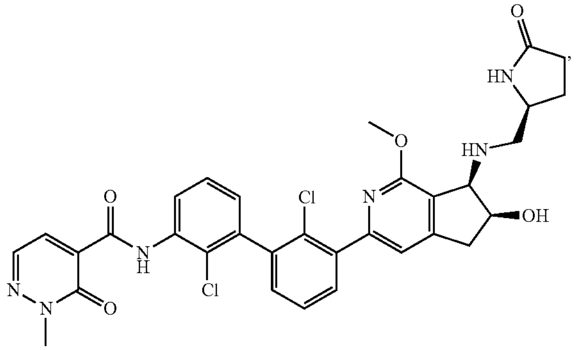

-continued
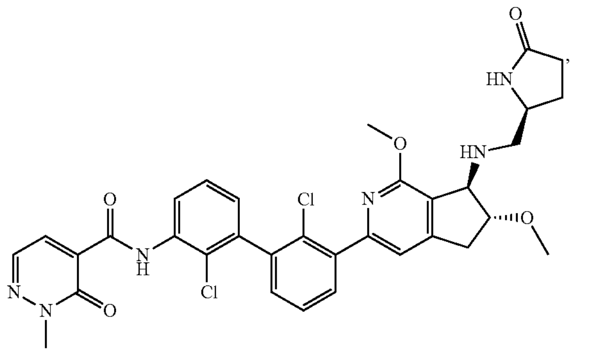
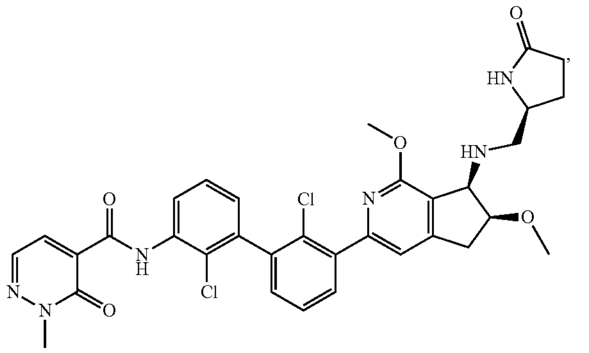
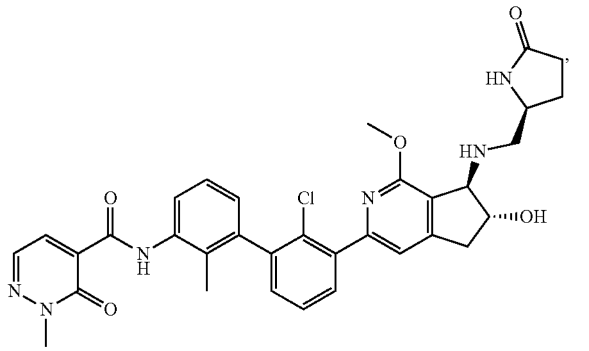
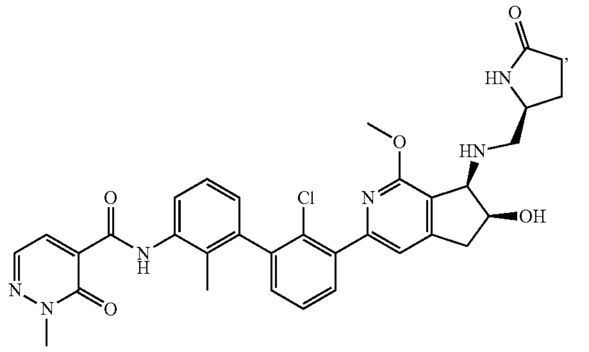
-continued
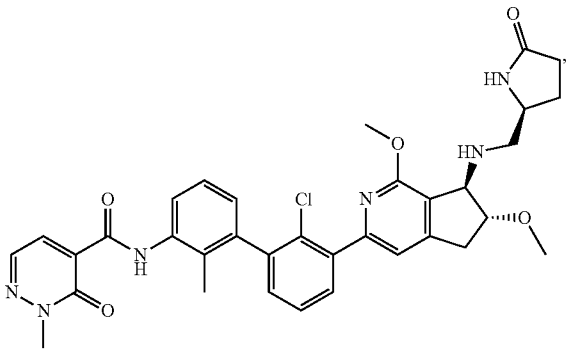
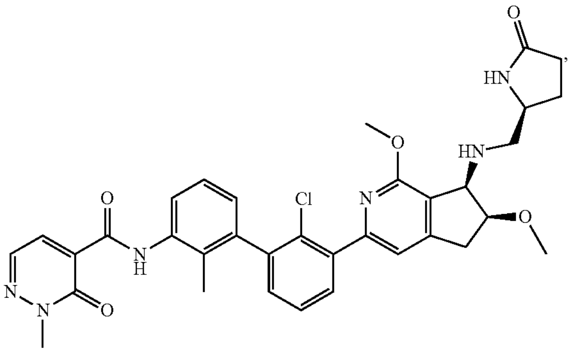
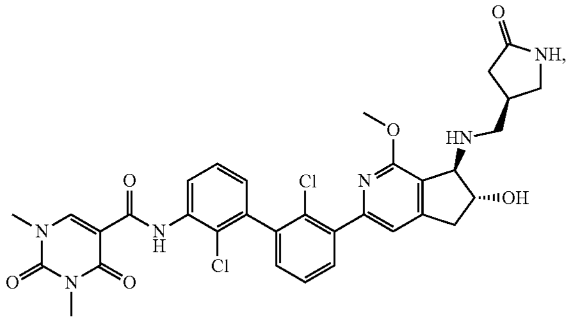
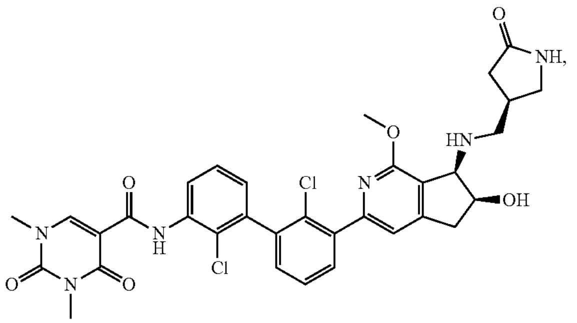
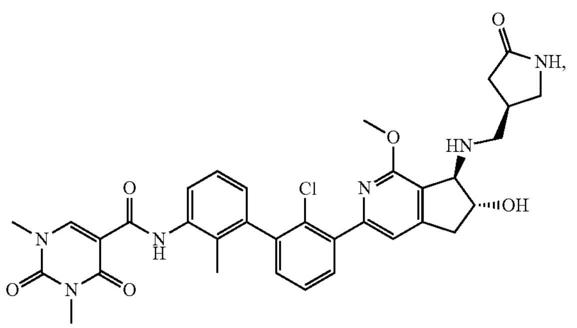

-continued
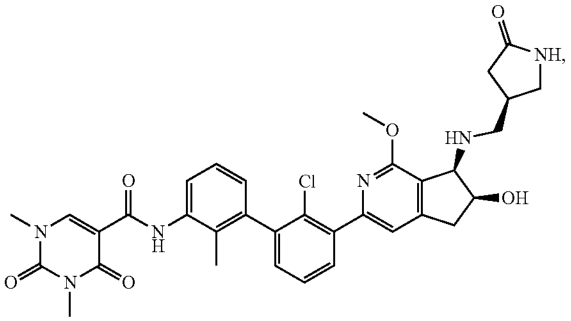
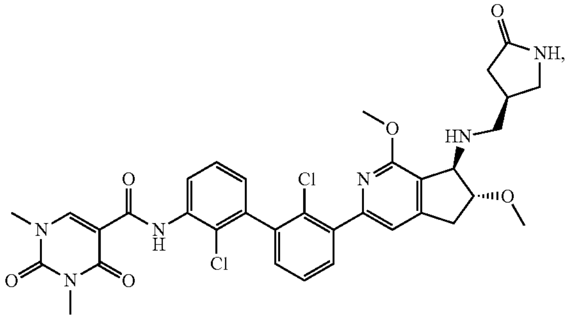
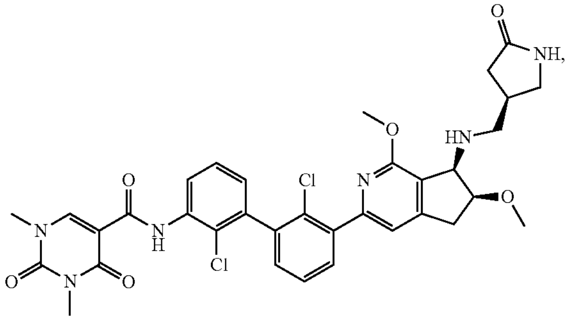
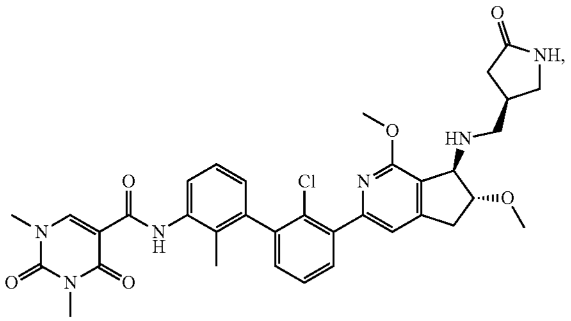
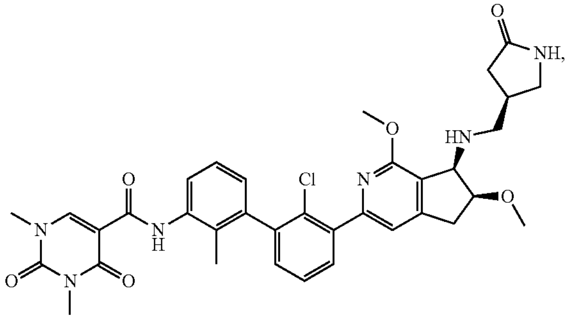
-continued
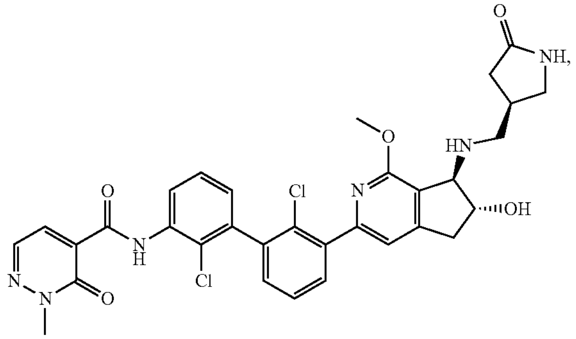
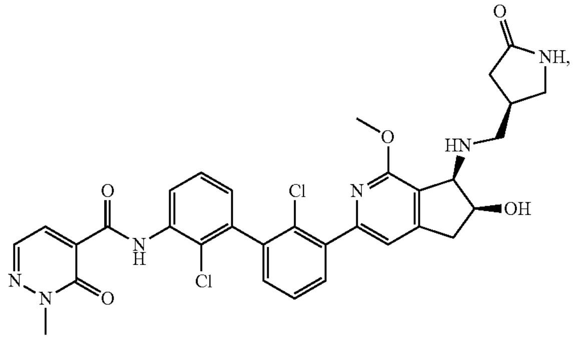
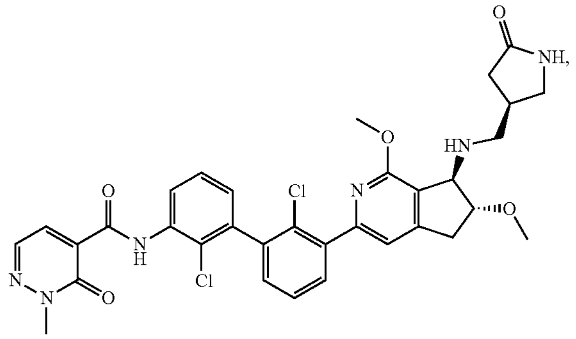
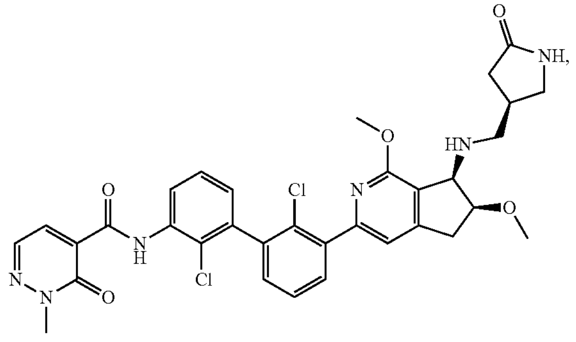
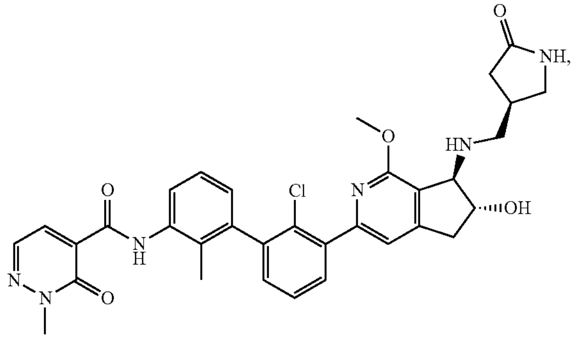

-continued
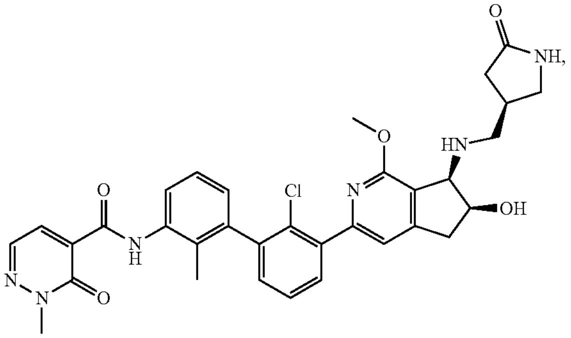
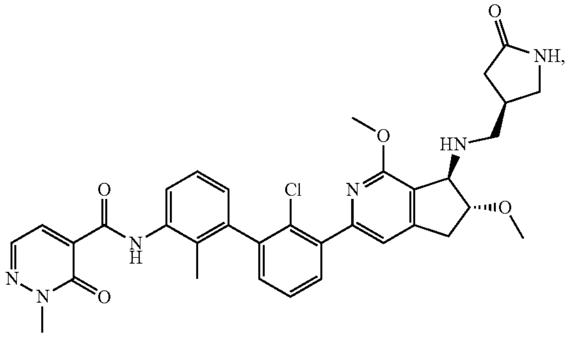
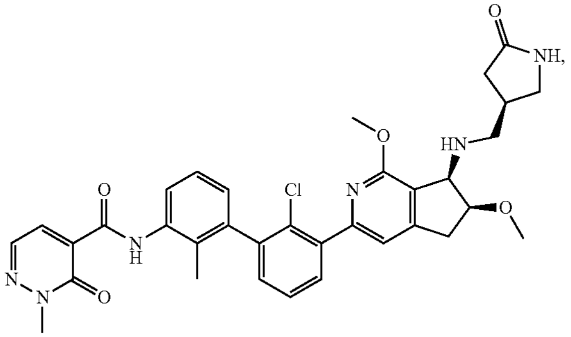
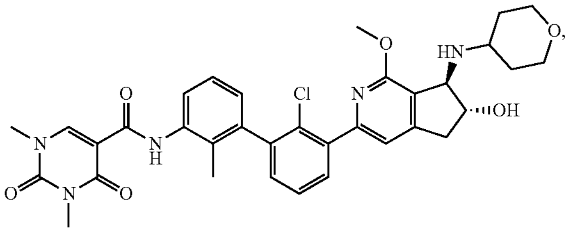
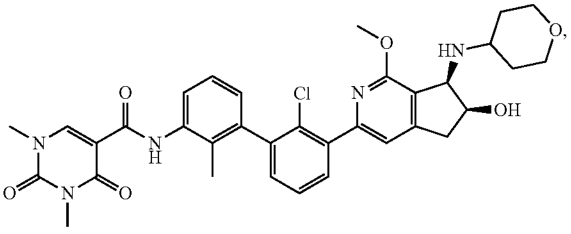
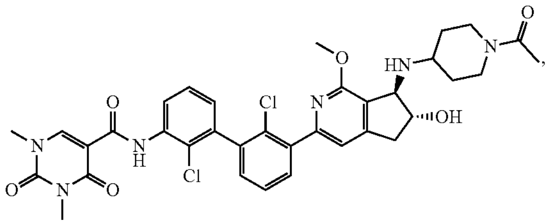
-continued
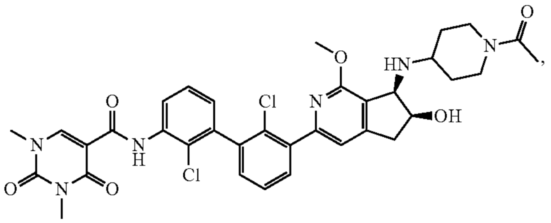
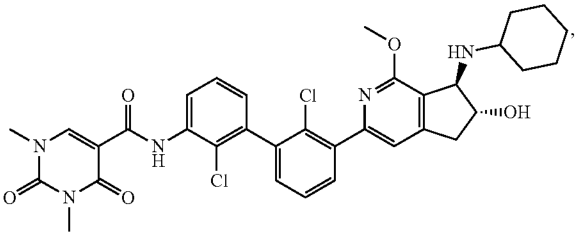
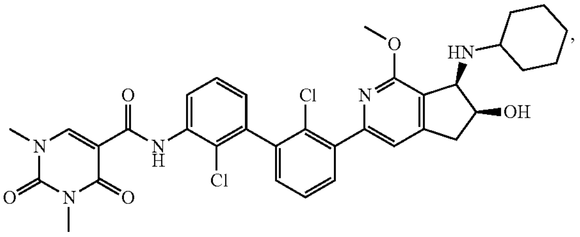
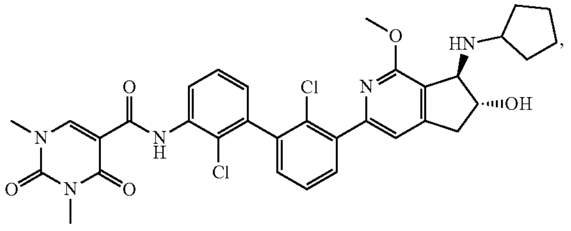
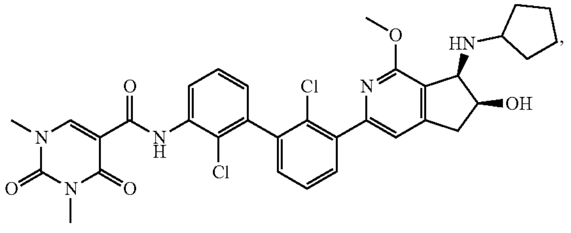
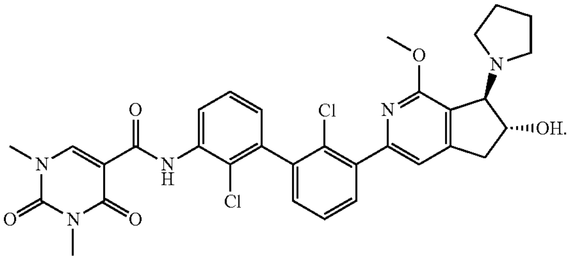
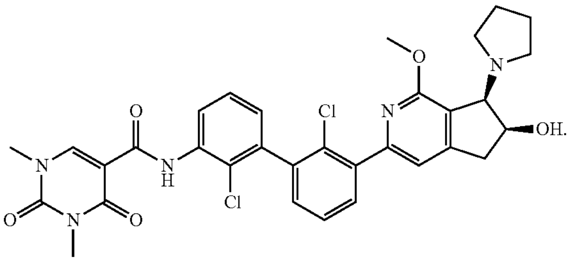

-continued
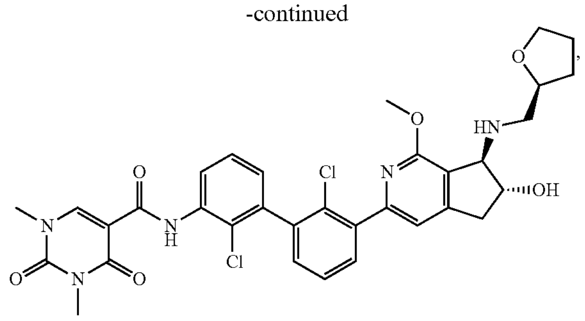
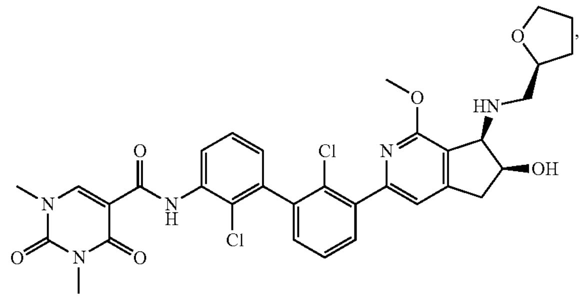
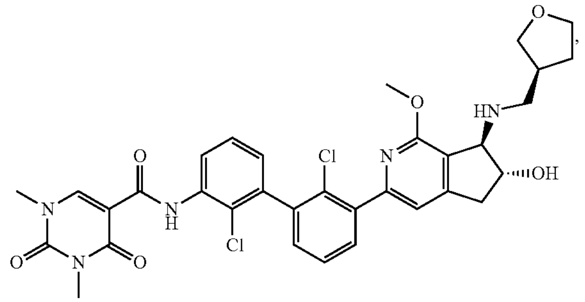
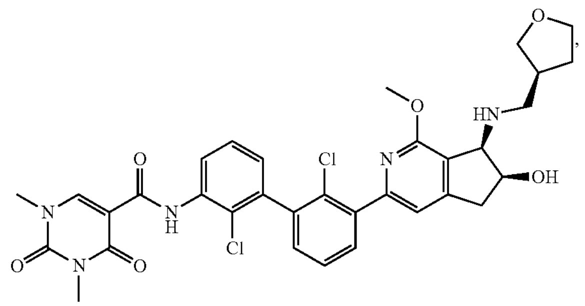
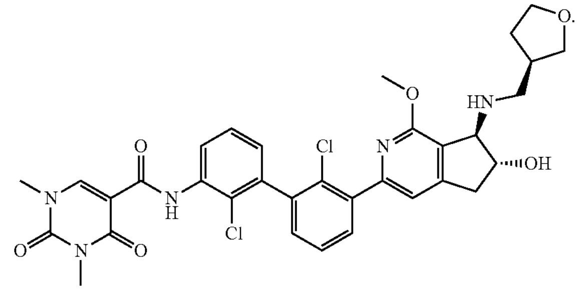
-continued
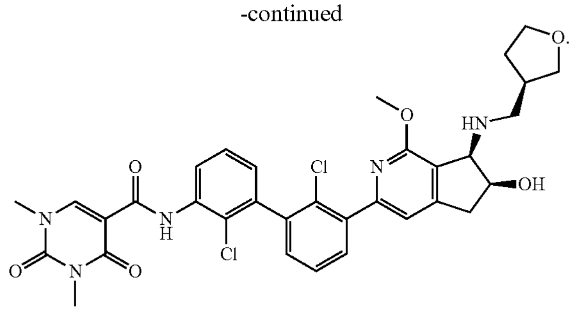
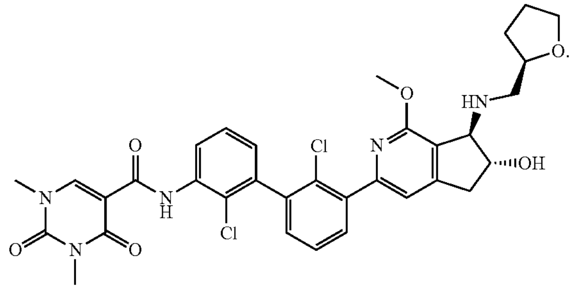
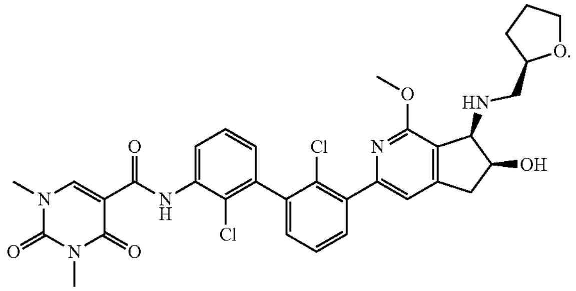
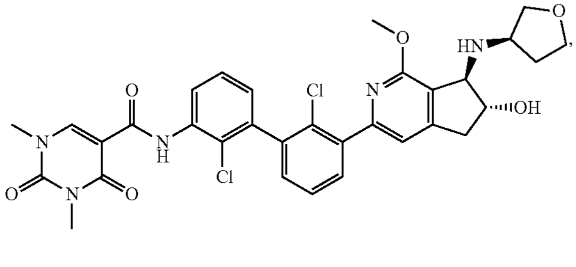
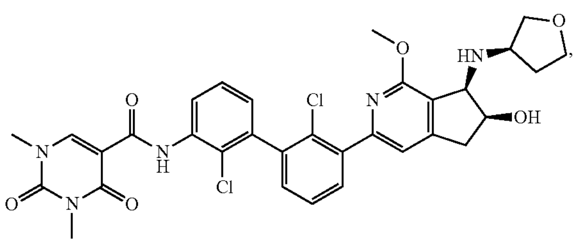
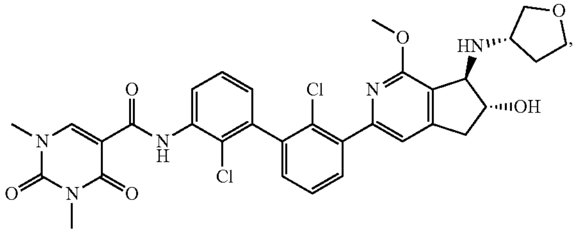

-continued
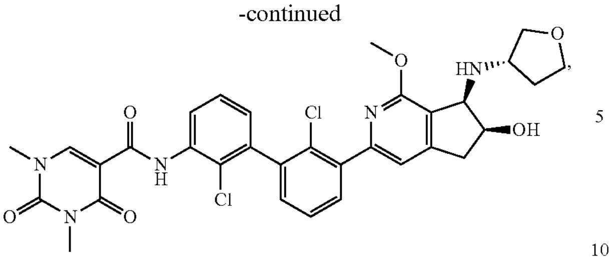
,
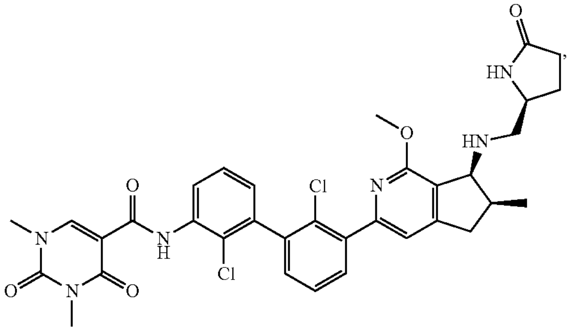
,
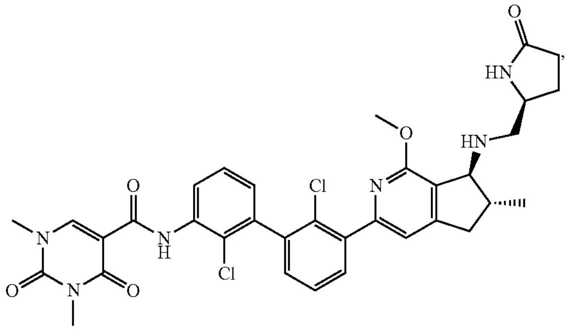
,
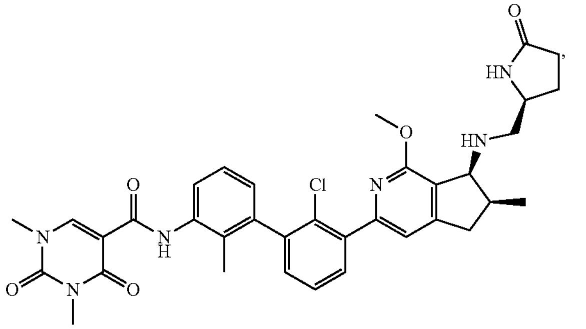
,
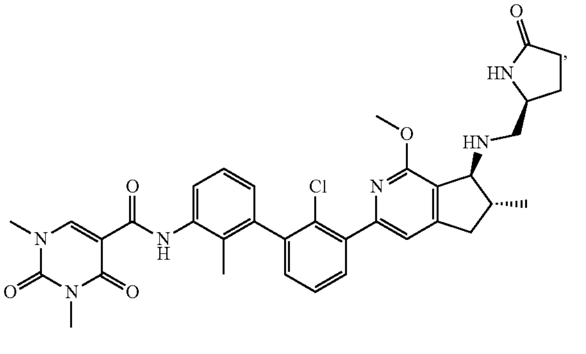
,
-continued
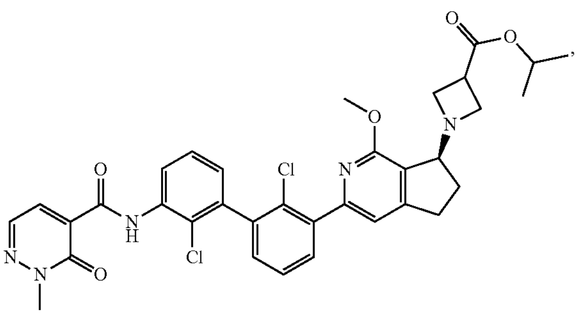
,
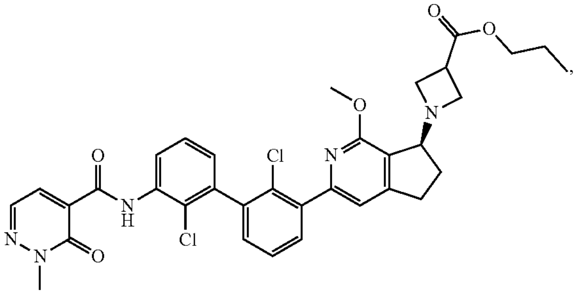
,
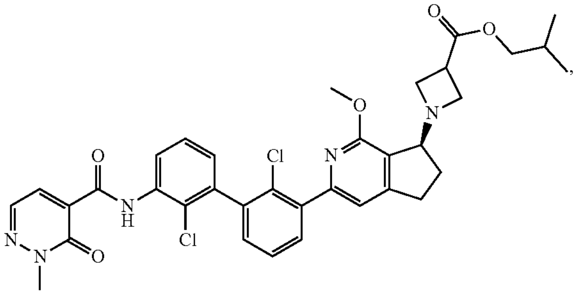
,
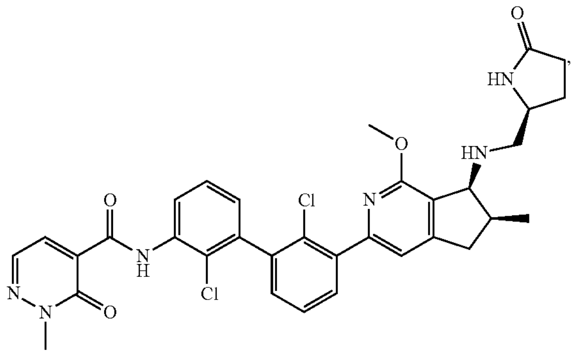
,
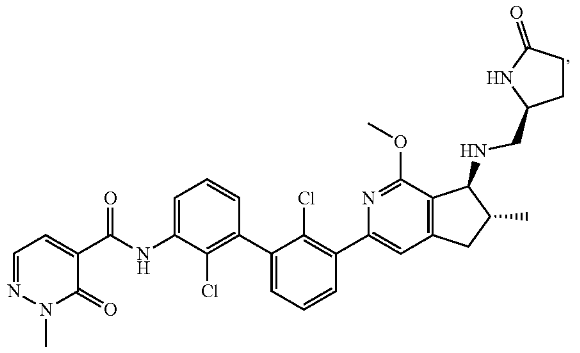
, -continued
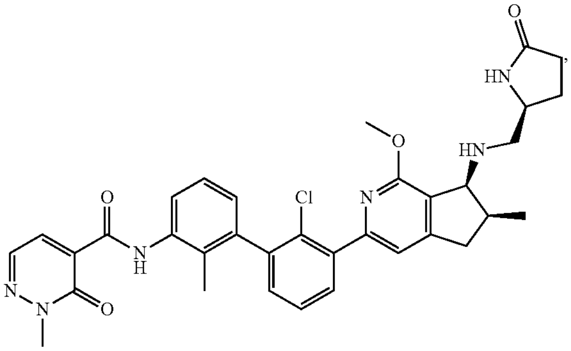
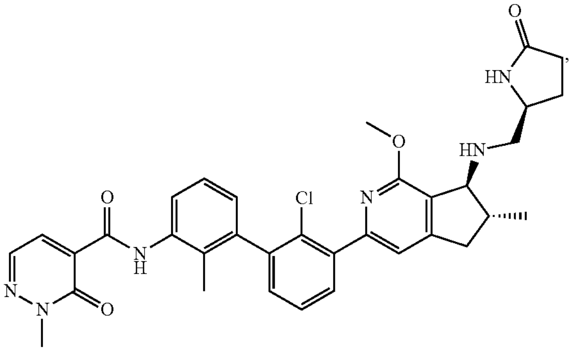
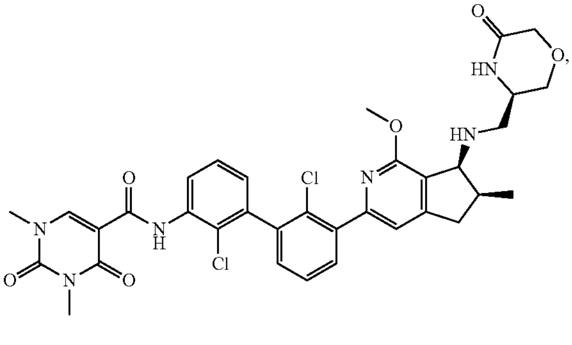
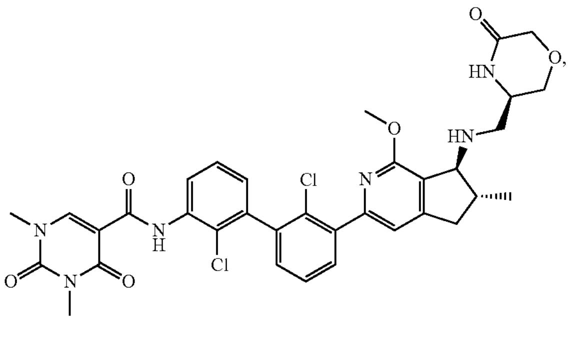
-continued
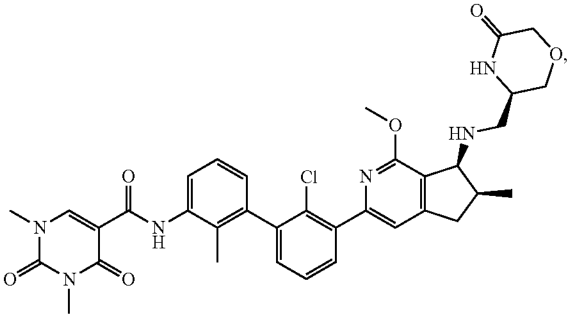
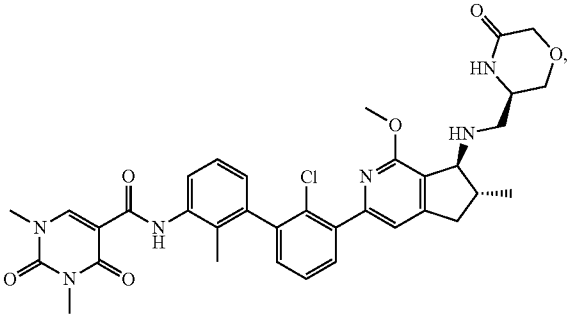
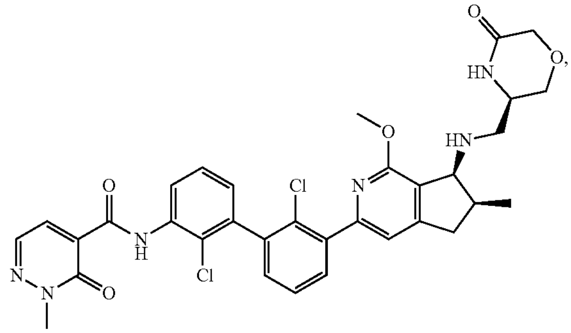
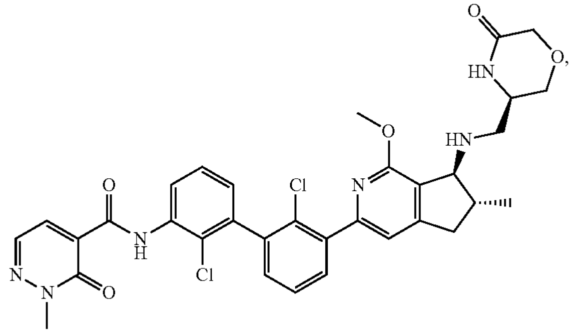
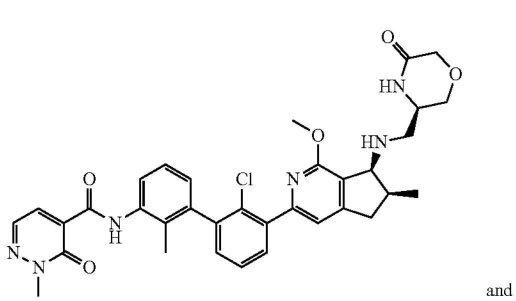
and -continued

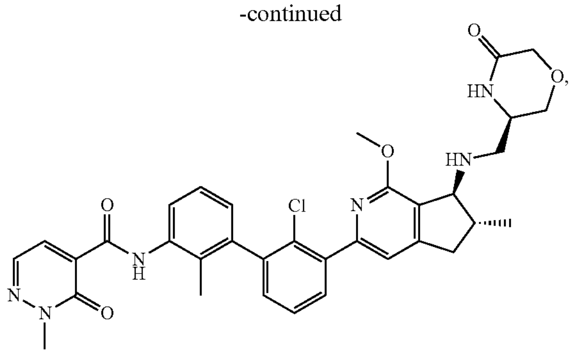

or a pharmaceutically acceptable salt of any of the foregoing.

Embodiment 148

The compound of Embodiment 1 selected from: A-1 to A-139, B-1, B-2, B-3, B-4, C-1, D-1, D-2, D-3, D-4, D-5, D-6, D-7, D-8a, D-8b, D-10, D-11, D-12, D-13, D-14, D-15, D-16, D-17, D-18, D-19, E-1, E-2, F-1, G-1, H-1, I-1, J-1, J-2, J-3, J-4, K1-a K-1b, L-1a, L-1b, M-1a, M-1b, M-2a, M-2b, M-3a and M-3b, or a pharmaceutically acceptable salt of any of the foregoing.

Embodiment 149

A pharmaceutical composition that can include an effective amount of a compound of any one of Embodiments 1-148, or a pharmaceutically acceptable salt thereof, and excipient.

Embodiment 150

A method for treating hepatitis B in a subject that can include administering to the subject in need thereof an effective amount of a compound of any one of Embodiments 1-148, or a pharmaceutically acceptable salt thereof.

Embodiment 151

A method for treating hepatocellular carcinoma (HCC) in a subject that can include administering to the subject in need thereof an effective amount of a compound of any one of Embodiments 1-148, or a pharmaceutically acceptable salt thereof.

Embodiment 152

The method of any one of Embodiments 150-151, that can further include administering surgery, radiation therapy, chemotherapy, targeted therapy, immunotherapy, hormonal therapy, or antiviral therapy.

Embodiment 153

A compound of any one of Embodiments 1-148, or a pharmaceutically acceptable salt thereof, for use in treating hepatitis B.

Embodiment 154

A compound of any one of Embodiments 1-148, or a pharmaceutically acceptable salt thereof, for use in treating hepatocellular carcinoma (HCC).

Embodiment 155

The compound of any one of Embodiments 153-154, that can further include administering surgery, radiation therapy, chemotherapy, targeted therapy, immunotherapy, hormonal therapy, or antiviral therapy.

Embodiment 156

Use of a compound of any one of Embodiments 1-148, or a pharmaceutically acceptable salt thereof, in the preparation of a medicament for use in treating hepatitis B.

Embodiment 157

Use of a compound of any one of Embodiments 1-148, or a pharmaceutically acceptable salt thereof, in the preparation of a medicament for use in treating hepatocellular carcinoma (HCC).

Embodiment 158

The use of any one of Embodiments 156-157, that can further include administering surgery, radiation therapy, chemotherapy, targeted therapy, immunotherapy, hormonal therapy, or antiviral therapy.

Methods for the Preparation

In this section, as in all other sections unless the context indicates otherwise, references to Formula (I), along with pharmaceutical acceptable salts thereof, include all other sub-groups and examples thereof as provided herein. The general preparations of some representative examples of compounds of Formula (I) are described herein, and are generally prepared from starting materials which are either commercially available or prepared by standard synthetic processes used by those skilled in the art.

In this section, as in all other sections unless the context indicates otherwise, references to Formula (I), Formula (II), Formula (III) and Formula (IV), along with pharmaceutical acceptable salts thereof, include all other sub-groups and examples thereof as provided herein. The general preparations of some representative examples of compounds of Formula (I), Formula (II), Formula (III), and Formula (IV) are described herein, and are generally prepared from starting materials which are either commercially available or prepared by standard synthetic processes used by those skilled in the art.

The following schemes a represent example preparations compounds of Formula (I), Formula (II), Formula (III) and Formula (IV), along with pharmaceutically acceptable salts thereof. Compounds of Formula (I), Formula (II), Formula (III) and Formula (IV), along with pharmaceutically acceptable salts thereof may also be prepared by analogous reaction protocols as described in the general schemes below, combined with standard synthetic processes used by those skilled in the art.

All variables shown in the schemes are defined as mentioned herein, unless otherwise is indicated or is clear from the context.

General Scheme 1

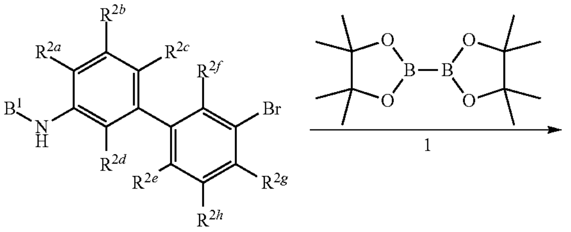

Intermediate II-1
Intermediate II-2
Intermediate II-3

-continued

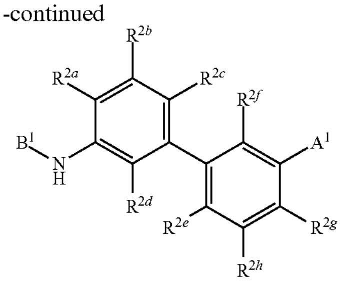

(I)

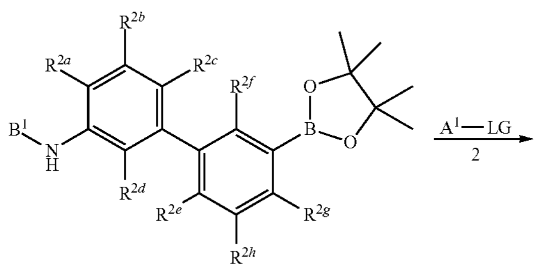

In general, compounds of Formula (I) can be prepared according to Scheme 1. In Scheme 1, LG is defined as Br or $C_1$. All other variables in Scheme 1 are defined according to descriptions provided herein. In Scheme 1, the following reaction conditions apply: (1) In the presence of suitable catalyst (for example, bis(triphenylphosphine)palladium(II) dichloride) in a suitable solvent, such as 1,4-dioxane, with a suitable base (for example, KOAc) at a suitable temperature (for example, 90° C.); (2) In the presence of suitable catalyst (for example bis(triphenylphosphine)palladium(II) dichloride) in a suitable solvent, such as 1,4-dioxane, with a suitable base, such as $K_2CO_3$ at a suitable temperature (for example 90° C.).

General Scheme 2

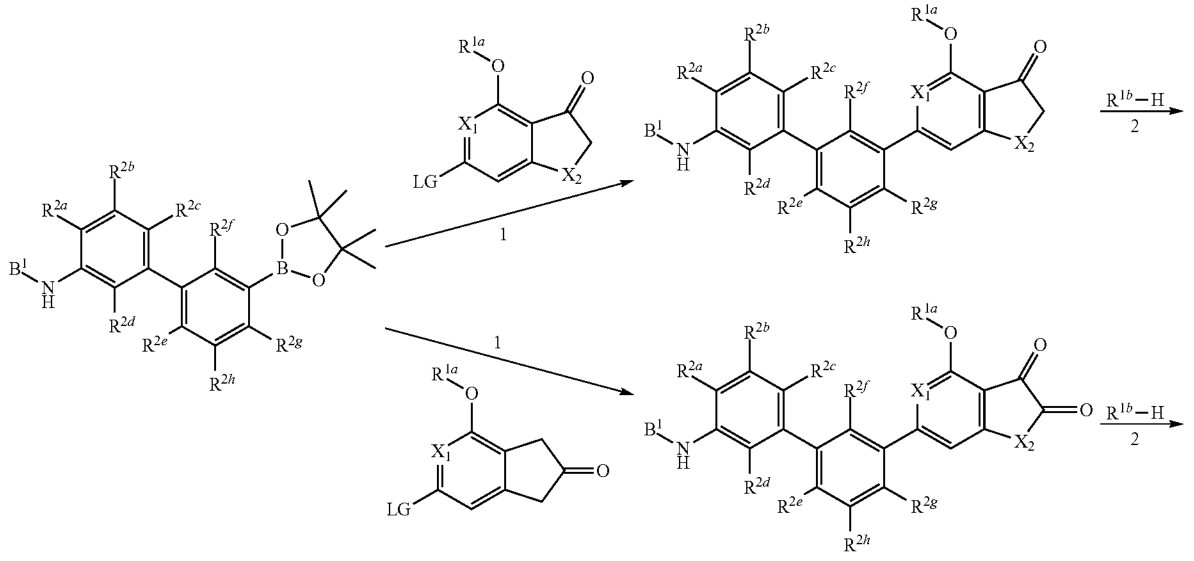

-continued

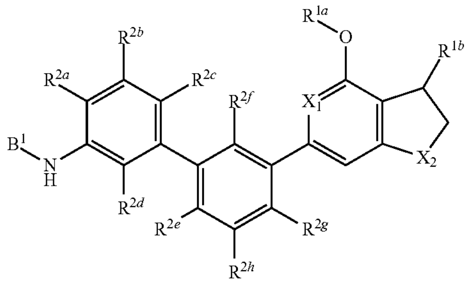

II

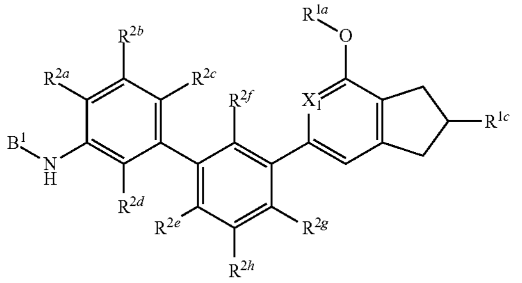

III

In general, compound with Formulae (II) and (III) can be prepared according to Scheme 2. In Scheme 2, the following reaction conditions apply: (1) In the presence of suitable catalyst (for example, bis(triphenylphosphine)palladium(II) dichloride) in a suitable solvent, such as 1,4-dioxane, with a suitable base (for example, $K_2CO_3$) at a suitable temperature (for example, 90° C.); (2) In the presence of an appropriate reductive reagent, such as sodium cyanoborohydride or sodium triacetoxyborohydride, in a suitable solvent (for example, DCM or MeOH) at a suitable temperature, such as approximately 20° C.

General Scheme 3

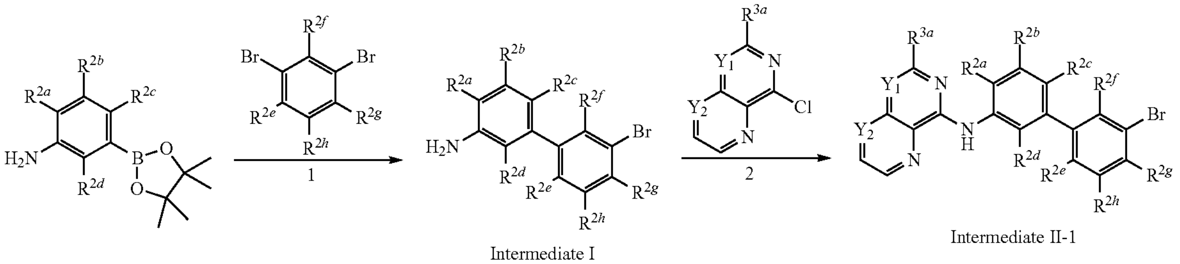

Intermediate I

Intermediate II-1

-continued

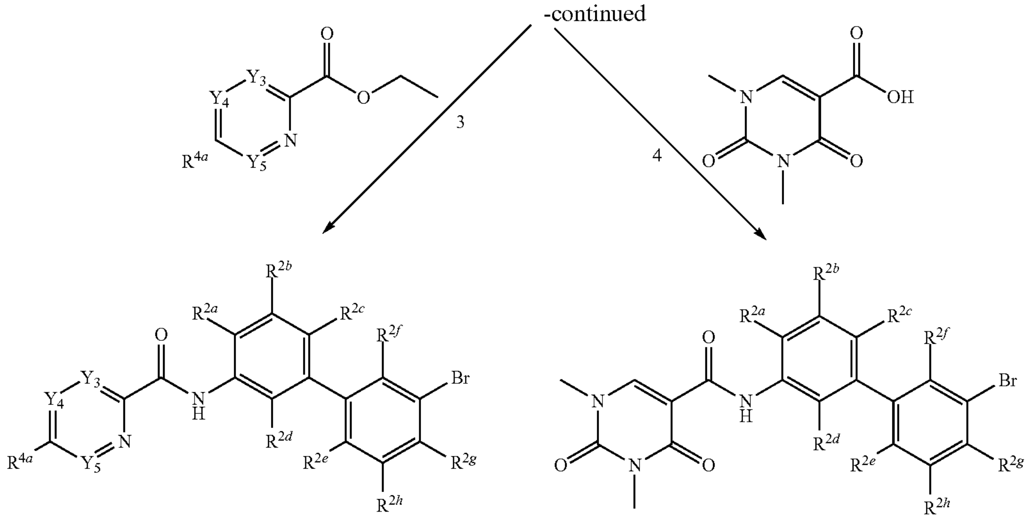

Intermediate II-2

Intermediate II-3

In general, Intermediates for preparing compounds with Formulae (I), (II) and (III) can be prepared according to Scheme 3 with suitable protection group. In Scheme 3, the following reaction conditions apply: (1) In the presence of suitable catalyst (for example, bis(triphenylphosphine)palladium(II) dichloride) in a suitable solvent, such as 1,4-dioxane, with a suitable base (for example, $K_2CO_3$) at a suitable temperature (for example, 90° C.); (2) In the presence of suitable acid (for example, HCL in 1,4-dioxane) in a suitable solvent (for example, t-BuOH) at a suitable temperature (for example, 100° C.); (3) In the presence of suitable base (for example, potassium tert-butoxide) in a suitable solvent, such as THF, at a suitable temperature (for example, 20° C.); (4) In the presence of suitable coupling reagents (for example, N,N,N',N'-tetramethylchloroformamidinium hexafluorophosphate and N-methylimidazole) in a suitable solvent (for example, acetonitrile) at a suitable temperature (for example, 50° C.).

General Scheme 4

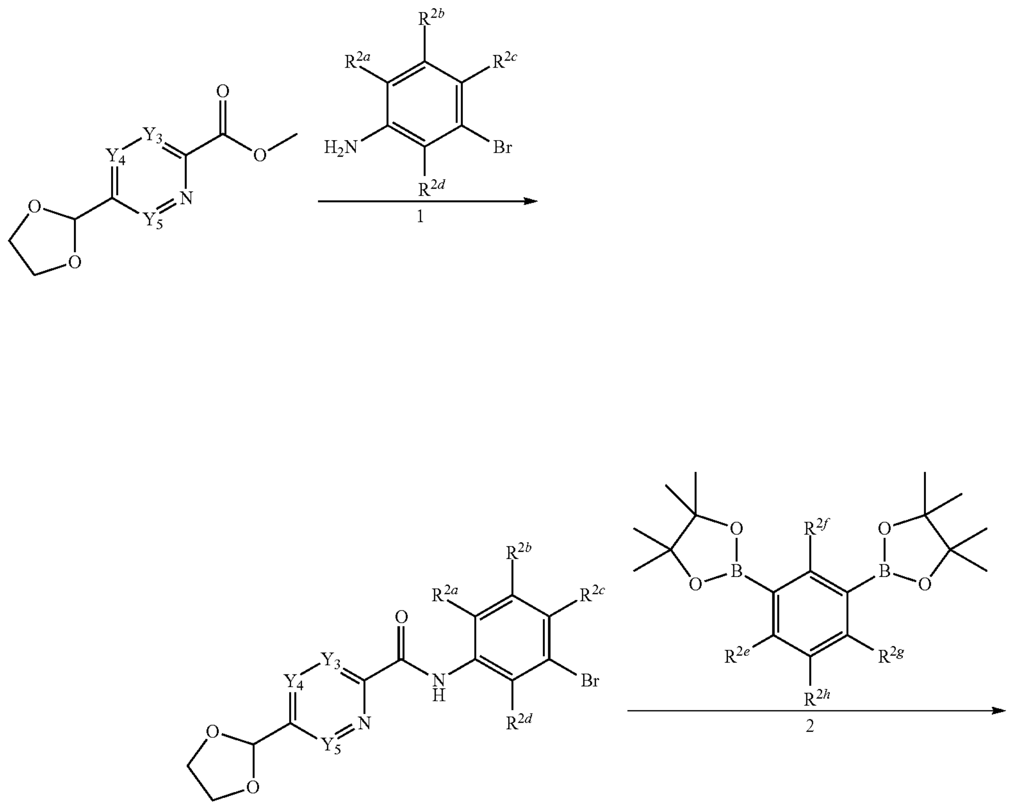

-continued

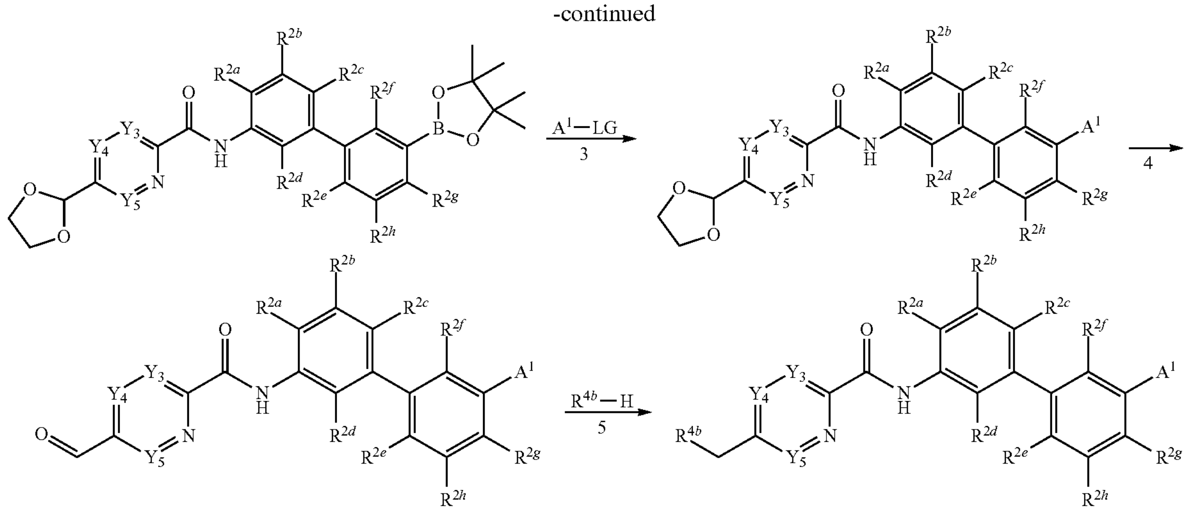

IV

In general, compounds with Formula (IV) be also prepared according to Scheme 4. In Scheme 4, the following reaction conditions apply: (1) In the presence of suitable base (for example, potassium tert-butoxide) in a suitable solvent, such as THF, at a suitable temperature (for example, 20° C.); (2) In the presence of suitable catalyst (for example, bis(triphenylphosphine)palladium(II) dichloride) in a suitable solvent, such as 1,4-dioxane, with a suitable base (for example, $K_2CO_3$) at a suitable temperature (for example, 90° C.); (3) In the presence of suitable catalyst (for example, bis(triphenylphosphine)palladium(II) dichloride) in a suitable solvent, such as 1,4-dioxane, with a suitable base (for example, $K_2CO_3$) at a suitable temperature (for example, 90° C.); (4) In the presence of a suitable acid, such as concentric HCl acid, in a suitable solvent (for example the mixture of $H_2O$ and THF), at a suitable temperature (for example approximately 20° C.); (5) In the presence of an appropriate reductive reagent, such as sodium cyanoborohydride or sodium triacetoxyborohydride, in a suitable solvent (for example, DCM or MeOH) at a suitable temperature, such as approximately 20° C.

Pharmaceutical Compositions

Some embodiments described herein relate to pharmaceutical compositions that comprise, consist essentially of, or consist of an effective amount of a compound described herein (such as a compound of Formula (I), or a pharmaceutically acceptable salt thereof) and a pharmaceutically acceptable carrier, excipient, or combination thereof. A pharmaceutical composition described herein is suitable for human and/or veterinary applications.

The terms "function" and "functional" as used herein refer to a biological, enzymatic, or therapeutic function.

The terms "effective amount" or "effective dose" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "pharmaceutically acceptable salts" includes relatively non-toxic, inorganic and organic acid, or base addition salts of compositions, including without limitation, analgesic agents, therapeutic agents, other materials, and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc, and the like. Salts may also be formed with suitable organic bases, including those that are non-toxic and strong enough to form such salts. For example, the class of such organic bases may include but are not limited to mono-, di-, and trialkylamines, including methylamine, dimethylamine, and triethylamine; mono-, di-, or trihydroxyalkylamines including mono-, di-, and triethanolamine; amino acids, including glycine, arginine and lysine; guanidine; N-methylglucosamine; N-methylglucamine; L-glutamine; N-methylpiperazine; morpholine; ethylenediamine; N-benzylphenethylamine; trihydroxymethyl aminoethane.

"Formulation", "pharmaceutical composition", and "composition" as used interchangeably herein are equivalent terms referring to a composition of matter for administration to a subject.

The term "pharmaceutically acceptable" means compatible with the treatment of a subject, and in particular, a human.

The terms "agent" refers to an active agent that has biological activity and may be used in a therapy. Also, an "agent" can be synonymous with "at least one agent," "compound," or "at least one compound," and can refer to any form of the agent, such as a derivative, analog, salt or a prodrug thereof. The agent can be present in various forms, components of molecular complexes, and pharmaceutically acceptable salts (e.g., hydrochlorides, hydrobromides, sulfates, phosphates, nitrates, borates, acetates, maleates, tartrates, and salicylates). The term "agent" can also refer to any pharmaceutical molecules or compounds, therapeutic molecules or compounds, matrix forming molecules or compounds, polymers, synthetic molecules and compounds, natural molecules and compounds, and any combination thereof.

The term "subject" as used herein has its ordinary meaning as understood in light of the specification and refers to an animal that is the object of treatment, inhibition, or amelioration, observation or experiment. "Animal" has its ordinary meaning as understood in light of the specification and includes cold- and warm-blooded vertebrates and/or invertebrates such as fish, shellfish, or reptiles and, in particular, mammals. "Mammal" has its ordinary meaning as understood in light of the specification, and includes but is not limited to mice, rats, rabbits, guinea pigs, dogs, cats, sheep, goats, cows, horses, primates, such as humans, monkeys, chimpanzees, or apes. In some embodiments, the subject is human.

Proper formulation is dependent upon the route of administration chosen. Techniques for formulation and administration of the compounds described herein are known to those skilled in the art. Multiple techniques of administering a compound exist in the art including, but not limited to, enteral, oral, rectal, topical, sublingual, buccal, intraaural, epidural, epicutaneous, aerosol, parenteral delivery, including intramuscular, subcutaneous, intra-arterial, intravenous, intraportal, intra-articular, intradermal, peritoneal, intramedullary injections, intrathecal, direct intraventricular, intraperitoneal, intranasal or intraocular injections. Pharmaceutical compositions will generally be tailored to the specific intended route of administration. Pharmaceutical compositions can also be administered to isolated cells from a patient or individual, such as T cells, Natural Killer cells, B cells, macrophages, lymphocytes, stem cells, bone marrow cells, or hematopoietic stem cells.

The pharmaceutical compound can also be administered in a local rather than systemic manner, for example, via injection of the compound directly into an organ, tissue, cancer, tumor or infected area, often in a depot or sustained release formulation. Furthermore, one may administer the compound in a targeted drug delivery system, for example, in a liposome coated with a tissue specific antibody. The liposomes may be targeted to and taken up selectively by the organ, tissue, cancer, tumor, or infected area.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

As used herein, a "carrier" refers to a compound, particle, solid, semi-solid, liquid, or diluent that facilitates the passage, delivery and/or incorporation of a compound to cells, tissues and/or bodily organs. For example, without limitation, a lipid nanoparticle (LNP) is a type of carrier that can encapsulate a compound, or a pharmaceutically acceptable salt thereof, as described herein to thereby protect the compound, or a pharmaceutically acceptable salt thereof, as described herein from degradation during passage through the bloodstream and/or to facilitate delivery to a desired organ, such as to the liver.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" has its ordinary meaning as understood in light of the specification, and refers to inert substances, compounds, or materials added to a pharmaceutical composition to provide, without limitation, bulk, consistency, stability, binding ability, lubrication, disintegrating ability etc., to the composition. Excipients with desirable properties include but are not limited to preservatives, adjuvants, stabilizers, solvents, buffers, diluents, solubilizing agents, detergents, surfactants, chelating agents, antioxidants, alcohols, ketones, aldehydes, ethylenediaminetetraacetic acid (EDTA), citric acid, salts, sodium chloride, sodium bicarbonate, sodium phosphate, sodium borate, sodium citrate, potassium chloride, potassium phosphate, magnesium sulfate sugars, dextrose, fructose, mannose, lactose, galactose, sucrose, sorbitol, cellulose, serum, amino acids, polysorbate 20, polysorbate 80, sodium deoxycholate, sodium taurodeoxycholate, magnesium stearate, octylphenol ethoxylate, benzethonium chloride, thimerosal, gelatin, esters, ethers, 2-phenoxyethanol, urea, or vitamins, or any combination thereof. The amount of the excipient may be found in a pharmaceutical composition at a percentage of 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 95%, 100% w/w or any percentage by weight in a range defined by any two of the aforementioned numbers.

The term "adjuvant" as used herein refers to a substance, compound, or material that stimulates the immune response and increase the efficacy of protective immunity and is administered in conjunction with an immunogenic antigen, epitope, or composition. Adjuvants serve to improve immune responses by enabling a continual release of antigen, upregulation of cytokines and chemokines, cellular recruitment at the site of administration, increased antigen uptake and presentation in antigen presenting cells, or activation of antigen presenting cells and inflammasomes. Commonly used adjuvants include but are not limited to alum, aluminum salts, aluminum sulfate, aluminum hydroxide, aluminum phosphate, calcium phosphate hydroxide, potassium aluminum sulfate, oils, mineral oil, paraffin oil, oil-in-water emulsions, detergents, MF59®, squalene, AS03, α-tocopherol, polysorbate 80, AS04, monophosphoryl lipid A, virosomes, nucleic acids, polyinosinic:polycytidylic acid, saponins, QS-21, proteins, flagellin, cytokines, chemokines, IL-1, IL-2, IL-12, IL-15, IL-21, imidazoquinolines, CpG oligonucleotides, lipids, phospholipids, dioleoyl phosphatidylcholine (DOPC), trehalose dimycolate, peptidoglycans, bacterial extracts, lipopolysaccharides, or Freund's Adjuvant, or any combination thereof.

The term "purity" of any given substance, compound, or material as used herein refers to the actual abundance of the substance, compound, or material relative to the expected abundance. For example, the substance, compound, or material may be at least 80, 85, 90, 91, 92, 93, 94, 95, 96, 97, 98, 99, or 100% pure, including all decimals in between. Purity may be affected by unwanted impurities, including but not limited to side products, isomers, enantiomers, degradation products, solvent, carrier, vehicle, or contaminants, or any combination thereof. Purity can be measured technologies including but not limited to chromatography, liquid chromatography, gas chromatography, spectroscopy, UV-visible spectrometry, infrared spectrometry, mass spectrometry, nuclear magnetic resonance, gravimetry, or titration, or any combination thereof.

Methods of Use

Some embodiments disclosed herein related to selecting a subject or patient in need. In some embodiments, a patient is selected who is in need of treatment, inhibition, amelioration, prevention or slowing of diseases or conditions associated with PD-L1 dysregulation. In some embodiments, such diseases or conditions associated with PD-L1 dysregulation may include, for example, cancer, HCC, viral infections, or HBV. In some embodiments, a subject can be selected who has previously been treated for the disease or disorder described herein. In some embodiments, a subject can be selected who has previously been treated for being at risk for the disease or disorder described herein. In some embodiments, a subject can be selected who has developed a recurrence of the disease or disorder described herein. In some embodiments, a subject can be selected who has developed resistance to therapies for the disease or disorder described herein. In some embodiments, a subject can be selected who may have any combination of the aforementioned selection criteria.

Compounds, and pharmaceutically acceptable salts thereof, disclosed herein can be evaluated for efficacy and toxicity using known methods. A non-limiting list of potential advantages of a compound, or a pharmaceutically acceptable salt thereof, described herein include improved stability, increased safety profile, increased efficacy, increased binding to the target, increased specificity for the target (for example, a cancer cell or virally infected cell).

The terms “treating,” “treatment,” “therapeutic,” or “therapy” as used herein has its ordinary meaning as understood in light of the specification, and do not necessarily mean total cure or abolition of the disease or condition. The term “treating” or “treatment” as used herein (and as well understood in the art) also means an approach for obtaining beneficial or desired results in a subject’s condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease’s transmission or spread, delaying or slowing of disease progression, amelioration or palliation of the disease state, diminishment of the reoccurrence of disease, and remission, whether partial or total and whether detectable or undetectable. “Treating” and “treatment” as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the subject. The length of the treatment period depends on a variety of factors, such as the severity of the condition, the age and genetic profile of the subject, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required.

Some embodiments described herein relate to a method of treating, inhibiting, ameliorating, preventing, or slowing the disease or disorder described herein. In some embodiments, the methods include administering to a subject identified as suffering from the disease or disorder described herein an effective amount of a compound, or a pharmaceutically acceptable salt thereof, described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating, inhibiting ameliorating, preventing, or slowing the disease or disorder described herein. Still other embodiments described herein relate to the use of a compound, or a pharmaceutically acceptable salt thereof, as described herein or a pharmaceutical composition that includes an effective amount of a compound, or a pharmaceutically acceptable salt thereof, as described herein for treating, inhibiting ameliorating, preventing, or slowing the disease or disorder described herein.

Some embodiments described herein relate to a method for inhibiting replication of a cancer cell or a virus that can include contacting the cell or virus or administering to a subject identified as suffering from a cancer or a viral infection with an effective amount of a compound, or a pharmaceutically acceptable salt thereof, described herein, or a pharmaceutical composition that includes an effective amount of a compound, or a pharmaceutically acceptable salt thereof, described herein. Other embodiments described herein relate to the use of an effective amount of a compound, or a pharmaceutically acceptable salt thereof, described herein, or a pharmaceutical composition that includes an effective amount of a compound, or a pharmaceutically acceptable salt thereof, described herein in the manufacture of a medicament for inhibiting replication of a cancer cell or virus. Still other embodiments described herein relate to an effective amount of a compound, or a pharmaceutically acceptable salt thereof, described herein, or a pharmaceutical composition that includes an effective amount of a compound, or a pharmaceutically acceptable salt thereof, described herein for inhibiting replication of a cancer cell or virus. In some embodiments, the cancer cell is an HCC cell. In some embodiments, the virus is hepatitis B.

Some embodiments described herein relate to a method for inhibiting cell proliferation, such as inhibiting cell proliferation of a cancer cell or cell infected with a virus, that can include administering to a subject identified as suffering from a disease wherein inhibiting cell proliferation is desirable with an effective amount of a compound, or a pharmaceutically acceptable salt thereof, described herein, or a pharmaceutical composition that includes effective amount of a compound, or a pharmaceutically acceptable salt thereof, described herein. Other embodiments described herein relate to the use of an effective amount of a compound, or a pharmaceutically acceptable salt thereof, described herein, or a pharmaceutical composition that includes an effective amount of a compound, or a pharmaceutically acceptable salt thereof, described herein in the manufacture of a medicament for inhibiting cell proliferation, such as inhibiting cell proliferation of a cancer cell or cell infected with a virus. Still other embodiments described herein relate to an effective amount of a compound, or a pharmaceutically acceptable salt thereof, described herein, or a pharmaceutical composition that includes an effective amount of a compound, or a pharmaceutically acceptable salt thereof, described herein for inhibiting cell proliferation, such as inhibiting cell proliferation of a cancer cell or cell infected with a virus. In some embodiments, the cancer cell is an HCC cell. In some embodiments, the cell infected with a virus is infected with hepatitis B virus.

Some embodiments described herein relate to a method of inducing apoptosis of a cell (for example, a cancer cell or cell infected with a virus) that can include contacting the cell with an effective amount of a compound, or a pharmaceutically acceptable salt thereof, described herein, or a pharmaceutical composition that includes an effective amount of a compound of Formula (I), or a pharmaceutically acceptable salt thereof, as described herein. Other embodiments described herein relate to using an effective amount of a compound, or a pharmaceutically acceptable salt thereof, as described herein or a pharmaceutical composition that includes an effective amount of a compound, or a pharmaceutically acceptable salt thereof, described herein in the manufacture of a medicament for inducing apoptosis of a cell, such as a cancer cell or cell infected with a virus. Still other embodiments described herein relate to the use of an effective amount of a compound, or a pharmaceutically acceptable salt thereof, as described herein or a pharmaceutical composition that includes an effective amount of a compound, or a pharmaceutically acceptable salt thereof, as described herein for inducing apoptosis of a cell, such as a cancer cell or cell infected with a virus. In some embodiments, the cancer cell is an HCC cell. In some embodiments, the cell infected with a virus is infected with hepatitis B virus.

Some embodiments described herein relate to a method of decreasing the viability of a cell (for example, a cancer cell or cell infected with a virus) that can include contacting the cell with an effective amount of a compound, or a pharmaceutically acceptable salt thereof, described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for decreasing the viability of a cell, such as a cancer cell or cell infected with a virus. Still other embodiments described herein relate to the use of an effective amount of a compound, or a pharmaceutically acceptable salt thereof, as described herein or a pharmaceutical composition that includes an effective amount of a compound, or a pharmaceutically acceptable salt thereof, as described herein for decreasing the viability of a cell, such as a cancer cell or cell infected with a virus. In some embodiments, the cancer cell is an HCC cell. In some embodiments, the cell infected with a virus is infected with hepatitis B virus.

Those of skill in the treatment of such diseases could determine the effective therapeutic daily amount from test results. An effective therapeutic daily amount would be from about 0.005 mg/kg to 50 mg/kg. in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight.

In some embodiments, the effective amount of a compound, or a pharmaceutically acceptable salt thereof, described herein is dosed more than one time. In some embodiments, the compound, or a pharmaceutically acceptable salt thereof, described herein can be administered every 1, 2, 3, 4, 5, 6, 7 days, or 1, 2, 3, 4 weeks, or 1, 2, 3, 4, 5, 6, 7, 8, 9, 10, 11, 12 months, or 1, 2, 3, 4, 5 years, or any period or combination thereof within the range defined by any two aforementioned times. In some embodiments, at least one loading dose and at least one maintenance dose is administered to the subject, where the at least one loading dose is a higher dose of a compound, or a pharmaceutically acceptable salt thereof, described herein than the at least one maintenance dose.

As used herein, the term "combination therapy" is intended to define therapies which comprise the use of a combination of two or more pharmaceutical compounds/agents or therapies. Thus, references to "combination therapy", "combinations" and the use of compounds/agents "in combination" in this application may refer to compounds/agents that are administered as part of the same overall treatment regimen. As such, the dosage or timing of each of the two or more compounds/agents may differ: each may be administered at the same time or at different times. Accordingly, the compounds/agents of the combination may be administered sequentially (e.g. before or after) or simultaneously, either in the same pharmaceutical formulation (i.e. together), or in different pharmaceutical formulations (i.e. separately). Each of the two or more compounds/agents in a combination therapy may also differ with respect to the route of administration.

The term "inhibitor", as used herein, refers to an enzyme inhibitor or receptor inhibitor which is a molecule that binds to an enzyme or receptor, and decreases and/or blocks its activity. The term may relate to a reversible or an irreversible inhibitor.

Cancer may be treated with surgery, radiation therapy, chemotherapy, targeted therapies, immunotherapy or hormonal therapies. Any of these mentioned therapies may be used in conjunction with another therapy as a combination therapy. Chemotherapeutic compounds include but are not limited to alemtuzumab, altretamine, azacitidine, bendamustine, bleomycin, bortezomib, busulfan, cabazitaxel, capecitabine, carboplatin, carmofur, carmustine, chlorambucil, chlormethine, cisplatin, cladribine, clofarabine, cyclophosphamide, cytarabine, dacarbazine, dactinomycin, daunorubicin, decitabine, denosumab, docetaxel, doxorubicin, epirubicin, estramustine, etoposide, everolimus, floxuridine, fludarabine, fluorouracil, fotemustine, gemcitabine, gemtuzumab, hydroxycarbamide, ibritumomab, idarubicin, ifosfamide, irinotecan, ixabepilone, lomustine, melphalan, mercaptopurine, methotrexate, mitomycin, mitoxantrone, nedaplatin, nelarabine, ofatumumab, oxaliplatin, paclitaxel, pemetrexed, pentostatin, pertuzumab, procarbazine, raltitrexed, streptozotocin, tegafur, temozolomide, temsirolimus, teniposide, tioguanine, topotecan, tositumomab, valrubicin, vinblastine, vincristine, vindesine, vinflunine, or vinorelbine, or any combination thereof.

As used herein, the term "protein kinase inhibitor" refers to inhibitors of protein kinases, serine/threonine kinases, tyrosine kinases, or dual-specificity kinases for the treatment of cancer or other illness. In some embodiments, the protein kinase inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the protein kinase inhibitor includes but is not limited to acalabrutinib, adavosertib, afatinib, alectinib, axitinib, binimetinib, bosutinib, brigatinib, cediranib, ceritinib, cetuximab, cobimetinib, crizotinib, cabozantinib, dacomitinib, dasatinib, entrectinib, erdafitinib, erlotinib, fostamatinib, gefitinib, ibrutinib, imatinib, lapatinib, lenvatinib, lestaurtinib, lortatinib, masitinib, momelotinib, mubritinib, neratinib, nilotinib, nintedanib, olmutinib, osimertinib, pacritinib, panitumumab, pazopanib, pegaptanib, ponatinib, radotinib, regorafenib, rociletinib, ruxolitinib, selumetinib, semaxanib, sorafenib, sunitinib, SU6656, tivozanib, toceranib, trametinib, trastuzumab, vandetanib, or vemurafenib, or any combination thereof.

As used herein, the term "checkpoint inhibitor" refers to an immunotherapy that targets immune checkpoints to stimulate immune function. In some embodiments, the checkpoint inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the immune checkpoint is the PD-1/PD-L1 checkpoint. In some embodiments, the PD-1 checkpoint includes but is not limited to nivolumab, pembrolizumab, spartalizumab, cemiplimab, camrelizumab, sintilimab, tislelizumab, toripalimab, AMP-224 or AMP-514, or any combination thereof. In some embodiments, the PD-L1 checkpoint inhibitor includes but is not limited to atezolizumab, avelumab, durvalumab, KN035, AUNP12, CA-170, or BMS-986189, or any combination thereof. In some embodiments, the immune checkpoint is the CTLA-4 checkpoint. In some embodiments, the CTLA-4 checkpoint inhibitor includes but is not limited to ipilimumab or tremilimumab, or any combination thereof.

As used herein, the term "VEGF inhibitor" refers to inhibitors of vascular endothelial growth factor (VEGF) or a VEGF receptor (VEGFR). In some embodiments, the VEGF inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the VEGF inhibitor includes but is not limited to aflibercept, axitinib, bevacizumab, brivanib, cabozantinib, cediranib, lenvatinib, linifinib, nintedanib, pazopanib, ponatinib, ramucirumab, regorafenib, semaxanib, sorafenib, sunitinib, tivozanib, toceranib, or vandetanib, or any combination thereof.

As used herein, the term "antiviral medication" refers to a pharmaceutical composition administered to treat a viral infection. In some embodiments, the viral infection is caused by adenovirus, Ebola virus, coronavirus, Epstein-Barr virus (EBV), Friend virus, hantavirus, hepatitis B virus (HBV), hepatitis C virus (HCV), herpes simplex virus, human immunodeficiency virus (HIV), human metapneumovirus, human papillomavirus (HPV), influenza virus, Japanese encephalitis virus, Kaposi's sarcoma-associated herpesvirus, lymphocytic choriomeningitis virus, parainfluenza virus, rabies virus, respiratory syncytial virus, rhinovirus, varicella zoster virus.

In some embodiments, the antiviral medication is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the antiviral medication is an interferon, a capsid assembly modulator, a sequence specific oligonucleotide, an entry inhibitor, or a small molecule immunomodulatory. In some embodiments, the antiviral medication includes but is not limited to AB-423, AB-506, ABI-H2158, vebicorvir (ABI-HO731), acyclovir, adapromine, adefovir, adefovir dipivoxil, alafenamide, amantadine, asunaprevir, baloxavir marboxil, beclabuvir, boceprevir, brivudine, cidofovir, ciluprevir, clevudine, cytarabine, daclatasvir, danoprevir, dasabuvir, deleobuvir, dipivoxil, edoxudine, elbasvir, entecavir, faldaprevir, famciclovir, favipiravir, filibuvir, fomivirsen, foscarnet, galidesivir, ganciclovir, glecaprevir, GLS4, grazoprevir, idoxuridine, imiquimod, IFN-$\alpha$, interferon alfa 2b, JNJ-440, JNJ-6379 (JNJ-56136379), lamivudine, laninamivir, ledipasvir, mericitabine, methisazone, MK-608, moroxydine, narlaprevir, NITD008, NZ-4, odalasvir, ombitasvir, oseltamivir, paritaprevir, peginterferon alfa-2a, penciclovir, peramivir, pibrentasvir, pimodivir, pleconaril, podophyllotoxin, presatovir, radalbuvir, ravidasvir, remdesivir, REP 2139, REP 2165, resiquimod, R07049389 (RG7907), ribavirin, rifampicin, rimantadine, ruzasvir, samatasvir, setrobuvir, simeprevir, sofosbuvir, sorivudine, sovaprevir, taribavirin, telaprevir, telbivudine, tenofovir, tenofovir disoproxil, tenofovir alfenamide, triazavirin, trifluridine, tromantadine, umifenovir, uprifosbuvir, valaciclovir, valgancicovir, vaniprevir, vedroprevir, velpatasvir, vidarabine, voxilaprevir, zanamivir, cledvudine, ANA-380/LB80380, thymalfasin (Zadaxin), ATI-2173, VIR-2218, RG6346, JNJ-73763989 (JNJ-3989), AB-729, BB-103, Hepcludex (Bulevirtide formerly Myrcludex B), hzVSF, morphothiadin, JNJ-56136379, EDP-514, QL-007, ABI-H3733, ZM-H1505R, B-836, VNRX-9945, GLP-26, ABI-4334, IONIS-HBVRx (GSK 3228836), EBT107, NASVAC, GS-4774, HepTcell, VBI-2601 (BRII-179), VVX001, VTP-300, CVI—HBV-002, AIC-649, HB-110, JNJ-64300535, CARG-201, PRGN-2013, SA104, VRON-0200, selgantolimod, RG7854, SBT-8230, YS—HBV-002, lenvervimab, Vir-3434, IMC-1109V, LTCR-H2-1, APG-1387, ASC42, EYP001, EDP-721, ENOB-HB-01, GV1001, CP101, DF-006, ALG-000184, ALG-010133, ALG-125097, ALG-020572, ALG-125755 or any combination thereof.

The term "% w/w" or "% wt/wt" as used herein has its ordinary meaning as understood in light of the specification and refers to a percentage expressed in terms of the weight of the ingredient or agent over the total weight of the composition multiplied by 100. The term "% v/v" or "% vol/vol" as used herein has its ordinary meaning as understood in the light of the specification and refers to a percentage expressed in terms of the liquid volume of the compound, substance, ingredient, or agent over the total liquid volume of the composition multiplied by 100.

EXAMPLES

Some aspects of the embodiments discussed above are disclosed in further detail in the following examples, which are not in any way intended to limit the scope of the present disclosure. Those in the art will appreciate that many other embodiments also fall within the scope of the present disclosure, as it is described herein above and in the claims.

Hereinafter, the term "rt", "r.t." or "RT" means room temperature; "h" means hours; "Me" means methyl; "MeOH" means methanol; "Et" means ethyl; "EtOH" means ethanol; "NaH" means sodium hydride; "$NaBH(AcO)_3$" or "$NaBH(OAc)_3$" means sodium triacetoxyborohydride; "EtOAc" means ethyl acetate; "TEA" or "$Et_3N$" means triethylamine; "DCM" means dichloromethane; "MeCN" or "ACN" means acetonitrile; "DMF" means -dimethyl formamide; "DMA" means dimethylacetamide; "$Pd(dppf)Cl_2$." means [1.1'-Bis(diphenylphosphino)ferrocene]-dichloropalladium(II); "THF" means tetrahydrofuran; "i-PrOH" or "iPrOH" means 2-propanol; "LC" means liquid chromatography; "LCMS" means Liquid Chromatography/Mass spectrometry; "HPLC" means high-performance liquid chromatography; "prep-HPLC" means preparative high-performance liquid chromatography; "TFA" means trifluoroacetic acid; "RP" means reversed phase; "min" means minute(s); "h" means hour(s); "PE" means petroleum ether; "v/v" means volume per volume; "Celite®" means diatomaceous earth; "DMSO" means dimethyl sulfoxide; "SFC" means Supercritical Fluid Chromatography; "DIPE" means diisopropyl ether; "DIPEA" or "DIEA" means N,N-diisopropylethylamine; "$Pd_2(dba)_3$" means Tris(dibenzylideneacetone)-dipalladium; "$Pd(OAc)_2$" means palladium(II) acetate; "AcOH" means acetic acid; "DMAP" means 4-(dimethylamino)pyridine; "t-BuOK", "BuO" or "KOtBu" means potassium tert-butoxide; "TLC" means thin layer chromatography; "prep-TLC" means preparative TLC; "KOAc" means potassium acetate.

For intermediates that were used in a next reaction step as a crude or as a partially purified intermediate, estimated mol amounts (in some cases indicated by ~) are indicated in the reaction protocols described below, or alternatively theoretical mol amounts are indicated.

The meanings of the abbreviations in the nuclear magnetic resonance spectra are provided as follows: s=singlet, d=doublet, dd=double doublet, dt=double triplet, ddd=doublet of doublets of doublets, Sept=septet, t=triplet, m=multiplet, br=broad, brs=broad singlet, q=quartet.

PREPARATION OF INTERMEDIATES

Example A1

Preparation of Intermediate 1

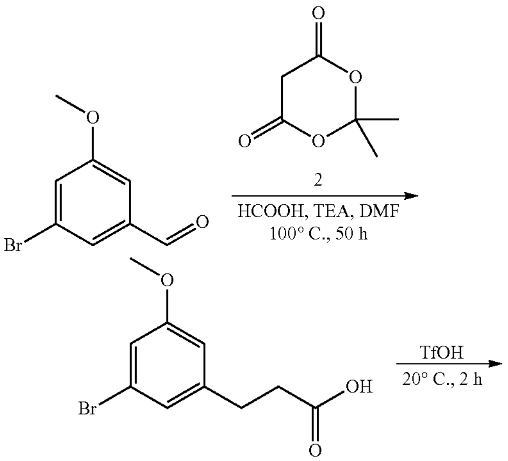

Intermediate 1-1

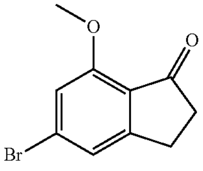

Intermediate 1

To HCOOH (16.5 mL, 419 mmol) at 0° C. was added TEA (23.3 mL, 167.41 mmol) dropwise at 0° C. The mixture was stirred at 0° C. for 30 min. To the mixture were added 3-Bromo-5-methoxybenzaldehyde (30 g, 140 mmol) and isopropylidene malonate (20.1 g, 140 mmol) in DMF (180 mL) dropwise at 25° C. The mixture was stirred at 100° C. for 50 h. Once the mixture was cooled to 0° C., the reaction was quenched with conc. HCl (120 mL) and diluted with water (800 mL). The mixture was extracted with DCM (2×400 mL). The combined organic layers were washed with NaOH (1N, 2×800 mL). The combined aqueous phases were acidified to pH ~2 with conc. HCl, and then extracted with EtOAc (2×300 mL). The combined organic layers were washed with brine (2×300 mL), dried over $Na_2SO_4$, filtered and concentrated to give Intermediate 1-1 (70 g) as a pink solid, which was used into the next step without further purification. $^1H$ NMR (400 MHz, $CDCl_3$) δ 6.96 (s, 1H), 6.91 (t, J=1.9 Hz, 1H), 6.69 (s, 1H), 3.78 (s, 3H), 2.95-2.88 (m, 2H), 2.70-2.62 (m, 2H).

A solution of Intermediate 1-1 (70 g, 270 mmol) in TfOH (150 mL) was stirred at 25° C. for 2 h. The reaction was quenched by the addition of ice water (1500 mL) at 0° C., extracted with DCM (3×600 mL). The combined organic layers were washed with $NaHCO_3$ (2×800 mL), dried over anhydrous $Na_2SO_4$ and concentrated to give a residue, which was purified by flash silica gel chromatography to give Intermediate 1 (12.6 g) as a yellow solid. $^1H$ NMR (400 MHz, $CDCl_3$) δ 7.19 (d, J=0.9 Hz, 1H), 6.93 (s, 1H), 3.94 (s, 3H), 3.11-2.97 (m, 2H), 2.73-2.59 (m, 2H).

Example A2

Preparation of Intermediate 2

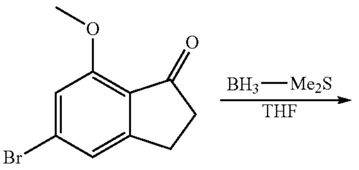

Intermediate 1

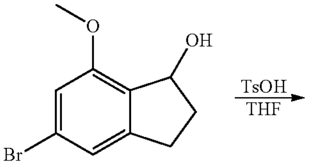

Intermediate 2-1

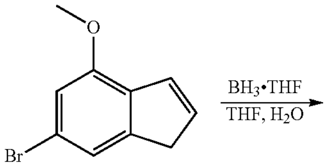

Intermediate 2-2

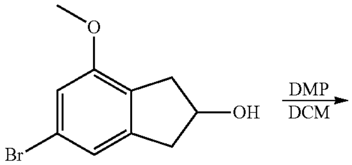

Intermediate 2-3

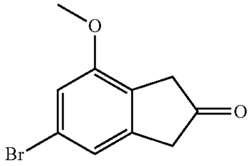

Intermediate 2

To a solution of compound Intermediate 1 (3.7 g, 15.4 mmol) in THF (120 mL) was added $BH_3$-$Me_2S$ (10 M, 2.61 mL) at −10° C. The mixture was stirred at 25° C. for 2 h. The reaction was quenched by the addition of ice water (200 mL) at 0° C., and then extracted with EtOAc (3×200 mL). The combined organic layers were washed with $NaHCO_3$ (2×150 mL), dried over anhydrous $Na_2SO_4$ and concentrated to give a residue, which was purified by flash silica gel chromatography (ISCO®; 20 g SepaFlash® Silica Flash Column, 0-10% EtOAc:PE) to give Intermediate 2-1 (3.68 g) as a white solid. $^1$H NMR (400 MHz, $CDCl_3$) δ 7.02 (s, 1H), 6.85 (s, 1H), 5.41 (dd, J=4.4, 7.1 Hz, 1H), 3.86 (s, 3H), 3.17-2.98 (m, 1H), 2.93-2.72 (m, 1H), 2.56-2.35 (m, 2H), 2.15-1.93 (m, 1H).

To a solution of Intermediate 2-1 (3.68 g, 15.1 mmol) in THF (350 mL) was added TsOH (782 mg, 4.54 mmol) at 25° C. The mixture was stirred at 60° C. for 16 h. The mixture was diluted with $H_2O$ (200 mL) and then extracted with EtOAc (3×150 mL). The combined organic layers were washed with brine (200 mL), dried over $Na_2SO_4$, filtered and concentrated to give a residue, which was purified by flash silica gel chromatography (ISCO®; 40 g SepaFlash® Silica Flash Column, 0~5% EtOAc:PE) to give Intermediate 2-2 (3.16 g) as a white solid. $^1$H NMR (400 MHz, $CDCl_3$) δ 7.26 (s, 1H), 7.01-6.90 (m, 2H), 6.45 (td, J=1.9, 5.6 Hz, 1H), 3.88 (s, 3H), 3.40 (s, 2H);

To a solution of Intermediate 2-2 (3.16 g, 14.0 mmol) in THF (60 mL) was added $BH_3$·THF (1 M, 42.12 mL) at 0° C. The mixture was stirred at 25° C. for 2 h. The reaction was quenched by the addition of ice water (100 mL) at 0° C. and extracted with EtOAc (3×100 mL). The combined organic layers were washed with $NaHCO_3$ (2×80 mL), dried over anhydrous $Na_2SO_4$ and concentrated to give a residue, which was purified by flash silica gel chromatography (ISCO®; 40 g SepaFlash® Silica Flash Column, 0~10% EtOAc:PE) to give Intermediate 2-3 (2.86 g) as a yellow oil.

To a solution of Intermediate 2-3 (2.86 g) in DCM (40 mL) was added Dess-Martin periodinane (7.48 g, 17.7 mmol) at 25° C. The mixture was stirred at 25° C. for 1 h. The mixture was diluted with $Na_2SO_3$ (100 mL) and extracted with DCM (3×80 mL). The combined organic layers were washed with brine (100 mL), dried over $Na_2SO_4$, filtered and concentrated to give a residue, which was purified by flash silica gel chromatography (ISCO®; 12 g SepaFlash® Silica Flash Column, 0-10% EtOAc:PE) to give Intermediate 2 (1.4 g) as a white solid. $^1$H NMR (400 MHz, $CDCl_3$) δ 7.08 (s, 1H), 6.93 (s, 1H), 3.85 (s, 3H), 3.53 (s, 2H), 3.40 (s, 2H).

Example A3

Preparation of Intermediate 3

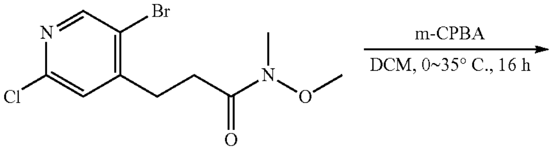

-continued

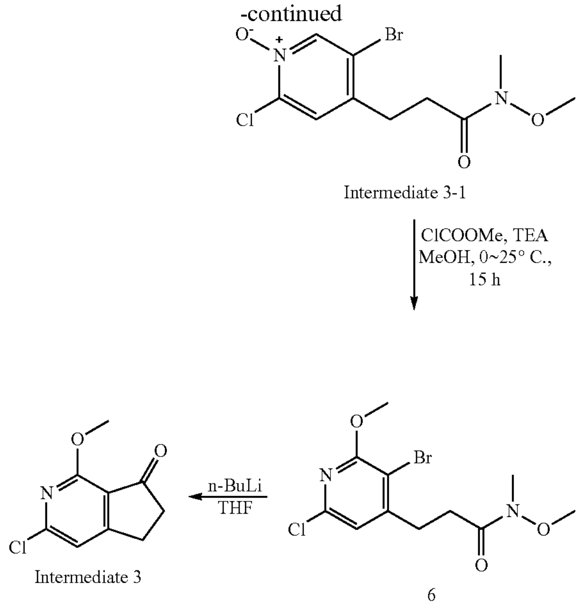

Intermediate 3-1

Intermediate 3

6

Intermediate 3-2

To a solution of 3-(5-bromo-2-chloro-4-pyridyl)-N-methoxy-N-methyl-propanamide (27.5 g, 89.4 mmol) in DCM (400 mL) was added m-CPBA (46.3 g, 268 mmol) at 0° C. The mixture was stirred at 35° C. for 16 h. The reaction was quenched with sat. aq. $Na_2S_2O_4$ (300 mL) and then extracted with DCM (2×100 mL). The combined organic layers were concentrated in vacuo. The residue was purified by flash silica gel chromatography to provide Intermediate 3-1 as a yellow solid. $^1$H NMR (400 MHz, $CDCl_3$) δ 8.50 (s, 1H), 7.48 (s, 1H), 3.67 (s, 3H), 3.18 (s, 3H), 3.06-2.99 (m, 2H), 2.81-2.75 (m, 2H).

To a solution of Intermediate 3-1 (26.8 g, 82.8 mmol) and methyl carbonochloridate (26.9 g, 285 mmol) in MeOH (150 mL) was added dropwise TEA (41.9 g, 414 mmol) at 0° C., and the mixture was stirred at 0° C. for 1.5 h. Additional methyl carbonochloridate (26.9 g, 285 mmol) was added, followed by the dropwise addition of TEA (41.9 g, 414 mmol) at 0° C. The mixture was stirred at 30° C. for 15 h, and then concentrated under reduced pressure. The mixture was diluted with 1M aq. NaOH (300 mL) and extracted with EtOAc (2×200 mL). The combined organic layers were washed with brine (2×100 mL), dried over anhydrous $Na_2SO_4$, filtered and concentrated under reduced pressure to give a residue. The residue was purified by flash silica gel chromatography to provide Intermediate 3-2 as a white solid (17 g, 61% yield). $^1$H NMR (400 MHz, $CDCl_3$) δ 6.87 (s, 1H), 4.00 (s, 3H), 3.66 (s, 3H), 3.19 (s, 3H), 3.06-3.01 (m, 2H), 2.74 (br t, 2H).

To a solution of Intermediate 3-2 (3.4 g, 10.1 mmol) in THF (40 mL) was added n-BuLi (2.5 M, 6.04 mL) at −70° C. The mixture was stirred at −70° C. for 0.5 h. The mixture was poured into sat.aq. $NH_4Cl$ (80 mL) and then extracted with EtOAc (2×100 mL). The combined organic layers were washed with brine (2×80 mL), dried over anhydrous $Na_2SO_4$, filtered and concentrated under reduced pressure to give a residue. The residue was purified by flash silica gel chromatography to provide Intermediate 3 as a white solid (1.45 g, 73% yield). $^1$H NMR (400 MHz, $CDCl_3$) δ 7.03 (s, 1H), 4.11 (s, 3H), 3.20-2.97 (m, 2H), 2.79-2.52 (m, 2H).

Example A4

Preparation of Intermediate 4

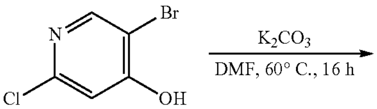

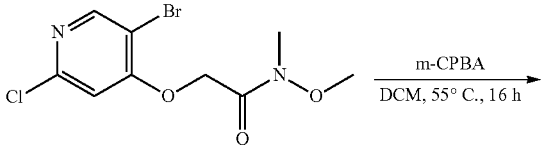

Intermediate 4-1

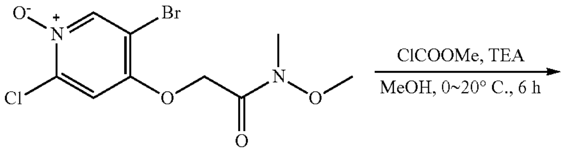

Intermediate 4-2

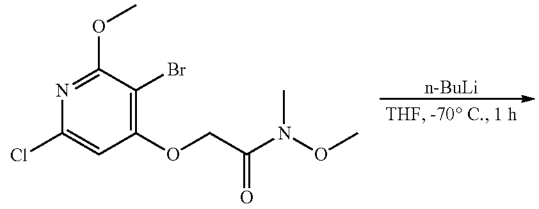

6
Intermediate 4-3

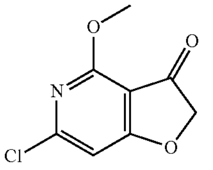

Intermediate 4

A mixture of 5-Bromo-2-chloro-pyridin-4-ol (3 g, 14.4 mmol), 2-bromo-N-methoxy-N-methyl-acetamide (3.93 g, 21.6 mmol) and $K_2CO_3$ (5.97 g, 43.2 mmol) in DMF (30 mL) was stirred at 60° C. for 16 h. The mixture was filtered and concentrated under reduced pressure to give a residue, which was purified by flash silica gel chromatography to give Intermediate 4-1 (3.5 g) as a white solid. $^1H$ NMR (400 MHz, $CDCl_3$) δ 8.38 (s, 1H), 6.73 (s, 1H), 4.99 (s, 2H), 3.80 (s, 3H), 3.26 (s, 3H).

A mixture of Intermediate 4-1 (2 g, 6.46 mmol), m-CPBA (6.69 g, 38.8 mmol) in DCM (50 mL) was stirred at 55° C. for 16 h. The crude mixture was poured into sat. aq. $Na_2S_2O_3$ (100 mL) and then extracted with DCM (2×50 mL). The combined organic layers were washed with brine (50 mL), dried over anhydrous $Na_2SO_4$, filtered and concentrated under reduced pressure to give a residue, which was purified by flash silica gel chromatography to give Intermediate 4-2 (1 g, 48% yield). $^1H$ NMR (400 MHz, $CDCl_3$) δ 8.50 (s, 1H), 6.93 (s, 1H), 4.99 (s, 2H), 3.80 (s, 3H), 3.25 (s, 3H).

To a solution of Intermediate 4-2 (1.7 g, 5.22 mmol) and methyl carbonochloridate (1.21 mL, 15.67 mmol) in MeOH (20 mL) was added dropwise TEA (1.59 g, 15.7 mmol, 2.18 mL) at 0° C. After addition, the mixture was stirred at 20° C. for 1 h. Additional methyl carbonochloridate (1.21 mL, 15.67 mmol) was added at 20° C., and then TEA (2.18 mL, 15.67 mmol) was added dropwise at 0° C. The mixture was stirred at 20° C. for 3 h and then concentrated under reduced pressure. The residue was diluted with $H_2O$ (40 mL) and then extracted with EtOAc (2×50 mL). The combined organic layers were washed with brine (30 mL×2), dried over anhydrous $Na_2SO_4$, filtered and concentrated under reduced pressure to give a residue, which was purified by flash silica gel chromatography to give Intermediate 4-3 (1.3 g, 73% yield) as a white solid. $^1H$ NMR (400 MHz, $CDCl_3$) δ 6.44 (s, 1H), 4.96 (s, 2H), 4.01 (s, 3H), 3.79 (s, 3H), 3.25 (s, 3H).

To a solution of Intermediate 4-3 (1.3 g, 3.83 mmol) in THF (15 mL) was added n-BuLi (2.5 M, 2.30 mL) at −70° C. under $N_2$. The mixture was stirred at −70° C. for 1 h. The reaction was quenched by addition sat. aq. $NH_4Cl$ (10 mL) at 0° C. and then extracted with EtOAc (3×20 mL). The combined organic layers were washed with brine (20 mL), dried over anhydrous $Na_2SO_4$, filtered and concentrated under reduced pressure to give a residue, which was purified by flash silica gel chromatography to give Intermediate 4 (534 mg, 70% yield) as a yellow solid. $^1H$ NMR (400 MHz, $CDCl_3$) δ 6.75 (s, 1H), 4.72 (s, 2H), 4.12 (s, 3H).

Example A4a

Preparation of Intermediate 4a

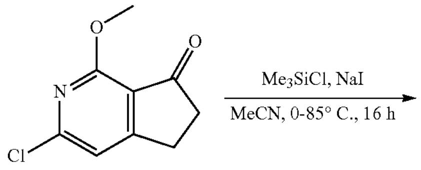

Intermediate 3

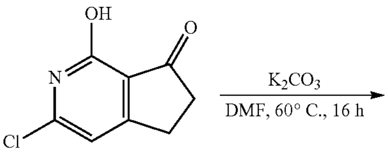

Intermediate 4a-1

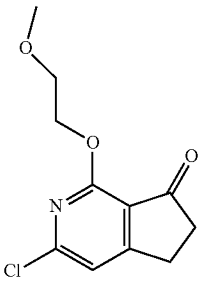

Intermediate 4a

To a mixture of Intermediate 3 (500 mg, 2.53 mmol) and NaI (1.14 g, 7.59 mmol) in MeCN (20 mL) was added dropwise chloro-trimethyl-silane (963 μL, 7.59 mmol) at 0° C. The mixture was stirred at 85° C. for 16 hours. The reaction mixture was filtered and concentrated under reduced pressure to give Intermediate 4a-1 (460 mg) as a yellow solid. MS: ES m/z calculated for $C_8H_7ClNO_2[M+H]^+$ 184.0 found 184.2.

To a solution of Intermediate 4a-1 (460 mg, 2.51 mmol) and 1-bromo-2-methoxy-ethane (471 μL, 5.01 mmol) in DMF (15 mL) was added $K_2CO_3$ (693 mg, 5.01 mmol). The mixture was stirred at 50° C. for 16 hours. The reaction mixture was filtered and concentrated under reduced pressure to give a residue, which was purified by prep-HPLC to give Intermediate 4a (150 mg) as a brown oil. MS: ES m/z calculated for $C_{11}H_{13}ClNO_3[M+H]^+$ 242.1 found 242.0; $^1H$ NMR (400 MHz, Chloroform-d) δ=7.02 (s, 1H), 4.71-4.55 (m, 2H), 3.87-3.73 (m, 2H), 3.46 (s, 3H), 3.17-3.03 (m, 2H), 2.80-2.64 (m, 2H).

Example A4b

Preparation of Intermediate 4b, 4b-A and 4b-B

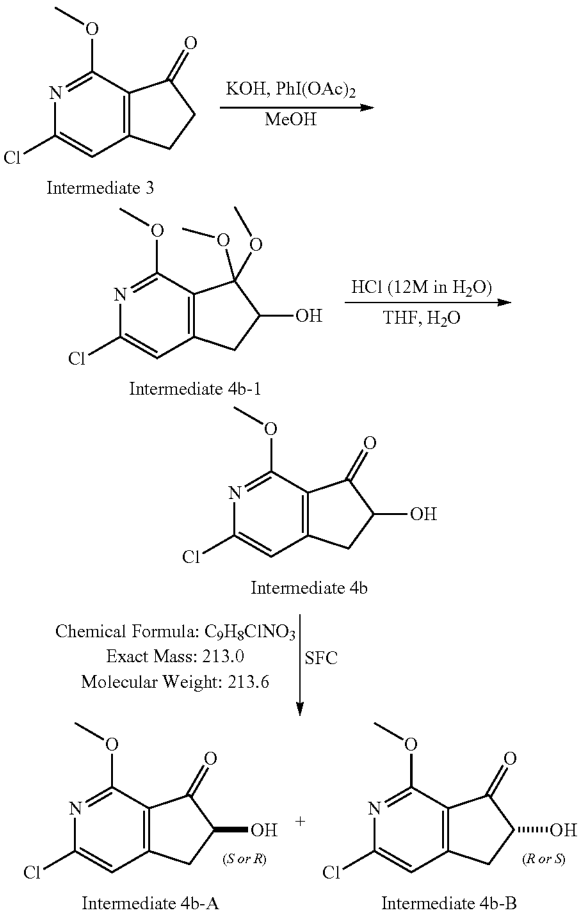

Intermediate 3

Intermediate 4b-1

Intermediate 4b

Intermediate 4b-A + Intermediate 4b-B

A solution of Intermediate 3 (250 mg, 1.27 mmol) and KOH (781 mg, 13.9 mmol) in MeOH (10 mL) was stirred for 30 minutes at 0° C. To the reaction mixture was added [acetoxy(phenyl)-$\lambda^3$-iodanyl]acetate (488.97 mg, 1.52 mmol, 1.2 eq). The resulting solution was stirred at 0° C. for 1 hour, followed by stirring at 25° C. for 16 hours. The reaction mixture was concentrated under reduced pressure to give crude Intermediate 4b-1 (1.3 g) as a black solid. MS: ES m/z calculated for $C_{11}H_{14}ClNO_4[M+H]^+$ 260.1 found 260.0.

To a solution of crude Intermediate 4b-1 (1.3 g) in THF (10 mL) and $H_2O$ (8 mL) was added Hydrochloric acid (12 M in $H_2O$, 417 μL). The mixture was stirred at 20° C. for 2 hours. The reaction mixture was diluted with Ethyl acetate (20 mL). The organic layer was washed with aq. $NaHCO_3$ (20 mL×3) and brine (20 mL), dried with anhydrous $Na_2SO_4$, filtered and concentrated under reduced pressure to give a residue, which was purified by prep-HPLC to give Intermediate 4b (350 mg) as a brown solid. MS: ES m/z calculated for $C_9H_9ClNO_3[M+H]^+$ 214.0 found 213.9; $^1H$ NMR (400 MHz, CHLOROFORM-d) δ=7.04 (s, 1H), 4.49 (dd, J=4.9, 7.8 Hz, 1H), 4.12 (s, 3H), 3.49 (dd, J=7.8, 17.6 Hz, 1H), 2.96 (ddd, J=0.7, 5.0, 17.6 Hz, 1H).

Intermediate 4b (350 mg) was separated by SFC (Column: Instrument: SFC-80; Column: DAICEL CHIRALCEL OX (250 mm*30 mm, 10 um); Condition: 0.1% $NH_3H_2O$ ETOH; Begin B: 25; End B: 25; FlowRate (ml/min): 70; Injections: 60) to give Intermediate 4b-A (130 mg, 99.6% ee) MS: ES m/z calculated for $C_9H_9ClNO_3[M+H]^+$ 214.0 found 213.9 and Intermediate 4b-B (145 mg, 98.9% ee) as brown solid. MS: ES m/z calculated for $C_9H_9ClNO_3[M+H]^+$ 214.0 found 213.9.

Example A4c

Preparation of Intermediate 4c

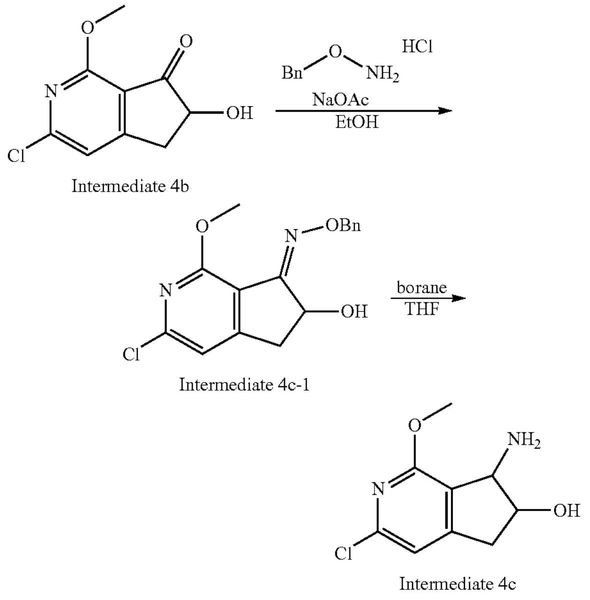

Intermediate 4b

Intermediate 4c-1

Intermediate 4c

A mixture of Intermediate 4b (100 mg, 468 μmol), O-benzylhydroxylamine hydrochloride salt (112 mg, 702 μmol) and NaOAc (115 mg, 1.40 mmol) in EtOH (3 mL) was stirred at 45° C. for 12 hours. The reaction mixture was filtered and concentrated under reduced pressure to give a residue, which was purified by flash silica gel chromatography to give Intermediate 4c-1 (100 mg) as a yellow liquid.

To a solution of Intermediate 4c-1 (88 mg) in THF (2 mL) was added borane (1 M in THF 828 μL) at 10° C. Then the reaction mixture was stirred at 50° C. for 16 hours. The reaction mixture was quenched by addition 1N NaOH, and then extracted with ethyl acetate (2×20 mL). The combined organic layers were washed with brine (20 mL), dried over anhydrous $Na_2SO_4$, filtered and concentrated under reduced pressure to give Intermediate 4c (32 mg) as a brown solid. MS: ES m/z calculated for $C_9H_{12}C_1N_2O_2[M+H]^+$ 215.1 found 214.9.

Example A4d

Preparation of Intermediate 4d

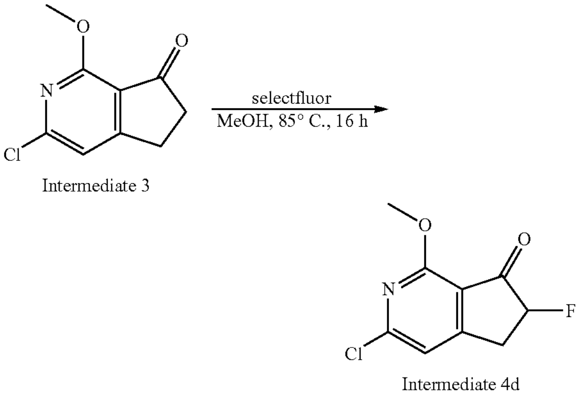

Intermediate 3

Intermediate 4d

To a solution of Intermediate 3 (300 mg, 1.52 mmol) in MeOH (3 mL) was added 1-(chloromethyl)-4-fluoro-1,4-diazoniabicyclo[2.2.2]octane ditetrafluoroborate (1.61 g, 4.55 mmol). The resulting mixture was stirred at 85° C. for 16 hours. The reaction mixture was filtered and concentrated under reduced pressure to give crude Intermediate 4d (310 mg) as a yellow solid. MS: ES m/z calculated for $C_9H_8ClFNO_2[M+H]^+$ 216.1 found 216.0.

Example A4e

Preparation of Intermediate 4e

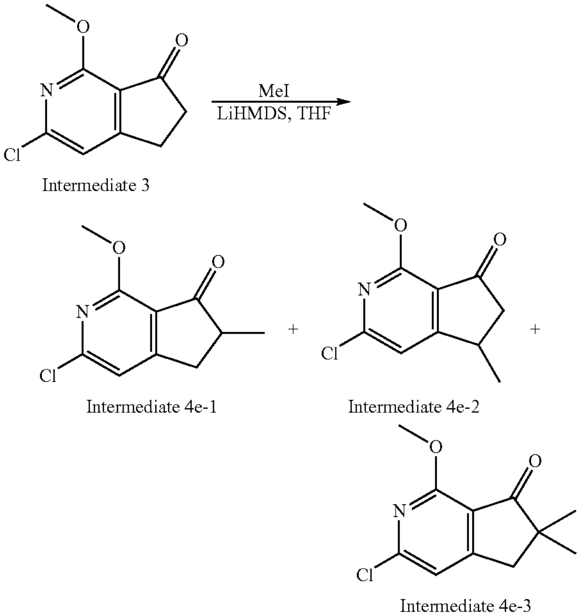

Intermediate 3

Intermediate 4e-1 + Intermediate 4e-2 +

Intermediate 4e-3

To a solution of Intermediate 3 (2 g, 10.12 mmol) and MeI (7.18 g, 50.60 mmol, 3.15 mL, 5 eq) in THF (20 mL) was added slowly LiHMDS (1 M, 20.24 mL, 2 eq) at −20° C. The mixture was stirred at −15° C. for 1 h, then the reaction was warmed up to 15° C. and stirred for 2 h. The reaction mixture was quenched by addition sat. $NH_4Cl$ (20 mL) at 0° C., then diluted with $H_2O$ (50 mL) and extracted with EtOAc (3×60 mL). The combined organic layers were washed with brine (1×100 mL), dried over anhydrous $Na_2SO_4$, filtered and concentrated under reduced pressure to give a residue, which was purified by flash silica gel chromatography to give Intermediate 4e-1 (70 mg) as a yellow oil, MS: ES m/z calculated for $C_{10}H_{11}ClNO_2[M+H]^+$ 212.0 found 211.9; Intermediate 4e-2 (300 mg) as a yellow oil, MS: ES m/z calculated for $C_{10}H_{11}ClNO_2[M+H]^+$ 212.0 found 211.9; and Intermediate 4e-3 (1.05 g) as a yellow oil, MS: ES m/z calculated for $C_{11}H_{13}ClNO_2[M+H]^+$ 226.1 found 226.0.

Example A5

Preparation of Intermediates 5-1a and 5-1b

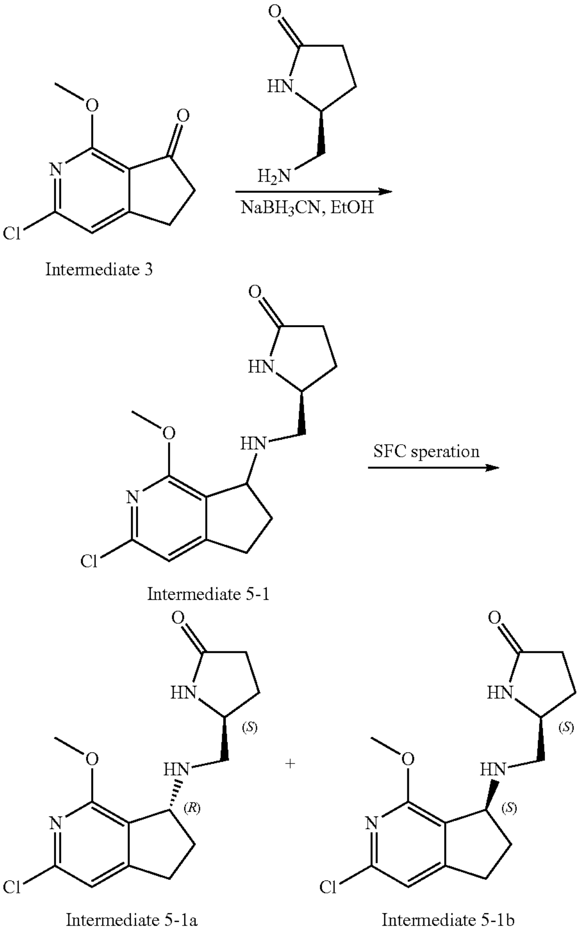

Intermediate 3

Intermediate 5-1

Intermediate 5-1a + Intermediate 5-1b

The mixture of Intermediate 3 (1.45 g, 7.34 mmol) and (5S)-5-(aminomethyl)pyrrolidin-2-one HCl salt (2.21 g, 14.7 mmol) in EtOH (20 mL) was stirred at 20-45° C. for 1 h. $NaBH_3CN$ (1.38 g, 22 mmol) was added into the mixture at 20° C. The mixture was stirred at 20-45° C. for 15 h, filtered and concentrated under reduced pressure to give a residue. The residue was diluted with $H_2O$ (80 mL) and extracted with EtOAc (2×100 mL). The combined organic layers were washed with brine (2×80 mL), dried over anhydrous $Na_2SO_4$, filtered and concentrated under reduced pressure to give a residue. The residue was purified by flash silica gel chromatography to give Intermediate 5-1 (2.2 g, 92% purity) as a yellow oil.

Intermediate 5-1 was further separated by SFC (Column: DAICEL CHIRALPAK IC (250 mm*50 mm, 10 um), Mobile phase: A: $CO_2$; B: IPA (0.1% $NH_3 \cdot H_2O$); Gradient: 55% B; Flow Rate (mL/min): 140; Injections: 300 min (3 mL per injection, Cycle time: ~6.8 min); Column temperature: 40° C.) to give pure enantiomers Intermediate 5-1a and Intermediate 5-1b. The absolute chiral centers of the intermediates are assigned based on a single crystal structure of Intermediate 5-1b.

Intermediate 5-1a (800 mg) was obtained as a yellow oil with SFC. Rt=3.44 minutes (SFC analytical Instrument: CAS-QD-ANA-SFC-SD (Agilent 1260 with DAD detector); Method: Column: Chrialpak IC-3 100×4.6 mm I.D., 3 m; Mobile phase: 40% of IPA (0.05%) in $CO_2$; Flow rate: 2.8 mL/min Column temperature: 40° C.). $^1$H NMR (400 MHz, $CD_3OD$) δ 6.96 (s, 1H), 4.51 (dd, J=3.9, 7.7 Hz, 1H), 3.98 (s, 3H), 3.91-3.80 (m, 1H), 3.61 (q, J=7.1 Hz, 1H), 3.18-3.02 (m, 1H), 2.95-2.74 (m, 3H), 2.52-2.40 (m, 1H), 2.39-2.25 (m, 3H), 2.08 (tdd, J=4.4, 8.9, 13.4 Hz, 1H), 1.92-1.76 (m, 1H).

Intermediate 5-1b (1.14 g) was obtained as a yellow solid with SFC. Rt=4.74 minutes (SFC analytical Instrument: CAS-QD-ANA-SFC-SD (Agilent 1260 with DAD detector) Method: Column: Chrialpak IC-3 100×4.6 mm I.D., 3 m Mobile phase: 40% of IPA (0.05%) in $CO_2$; Flow rate: 2.8 mL/min Column temperature: 40° C.). $^1$H NMR (400 MHz, $CD_3OD$) δ 6.91 (s, 1H), 4.37 (dd, J=4.8, 7.5 Hz, 1H), 3.96 (s, 3H), 3.86-3.74 (m, 1H), 3.05 (ddd, J=5.9, 8.8, 17.1 Hz, 1H), 2.89-2.68 (m, 2H), 2.59 (dd, J=7.1, 11.9 Hz, 1H), 2.46-2.19 (m, 4H), 1.97 (tdd, J=5.3, 8.4, 13.5 Hz, 1H), 1.89-1.72 (m, 1H).

The single crystal of Intermediate 5-1b's formate salt was obtained. The crystal was a colorless needle with the following dimensions: 0.30×0.04×0.04 mm$^3$. The symmetry of the crystal structure was assigned the monoclinic space group $P2_1$ with the following parameters: a=20.8793(7) Å, b=5.8084(2) Å, c=28.1836(9) Å, α=90°, β=102.238(3°), γ=90°, V=3340.3(2) Å3, Z=8, Dc=1.359 g/cm3, F(000)=1440.0, μ(CuKα)=2.236 mm-1, and T=149.99(10) K. FIGS. 1A and 1B show the absolute configuration structure and ORTEP crystal structure of the formate salt of Intermediate 5-1b.

The intermediates in Table A-1 were prepared using similar methodologies are described for preparing Intermediate 5-1a and 5-1b.

TABLE A-1

| Intermediate No. | Structure | SFC Method | Retention time (minute) | Starting Materials |
|---|---|---|---|---|
| 5-2a | 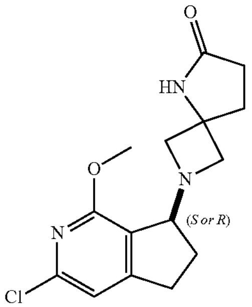 [SMILES: COc1nc(Cl)cc2c1[C@@H](N1CC3(CCC(=O)N3)C1)CC2] | E | 3.33 | Intermediate 3 2,5-Diazaspiro[3.4] octan-6-one hydrochloride |
| 5-2b | 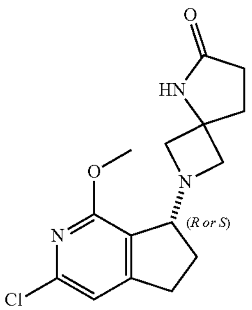 [SMILES: COc1nc(Cl)cc2c1[C@H](N1CC3(CCC(=O)N3)C1)CC2] | E | 4.00 | Intermediate 3 2,5-Diazaspiro[3.4] octan-6-one hydrochloride |

TABLE A-1-continued
| Intermediate No. | Structure | SFC Method | Retention time (minute) | Starting Materials |
|---|---|---|---|---|
| 5-3a | 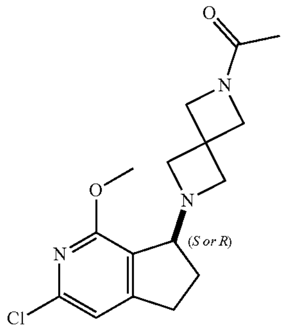 [SMILES: COc1nc(Cl)cc2c1[C@@H](N1CC3(CN(C(C)=O)C3)C1)CC2] | F | 1.19 | Intermediate 3 1-(2,6-diazaspiro[3.3] heptan-2-yl)ethan-1-one |
| 5-3b | 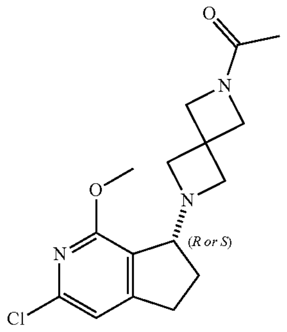 [SMILES: COc1nc(Cl)cc2c1[C@H](N1CC3(CN(C(C)=O)C3)C1)CC2] | F | 1.34 | Intermediate 3 1-(2,6-diazaspiro[3.3] heptan-2-yl)ethan-1-one |
| 6-1a | 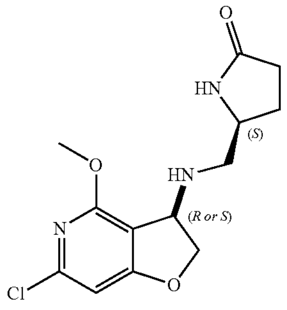 | I | 1.36 | Intermediate 4 (5S)-5-(aminomethyl) pyrrolidin-2-one HCl |
| 6-1b | 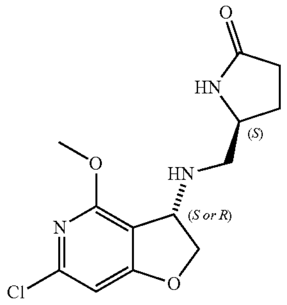 | I | 1.67 | Intermediate 4 (5S)-5-(aminomethyl) pyrrolidin-2-one HCl |

TABLE A-1-continued
| Intermediate No. | Structure | SFC Method | Retention time (minute) | Starting Materials |
|---|---|---|---|---|
| 6-2a | 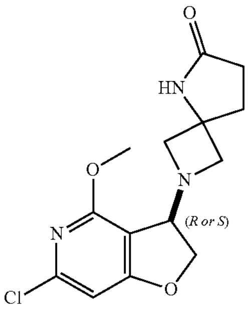 [SMILES: COc1nc(Cl)cc2c1[C@@H](N1CC3(CCC(=O)N3)C1)CO2] | G | 1.51 | Intermediate 4 2,5-Diazaspiro[3.4] octan-6-one hydrochloride |
| 6-2b | 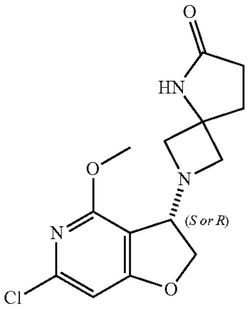 [SMILES: COc1nc(Cl)cc2c1[C@H](N1CC3(CCC(=O)N3)C1)CO2] | G | 2.10 | Intermediate 4 2,5-Diazaspiro[3.4] octan-6-one hydrochloride |
| 5-4a | 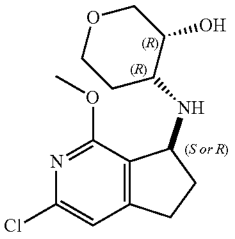 | J | 1.98 | Intermediate 3 (3R,4R)-4-Aminooxan-3-ol hydrochloride |
| 5-4b | 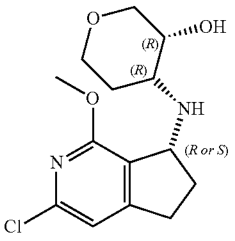 | J | 1.83 | Intermediate 3 (3R,4R)-4-Aminooxan-3-ol hydrochloride |
| 5-5a | 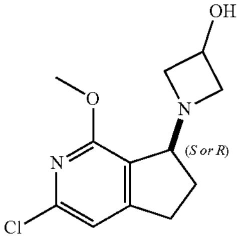 [SMILES: COc1nc(Cl)cc2c1[C@@H](N1CC(O)C1)CC2] | L | 3.28 | Intermediate 3 3-Hydroxyazetidine Hydrochloride |

TABLE A-1-continued

| Intermediate No. | Structure | SFC Method | Retention time (minute) | Starting Materials |
|---|---|---|---|---|
| 5-5b | 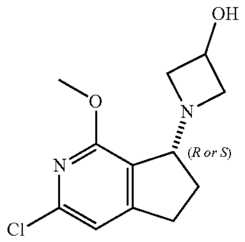 [SMILES: COc1nc(Cl)cc2c1[C@H](N1CC(O)C1)CC2] | L | 3.58 | Intermediate 3<br>3-Hydroxyazetidine<br>Hydrochloride |
| 5-6a | 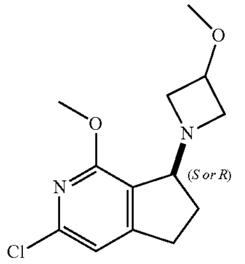 [SMILES: COc1nc(Cl)cc2c1[C@@H](N1CC(OC)C1)CC2] | L | 1.96 | Intermediate 3<br>3-methoxyazetidine<br>hydrochloride |
| 5-6b | 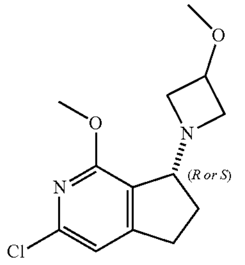 [SMILES: COc1nc(Cl)cc2c1[C@H](N1CC(OC)C1)CC2] | L | 2.14 | Intermediate 3<br>3-methoxyazetidine<br>hydrochloride |
| 5-7a | 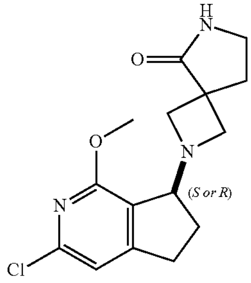 [SMILES: COc1nc(Cl)cc2c1[C@@H](N1CC3(CCNC3=O)C1)CC2] | K | 1.69 | Intermediate 3<br>2,6-<br>Diazaspiro[3.4]octan-<br>5-one<br>hydrochloride |
| 5-7b | 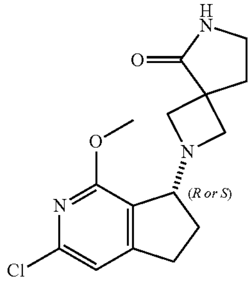 [SMILES: COc1nc(Cl)cc2c1[C@H](N1CC3(CCNC3=O)C1)CC2] | K | 1.80 | Intermediate 3<br>2,6-<br>Diazaspiro[3.4]octan-<br>5-one hydrochloride |

TABLE A-1-continued

| Intermediate No. | Structure | SFC Method | Retention time (minute) | Starting Materials |
|---|---|---|---|---|
| 5-8a | 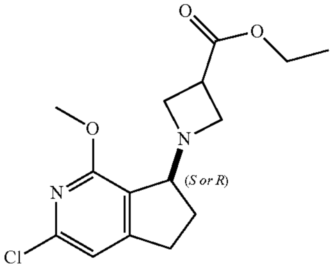 [SMILES: CCOC(=O)C1CN([C@H]2CCc3cc(Cl)nc(OC)c32)C1] | J | 0.76 | Intermediate 3 Ethyl Azetidine-3-carboxylate Hydrochloride |
| 5-8b | 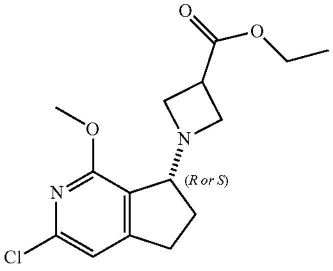 [SMILES: CCOC(=O)C1CN([C@@H]2CCc3cc(Cl)nc(OC)c32)C1] | J | 0.96 | Intermediate 3 Ethyl Azetidine-3-carboxylate Hydrochloride |
| 5-9a | 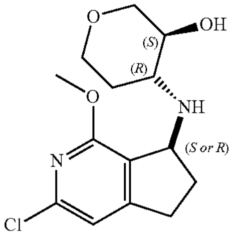 | J | 1.02 | Intermediate 3 (3S,4R)-4-aminotetrahydro-2H-pyran-3-ol hydrochloride |
| 5-9b | 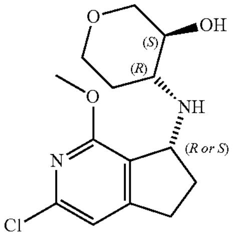 | J | 1.31 | Intermediate 3 (3S,4R)-4-aminotetrahydro-2H-pyran-3-ol hydrochloride |
| 5-10a | 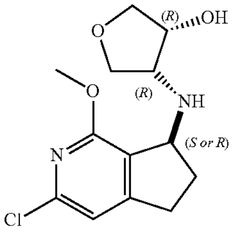 | N | 1.62 | Intermediate 3 (3R,4R)-4-aminotetrahydrofuran-3-ol hydrochloride |
| 5-10b | 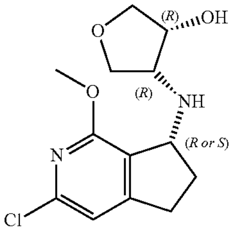 | N | 1.81 | Intermediate 3 (3R,4R)-4-aminotetrahydrofuran-3-ol hydrochloride |

TABLE A-1-continued
| Intermediate No. | Structure | SFC Method | Retention time (minute) | Starting Materials |
|---|---|---|---|---|
| 511a | 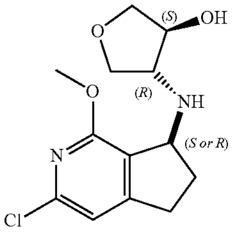 | M | 1.64 | Intermediate 3 (3S,4R)-4-Aminotetrahydro-3-furanol |
| 5-11b | 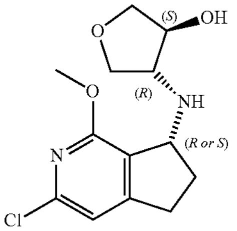 | M | 1.78 | Intermediate 3 (3S,4R)-4-Aminotetrahydro-3-furanol |
| 5-12a | 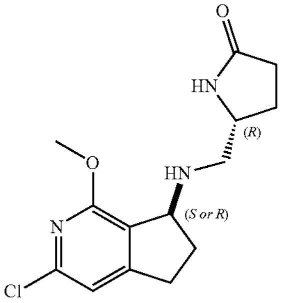 | O | 2.10 | Intermediate 3 (5R)-5-(aminomethyl) pyrrolidin-2-one HCl |
| 5-12b | 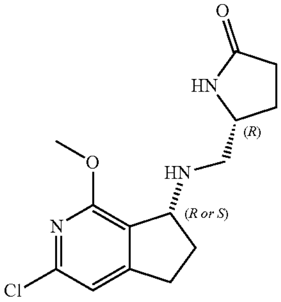 | O | 2.33 | Intermediate 3 (5R)-5-(aminomethyl)pyrrol-idin-2-one HCl |
| 5-13a | 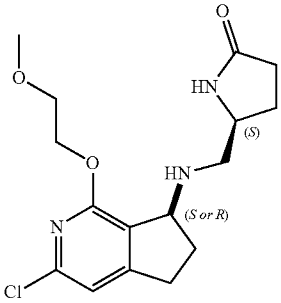 | J | 1.48 | Intermediate 4a (5S)-5-(aminomethyl) pyrrolidin-2-one HCl |

TABLE A-1-continued

| Intermediate No. | Structure | SFC Method | Retention time (minute) | Starting Materials |
|---|---|---|---|---|
| 5-13b | 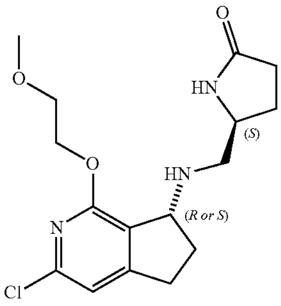 | J | 1.89 | Intermediate 4a (5S)-5-(aminomethyl) pyrrolidin-2-one HCl |
| 5-14a | 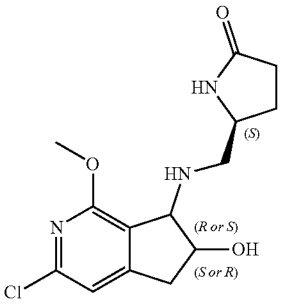 | G | 1.69 | Intermediate 4b-A (5S)-5-(aminomethyl) pyrrolidin-2-one HCl |
| 5-14b | 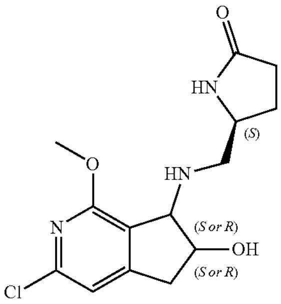 | G | 2.37 | Intermediate 4b-A (5S)-5-(aminomethyl) pyrrolidin-2-one HCl |
| 5-15a | 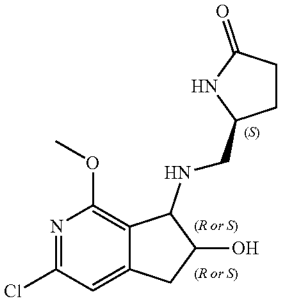 | P | 1.99 | Intermediate 4b-B (5S)-5-(aminomethyl) pyrrolidin-2-one HCl |
| 5-15b | 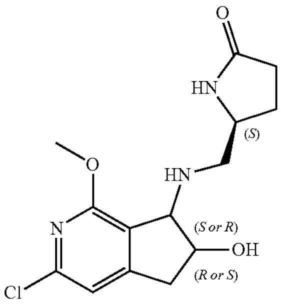 | P | 2.72 | Intermediate 4b-B (5S)-5-(aminomethyl) pyrrolidin-2-one HCl |

TABLE A-1-continued

| Intermediate No. | Structure | SFC Method | Retention time (minute) | Starting Materials |
|---|---|---|---|---|
| 5-16a | 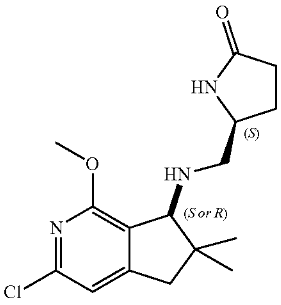 | P | 1.61 | Intermediate 4e-3 (5S)-5-(aminomethyl) pyrrolidin-2-one HCl |
| 5-16b | 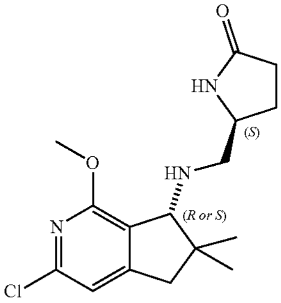 | P | 1.85 | Intermediate 4e-3 (5S)-5-(aminomethyl) pyrrolidin-2-one HCl |
| 5-17a | 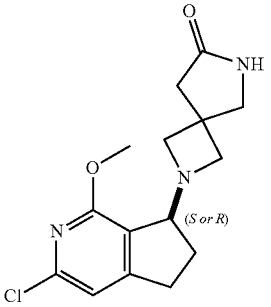 [SMILES: COc1nc(Cl)cc2c1[C@@H](N1CC3(CNC(=O)C3)C1)CC2] | M | 2.47 | Intermediate 3 2,6-diazaspiro[3.4]octan-7-one hydrochloride |
| 5-17b | 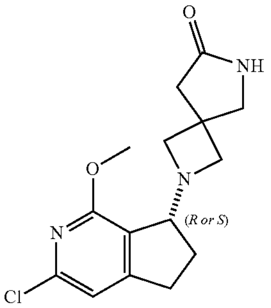 [SMILES: COc1nc(Cl)cc2c1[C@H](N1CC3(CNC(=O)C3)C1)CC2] | M | 2.67 | Intermediate 3 2,6-diazaspiro[3.4]octan-7-one hydrochloride |
| 5-18a | 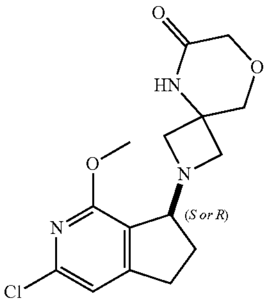 [SMILES: COc1nc(Cl)cc2c1[C@@H](N1CC3(COCC(=O)N3)C1)CC2] | G | 1.411 | Intermediate 3 8-oxa-2,5-diazaspiro[3.5]nonan-6-one hydrochloride |

TABLE A-1-continued

| Intermediate No. | Structure | SFC Method | Retention time (minute) | Starting Materials |
|---|---|---|---|---|
| 5-18b | 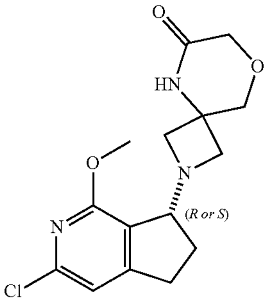 [SMILES: COc1nc(Cl)cc2c1[C@H](N1CC3(COCC(=O)N3)C1)CC2] | G | 1.675 | Intermediate 3 8-oxa-2,5-diazaspiro[3.5]nonan-6-one hydrochloride |
| 5-19a | 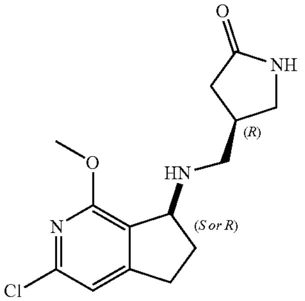 | Q | 1.97 | Intermediate 3 (R)-4-(aminomethyl) pyrrolidin-2-one hydrochloride |
| 5-19b | 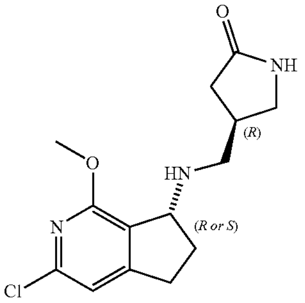 | Q | 2.16 | Intermediate 3 (R)-4-(aminomethyl) pyrrolidin-2-one hydrochloride |

SFC Method E: Column: UniChiral ND 100×4.6 mm I.D., 5 m; Mobile phase: A: $CO_2$; B: iso-propanol (0.05% DEA); Gradient: from 5% to 40% of B in 4.5 min and hold 40% for 0.5 min, then 5% of B for 1 min; Flow rate: 2.8 mL/min; Column temperature: 40° C.

SFC Method F: Column: Chiralpak AD-3 100×4.6 mm I.D., 3 m; Mobile phase: A: $CO_2$, B: Ethanol (0.05% DEA); Gradient: from 5% to 40% of B in 4.5 min and hold 40% for 2.5 min, then 5% of B for 1 min; Flow rate: 2.8 mL/min; Column temperature: 40° C.

SFC Method G: Column: Chiralpak AD-3 50×4.6 mm I.D., 3 m; Mobile phase: A: $CO_2$, B: Ethanol (0.05% DEA); Gradient: from 5% to 40% of B in 2.5 min and hold 40% for 0.5 min, then 5% of B for 1 min; Flow rate: 4 mL/min; Column temperature: 35° C.

SFC Method H: Column: Lux Cellulose-2 100×4.6 mm I.D., 3 m; Mobile phase: A: $CO_2$; B: IPA (0.05% DEA); Gradient: from 5% to 40% of B in 4.5 min and hold 40% for 2.5 min, then 5% of B for 1 min; Flow rate: 2.5 mL/min; Column temperature: 40° C.

SFC Method I: Column: Chiralpak AY-3 50×4.6 mm I.D., 3 m; Mobile phase: A: $CO_2$; B: IPA (0.05% DEA); Gradient: from 5% to 40% of B in 2.5 min and hold 40% for 0.5 min, then 5% of B for 1 min; Flow rate: 4 mL/min; Column temperature: 35° C.

SFC Method J: Column: Chiralpak AY-3 50×4.6 mm I.D., 3 m; Mobile phase: A: $CO_2$; B: Ethanol (0.05% DEA); Gradient: from 5% to 40% of B in 2.5 min and hold 40% for 0.5 min, then 5% of B for 1 min; Flow rate: 4 mL/min; Column temperature: 35° C.

SFC Method K: Column: (S,S)-Whelk-O-1.8 50×4.6 mm I.D., 1.8 m; Mobile phase: A: $CO_2$; B: methanol (0.05% DEA); Gradient: from 10% to 40% of B in 2 min and hold 40% for 1 min, then 5% of B for 1 min; Flow rate: 2.8 mL/min; Column temperature: 35° C.

SFC Method L: Column: Lux Cellulose-2 100×4.6 mm I.D., 3 m; Mobile phase: A: $CO_2$; B: IPA (0.05% DEA); Gradient: from 5% to 40% of B in 4.5 min, then 5% of B for 2.5 min, then 5% of B for 1 min; Flow rate: 2.5 mL/min; Column temperature: 40° C.

SFC Method M: Column: MChiral NS-3 100×4.6 mm I.D., 3 m Mobile phase: A: CO2 B: IPA (0.05% DEA) Gradient: from 5% to 40% of B in 2 min and hold 40% for 1 min, then 5% of B for 1 min Flow rate: 2.8 mL/min; Column temp.: 35° C.

SFC Method N: Column: Chiralcel OJ-3 100×4.6 mm I.D., 3 m Mobile phase: A: CO2 B: ethanol (0.05% DEA) Gradient: from 5% to 40% of B in 2 min and hold 40% for 1 min, then 5% of B for 1 min Flow rate: 2.8 mL/min; Column temp.: 35° C.

SFC Method O: Column: Chiralpak AS-3 50×4.6 mm I.D., 3 m; Mobile phase: A: $CO_2$; B: Ethanol (0.05% DEA); Gradient: from 5% to 40% of B in 2.5 min, then 40% of B for 0.5 min, then 5% of B for 1 min; Flow rate: 4 mL/min; Column temperature: 35° C.

SFC Method P: Column: Chiralpak IG 50×4.6 mm I.D., 3 m; Mobile phase: A: $CO_2$; B: Ethanol (0.05% DEA); Gradient: from 5% to 40% of B in 2.5 min, then 40% of B for 0.5 min, then 5% of B for 1 min; Flow rate: 4 mL/min; Column temperature: 35° C.

SFC Method Q: Column: Chiralpak IC-3 50×4.6 mm I.D., 3 m; Mobile phase: A: CO2 B: Methanol (0.05% DEA); Gradient: from 20% to 40% of B in 2.5 min and hold 40% of 0.5 min, then 20% of B for 1 min; Flow rate: mL/min; Column temp.: 35° C.

Example A6

Preparation of Intermediate 7-1

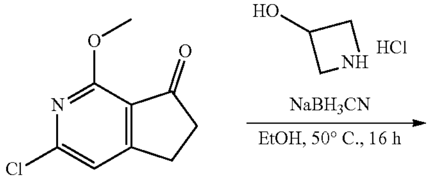

Intermediate 3

-continued

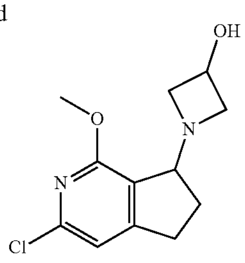

Intermediate 7-1

To a solution of Intermediate 3 (500 mg, 2.53 mmol) in EtOH (6 mL) was added 3-Hydroxyazetidine hydrochloride (416 mg, 3.80 mmol). The mixture was stirred at 50° C. for 1 h. After adding $NaBH_3CN$ (477 mg, 7.59 mmol) at 25° C. into the mixture, the resulting mixture was stirred at 50° C. for 15 h to give a yellow mixture. The reaction was quenched with $H_2O$ (30 mL) and then extracted with EtOAc (3×30 mL). The combined organic layers were dried over $Na_2SO_4$, filtered and concentrated under reduced pressure to give a residue, which was purified by prep-HPLC to give Intermediate 7-1 (280 mg, 39% yield, 90% purity) as a yellow solid. MS: ES m/z calculated for $C_{12}H_{16}ClN_2O_2[M+H]^+$ 255.1 found 255.0.

The intermediates shown in Table A-2 were prepared by an analogous reaction protocol as was used for the preparation of Intermediate 7-1 using the appropriate starting materials.

TABLE A-2

| Intermediate No. | Structure | Starting Materials |
|---|---|---|
| 7-2 | 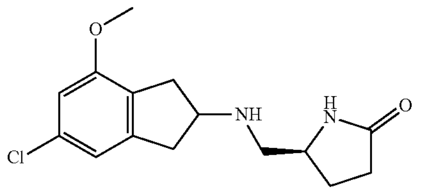 [SMILES: COc1cc(Cl)cc2c1CC(NC[C@@H]1CCC(=O)N1)C2] | (5S)-5-(aminomethyl)pyrrolidin-2-one HCl salt Intermediate 2 |
| 7-3 | 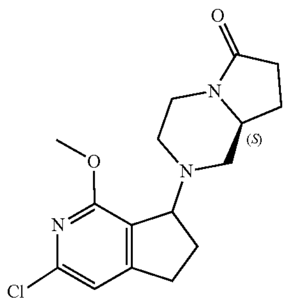 | (8aS)-Hexahydropyrrolo[1,2-a]pyrazin-6(2H)-one hydrochloride Intermediate 3 |
| 7-4 | 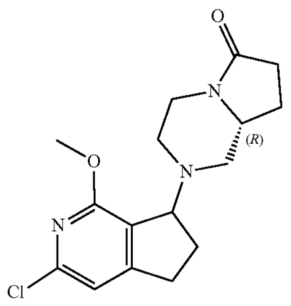 | (8aR)-Hexahydropyrrolo[1,2-a]pyrazin-6(2H)-one hydrochloride Intermediate 3 |

TABLE A-2-continued

| Intermediate No. | Structure | Starting Materials |
| --- | --- | --- |
| 7-5 | 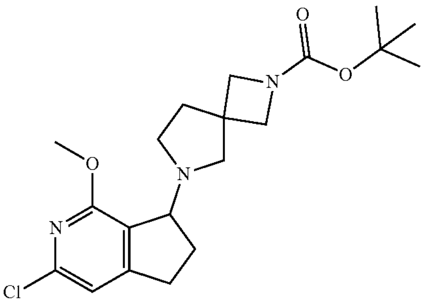 [SMILES: COc1nc(Cl)cc2c1C(N1CCC3(CN(C(=O)OC(C)(C)C)C3)C1)CC2] | tert-butyl 2,6-diazaspiro[3.4]octane-2-carboxylate Intermediate 3 |
| 7-6 | 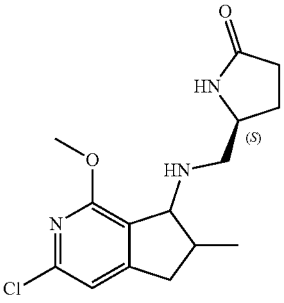 | (5S)-5-(aminomethyl)pyrrolidin-2-one HCl salt Intermediate 4e-1 |
| 7-7 | 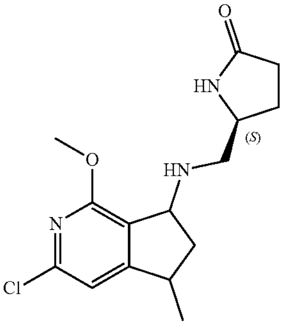 | (5S)-5-(aminomethyl)pyrrolidin-2-one HCl salt Intermediate 4e-2 |

Example 7

Preparation Intermediate 8-1

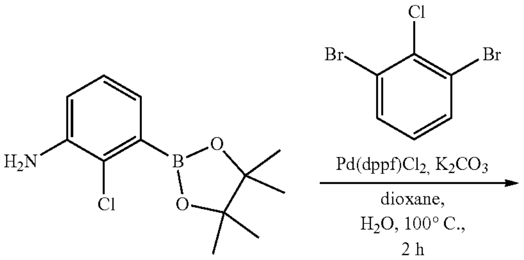

-continued

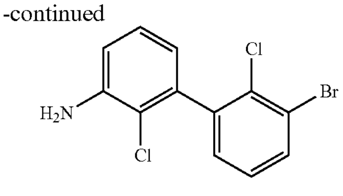

Intermediate 8-1

A mixture of 2-Chloro-3-(4,4,5,5-tetramethyl-1,3,2-dioxaborolan-2-yl)aniline (2.1 g, 8.28 mmol), 1,3-Dibromo-2-chlorobenzene (4.48 g, 16.6 mmol), Pd(dppf)Cl$_2$ (606 mg, 828 mmol) and $K_2CO_3$ (3.43 g, 24.9 mmol) in dioxane (25 mL) and $H_2O$ (2.5 mL) was degassed and purged with $N_2$ (3×). After stirring the mixture at 100° C. for 2 h under $N_2$ atmosphere, the reaction was quenched with $H_2O$ (30 mL) and then extracted with EtOAc (3×30 mL). The combined organic layers were dried over $Na_2SO_4$, filtered and concentrated under reduced pressure to give a residue, which was purified by flash silica gel chromatography to give Intermediate 8-1 (1.4 g) as a yellow solid. MS: ES m/z calculated for $C_{12}H_9BrCl_2N$ $[M+H]^+$ 315.9, found 316.0.

The intermediates shown in Table A-3 were prepared by an analogous reaction protocol as was used for the preparation of Intermediate 8-1 using the appropriate starting materials.

TABLE A-3

| Intermediate No. | Structure | Starting Materials |
|---|---|---|
| 8-2 | 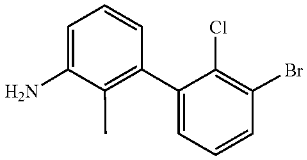 | 2-Methyl-3-(4,4,5,5-tetramethyl-1,3,2-dioxaborolan-2-yl)aniline 1,3-Dibromo-2-chlorobenzene |
| 8-3 | 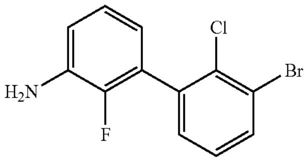 [SMILES: Cc1c(N)cccc1-c1cccc(Br)c1C] | 2-Fluoro-3-(4,4,5,5-tetramethyl-1,3,2-dioxaborolan-2-yl)aniline 1,3-Dibromo-2-chlorobenzene |
| 8-4 | 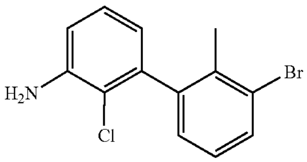 [SMILES: Cc1c(Br)cccc1-c1cccc(N)c1F] | 2-Chloro-3-(4,4,5,5-tetramethyl-1,3,2-dioxaborolan-2-yl)aniline 1,3-Dibromo-2-methylbenzene |
| 8-5 | 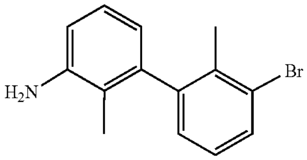 | 2-Methyl-3-(4,4,5,5-tetramethyl-1,3,2-dioxaborolan-2-yl)aniline 1,3-Dibromo-2-methylbenzene |
| 8-6 | 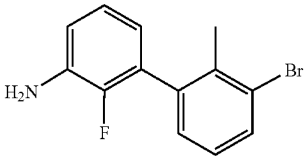 | 2-Fluoro-3-(4,4,5,5-tetramethyl-1,3,2-dioxaborolan-2-yl)aniline 1,3-Dibromo-2-methylbenzene |
| 8-7 | 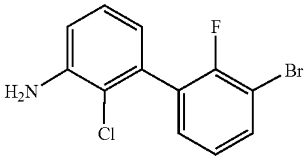 [SMILES: Nc1cccc(-c2cccc(Br)c2F)c1Cl] | 2-Chloro-3-(4,4,5,5-tetramethyl-1,3,2-dioxaborolan-2-yl)aniline 1,3-Dibromo-2-fluorobenzene |
| 8-8 | 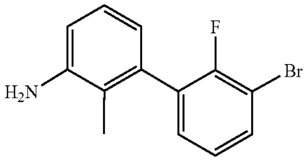 [SMILES: Cc1c(N)cccc1-c1cccc(Br)c1F] | 2-Methyl-3-(4,4,5,5-tetramethyl-1,3,2-dioxaborolan-2-yl)aniline 1,3-Dibromo-2-fluorobenzene |

TABLE A-3-continued

| Intermediate No. | Structure | Starting Materials |
|---|---|---|
| 8-9 | 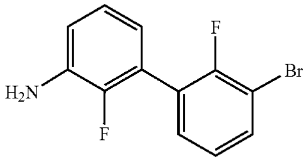 [SMILES: Nc1cccc(-c2cccc(Br)c2F)c1F] | 2-Fluoro-3-(4,4,5,5-tetramethyl-1,3,2-dioxaborolan-2-yl)aniline 1,3-Dibromo-2-fluorobenzene |
| 8-10 | 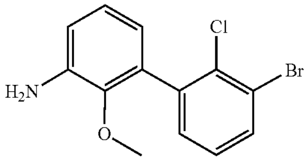 [SMILES: COc1c(N)cccc1-c1cccc(Br)c1Cl] | 2-Methoxy-3-(tetramethyl-1,3,2-dioxaborolan-2-yl)aniline 1,3-Dibromo-2-chlorobenzene |
| 8-11 | 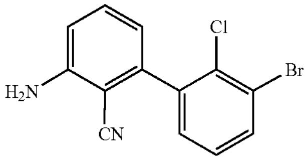 [SMILES: N#Cc1c(Br)cccc1-c1cccc(N)c1Cl] | 2-amino-6-(4,4,5,5-tetramethyl-1,3,2-dioxaborolan-2-yl)benzonitrile 1,3-Dibromo-2-chlorobenzene |
| 8-12 | 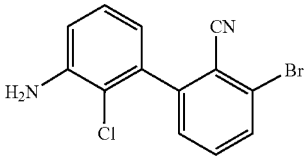 | 2-Chloro-3-(4,4,5,5-tetramethyl-1,3,2-dioxaborolan-2-yl)aniline 2,6-dibromobenzonitrile |
| 8-14 | 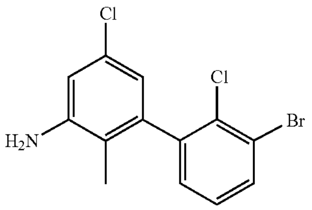 | 5-chloro-2-methyl-3-(4,4,5,5-tetramethyl-1,3,2-dioxaborolan-2-yl)aniline 1,3-Dibromo-2-chlorobenzene |
| 8-15 | 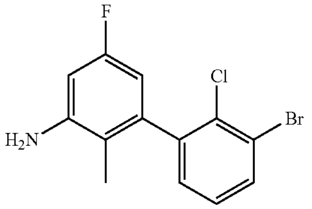 | 5-fluoro-2-methyl-3-(4,4,5,5-tetramethyl-1,3,2-dioxaborolan-2-yl)phenylamine 1,3-Dibromo-2-chlorobenzene |
| 8-15a | 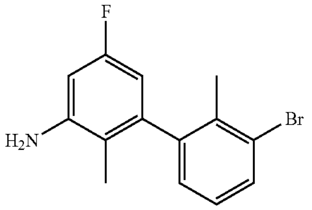 [SMILES: Cc1c(N)cc(F)cc1-c1cccc(Br)c1C] | 5-fluoro-2-methyl-3-(4,4,5,5-tetramethyl-1,3,2-dioxaborolan-2-yl)phenylamine 1,3-dibromo-2-methylbenzene |
| 8-16 | 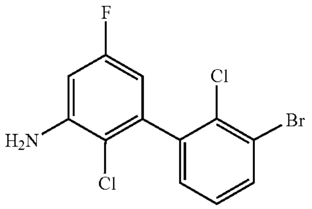 | 2-Chloro-5-fluoro-3-(4,4,5,5-tetramethyl-1,3,2-dioxaborolan-2-yl)aniline 1,3-Dibromo-2-chlorobenzene |

TABLE A-3-continued

| Intermediate No. | Structure | Starting Materials |
|---|---|---|
| 8-18 | 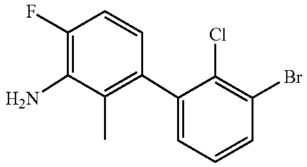 [SMILES: Cc1c(-c2cccc(Br)c2Cl)ccc(F)c1N] | 6-fluoro-2-methyl-3-(4,4,5,5-tetramethyl-1,3,2-dioxaborolan-2-yl)aniline 1,3-Dibromo-2-chlorobenzene |
| 8-20 | 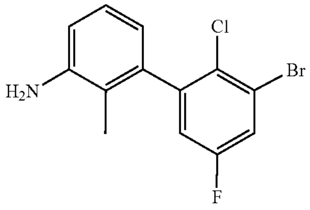 [SMILES: Cc1c(N)cccc1-c1cc(F)cc(Br)c1Cl] | 2-Methyl-3-(4,4,5,5-tetramethyl-1,3,2-dioxaborolan-2-yl)aniline 1,3-dibromo-2-chloro-5-fluorobenzene |
| 8-21 | 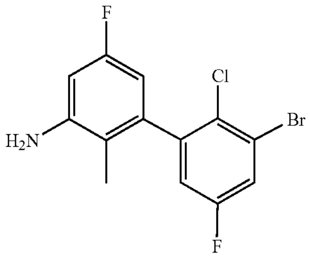 [SMILES: Cc1c(N)cc(F)cc1-c1cc(F)cc(Br)c1Cl] | 5-fluoro-2-methyl-3-(4,4,5,5-tetramethyl-1,3,2-dioxaborolan-2-yl)phenylamine 1,3-dibromo-2-chloro-5-fluorobenzene |
| 8-22 | 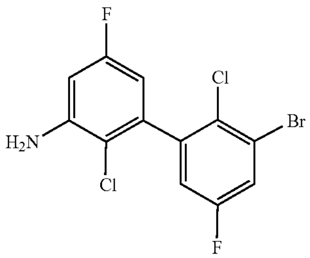 [SMILES: Nc1cc(F)cc(-c2cc(F)cc(Br)c2Cl)c1Cl] | 2-chloro-5-fluoro-3-(4,4,5,5-tetramethyl-1,3,2-dioxaborolan-2-yl)aniline 1,3-dibromo-2-chloro-5-fluorobenzene |
| 8-23 | 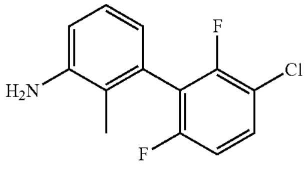 [SMILES: Cc1c(N)cccc1-c1c(F)ccc(Cl)c1F] | 2-Methyl-3-(4,4,5,5-tetramethyl-1,3,2-dioxaborolan-2-yl)aniline 2-bromo-4-chloro-1,3-difluorobenzene |
| 8-24 | 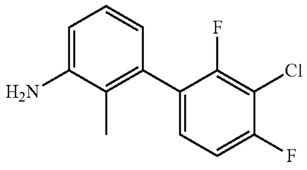 [SMILES: Cc1c(N)cccc1-c1ccc(F)c(Cl)c1F] | 2-Methyl-3-(4,4,5,5-tetramethyl-1,3,2-dioxaborolan-2-yl)aniline 1-bromo-3-chloro-2,4-difluorobenzene |

Example A8

Preparation Intermediate 10-1

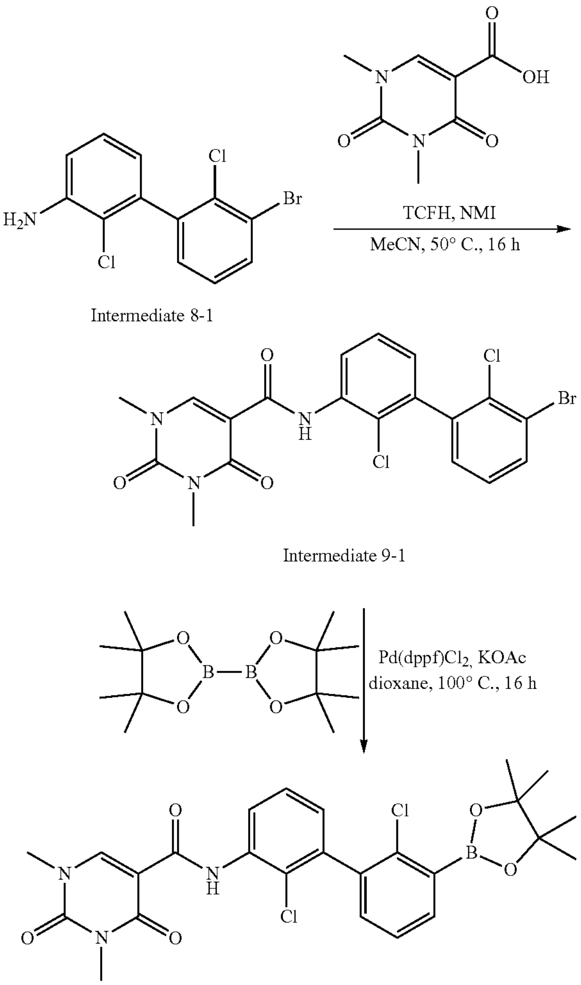

Intermediate 8-1

Intermediate 9-1

Intermediate 10-1

To a solution of compound Intermediate 8-1 (300 mg, 946 µmol) and 1,3-dimethyl-2,4-dioxopyrimidine-5-carboxylic acid (145 mg, 789 µmol) in MeCN (4 mL) were added N,N,N',N'-tetramethylchloroformamidinium hexafluorophosphate (TCFH, 443 mg, 1.58 mmol) and N-methylimidazole (NMI, 157.16 µL, 1.97 mmol). The mixture was stirred at 50° C. for 16 h. The reaction was quenched with $H_2O$ (20 mL) and then extracted with EtOAc (3×20 mL). The combined organic layers were dried over $Na_2SO_4$, filtered and concentrated under reduced pressure to give a residue, which was purified by flash silica gel chromatography to give Intermediate 9-1 (420 mg, crude) as a yellow solid. MS: ES m/z calculated for $C_{19}H_{14}BrCl_2N_3O_3Na[M+Na]^+$504.0 found 504.0.

A mixture of crude Intermediate 9-1 (420 mg), Bis (pinacolato)diboron (132 mg, 521 µmol), KOAc (128 mg, 1.30 mmol) and $Pd(dppf)Cl_2$ (31.8 mg, 43.5 µmol) in dioxane (3 mL) was degassed and purged with $N_2$ (3×). The mixture was stirred at 100° C. for 16 h under $N_2$ atmosphere, filtered and concentrated under reduced pressure to give a residue, which was purified by flash silica gel chromatography (ISCO®; 4 g SepaFlash® Silica Flash Column, 0-50% EtOAc:PE) to give Intermediate 10-1 (330 mg) as a yellow solid. MS: ES m/z calculated for $C_{25}H_{27}BCl_2N_3O_5[M+H]^+$ 530.1 found 530.1.

Example A8a

Preparation Intermediate 9-2

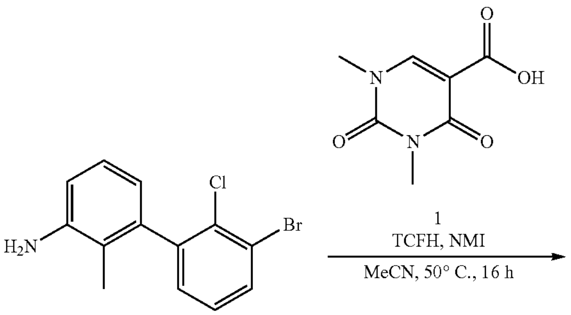

8-2

-continued

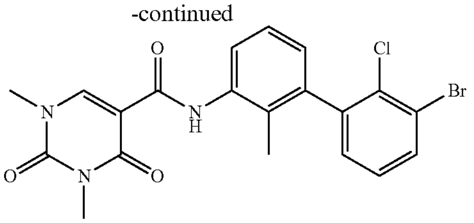

9-2

To a solution of Intermediate 8-2 (850 mg, 2.87 mmol) and 1,3-dimethyl-2,4-dioxopyrimidine-5-carboxylic acid (580 mg, 3.15 mmol) in MeCN (8 mL) were added N,N,N',N'-tetramethylchloroformamidinium hexafluorophosphate (TCFH) (1.61 g, 5.73 mmol) and N-methylimidazole (NMI) (571 μL 7.16 mmol). The reaction mixture was stirred at 50° C. for 16 hours. The reaction mixture was filtered, and the crude product was triturated with EtOAc (30 mL) at 25° C. for 10 min. The solid residue was filtered and dried to give Intermediate 9-2 (1 g) as a white solid.

The intermediates shown in Table A-4 were prepared by an analogous reaction protocol as was used for the preparation of Intermediate 9-2 using the appropriate starting materials.

TABLE A-4

| Intermediate No. | Structure | Starting Materials |
|---|---|---|
| 9-3 | 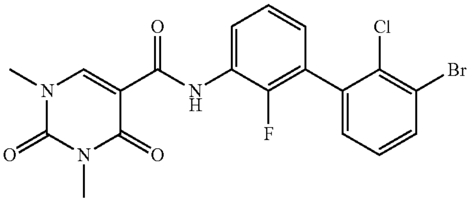 [SMILES: Cn1cc(C(=O)Nc2cccc(-c3cccc(Br)c3Cl)c2F)c(=O)n(C)c1=O] | 1,3-dimethyl-2,4-dioxopyrimidine-5-carboxylic acid Intermediate 8-3 |
| 9-4 | 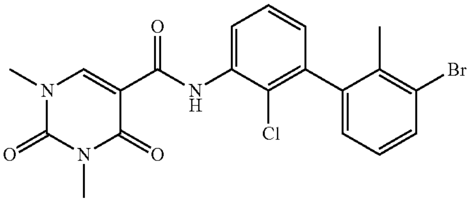 | 1,3-dimethyl-2,4-dioxopyrimidine-5-carboxylic acid Intermediate 8-4 |
| 9-5 | 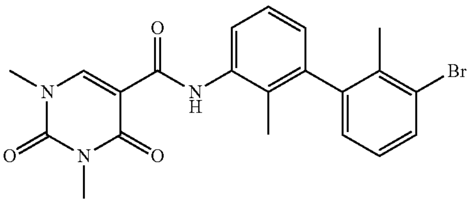 [SMILES: Cc1c(Br)cccc1-c1cccc(NC(=O)c2cn(C)c(=O)n(C)c2=O)c1C] | 1,3-dimethyl-2,4-dioxopyrimidine-5-carboxylic acid Intermediate 8-5 |
| 9-6 | 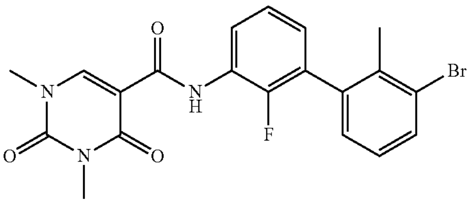 [SMILES: Cc1c(Br)cccc1-c1cccc(NC(=O)c2cn(C)c(=O)n(C)c2=O)c1F] | 1,3-dimethyl-2,4-dioxopyrimidine-5-carboxylic acid Intermediate 8-6 |

TABLE A-4-continued

| Intermediate No. | Structure | Starting Materials |
| --- | --- | --- |
| 9-7 | 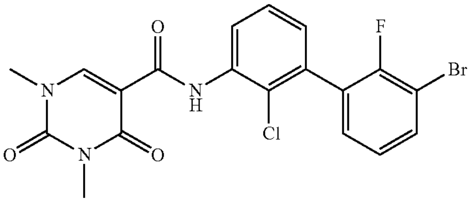 [SMILES: Cn1cc(C(=O)Nc2cccc(-c3cccc(Br)c3F)c2Cl)c(=O)n(C)c1=O] | 1,3-dimethyl-2,4-dioxopyrimidine-5-carboxylic acid<br>Intermediate 8-7 |
| 9-8 | 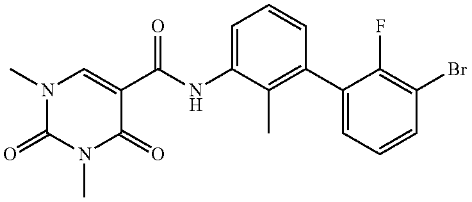 [SMILES: Cc1c(NC(=O)c2cn(C)c(=O)n(C)c2=O)cccc1-c1cccc(Br)c1F] | 1,3-dimethyl-2,4-dioxopyrimidine-5-carboxylic acid<br>Intermediate 8-8 |
| 9-9 | 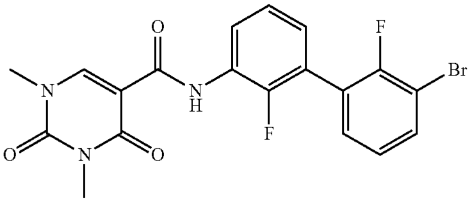 [SMILES: Cn1cc(C(=O)Nc2cccc(-c3cccc(Br)c3F)c2F)c(=O)n(C)c1=O] | 1,3-dimethyl-2,4-dioxopyrimidine-5-carboxylic acid<br>Intermediate 8-9 |
| 9-10 | 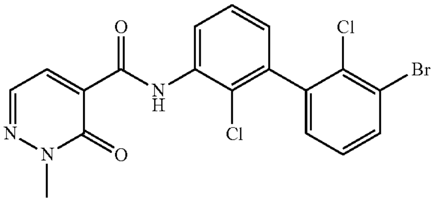 [SMILES: Cn1nccc(C(=O)Nc2cccc(-c3cccc(Br)c3Cl)c2Cl)c1=O] | 2-Methyl-3-oxo-2,3-dihydropyridazine-4-carboxylic acid<br>Intermediate 8-1 |
| 9-11 | 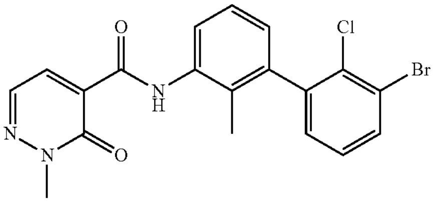 [SMILES: Cc1c(NC(=O)c2ccnn(C)c2=O)cccc1-c1cccc(Br)c1Cl] | 2-Methyl-3-oxo-2,3-dihydropyridazine-4-carboxylic acid<br>Intermediate 8-2 |
| 9-12 | 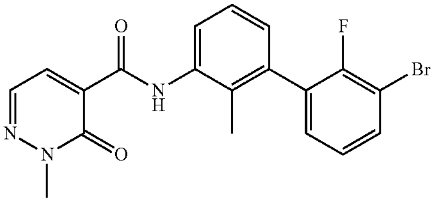 [SMILES: Cc1c(NC(=O)c2ccnn(C)c2=O)cccc1-c1cccc(Br)c1F] | 2-Methyl-3-oxo-2,3-dihydropyridazine-4-carboxylic acid<br>Intermediate 8-8 |
| 9-13 | 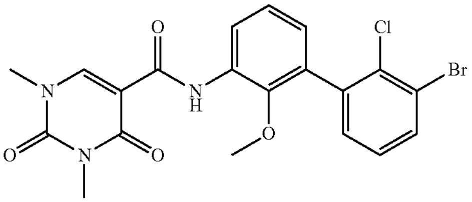 | 1,3-dimethyl-2,4-dioxopyrimidine-5-carboxylic acid<br>Intermediate 8-10 |

TABLE A-4-continued

| Intermediate No. | Structure | Starting Materials |
| --- | --- | --- |
| 9-14 | 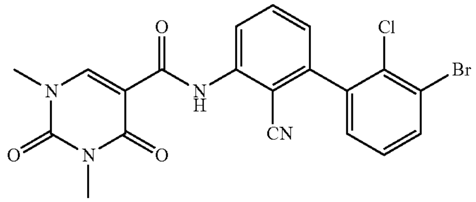 [SMILES: Cn1cc(C(=O)Nc2cccc(-c3cccc(Br)c3Cl)c2C#N)c(=O)n(C)c1=O] | 1,3-dimethyl-2,4-dioxopyrimidine-5-carboxylic acid Intermediate 8-11 |
| 9-15 | 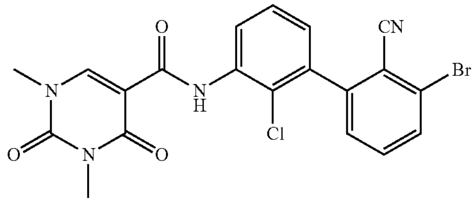 | 1,3-dimethyl-2,4-dioxopyrimidine-5-carboxylic acid Intermediate 8-12 |
| 9-17 | 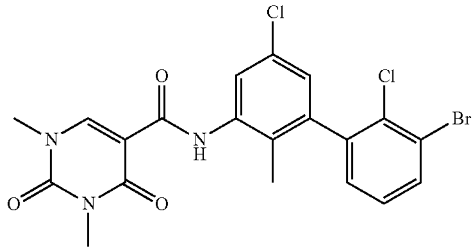 | 1,3-dimethyl-2,4-dioxopyrimidine-5-carboxylic acid Intermediate 8-14 |
| 9-18 | 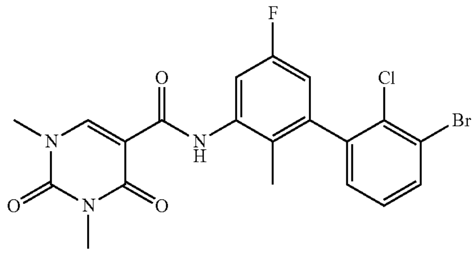 [SMILES: Cc1c(NC(=O)c2cn(C)c(=O)n(C)c2=O)cc(F)cc1-c1cccc(Br)c1Cl] | 1,3-dimethyl-2,4-dioxopyrimidine-5-carboxylic acid Intermediate 8-15 |
| 9-19 | 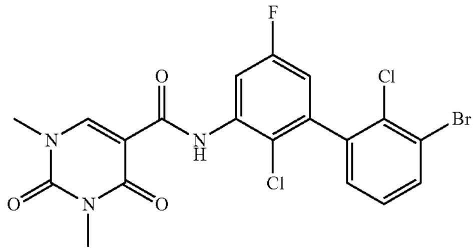 [SMILES: Cn1cc(C(=O)Nc2cc(F)cc(-c3cccc(Br)c3Cl)c2Cl)c(=O)n(C)c1=O] | 1,3-dimethyl-2,4-dioxopyrimidine-5-carboxylic acid Intermediate 8-16 |
| 9-21 | 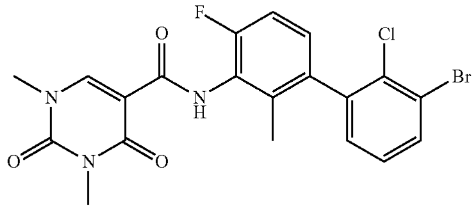 [SMILES: Cc1c(-c2cccc(Br)c2Cl)ccc(F)c1NC(=O)c1cn(C)c(=O)n(C)c1=O] | 1,3-dimethyl-2,4-dioxopyrimidine-5-carboxylic acid Intermediate 8-18 |

TABLE A-4-continued

| Intermediate No. | Structure | Starting Materials |
|---|---|---|
| 9-23 | 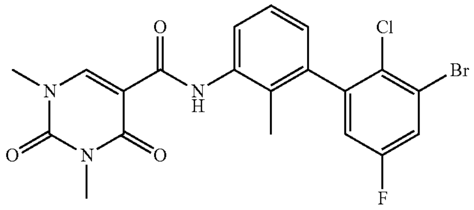 [SMILES: Cc1c(NC(=O)c2cn(C)c(=O)n(C)c2=O)cccc1-c1cc(F)cc(Br)c1Cl] | 1,3-dimethyl-2,4-dioxopyrimidine-5-carboxylic acid Intermediate 8-20 |
| 9-24 | 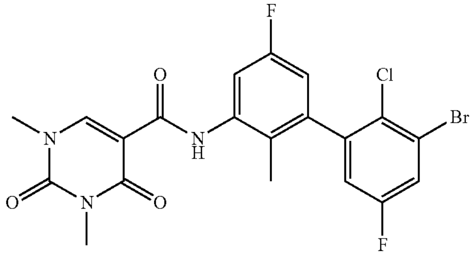 [SMILES: Cc1c(NC(=O)c2cn(C)c(=O)n(C)c2=O)cc(F)cc1-c1cc(F)cc(Br)c1Cl] | 1,3-dimethyl-2,4-dioxopyrimidine-5-carboxylic acid Intermediate 8-21 |
| 9-25 | 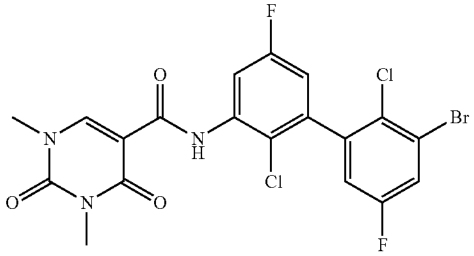 [SMILES: Cn1cc(C(=O)Nc2cc(F)cc(-c3cc(F)cc(Br)c3Cl)c2Cl)c(=O)n(C)c1=O] | 1,3-dimethyl-2,4-dioxopyrimidine-5-carboxylic acid Intermediate 8-22 |
| 9-26 | 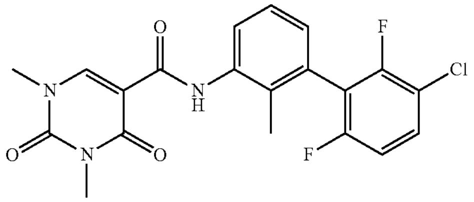 [SMILES: Cc1c(NC(=O)c2cn(C)c(=O)n(C)c2=O)cccc1-c1c(F)ccc(Cl)c1F] | 1,3-dimethyl-2,4-dioxopyrimidine-5-carboxylic acid Intermediate 8-23 |
| 9-27 | 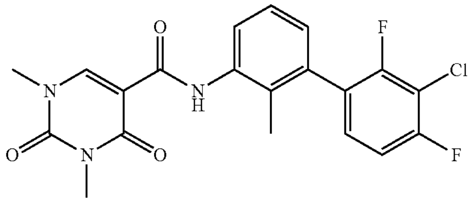 [SMILES: Cc1c(NC(=O)c2cn(C)c(=O)n(C)c2=O)cccc1-c1ccc(F)c(Cl)c1F] | 1,3-dimethyl-2,4-dioxopyrimidine-5-carboxylic acid Intermediate 8-24 |
| 9-28a | 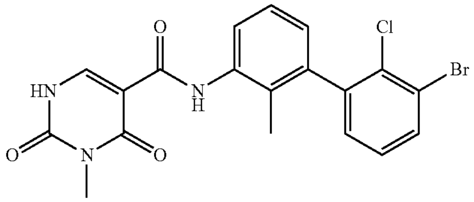 [SMILES: Cc1c(NC(=O)c2c[nH]c(=O)n(C)c2=O)cccc1-c1cccc(Br)c1Cl] | 1,2,3,6-Tetrahydro-l-methyl-2,6-dioxo-5-pyrimidinecarboxylic acid Intermediate 8-2 |
| 9-28b | 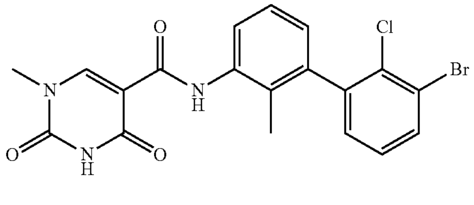 [SMILES: Cc1c(NC(=O)c2cn(C)c(=O)[nH]c2=O)cccc1-c1cccc(Br)c1Cl] | 1,2,3,4-Tetrahydro-1-methyl-2,4-dioxo-5-pyrimidinecarboxylic acid Intermediate 8-2 |

TABLE A-4-continued

| Intermediate No. | Structure | Starting Materials |
|---|---|---|
| 9-29 | 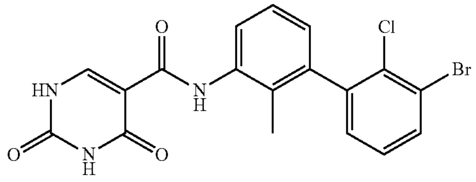 [SMILES: Cc1c(NC(=O)c2c[nH]c(=O)[nH]c2=O)cccc1-c1cccc(Br)c1Cl] | 1,2,3,4-Tetrahydro-2,4-dioxo-5-pyrimidinecarboxylic acid<br>Intermediate 8-2 |
| 9-30 | 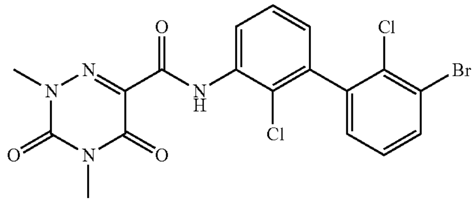 | 2,3,4,5-Tetrahydro-2,4-dimethyl-3,5-dioxo-1,2,4-triazine-6-carboxylic acid<br>Intermediate 8-1 |
| 9-31 | 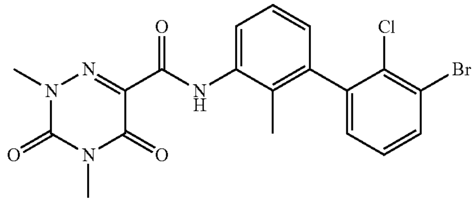 | 2,3,4,5-Tetrahydro-2,4-dimethyl-3,5-dioxo-1,2,4-triazine-6-carboxylic acid<br>Intermediate 8-2 |
| 9-32 | 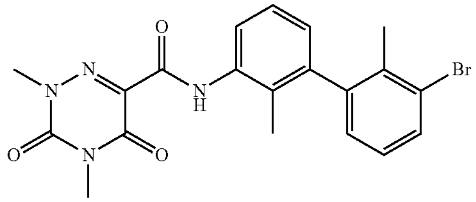 [SMILES: Cc1c(Br)cccc1-c1cccc(NC(=O)c2nn(C)c(=O)n(C)c2=O)c1C] | 2,3,4,5-Tetrahydro-2,4-dimethyl-3,5-dioxo-1,2,4-triazine-6-carboxylic acid<br>Intermediate 8-5 |
| 9-33 | 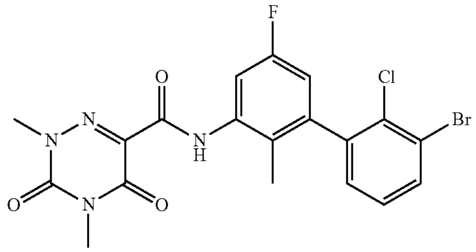 | 2,3,4,5-Tetrahydro-2,4-dimethyl-3,5-dioxo-1,2,4-triazine-6-carboxylic acid<br>Intermediate 8-15 |
| 9-33a | 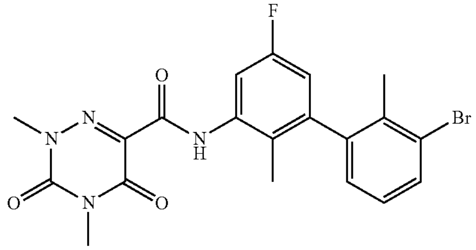 [SMILES: Cc1c(Br)cccc1-c1cc(F)cc(NC(=O)c2nn(C)c(=O)n(C)c2=O)c1C] | 2,3,4,5-Tetrahydro-2,4-dimethyl-3,5-dioxo-1,2,4-triazine-6-carboxylic acid<br>Intermediate 8-15a |
| 9-34 | 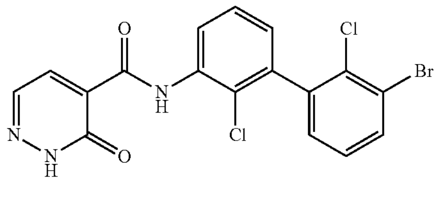 | 3-hydroxy-4-pyridazinecarboxylic acid<br>Intermediate 8-1 |

TABLE A-4-continued

| Intermediate No. | Structure | Starting Materials |
|---|---|---|
| 9-35 | 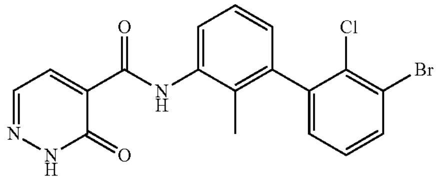 [SMILES: O=C(Nc1cccc(-c2cccc(Br)c2Cl)c1Cl)c1ccn[nH]c1=O] | 3-hydroxy-4-pyridazinecarboxylic acid<br>Intermediate 8-2 |
| 9-36 | 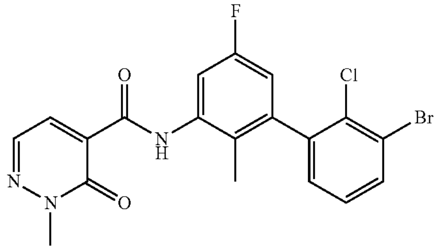 [SMILES: Cc1c(NC(=O)c2ccnn(C)c2=O)cc(F)cc1-c1cccc(Br)c1Cl] | 2-Methyl-3-oxo-2,3-dihydropyridazine-4-carboxylic acid<br>Intermediate 8-15 |

Example A8b

Preparation Intermediate 10-2

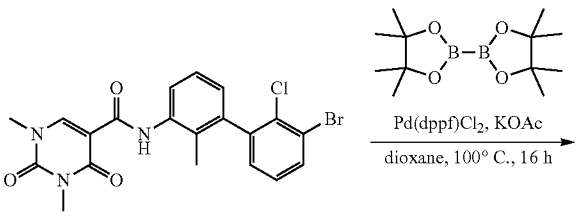

Intermediate 9-2

-continued

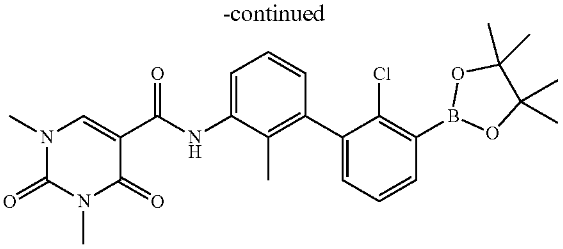

Intermediate 10-2

A mixture of Intermediate 9-2 (1.0 g), Bis(pinacolato) diboron (823 mg, 3.24 mmol), KOAc (636 mg, 6.48 mmol) and Pd(dppf)$Cl_2$ (158 mg, 216 μmol) in dioxane (10 mL) was degassed and purged with $N_2$ (3×). The mixture was stirred at 100° C. for 16 h under $N_2$ atmosphere. The mixture was filtered and concentrated under reduced pressure to give a residue, which was purified by flash silica gel column to give Intermediate 10-2 (780 mg) as a white solid. MS: ES m/z calculated for $C_{26}H_{30}BClN_3O_5[M+H]^+$ 510.2 found 510.0.

The intermediates shown in Table A-5 were prepared by an analogous reaction protocol as was used for the preparation of Intermediate 10-2 using the appropriate starting materials.

TABLE A-5

| Intermediate No. | Structure | Starting Materials |
|---|---|---|
| 10-3 | 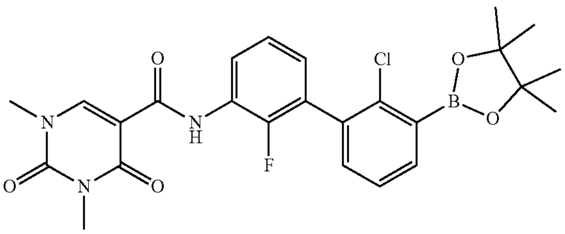 [SMILES: Cn1cc(C(=O)Nc2cccc(-c3cccc(B4OC(C)(C)C(C)(C)O4)c3Cl)c2F)c(=O)n(C)c1=O] | Bis(pinacolato)diboron<br>Intermediate 9-3 |

TABLE A-5-continued
| Intermediate No. | Structure | Starting Materials |
|---|---|---|
| 10-4 | 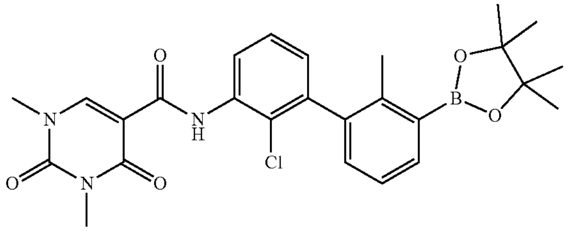 [SMILES: Cc1c(B2OC(C)(C)C(C)(C)O2)cccc1-c1cccc(NC(=O)c2cn(C)c(=O)n(C)c2=O)c1Cl] | Bis(pinacolato)diboron<br>Intermediate 9-4 |
| 10-5 | 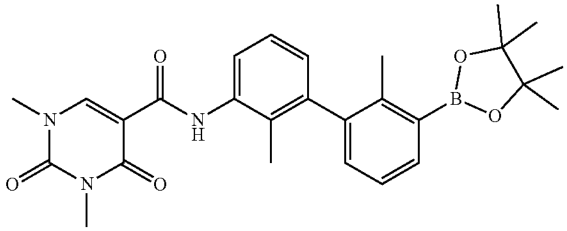 [SMILES: Cc1c(NC(=O)c2cn(C)c(=O)n(C)c2=O)cccc1-c1cccc(B2OC(C)(C)C(C)(C)O2)c1C] | Bis(pinacolato)diboron<br>Intermediate 9-5 |
| 10-6 | 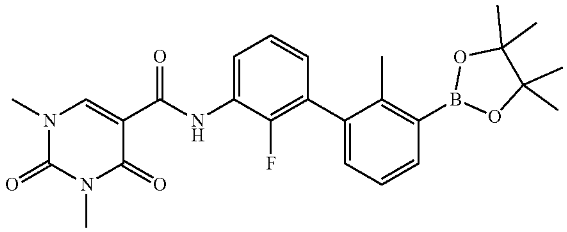 [SMILES: Cc1c(B2OC(C)(C)C(C)(C)O2)cccc1-c1cccc(NC(=O)c2cn(C)c(=O)n(C)c2=O)c1F] | Bis(pinacolato)diboron<br>Intermediate 9-6 |
| 10-7 | 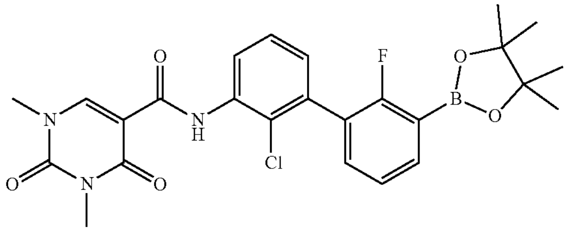 [SMILES: Cn1cc(C(=O)Nc2cccc(-c3cccc(B4OC(C)(C)C(C)(C)O4)c3F)c2Cl)c(=O)n(C)c1=O] | Bis(pinacolato)diboron<br>Intermediate 9-7 |
| 10-8 | 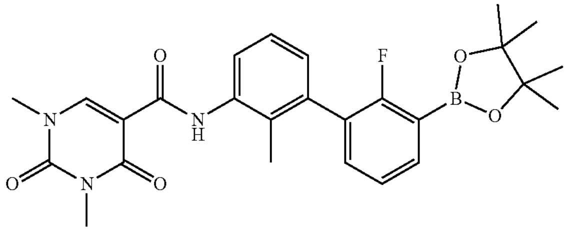 [SMILES: Cc1c(NC(=O)c2cn(C)c(=O)n(C)c2=O)cccc1-c1cccc(B2OC(C)(C)C(C)(C)O2)c1F] | Bis(pinacolato)diboron<br>Intermediate 9-8 |
| 10-9 | 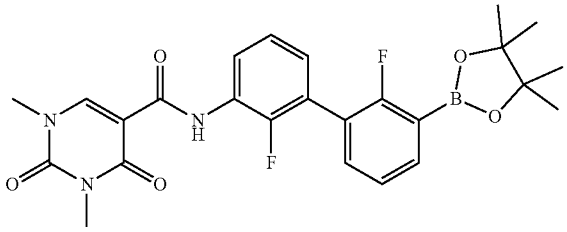 [SMILES: Cn1cc(C(=O)Nc2cccc(-c3cccc(B4OC(C)(C)C(C)(C)O4)c3F)c2F)c(=O)n(C)c1=O] | Bis(pinacolato)diboron<br>Intermediate 9-9 |

TABLE A-5-continued
| Intermediate No. | Structure | Starting Materials |
|---|---|---|
| 10-10 | 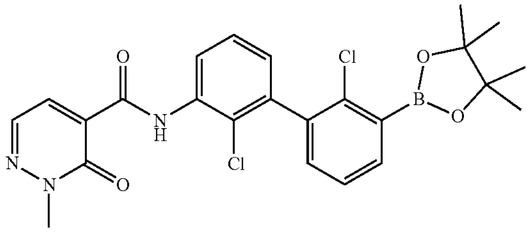 [SMILES: Cn1nccc(C(=O)Nc2cccc(-c3cccc(B4OC(C)(C)C(C)(C)O4)c3Cl)c2Cl)c1=O] | Bis(pinacolato)diboron Intermediate 9-10 |
| 10-11 | 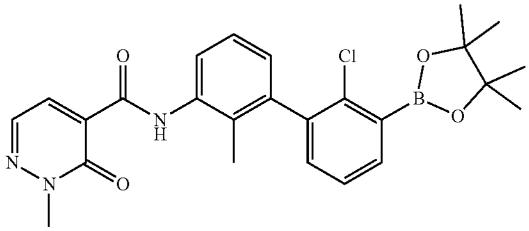 [SMILES: Cc1c(NC(=O)c2ccnn(C)c2=O)cccc1-c1cccc(B2OC(C)(C)C(C)(C)O2)c1Cl] | Bis(pinacolato)diboron Intermediate 9-11 |
| 10-12 | 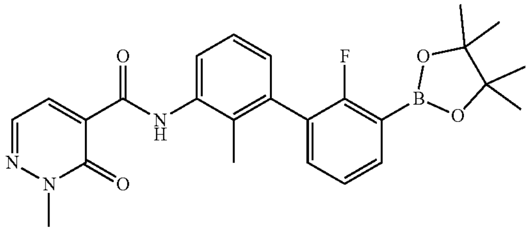 [SMILES: Cc1c(NC(=O)c2ccnn(C)c2=O)cccc1-c1cccc(B2OC(C)(C)C(C)(C)O2)c1F] | Bis(pinacolato)diboron Intermediate 9-12 |
| 10-13 | 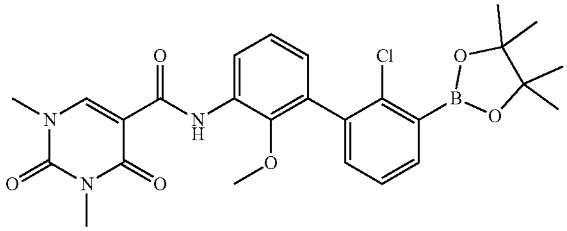 [SMILES: COc1c(NC(=O)c2cn(C)c(=O)n(C)c2=O)cccc1-c1cccc(B2OC(C)(C)C(C)(C)O2)c1Cl] | Bis(pinacolato)diboron Intermediate 9-13 |
| 10-14 | 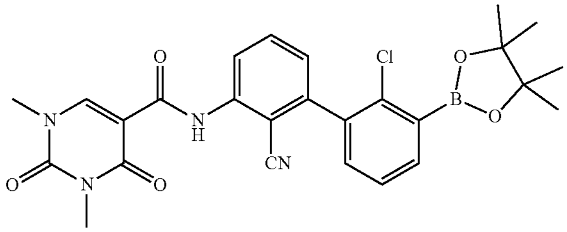 [SMILES: Cn1cc(C(=O)Nc2cccc(-c3cccc(B4OC(C)(C)C(C)(C)O4)c3Cl)c2C#N)c(=O)n(C)c1=O] | Bis(pinacolato)diboron Intermediate 9-14 |
| 10-15 | 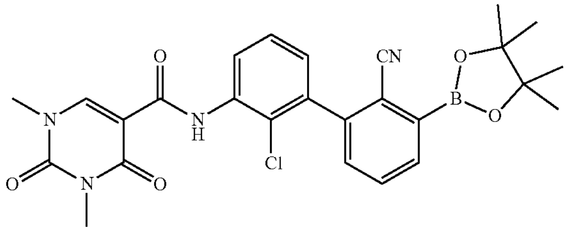 [SMILES: Cn1cc(C(=O)Nc2cccc(-c3cccc(B4OC(C)(C)C(C)(C)O4)c3C#N)c2Cl)c(=O)n(C)c1=O] | Bis(pinacolato)diboron Intermediate 9-15 |

TABLE A-5-continued
| Intermediate No. | Structure | Starting Materials |
| --- | --- | --- |
| 10-17 | 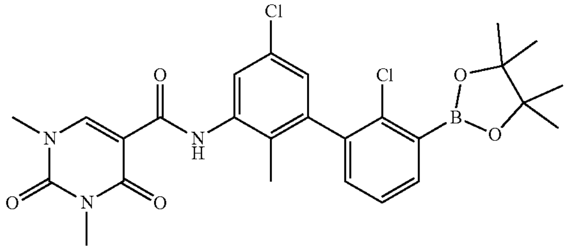 | Bis(pinacolato)diboron Intermediate 9-17 |
| 10-18 | 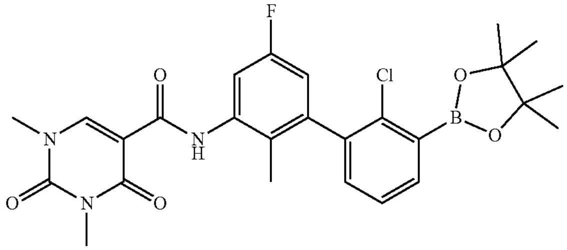 [SMILES: Cc1c(NC(=O)c2cn(C)c(=O)n(C)c2=O)cc(F)cc1-c1cccc(B2OC(C)(C)C(C)(C)O2)c1Cl] | Bis(pinacolato)diboron Intermediate 9-18 |
| 10-19 | 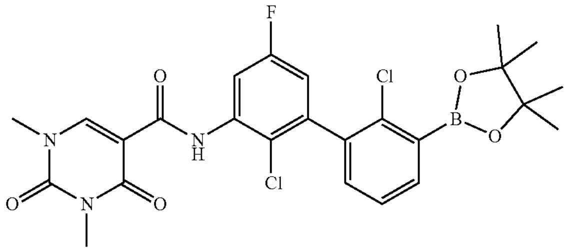 [SMILES: Cn1cc(C(=O)Nc2cc(F)cc(-c3cccc(B4OC(C)(C)C(C)(C)O4)c3Cl)c2Cl)c(=O)n(C)c1=O] | Bis(pinacolato)diboron Intermediate 9-19 |
| 10-21 | 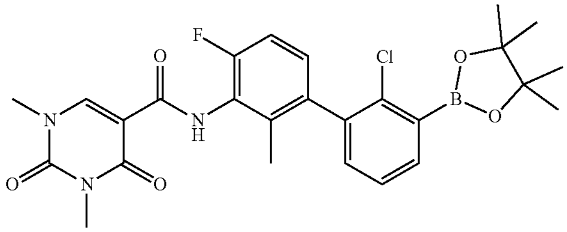 [SMILES: Cc1c(-c2cccc(B3OC(C)(C)C(C)(C)O3)c2Cl)ccc(F)c1NC(=O)c1cn(C)c(=O)n(C)c1=O] | Bis(pinacolato)diboron Intermediate 9-21 |
| 10-23 | 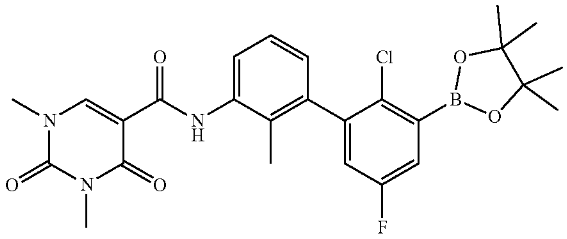 [SMILES: Cc1c(NC(=O)c2cn(C)c(=O)n(C)c2=O)cccc1-c1cc(F)cc(B2OC(C)(C)C(C)(C)O2)c1Cl] | Bis(pinacolato)diboron Intermediate 9-23 |
| 10-24 | 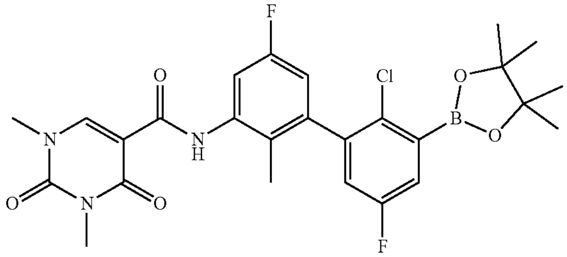 [SMILES: Cc1c(NC(=O)c2cn(C)c(=O)n(C)c2=O)cc(F)cc1-c1cc(F)cc(B2OC(C)(C)C(C)(C)O2)c1Cl] | Bis(pinacolato)diboron Intermediate 9-24 |

TABLE A-5-continued
| Intermediate No. | Structure | Starting Materials |
|---|---|---|
| 10-25 | 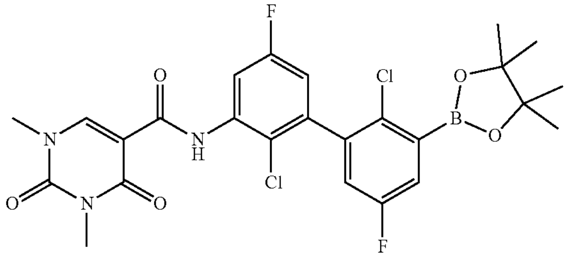 [SMILES: Cn1cc(C(=O)Nc2cc(F)cc(-c3cc(F)cc(B4OC(C)(C)C(C)(C)O4)c3Cl)c2Cl)c(=O)n(C)c1=O] | Bis(pinacolato)diboron Intermediate 9-25 |
| 10-26 | 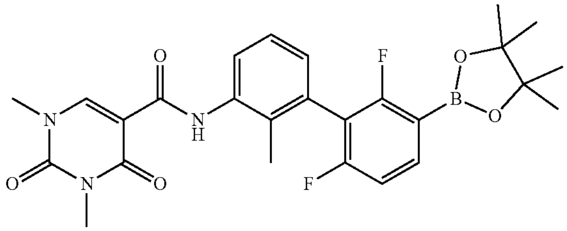 [SMILES: Cc1c(NC(=O)c2cn(C)c(=O)n(C)c2=O)cccc1-c1c(F)ccc(B2OC(C)(C)C(C)(C)O2)c1F] | Bis(pinacolato)diboron Intermediate 9-26 |
| 10-27 | 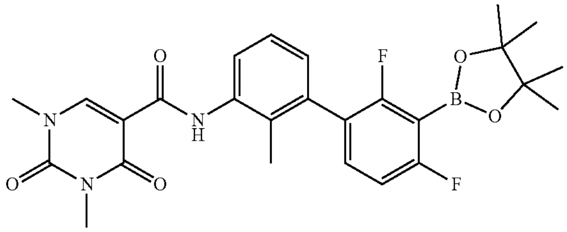 [SMILES: Cc1c(NC(=O)c2cn(C)c(=O)n(C)c2=O)cccc1-c1ccc(F)c(B2OC(C)(C)C(C)(C)O2)c1F] | Bis(pinacolato)diboron Intermediate 9-27 |
| 10-28a | 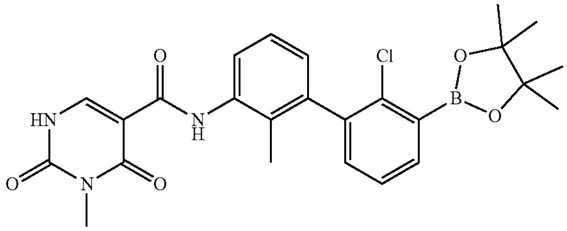 [SMILES: Cc1c(NC(=O)c2c[nH]c(=O)n(C)c2=O)cccc1-c1cccc(B2OC(C)(C)C(C)(C)O2)c1Cl] | Bis(pinacolato)diboron Intermediate 9-28a |
| 10-28b | 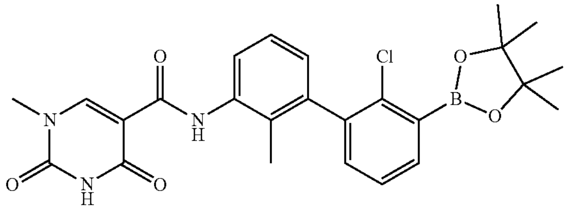 [SMILES: Cc1c(NC(=O)c2cn(C)c(=O)[nH]c2=O)cccc1-c1cccc(B2OC(C)(C)C(C)(C)O2)c1Cl] | Bis(pinacolato)diboron Intermediate 9-28b |
| 10-29 | 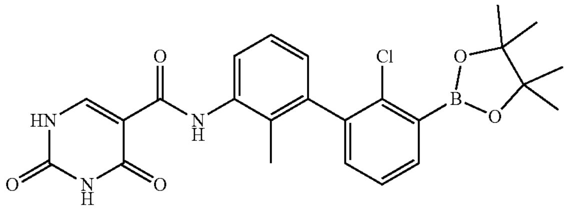 [SMILES: Cc1c(NC(=O)c2c[nH]c(=O)[nH]c2=O)cccc1-c1cccc(B2OC(C)(C)C(C)(C)O2)c1Cl] | Bis(pinacolato)diboron Intermediate 9-29 |

TABLE A-5-continued
| Intermediate No. | Structure | Starting Materials |
| --- | --- | --- |
| 10-30 | 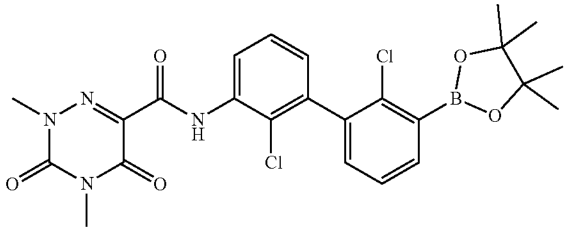 [SMILES: Cn1nc(C(=O)Nc2cccc(-c3cccc(B4OC(C)(C)C(C)(C)O4)c3Cl)c2Cl)c(=O)n(C)c1=O] | Bis(pinacolato)diboron Intermediate 9-30 |
| 10-31 | 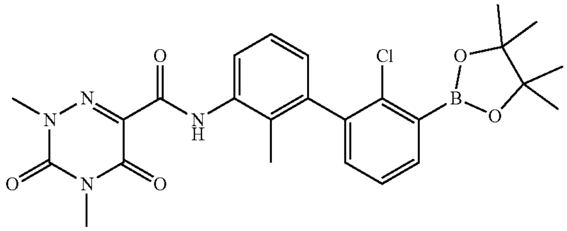 [SMILES: Cc1c(NC(=O)c2nn(C)c(=O)n(C)c2=O)cccc1-c1cccc(B2OC(C)(C)C(C)(C)O2)c1Cl] | Bis(pinacolato)diboron Intermediate 9-31 |
| 10-32 | 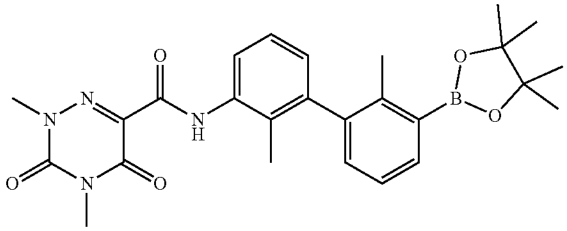 | Bis(pinacolato)diboron Intermediate 9-32 |
| 10-33 | 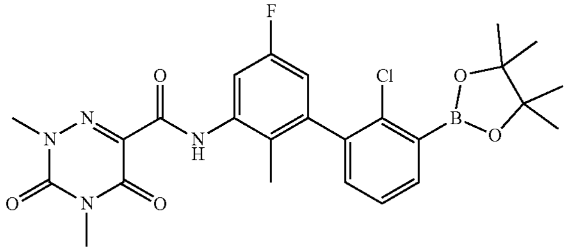 [SMILES: Cc1c(NC(=O)c2nn(C)c(=O)n(C)c2=O)cc(F)cc1-c1cccc(B2OC(C)(C)C(C)(C)O2)c1Cl] | Bis(pinacolato)diboron Intermediate 9-33 |
| 10-34 | 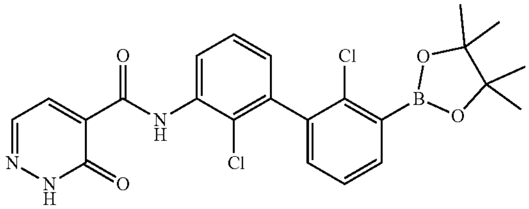 [SMILES: CC1(C)OB(c2cccc(-c3cccc(NC(=O)c4ccn[nH]c4=O)c3Cl)c2Cl)OC1(C)C] | Bis(pinacolato)diboron Intermediate 9-34 |
| 10-35 | 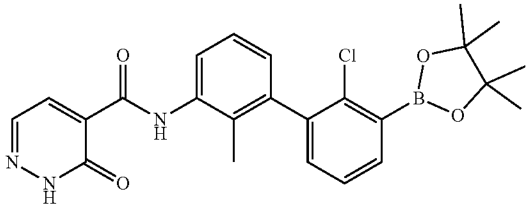 [SMILES: Cc1c(NC(=O)c2ccn[nH]c2=O)cccc1-c1cccc(B2OC(C)(C)C(C)(C)O2)c1Cl] | Bis(pinacolato)diboron Intermediate 9-35 |

TABLE A-5-continued

| Intermediate No. | Structure | Starting Materials |
| --- | --- | --- |
| 10-36 | 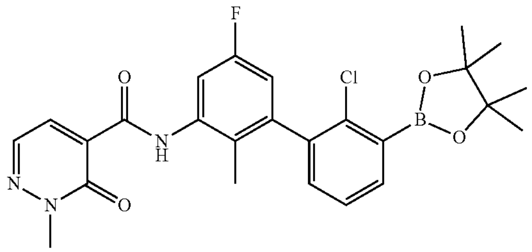 [SMILES: Cc1c(NC(=O)c2ccnn(C)c2=O)cc(F)cc1-c1cccc(B2OC(C)(C)C(C)(C)O2)c1Cl] | Bis(pinacolato)diboron<br>Intermediate 9-36 |

Example A9

Preparation Intermediate 12-1

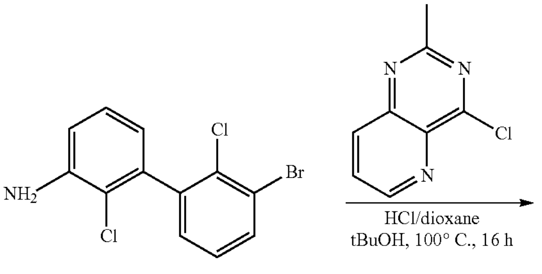

Intermediate 8-1

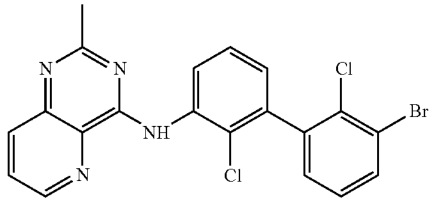

Intermediate 11-1

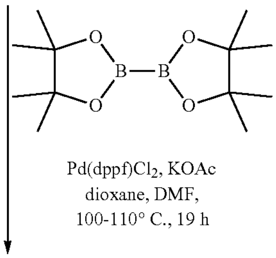

-continued

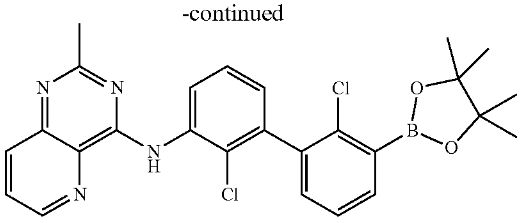

Intermediate 12-1

A mixture of Intermediate 8-1 (200 mg, 631 μmol), 4-chloro-2-methylpyrido[3,2-d]pyrimidine (113 mg, 631 μmol) and HCl/dioxane (4 M, 156 μL) in t-BuOH (3.5 mL) was stirred at 100° C. for 16 h. The mixture was concentrated under reduced pressure to give a residue, which was triturated with EtOAc (20 mL) to give Intermediate 11-1 (211 mg, crude) as an off-white solid. MS: ES m/z calculated for $C_{20}H_{14}BrCl_2N_4[M+H]^+$ 459.0, found 458.9.

A mixture of Intermediate 11-1 (100 mg, 217 μmol), Bis(pinacolato)diboron (166 mg, 652 μmol), KOAc (597 mg, 6.08 mmol) and $Pd(dppf)Cl_2$ (15.9 mg, 21.7 μmol) in dioxane (2.5 mL) was degassed and stirred at 100° C. for 16 h under $N_2$ atmosphere. After adding DMF (1 mL) into the mixture, the resulting mixture was stirred at 110° C. for 3 h under $N_2$ atmosphere. The mixture was partitioned between EtOAc (50 mL) and $H_2O$ (50 mL). The organic layer was separated, washed with brine (50 mL), dried over $Na_2SO_4$, filtered and concentrated under reduced pressure to give a residue, which was purified by flash silica gel chromatography to give Intermediate 12-1 (244 mg, crude) as a brown solid. MS: ES m/z calculated for $C_{26}H_{26}BCl_2N_4O_2[M+H]^+$ 507.1, found 507.1.

The intermediates shown in Table A-6 were prepared by an analogous reaction protocol as was used for the preparation of Intermediate 12-1 using the appropriate starting materials.

TABLE A-6

| Intermediate No. | Structure | Starting Materials |
| --- | --- | --- |
| 12-2 | 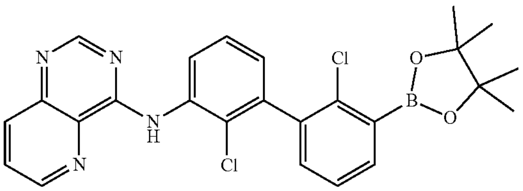 [SMILES: CC1(C)OB(c2cccc(-c3cccc(Nc4ncnc5cccnc45)c3Cl)c2Cl)OC1(C)C] | 4-Chloropyrido[3,2-d]pyrimidine<br>Intermediate 8-1 |

TABLE A-6-continued

| Intermediate No. | Structure | Starting Materials |
| --- | --- | --- |
| 12-3 | 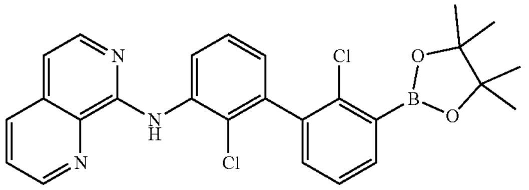 [SMILES: CC1(C)OB(c2cccc(-c3cccc(Nc4nccc5cccnc45)c3Cl)c2Cl)OC1(C)C] | 8-Chloro-1,7-naphthyridine<br>Intermediate 8-1 |
| 12-4 | 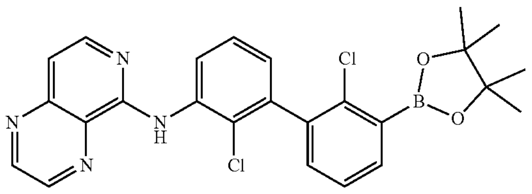 [SMILES: CC1(C)OB(c2cccc(-c3cccc(Nc4nccc5nccnc45)c3Cl)c2Cl)OC1(C)C] | 5-chloropyrido[4,3-b]pyrazine<br>Intermediate 8-1 |

Example A10

Preparation Intermediate 13-1

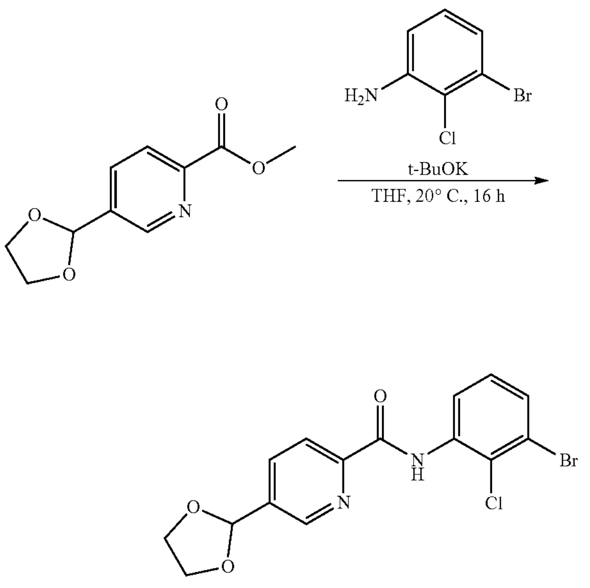

Intermediate 13-1

To a solution of methyl 5-(1,3-dioxolan-2-yl)pyridine-2-carboxylate (800 mg, 3.82 mmol) and 3-Bromo-2-chloroaniline (790 mg, 3.82 mmol) in THF (6 mL) was added t-BuOK (644 mg, 5.74 mmol). The mixture was stirred at 20° C. for 16 h to give a yellow solution. After the mixture's pH was adjusted to be ~7 with aq. $NH_4Cl$, the mixture was diluted with $H_2O$ (20 mL) and extracted with EtOAc (3×20 mL). The combined organic layers were dried over anhydrous $Na_2SO_4$, filtered and concentrated under reduced pressure to give a residue, which was purified by flash silica gel chromatography to give Intermediate 13-1 (950 mg) as a yellow solid. MS: ES m/z calculated for $C_{15}H_{13}BrClN_2O_3$ $[M+H]^+$ 383.0, found 382.9.

Example A11

Preparation of Intermediate 14-1

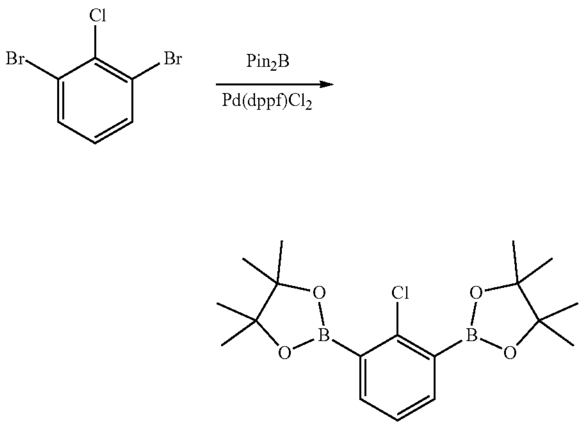

Intermediate 14-1

To a mixture of 1,3-dibromo-2-chloro-benzene (50 g, 185 mmol) and 4,4,5,5-tetramethyl-2-(4,4,5,5-tetramethyl-1,3,2-dioxaborolan-2-yl)-1,3,2-dioxaborolane (93.9 g, 370 mmol) in dioxane (400 mL) were added KOAc (90.76 g, 924.73 mmol, 5 eq.) and $Pd(dppf)Cl_2$ (13.53 g, 18.49 mmol, 0.1 eq.) at 25° C. under $N_2$. The mixture was stirred at 110° C. for 12 h. The mixture was evaporated and diluted with water (500 mL). The mixture was extracted with MTBE (2×500 mL). The combined organic layers were evaporated to give the crude product. The crude product was triturated with MeOH (150 mL) to give Intermediate 14-1 (41.3 g, 61% yield) as white solid. $^1H$ NMR: (400 MHz, $CDCl_3$) δ 7.59 (d, J=7.2 Hz, 2H), 7.13 (t, J=7.2 Hz, 1H), 1.29 (s, 24H).

Example A12

Preparation Intermediate 15-1

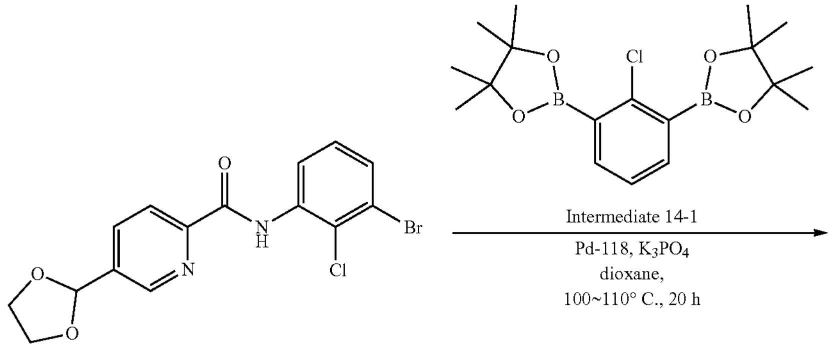

Intermediate 13-1

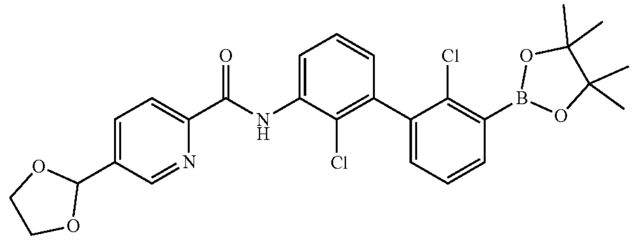

Intermediate 15-1

A mixture of Intermediate 13-1 (950 mg, 2.35 mmol), Intermediate 14-1 (2.57 g, 7.05 mmol) and Pd-118 (153 mg, 235 μmol), $K_3PO_4$ (1.50 g, 7.05 mmol) in dioxane (10 mL) was degassed and purged with $N_2$ (3×). The mixture was stirred at 100° C. for 16 h under $N_2$ atmosphere to give a black mixture. LC-MS showed Intermediate 13-1 was not consumed completely. To the mixture were added additional Intermediate 14-1 (2.57 g, 7.05 mmol), Pd-118 (153 mg, 235 μmol), $K_3PO_4$ (1.50 g, 7.05 mmol) and dioxane (10 mL). The mixture was degassed and purged with $N_2$ (3×), and then the mixture was stirred at 110° C. for 4 h under $N_2$. The reaction was quenched with $H_2O$ (30 mL) and then extracted with EtOAc (3×30 mL). The combined organic layers were dried over $Na_2SO_4$, filtered and concentrated under reduced pressure to give a residue, which was purified by flash silica gel chromatography to give Intermediate 15-1 (550 mg) as a yellow solid. MS: ES m/z calculated for $C_{27}H_{28}BCl_2N_2O_5$ $[M+H]^+$ 541.1, found 541.1.

Example A13

Preparation Intermediate 17-1

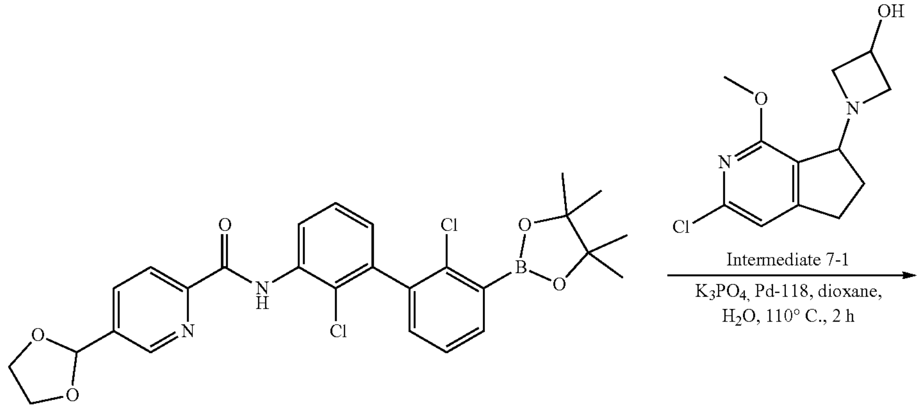

Intermediate 15-1

-continued

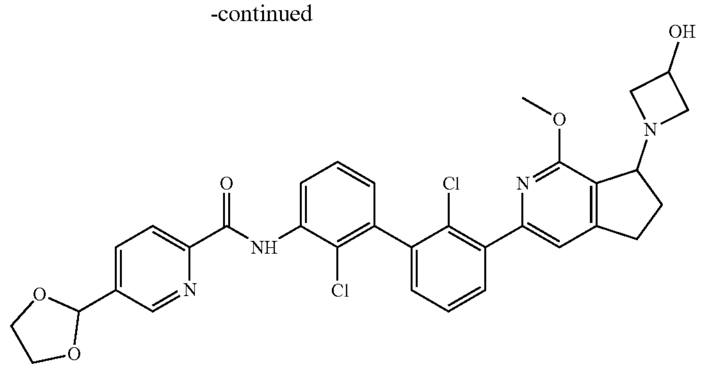

Intermediate 16-1

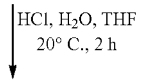

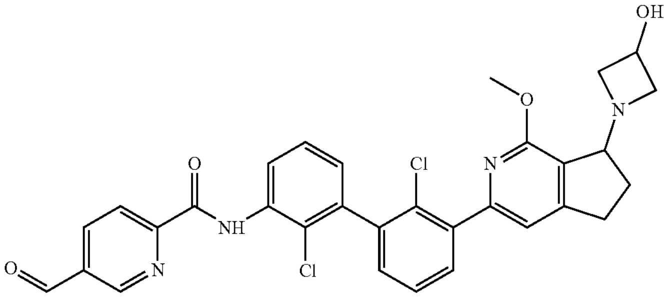

Intermediate 17-1

A mixture of Intermediate 15-1 (127 mg, 236 μmol), Intermediate 7-1 (50 mg, 196 μmol), Pd-118 (12.8 mg, 19.6 μmol) and $K_3PO_4$ (125 mg, 589 μmol) in dioxane (3 mL) and $H_2O$ (0.3 mL) was degassed and purged with $N_2$ (3×). The mixture was stirred at 110° C. for 2 h under $N_2$ atmosphere to give a black mixture. The reaction was quenched with $H_2O$ (30 mL) and then extracted with EtOAc (3×30 mL). The combined organic layers were dried over anhydrous $Na_2SO_4$, filtered and concentrated under reduced pressure to give a residue, which was purified by prep-HPLC to give Intermediate 16-1 (35 mg) as a yellow solid. MS: ES m/z calculated for $C_{33}H_{31}Cl_2N_4O_5[M+H]^+$ 633.2, found 633.1.

A mixture of Intermediate 16-1 (20 mg) in THF (0.7 mL) was added $H_2O$ (0.6 mL) and aq. HCl (12 M, 0.2 mL), and then the mixture was stirred at 20° C. for 2 h to give a yellow solution. The mixture was diluted with THF (30 mL), and then concentrated to give Intermediate 17-1 (15 mg, crude) as a yellow solid. MS: ES m/z calculated for $C_{31}H_{27}Cl_2N_4O_4[M+H]^+$ 589.1, found 589.1.

Example A14

Preparation of Intermediate 18-1

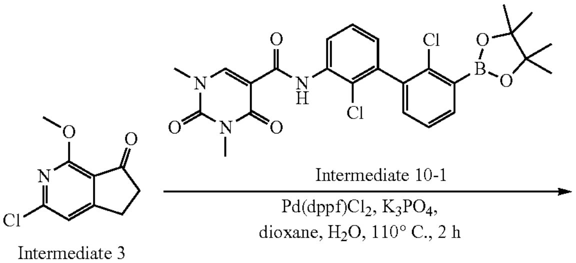

Intermediate 3

-continued

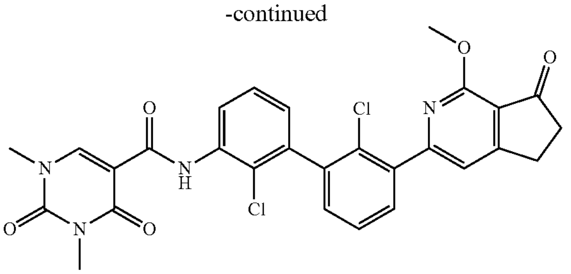

Intermediate 18-1

To the solvent mixture of dioxane (3 mL) and $H_2O$ (0.3 mL) were added Intermediate 10-1 (150 mg, 283 μmol), Intermediate 3 (56 mg, 283 μmol), $K_3PO_4$ (180 mg, 849 μmol) and Pd(dppf)$Cl_2$ (21 mg, 29 μmol). The reaction mixture was degassed and purged with $N_2$ for 3 times. Then the reaction mixture was stirred at 110° C. for 2 hours under $N_2$ atmosphere. The reaction mixture was concentrated under reduced pressure to give a residue, which was purified by prep-HPLC to give Intermediate 18-1 (27 mg) as a white solid. MS: ES m/z calculated for $C_{28}H_{23}Cl_2N_4O_5[M+H]^+$ 565.1, found 565.3; $^1H$ NMR (400 MHz, CHLOROFORM-d) 6=11.50 (s, 1H), 8.58 (d, J=8.3 Hz, 1H), 8.53 (s, 1H), 7.68 (dd, J=1.3, 7.6 Hz, 1H), 7.46 (t, J=7.6 Hz, 1H), 7.42-7.32 (m, 3H), 7.12-7.06 (m, 1H), 4.16 (s, 3H), 3.59 (s, 3H), 3.46 (s, 3H), 3.20-3.12 (m, 2H), 2.79-2.70 (m, 2H).

The intermediate shown in Table A-7 was prepared by an analogous reaction protocol as was used for the preparation of Intermediate 18-1 using the appropriate starting materials.

TABLE A-7

| Intermediate No. | Structure | Starting Materials |
|---|---|---|
| 18-2 | 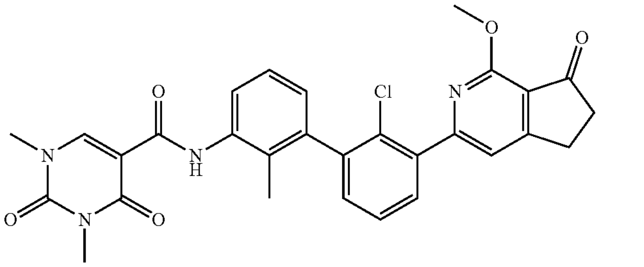 [SMILES: COc1nc(-c2cccc(-c3cccc(NC(=O)c4cn(C)c(=O)n(C)c4=O)c3C)c2Cl)cc2c1C(=O)CC2] | Intermediate 10-2<br>Intermediate 3 |
| 18-3 | 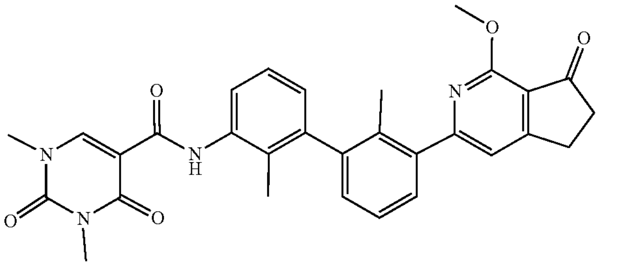 [SMILES: COc1nc(-c2cccc(-c3cccc(NC(=O)c4cn(C)c(=O)n(C)c4=O)c3C)c2C)cc2c1C(=O)CC2] | Intermediate 10-5<br>Intermediate 3 |
| 18-4 | 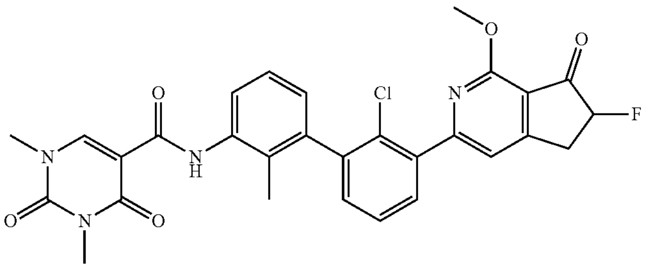 [SMILES: COc1nc(-c2cccc(-c3cccc(NC(=O)c4cn(C)c(=O)n(C)c4=O)c3C)c2Cl)cc2c1C(=O)C(F)C2] | Intermediate 10-2<br>Intermediate 4d |

Preparation of Compounds

Example 1

Preparation of Compound A-1

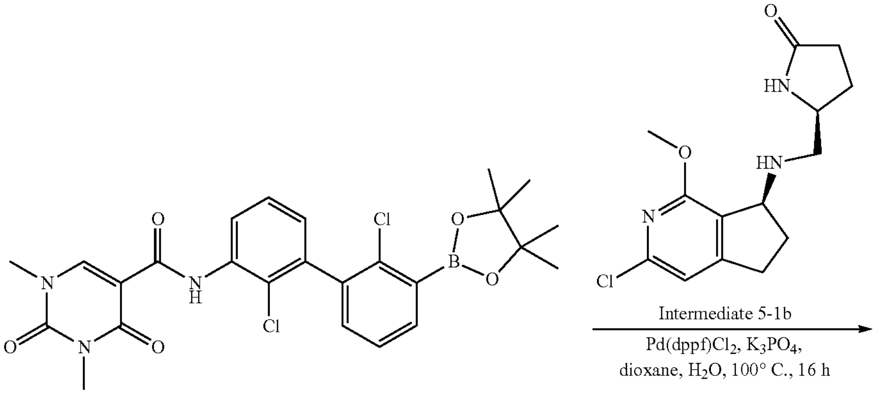

Intermediate 10-1

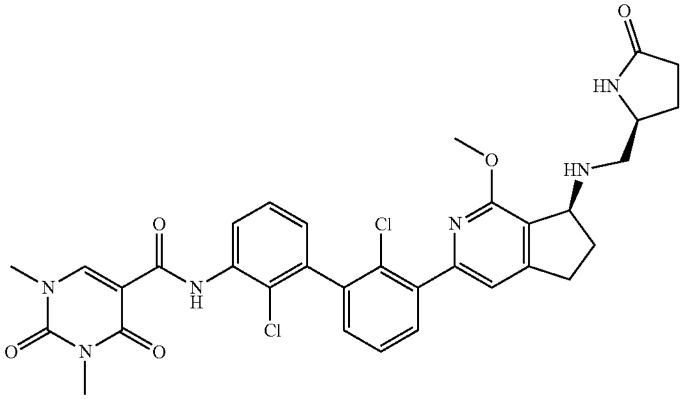

Compound A-1

A mixture of Intermediate 10-1 (60 mg), Intermediate 5-1b (26 mg, 87.1 mol), $K_3PO_4$ (50.4 mg, 238 μmol) and Pd-118 (5.2 mg, 7.9 μmol) in dioxane (2 mL) and $H_2O$ (0.2 mL) was degassed and purged with $N_2$ (3×). The mixture was stirred at 100° C. for 16 h under $N_2$ atmosphere to give a black mixture. The reaction was quenched with $H_2O$ (20 mL) and then extracted with EtOAc (3×20 mL). The combined organic layers were dried over $Na_2SO_4$, filtered and concentrated under reduced pressure to give a residue, which was purified by prep-HPLC to give Compound A-1 (15.7 mg, 98% purity) as a white solid.

Example 1a

Preparation of Compound A-2

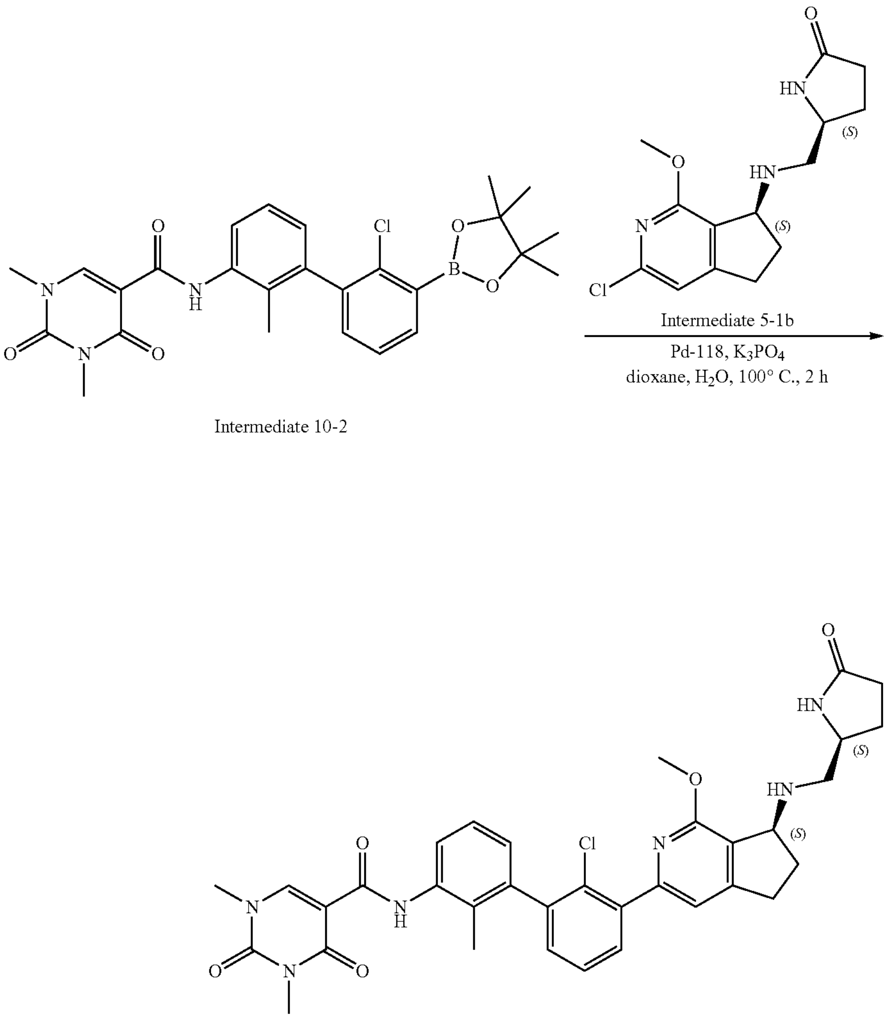

Intermediate 10-2

Compound A-2

A mixture of compound Intermediate 10-2 (240 mg), Intermediate 5-1b (107 mg, 363 μmol), ditert-butyl(cyclopentyl)phosphane; dichloropalladium; iron (Pd-118, 22 mg, 33 μmol) and $K_3PO_4$ (210 mg, 989 μmol) in dioxane (2.5 mL) and $H_2O$ (0.25 mL) was degassed and purged with $N_2$ (3×). The mixture was stirred at 100° C. for 2 h under $N_2$ atmosphere. The mixture was filtered and concentrated under reduced pressure to give a residue, which was purified by prep-HPLC to give Compound A-2 (56 mg) as an off-white solid.

The compounds shown below in Table 1 were prepared by an analogous reaction protocol as was used for the preparation of Compound A-2 using the appropriate starting materials.

TABLE 1
| Cmpd No. | Structure | Starting materials |
| --- | --- | --- |
| A-3 | 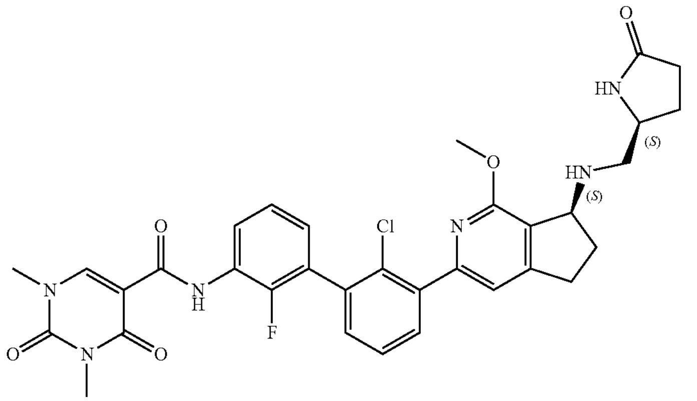 | Intermediate 10-3<br>Intermediate 5-1b |
| A-4 | 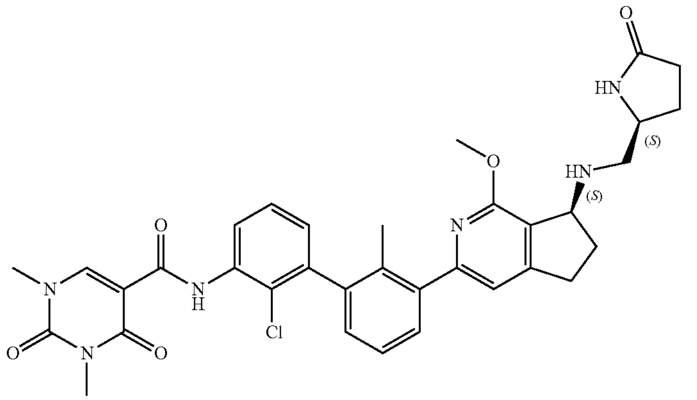 | Intermediate 10-4<br>Intermediate 5-1b |
| A-5 | 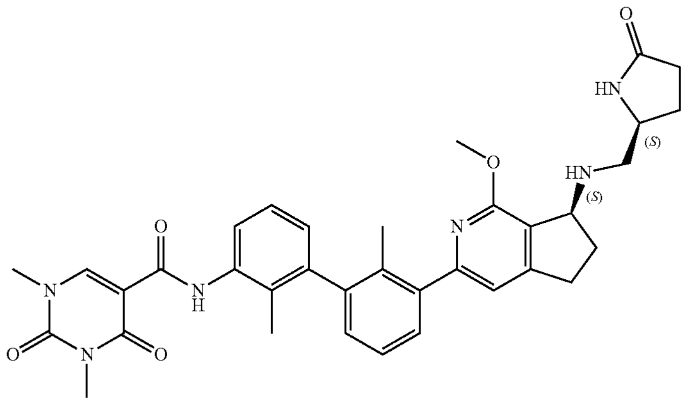 | Intermediate 10-5<br>Intermediate 5-1b |

TABLE 1-continued
| Cmpd No. | Structure | Starting materials |
|---|---|---|
| A-6 | 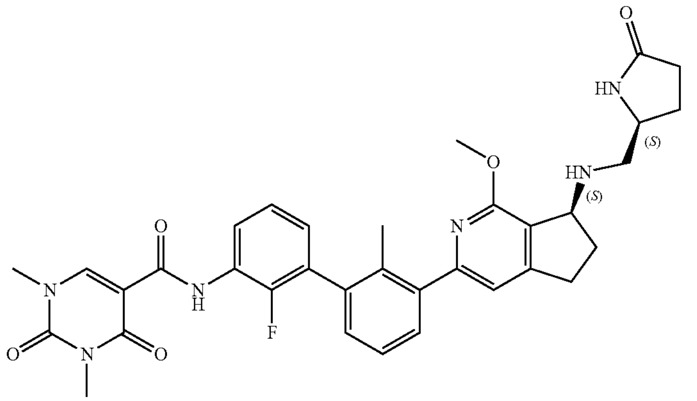 | Intermediate 10-6<br>Intermediate 5-1b |
| A-7 | 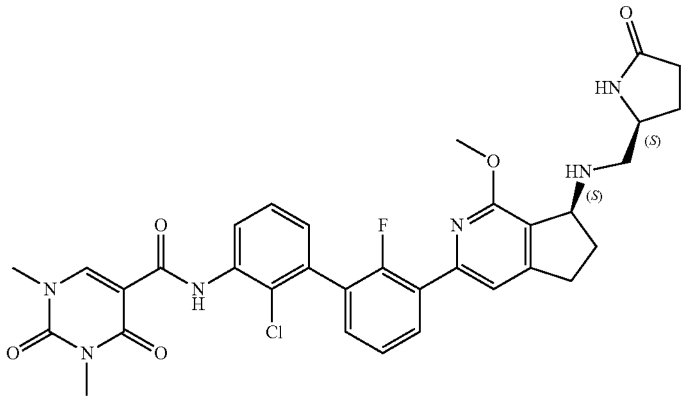 | Intermediate 10-7<br>Intermediate 5-1b |
| A-8 | 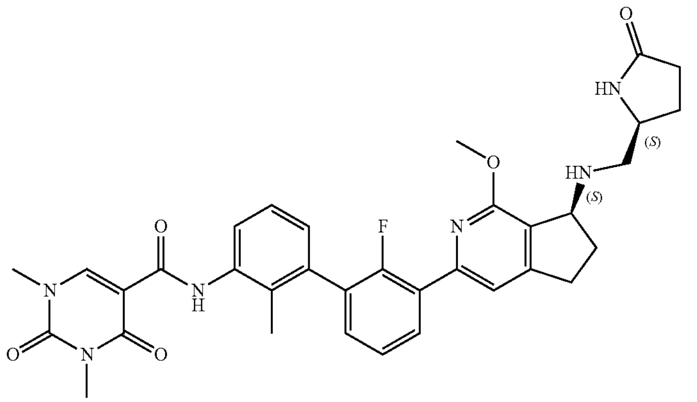 | Intermediate 10-8<br>Intermediate 5-1b |

TABLE 1-continued
| Cmpd No. | Structure | Starting materials |
|---|---|---|
| A-9 | 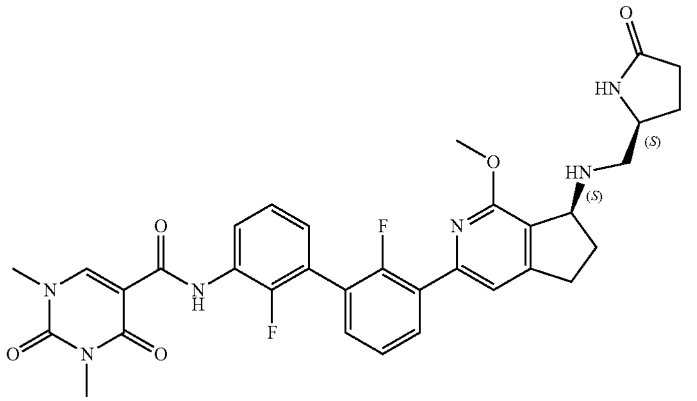 | Intermediate 10-9<br>Intermediate 5-1b |
| A-10 | 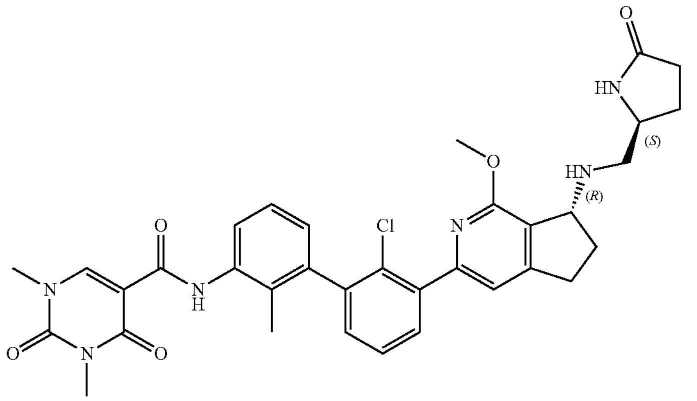 | Intermediate 10-2<br>Intermediate 5-1a |
| A-11 | 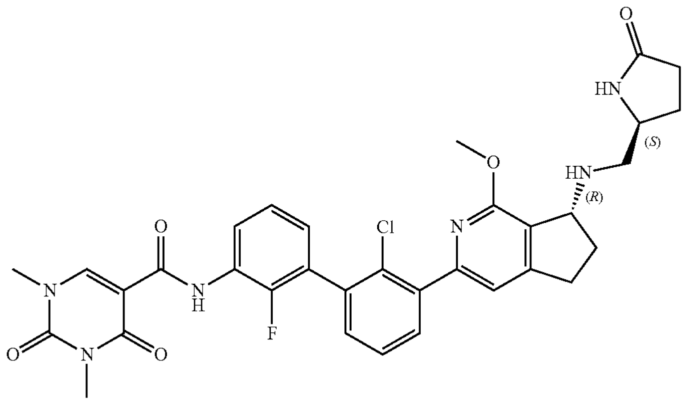 | Intermediate 10-3<br>Intermediate 5-1a |

TABLE 1-continued
| Cmpd No. | Structure | Starting materials |
|---|---|---|
| A-12 | 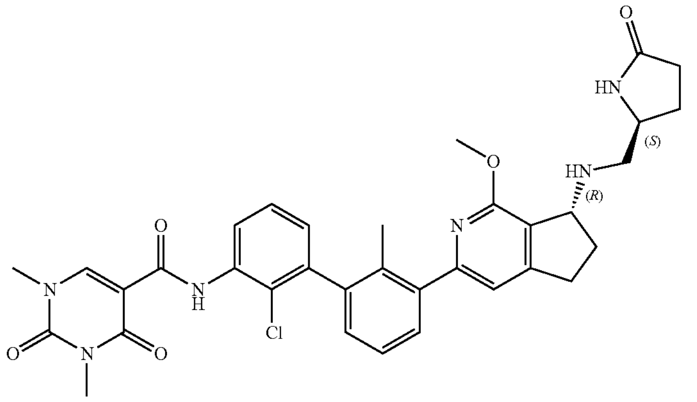 | Intermediate 10-4<br>Intermediate 5-1a |
| A-13 | 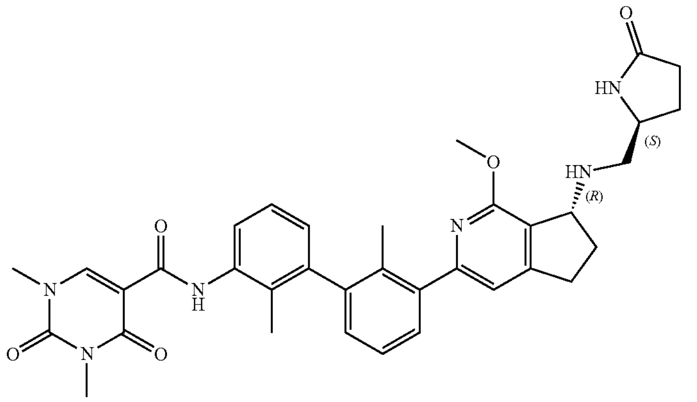 | Intermediate 10-5<br>Intermediate 5-1a |
| A-14 | 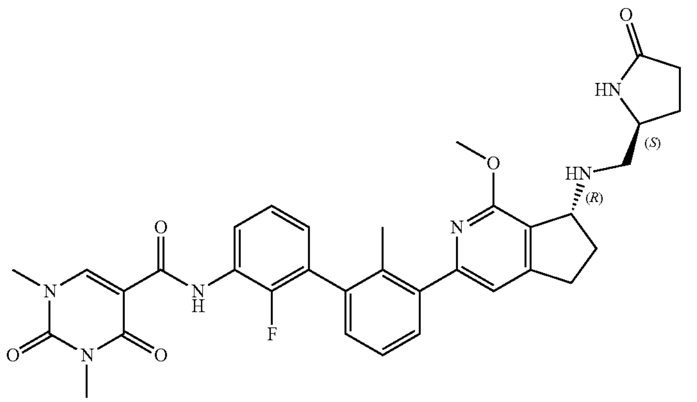 | Intermediate 10-6<br>Intermediate 5-1a |

TABLE 1-continued
| Cmpd No. | Structure | Starting materials |
|---|---|---|
| A-15 | 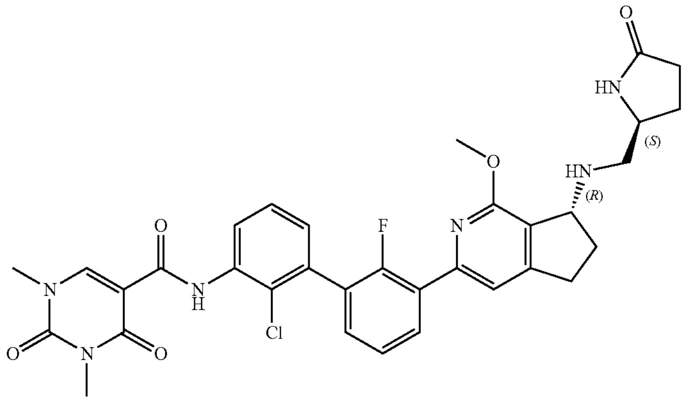 | Intermediate 10-7<br>Intermediate 5-1a |
| A-16 | 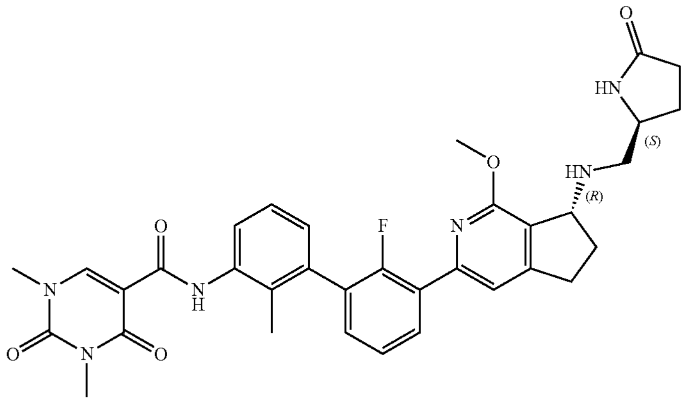 | Intermediate 10-8<br>Intermediate 5-1a |
| A-17 | 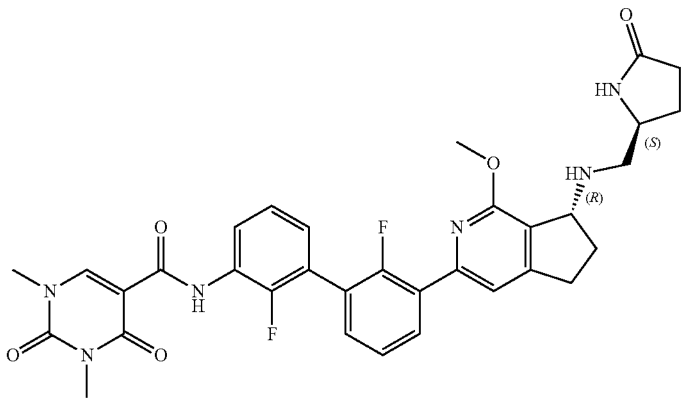 | Intermediate 10-9<br>Intermediate 5-1a |

TABLE 1-continued
| Cmpd No. | Structure | Starting materials |
|---|---|---|
| A-18 | 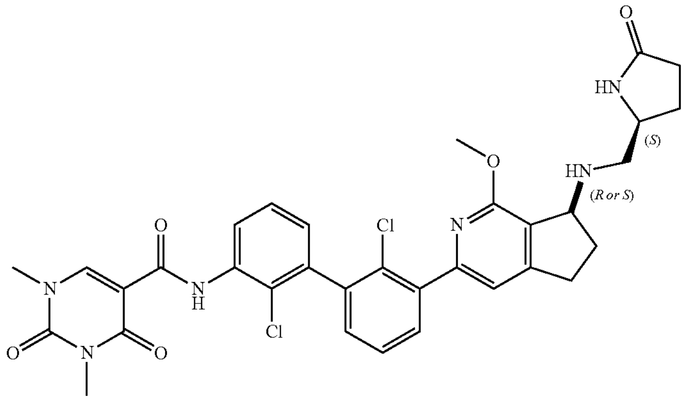 | Intermediate 10-1<br>Intermediate 6-1a |
| A-19 | 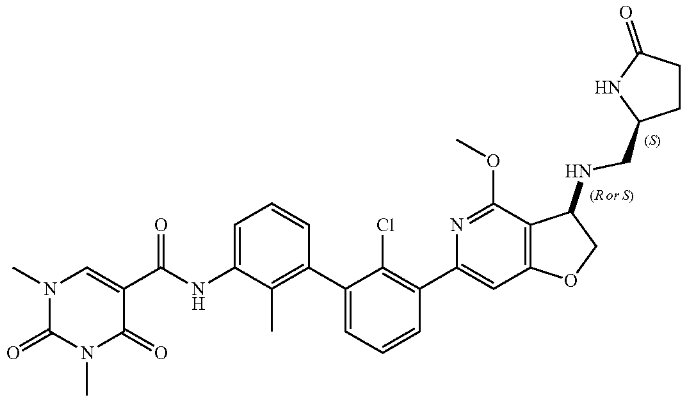 | Intermediate 10-2<br>Intermediate 6-1a |
| A-20 | 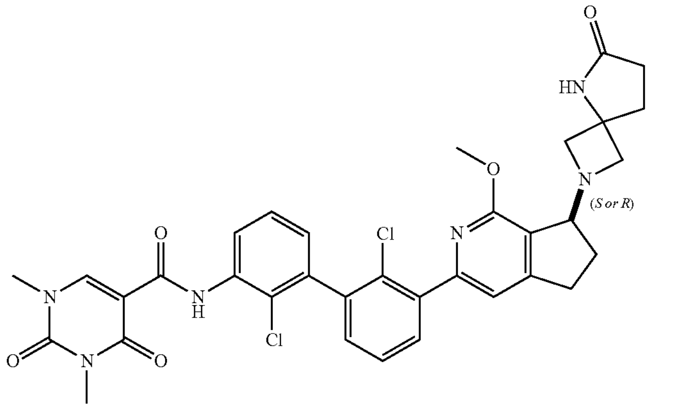 | Intermediate 10-1<br>Intermediate 5-2a |

TABLE 1-continued
| Cmpd No. | Structure | Starting materials |
|---|---|---|
| A-21 | 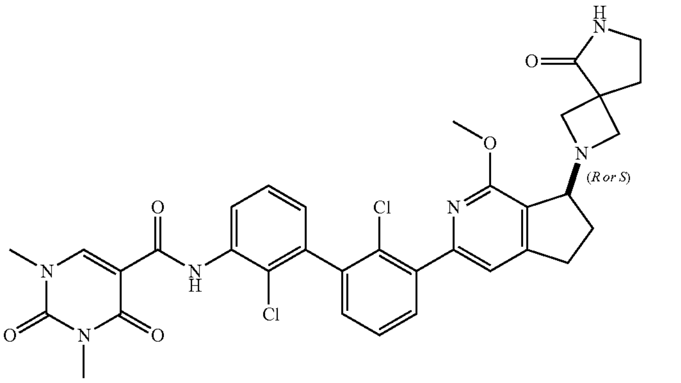 | Intermediate 10-1<br>Intermediate 5-7a |
| A-22 | 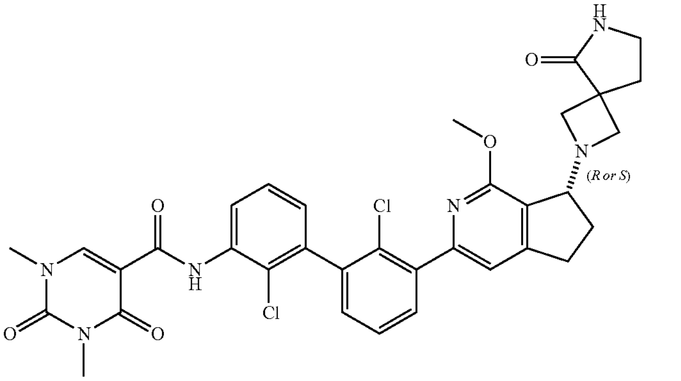 | Intermediate 10-1<br>Intermediate 5-7b |
| A-23 | 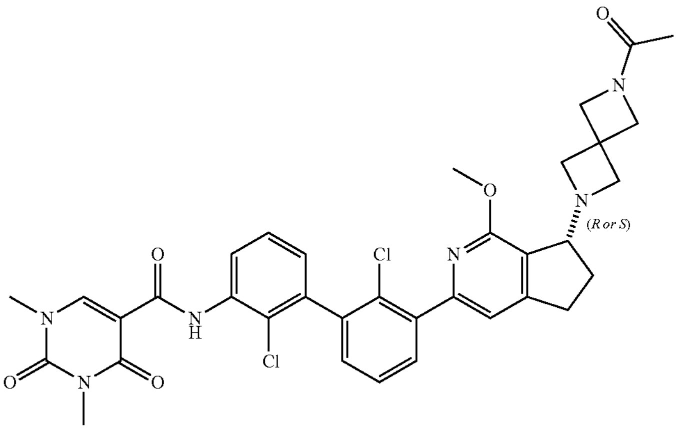 | Intermediate 10-1<br>Intermediate 5-3b |
| A-24 | 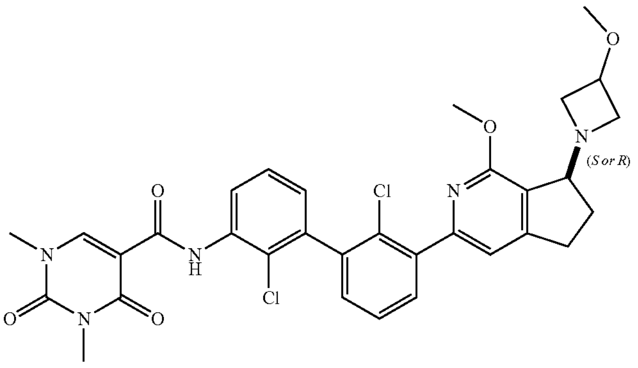 | Intermediate 10-1<br>Intermediate 5-6a |

TABLE 1-continued
| Cmpd No. | Structure | Starting materials |
| --- | --- | --- |
| A-25 | 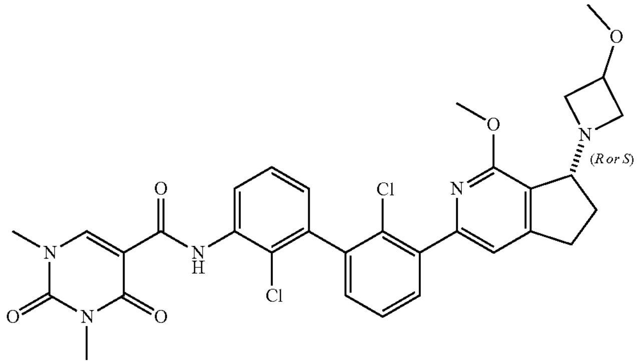 | Intermediate 10-1<br>Intermediate 5-6b |
| A-26 | 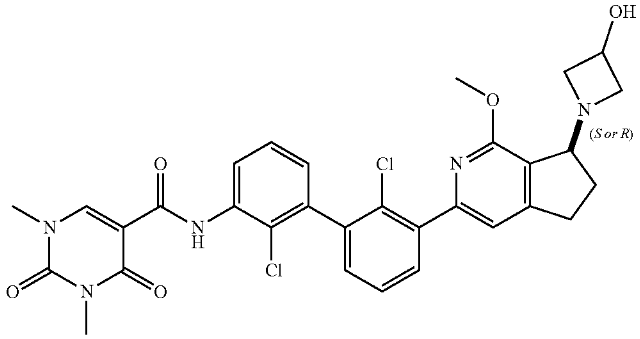 | Intermediate 10-1<br>Intermediate 5-5a |
| A-27 | 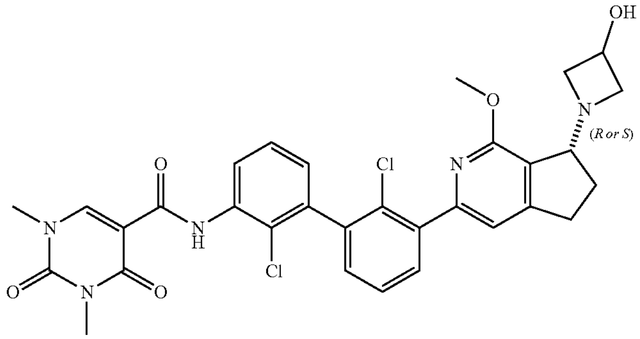 | Intermediate 10-1<br>Intermediate 5-5b |
| A-28 | 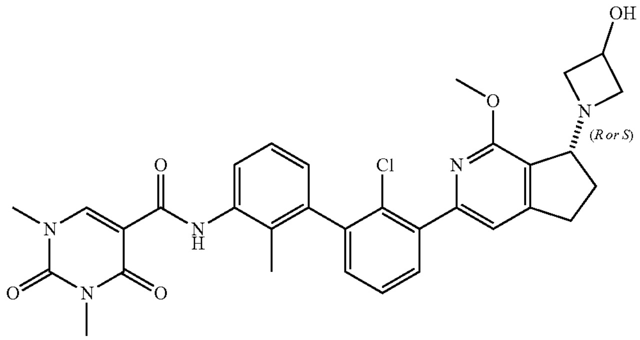 | Intermediate 10-1<br>Intermediate 5-5b |

TABLE 1-continued
| Cmpd No. | Structure | Starting materials |
|---|---|---|
| A-29 | 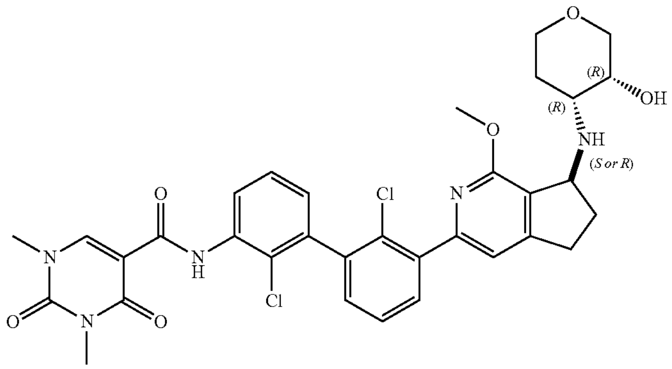 | Intermediate 10-1<br>Intermediate 5-4a |
| A-30 | 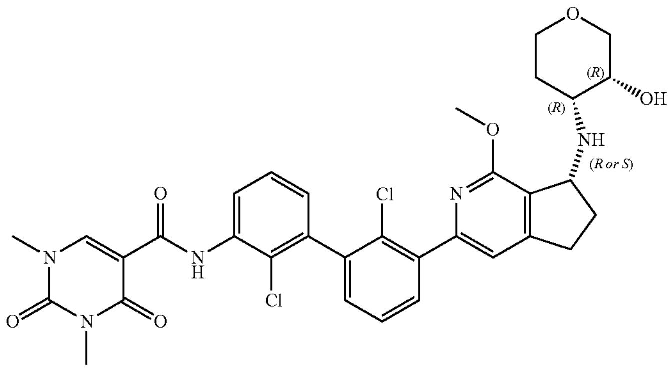 | Intermediate 10-1<br>Intermediate 5-4b |
| A-31 | 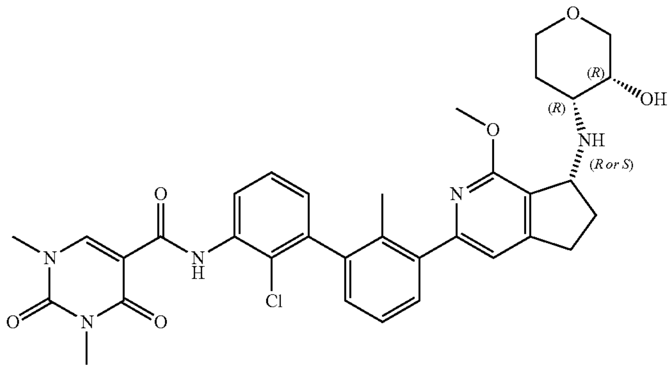 | Intermediate 10-4<br>Intermediate 5-4b |
| A-32 | 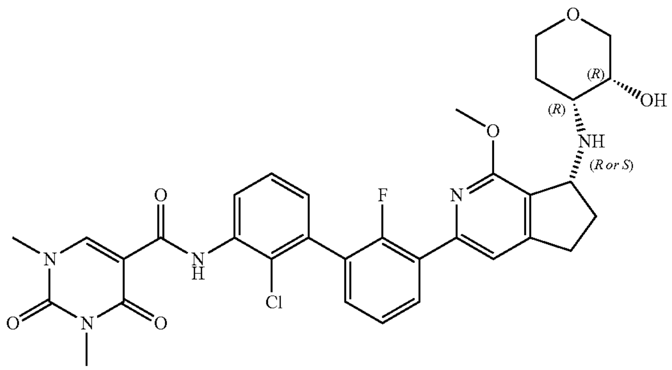 | Intermediate 10-7<br>Intermediate 5-4b |

TABLE 1-continued
| Cmpd No. | Structure | Starting materials |
| --- | --- | --- |
| A-33 | 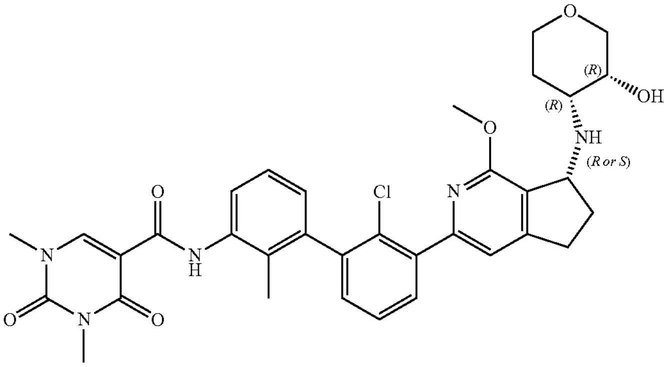 | Intermediate 10-2<br>Intermediate 5-4b |
| A-34 | 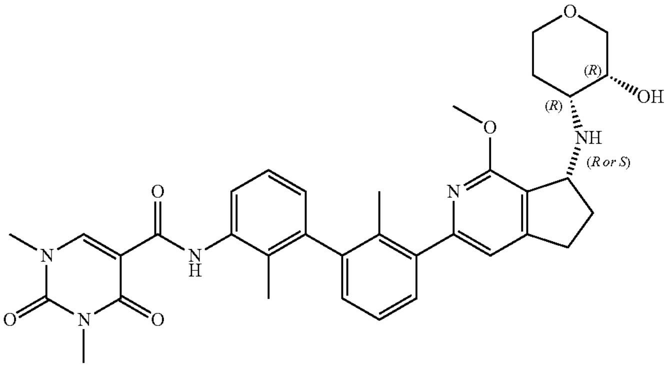 | Intermediate 10-5<br>Intermediate 5-4b |
| A-35 | 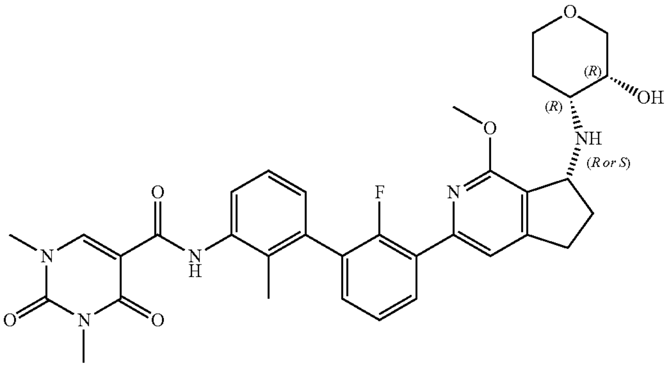 | Intermediate 10-8<br>Intermediate 5-4b |
| A-36 | 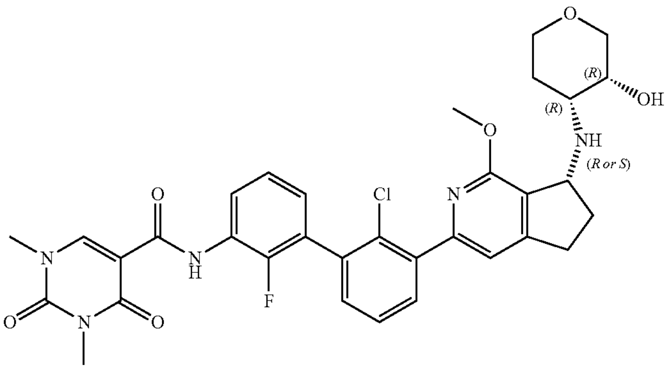 | Intermediate 10-3<br>Intermediate 5-4b |

TABLE 1-continued
| Cmpd No. | Structure | Starting materials |
|---|---|---|
| A-37 | 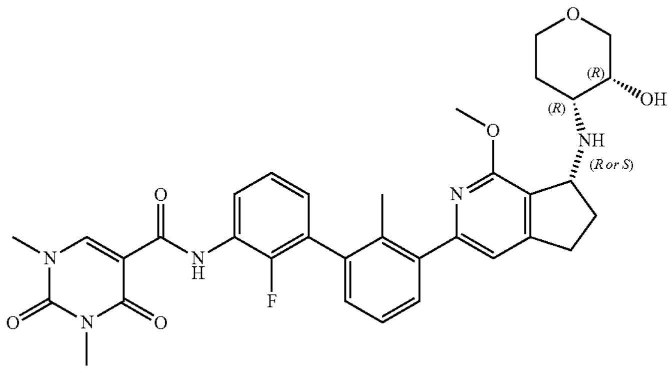 | Intermediate 10-6<br>Intermediate 5-4b |
| A-38 | 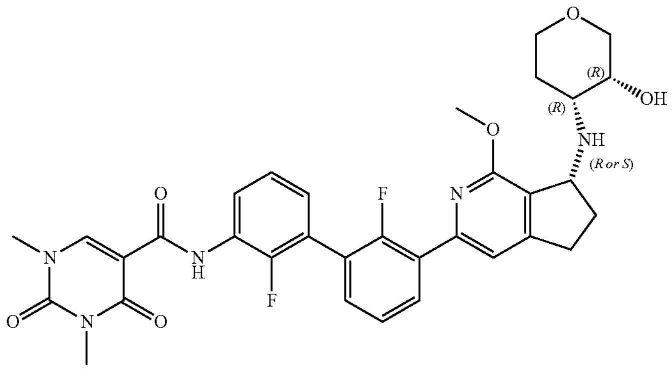 | Intermediate 10-9<br>Intermediate 5-4b |
| A-39 | 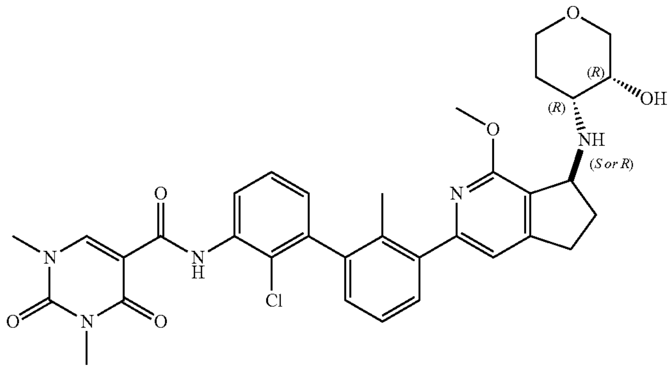 | Intermediate 10-4<br>Intermediate 5-4a |
| A-40 | 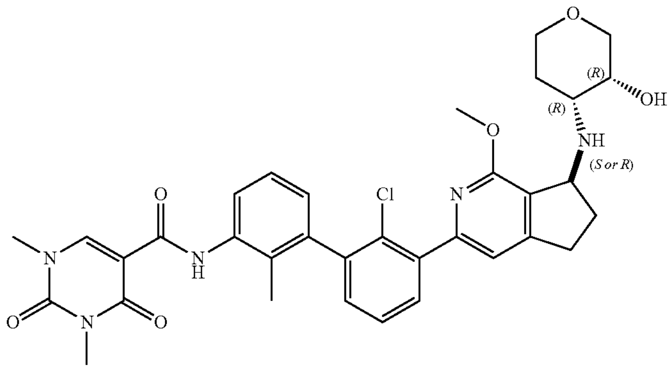 | Intermediate 10-2<br>Intermediate 5-4a |

TABLE 1-continued
| Cmpd No. | Structure | Starting materials |
|---|---|---|
| A-41 | 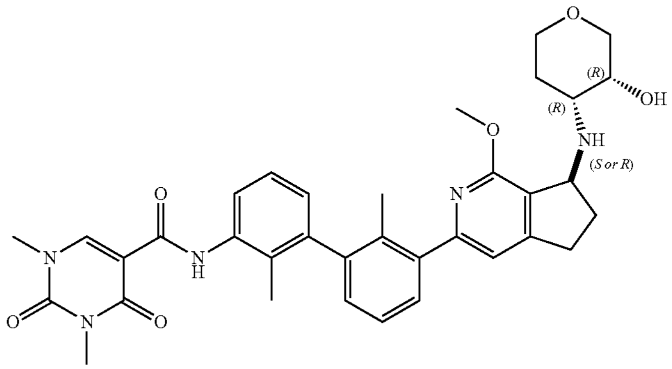 | Intermediate 10-5<br>Intermediate 5-4a |
| A-42 | 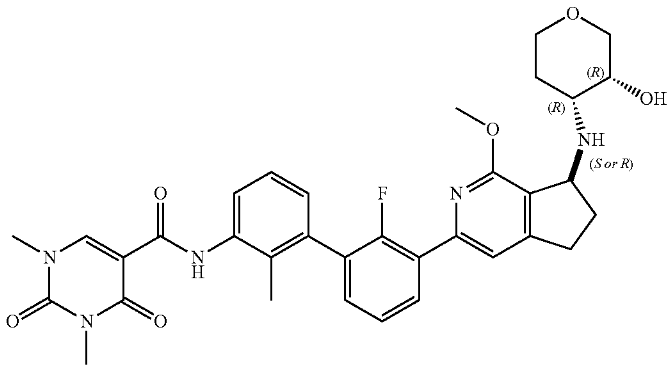 | Intermediate 10-8<br>Intermediate 5-4a |
| A-43 | 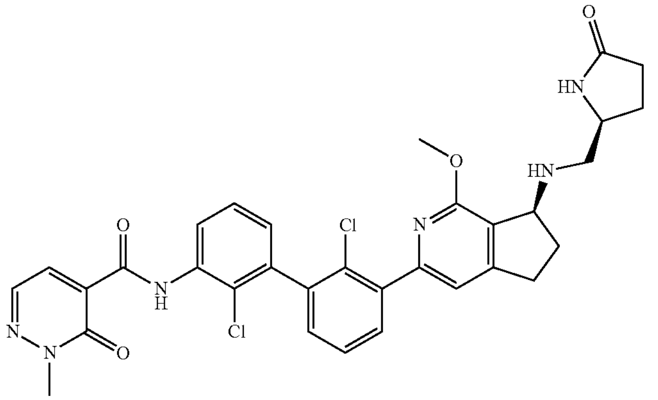 [SMILES: COc1nc(-c2cccc(-c3cccc(NC(=O)c4ccnn(C)c4=O)c3Cl)c2Cl)cc2c1[C@@H](NC[C@@H]1CCC(=O)N1)CC2] | Intermediate 10-10<br>Intermediate 5-1b |
| A-44 | 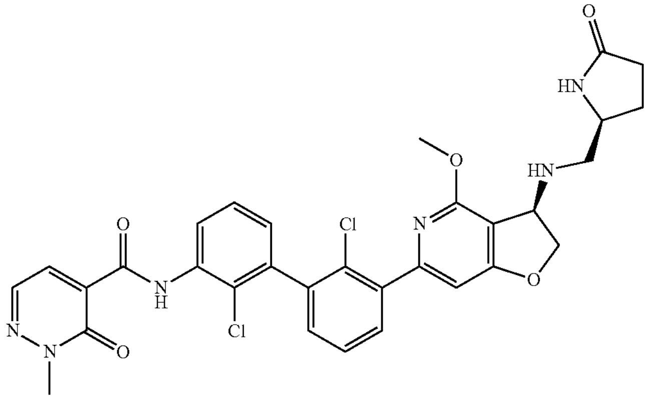 [SMILES: COc1nc(-c2cccc(-c3cccc(NC(=O)c4ccnn(C)c4=O)c3Cl)c2Cl)cc2c1[C@@H](NC[C@@H]1CCC(=O)N1)CO2] | Intermediate 10-10<br>Intermediate 6-1a |

TABLE 1-continued
| Cmpd No. | Structure | Starting materials |
|---|---|---|
| A-45 | 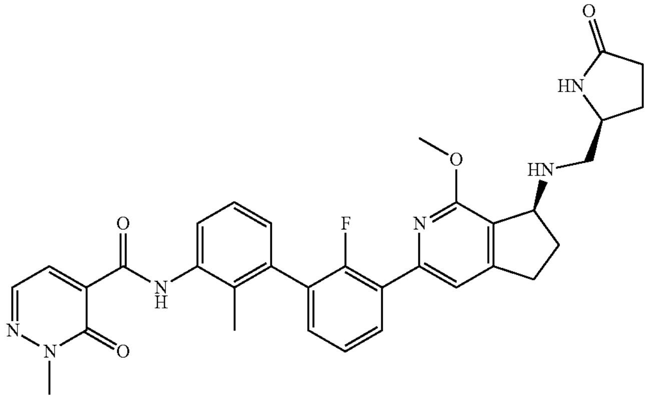 [SMILES: COc1nc(-c2cccc(-c3cccc(NC(=O)c4ccnn(C)c4=O)c3C)c2F)cc2c1[C@@H](NC[C@@H]1CCC(=O)N1)CC2] | Intermediate 10-12<br>Intermediate 5-1b |
| A-46 | 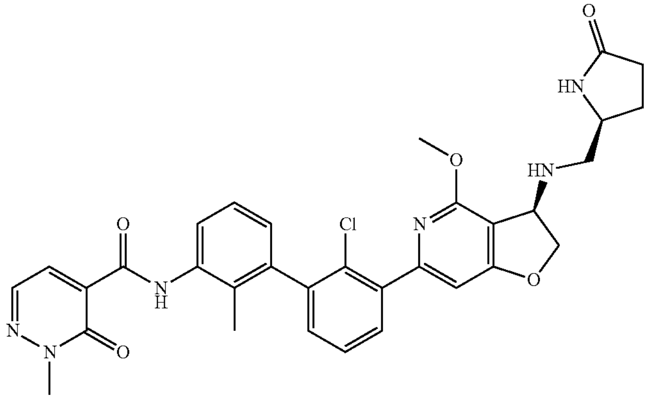 [SMILES: COc1nc(-c2cccc(-c3cccc(NC(=O)c4ccnn(C)c4=O)c3C)c2Cl)cc2c1[C@@H](NC[C@@H]1CCC(=O)N1)CO2] | Intermediate 10-11<br>Intermediate 6-1a |
| A-47 | 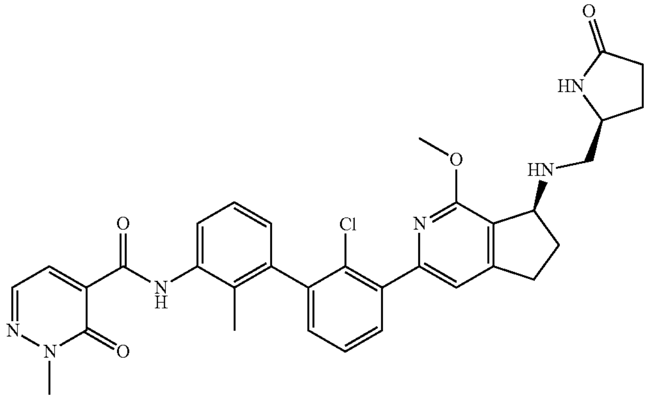 [SMILES: COc1nc(-c2cccc(-c3cccc(NC(=O)c4ccnn(C)c4=O)c3C)c2Cl)cc2c1[C@@H](NC[C@@H]1CCC(=O)N1)CC2] | Intermediate 10-11<br>Intermediate 5-1b |
| A-48 | 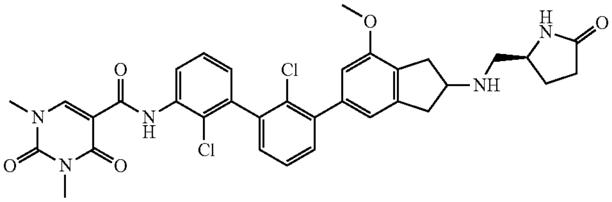 [SMILES: COc1cc(-c2cccc(-c3cccc(NC(=O)c4cn(C)c(=O)n(C)c4=O)c3Cl)c2Cl)cc2c1CC(NC[C@@H]1CCC(=O)N1)C2] | Intermediate 10-1<br>Intermediate 7-2 |

TABLE 1-continued
| Cmpd No. | Structure | Starting materials |
|---|---|---|
| A-49 | 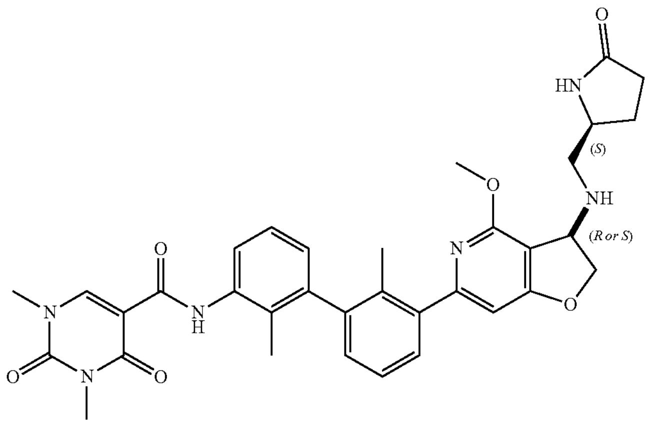 | Intermediate 10-5<br>Intermediate 6-1a |
| A-50 | 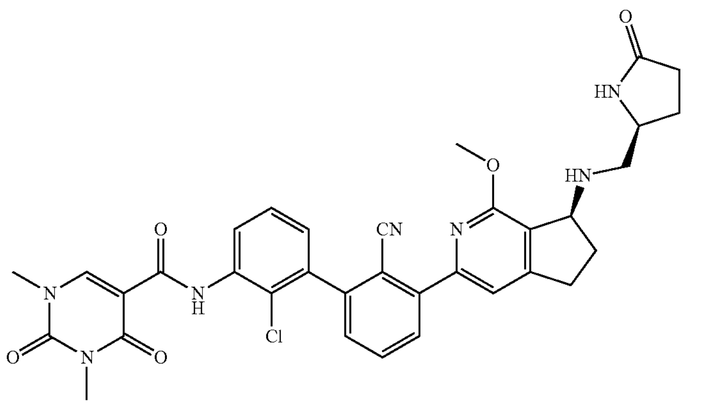 [SMILES: COc1nc(-c2cccc(-c3cccc(NC(=O)c4cn(C)c(=O)n(C)c4=O)c3Cl)c2C#N)cc2c1[C@@H](NC[C@@H]1CCC(=O)N1)CC2] | Intermediate 10-15<br>Intermediate 5-1b |
| A-51 | 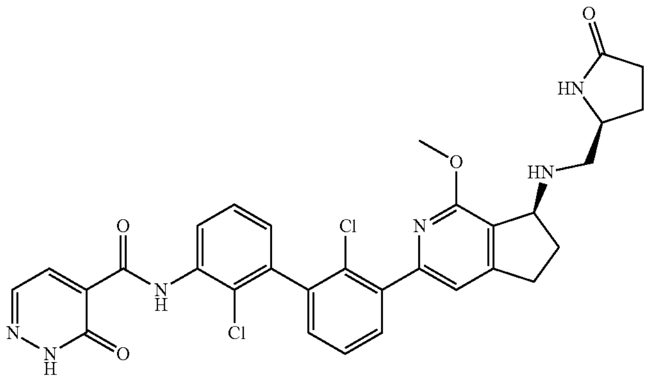 [SMILES: COc1nc(-c2cccc(-c3cccc(NC(=O)c4ccn[nH]c4=O)c3Cl)c2Cl)cc2c1[C@@H](NC[C@@H]1CCC(=O)N1)CC2] | Intermediate 10-34<br>Intermediate 5-1b |
| A-52 | 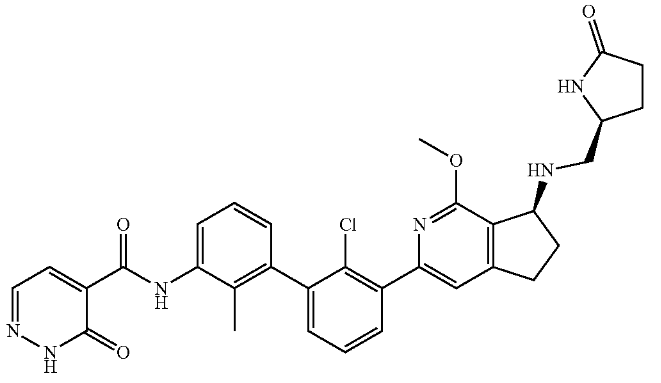 [SMILES: COc1nc(-c2cccc(-c3cccc(NC(=O)c4ccn[nH]c4=O)c3C)c2Cl)cc2c1[C@@H](NC[C@@H]1CCC(=O)N1)CC2] | Intermediate 10-35<br>Intermediate 5-1b |

TABLE 1-continued
| Cmpd No. | Structure | Starting materials |
| --- | --- | --- |
| A-53 | 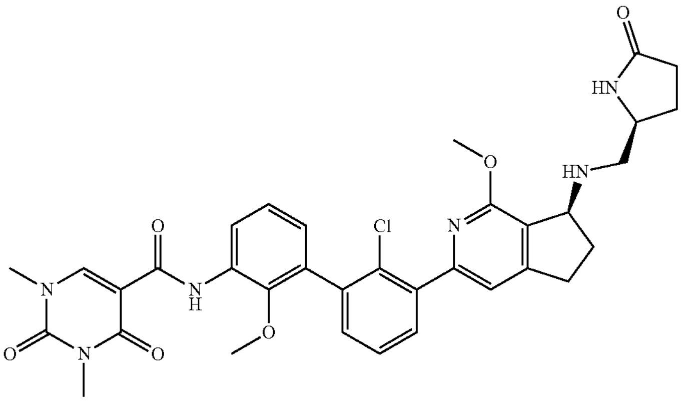 [SMILES: COc1nc(-c2cccc(-c3cccc(NC(=O)c4cn(C)c(=O)n(C)c4=O)c3OC)c2Cl)cc2c1[C@@H](NC[C@@H]1CCC(=O)N1)CC2] | Intermediate 10-13<br>Intermediate 5-1b |
| A-54 | 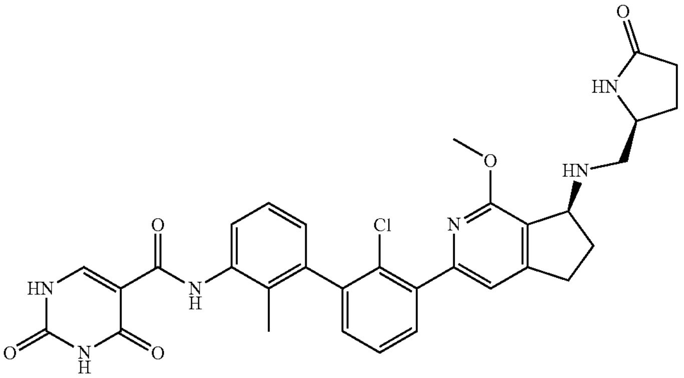 [SMILES: COc1nc(-c2cccc(-c3cccc(NC(=O)c4c[nH]c(=O)[nH]c4=O)c3C)c2Cl)cc2c1[C@@H](NC[C@@H]1CCC(=O)N1)CC2] | Intermediate 10-29<br>Intermediate 5-1b |
| A-55 | 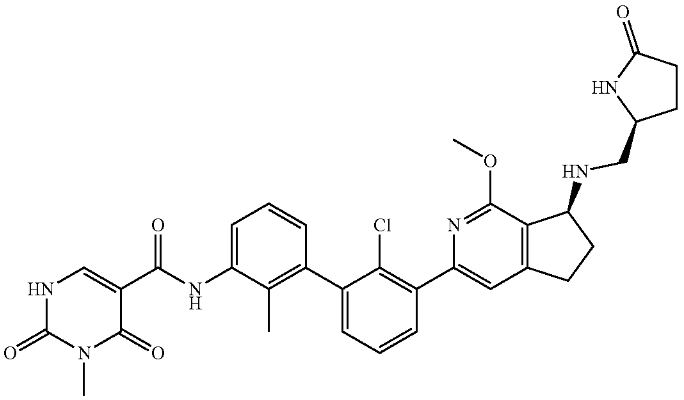 [SMILES: COc1nc(-c2cccc(-c3cccc(NC(=O)c4c[nH]c(=O)n(C)c4=O)c3C)c2Cl)cc2c1[C@@H](NC[C@@H]1CCC(=O)N1)CC2] | Intermediate 10-28a<br>Intermediate 5-1b |
| A-56 | 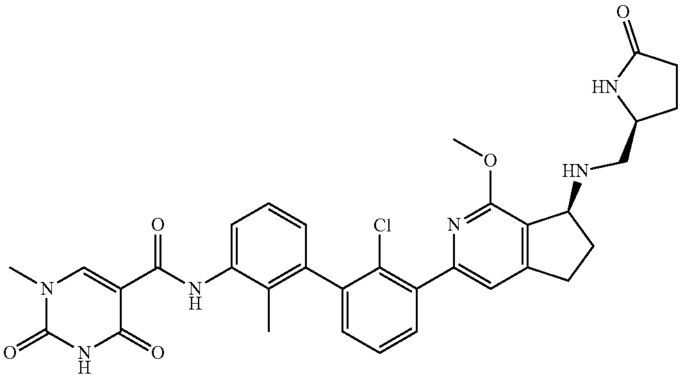 [SMILES: COc1nc(-c2cccc(-c3cccc(NC(=O)c4cn(C)c(=O)[nH]c4=O)c3C)c2Cl)cc2c1[C@@H](NC[C@@H]1CCC(=O)N1)CC2] | Intermediate 10-28b<br>Intermediate 5-1b |

TABLE 1-continued
| Cmpd No. | Structure | Starting materials |
|---|---|---|
| A-57 | 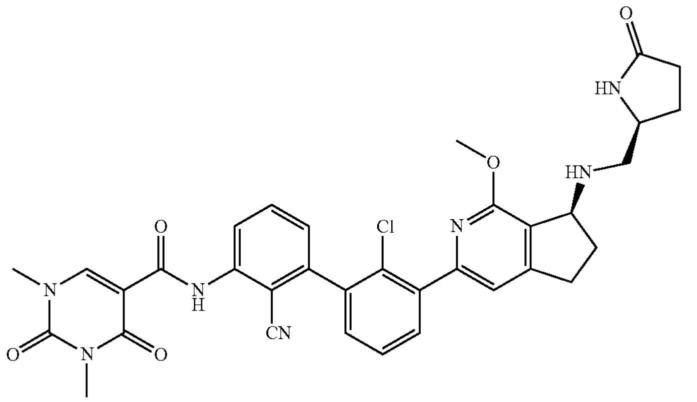 [SMILES: COc1nc(-c2cccc(-c3cccc(NC(=O)c4cn(C)c(=O)n(C)c4=O)c3C#N)c2Cl)cc2c1[C@@H](NC[C@@H]1CCC(=O)N1)CC2] | Intermediate 10-14<br>Intermediate 5-1b |
| A-58 | 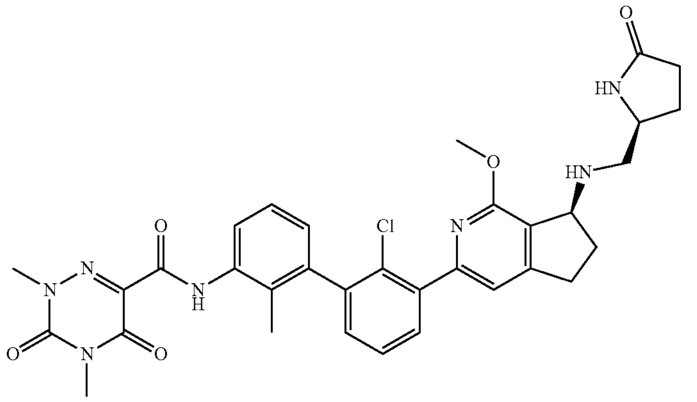 [SMILES: COc1nc(-c2cccc(-c3cccc(NC(=O)c4nn(C)c(=O)n(C)c4=O)c3C)c2Cl)cc2c1[C@@H](NC[C@@H]1CCC(=O)N1)CC2] | Intermediate 10-31<br>Intermediate 5-1b |
| A-59 | 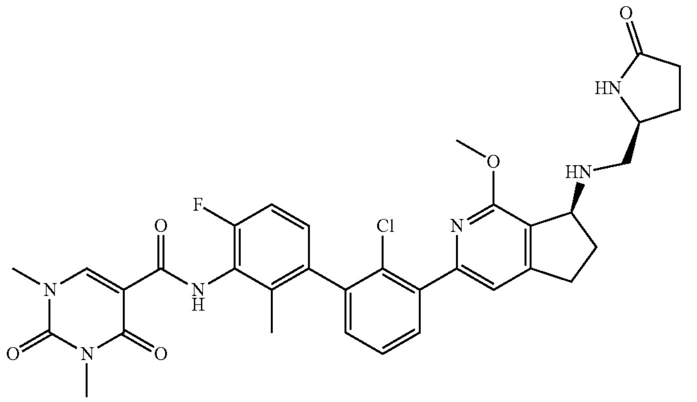 [SMILES: COc1nc(-c2cccc(-c3ccc(F)c(NC(=O)c4cn(C)c(=O)n(C)c4=O)c3C)c2Cl)cc2c1[C@@H](NC[C@@H]1CCC(=O)N1)CC2] | Intermediate 10-21<br>Intermediate 5-1b |

TABLE 1-continued
| Cmpd No. | Structure | Starting materials |
|---|---|---|
| A-60 | 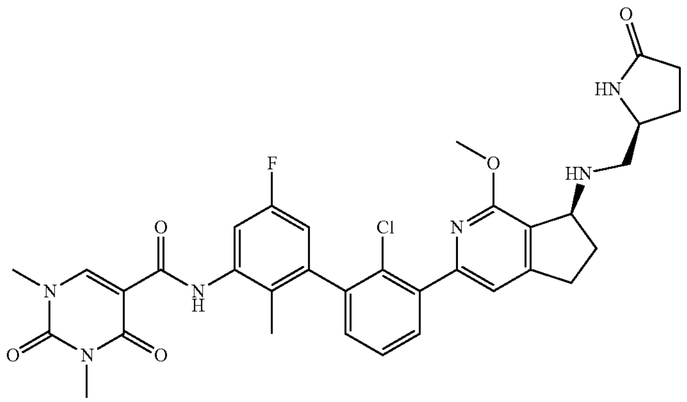 [SMILES: COc1nc(-c2cccc(-c3cc(F)cc(NC(=O)c4cn(C)c(=O)n(C)c4=O)c3C)c2Cl)cc2c1[C@@H](NC[C@@H]1CCC(=O)N1)CC2] | Intermediate 10-18<br>Intermediate 5-1b |
| A-61 | 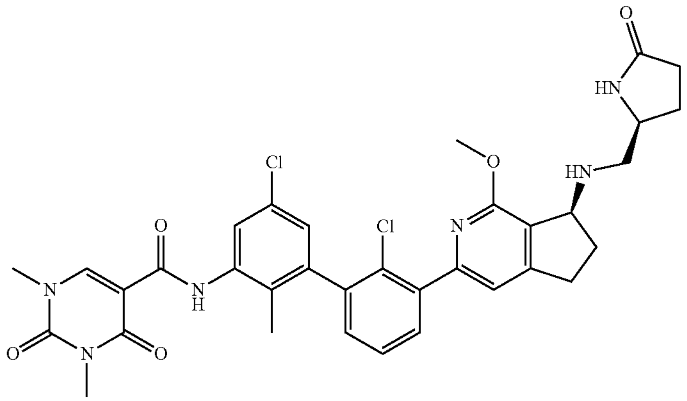 [SMILES: COc1nc(-c2cccc(-c3cc(Cl)cc(NC(=O)c4cn(C)c(=O)n(C)c4=O)c3C)c2Cl)cc2c1[C@@H](NC[C@@H]1CCC(=O)N1)CC2] | Intermediate 10-17<br>Intermediate 5-1b |
| A-62 | 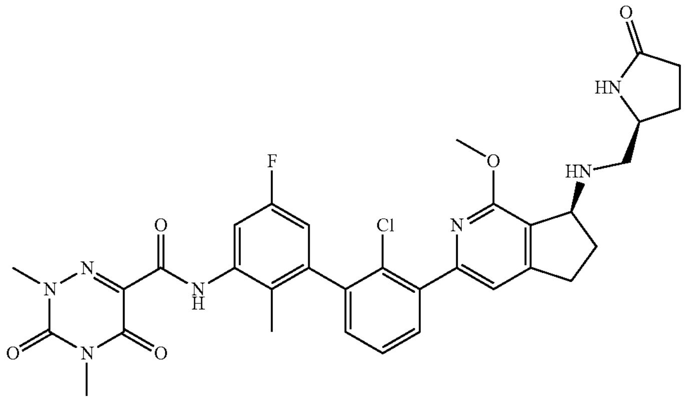 [SMILES: COc1nc(-c2cccc(-c3cc(F)cc(NC(=O)c4nn(C)c(=O)n(C)c4=O)c3C)c2Cl)cc2c1[C@@H](NC[C@@H]1CCC(=O)N1)CC2] | Intermediate 10-33<br>Intermediate 5-1b |

TABLE 1-continued
| Cmpd No. | Structure | Starting materials |
| --- | --- | --- |
| A-63 | 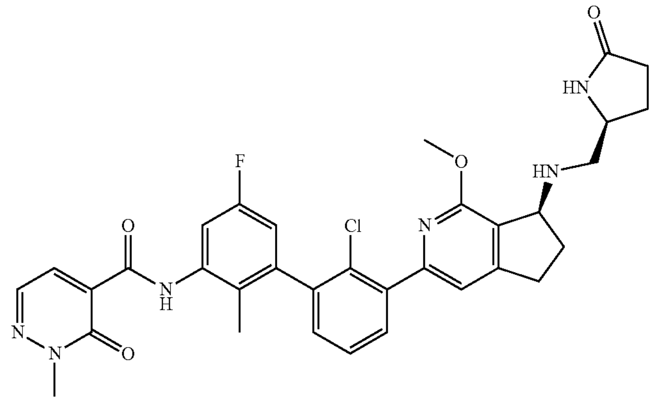 [SMILES: COc1nc(-c2cccc(-c3cc(F)cc(NC(=O)c4ccnn(C)c4=O)c3C)c2Cl)cc2c1[C@@H](NC[C@@H]1CCC(=O)N1)CC2] | Intermediate 10-36<br>Intermediate 5-1b |
| A-64 | 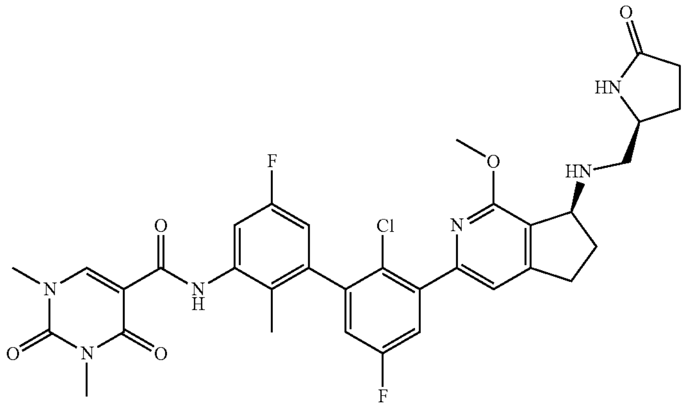 [SMILES: COc1nc(-c2cc(F)cc(-c3cc(F)cc(NC(=O)c4cn(C)c(=O)n(C)c4=O)c3C)c2Cl)cc2c1[C@@H](NC[C@@H]1CCC(=O)N1)CC2] | Intermediate 10-24<br>Intermediate 5-1b |
| A-65 | 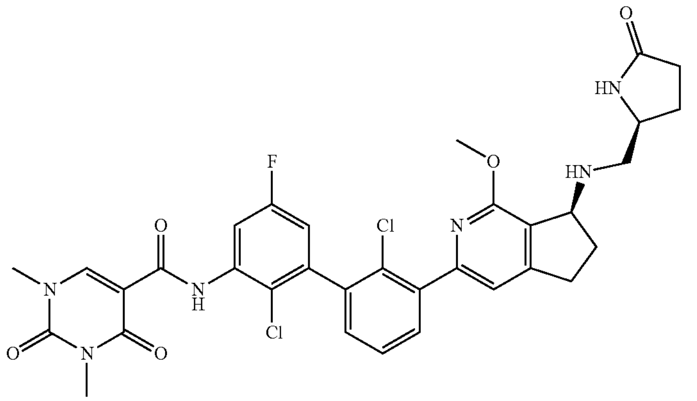 | Intermediate 10-19<br>Intermediate 5-1b |

TABLE 1-continued
| Cmpd No. | Structure | Starting materials |
| --- | --- | --- |
| A-66 | 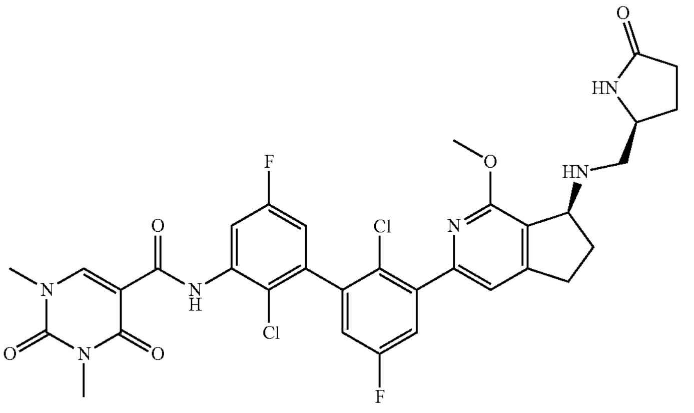 [SMILES: COc1nc(-c2cc(F)cc(-c3cc(F)cc(NC(=O)c4cn(C)c(=O)n(C)c4=O)c3Cl)c2Cl)cc2c1[C@@H](NC[C@@H]1CCC(=O)N1)CC2] | Intermediate 10-25<br>Intermediate 5-1b |
| A-67 | 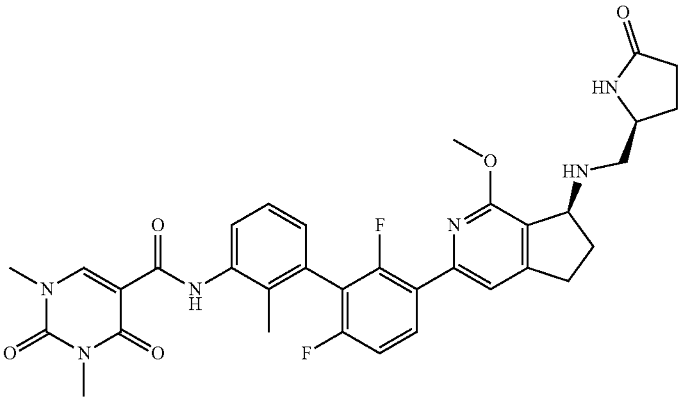<br>atropoisomer R or S | Intermediate 10-26<br>Intermediate 5-1b |
| A-68 | 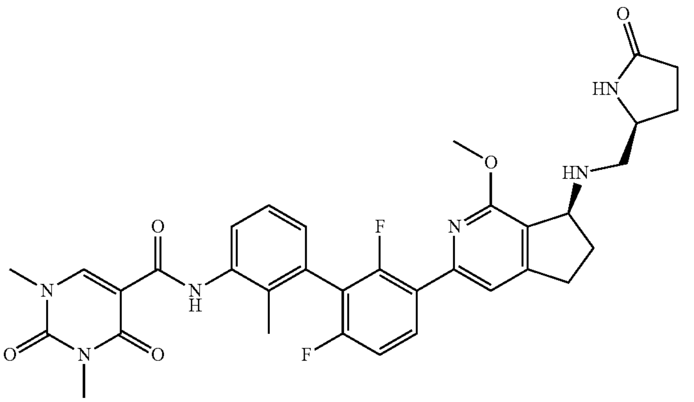<br>atropoisomer S or R | Intermediate 10-26<br>Intermediate 5-1b |

TABLE 1-continued
| Cmpd No. | Structure | Starting materials |
|---|---|---|
| A-69 | 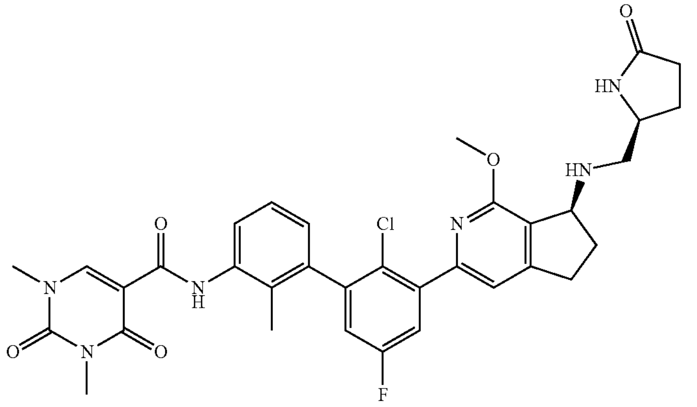 [SMILES: COc1nc(-c2cc(F)cc(-c3cccc(NC(=O)c4cn(C)c(=O)n(C)c4=O)c3C)c2Cl)cc2c1[C@@H](NC[C@@H]1CCC(=O)N1)CC2] | Intermediate 10-23<br>Intermediate 5-1b |
| A-70 | 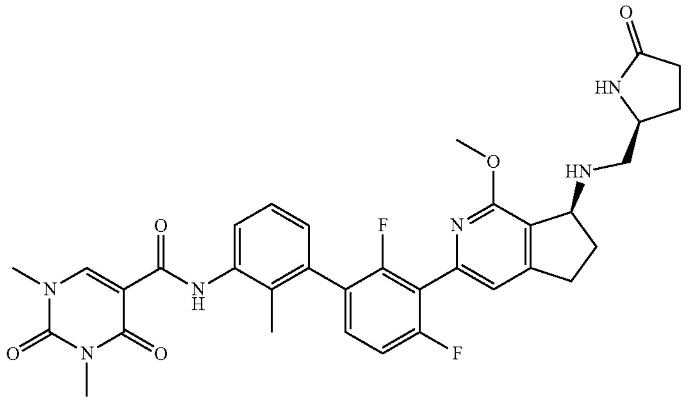 [SMILES: COc1nc(-c2c(F)ccc(-c3cccc(NC(=O)c4cn(C)c(=O)n(C)c4=O)c3C)c2F)cc2c1[C@@H](NC[C@@H]1CCC(=O)N1)CC2] | Intermediate 10-27<br>Intermediate 5-1b |
| A-71 | 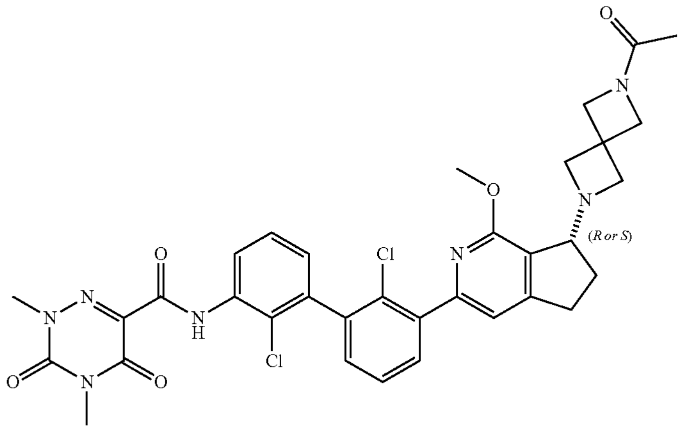 [SMILES: COc1nc(-c2cccc(-c3cccc(NC(=O)c4nn(C)c(=O)n(C)c4=O)c3Cl)c2Cl)cc2c1[C@H](N1CC3(CN(C(C)=O)C3)C1)CC2] | Intermediate 10-30<br>Intermediate 5-3b |

TABLE 1-continued
| Cmpd No. | Structure | Starting materials |
|---|---|---|
| A-72 | 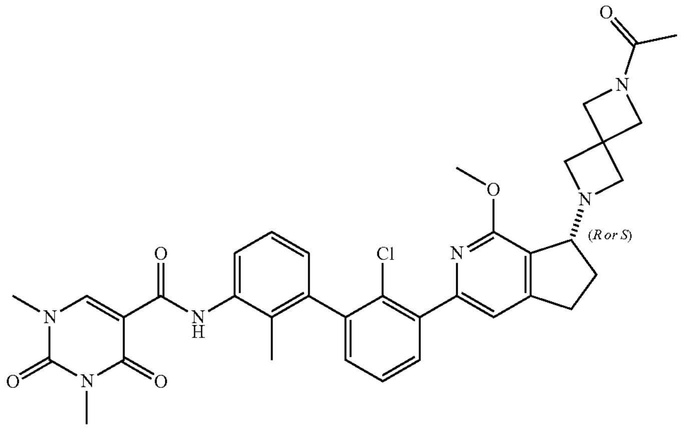 [SMILES: COc1nc(-c2cccc(-c3cccc(NC(=O)c4cn(C)c(=O)n(C)c4=O)c3C)c2Cl)cc2c1[C@H](N1CC3(CN(C(C)=O)C3)C1)CC2] | Intermediate 10-2<br>Intermediate 5-3b |
| A-73 | 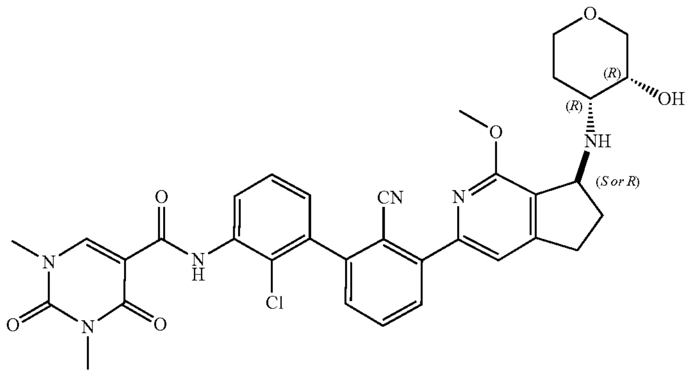 | Intermediate 10-15<br>Intermediate 5-4a |
| A-74 | 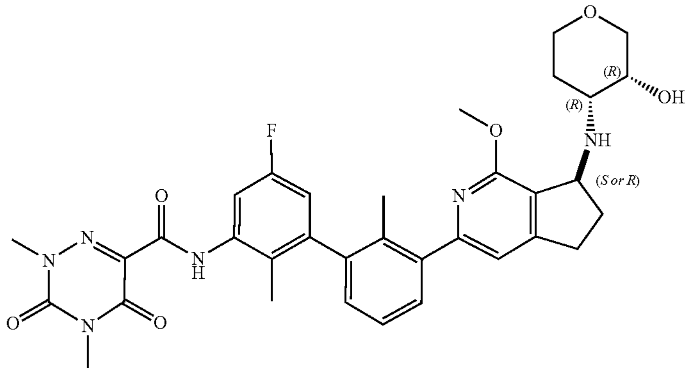 | Intermediate 10-33a<br>Intermediate 5-4a |
| A-75 | 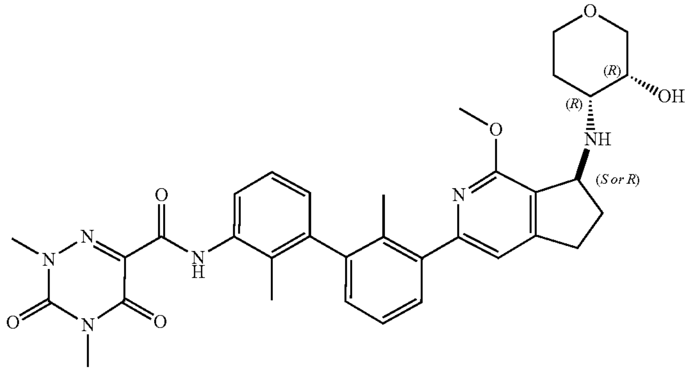 | Intermediate 10-32<br>Intermediate 5-4a |

TABLE 1-continued
| Cmpd No. | Structure | Starting materials |
|---|---|---|
| A-76 | 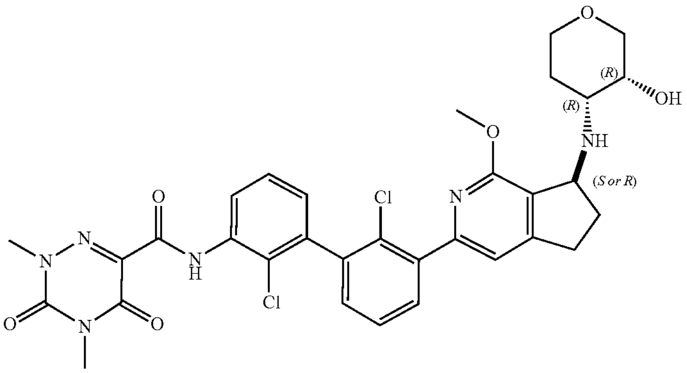 | Intermediate 10-30<br>Intermediate 5-4a |
| A-77 | 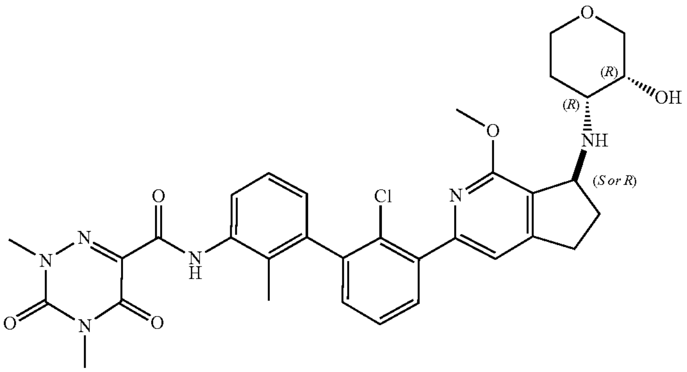 | Intermediate 10-31<br>Intermediate 5-4a |
| A-79 | 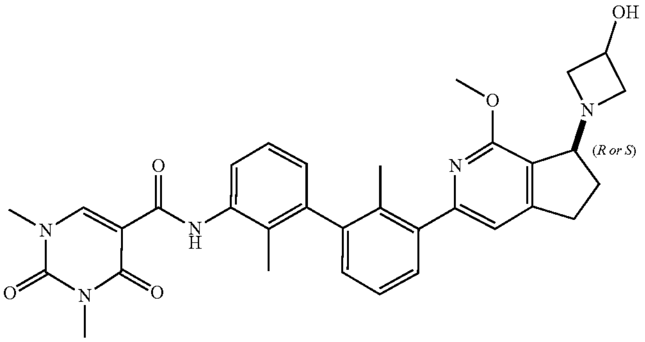 [SMILES: COc1nc(-c2cccc(-c3cccc(NC(=O)c4cn(C)c(=O)n(C)c4=O)c3C)c2C)cc2c1[C@@H](N1CC(O)C1)CC2] | Intermediate 10-5<br>Intermediate 5-5a |
| A-80 | 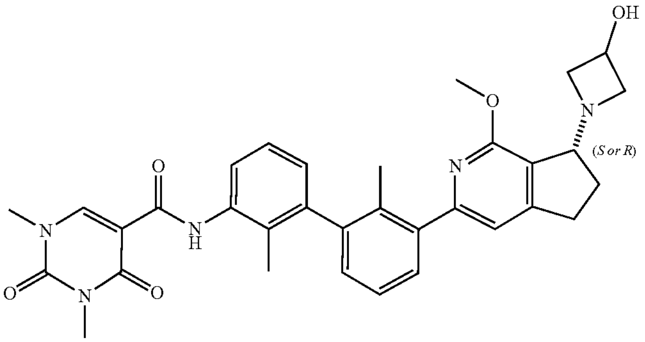 [SMILES: COc1nc(-c2cccc(-c3cccc(NC(=O)c4cn(C)c(=O)n(C)c4=O)c3C)c2C)cc2c1[C@H](N1CC(O)C1)CC2] | Intermediate 10-5<br>Intermediate 5-5b |

TABLE 1-continued
| Cmpd No. | Structure | Starting materials |
| --- | --- | --- |
| A-81 | 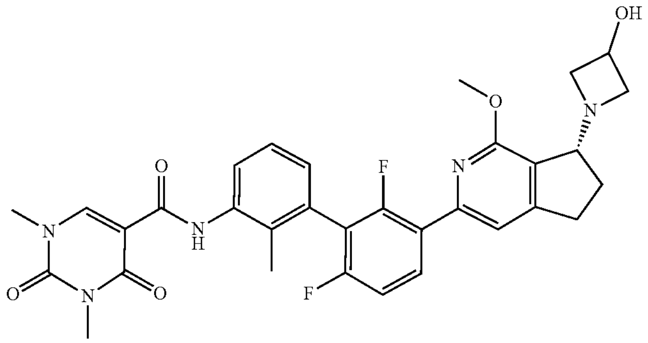<br>Atropiosmer R or S | Intermediate 10-26<br>Intermediate 5-5b |
| A-82 | 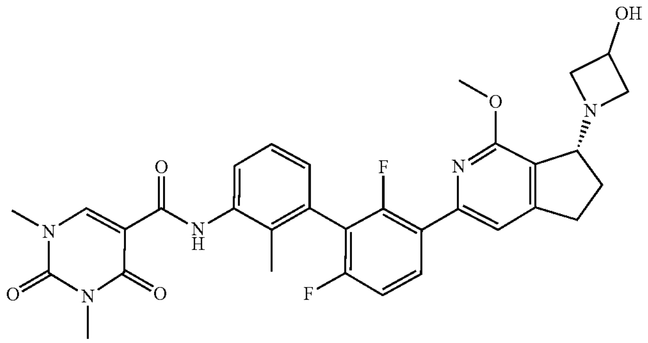<br>Atropiosmer S or R | Intermediate 10-26<br>Intermediate 5-5b |
| A-83 | 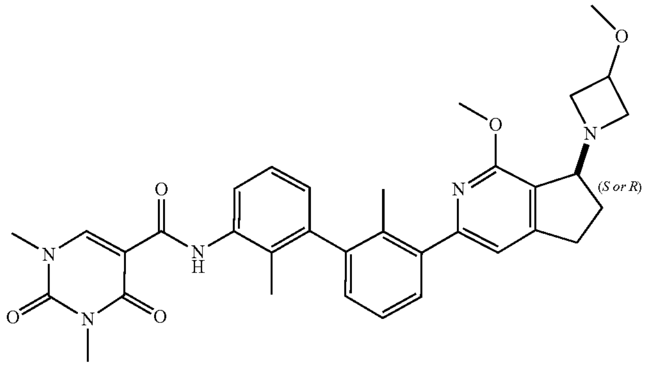 [SMILES: COc1nc(-c2cccc(-c3cccc(NC(=O)c4cn(C)c(=O)n(C)c4=O)c3C)c2C)cc2c1[C@@H](N1CC(OC)C1)CC2] | Intermediate 10-5<br>Intermediate 5-6a |
| A-84 | 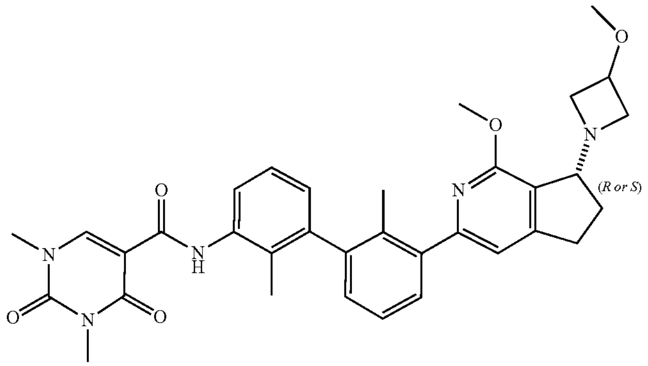 [SMILES: COc1nc(-c2cccc(-c3cccc(NC(=O)c4cn(C)c(=O)n(C)c4=O)c3C)c2C)cc2c1[C@H](N1CC(OC)C1)CC2] | Intermediate 10-5<br>Intermediate 5-6b |

TABLE 1-continued
| Cmpd No. | Structure | Starting materials |
|---|---|---|
| A-85 | 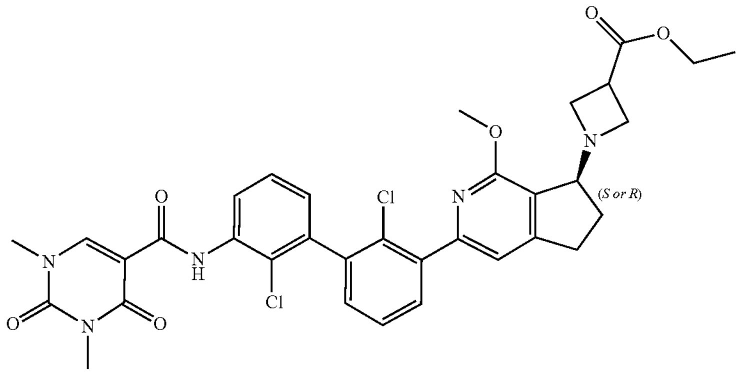 [SMILES: CCOC(=O)C1CN([C@H]2CCc3cc(-c4cccc(-c5cccc(NC(=O)c6cn(C)c(=O)n(C)c6=O)c5Cl)c4Cl)nc(OC)c32)C1] | Intermediate 10-1<br>Intermediate 5-8a |
| A-86 | 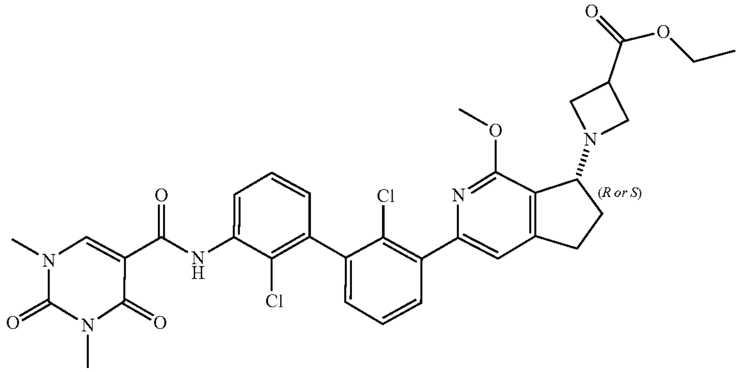 [SMILES: CCOC(=O)C1CN([C@@H]2CCc3cc(-c4cccc(-c5cccc(NC(=O)c6cn(C)c(=O)n(C)c6=O)c5Cl)c4Cl)nc(OC)c32)C1] | Intermediate 10-1<br>Intermediate 5-8b |
| A-87 | 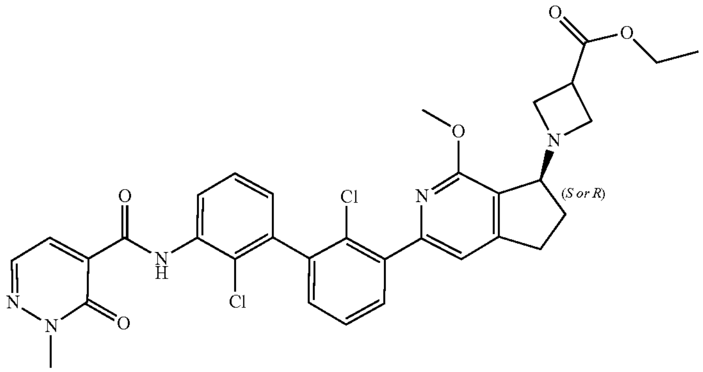 [SMILES: CCOC(=O)C1CN([C@H]2CCc3cc(-c4cccc(-c5cccc(NC(=O)c6ccnn(C)c6=O)c5Cl)c4Cl)nc(OC)c32)C1] | Intermediate 10-10<br>Intermediate 5-8a |
| A-88 | 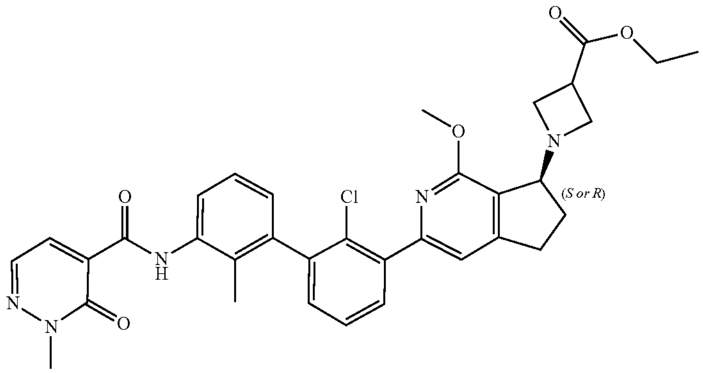 [SMILES: CCOC(=O)C1CN([C@H]2CCc3cc(-c4cccc(-c5cccc(NC(=O)c6ccnn(C)c6=O)c5C)c4Cl)nc(OC)c32)C1] | Intermediate 10-11<br>Intermediate 5-8a |

TABLE 1-continued
| Cmpd No. | Structure | Starting materials |
|---|---|---|
| A-89 | 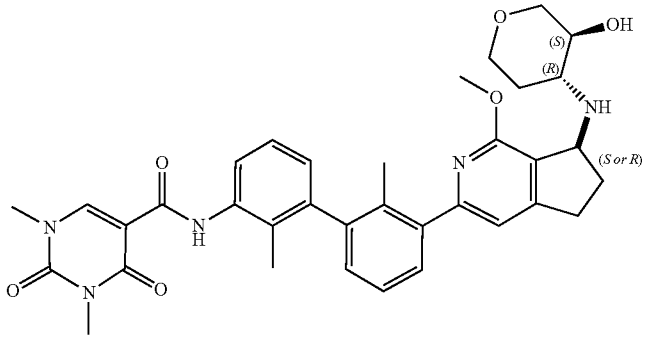 | Intermediate 10-5<br>Intermediate 5-9a |
| A-90 | 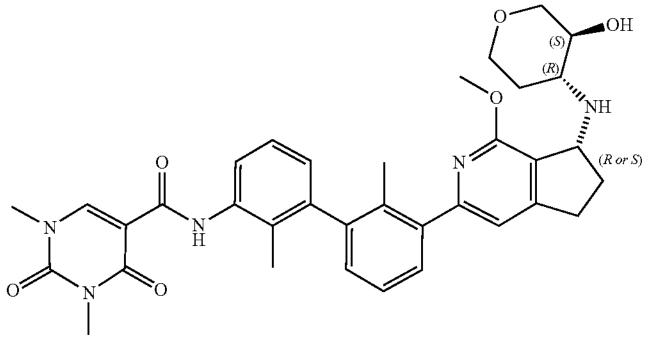 | Intermediate 10-5<br>Intermediate 5-9b |
| A-91 | 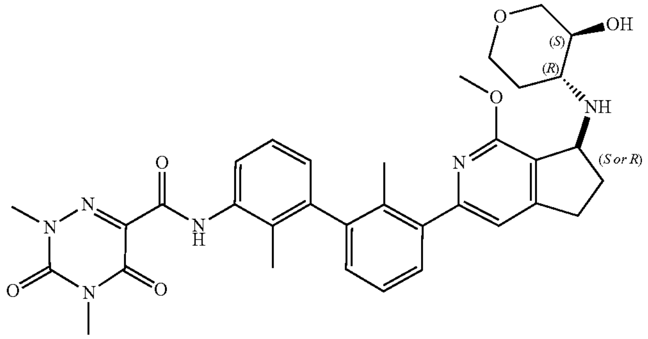 | Intermediate 10-32<br>Intermediate 5-9a |
| A-92 | 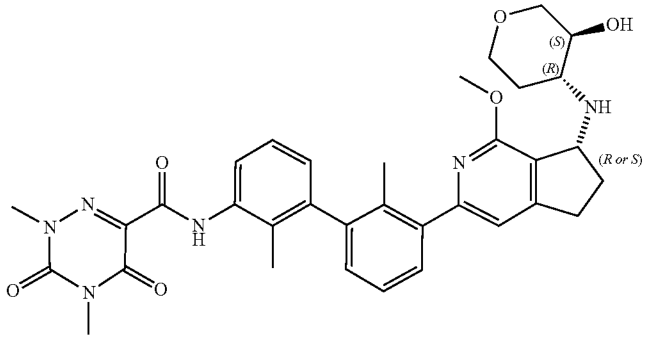 | Intermediate 10-32<br>Intermediate 5-9b |

TABLE 1-continued
| Cmpd No. | Structure | Starting materials |
|---|---|---|
| A-93 | 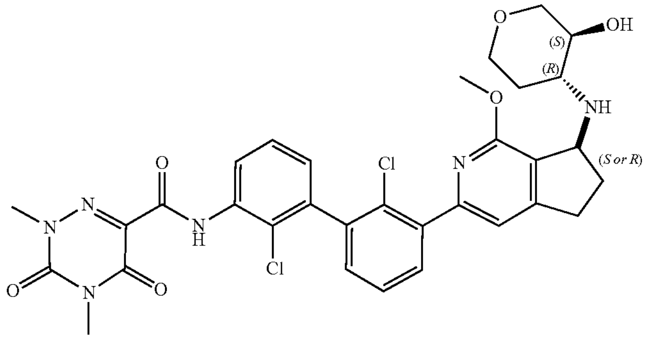 | Intermediate 10-30<br>Intermediate 5-9a |
| A-94 | 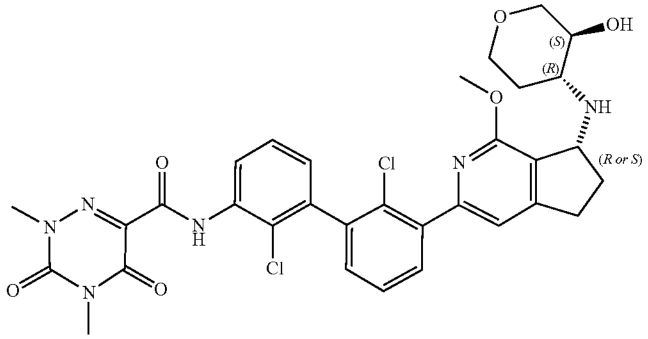 | Intermediate 10-30<br>Intermediate 5-9b |
| A-95 | 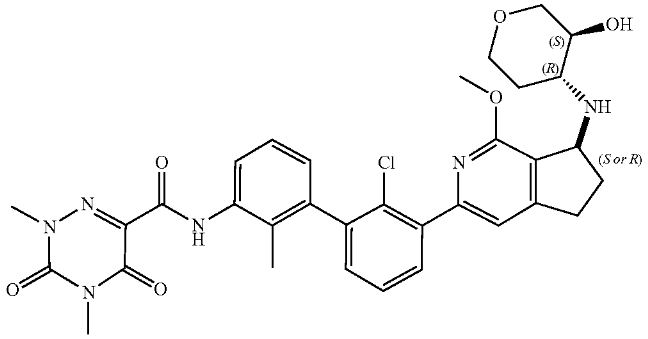 | Intermediate 10-31<br>Intermediate 5-9a |
| A-96 | 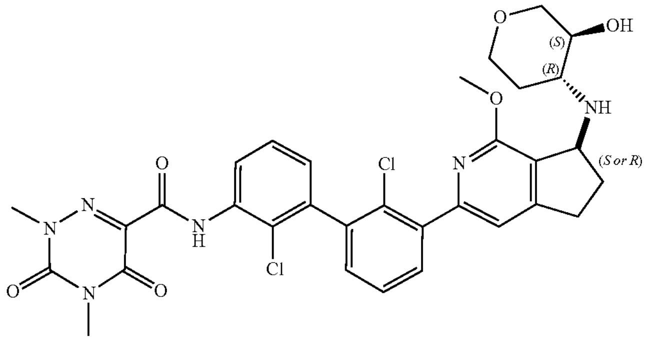 | Intermediate 10-31<br>Intermediate 5-9b |

TABLE 1-continued
| Cmpd No. | Structure | Starting materials |
|---|---|---|
| A-97 | 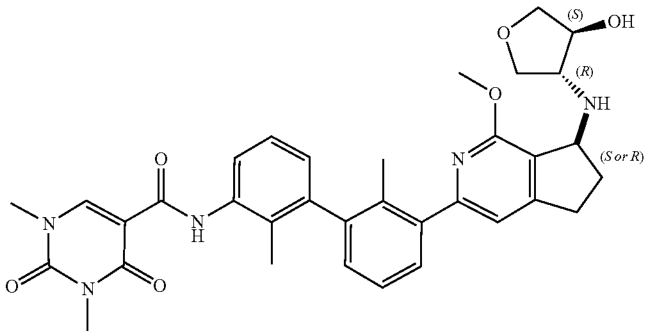 | Intermediate 10-5<br>Intermediate 5-11a |
| A-98 | 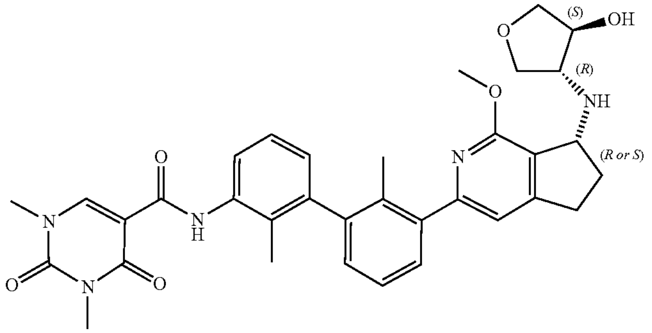 | Intermediate 10-5<br>Intermediate 5-1 lb |
| A-99 | 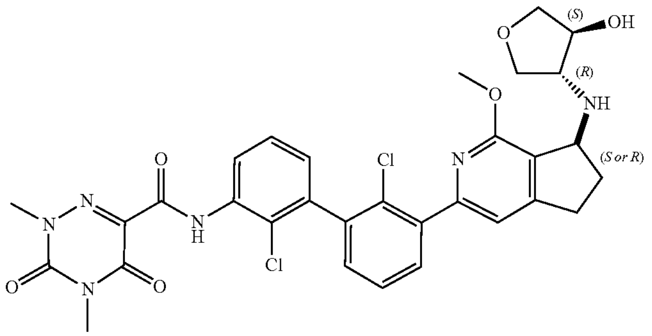 | Intermediate 10-30<br>Intermediate 5-11a |
| A-100 | 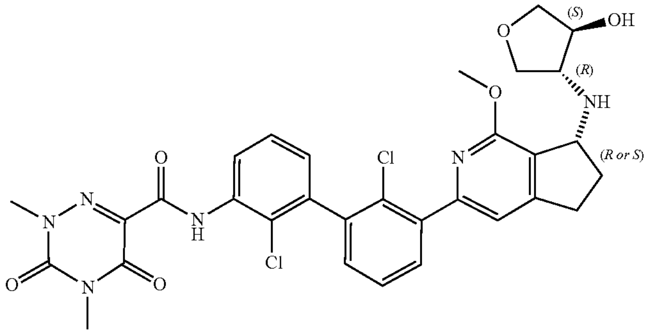 | Intermediate 10-30<br>Intermediate 5-1lb |

TABLE 1-continued
| Cmpd No. | Structure | Starting materials |
|---|---|---|
| A-101 | 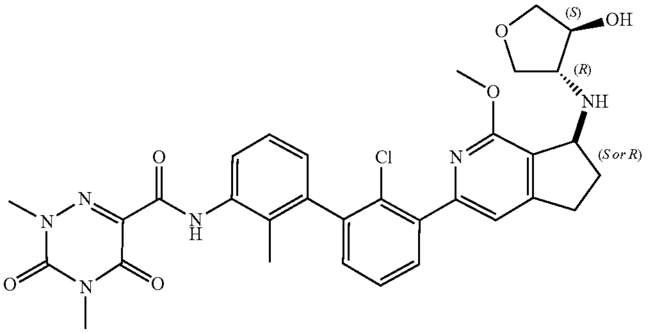 | Intermediate 10-31<br>Intermediate 5-11a |
| A-102 | 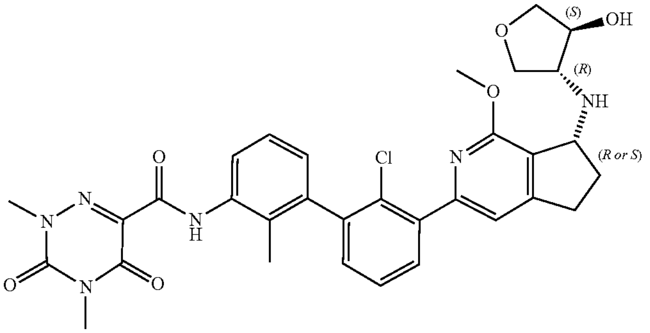 | Intermediate 10-31<br>Intermediate 5-11b |
| A-103 | 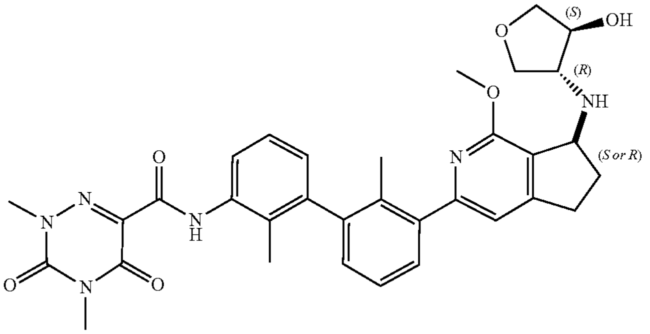 | Intermediate 10-32<br>Intermediate 5-11a |
| A-104 | 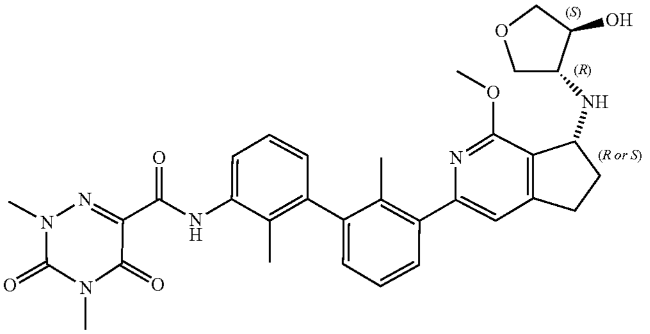 | Intermediate 10-32<br>Intermediate 5-11b |

TABLE 1-continued
| Cmpd No. | Structure | Starting materials |
|---|---|---|
| A-105 | 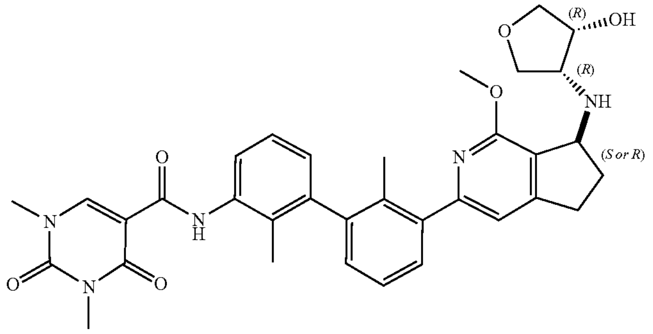 | Intermediate 10-5<br>Intermediate 5-10a |
| A-106 | 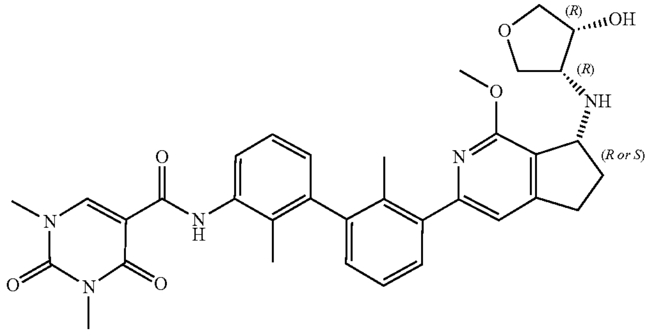 | Intermediate 10-5<br>Intermediate 5-10b |
| A-107 | 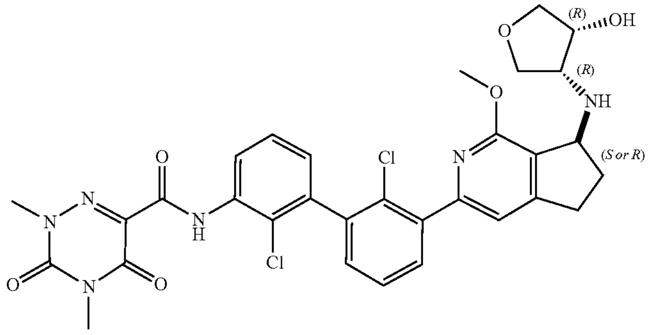 | Intermediate 10-30<br>Intermediate 5-10a |
| A-108 | 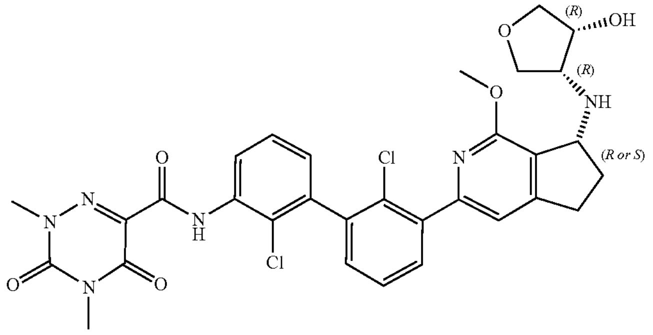 | Intermediate 10-30<br>Intermediate 5-10b |

TABLE 1-continued
| Cmpd No. | Structure | Starting materials |
|---|---|---|
| A-109 | 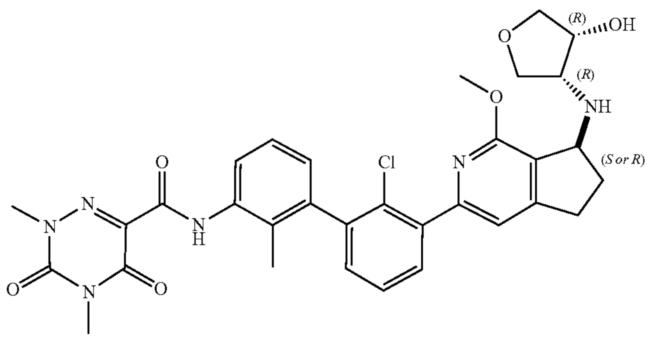 | Intermediate 10-31<br>Intermediate 5-10a |
| A-110 | 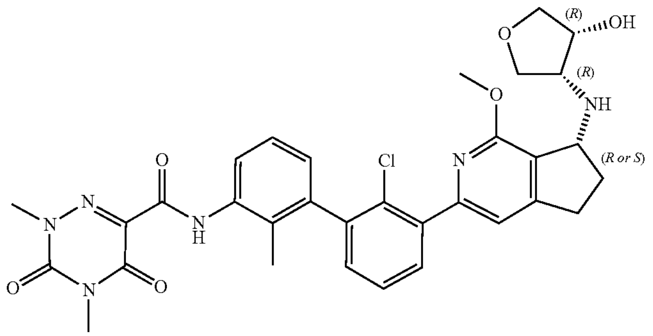 | Intermediate 10-31<br>Intermediate 5-10b |
| A-111 | 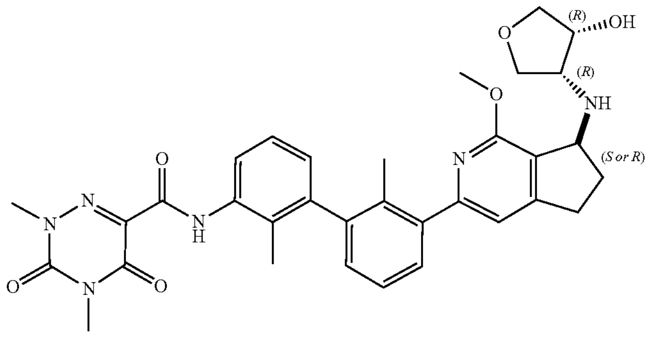 | Intermediate 10-32<br>Intermediate 5-10a |
| A-112 | 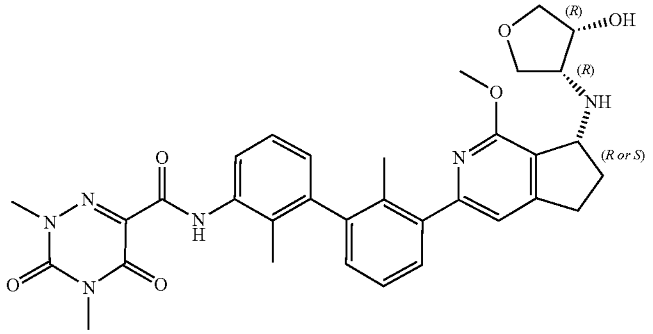 | Intermediate 10-32<br>Intermediate 5-10b |

TABLE 1-continued
| Cmpd No. | Structure | Starting materials |
| --- | --- | --- |
| A-113 | 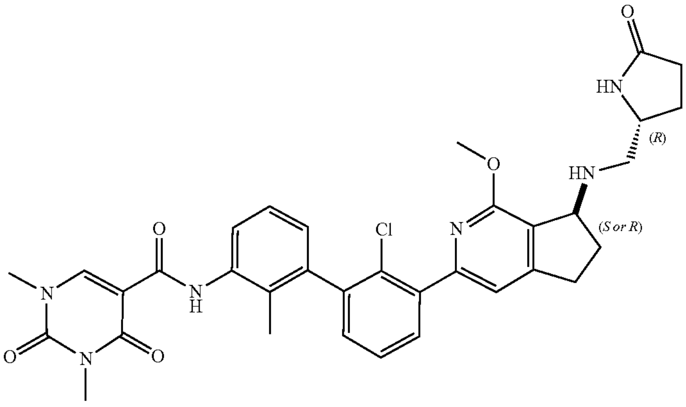 | Intermediate 10-2<br>Intermediate 5-12a |
| A-114 | 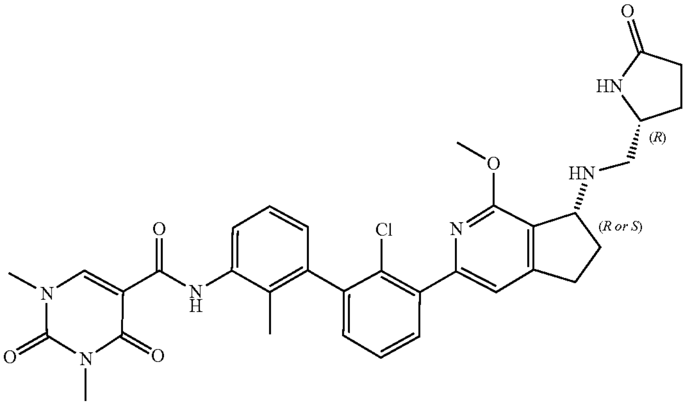 | Intermediate 10-2<br>Intermediate 5-12b |
| A-115 | 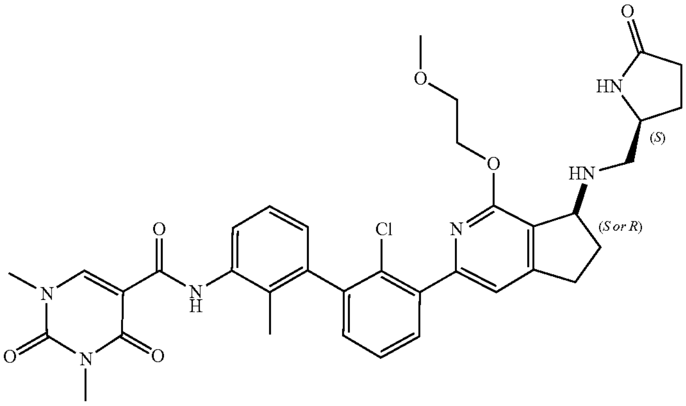 | Intermediate 10-2<br>Intermediate 5-13a |

TABLE 1-continued
| Cmpd No. | Structure | Starting materials |
|---|---|---|
| A-116 | 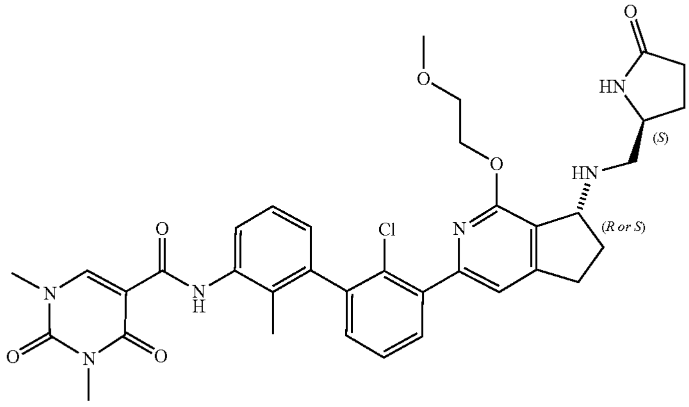 | Intermediate 10-2<br>Intermediate 5-13b |
| A-117 | 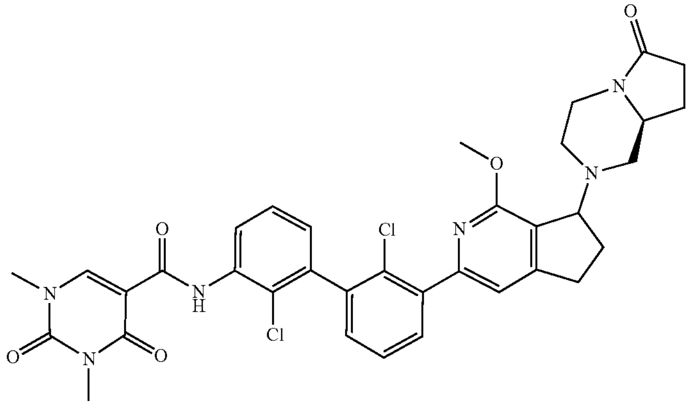 [SMILES: COc1nc(-c2cccc(-c3cccc(NC(=O)c4cn(C)c(=O)n(C)c4=O)c3Cl)c2Cl)cc2c1C(N1CCN3C(=O)CC[C@H]3C1)CC2] | Intermediate 10-1<br>Intermediate 7-3 |
| A-118 | 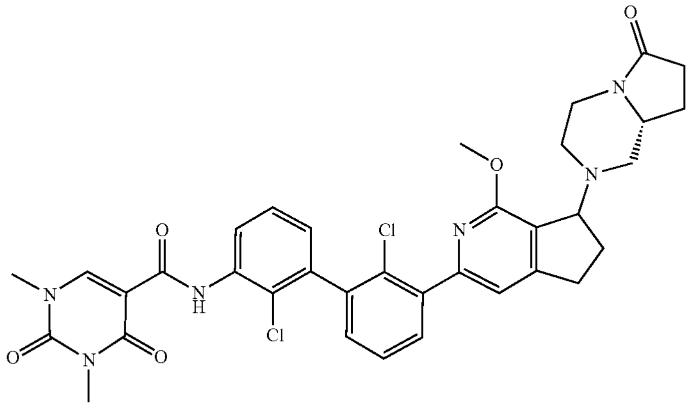 [SMILES: COc1nc(-c2cccc(-c3cccc(NC(=O)c4cn(C)c(=O)n(C)c4=O)c3Cl)c2Cl)cc2c1C(N1CCN3C(=O)CC[C@@H]3C1)CC2] | Intermediate 10-1<br>Intermediate 7-4 |

TABLE 1-continued
| Cmpd No. | Structure | Starting materials |
|---|---|---|
| A-119 | 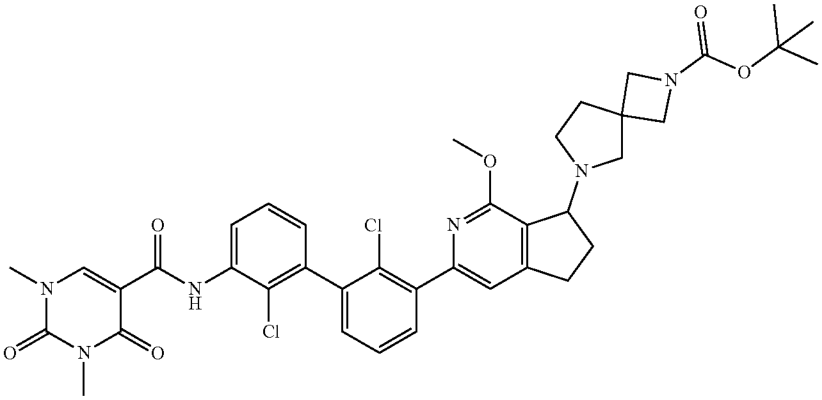 [SMILES: COc1nc(-c2cccc(-c3cccc(NC(=O)c4cn(C)c(=O)n(C)c4=O)c3Cl)c2Cl)cc2c1C(N1CCC3(CN(C(=O)OC(C)(C)C)C3)C1)CC2] | Intermediate 10-1<br>Intermediate 7-5 |
| A-120 | 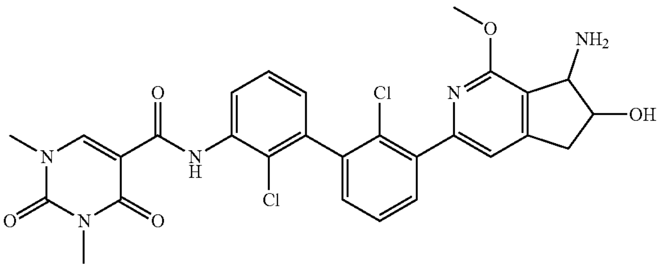 [SMILES: COc1nc(-c2cccc(-c3cccc(NC(=O)c4cn(C)c(=O)n(C)c4=O)c3Cl)c2Cl)cc2c1C(N)C(O)C2] | Intermediate 10-1<br>Intermediate 4c |
| A-121 | 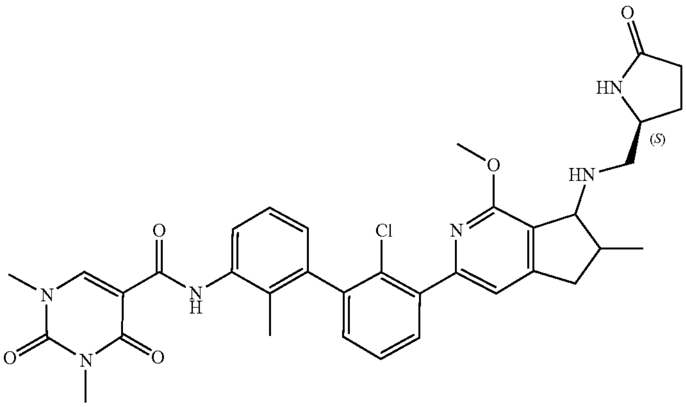 | Intermediate 10-2<br>Intermediate 7-6 |
| A-122 | 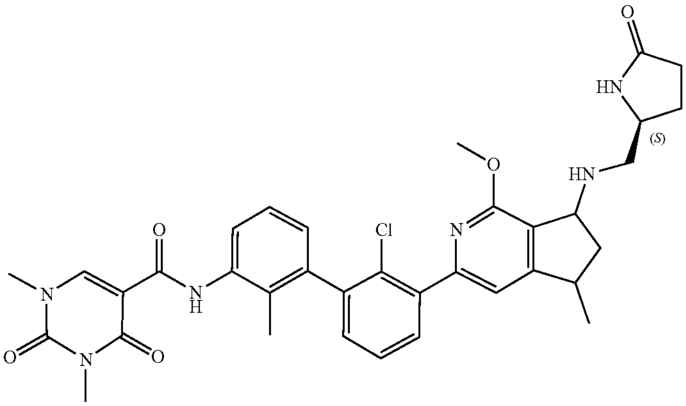 | Intermediate 10-2<br>Intermediate 7-7 |

TABLE 1-continued
| Cmpd No. | Structure | Starting materials |
|---|---|---|
| A-123 | 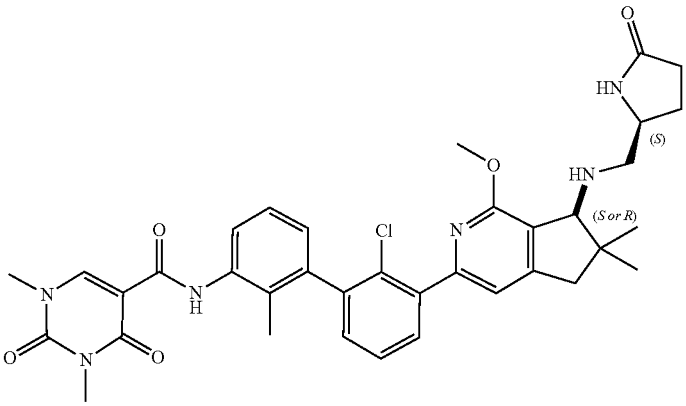 | Intermediate 10-2<br>Intermediate 5-16a |
| A-124 | 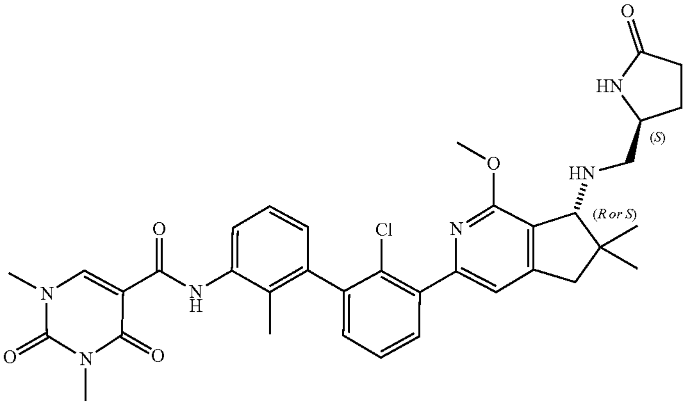 | Intermediate 10-2<br>Intermediate 5-16b |
| A-125 | 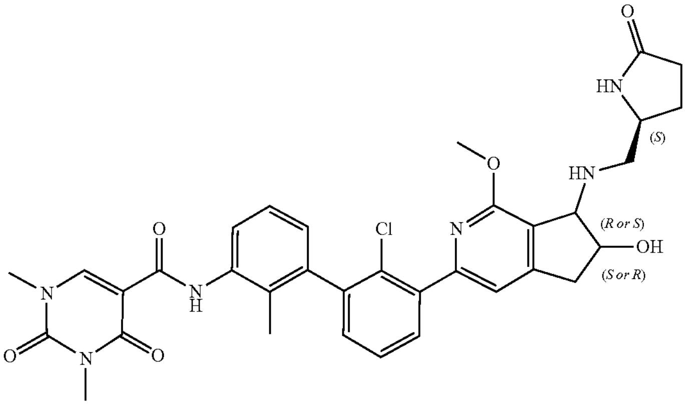 | Intermediate 10-2<br>Intermediate 5-14a |

TABLE 1-continued
| Cmpd No. | Structure | Starting materials |
|---|---|---|
| A-126 | 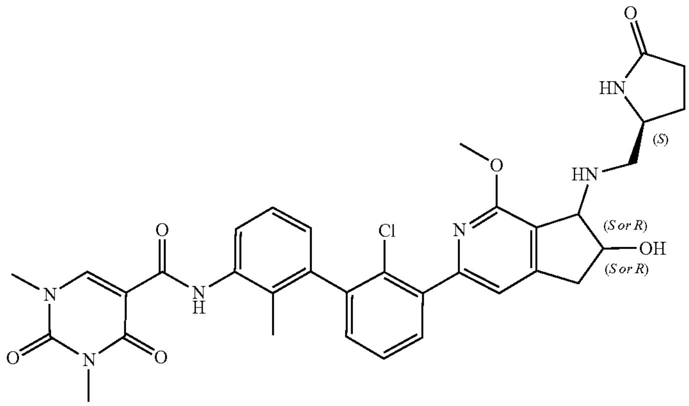 | Intermediate 10-2<br>Intermediate 5-14b |
| A-127 | 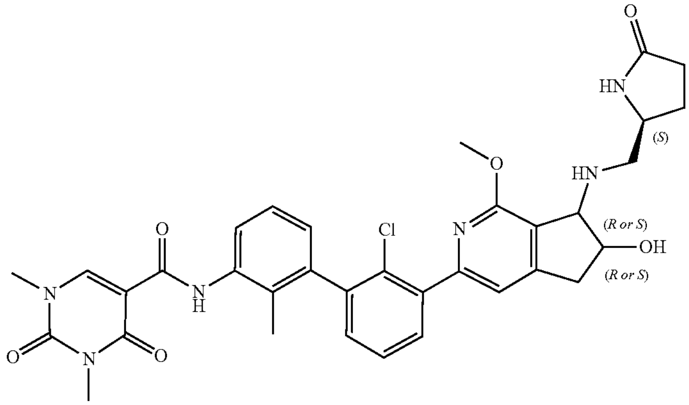 | Intermediate 10-2<br>Intermediate 5-15a |
| A-128 | 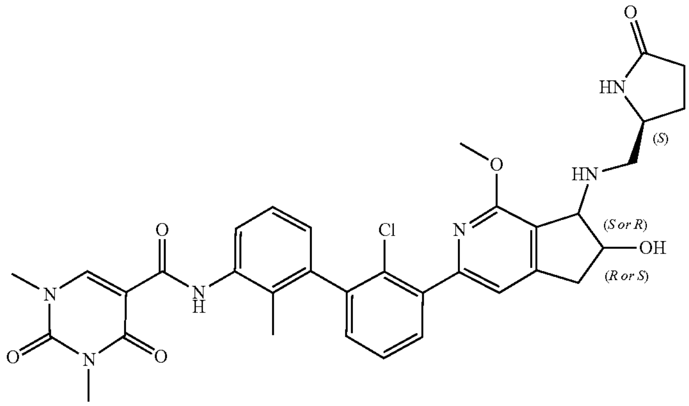 | Intermediate 10-2<br>Intermediate 5-15b |

TABLE 1-continued
| Cmpd No. | Structure | Starting materials |
|---|---|---|
| A-129 | 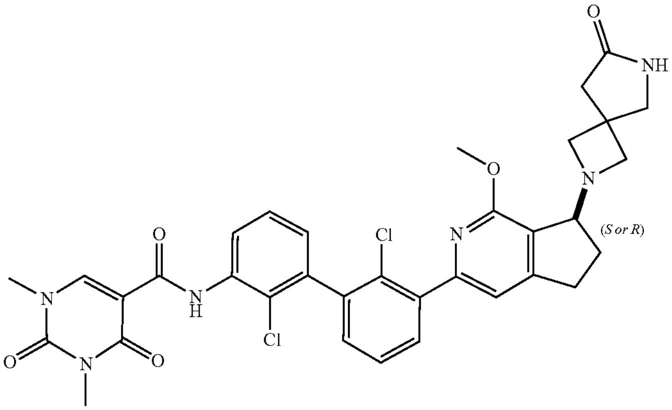 [SMILES: COc1nc(-c2cccc(-c3cccc(NC(=O)c4cn(C)c(=O)n(C)c4=O)c3Cl)c2Cl)cc2c1[C@@H](N1CC3(CNC(=O)C3)C1)CC2] | Intermediate 10-1<br>Intermediate 5-17a |
| A-130 | 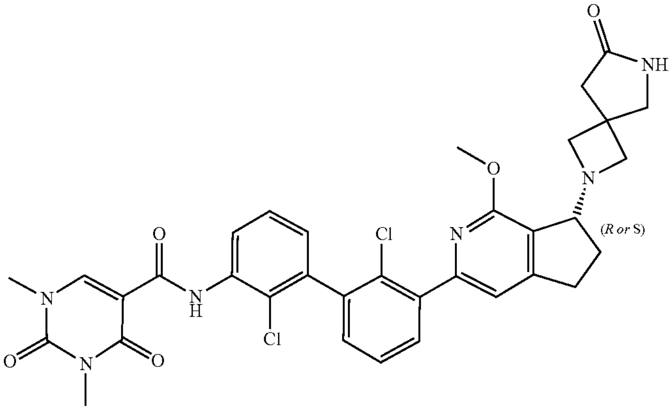 | Intermediate 10-1<br>Intermediate 5-17b |
| A-131 | 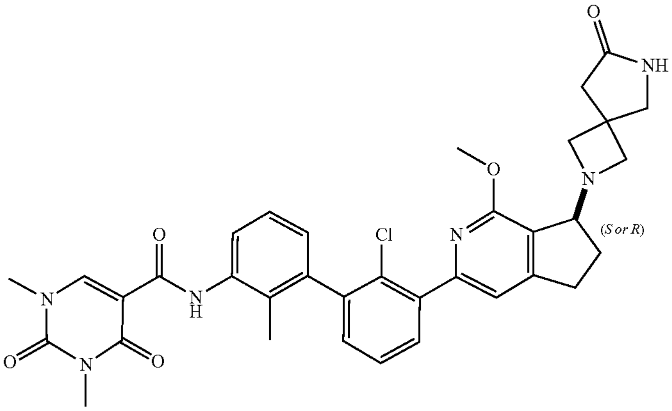 [SMILES: COc1nc(-c2cccc(-c3cccc(NC(=O)c4cn(C)c(=O)n(C)c4=O)c3C)c2Cl)cc2c1[C@@H](N1CC3(CNC(=O)C3)C1)CC2] | Intermediate 10-2<br>Intermediate 5-17a |

TABLE 1-continued
| Cmpd No. | Structure | Starting materials |
|---|---|---|
| A-132 | 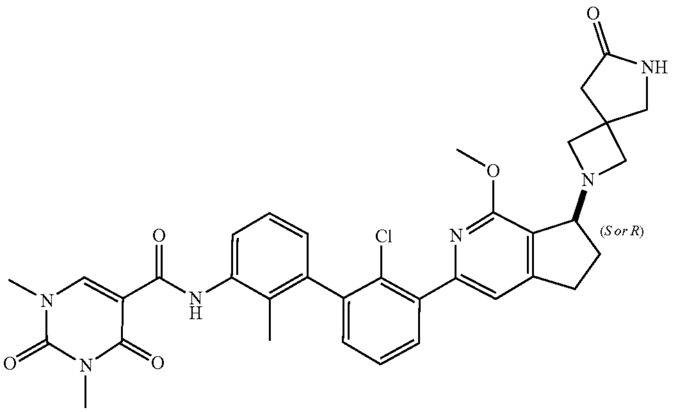 [SMILES: COc1nc(-c2cccc(-c3cccc(NC(=O)c4cn(C)c(=O)n(C)c4=O)c3C)c2Cl)cc2c1[C@@H](N1CC3(CNC(=O)C3)C1)CC2] | Intermediate 10-2<br>Intermediate 5-17b |
| A-133 | 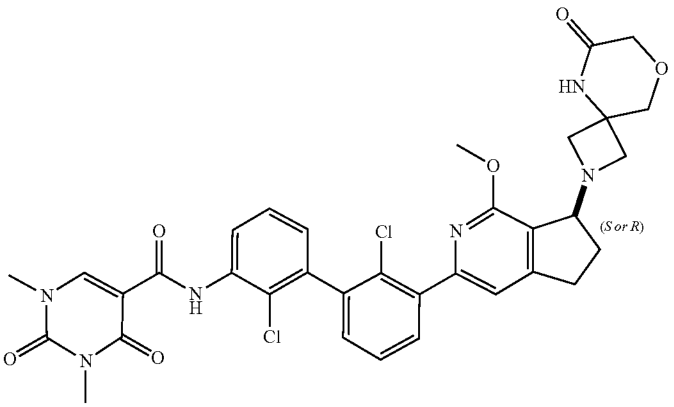 [SMILES: COc1nc(-c2cccc(-c3cccc(NC(=O)c4cn(C)c(=O)n(C)c4=O)c3Cl)c2Cl)cc2c1[C@@H](N1CC3(COCC(=O)N3)C1)CC2] | Intermediate 10-1<br>Intermediate 5-18a |
| A-134 | 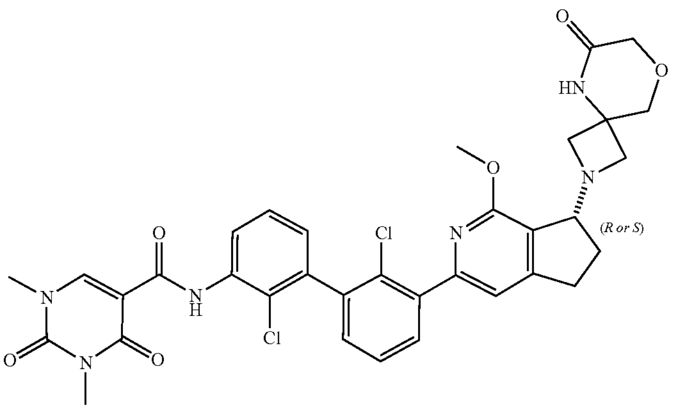 [SMILES: COc1nc(-c2cccc(-c3cccc(NC(=O)c4cn(C)c(=O)n(C)c4=O)c3Cl)c2Cl)cc2c1[C@H](N1CC3(COCC(=O)N3)C1)CC2] | Intermediate 10-1<br>Intermediate 5-18b |

TABLE 1-continued
| Cmpd No. | Structure | Starting materials |
| --- | --- | --- |
| A-135 | 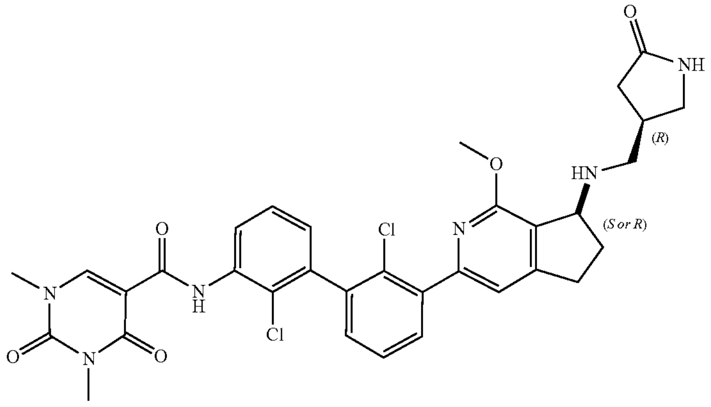 | Intermediate 10-1<br>Intermediate 5-19a |
| A-136 | 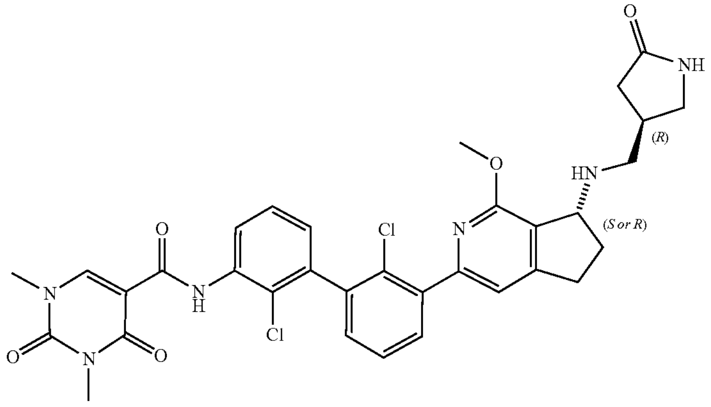 | Intermediate 10-1<br>Intermediate 5-19b |
| A-137 | 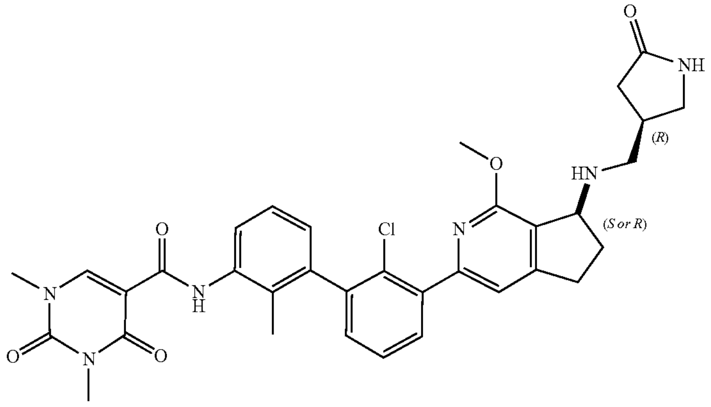 | Intermediate 10-2<br>Intermediate 5-19a |

TABLE 1-continued
| Cmpd No. | Structure | Starting materials |
| --- | --- | --- |
| A-138 | 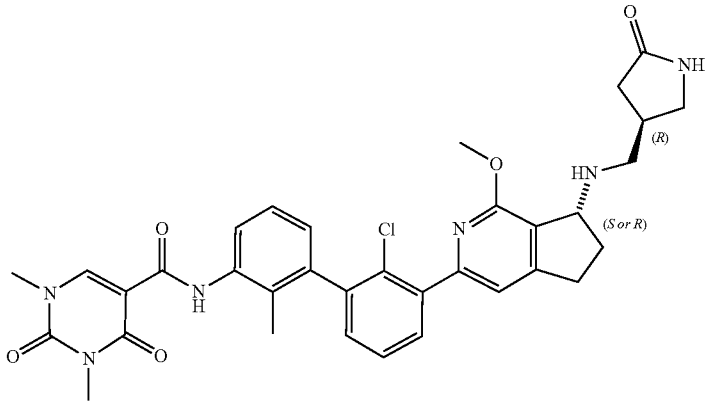 | Intermediate 10-2<br>Intermediate 5-19b |
| A-139 | 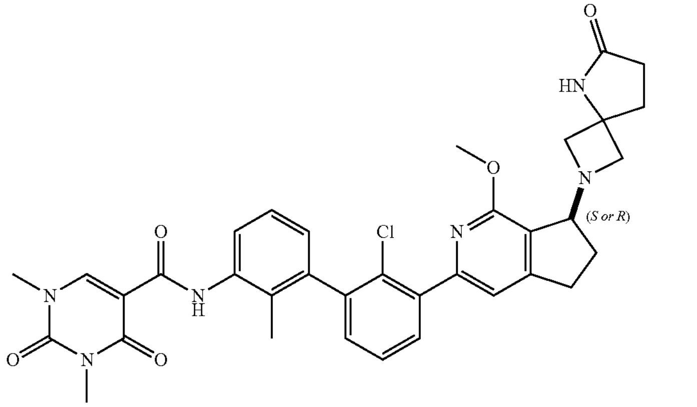 [SMILES: COc1nc(-c2cccc(-c3cccc(NC(=O)c4cn(C)c(=O)n(C)c4=O)c3C)c2Cl)cc2c1[C@@H](N1CC3(CCC(=O)N3)C1)CC2] | Intermediate 10-2<br>Intermediate 5-2a |
Example 2
Preparation of Compound B-1
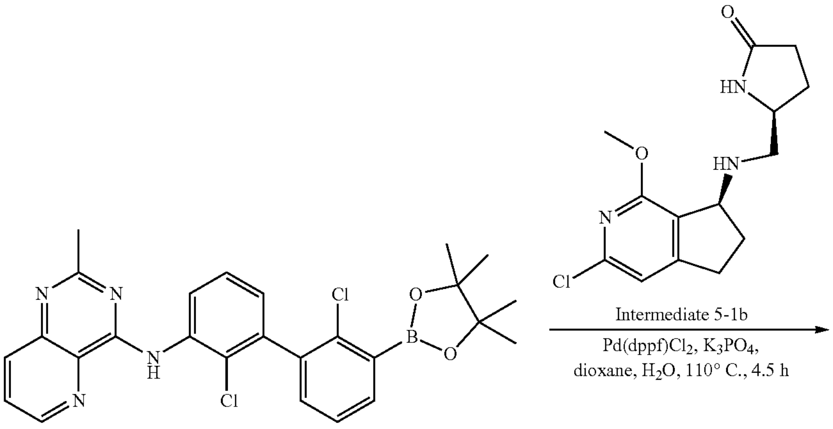
Intermediate 12-1

-continued

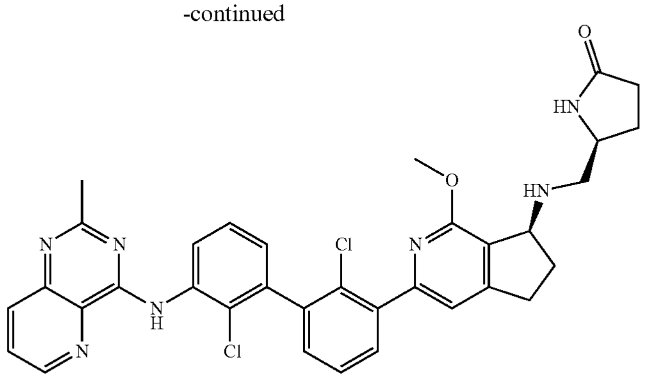

Compound B-1

A mixture of Intermediate 12-1 (64 mg, 126 μmol), Intermediate 5-1b (18 mg, 63 μmol), Pd(dppf)$Cl_2$ (4.62 mg, 6.31 μmol) and $K_3PO_4$ (40 mg, 189 μmol) in dioxane (1 mL) and $H_2O$ (0.1 mL) was degassed and purged with $N_2$ (3×). After the mixture was stirred at 110° C. for 4.5 h under $N_2$ atmosphere, the mixture was filtered and concentrated to give a residue, which was purified by prep-HPLC to give Compound B-1 (8.8 mg) as a yellow solid.

The compounds shown below in Table 2 were prepared by an analogous reaction protocol as was used for the preparation of Compound B-1 using the appropriate starting materials.

TABLE 2

| Cmpd No. | Structure | Starting Materials |
|---|---|---|
| B-2 | 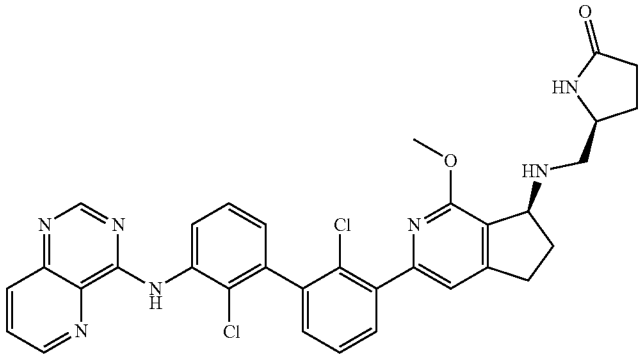 [SMILES: COc1nc(-c2cccc(-c3cccc(Nc4nccc5cccnc45)c3Cl)c2Cl)cc2c1[C@@H](NC[C@@H]1CCC(=O)N1)CC2] | Intermediate 12-2<br>Intermediate 5-1b |
| B-3 | 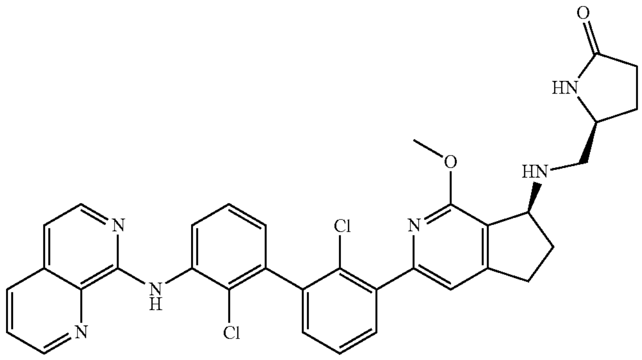 | Intermediate 12-3<br>Intermediate 5-1b |

TABLE 2-continued

| Cmpd No. | Structure | Starting Materials |
|---|---|---|
| B-4 | 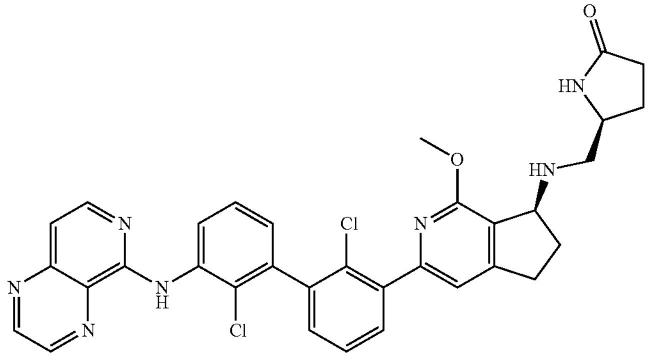 [SMILES: COc1nc(-c2cccc(-c3cccc(Nc4nccc5nccnc45)c3Cl)c2Cl)cc2c1[C@@H](NC[C@@H]1CCC(=O)N1)CC2] | Intermediate 12-4<br>Intermediate 5-1b |

Example 3

Preparation of Compound C-1

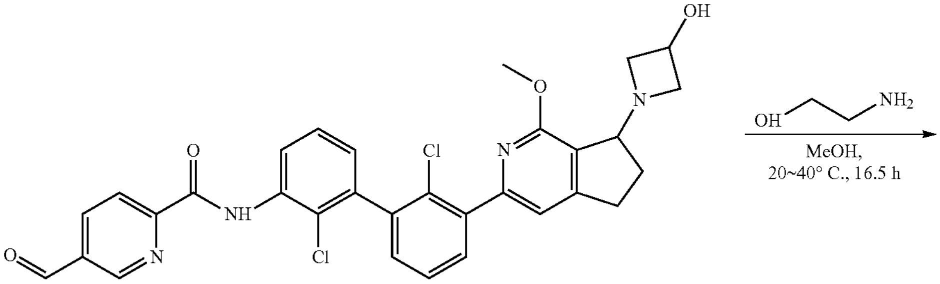

Intermediate 17-1

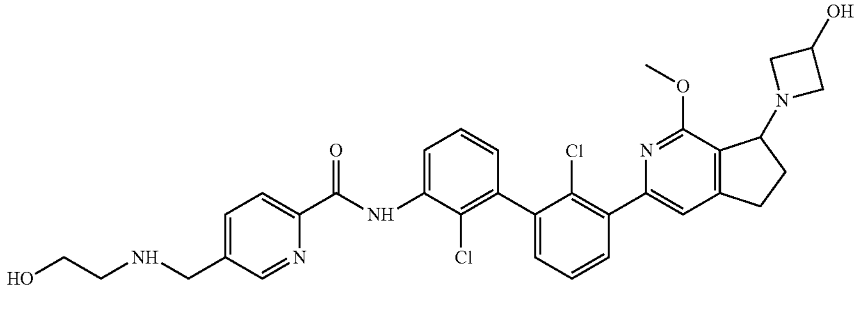

Compound C-1

The mixture of Intermediate 17-1 (37 mg, 62.8 μmol) and 2-aminoethan-1-ol (5.7 μL, 94.2 μmol) in MeOH (2 mL) was stirred at 20° C. for 0.5 h. After adding $NaBH_3CN$ (11.8 mg, 188 μmol) into the mixture, the reaction mixture was stirred at 40° C. for 16 hours. The reaction mixture was concentrated under reduced pressure, diluted with $H_2O$ (20 mL) and extracted with EtOAc (20 mL×3). The combined organic layers were dried over $Na_2SO_4$, filtered and concentrated under reduced pressure to give a residue, which was purified by prep-HPLC to give Compound C-1 (11 mg) as a yellow solid.

Example 3a

Preparation of Compound D-1

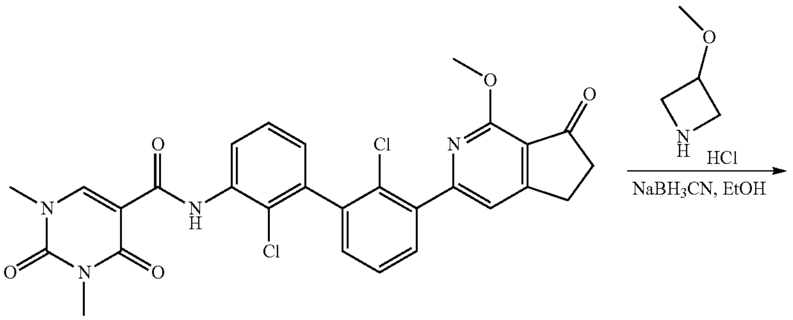

Intermediate 18-1

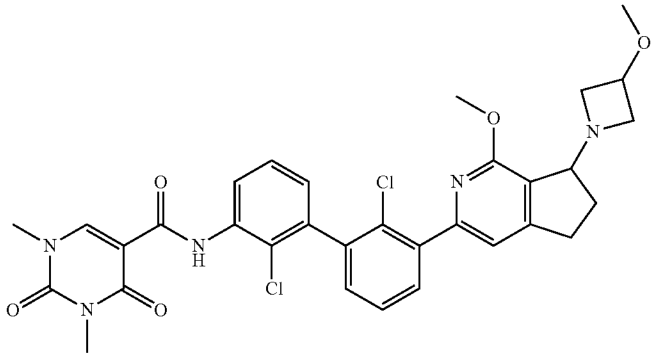

Compound D-1

A mixture of Intermediate 18-1 (100 mg, 177 μmol), 3-methoxyazetidine hydrochloride (44 mg, 354 μmol) and $NaBH_3CN$ (33 mg, 531 μmol) in EtOH (2 mL) was stirred at 50° C. for 16 h. The mixture was filtered and concentrated under reduced pressure to give a residue, which was purified by prep-HPLC to give compound D-1 (23 mg) as an off-white solid.

The compounds shown below in Table 3 were prepared by an analogous reaction protocol as was used for the preparation of Compound D-1 using the appropriate starting materials.

TABLE 3

| Cmpd No. | Structure | Starting Materials |
|---|---|---|
| D-2 | 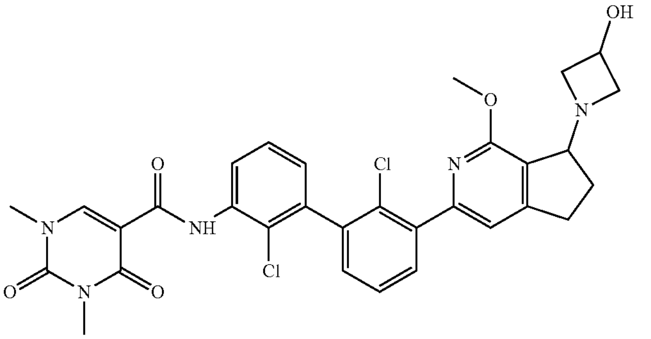 [SMILES: COc1nc(-c2cccc(-c3cccc(NC(=O)c4cn(C)c(=O)n(C)c4=O)c3Cl)c2Cl)cc2c1C(N1CC(O)C1)CC2] | 3-Hydroxyazetidine Hydrochloride Intermediate 18-1 |

TABLE 3-continued
| Cmpd No. | Structure | Starting Materials |
| --- | --- | --- |
| D-3 | 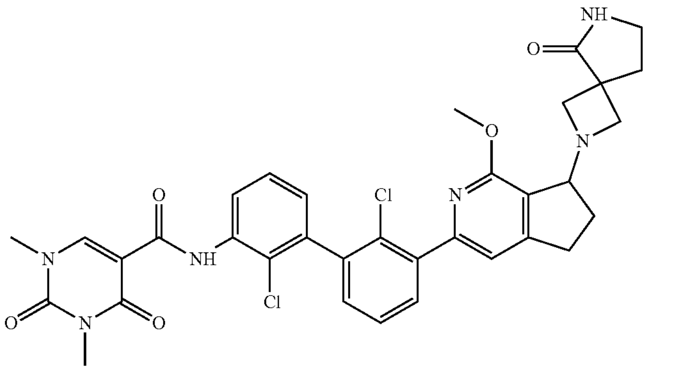 [SMILES: COc1nc(-c2cccc(-c3cccc(NC(=O)c4cn(C)c(=O)n(C)c4=O)c3Cl)c2Cl)cc2c1C(N1CC3(CCNC3=O)C1)CC2] | 2,6-Diazaspiro[3.4]octan-5-one hydrochloride Intermediate 18-1 |
| D-4 | 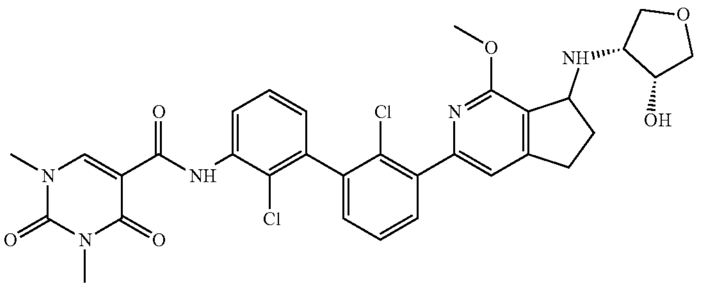 [SMILES: COc1nc(-c2cccc(-c3cccc(NC(=O)c4cn(C)c(=O)n(C)c4=O)c3Cl)c2Cl)cc2c1C(N[C@@H]1COC[C@@H]1O)CC2] | (3R,4R)-4-aminooxolan-3-ol Intermediate 18-1 |
| D-5 | 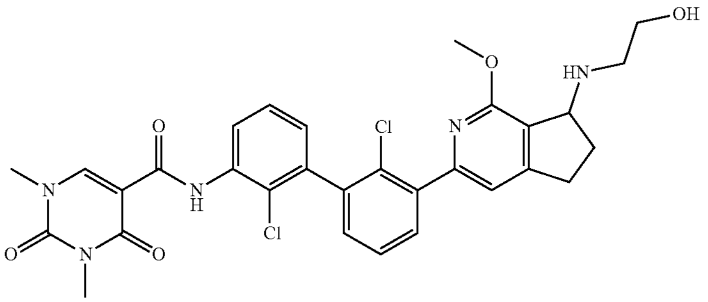 [SMILES: COc1nc(-c2cccc(-c3cccc(NC(=O)c4cn(C)c(=O)n(C)c4=O)c3Cl)c2Cl)cc2c1C(NCCO)CC2] | Ethanolamine Intermediate 18-1 |
| D-6 | 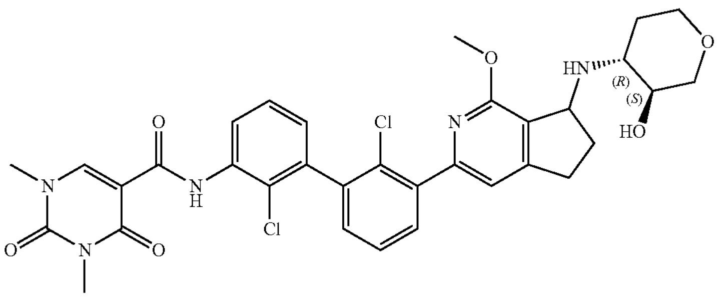 | (3S,4R)-4-aminooxan-3-ol hydrochloride Intermediate 18-1 |
| D-7 | 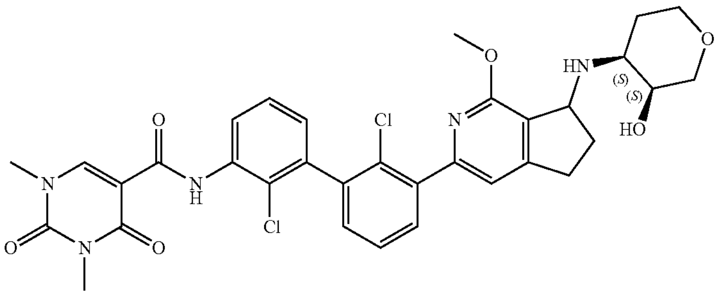 | (3S,4S)-4-aminooxan-3-ol hydrochloride Intermediate 18-1 |

TABLE 3-continued
| Cmpd No. | Structure | Starting Materials |
|---|---|---|
| D-8a | 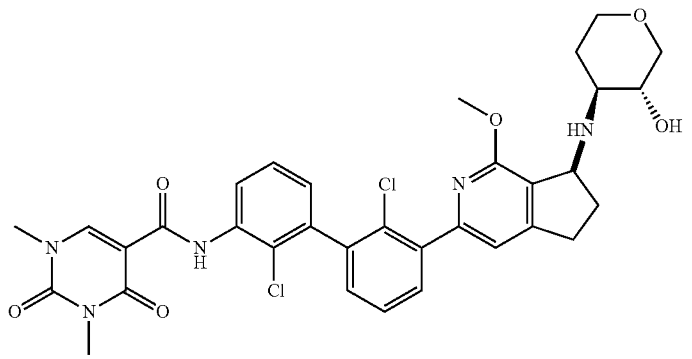 | (3R,4S)-4-aminooxan-3-ol hydrochloride Intermediate 18-1 |
| D-8b | 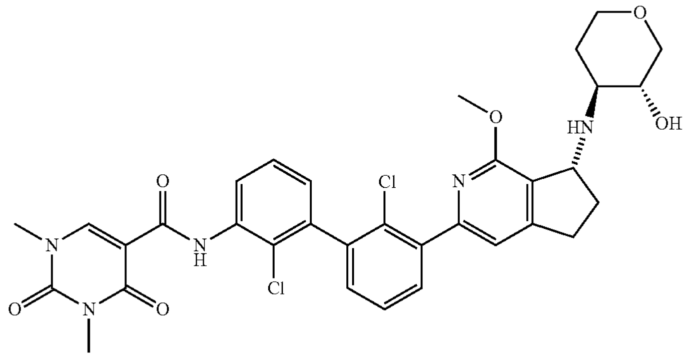 | (3R,4S)-4-aminooxan-3-ol hydrochloride Intermediate 18-1 |
| D-9 | 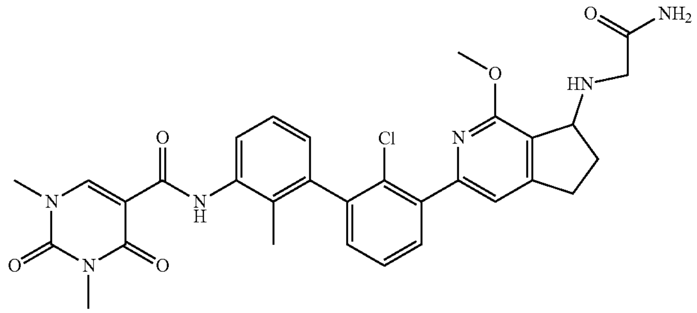 [SMILES: COc1nc(-c2cccc(-c3cccc(NC(=O)c4cn(C)c(=O)n(C)c4=O)c3C)c2Cl)cc2c1C(NCC(N)=O)CC2] | Glycinamide hydrochloride Intermediate 18-2 |
| D-10 | 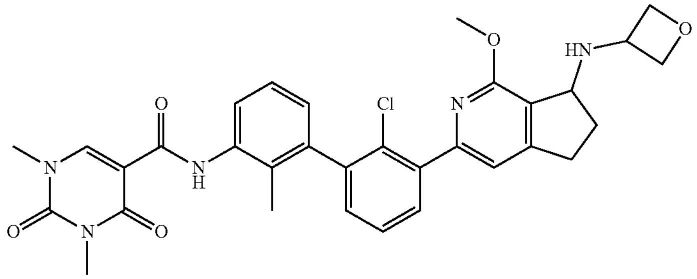 [SMILES: COc1nc(-c2cccc(-c3cccc(NC(=O)c4cn(C)c(=O)n(C)c4=O)c3C)c2Cl)cc2c1C(NC1COC1)CC2] | Oxetan-3-amine Intermediate 18-2 |

TABLE 3-continued
| Cmpd No. | Structure | Starting Materials |
|---|---|---|
| D-11 | 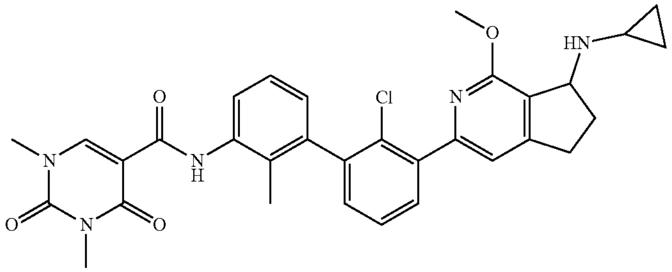 [SMILES: COc1nc(-c2cccc(-c3cccc(NC(=O)c4cn(C)c(=O)n(C)c4=O)c3C)c2Cl)cc2c1C(NC1CC1)CC2] | Cyclopropylamine Intermediate 18-2 |
| D-12 | 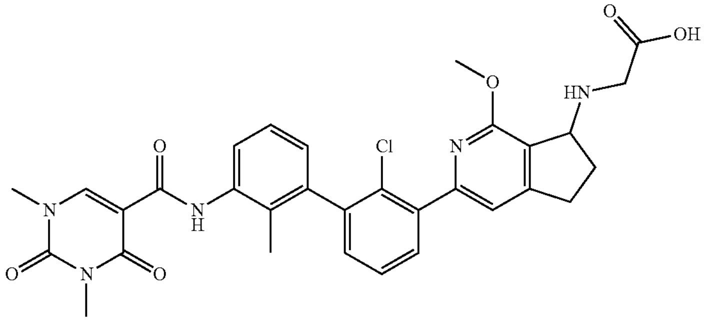 [SMILES: COc1nc(-c2cccc(-c3cccc(NC(=O)c4cn(C)c(=O)n(C)c4=O)c3C)c2Cl)cc2c1C(NCC(=O)O)CC2] | Glycine Intermediate 18-2 |
| D-13 | 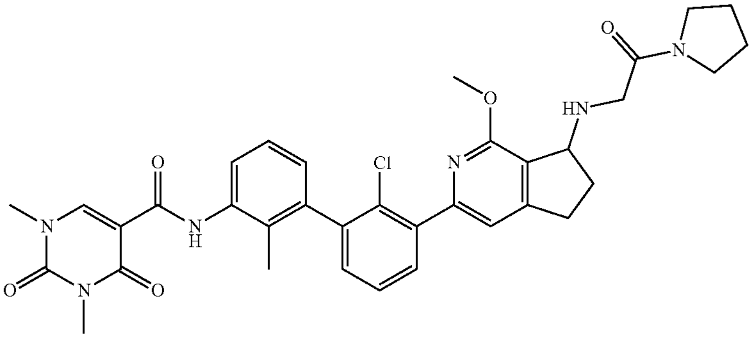 [SMILES: COc1nc(-c2cccc(-c3cccc(NC(=O)c4cn(C)c(=O)n(C)c4=O)c3C)c2Cl)cc2c1C(NCC(=O)N1CCCC1)CC2] | 2-Amino-1-(pyrrolidin-1-yl)ethanone hydrochloride Intermediate 18-2 |
| D-14 | 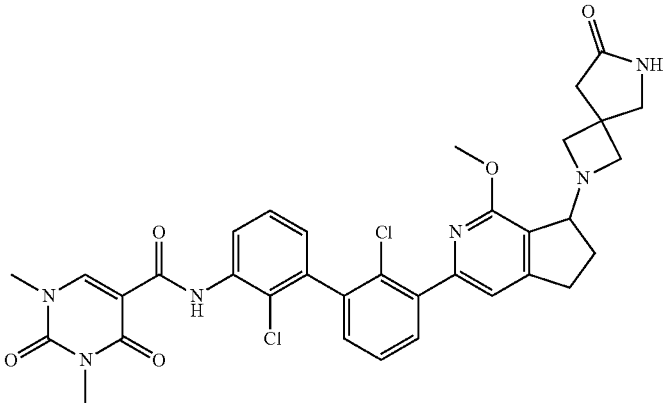 [SMILES: COc1nc(-c2cccc(-c3cccc(NC(=O)c4cn(C)c(=O)n(C)c4=O)c3Cl)c2Cl)cc2c1C(N1CC3(CNC(=O)C3)C1)CC2] | 2,6-Diazaspiro[3.4] octan-7-one Intermediate 18-1 |

TABLE 3-continued
| Cmpd No. | Structure | Starting Materials |
|---|---|---|
| D-15 | 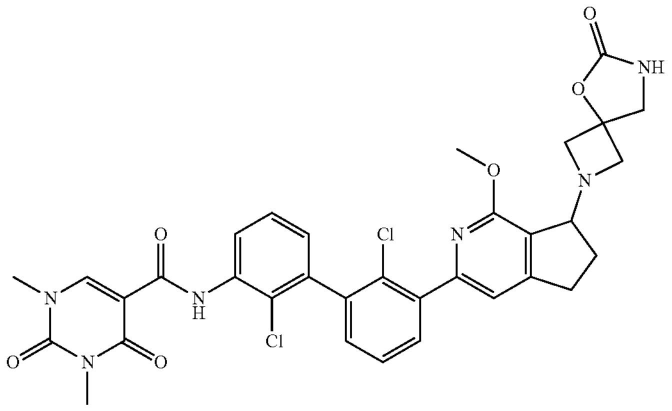 [SMILES: COc1nc(-c2cccc(-c3cccc(NC(=O)c4cn(C)c(=O)n(C)c4=O)c3Cl)c2Cl)cc2c1C(N1CC3(CNC(=O)O3)C1)CC2] | 5-oxa-2,7-diazaspiro[3.4]octan-6-one Intermediate 18-1 |
| D-16 | 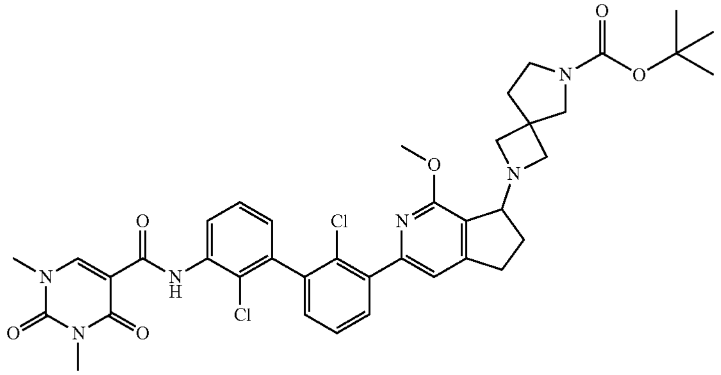 [SMILES: COc1nc(-c2cccc(-c3cccc(NC(=O)c4cn(C)c(=O)n(C)c4=O)c3Cl)c2Cl)cc2c1C(N1CC3(CCN(C(=O)OC(C)(C)C)C3)C1)CC2] | tert-butyl 2,6-diazaspiro[3.4]octane-6-carboxylate Intermediate 18-1 |
| D-17 | 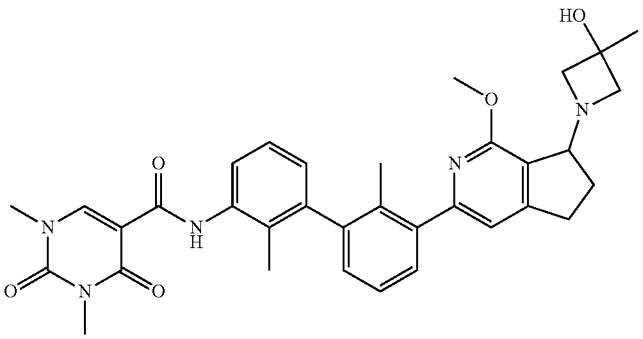 [SMILES: COc1nc(-c2cccc(-c3cccc(NC(=O)c4cn(C)c(=O)n(C)c4=O)c3C)c2C)cc2c1C(N1CC(C)(O)C1)CC2] | 3-Hydroxy-3-methylazetidine hydrochloride Intermediate 18-3 |
| D-18 | 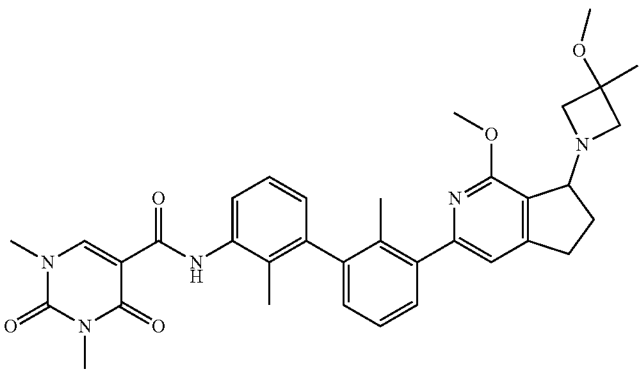 [SMILES: COc1nc(-c2cccc(-c3cccc(NC(=O)c4cn(C)c(=O)n(C)c4=O)c3C)c2C)cc2c1C(N1CC(C)(OC)C1)CC2] | 3-methoxy-3-methylazetidine hydrochloride Intermediate 18-3 |

TABLE 3-continued

| Cmpd No. | Structure | Starting Materials |
|---|---|---|
| D-19 | 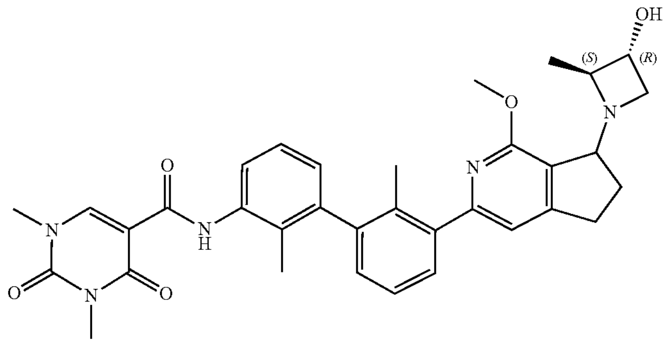 | (2S,3R)-2-Methyl-3-azetidinol Intermediate 18-3 |

Example 3b

Preparation of Compound E-1

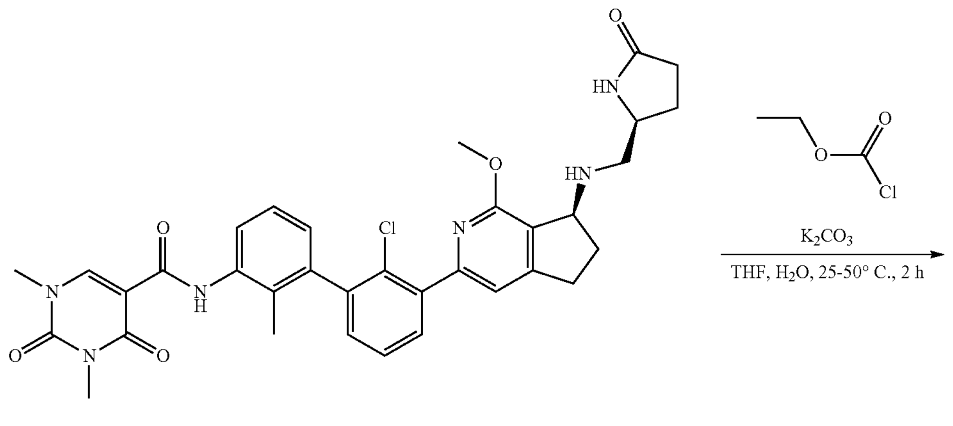

Compound A-2

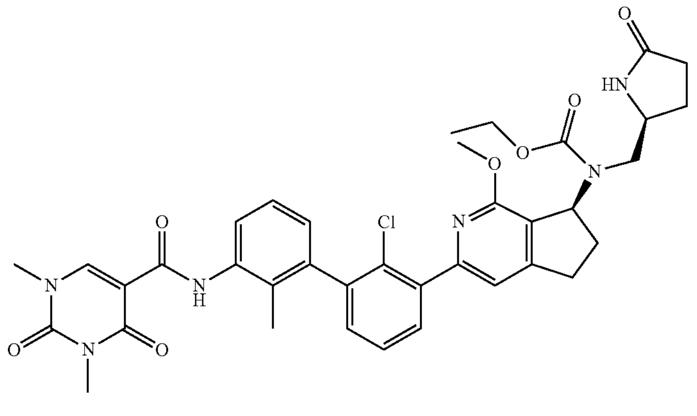

Compound E-1

To a solution of Compound A-2 (120 mg) in THF (3 mL) were added $K_2CO_3$ (46 mg, 336 μmol) and ethyl chloroformate (40 μL, 420 μmol). The mixture was stirred at 25° C. for 2 h. The mixture was filtered and concentrated under reduced pressure to give a residue, which was purified by prep-HPLC to give Compound E-1 (17 mg, 99% purity) as a yellow solid.

The compounds shown below in Table 4 were prepared by an analogous reaction protocol as was used for the preparation of Compound E-1 using the appropriate starting materials.
TABLE 4
| Cmpd No. | Structure | Starting Materials |
|---|---|---|
| E-2 | 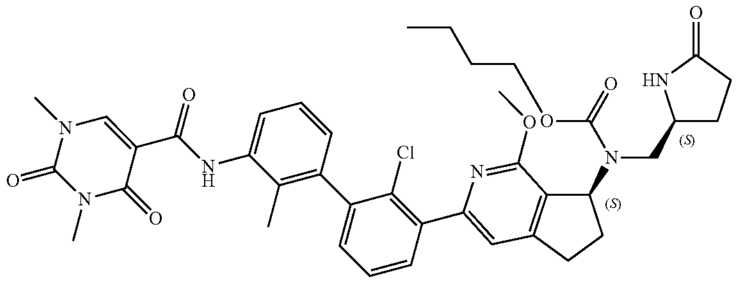 | A-2<br>n-Butyl Chloroformate |
| E-3 | 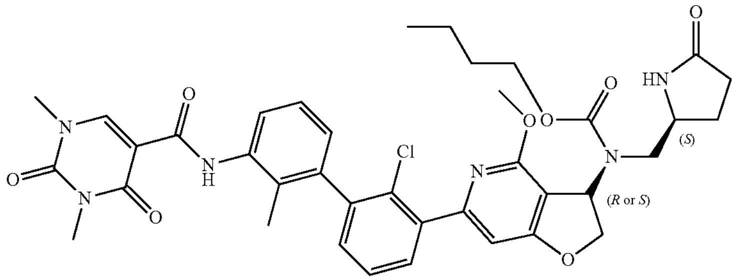 | A-19<br>Ethyl chloroformate |
Example 3c
Preparation of Compound F-1
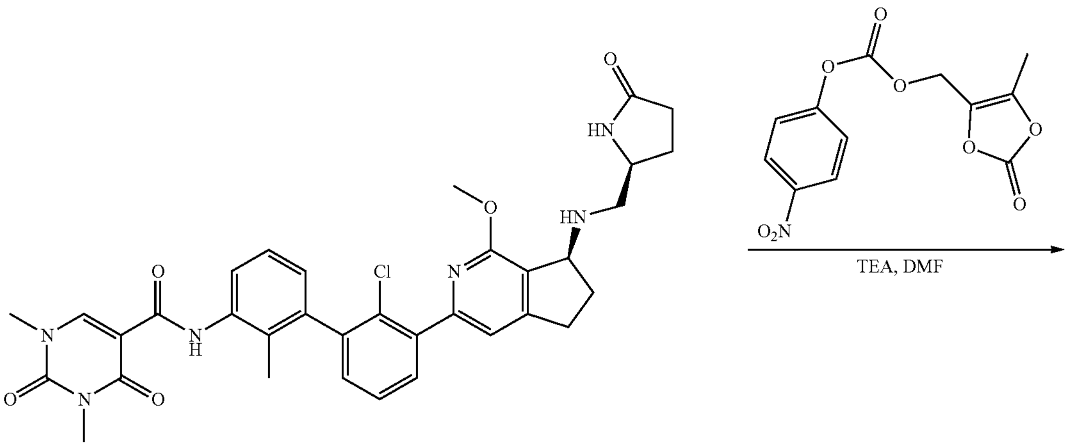
Compound A-2

-continued

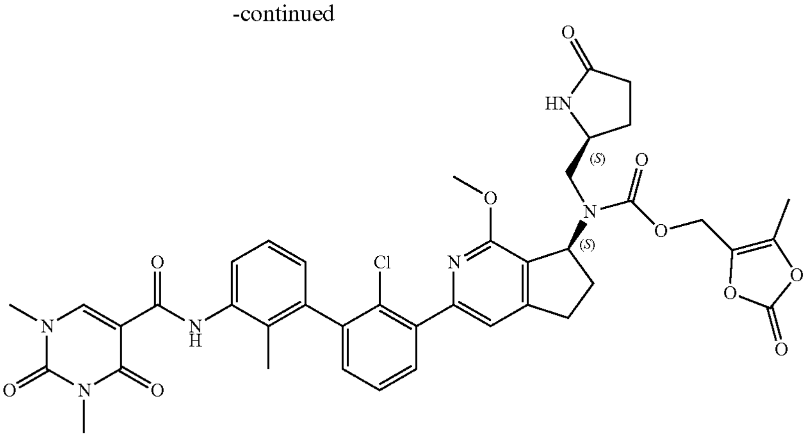

Compound F-1

To a solution of Compound A-2 (75 mg, 117 μmol) and (5-methyl-2-oxo-1,3-dioxol-4-yl)methyl 4-nitrophenyl carbonate (69 mg, 233 μmol) in DMF (1 mL) was added TEA (49 μL, 350 μmol). The mixture was stirred at 60° C. for 48 h. The mixture was concentrated under reduced pressure to give a residue, which was purified by prep-HPLC twice to give Compound F-1 (3.0 mg, 96% purity) as a white solid.

Example 3d

Preparation of Compound G-1

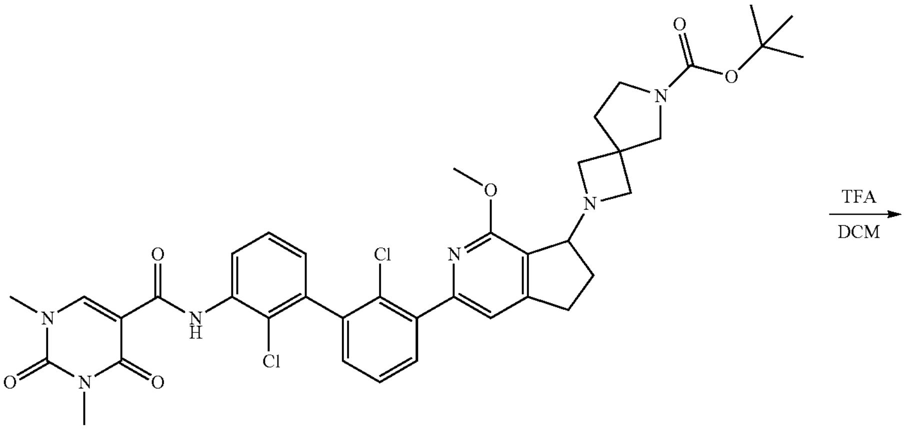

Compound D-16

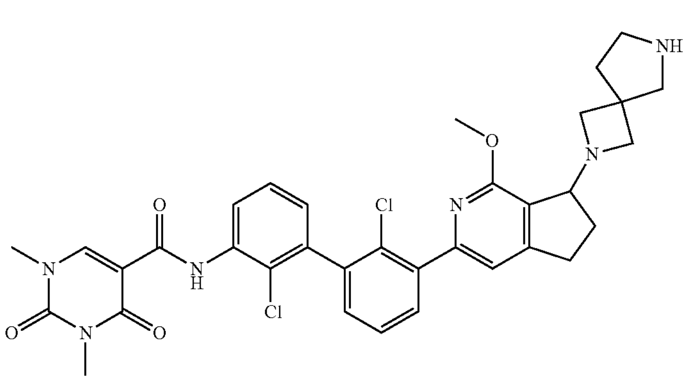

Compound G-1

To a solution of Compound D-16 (80 mg, 105 μmol) in DCM (2 mL) was added TFA (2 mL). The mixture was stirred at 20° C. for 0.5 h to give a colorless solution. The mixture was concentrated under reduced pressure to give a residue, which was purified by prep-HPLC to give Compound G-1 (6.27 mg, 97% purity) as a white solid.

Example 3e

Preparation of Compound H-1

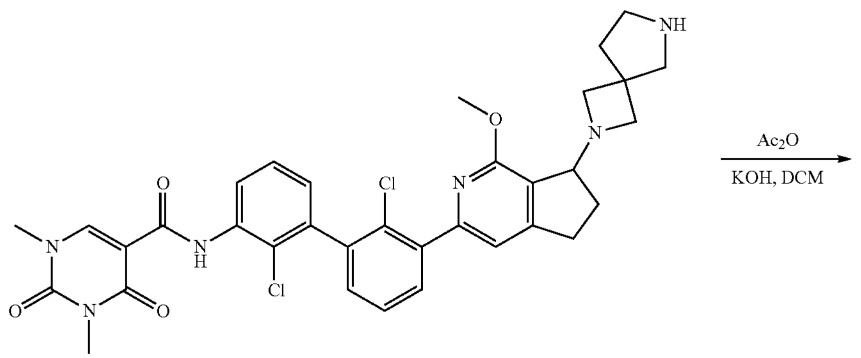

Compound G-1

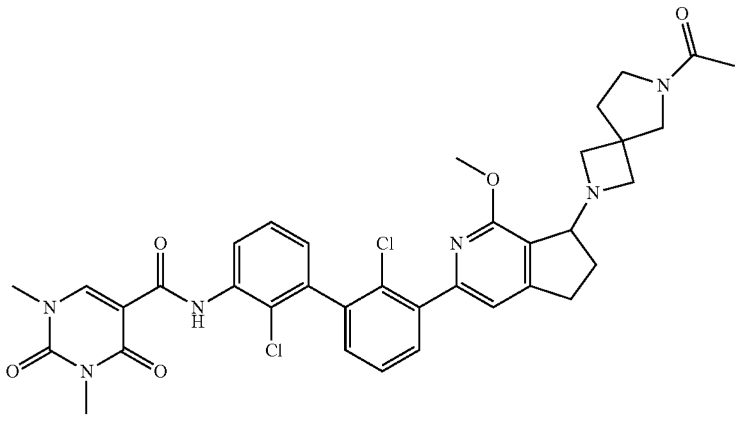

Compound H-1

To a solution of Compound G-1 (40 mg, 61 μmol) in DCM (2 mL) were added KOH (10 mg, 181 μmol) and acetic anhydride (6.0 μL, 60 μmol). The mixture was stirred at 20° C. for 2 h to give a yellow solution. The mixture was concentrated under reduced pressure to give a residue, which was purified by prep-HPLC to give Compound H-1 (9.48 mg) as a white solid.

Example 3f

Preparation of Compound I-1

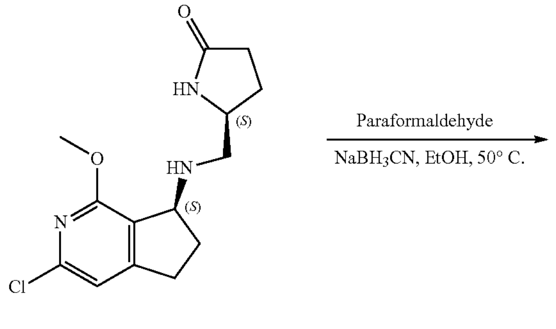

Intermediate 5-1b

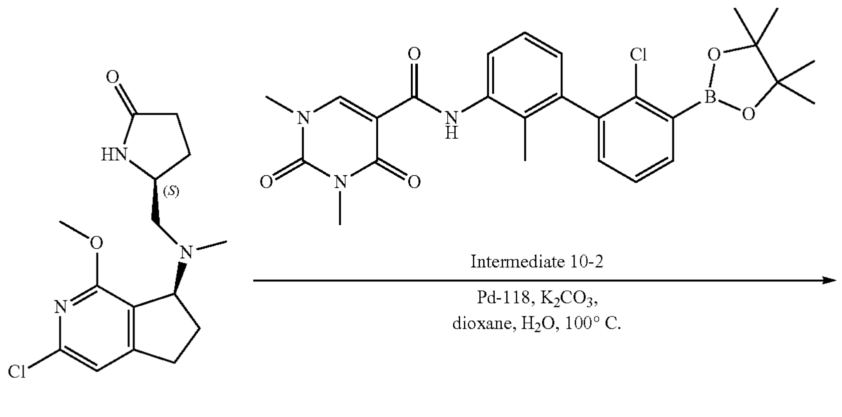

Intermediate I-1-1

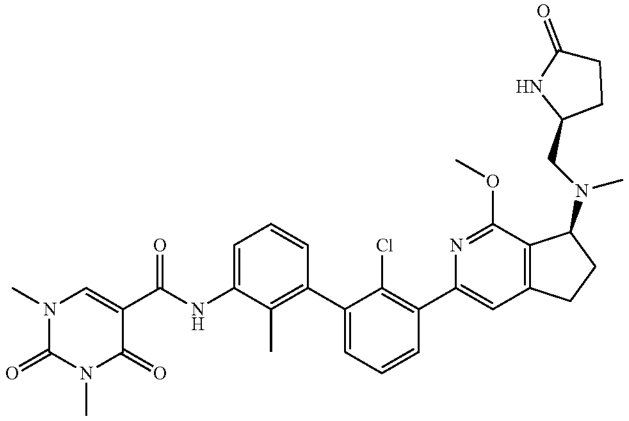

Compound I-1

A mixture of Intermediate 5-1b (50 mg, 169 μmol) and paraformaldehyde (15 mg, 507 μmol) in EtOH (1 mL) was stirred at 50° C. for 15 h. After adding $NaBH_3CN$ (53 mg, 845 μmol), the mixture was stirred at 50° C. for 1 h. The mixture was filtered and concentrated under reduced pressure to give a residue, which was purified by prep-TLC to give Intermediate I-1-1 (30 mg) as a liquid. MS: ES m/z calculated for $C_{15}H2_1C_1N_3O_2[M+H]^+$ 310.1, found 310.1.

A mixture of Intermediate I-1-1 (30 mg), Intermediate 10-2 (54 mg, 107 μmol), [1,1'-Bis(di-tert-butylphosphino) ferrocene]dichloropalladium(II) (6.3 mg, 9.68 μmol), $K_2CO_3$ (40 mg, 291 μmol) in dioxane (2 mL) and $H_2O$ (0.2 mL) was degassed and then purged with $N_2$ (3×). The mixture was stirred at 100° C. for 16 h under $N_2$ atmosphere. The mixture was filtered and concentrated under reduced pressure to give a residue, which was purified by prep-HPLC to give Compound I-1 (2.4 mg) as an off-white solid.

Example 3g

Preparation of Compound J-1

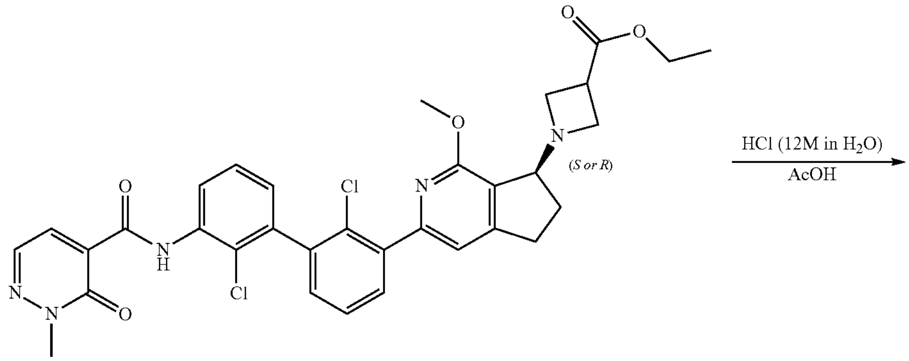

Compound A-87

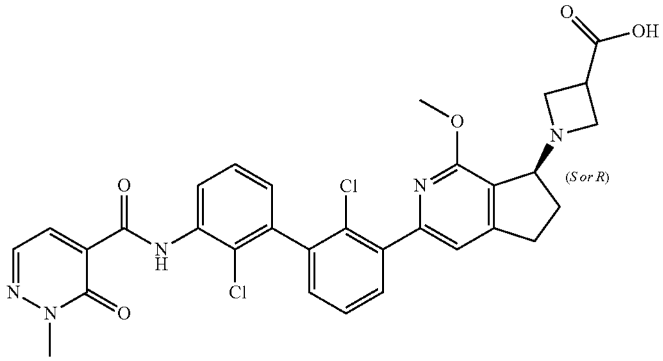

Compound J-1

A mixture of Compound A-87 (90 mg, 139 μmol) with HCl acid (12 M in $H_2O$, 1 mL) and AcOH (1 mL) was stirred at 20° C. for 16 h. The mixture was filtered and concentrated under reduced pressure to give a residue, which was purified by prep-HPLC to give Compound J-1 (12 mg) as an off-white solid.

The compounds shown below in Table 5 were prepared by an analogous reaction protocol as used for the preparation of Compound J-1 using the appropriate starting materials.

TABLE 5

| Cmpd No. | Structure | Starting Materials |
|---|---|---|
| J-2 | 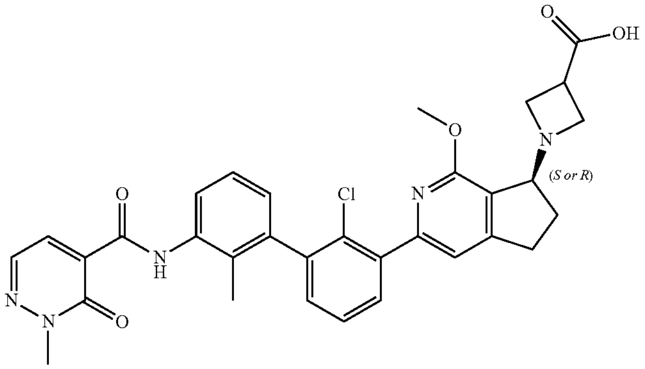 [SMILES: COc1nc(-c2cccc(-c3cccc(NC(=O)c4ccnn(C)c4=O)c3C)c2Cl)cc2c1[C@@H](N1CC(C(=O)O)C1)CC2] | Compound A-88 |

TABLE 5-continued
| Cmpd No. | Structure | Starting Materials |
|---|---|---|
| J-3 | 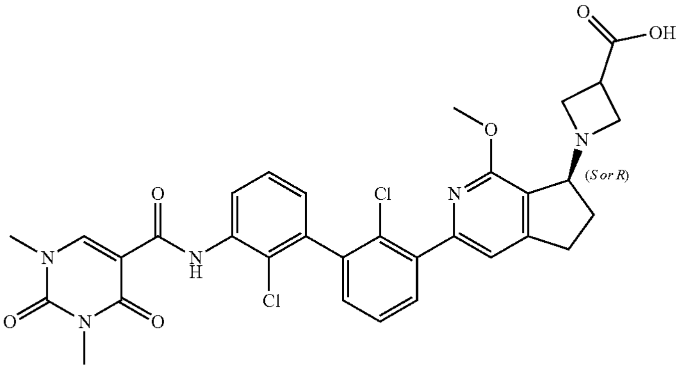 [SMILES: COc1nc(-c2cccc(-c3cccc(NC(=O)c4cn(C)c(=O)n(C)c4=O)c3Cl)c2Cl)cc2c1[C@@H](N1CC(C(=O)O)C1)CC2] | Compound A-85 |
| J-4 | 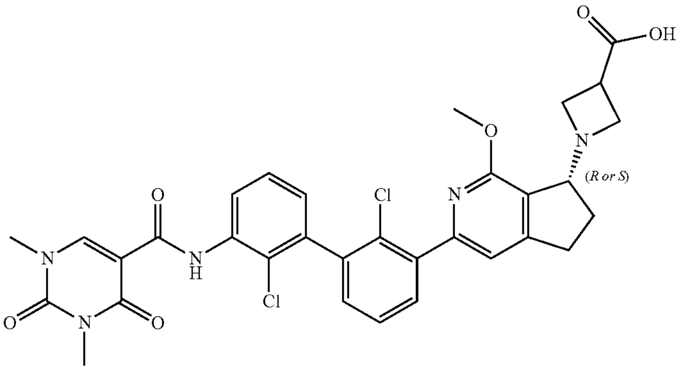 [SMILES: COc1nc(-c2cccc(-c3cccc(NC(=O)c4cn(C)c(=O)n(C)c4=O)c3Cl)c2Cl)cc2c1[C@H](N1CC(C(=O)O)C1)CC2] | Compound A-86 |
Example 3h
Preparation of Compound K-1a & K-1b
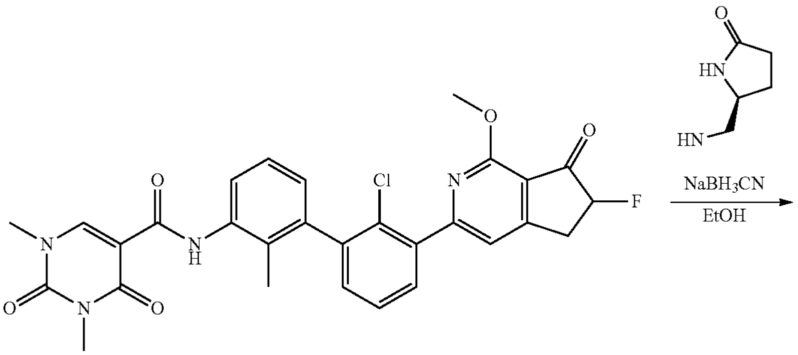
Intermediate 18-4

-continued

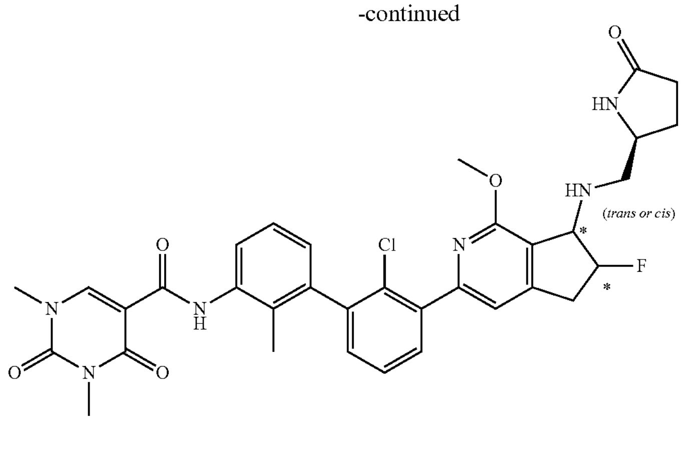

Compound K-1a

+

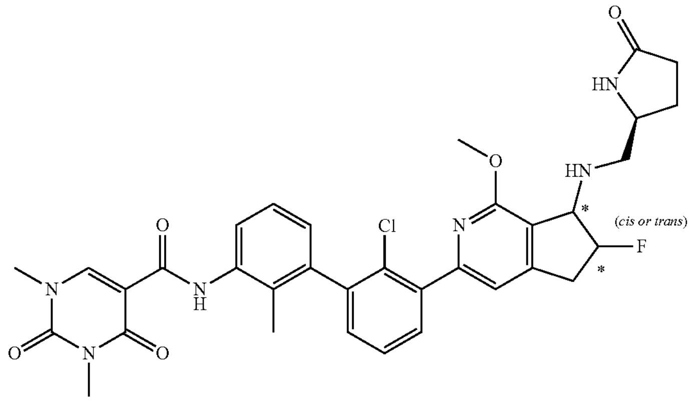

Compound K-1b

To a solution of Intermediate 18-4 (50 mg, 88.81 μmol) in MeOH (1 mL) was added (5S)-5-(aminomethyl) pyrrolidin-2-one HCl salt (20 mg, 133 μmol). The mixture was stirred at 50° C. for 13 h. To the mixture was added $NaBH_3CN$ (17 mg, 266 μmol) at 20° C. The mixture was stirred at 50° C. for 3 h. The mixture was filtered to give a filtrate, which was purified by prep-HPLC to give Compound K-1a (3.3 mg) as a white solid and Compound K-1b (3.81 mg) as white solid.

Example 3i

Preparation of Compound L-1a & L-1b

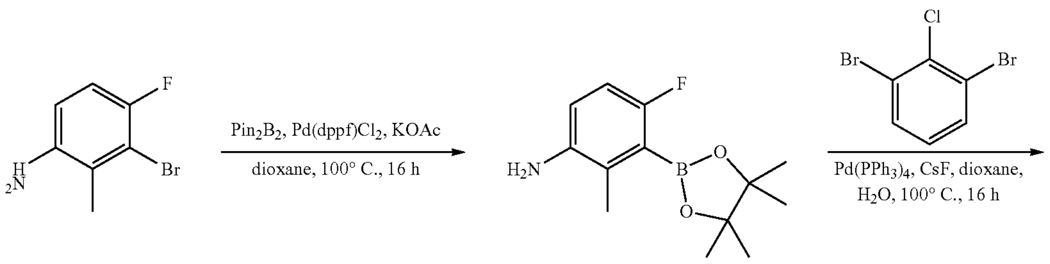

L-1-4

-continued
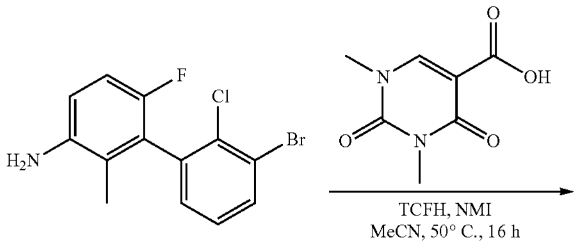
L-1-3
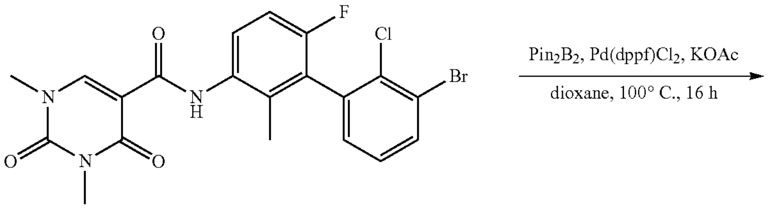
L-1-2
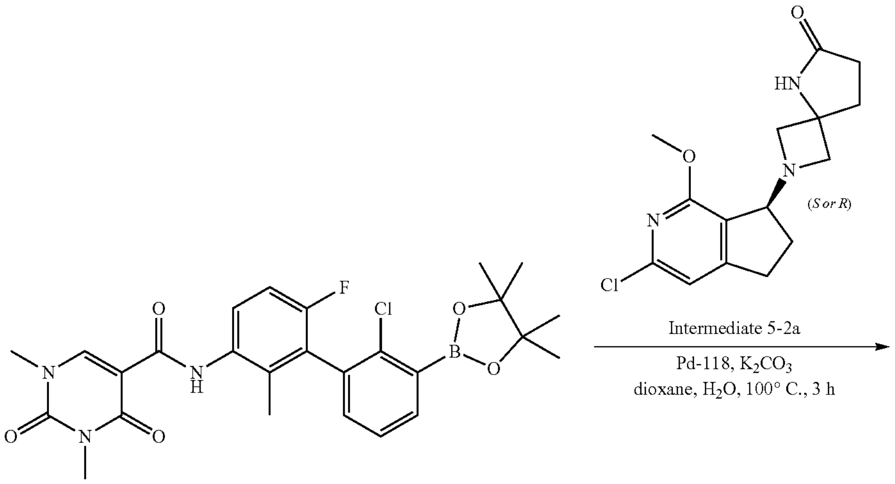
L-1-1
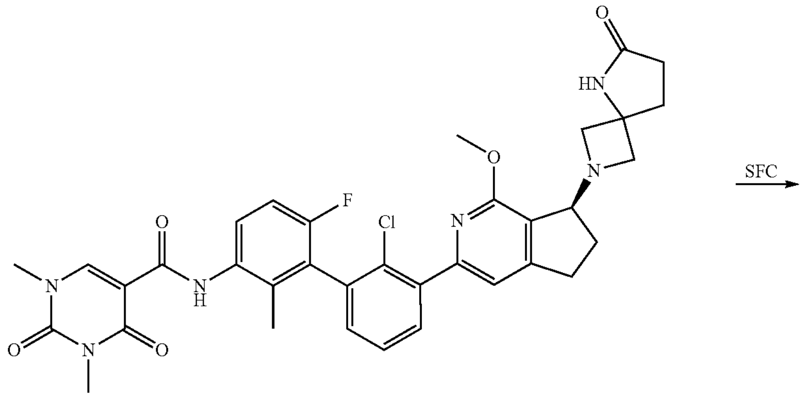
L-1

-continued

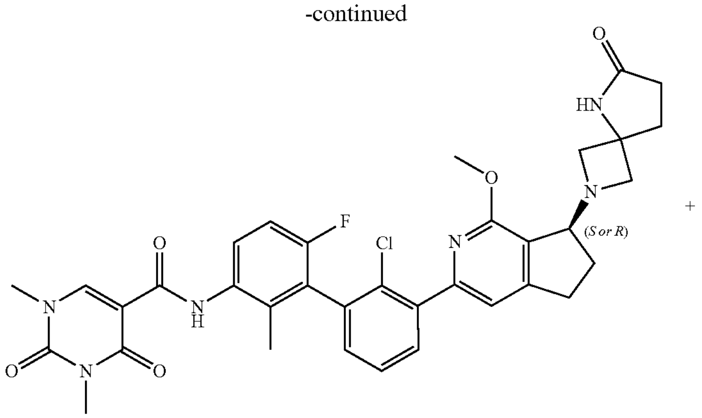

Atropisomer - (R or S)
L-1a

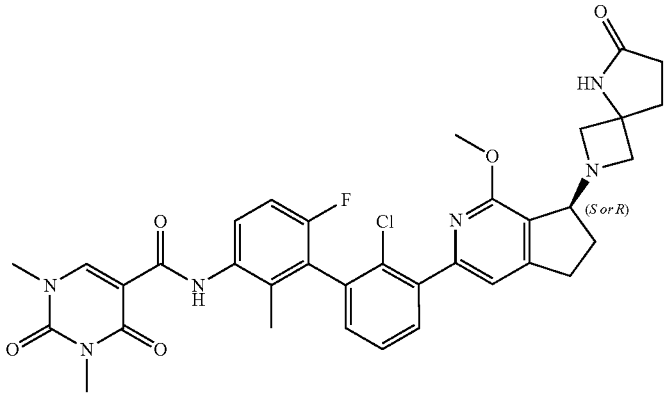

Atropisomer - (S or R)
L-1b

A mixture of 3-Bromo-4-fluoro-2-methylaniline (390 mg, 1.91 mmol), Bis(pinacolato)diboron (1.21 g, 4.78 mmol), Pd(dppf)$Cl_2$ (140 mg, 191 μmol) and AcOK (563 mg, 5.73 mmol) in dioxane (10 mL) was degassed and purged with $N_2$ (3×). The mixture was stirred at 100° C. for 16 h under $N_2$ atmosphere. The mixture was filtered and concentrated under reduced pressure to give a residue, which was purified by flash silica gel chromatography to give Intermediate L-1-4 (390 mg). MS: ES m/z calculated for $C_{13}H_{20}BFNO_2$ $[M+H]^+$ 252.1, found 252.3.

A mixture of Intermediate L-1-4 (390 mg), 1,3-dibromo-2-chlorobenzene (840 mg, 3.11 mmol), $Pd(PPh_3)_4$(180 mg, 155 μmol) and CsF (708 mg, 4.66 mmol) in dioxane (5 mL) and $H_2O$ (0.5 mL) was degassed and purged with $N_2$ (3×). The mixture was stirred at 100° C. for 16 h under $N_2$ atmosphere. The mixture was filtered and concentrated under reduced pressure to give a residue, which was purified by flash silica gel chromatography to give Intermediate L-1-3 (190 mg) was obtained as a yellow liquid. MS: ES m/z calculated for $C_{13}H_{11}BrClFN_2$$[M+H]^+$ 314.0, found 314.0.

To a solution of Intermediate L-1-3 (190 mg) and 1,3-dimethyl-2,4-dioxo-1,2,3,4-tetrahydro-5-pyrimidinecarboxylic acid (167 mg, 906 μmol) in MeCN (3 mL) was added chloro-N,N,N',N'-tetramethylformamidinium hexafluorophosphate (TCFH, 339 mg, 1.21 mmol) and N-methyl imidazole (NMI, 124 mg, 1.51 mmol). The mixture was stirred at 50° C. for 16 h to give a yellow mixture. The mixture was filtered and concentrated under reduced pressure to give a residue, which was triturated with ethyl acetate at 25° C. for 1 h to give Intermediate L-1-2 (130 mg) as a white solid. MS: ES m/z calculated for $C_{20}H_{17}BrClFN_3O_3$ $[M+H]^+$ 480.0, found 480.0.

A mixture of Intermediate L-1-2 (130 mg, 270 μmol), bis(pinacolato)diboron (172 mg, 676 μmol), Pd(dppf)$Cl_2$ (20 mg, 27 μmol) and KOAc (80 mg, 811 μmol) in dioxane (5 mL) was degassed and purged with $N_2$ (3×). The mixture was stirred at 100° C. for 16 h under $N_2$ atmosphere. The mixture was filtered and concentrated under reduced pressure to give a residue, which was purified by flash silica gel chromatography to give Intermediate L-1-1 (230 mg) as a yellow liquid. MS: ES m/z calculated for $C_{26}H_{29}BClFN_3O_5$ $[M+H]^+$ 528.2, found 528.3.

A mixture of Intermediate L-1-1 (76 mg, 144 μmol), Intermediate 5-2a (37 mg, 120 μmol), $K_2CO_3$ (50 mg, 360 μmol) and Pd-118 (7.8 mg, 12 μmol) in dioxane (1.5 mL) and $H_2O$ (0.15 mL) was degassed and purged with $N_2$ (3×). The mixture was stirred at 100° C. for 3 h under $N_2$ atmosphere. The mixture was filtered and concentrated under reduced pressure to give a residue, which was purified by prep-HPLC to give Compound L-1 (34 mg, 99% purity) as a yellow solid. MS: ES m/z calculated for $C_{35}H_{34}ClFN_6O_5$$[M+H]^+$ 673.23, found 673.6.

Compound L-1 (10 mg) was separated by SFC (Instrument: SFC-80; Column: DAICEL CHIRALPAK AS (250 mm*30 mm, 10 um); Condition: A: $CO_2$; B: 0.1% $NH_3H_2O$ ETOH; Begin B: 60; End B: 60; Flow Rate (mL/min): 80;

Injections: 90) to give Compound L-1a (2.46 mg, 98% purity, 96% ee) and Compound L-1b (2.95 mg, 98% purity, 100% ee) as white solid.
Example 3J-1
Preparation of Compound M-1a & M-1b
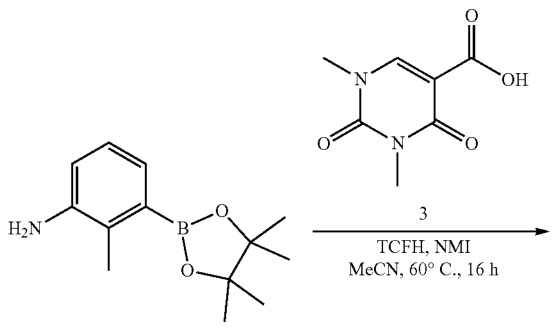
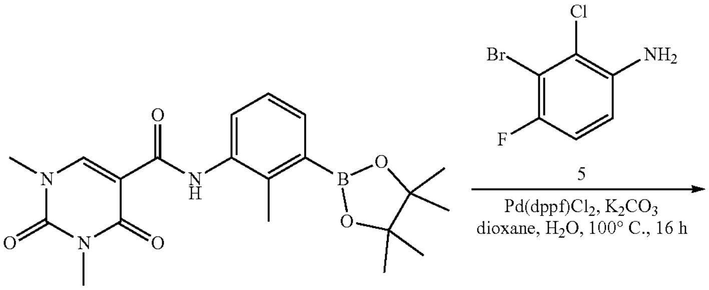
M-1-4
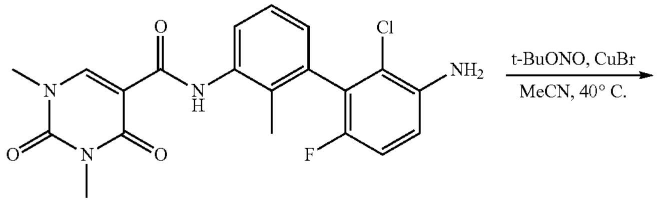
M-1-3
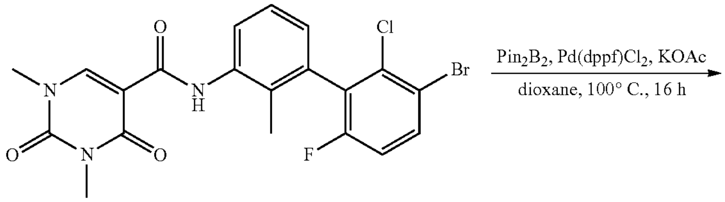
M-1-2

-continued
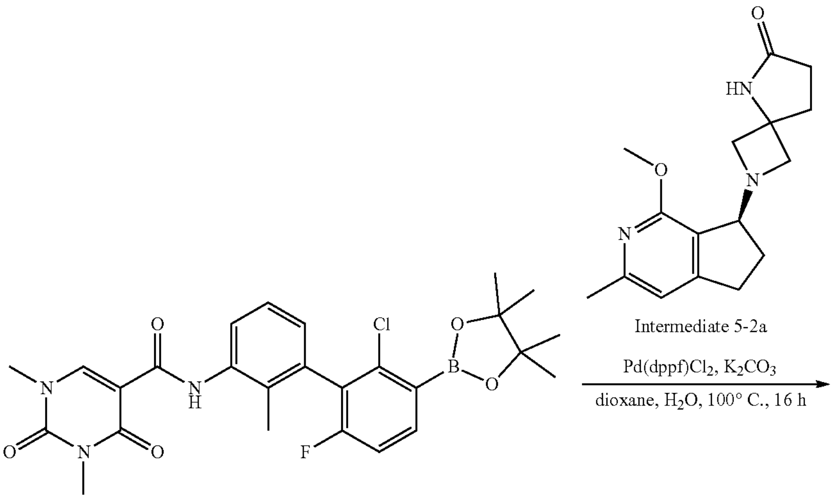
M-1-1
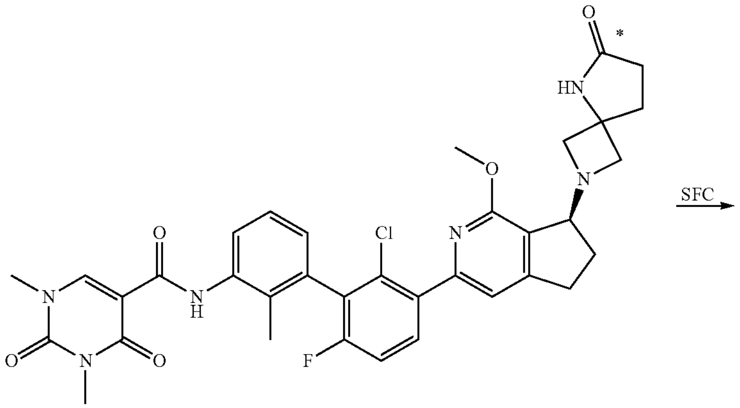
M-1
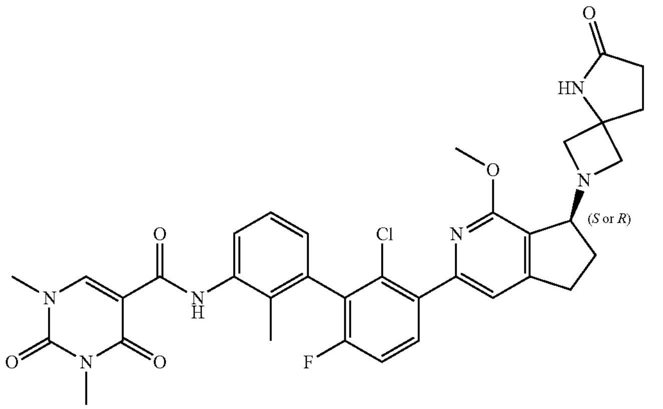
Atropisomer -(R or S)
M-1a
+

-continued

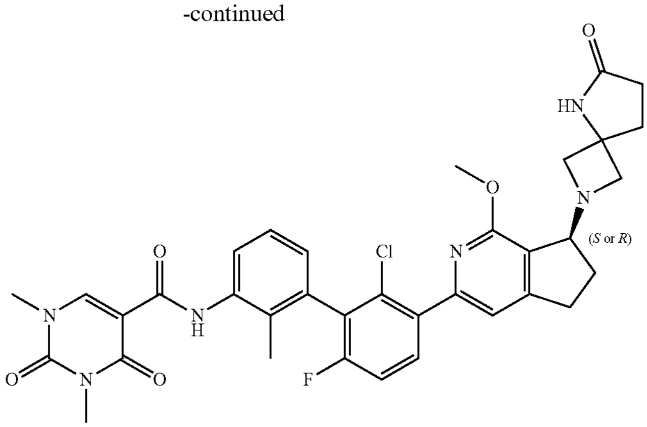

Atropisomer -(R or S)

M-1b

To a solution of 2-methyl-3-(4,4,5,5-tetramethyl-1,3,2-dioxaborolan-2-yl)aniline (3.80 g, 16.3 mmol) and 1,3-dimethyl-2,4-dioxo-1,2,3,4-tetrahydro-5-pyrimidinecarboxylic acid (3 g, 16.29 mmol) in MeCN (30 mL) was added chloro-N,N,N',N'-tetramethylformamidinium hexafluorophosphate (TCFH, 9.14 g, 32.6 mmol) and N-methyl imidazole (NMI, 3.34 g, 40.73 mmol, 3.25 mL). The mixture was stirred at 60° C. for 16 h. The mixture was filtered and concentrated under reduced pressure to give a residue, which was triturated with EtOAc (30 mL) at 25° C. for 10 min to give Intermediate M-1-4 (4.5 g) as a white solid.

A mixture of Intermediate M-1-4 (3.5 g, 8.77 mmol), 3-bromo-2-chloro-4-fluorobenzenamine (1.97 g, 8.77 mmol), $K_2CO_3$ (3.63 g, 26.3 mmol) and Pd(dppf)$Cl_2$ (641 mg, 877 μmol) in dioxane (35 mL) and $H_2O$ (3.5 mL) was degassed and purged with $N_2$ (3×). The mixture was stirred at 100° C. for 16 h under $N_2$ atmosphere. The mixture was filtered and concentrated under reduced pressure to give a residue, which was purified by flash silica gel chromatography to give Intermediate M-1-3 (2.2 g) as a yellow solid. MS: ES m/z calculated for $C_{20}H_{19}ClFN_4O_3$[M+H]$^+$ 417.0, found 417.1.

To a solution of Intermediate M-1-3 (1.7 g, 4.08 mmol) in MeCN (15 mL) was added CuBr (878 mg, 6.12 mmol) and isopentyl nitrite (956 mg, 8.16 mmol). The mixture was stirred at 40° C. for 16 h. The mixture was filtered and concentrated under reduced pressure to give a residue, which was purified by flash silica gel chromatography to give Intermediate M-1-2 (1.2 g) as a yellow solid.

A mixture of Intermediate M-1-2 (1.49 g, 3.10 mmol), bis(pinacolato)diboron (866 mg, 3.41 mmol), KOAc (913 mg, 9.30 mmol) and Pd(dppf)$Cl_2$ (227 mg, 310 μmol, 0.1 eq.) in dioxane (15 mL) was degassed and purged with $N_2$ (3×). The mixture was stirred at 100° C. for 16 h under $N_2$ atmosphere. The mixture was filtered and concentrated to give a residue, which was purified by flash silica gel chromatography (ISCO®; 12 g SepaFlash® Silica Flash Column, Eluent of 0-50% ethyl acetate/petroleum ether gradient @ 60 mL/min) to give Intermediate M-1-1 (1.1 g, 43.99% yield, 70% purity) as a yellow solid. MS: ES m/z calculated for $C_{26}$H29BClF$N_3O_5$[M+H]$^+$ 528.2, found 528.1.

A mixture of Intermediate M-1-1 (211 mg), Intermediate 5-2a (80 mg, 260 μmol), $K_2CO_3$ (108 mg, 780 μmol) and Pd-118 (16.9 mg, 26 μmol) in dioxane (2 mL) and $H_2O$ (0.2 mL) was degassed and purged with $N_2$ (3×). The mixture was stirred at 100° C. for 16 h under $N_2$ atmosphere. The mixture was filtered and concentrated under reduced pressure to give a residue, which was purified by prep-HPLC to give Compound M-1 (45 mg) as a white solid. MS: ES m/z calculated for $C_{35}H_{35}ClFN_6O_5$[M+H]$^+$ 673.2, found 673.5.

Compound M-1 (45 mg) was separated by SFC (Instrument: SFC-80; Column: DAICEL CHIRALPAK AD (250 mm*30 mm, 10 um); Condition: A: $CO_2$; B: 0.1% $NH_3H_2O$ EtOH; Begin B: 60; End B: 60; Flow Rate (mL/min): 80; Injections: 90). The separated peaks were purified by purified by prep-HPLC, Column: Xtimate C18 100*30 mm*10 um; Condition: water (0.225% FA)-ACN; Begin B: 25; End B: 55; Gradient Time (min): 10; 100% B Hold Time (min): 2; Injections: 1) to give Compound M-1a (4.77 mg, 100% ee, >99% purity) and Compound M-1b (5.01 mg, 99% ee, >99% purity) as a white solid.

Example 3J-2
Preparation of Compound M-2a & M-2b
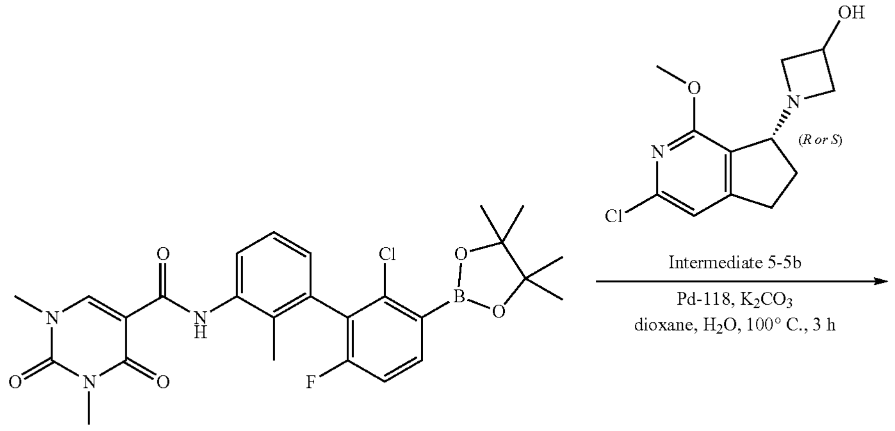
M-1-1
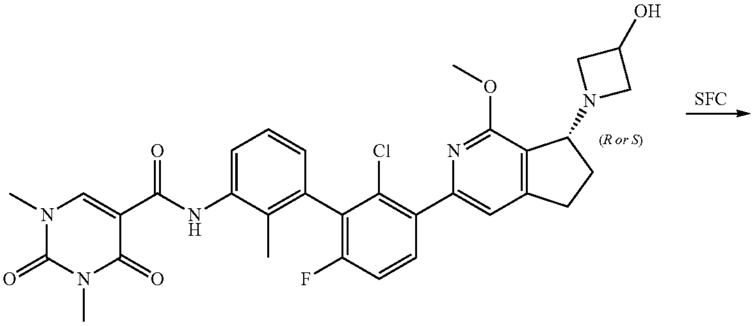
M-2
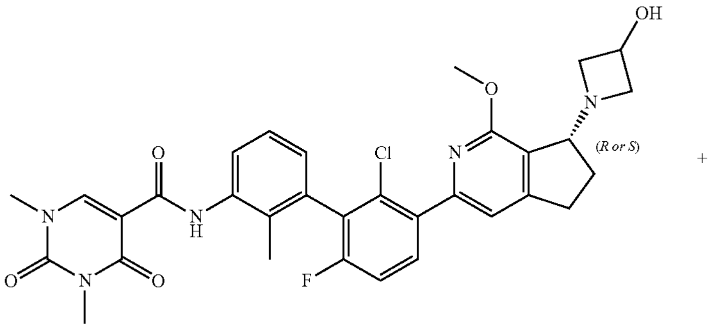
Atropisomer -(R or S)
M-2a -continued

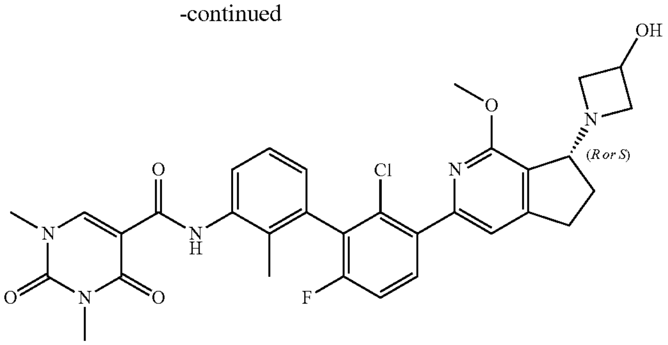

Atropisomer -(S or R)
M-2b

A solution of Intermediate M-1-1 (150 mg, 284 μmol), Intermediate 5-5b (60 mg, 237 μmol), $K_2CO_3$ (98 mg, 711 μmol) and Pd-118 (15 mg, 24 μmol) in dioxane (2 mL) and $H_2O$ (0.2 mL) was degassed and purged with $N_2$ (3×). The mixture was stirred at 100° C. for 3 h under $N_2$ atmosphere. The mixture filtered and concentrated under reduced pressure to give a residue, which was purified by prep-HPLC to give Compound M-2 (32 mg) as an off-white solid. MS: ES m/z calculated for $C_{32}H_{31}ClFN_5O_5[M+H]^+$ 621.2, found 620.5.

Compound M-2 (32 mg) was separated by SFC (Instrument: SFC-80; Column: DAICEL CHIRALPAK AS (250 mm*30 mm, 10 um); Condition: A: $CO_2$; B: 0.1% $NH_3H_2O$ EtOH; Begin B: 30; End B: 30; Flow Rate (mL/min): 70; Injections: 90) to give Compound M-2a (7.5 mg, 94.5% ee, 96% purity) as a white solid and Compound M-2b (6.6 mg, 97.3% ee, 96% purity) as a white solid.

Example 3J-3

Preparation of Compound M-3a & M-3b

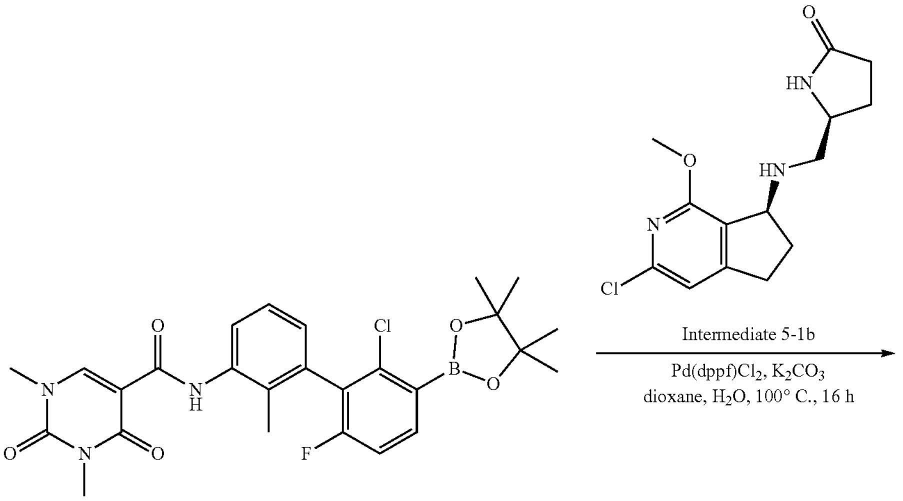

M-1-1

-continued

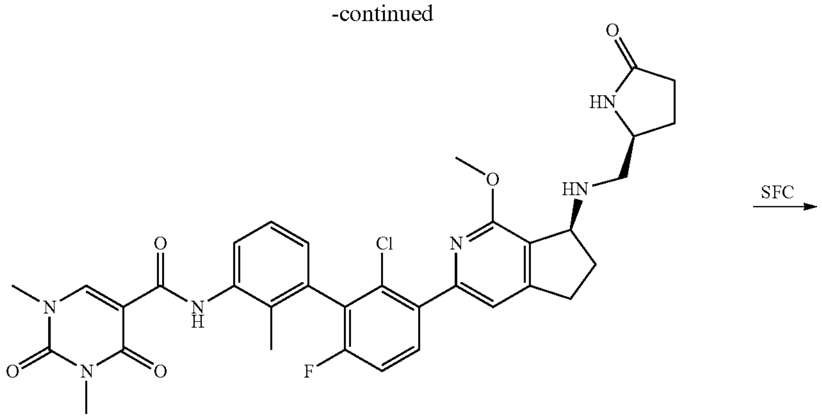

M-3

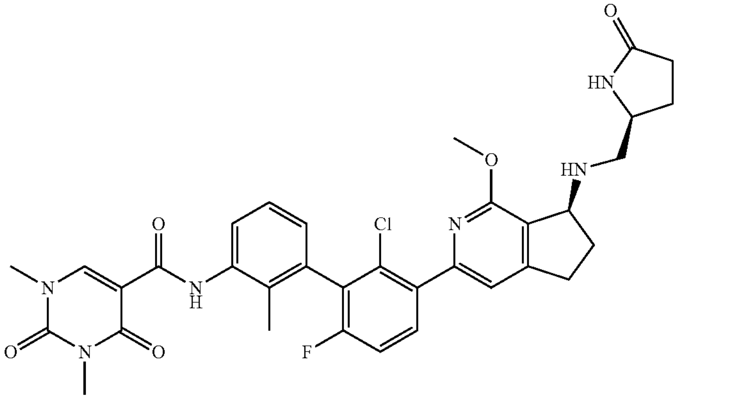

+

Atropisomer -(R or S)
M-3a

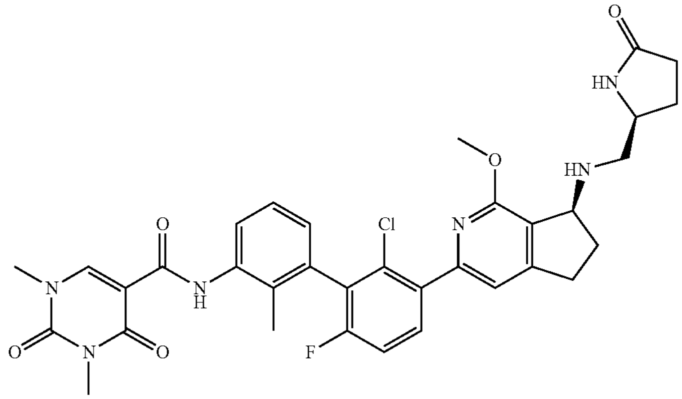

Atropisomer -(S or R)
M-3b

A mixture of Intermediate M-1-1 (151 mg), Intermediate 5-1b (55 mg, 186 μmol), $K_2CO_3$ (77 mg, 558 μmol) and Pd-118 (12 mg, 18.6 μmol) in dioxane (2 mL) and $H_2O$ (0.2 mL) was degassed and purged with $N_2$ (3×). The mixture was stirred at 100° C. for 16 h under $N_2$ atmosphere. The mixture was filtered and concentrated under reduced pressure to give a residue, which was purified by prep-HPLC to give Compound M-3 (80 mg) as a brown solid. MS: ES m/z calculated for $C_{34}H_{35}ClFN_6O_5[M+H]^+$ 661.2, found 661.2.

Compound M-3 (80 mg) was separated by SFC (Instrument: SFC-80; Column: Column: DAICEL CHIRALPAK OD (250 mm*30 mm, 10 um); Condition: A: $CO_2$; B: 0.1% $NH_3H_2O$ MeOH; Begin B: 60; End B: 60; Flow Rate (mL/min): 80; Injections: 150). The two separate peaks were re-purified by prep-HPLC to give Compound M-3a (16.5 mg, 96.38% ee, 99.76% purity) and Compound M-3b (6.5 mg, 96.98% ee, 99.71% purity) as a white solid.

Example 4
Additional Compounds
Other compounds, including those provided in Embodiments 145-147 and below, can be prepared applying similar procedures as those described herein.
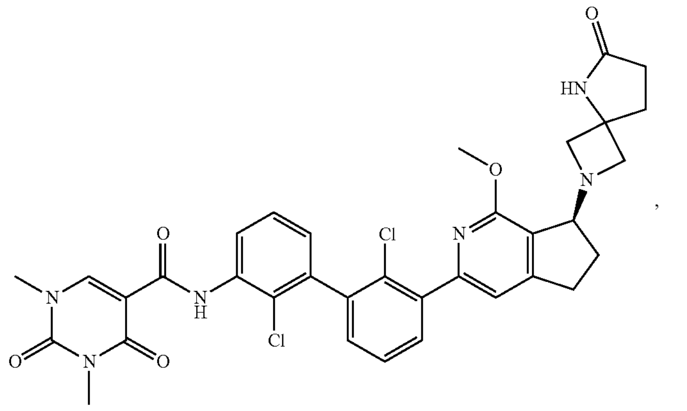
,
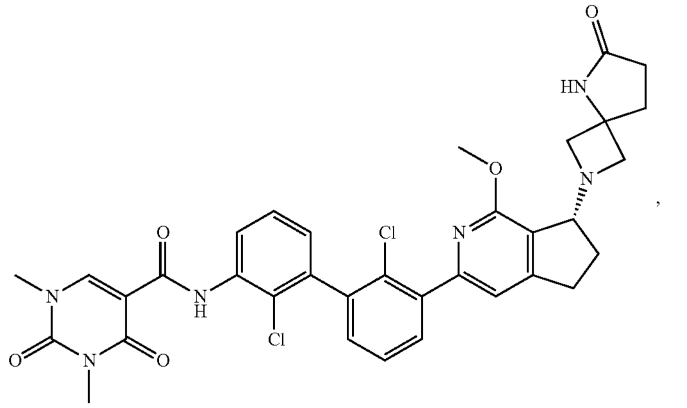
,
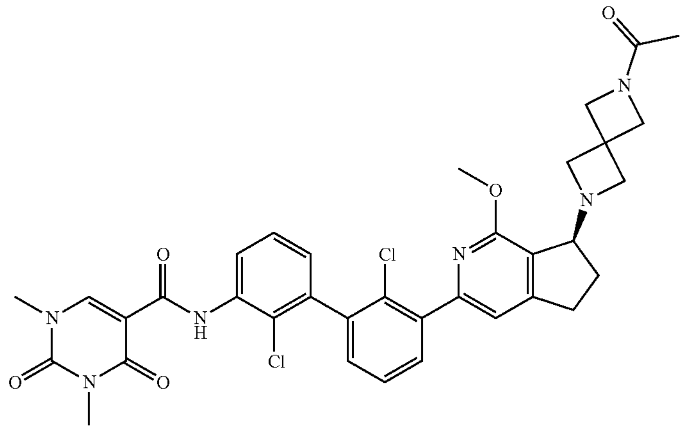
, -continued
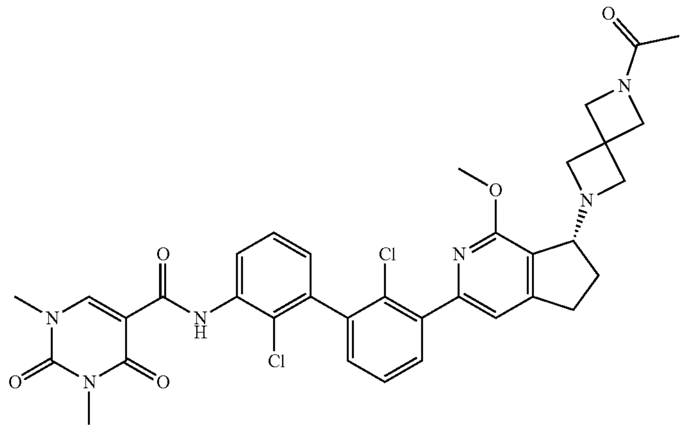
,
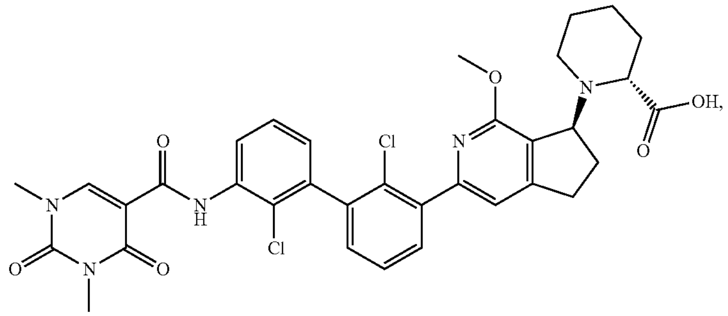
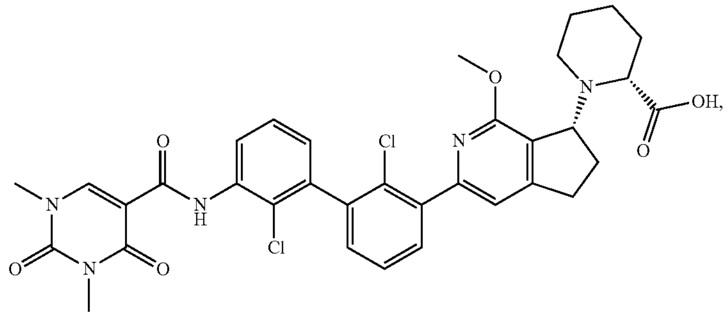
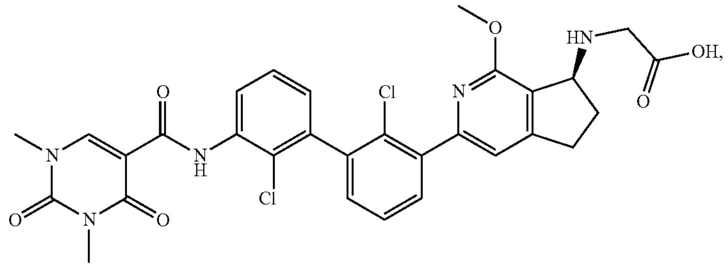
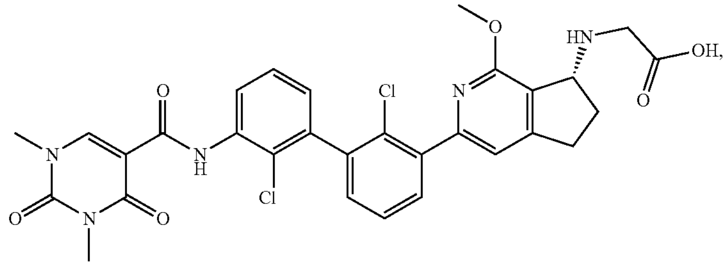

-continued
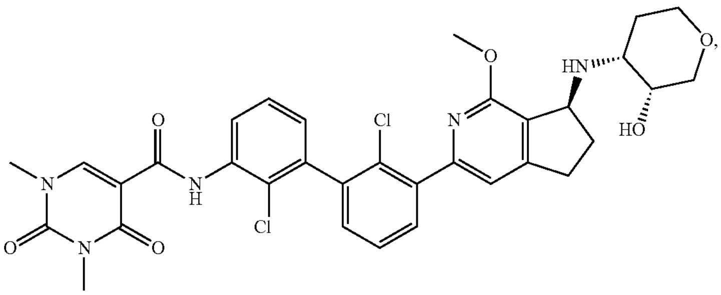
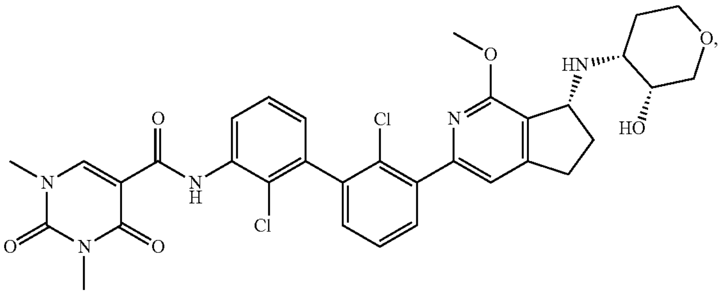
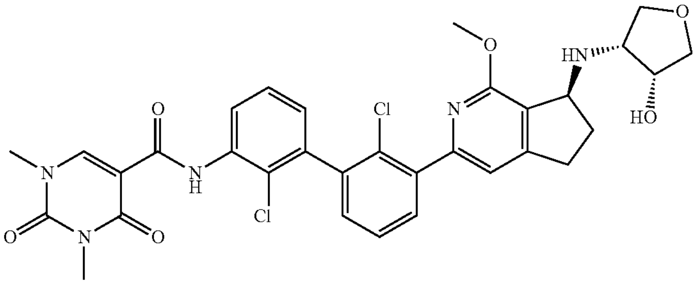
,
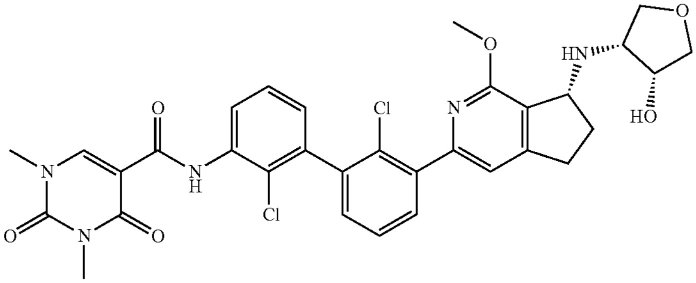
,
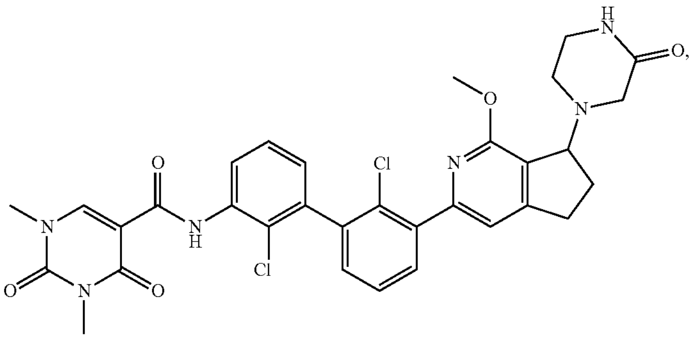

-continued
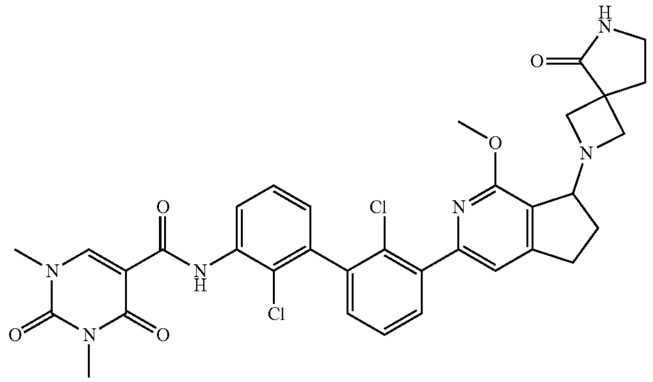
,
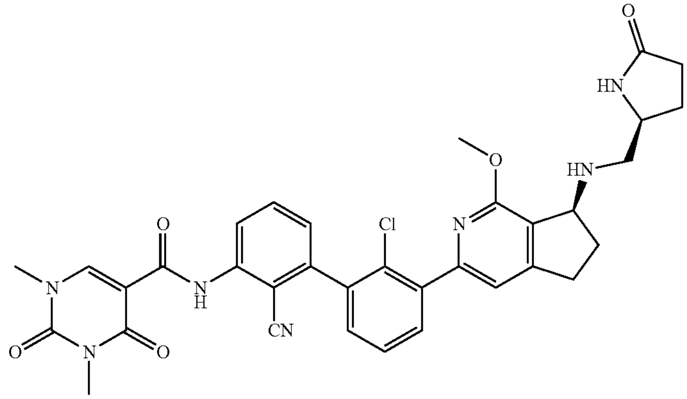
,
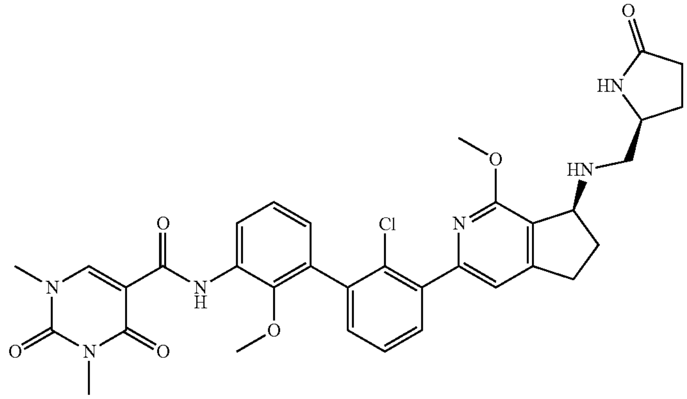
,
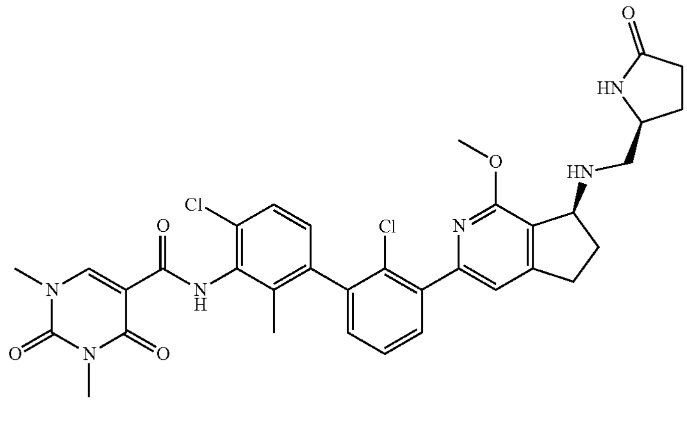
,

-continued
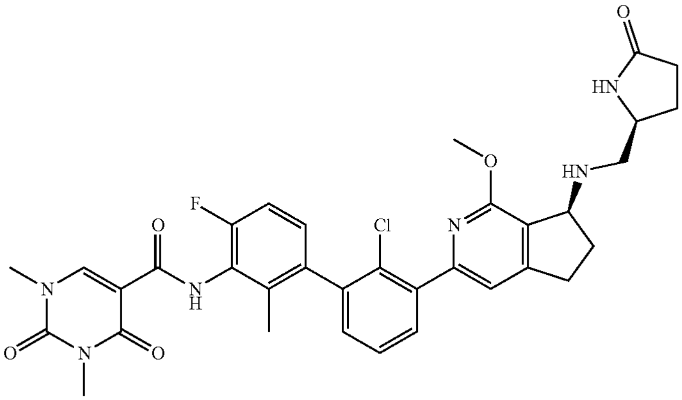
,
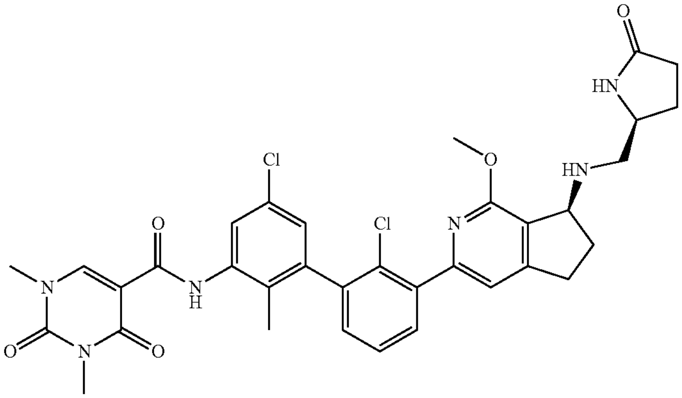
,
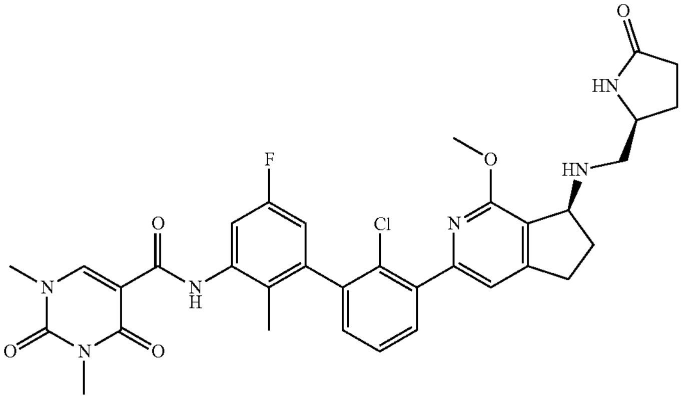
,
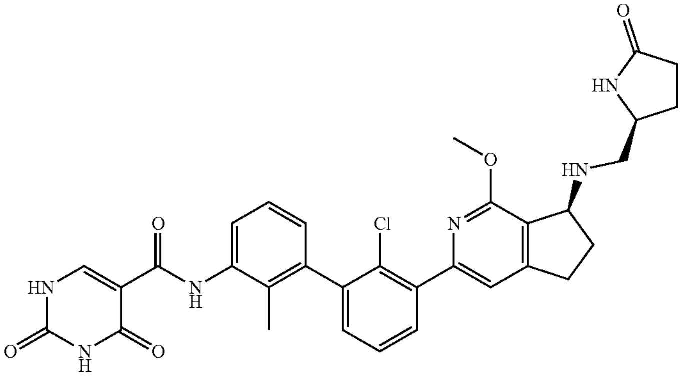
,

-continued
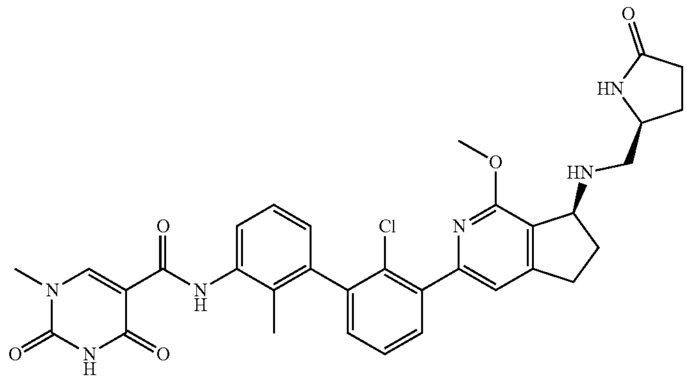
,
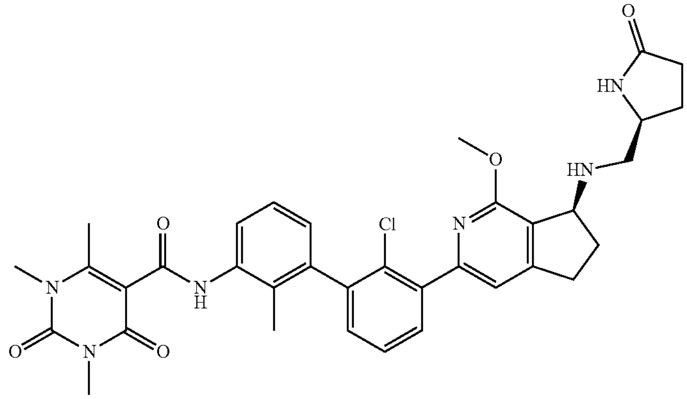
,
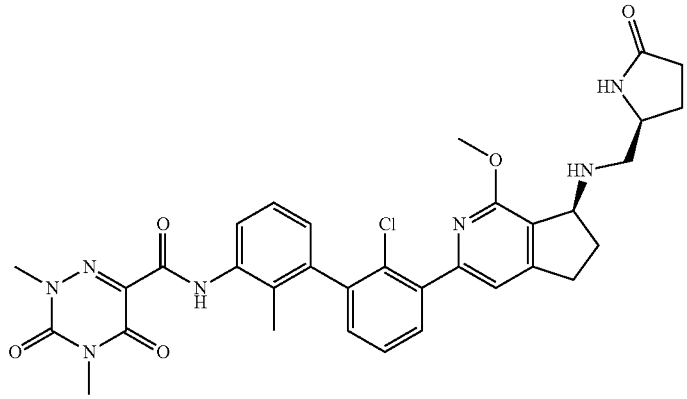
,
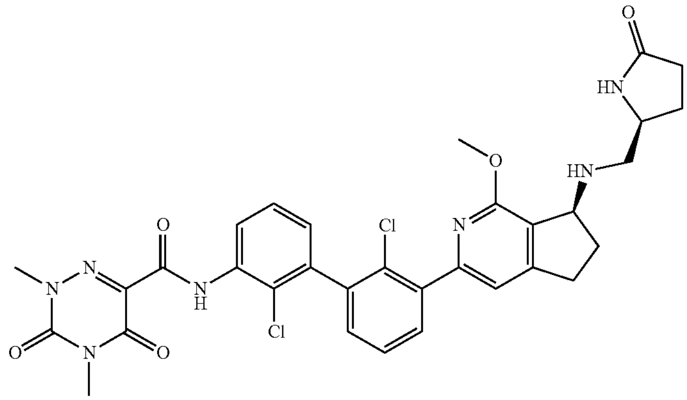
,

-continued
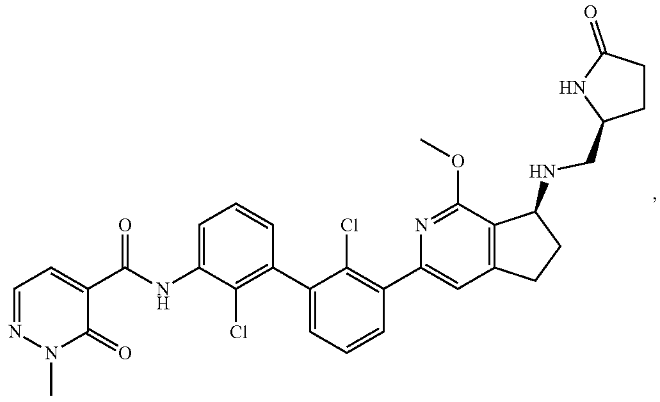
,
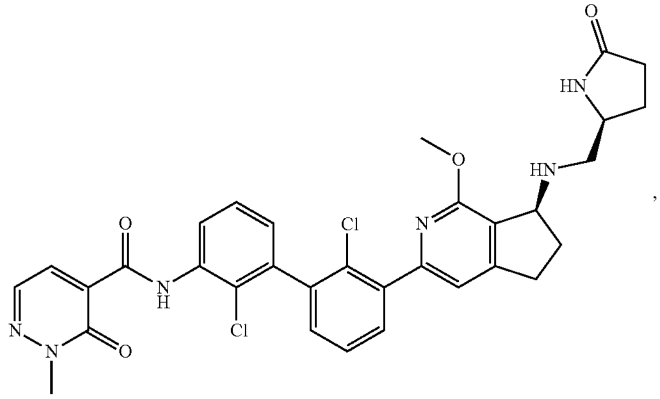
,
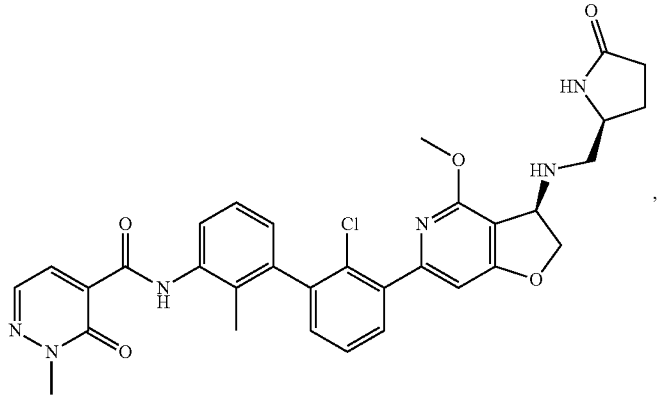
,
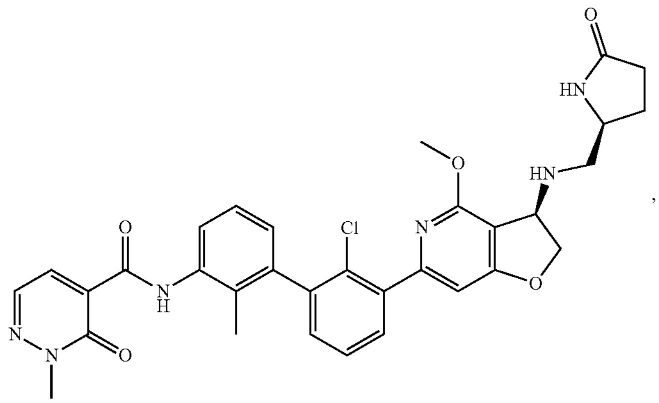
,

-continued
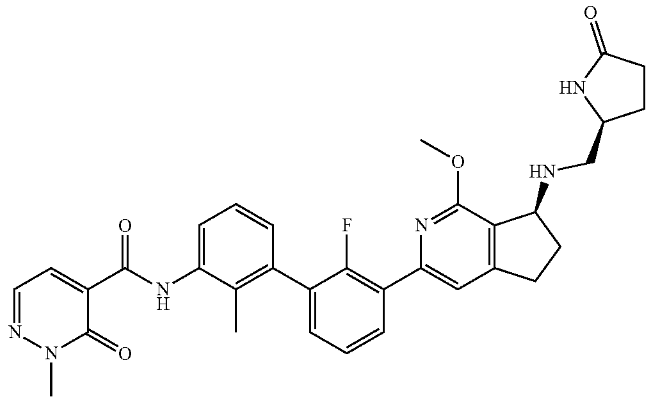
,
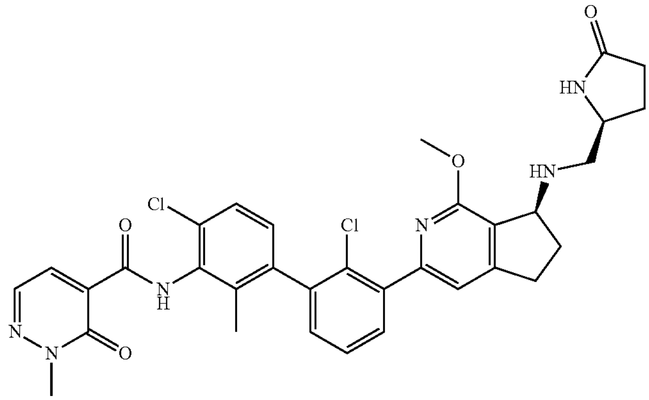
,
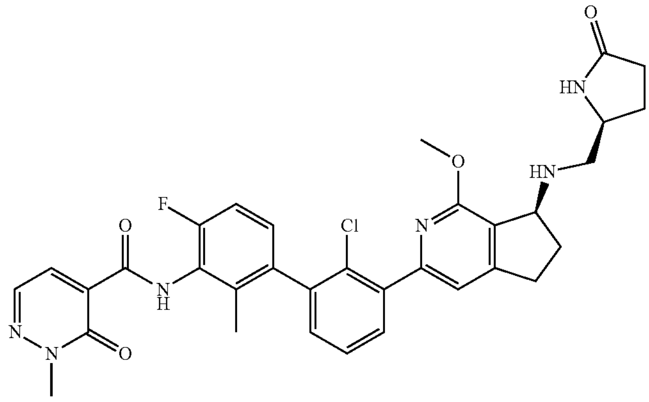
,
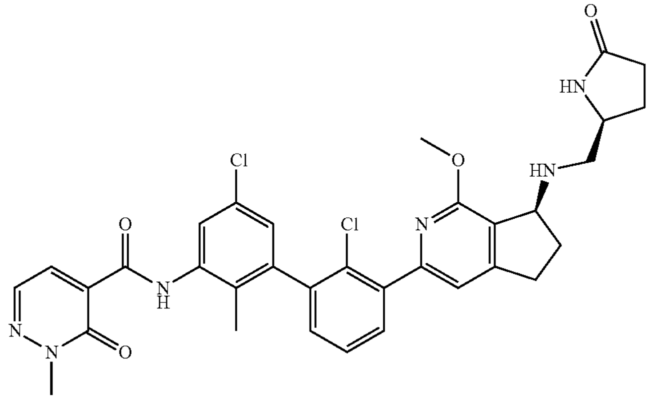
,

-continued
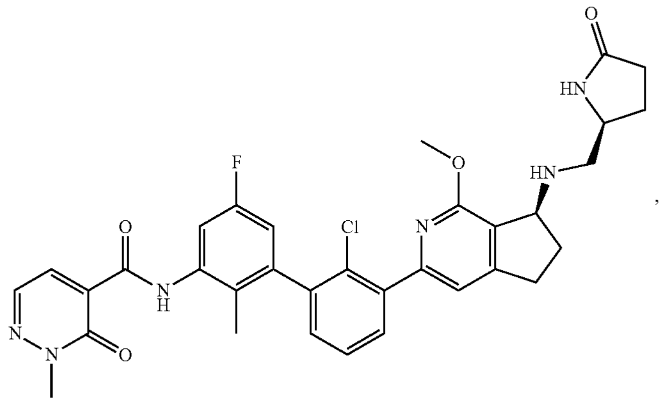
,
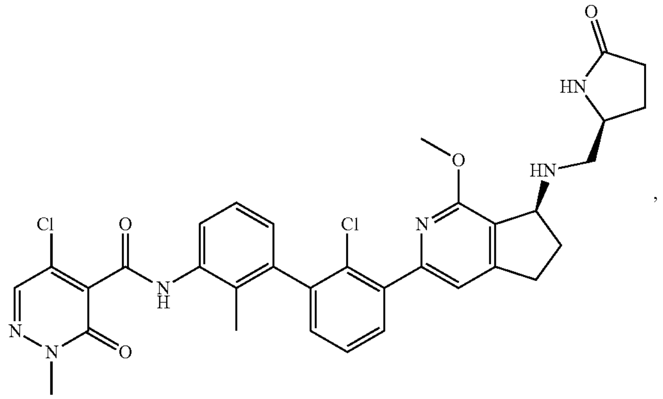
,
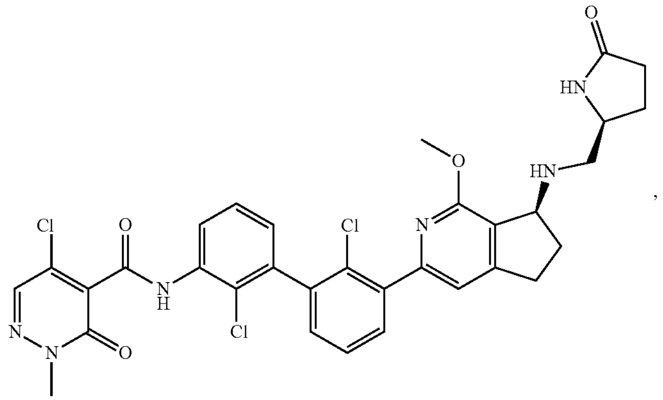
,
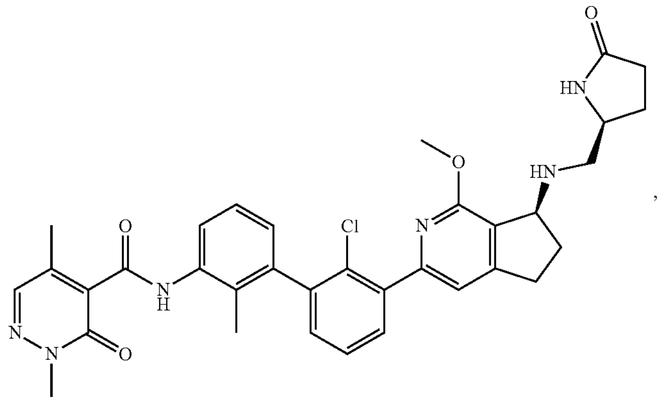
,

-continued
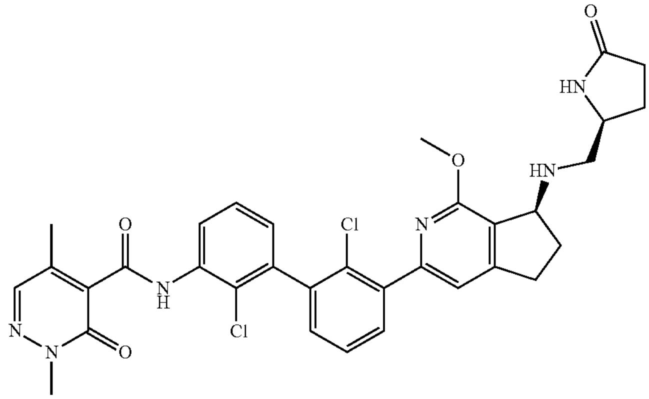
,
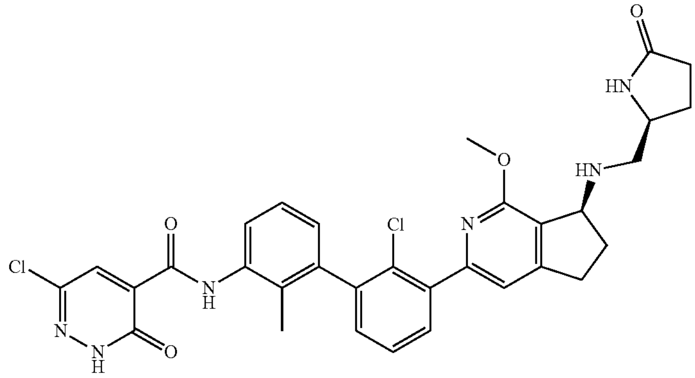
,
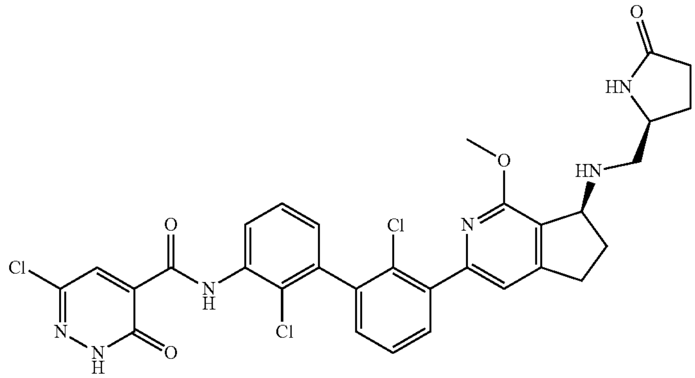
,
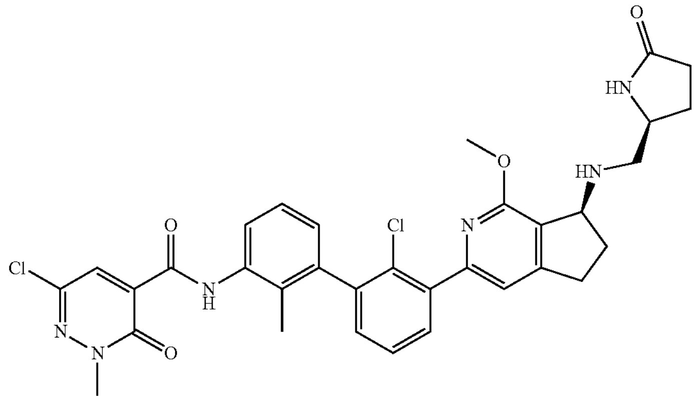
,

-continued
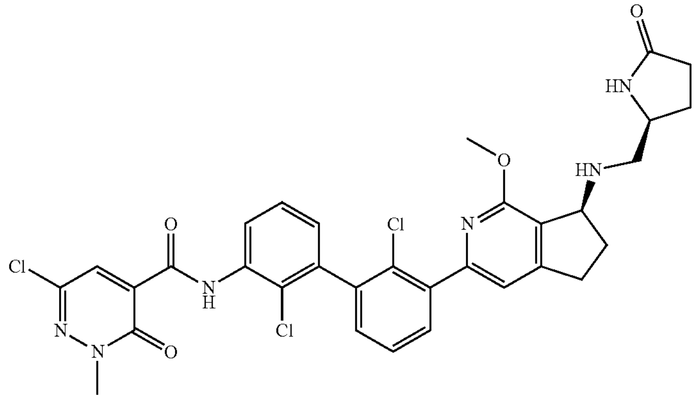
,
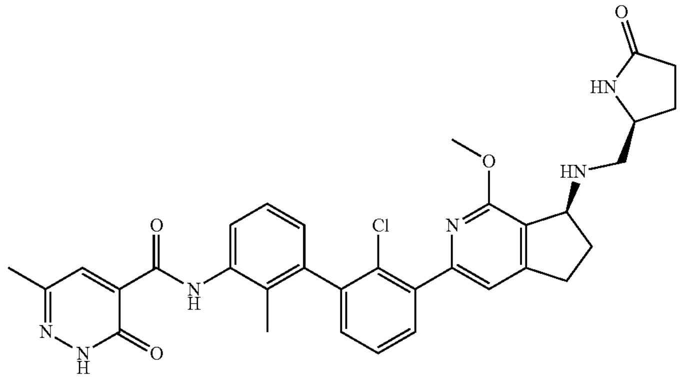
,
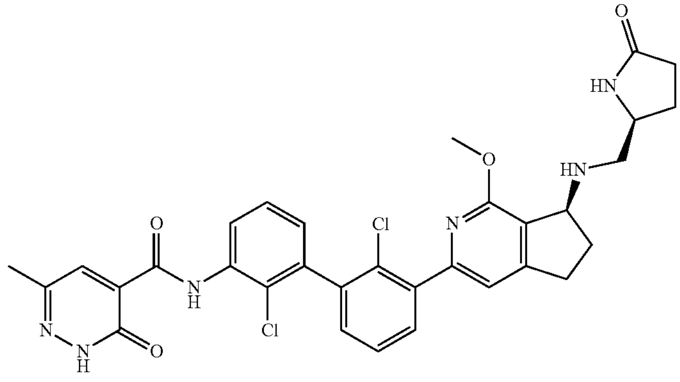
,
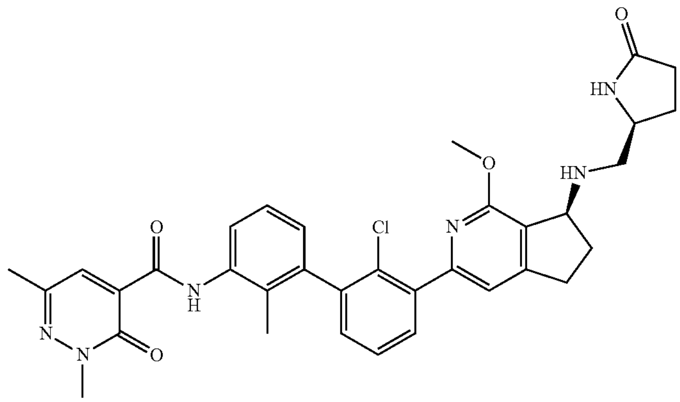
,

-continued
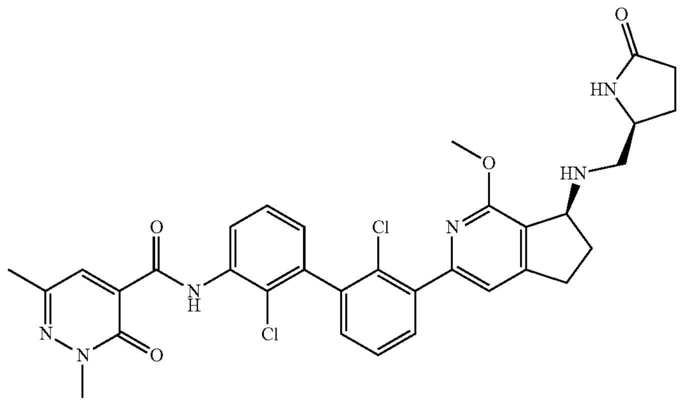
,
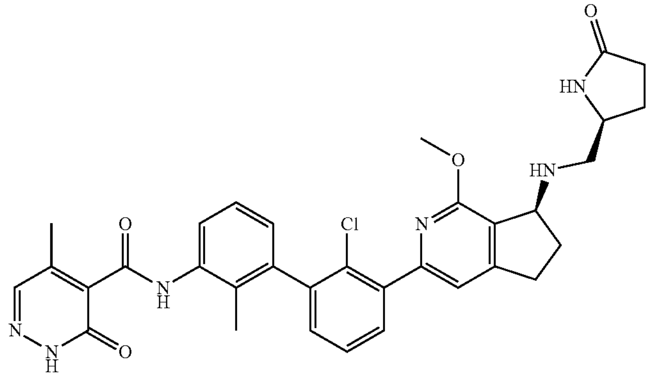
,
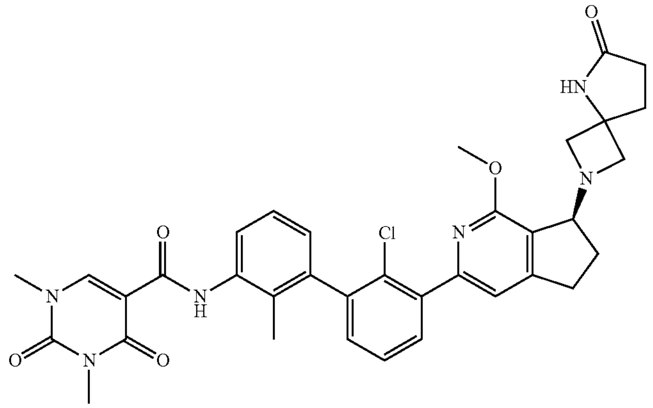
,
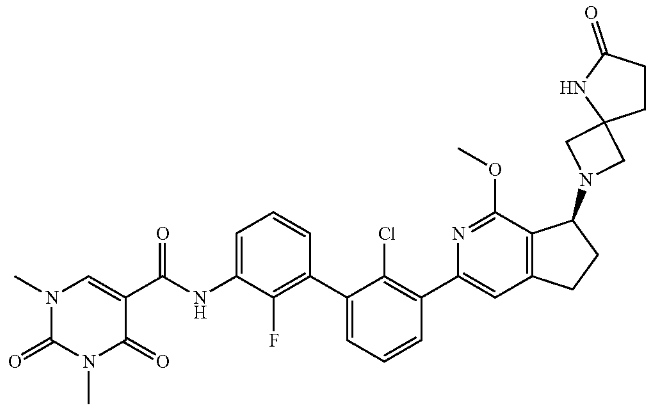
,

-continued
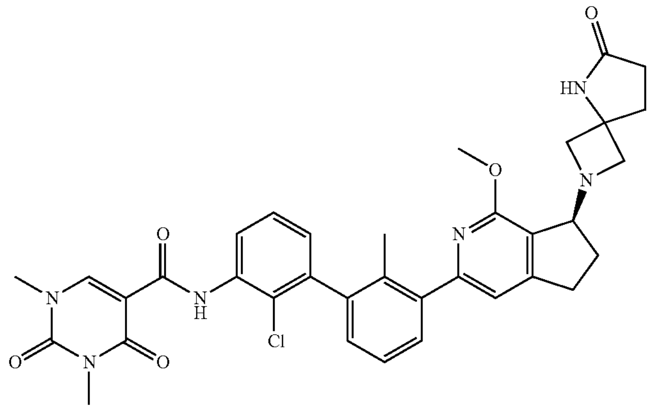
,
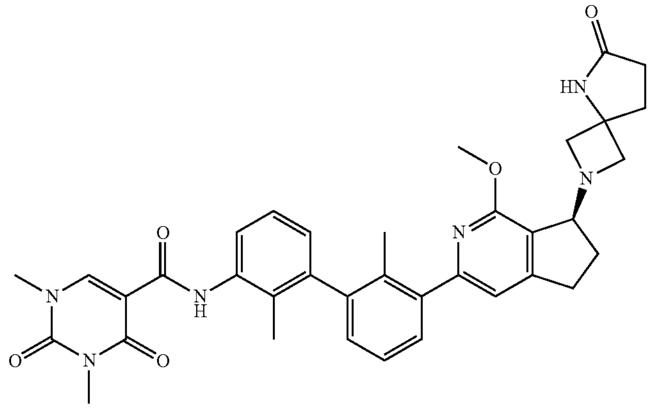
,
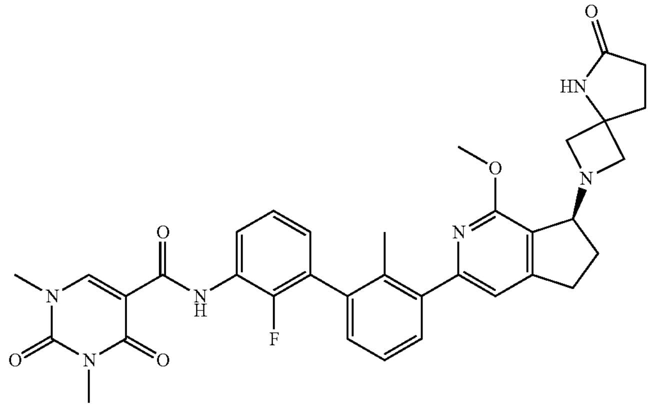
,
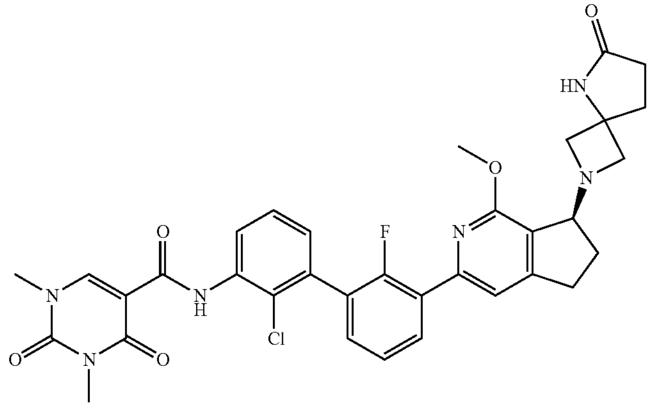
,

-continued
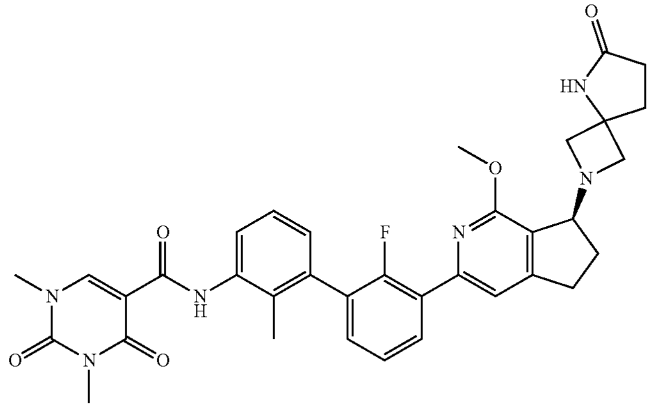
,
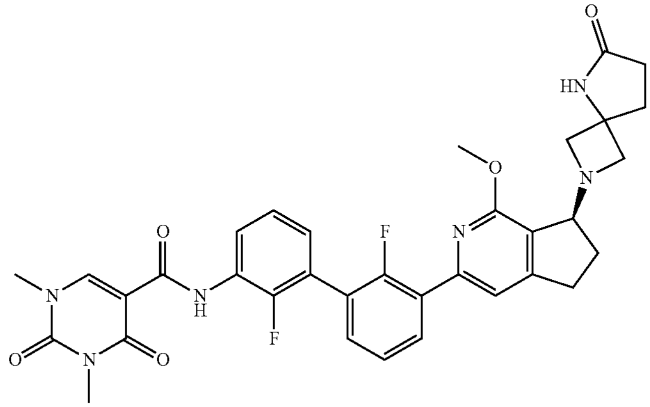
,
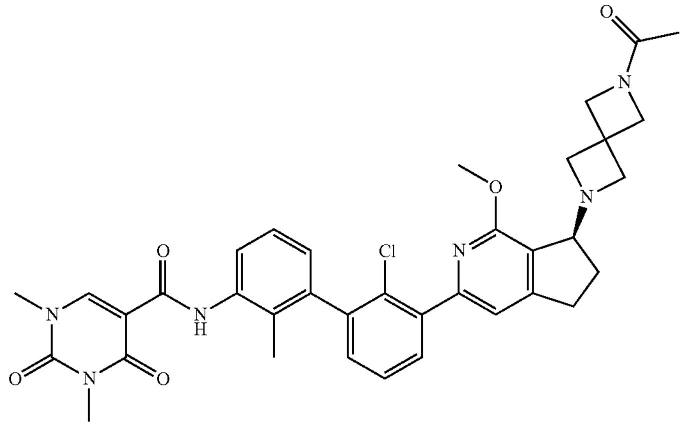
,
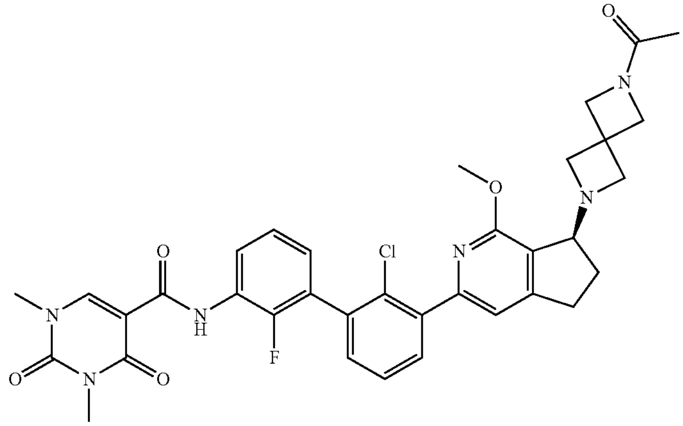
,

-continued
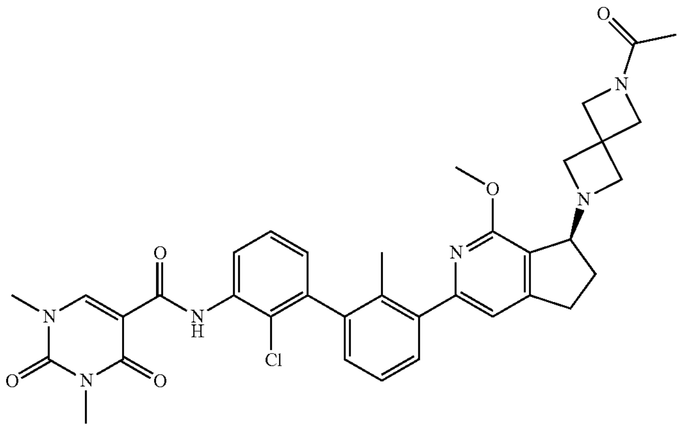
,
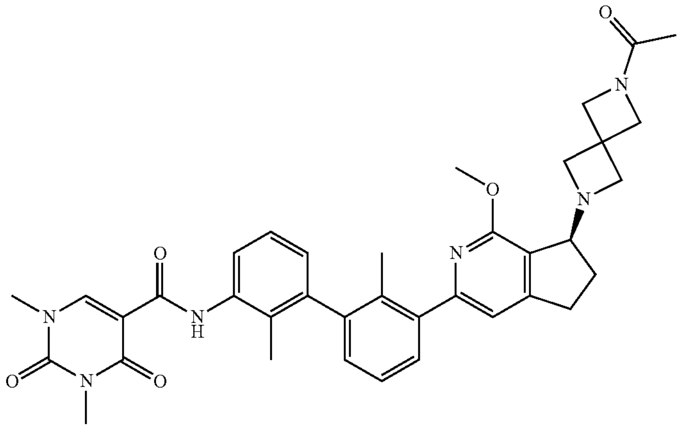
,
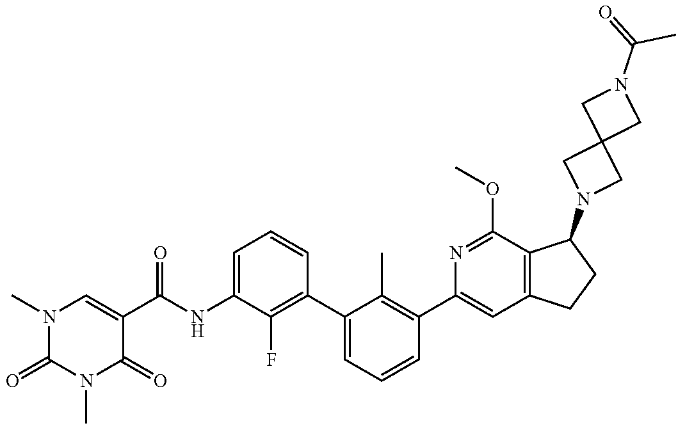
,
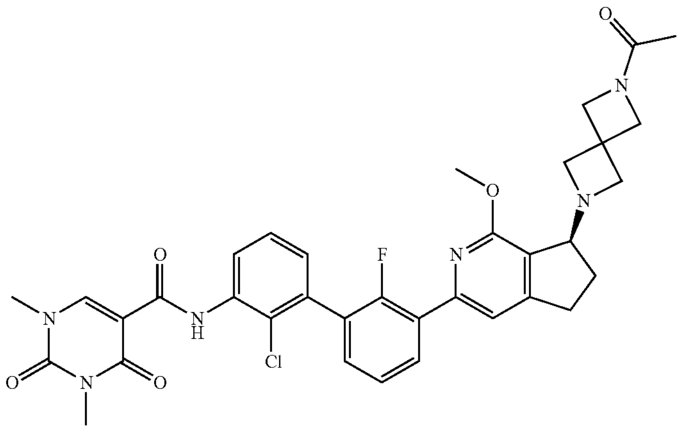
,

-continued
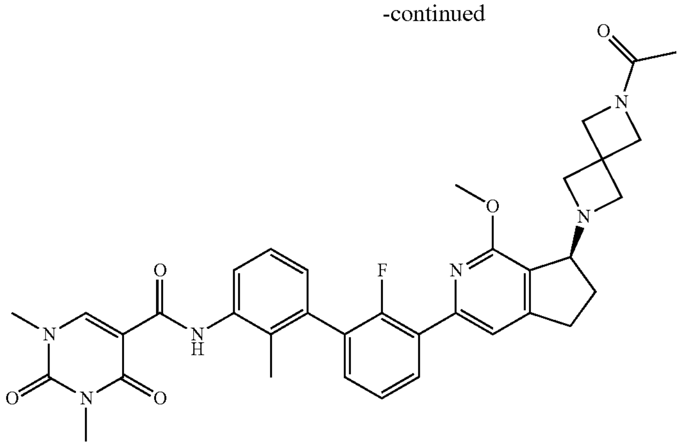
,
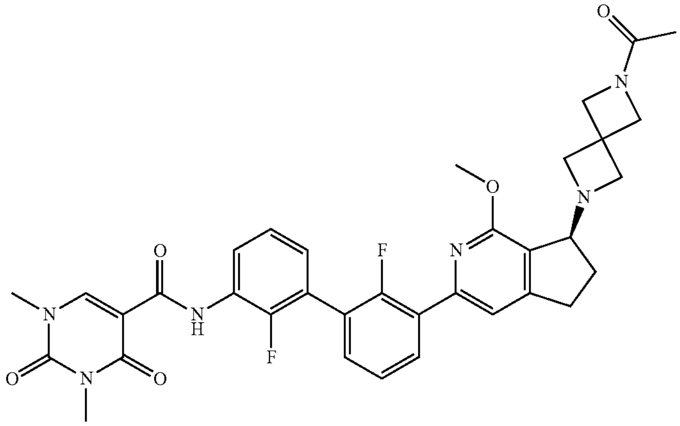
,
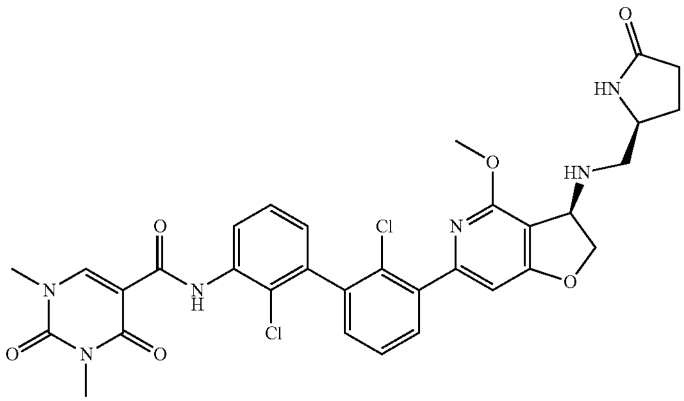
,
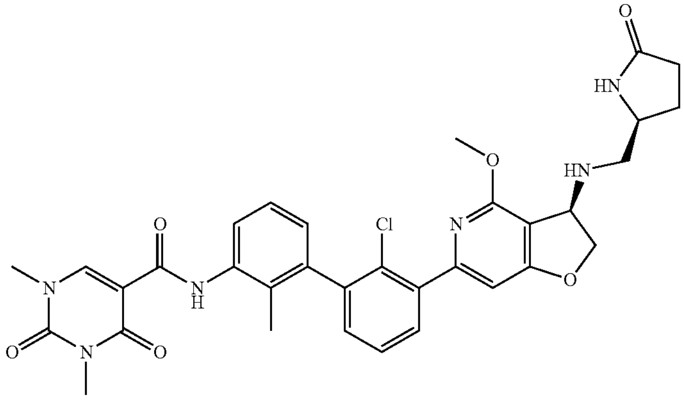
,

-continued
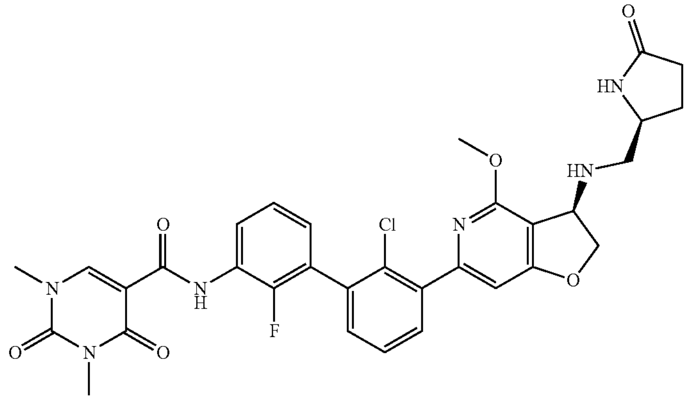
,
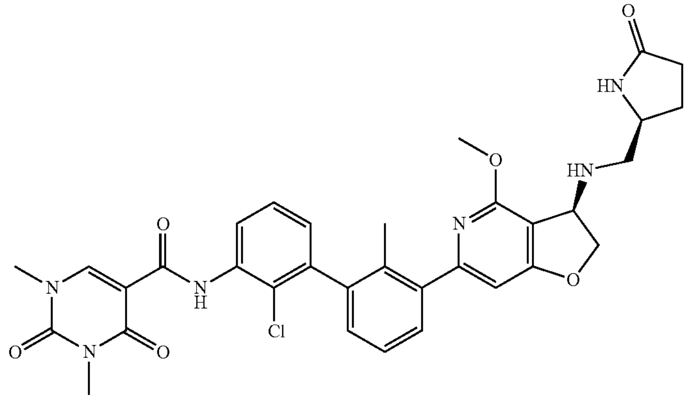
,
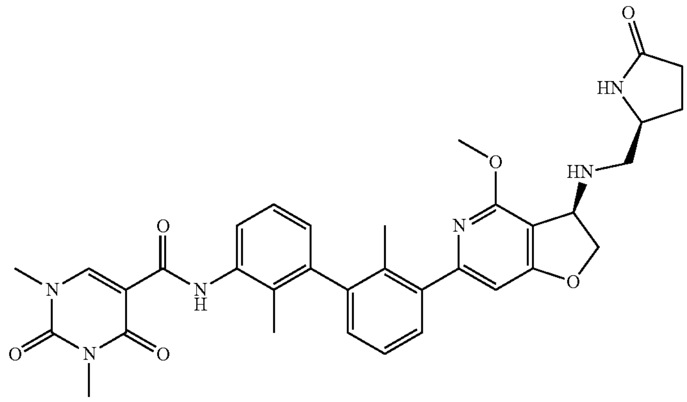
,
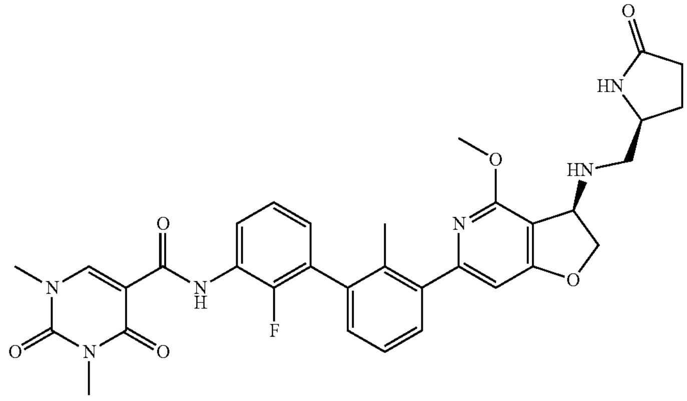
,

-continued
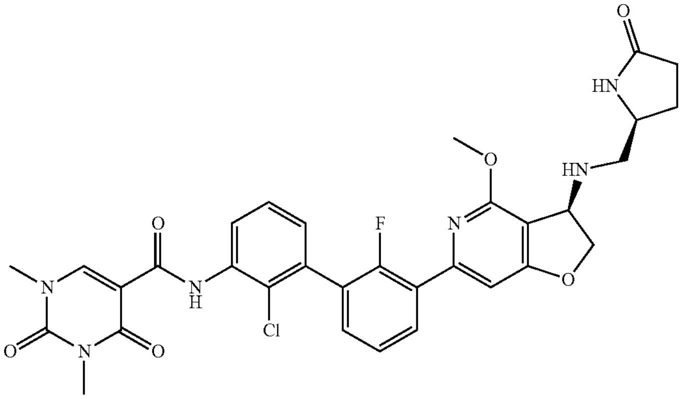
,
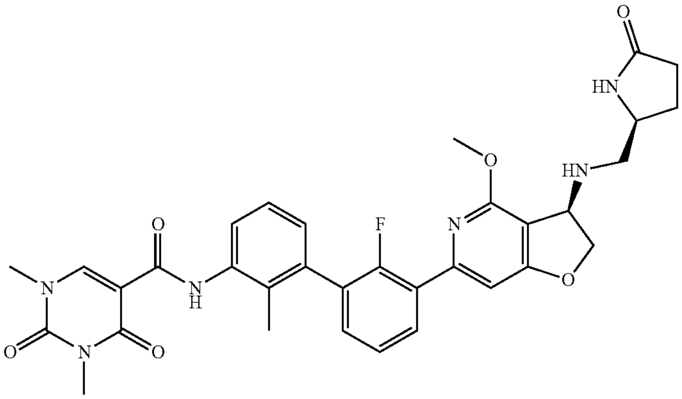
,
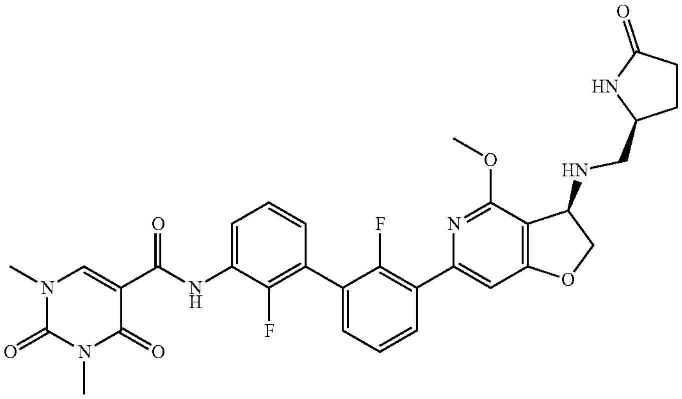
,
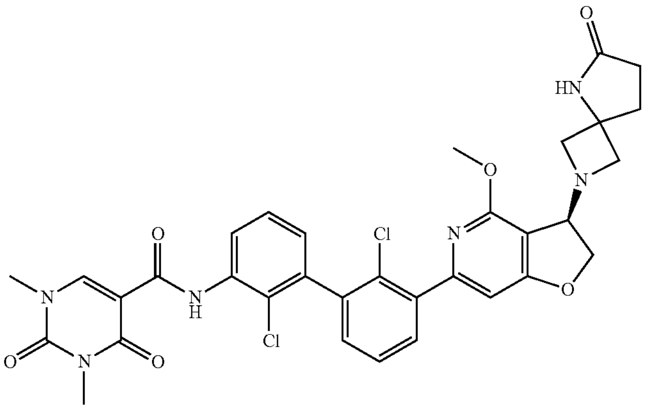
,

-continued
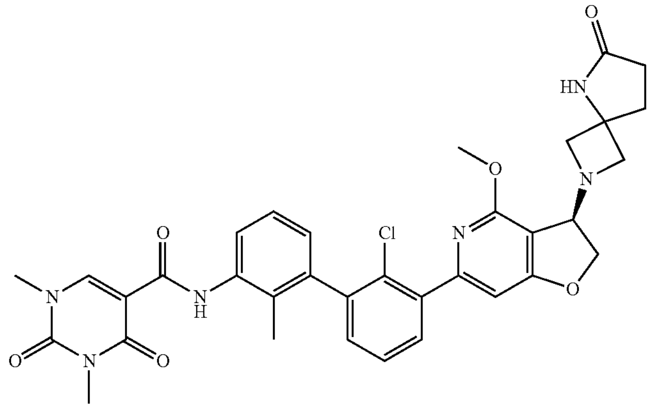
,
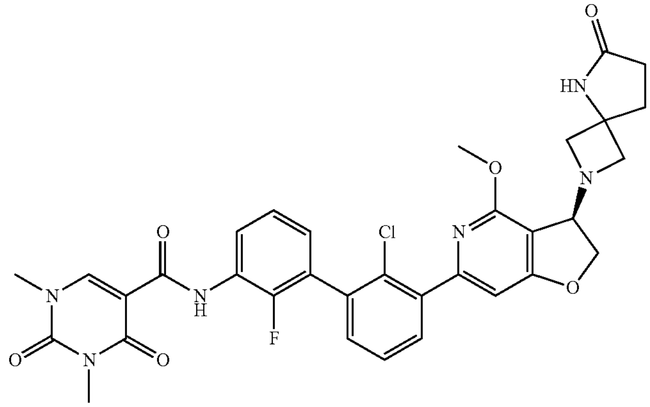
,
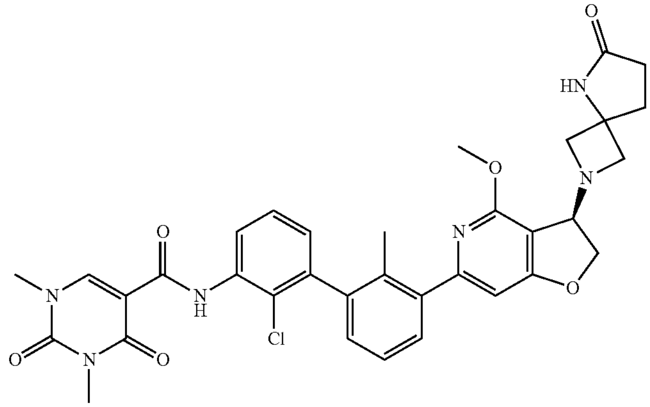
,
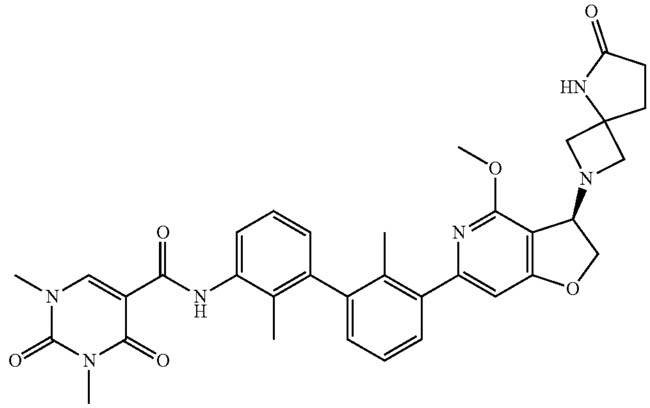
,

-continued
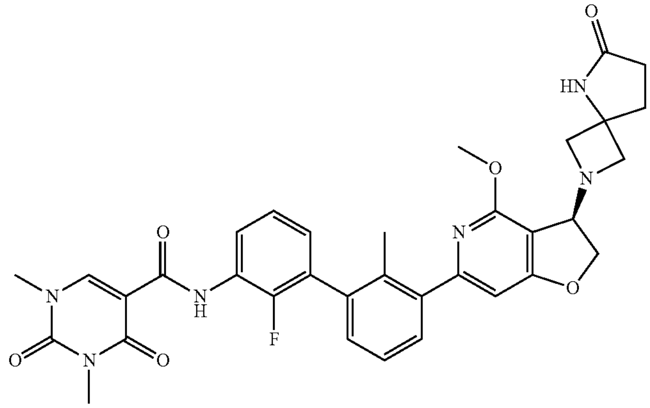
,
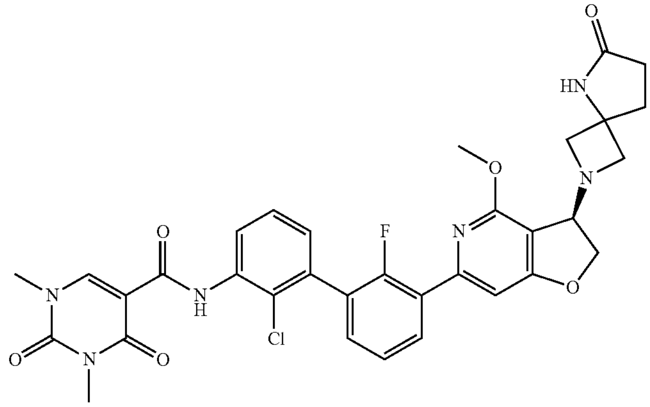
,
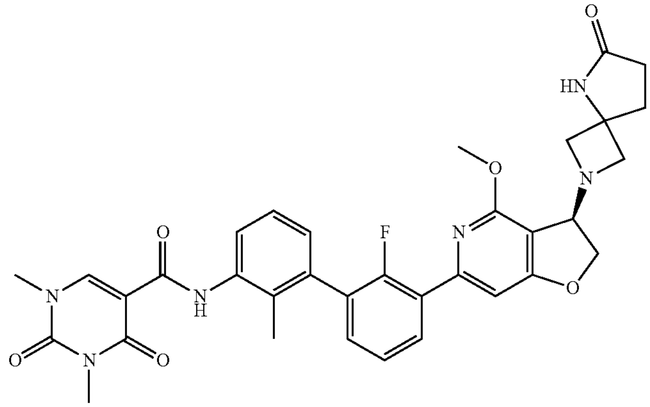
,
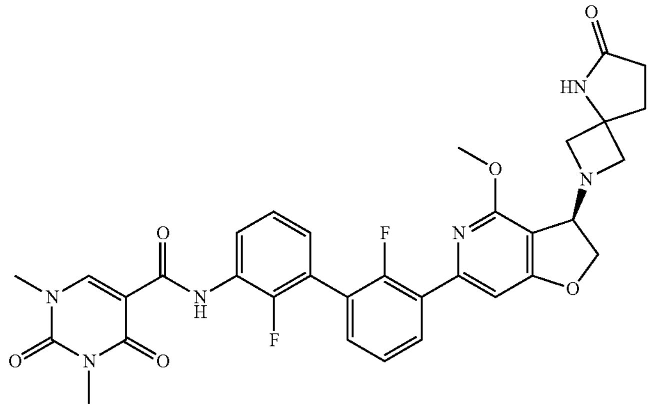
,

-continued
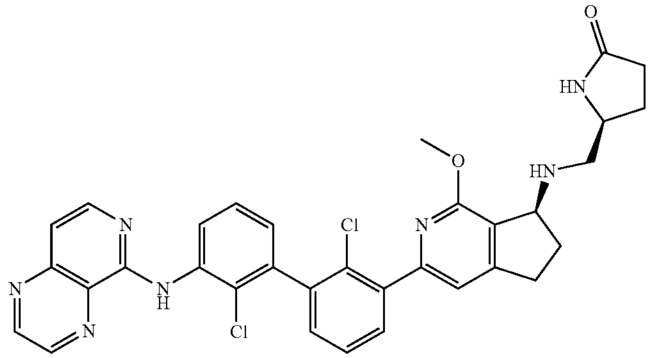
,
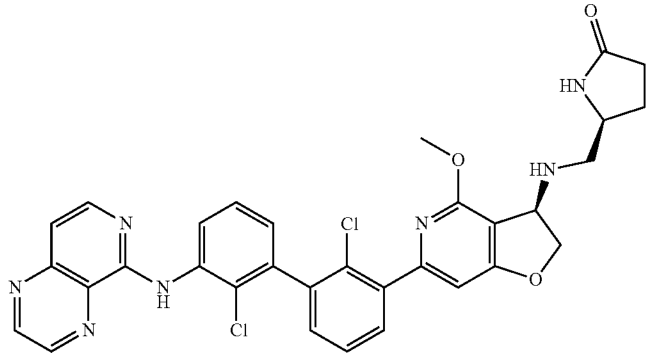
,
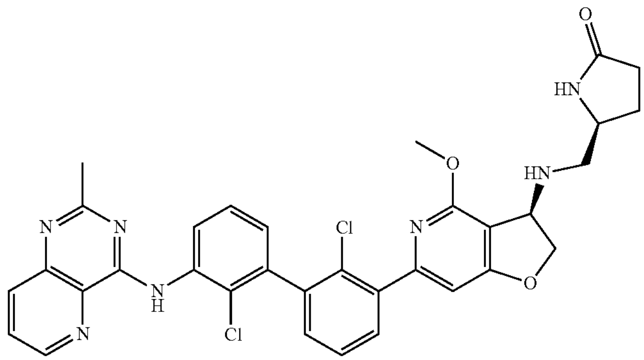
,
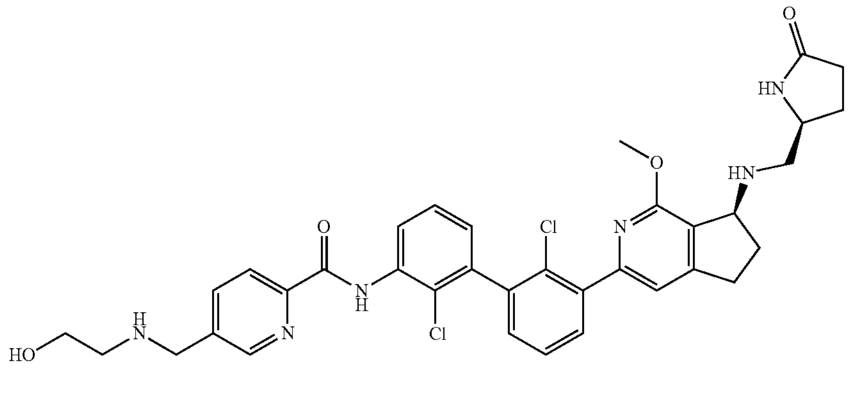
,

-continued
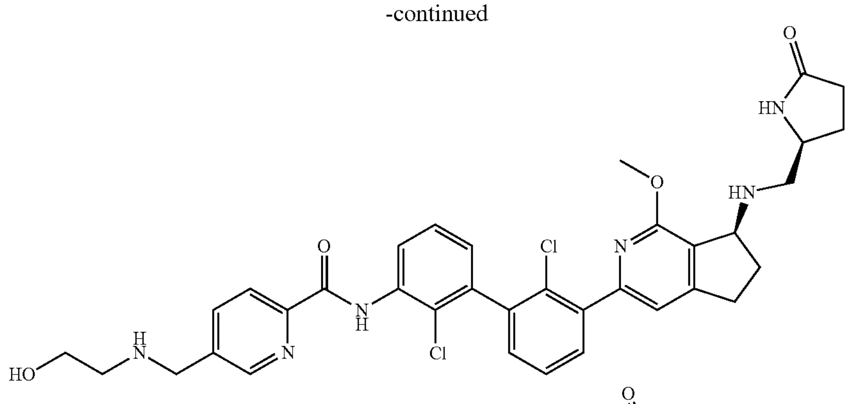
,
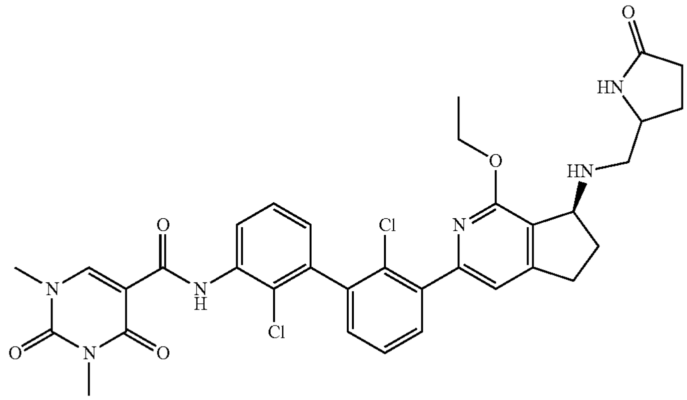
,
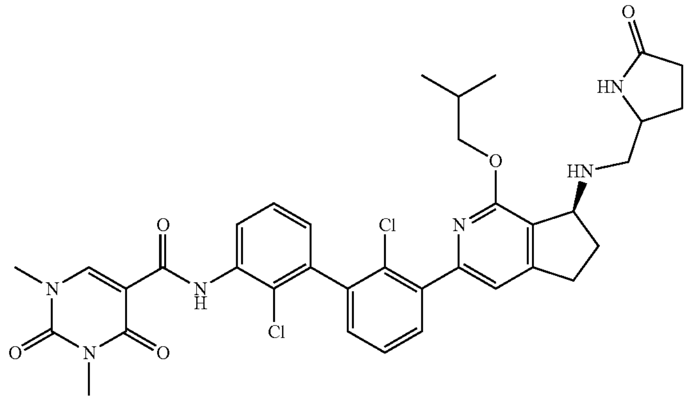
,
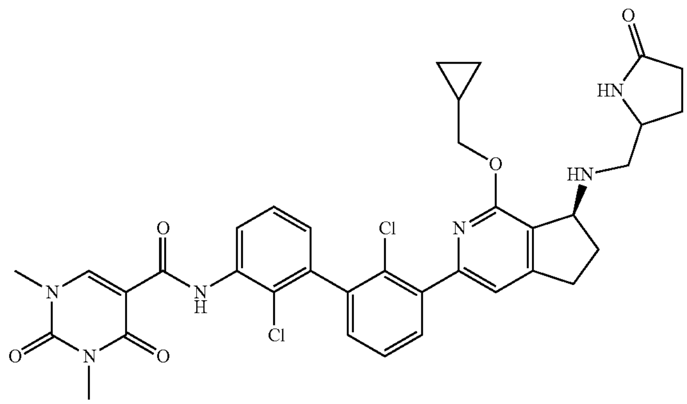
,

-continued
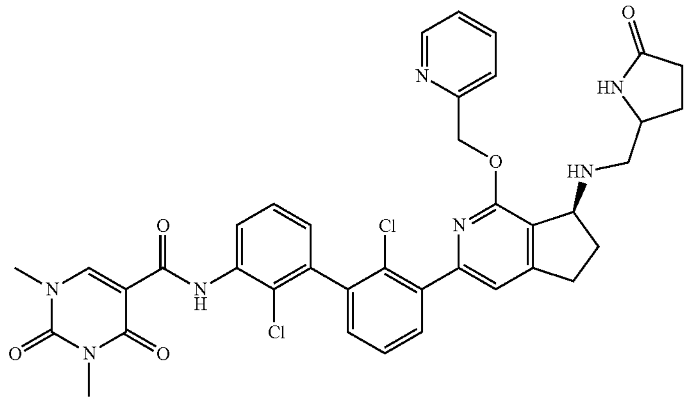
,
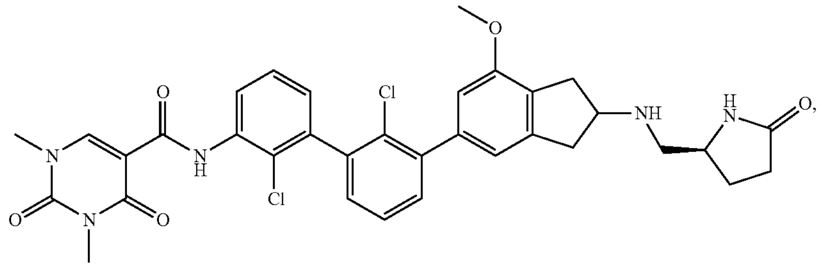
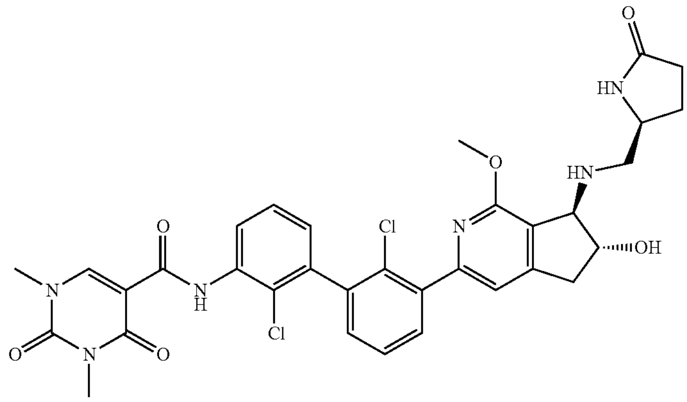
,
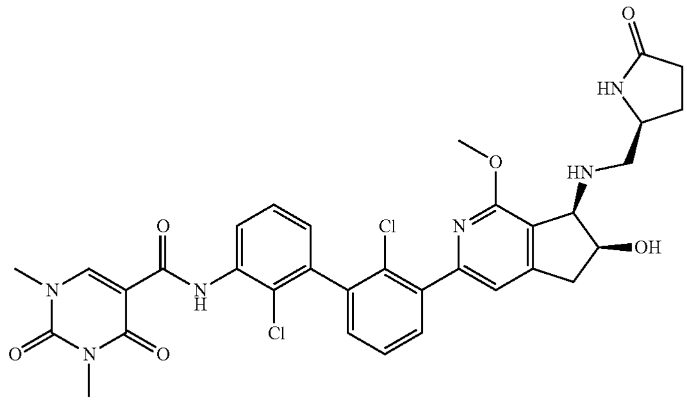
,

-continued
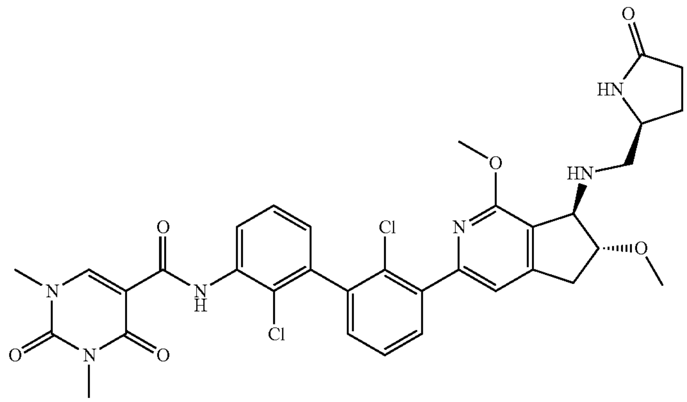
,
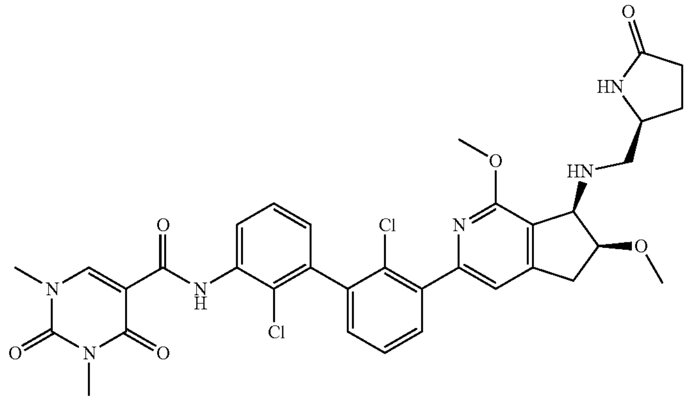
,
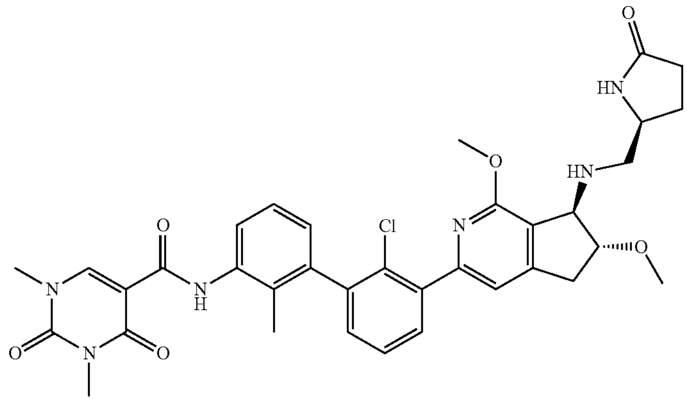
,
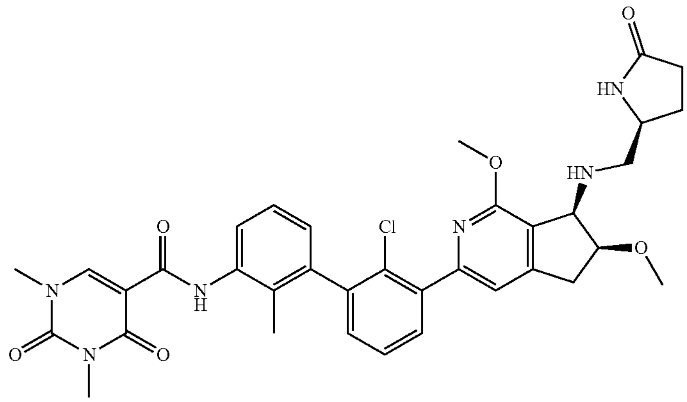
,

-continued
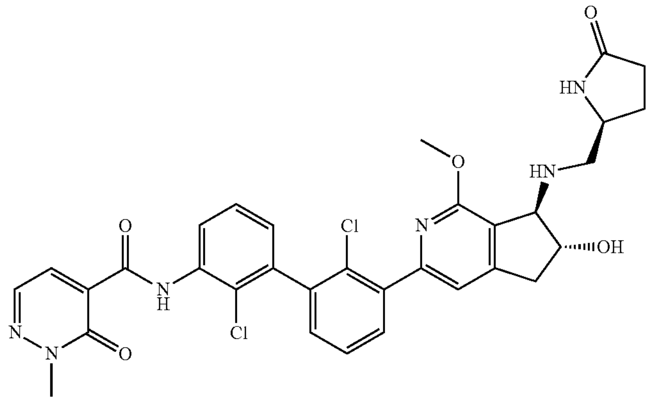
,
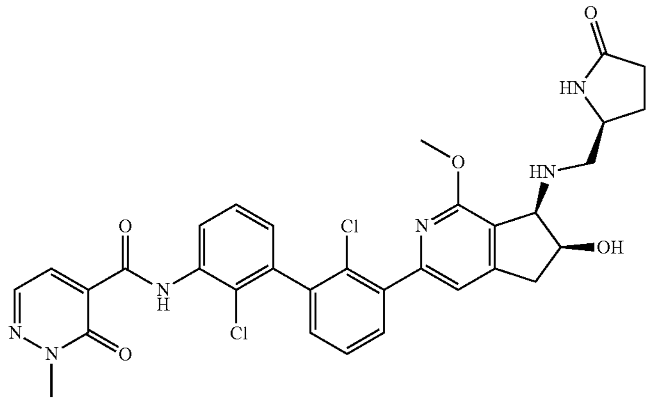
,
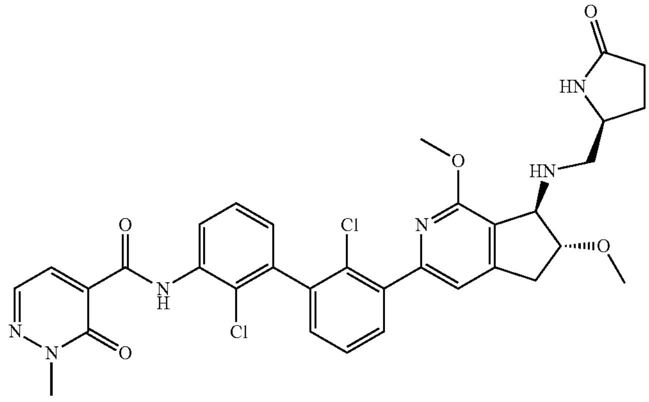
,
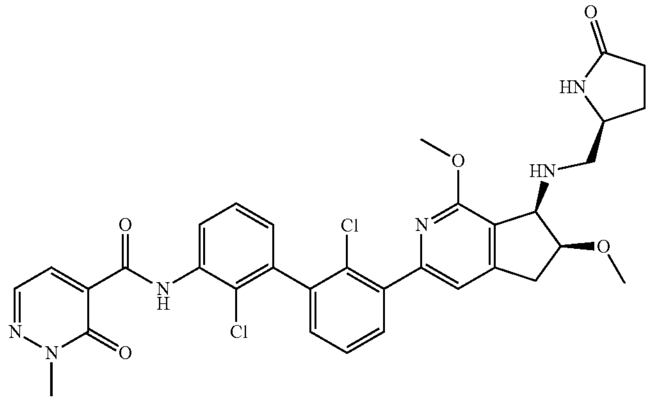
,

-continued
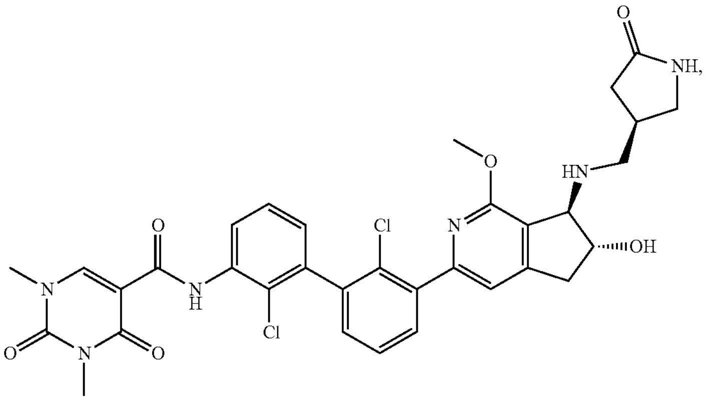
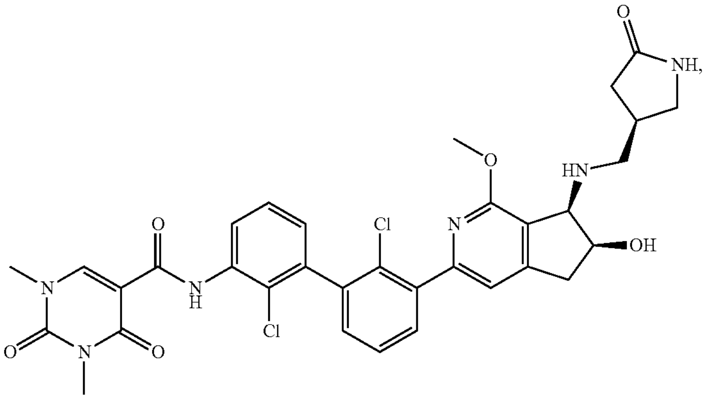
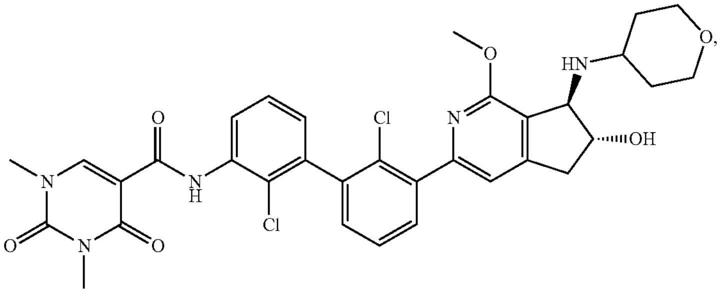
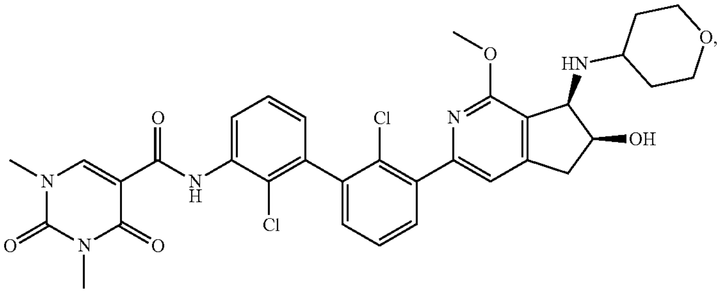
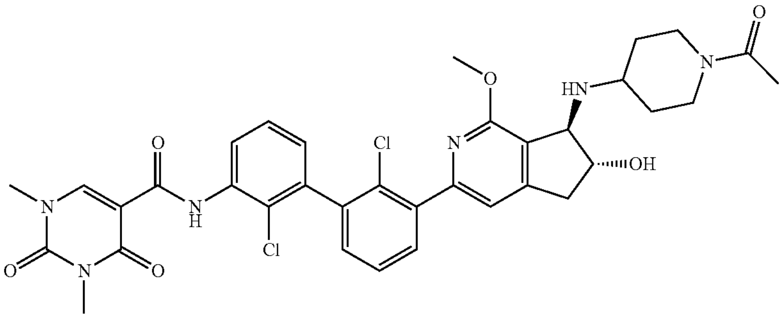
,

-continued
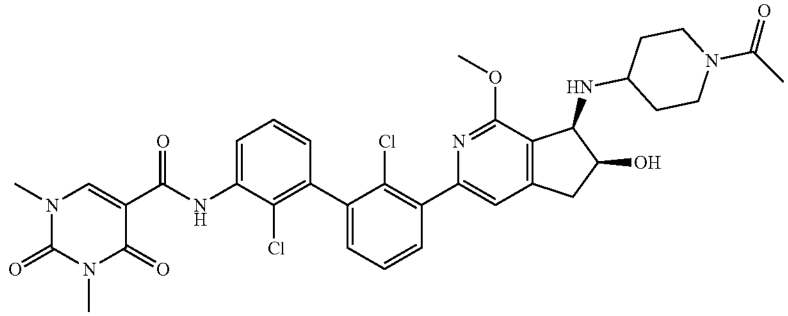
,
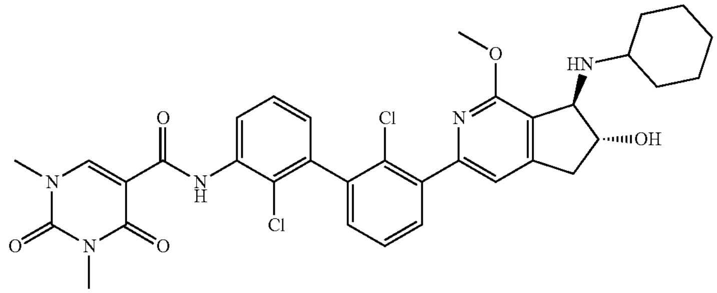
,
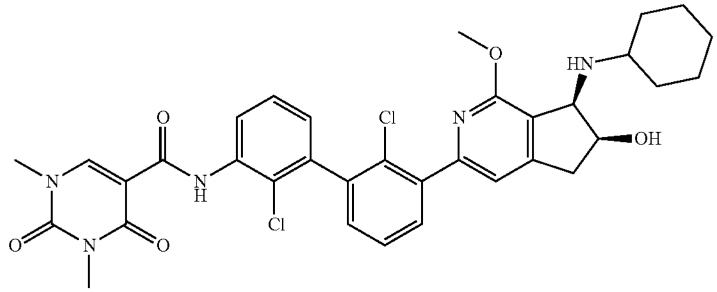
,
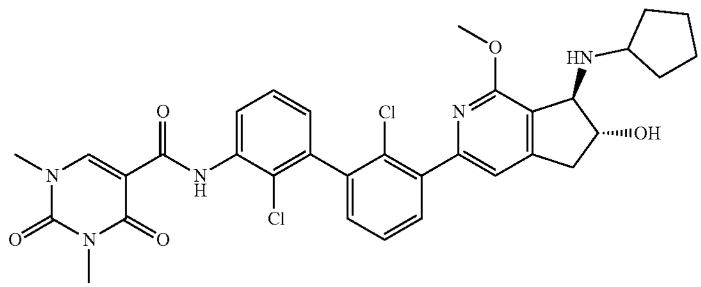
,
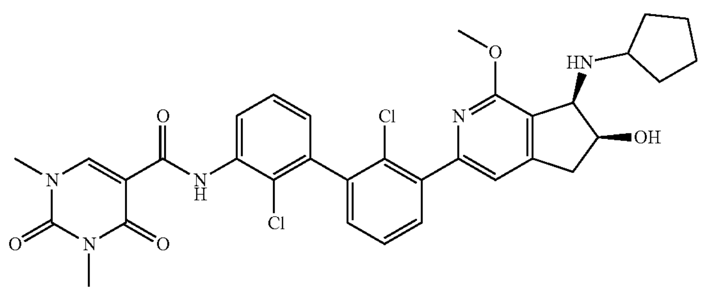
, -continued
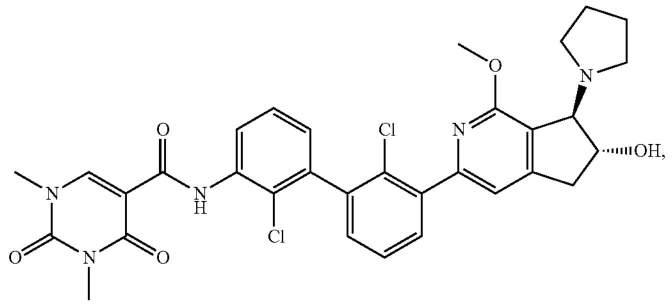
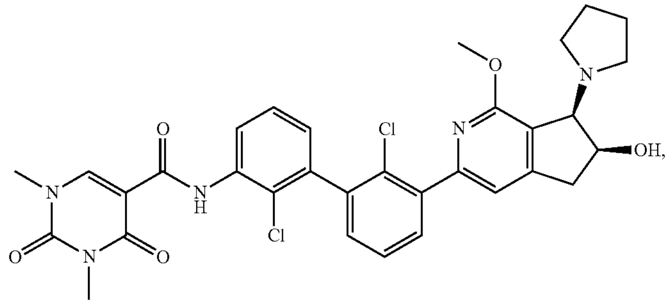
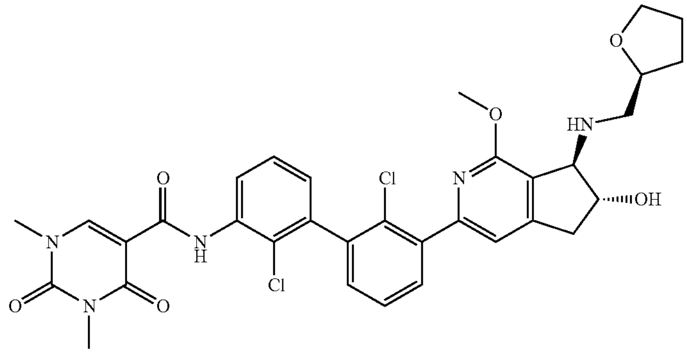
,
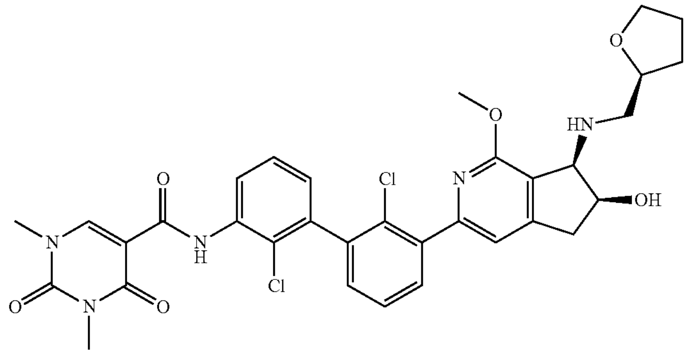
,
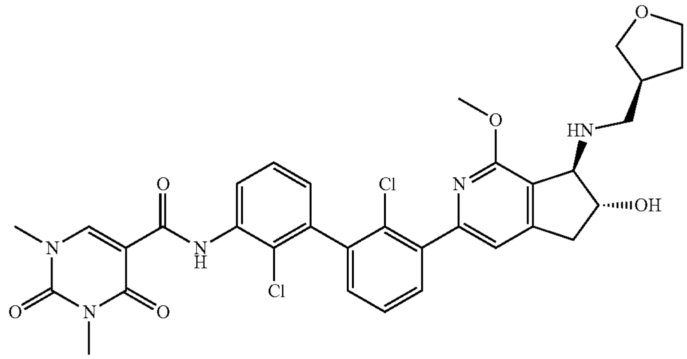
, -continued
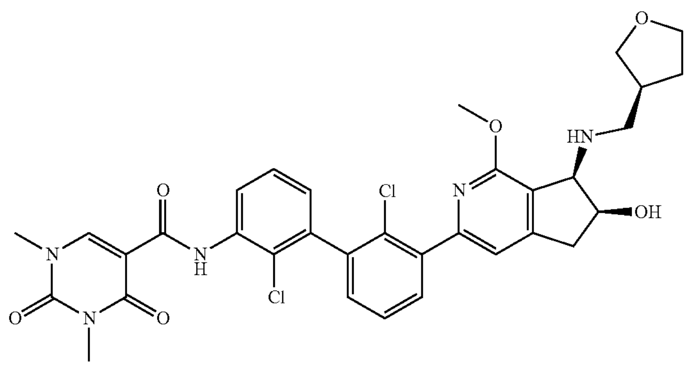
,
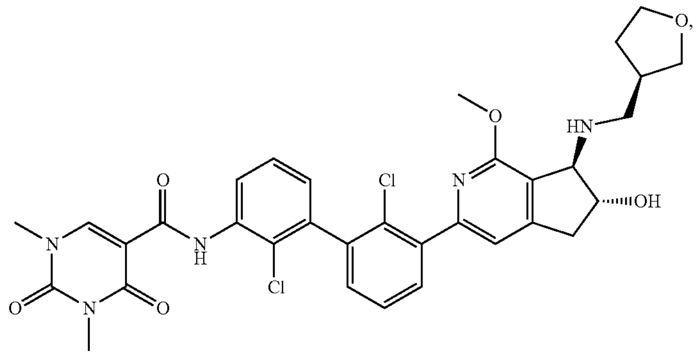
,
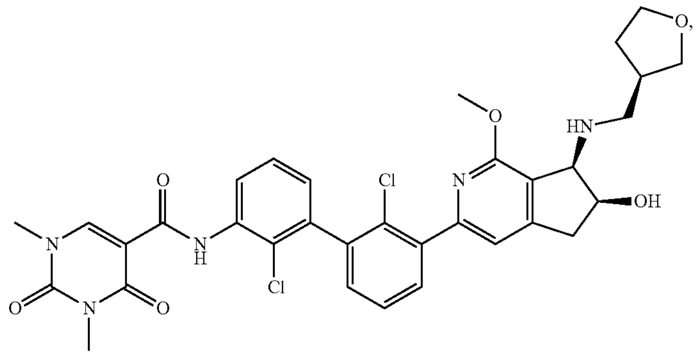
,
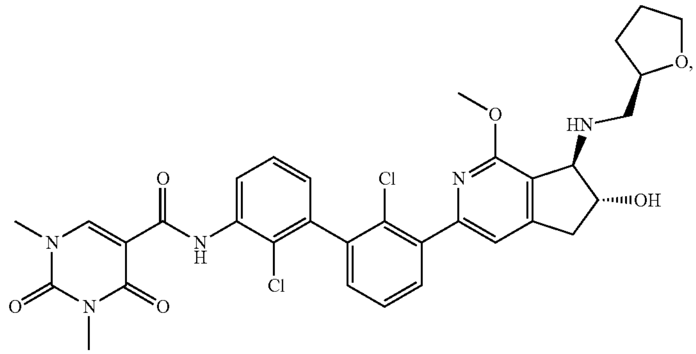
, -continued
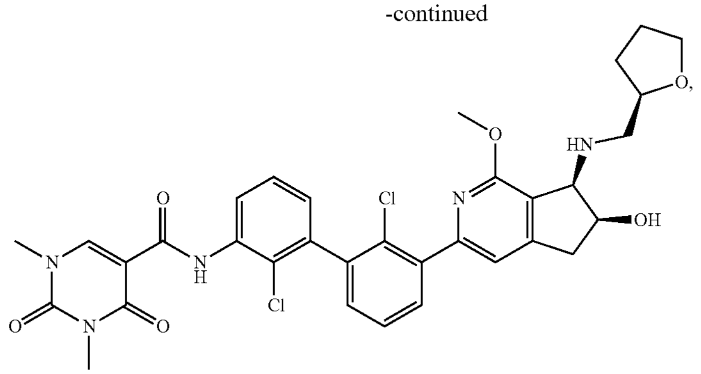
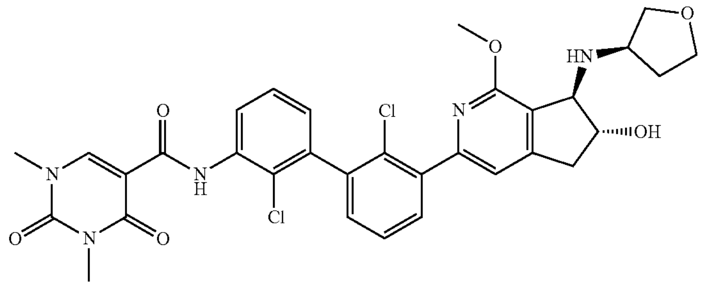
,
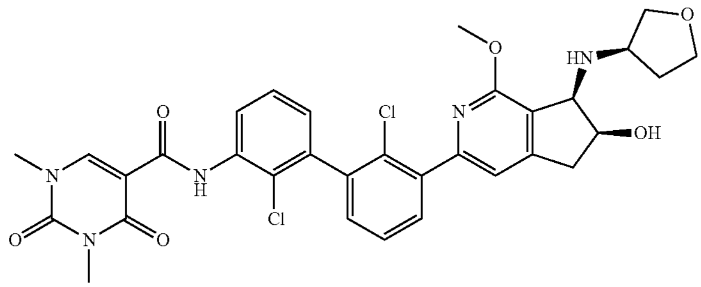
,
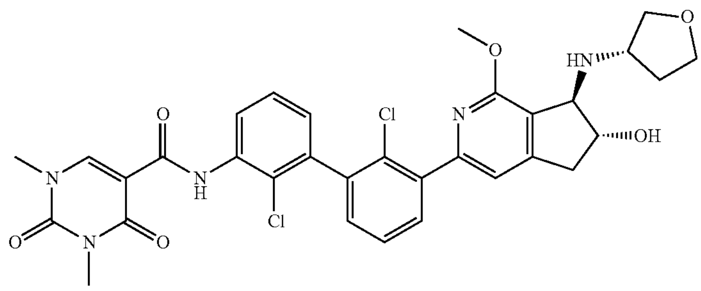
,
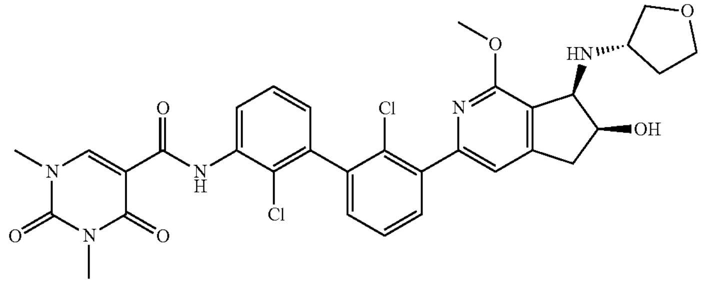
, -continued
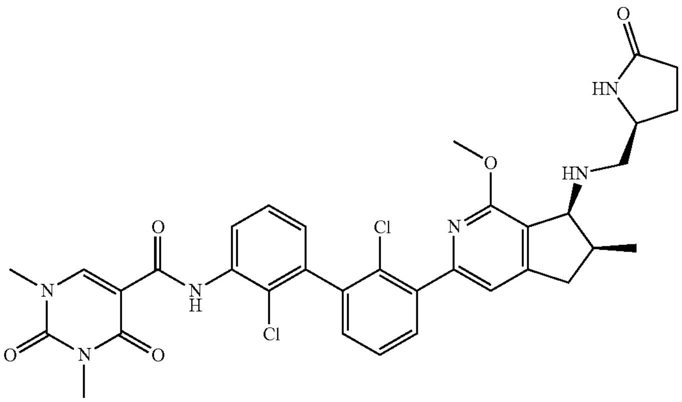
,
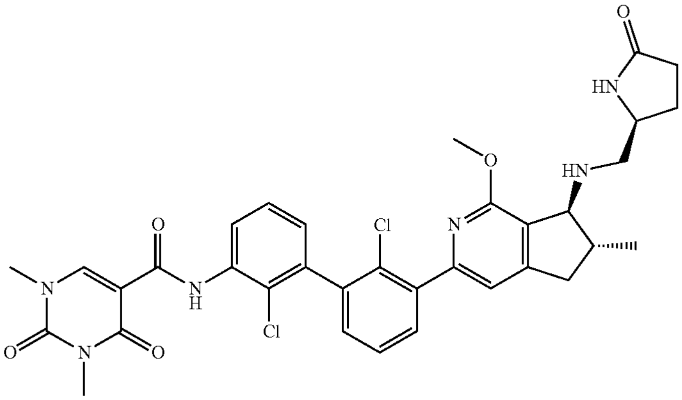
,
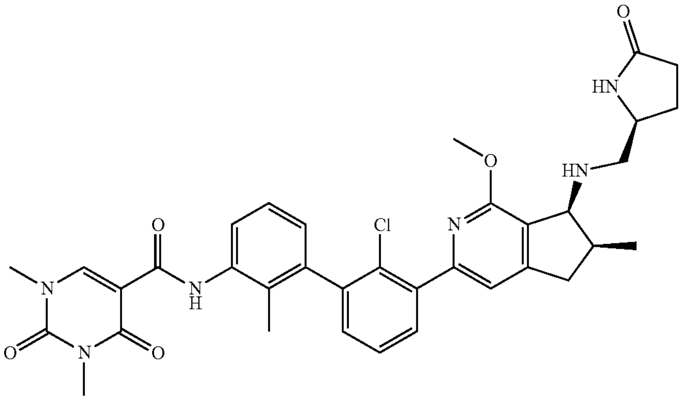
,
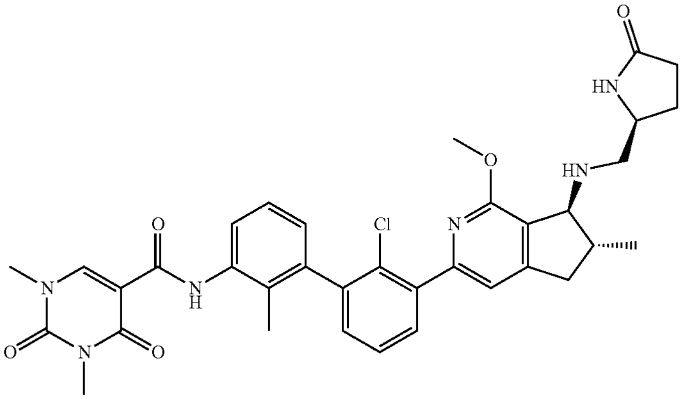
, -continued
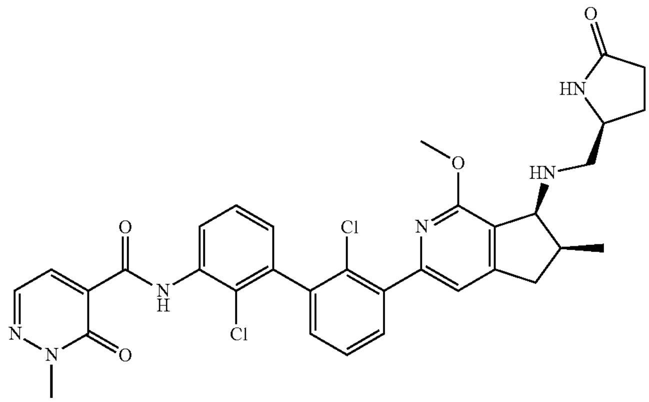
,
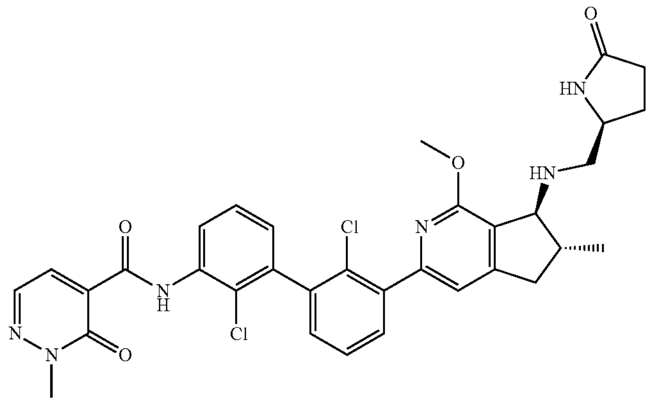
,
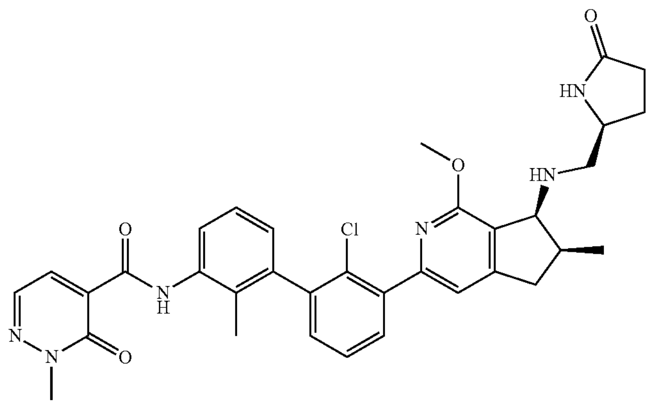
,
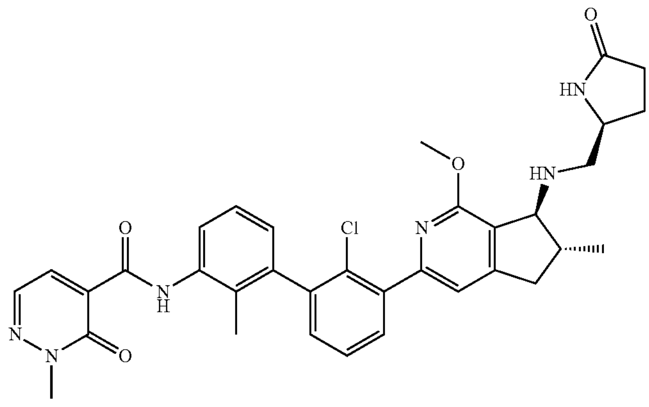
, -continued
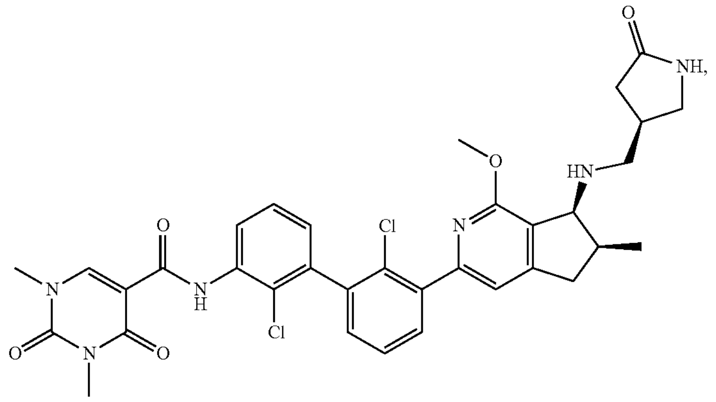
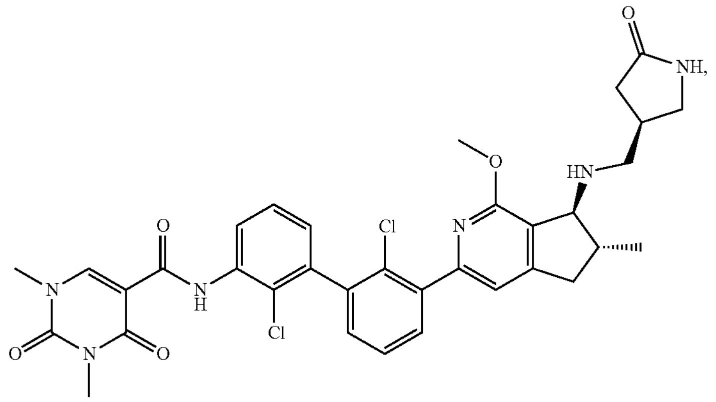
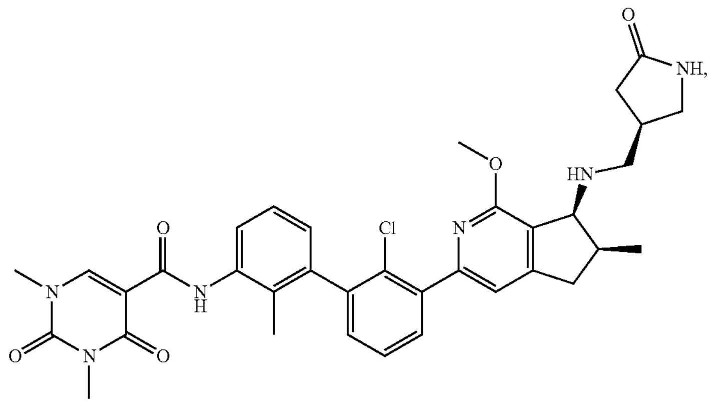
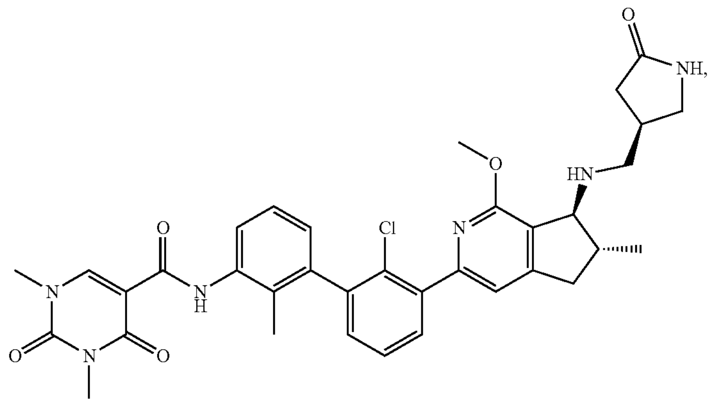

-continued
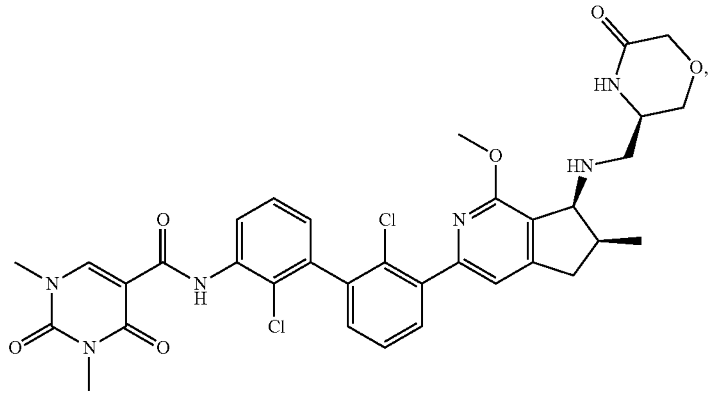
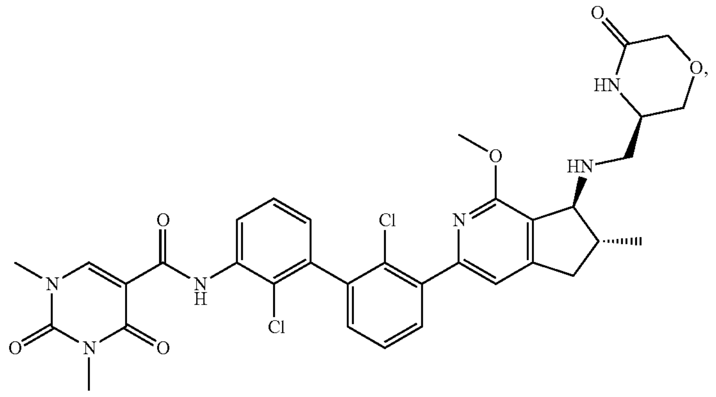
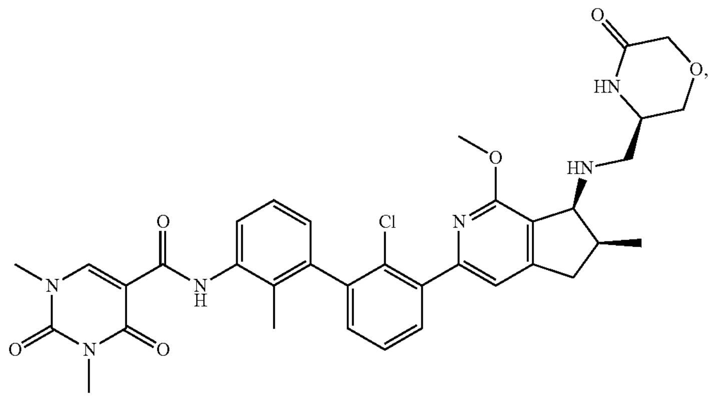
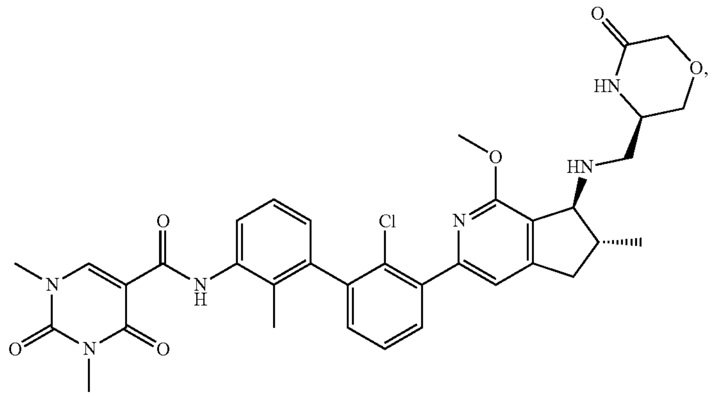

-continued
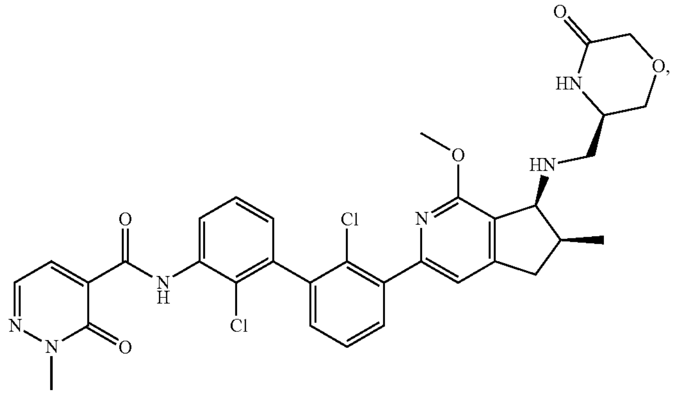
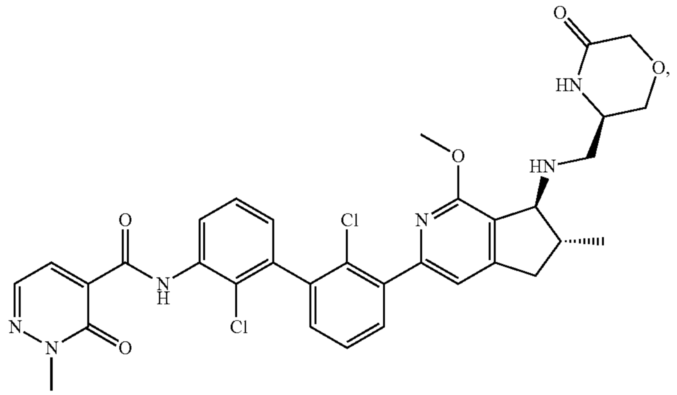
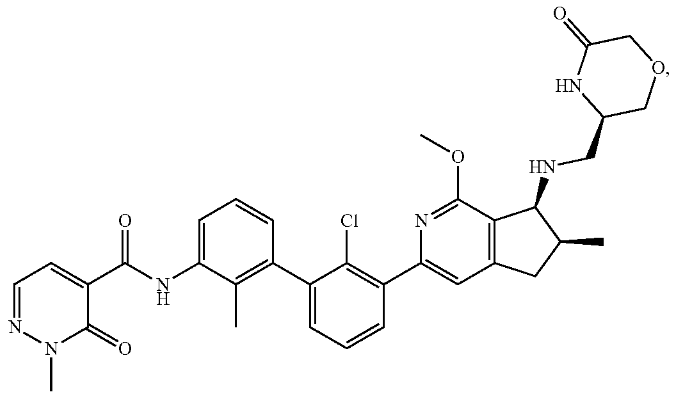
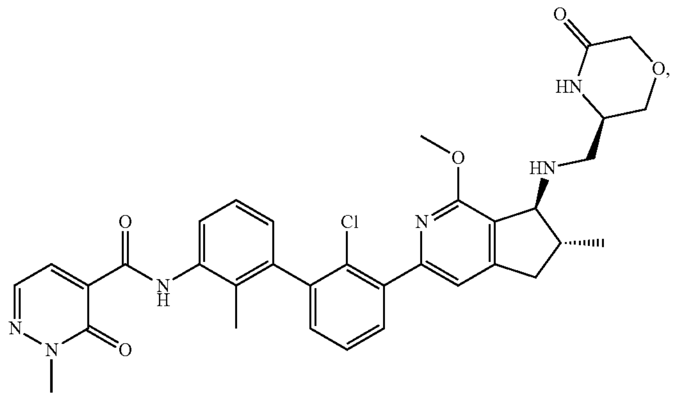

-continued

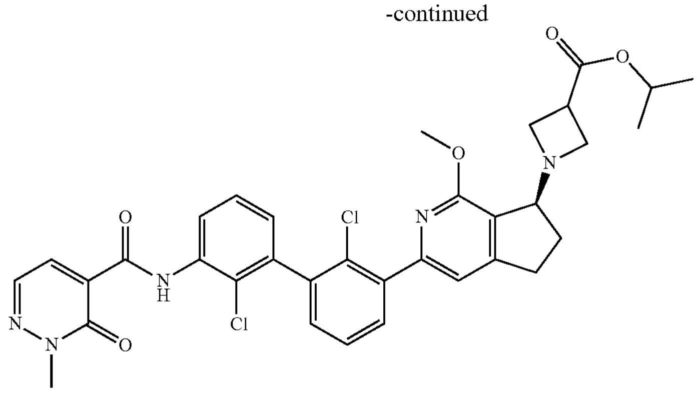

,

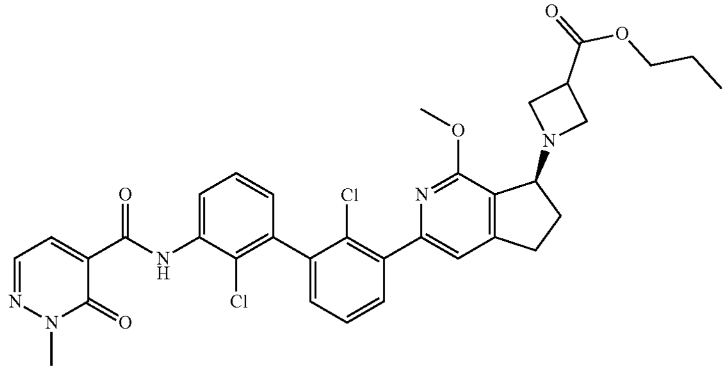

and

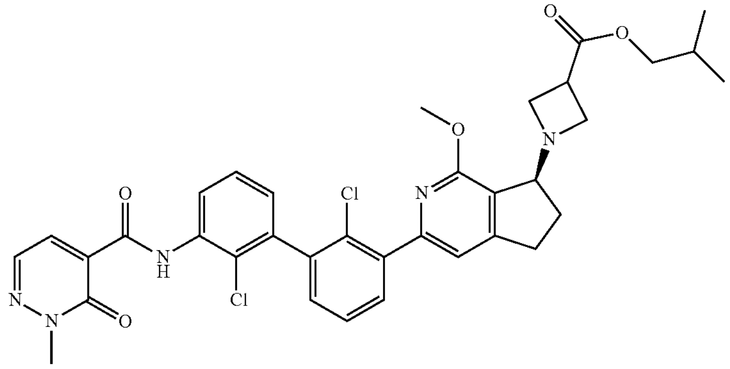

, (including pharmaceutically acceptable salts thereof).

Example A

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+Na]^+$, $[M+HCOO]^-$, etc.). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof Quadrupole Time-off light mass spectrometers, "CLND", ChemiLuminescent Nitrogen Detector, "ELSD" Evaporative Light Scanning Detector.

TABLE A

LCMS Method Codes

| Method code | Instrument | Column | Mobile phase | Gradient | Flow T | Run Time |
|---|---|---|---|---|---|---|
| 1 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 50 | 4.0 |
| 2 | Shimadzu LCMS2020 | Chromolith ® Flash RP-18e 25-3 mm | A: water(4 L) + TFA(1.5 mL) B: acetonitrile (4 L) + TFA (0.75 mL) | from 95% A to 5% A in 0.7 minutes and holding at 5% for 0.4 minutes, to 95% A in 0.01 min held for 0.49 min | 1.5 50 | 1.5 |
| 3 | Shimadzu LC20-MS2020 | Agilent Pursit 5 C18 20*2.0 mm | A: water(4 L) + TFA(1.5 mL) B: acetonitrile (4 L) + TFA (0.75 mL) | from 95% A to 5% A in 0.7 minutes and holding at 5% for 0.4 minutes, to 95% A in 0.01 min held for 0.39 min | 1.5 50 | 1.5 |
| 4 | Shimadzu LCMS2020 | Xbrige Shield RP-18, 5 um, 2.1*50 mm | A: water(4 L) + $NH_3H_2O$ (0.8 mL) B: acetonitrile (4 L) | from 90% A to 20% A in 3 minutes and holding at 20% for 0.5 minutes, to 90% A in 0.01 min held for 0.49 min | 1.0 50 | 4.0 |
| 5 | Shimadzu LCMS2020 | Xtimate ® C18 2.1*30 mm, 3 um | A: water(4 L) + TFA(1.5 mL) B: acetonitrile (4 L) + TFA (0.75 mL) | from 95% A to 5% A in 3 minutes and holding at 5% for 0.5 minutes, to 95% A in 0.01 min held for 0.49 min | 1.0 50 | 4.0 |
| 6 | Shimadzu LCMS2020 | Xtimate ® C18 2.1*30 mm, 3 um | A: water(4 L) + TFA(1.5 mL) B: acetonitrile (4 L) + TFA (0.75 mL) | from 95% A to 5% A in 3 minutes and holding at 5% for 0.5 minutes, to 95% A in 0.01 min held for 0.49 min | 1.2 50 | 4.0 |
| 7 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 50 | 4.0 |
| 8 | Shimadzu LCMS2020 | Xtimate ® C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.2 50 | 4.0 |
| 9 | Shimadzu LCMS2020 | Xtimate C18 2.1*30 mm, 3 um | A: water(4 L) + TFA(1.5 mL) B: acetonitrile (4 L) + TFA (0.75 mL) | From 100% A to 40% A in 3 minutes, to 10% A in 0.01 min and holding at 10% for 0.5 minutes, to 0% A in 0.01 min held for 0.49 min | 1.2 50 | 4.0 |
| 10 | Shimadzu LCMS2020 | Xtimate C18 2.1*30 mm, 3 um | A: water(4 L) + TFA(1.5 mL) B: acetonitrile (4 L) + TFA (0.75 mL) | From 100% A to 40% A in 3 minutes, to 10% A in 0.01 min and holding at 10% for 0.5 minutes, to 0% A in 0.01 min held for 0.49 min | 1.0 50 | 4.0 |
| 11 | Shimadzu LCMS2020 | Xtimate C18 2.1*30 mm, 3 um | A: water(4 L) + TFA(1.5 mL) B: acetonitrile (4 L) + TFA (0.75 mL) | From 100% A to 40% A in 6 minutes, to 10% A in 0.01 min and holding at 10% for 0.5 minutes, to 0% A in 0.01 min held for 0.49 min | 1.0 50 | 7.0 |

Flow expressed in mL/min;
column temperature (T) in ° C.;
Run time in minutes.

TABLE B

| Cmpd No. | $R_t$ | LC/MS | LCMS Method |
|---|---|---|---|
| | LCMS | | |
| A-1 | 1.35 | 640.4 | 1 |
| B-1 | 1.28 | 634.4 | 1 |
| C-1 | 1.61 | 663.4 | 1 |
| A-2 | 1.54 | 643.5 | 7 |
| A-3 | 1.53 | 647.4 | 7 |
| A-4 | 1.60 | 643.5 | 7 |
| A-5 | 1.59 | 623.5 | 7 |
| A-6 | 1.57 | 627.5 | 7 |
| A-7 | 1.60 | 647.5 | 7 |
| A-8 | 1.56 | 627.5 | 7 |
| A-9 | 1.55 | 631.4 | 7 |
| A-10 | 1.55 | 643.5 | 7 |
| A-11 | 2.19 | 647.2 | 4 |
| A-12 | 2.28 | 643.2 | 4 |
| A-13 | 1.58 | 623.5 | 7 |
| A-14 | 1.56 | 627.5 | 7 |
| A-15 | 2.23 | 647.3 | 4 |
| A-16 | 1.56 | 627.5 | 7 |
| A-17 | 1.59 | 631.5 | 7 |
| A-18 | 1.56 | 665.4 | 7 |
| A-19 | 1.65 | 645.4 | 7 |
| A-20 | 1.62 | 675.4 | 7 |
| A-21 | 1.61 | 675.4 | 7 |
| A-22 | 1.62 | 675.4 | 7 |
| A-23 | 1.62/1.65 | 689.5/689.4 | 7 |
| A-24 | 1.87 | 636.4 | 7 |
| A-25 | 1.74 | 636.4 | 7 |
| A-26 | 1.63 | 622.4 | 7 |
| A-27 | 1.62 | 622.4 | 7 |
| A-28 | 1.80 | 602.4 | 7 |
| A-29 | 1.69 | 666.2 | 5 |
| A-30 | 1.62 | 666.4 | 7 |
| A-31 | 1.64 | 646.4 | 7 |
| A-32 | 1.66 | 650.4 | 7 |
| A-33 | 1.59 | 646.5 | 7 |
| A-34 | 1.64 | 626.5 | 7 |
| A-35 | 1.61 | 630.5 | 7 |
| A-36 | 1.58 | 650.4 | 7 |
| A-37 | 1.61 | 630.5 | 7 |
| A-38 | 1.63 | 634.5 | 7 |
| A-39 | 1.86 | 646.5 | 7 |
| A-40 | 1.67 | 646.5 | 7 |
| A-41 | 1.77 | 626.5 | 7 |
| A-42 | 1.84 | 630.6 | 7 |
| A-43 | 1.80 | 633.4 | 7 |
| A-44 | 1.77 | 635.4 | 7 |
| A-45 | 1.74 | 597.5 | 7 |
| A-46 | 1.72 | 615.4 | 7 |
| A-47 | 1.72 | 613.5 | 7 |
| A-48 | 1.64 | 662.4 | 7 |
| A-49 | 1.68 | 625.5 | 7 |
| A-50 | 1.44 | 654.5 | 7 |
| A-51 | 1.57 | 619.4 | 7 |
| A-52 | 1.50 | 599.4 | 7 |
| A-53 | 1.60 | 659.5 | 7 |
| A-54 | 1.36 | 615.5 | 7 |
| A-55 | 1.51 | 629.5 | 7 |
| A-56 | 3.42 | 629.2 | 11 |
| A-57 | 1.51 | 654.5 | 7 |
| A-58 | 1.49 | 644.6 | 7 |
| A-59 | 1.57 | 661.5 | 7 |
| A-60 | 1.71 | 661.5 | 7 |
| A-61 | 1.82 | 677.5 | 7 |
| A-62 | 1.70 | 662.6 | 7 |
| A-63 | 1.88 | 631.5 | 7 |
| A-64 | 1.76 | 679.3 | 8 |
| A-65 | 1.80 | 681.4 | 7 |
| A-66 | 1.84 | 699.5 | 7 |
| A-67 | 1.64 | 645.5 | 7 |
| A-68 | 1.66 | 645.5 | 7 |
| A-69 | 1.72 | 661.5 | 7 |
| A-70 | 1.65 | 645.5 | 7 |
| A-71 | 1.63 | 690.2 | 5 |
| A-72 | 1.66 | 669.3 | 5 |
| A-73 | 1.43 | 657.5 | 5 |
| A-74 | 1.66 | 645.3 | 5 |

TABLE B-continued

| Cmpd No. | $R_t$ | LC/MS | LCMS Method |
|---|---|---|---|
| | LCMS | | |
| A-75 | 1.58 | 627.3 | 5 |
| A-76 | 1.67 | 667.5 | 7 |
| A-77 | 1.59 | 647.5 | 7 |
| A-79 | 1.71 | 582.5 | 7 |
| A-80 | 1.72 | 582.5 | 7 |
| A-81 | 1.57 | 604.5 | 7 |
| A-82 | 1.61 | 604.4 | 7 |
| A-83 | 1.76 | 596.5 | 7 |
| A-84 | 1.78 | 596.5 | 7 |
| A-85 | 1.90 | 678.5 | 7 |
| A-86 | 1.90 | 678.5 | 7 |
| A-87 | 1.83 | 648.4 | 7 |
| A-88 | 1.77 | 628.5 | 7 |
| A-89 | 1.75 | 626.5 | 7 |
| A-90 | 1.74 | 626.5 | 7 |
| A-91 | 1.62 | 627.5 | 8 |
| A-92 | 1.62 | 627.3 | 8 |
| A-93 | 1.65 | 667.4 | 7 |
| A-94 | 1.67 | 667.4 | 7 |
| A-95 | 1.58 | 647.3 | 7 |
| A-96 | 1.61 | 647.5 | 7 |
| A-97 | 1.64 | 612.5 | 5 |
| A-98 | 1.62 | 612.5 | 5 |
| A-99 | 1.59 | 653.2 | 5 |
| A-100 | 1.58 | 653.3 | 5 |
| A-101 | 1.51 | 633.5 | 5 |
| A-102 | 1.52 | 633.6 | 5 |
| A-103 | 1.55 | 613.5 | 5 |
| A-104 | 1.55 | 613.6 | 5 |
| A-105 | 1.64 | 612.5 | 5 |
| A-106 | 1.66 | 612.5 | 5 |
| A-107 | 1.59 | 653.2 | 5 |
| A-108 | 1.60 | 653.2 | 5 |
| A-109 | 1.51 | 633.5 | 5 |
| A-110 | 1.54 | 633.5 | 5 |
| A-111 | 1.54 | 613.6 | 5 |
| A-112 | 1.60 | 613.3 | 5 |
| A-113 | 1.62 | 643.5 | 7 |
| A-114 | 1.63 | 643.5 | 7 |
| A-115 | 1.56 | 687.6 | 7 |
| A-116 | 1.56 | 687.6 | 7 |
| A-117 | 1.61 | 689.5 | 7 |
| A-118 | 1.60 | 689.4 | 7 |
| A-119 | 1.91 | 761.5 | 7 |
| A-120 | 1.66 | 582.3 | 7 |
| A-121 | 1.81 | 657.5 | 7 |
| A-122 | 1.80 | 657.6 | 7 |
| A-123 | 1.48 | 671.5 | 5 |
| A-124 | 1.47 | 671.5 | 5 |
| A-125 | 1.36 | 659.5 | 7 |
| A-126 | 1.39 | 659.5 | 7 |
| A-127 | 1.35 | 659.6 | 7 |
| A-128 | 1.38 | 659.5 | 7 |
| A-129 | 1.48 | 675.5 | 7 |
| A-130 | 1.49 | 675.5 | 7 |
| A-131 | 1.44 | 655.5 | 7 |
| A-132 | 1.43 | 655.5 | 7 |
| A-133 | 1.44 | 691.5 | 7 |
| A-134 | 1.46 | 691.5 | 7 |
| A-135 | 1.45 | 663.5 | 7 |
| A-136 | 1.45 | 663.5 | 7 |
| A-137 | 1.40 | 643.5 | 7 |
| A-138 | 1.42 | 643.5 | 7 |
| A-139 | 2.03 | 655.5 | 10 |
| B-2 | 1.74 | 626.4 | 7 |
| B-3 | 1.56 | 625.4 | 7 |
| B-4 | 1.50 | 626.4 | 7 |
| D-1 | 2.32 | 636.4 | 10 |
| D-2 | 1.64 | 622.4 | 7 |
| D-3 | 1.62 | 675.4 | 7 |
| D-4 | 1.61 | 652.4 | 7 |
| D-5 | 1.59 | 610.4 | 7 |
| D-6 | 1.64 | 666.4 | 7 |
| D-7 | 1.62 | 666.4 | 7 |
| D-8a | 1.651 | 666.5 | 7 |
| D-8b | 1.650 | 666.5 | 7 |

TABLE B-continued

| LCMS | | | |
|---|---|---|---|
| Cmpd No. | $R_t$ | LC/MS | LCMS Method |
| D-9 | 1.70 | 603.5 | 7 |
| D-10 | 1.73 | 602.5 | 7 |
| D-11 | 1.83 | 586.5 | 7 |
| D-12 | 1.24 | 604.2 | 4 |
| D-13 | 2.29 | 657.3 | 4 |
| D-14 | 1.76 | 675.5 | 7 |
| D-15 | 2.19 | 677.4 | 10 |
| D-16 | 1.91 | 761.5 | 5 |
| D-17 | 1.76 | 596.6 | 7 |
| D-18 | 1.84 | 610.6 | 7 |
| D-19 | 1.78 | 596.6 | 7 |
| E-1 | 2.35 | 715.5 | 7 |
| E-2 | 2.54 | 743.5 | 7 |
| E-3 | 2.27 | 717.5 | 7 |
| F-1 | 2.23 | 799.5 | 7 |
| G-1 | 1.58 | 661.5 | 5 |
| H-1 | 1.71 | 703.5 | 5 |
| I-1 | 1.61 | 657.5 | 7 |
| J-1 | 1.67 | 620.4 | 7 |
| J-2 | 1.64 | 600.5 | 7 |
| J-3 | 1.77 | 650.4 | 7 |
| J-4 | 1.77 | 650.5 | 7 |
| K-1a | 1.46 | 661.6 | 7 |
| K-1b | 1.55 | 661.6 | 7 |
| L-1a | 1.42 | 673.5 | 7 |
| L-1b | 1.43 | 673.5 | 7 |
| M-1a | 1.44 | 673.5 | 7 |
| M-1b | 1.44 | 673.5 | 7 |
| M-2a | 1.45 | 620.1 | 7 |
| M-2b | 1.45 | 620.1 | 7 |
| M-3a | 1.40 | 661.5 | 7 |
| M-3b | 1.42 | 661.5 | 7 |

Retention time ($R_t$) in min;
LC/MS: without indication the mass is corresponding to $[M + H]^+$

Example B

Nuclear Magnetic Resonance Spectroscopy

For a number of compounds, $^1$H NMR spectra were recorded on a Bruker DPX-360 operating a 360 MHz, on a Bruker Avance 600 operating at 600 z, on a Bruker Avance 400 operating at 400 MHz, or on a Varian 400MR spectrometer operating at 400 MHz. As solvents CHLOROFORM-$d_3$ (deuterated chloroform, $CDCl_3$) and/or DMSO-$d_6$ (deuterated DMSO, dimethyl-$d_6$ sulfoxide) were used. Chemical shifts (d) are reported in parts per million (ppm) relative to tetramethylsilane (TMS), which was used as internal standard.

Compound A-1: $^1$H-NMR (400 MHz, CHLOROFORM-$d_3$) δ=11.48 (s, 1H), 8.57 (dd, J=1.4, 8.3 Hz, 1H), 8.53 (s, 1H), 7.63 (d, J=7.9 Hz, 1H), 7.39 (td, J=7.8, 15.4 Hz, 2H), 7.29 (br d, J=1.6 Hz, 1H), 7.21 (br s, 1H), 7.09 (dd, J=1.3, 7.6 Hz, 1H), 4.62-4.31 (m, 1H), 4.05 (s, 3H), 3.90 (br dd, J=3.6, 6.8 Hz, 1H), 3.59 (s, 3H), 3.46 (s, 3H), 3.31-3.12 (m, 1H), 3.07-2.96 (m, 1H), 2.94-2.83 (m, 1H), 2.77-2.60 (m, 1H), 2.38 (br t, J=8.1 Hz, 3H), 2.33-2.25 (m, 1H), 2.15-2.01 (m, 1H), 1.85-1.73 (m, 2H).

Compound A-2: $^1$H-NMR (400 MHz, CHLOROFORM-$d_3$) δ=10.92 (br d, J=4.6 Hz, 1H), 8.61-8.51 (m, 1H), 8.22 (br d, J=8.0 Hz, 1H), 7.59 (ddd, J=1.5, 4.4, 7.5 Hz, 1H), 7.40 (br t, J=7.3 Hz, 1H), 7.36-7.27 (m, 2H), 7.21 (d, J=7.6 Hz, 1H), 7.03 (d, J=7.5 Hz, 1H), 6.98-6.64 (m, 1H), 5.33-4.38 (m, 1H), 4.13-3.93 (m, 4H), 3.64-3.58 (m, 3H), 3.45 (s, 3H), 3.28-3.19 (m, 1H), 3.03 (br d, J=12.8 Hz, 1H), 2.94-2.86 (m, 1H), 2.76-2.66 (m, 1H), 2.44 (br d, J=6.6 Hz, 1H), 2.39-2.34 (m, 2H), 2.30 (br dd, J=6.4, 13.8 Hz, 2H), 2.22-2.17 (m, 4H), 1.78-1.73 (m, 1H).

Compound A-71: $^1$H-NMR (400 MHz, CHLOROFORM-$d_3$) δ=11.43 (s, 1H), 8.66 (d, J=8.3 Hz, 1H), 8.00 (s, 1H), 7.63 (br d, J=8.1 Hz, 1H), 7.49-7.39 (m, 2H), 7.37-7.29 (m, 2H), 7.14 (d, J=7.5 Hz, 1H), 4.72-4.48 (m, 2H), 4.40-4.03 (m, 9H), 3.94-3.62 (m, 5H), 3.49 (s, 3H), 3.02-2.92 (m, 1H), 2.63-2.29 (m, 2H), 1.92-1.85 (m, 3H).

Compound A-87: $^1$H-NMR (400 MHz, CHLOROFORM-$d_3$) δ=12.24 (s, 1H), 8.64 (dd, J=1.4, 8.3 Hz, 1H), 8.33 (d, J=4.1 Hz, 1H), 8.06 (d, J=4.3 Hz, 1H), 7.63 (ddd, J=1.7, 6.1, 7.7 Hz, 1H), 7.43-7.40 (m, 1H), 7.39-7.37 (m, 1H), 7.31-7.28 (m, 1H), 7.19 (d, J=5.1 Hz, 1H), 7.14-7.10 (m, 1H), 4.18 (dq, J=0.8, 7.1 Hz, 2H), 4.05 (br d, J=6.0 Hz, 1H), 4.01 (d, J=1.4 Hz, 3H), 3.97 (s, 3H), 3.68 (br dd, J=7.3, 14.9 Hz, 2H), 3.58 (br t, J=6.9 Hz, 1H), 3.46 (br t, J=7.2 Hz, 1H), 3.34-3.27 (m, 1H), 3.17-3.09 (m, 1H), 2.84-2.76 (m, 1H), 2.14-2.06 (m, 1H), 2.02-1.95 (m, 1H), 1.29 (dt, J=0.9, 7.1 Hz, 3H).

Compound A-126: $^1$H-NMR (400 MHz, CHLOROFORM-$d_3$) δ=10.91 (s, 1H), 8.54 (s, 1H), 8.22 (d, J=8.0 Hz, 1H), 7.56 (br d, J=7.4 Hz, 1H), 7.39 (t, J=7.6 Hz, 1H), 7.34-7.28 (m, 2H), 7.19 (s, 1H), 7.03 (br d, J=7.5 Hz, 1H), 6.34 (br s, 1H), 4.49-4.42 (m, 1H), 4.25 (br d, J=3.9 Hz, 1H), 4.06 (s, 3H), 3.94 (br d, J=4.0 Hz, 1H), 3.59 (s, 3H), 3.45 (s, 3H), 3.09-3.03 (m, 3H), 2.75 (br dd, J=7.9, 12.2 Hz, 1H), 2.44-2.39 (m, 2H), 2.37-2.30 (m, 2H), 2.19 (s, 3H), 1.91-1.85 (m, 1H).

Compound A-129: $^1$H-NMR (400 MHz, CHLOROFORM-$d_3$) δ=11.48 (s, 1H), 8.59-8.52 (m, 2H), 8.26 (s, 1H), 7.67-7.61 (m, 1H), 7.45-7.35 (m, 2H), 7.32-7.28 (m, 1H), 7.22 (s, 1H), 7.11-7.06 (m, 1H), 5.87 (br s, 1H), 4.25 (br d, J=7.0 Hz, 1H), 4.02 (d, J=1.4 Hz, 3H), 3.88 (br t, J=7.8 Hz, 1H), 3.81-3.75 (m, 1H), 3.67-3.58 (m, 7H), 3.45 (s, 3H), 3.19 (br d, J=8.5 Hz, 1H), 2.86-2.79 (m, 1H), 2.55 (d, J=2.6 Hz, 2H), 2.28-2.18 (m, 1H), 2.11 (br d, J=7.4 Hz, 1H).

Compound A-130: $^1$H-NMR (400 MHz, CHLOROFORM-$d_3$) δ=11.48 (s, 1H), 8.60-8.47 (m, 2H), 8.26 (s, 1H), 7.63 (ddd, J=1.6, 3.3, 7.7 Hz, 1H), 7.40 (td, J=7.9, 17.0 Hz, 2H), 7.30 (d, J=1.5 Hz, 1H), 7.22 (s, 1H), 7.09 (ddd, J=1.4, 3.0, 7.5 Hz, 1H), 5.72 (br s, 1H), 4.20 (br d, J=6.9 Hz, 1H), 4.02 (d, J=1.3 Hz, 3H), 3.81 (br t, J=6.4 Hz, 1H), 3.77-3.71 (m, 1H), 3.66-3.53 (m, 6H), 3.46 (s, 3H), 3.26-3.15 (m, 1H), 2.86-2.78 (m, 1H), 2.55 (d, J=1.5 Hz, 2H), 2.20-2.17 (m, 1H), 2.10-2.05 (m, 1H).

Compound A-131: $^1$H-NMR (400 MHz, CHLOROFORM-$d_3$) δ=10.91 (s, 1H), 8.54 (s, 1H), 8.22 (d, J=8.0 Hz, 1H), 7.59 (td, J=2.0, 7.6 Hz, 1H), 7.40 (t, J=7.6 Hz, 1H), 7.34-7.28 (m, 2H), 7.21 (d, J=3.8 Hz, 1H), 7.03 (br d, J=7.6 Hz, 1H), 5.72 (s, 1H), 4.27 (br d, J=5.6 Hz, 1H), 4.03 (s, 3H), 3.91 (br d, J=6.6 Hz, 1H), 3.85-3.77 (m, 1H), 3.71-3.56 (m, 7H), 3.45 (s, 3H), 3.29-3.18 (m, 1H), 2.97 (s, 1H), 2.89 (s, 1H), 2.88-2.81 (m, 1H), 2.56 (s, 2H), 2.23-2.18 (m, 4H).

Compound A-132: $^1$H-NMR (400 MHz, CHLOROFORM-$d_3$) δ=10.91 (s, 1H), 8.55 (s, 1H), 8.22 (d, J=8.0 Hz, 1H), 7.59 (td, J=1.9, 7.6 Hz, 1H), 7.43-7.36 (m, 1H), 7.34-7.29 (m, 1H), 7.26-7.24 (m, 1H), 7.21 (d, J=3.4 Hz, 1H), 7.05-7.00 (m, 1H), 5.88 (s, 1H), 4.24 (br d, J=7.0 Hz, 1H), 4.02 (s, 3H), 3.87 (br t, J=6.8 Hz, 1H), 3.78 (br dd, J=4.6, 8.3 Hz, 1H), 3.67-3.57 (m, 7H), 3.45 (s, 3H), 3.23-3.17 (m, 1H), 2.86-2.78 (m, 1H), 2.55 (s, 2H), 2.19 (d, J=3.1 Hz, 4H), 2.14-2.05 (m, 1H).

Compound A-135: $^1$H-NMR (400 MHz, CHLOROFORM-$d_3$) δ=11.49 (s, 1H), 8.61-8.49 (m, 2H), 7.63 (br d, J=7.6 Hz, 1H), 7.44-7.34 (m, 2H), 7.32-7.29 (m, 1H), 7.24 (br s, 1H), 7.08 (br d, J=7.5 Hz, 1H), 6.03 (br s, 1H), 4.65 (br d, J=2.3 Hz, 1H), 4.08-3.99 (m, 3H), 3.71-3.63 (m, 1H), 3.59 (s, 3H), 3.45 (s, 3H), 3.36-3.25 (m, 2H), 3.03-2.88 (m, 4H), 2.62-2.47 (m, 3H), 2.19-2.13 (m, 2H).

Compound A-136: $^1$H-NMR (400 MHz, CHLOROFORM-$d_3$) δ=11.49 (s, 1H), 8.81-8.38 (m, 2H), 7.63 (br d, J=7.5 Hz, 1H), 7.40 (td, J=7.8, 19.1 Hz, 2H), 7.31 (br s, 1H), 7.24 (br s, 1H), 7.09 (br d, J=7.6 Hz, 1H), 6.06 (br s, 1H), 4.74 (br d, J=3.8 Hz, 1H), 4.11-3.99 (m, 3H), 3.71-3.57 (m, 4H), 3.46 (s, 3H), 3.42-3.28 (m, 2H), 3.11-2.99 (m, 2H), 2.99-2.88 (m, 2H), 2.65-2.47 (m, 3H), 2.24-2.18 (m, 2H).

Compound A-137: $^1$H-NMR (400 MHz, CHLOROFORM-$d_3$) δ=10.91 (s, 1H), 8.55 (s, 1H), 8.22 (br d, J=8.1 Hz, 1H), 7.59 (br d, J=6.9 Hz, 1H), 7.40 (t, J=7.6 Hz, 1H), 7.34-7.30 (m, 1H), 7.26-7.24 (m, 1H), 7.22 (s, 1H), 7.06-7.00 (m, 1H), 5.96 (br s, 1H), 4.63 (br d, J=1.1 Hz, 1H), 4.10-3.98 (m, 3H), 3.70-3.56 (m, 4H), 3.45 (s, 3H), 3.35-3.20 (m, 2H), 3.02-2.83 (m, 4H), 2.67-2.43 (m, 3H), 2.19 (br d, J=1.9 Hz, 5H).

Compound A-138: $^1$H-NMR (400 MHz, CHLOROFORM-$d_3$) δ=10.91 (s, 1H), 8.55 (s, 1H), 8.22 (br d, J=8.1 Hz, 1H), 7.59 (br d, J=7.1 Hz, 1H), 7.40 (br t, J=7.3 Hz, 1H), 7.34-7.29 (m, 2H), 7.24 (br s, 1H), 7.06-7.00 (m, 1H), 6.03 (br s, 1H), 4.70 (br d, J=2.3 Hz, 1H), 4.11-3.98 (m, 3H), 3.71-3.55 (m, 4H), 3.45 (s, 3H), 3.40-3.25 (m, 2H), 3.08-2.85 (m, 4H), 2.65-2.45 (m, 3H), 2.19 (br d, J=2.8 Hz, 5H).

Compound 139: $^1$H-NMR (400 MHz, DMSO-$d_6$) δ=11.06 (d, J=2.9 Hz, 1H), 8.75 (s, 1H), 8.25 (d, J=8.3 Hz, 1H), 8.13 (s, 1H), 8.10 (s, 1H), 7.62-7.57 (m, 1H), 7.51 (t, J=7.6 Hz, 1H), 7.37-7.29 (m, 2H), 7.19 (s, 1H), 6.98 (dd, J=3.4, 7.3 Hz, 1H), 3.90 (s, 4H), 3.50 (s, 4H), 3.27 (s, 3H), 3.25 (br s, 2H), 3.19-3.16 (m, 1H), 3.03-2.96 (m, 1H), 2.77 (br dd, J=7.8, 17.2 Hz, 1H), 2.19-2.11 (m, 4H), 2.09 (d, J=6.4 Hz, 3H), 2.02 (br dd, J=7.8, 13.9 Hz, 1H), 1.91-1.85 (m, 1H).

Compound J-1: $^1$H-NMR (400 MHz, CHLOROFORM-$d_3$) δ=12.23 (d, J=4.0 Hz, 1H), 8.64 (dd, J=1.4, 8.3 Hz, 1H), 8.33 (d, J=4.3 Hz, 1H), 8.06 (d, J=4.1 Hz, 1H), 7.65 (dd, J=1.7, 7.7 Hz, 1H), 7.44-7.37 (m, 2H), 7.35-7.27 (m, 2H), 7.25 (d, J=2.4 Hz, 1H), 7.11 (td, J=1.3, 7.6 Hz, 1H), 4.57 (br d, J=7.5 Hz, 2H), 4.28 (br s, 1H), 4.25-4.19 (m, 1H), 4.11 (br t, J=9.4 Hz, 1H), 4.02 (d, J=3.4 Hz, 3H), 3.97 (s, 3H), 3.48 (br dd, J=8.7, 16.1 Hz, 1H), 3.17 (br s, 1H), 2.93-2.85 (m, 1H), 2.62-2.51 (m, 1H), 2.37-2.27 (m, 1H).

Compound H-1: $^1$H-NMR (400 MHz, DMSO-$d_6$) δ=11.62 (d, J=2.9 Hz, 1H), 8.79 (s, 1H), 8.57 (dd, J=1.3, 8.3 Hz, 1H), 8.17 (s, 1H), 7.64 (d, J=7.6 Hz, 1H), 7.55-7.45 (m, 2H), 7.40 (dd, J=1.5, 7.5 Hz, 1H), 7.19 (s, 1H), 7.14 (ddd, J=1.4, 3.4, 7.6 Hz, 1H), 3.95-3.87 (m, 4H), 3.50 (br s, 1H), 3.51 (s, 4H), 3.34-3.32 (m, 2H), 3.27 (s, 3H), 3.25-3.23 (m, 1H), 3.18-3.06 (m, 3H), 3.02-2.95 (m, 1H), 2.76 (br dd, J=8.6, 16.8 Hz, 1H), 2.05-1.95 (m, 2H), 1.93-1.86 (m, 5H).

Compound L-1a: $^1$H-NMR (400 MHz, DMSO-$d_6$) δ=10.99 (s, 1H), 8.75 (s, 1H), 8.20 (dd, J=5.4, 9.0 Hz, 1H), 8.11 (s, 1H), 7.66 (br d, J=7.5 Hz, 1H), 7.55 (t, J=7.6 Hz, 1H), 7.39 (br d, J=7.4 Hz, 1H), 7.25-7.18 (m, 2H), 3.90 (s, 3H), 3.87 (br d, J=6.5 Hz, 1H), 3.50 (s, 3H), 3.27 (br s, 4H), 3.21-3.20 (m, 1H), 3.14 (br d, J=6.8 Hz, 1H), 3.09-2.94 (m, 2H), 2.77 (br dd, J=8.1, 16.8 Hz, 1H), 2.15 (br dd, J=5.4, 10.9 Hz, 4H), 2.04 (s, 3H), 1.99 (br s, 1H), 1.91-1.85 (m, 1H).

Compound L-1b: $^1$H-NMR (400 MHz, DMSO-$d_6$) δ=11.00 (s, 1H), 8.75 (s, 1H), 8.20 (dd, J=5.6, 8.8 Hz, 1H), 8.11 (s, 1H), 7.65 (br d, J=7.3 Hz, 1H), 7.55 (t, J=7.6 Hz, 1H), 7.42-7.35 (m, 1H), 7.24-7.19 (m, 2H), 3.90 (s, 3H), 3.86 (br d, J=6.5 Hz, 1H), 3.50 (s, 3H), 3.27 (br s, 4H), 3.21 (br s, 1H), 3.14 (br d, J=6.9 Hz, 1H), 2.98 (br d, J=8.8 Hz, 2H), 2.77 (br dd, J=8.9, 16.2 Hz, 1H), 2.19-2.11 (m, 4H), 2.06 (s, 3H), 1.99 (br d, J=6.4 Hz, 1H), 1.89 (br d, J=7.3 Hz, 1H).

Compound M-2a: $^1$H-NMR (400 MHz, CHLOROFORM-$d_3$) δ=10.94 (s, 1H), 8.54 (s, 1H), 8.29 (br d, J=8.1 Hz, 1H), 7.62 (dd, J=6.1, 8.5 Hz, 1H), 7.38-7.37 (m, 1H), 7.38-7.33 (m, 1H), 7.22-7.17 (m, 2H), 7.04 (br d, J=7.5 Hz, 1H), 4.42 (br s, 1H), 4.27 (br s, 1H), 4.30-4.21 (m, 1H), 4.08-3.97 (m, 4H), 3.91-3.79 (m, 1H), 3.71-3.63 (m, 1H), 3.59 (s, 3H), 3.45 (s, 4H), 3.33-3.25 (m, 1H), 2.85 (br dd, J=8.5, 16.9 Hz, 1H), 2.28-2.21 (m, 1H), 2.19 (s, 3H), 2.14-2.04 (m, 2H).

Compound M-2b: $^1$H-NMR (400 MHz, CHLOROFORM-$d_3$) δ=10.94 (s, 1H), 8.54 (s, 1H), 8.30 (d, J=7.9 Hz, 1H), 7.62 (dd, J=6.1, 8.6 Hz, 1H), 7.35 (br t, J=8.0 Hz, 2H), 7.21 (br s, 1H), 7.05-7.00 (m, 1H), 4.76-4.54 (m, 2H), 4.53-4.40 (m, 1H), 4.29-4.15 (m, 2H), 4.13-3.99 (m, 4H), 3.98-3.87 (m, 1H), 3.59 (s, 3H), 3.46 (s, 3H), 2.94 (br dd, J=8.3, 17.0 Hz, 1H), 2.48-2.24 (m, 3H), 2.19 (s, 3H).

Compound M-3a: $^1$H-NMR (400 MHz, CHLOROFORM-$d_3$) δ=10.95 (s, 1H), 8.63-8.51 (m, 1H), 8.29 (br d, J=7.6 Hz, 1H), 7.61 (dd, J=6.1, 8.5 Hz, 1H), 7.36 (t, J=7.8 Hz, 1H), 7.21-7.14 (m, 2H), 7.07-7.00 (m, 1H), 6.69 (br s, 1H), 4.47 (br dd, J=4.1, 7.3 Hz, 1H), 4.03 (s, 3H), 3.95 (br d, J=6.9 Hz, 1H), 3.60 (s, 3H), 3.45 (s, 3H), 3.17 (td, J=7.8, 15.8 Hz, 1H), 2.99 (br dd, J=3.1, 12.1 Hz, 1H), 2.94-2.82 (m, 1H), 2.65 (br dd, J=9.3, 11.9 Hz, 1H), 2.46-2.25 (m, 6H), 2.19 (s, 3H), 1.82-1.72 (m, 1H).

Compound M-3b: $^1$H-NMR (400 MHz, CHLOROFORM-$d_3$) δ=10.94 (s, 1H), 9.84-9.55 (m, 1H), 8.55 (s, 1H), 8.29 (br d, J=8.1 Hz, 1H), 8.14-7.95 (m, 1H), 7.77-7.57 (m, 1H), 7.34 (t, J=7.9 Hz, 1H), 7.26-7.11 (m, 2H), 7.07-6.99 (m, 1H), 4.96-4.74 (m, 1H), 4.46-3.88 (m, 4H), 3.59 (s, 4H), 3.45 (d, J=3.6 Hz, 3H), 3.30-2.89 (m, 3H), 2.78-2.12 (m, 7H), 2.10-1.80 (m, 1H).

Example C

PDL1/PD1 Binding Assay

Compounds to be tested were serially diluted in DMSO, and further diluted in assay buffer (25 mM Hepes pH 7.4, 150 mM NaCl, 0.005% Tween 20, BSA 0.01%). Diluted compounds were added to the wells with final concentration of DMSO at 1%. PDL1-6×His protein was added to the wells, mixed well with compound. The plates were incubated for 30 min at room temperature. PD1-Fc-Avi-Biotin protein was added to the wells. Final concentration of PDL1 and PD1 protein is 0.3 nM and 2.5 nM, respectively. After a binding time of 30 min at room temperature, Anti-6×His Acceptor beads (final concentration 20 ug/ml) were added to the wells, and the incubation continued for 1 h. Streptavidin Donor beads (final concentration 20 ug/mL) were added at reduced light. The plates were sealed with foil and incubated in the dark for additional 1 h or overnight before reading on an Envision reader. The $IC_{50}$ values were determined by fitting the curves using a four-parameter equation in Graphpad Prism 8.

Example D

PD-1/PD-L1 NFAT Reporter Assay

Cellular activity of the compounds was assessed using a co-culture reporter assay in which TCR-mediated NFAT activity of Jurkat T cells is constitutively inhibited by the engagement of PD-1 by PD-L1 expressing CHO cells. Blocking the PD-1/PD-L1 interaction will release the inhibitory signal and results in TCR signaling and NFAT-mediated luciferase activity.

CHO cells expressing surface-bound anti-CD3 antibodies and PD-L1 were first seeded overnight and treated with the compounds. Jurkat cells overexpressing PD-1 and a luciferase construct under NFAT promoter were then immediately seeded on the monolayer of CHO cells. The co-culture was then incubated for 6 hrs at 37° C. Luciferase activity was assessed by adding the ONE-Glo reagent and measuring luminescence with a plate reader. $EC_{50}$ values were determined from the fit of the dose-response curves.

Compounds described herein, as exemplified in the Examples, showed $EC_{50}$ or $IC_{50}$ values in the following ranges: A: $IC_{50}$ or $EC_{50} \leq 10$ nM; B: 10 nM<$IC_{50}$ or $EC_{50} \leq 100$ nM; C: 100 nM<$IC_{50}$ or $EC_{50} \leq 1000$ nM; D: 1000 nM<$IC_{50}$ or $EC_{50} \leq 10000$ nM; E: $IC_{50}$ or $EC_{50}$>10000 nM; F: $IC_{50}$ or $EC_{50}$>5000 nM; n.d.=not determined; n.r.=$EC_{50}$ not reached in the range of tested concentrations starting from 1 nM to 10000 nM.

TABLE C

| Cmpd No. | PD-1/ PD-L1 PPI IC50 | Jurkat NFAT $EC_{50}$ |
|---|---|---|
| A-1 | A | A |
| B-1 | A | B |
| C-1 | A | B |
| A-2 | A | A |
| A-3 | A | A |
| A-4 | A | A |
| A-5 | A | A |
| A-6 | A | B |
| A-7 | A | A |
| A-8 | A | A |
| A-9 | | B |
| A-10 | A | n.r |
| A-11 | A | n.r |
| A-12 | A | n.r |
| A-13 | A | n.r |
| A-14 | A | n.r |
| A-15 | A | n.r |
| A-16 | A | n.r |
| A-17 | A | C |
| A-18 | A | A |
| A-19 | A | B |
| A-20 | A | B |
| A-21 | A | C |
| A-22 | A | A |
| A-23 | A | A |
| A-24 | A | n.r |
| A-25 | A | A |
| A-26 | A | n.r |
| A-27 | A | A |
| A-28 | A | A |
| A-29 | A | A |
| A-30 | A | C |
| A-31 | A | D |
| A-32 | A | n.r |
| A-33 | A | A |
| A-34 | A | n.r |
| A-35 | A | n.r |
| A-36 | A | n.r |
| A-37 | A | n.r |
| A-38 | A | n.r |
| A-39 | A | A |
| A-40 | A | A |
| A-41 | A | A |
| A-42 | A | B |
| A-43 | A | A |
| A-44 | A | B |
| A-45 | A | B |
| A-46 | A | A |
| A-47 | A | A |
| A-48 | | C |
| A-49 | A | B |
| A-50 | | B |
| A-51 | A | A |
| A-52 | A | B |
| A-53 | A | C |
| A-54 | A | B |

TABLE C-continued

| Cmpd No. | PD-1/ PD-L1 PPI IC50 | Jurkat NFAT $EC_{50}$ |
|---|---|---|
| A-55 | A | A |
| A-56 | A | B |
| A-57 | A | A |
| A-58 | A | A |
| A-59 | A | B |
| A-60 | A | A |
| A-61 | A | B |
| A-62 | A | A |
| A-63 | A | A |
| A-64 | A | A |
| A-65 | A | A |
| A-66 | A | B |
| A-67 | A | A |
| A-68 | A | B |
| A-69 | A | A |
| A-70 | A | B |
| A-71 | | A |
| A-72 | A | B |
| A-73 | | B |
| A-74 | A | B |
| A-75 | A | B |
| A-76 | | A |
| A-77 | | A |
| A-79 | B | F |
| A-80 | A | B |
| A-81 | | B |
| A-82 | | B |
| A-83 | A | B |
| A-84 | B | F |
| A-85 | A | B |
| A-86 | C | F |
| A-87 | A | B |
| A-88 | A | B |
| A-89 | B | D |
| A-90 | A | B |
| A-91 | A | D |
| A-92 | A | B |
| A-93 | A | C |
| A-94 | A | A |
| A-95 | A | C |
| A-96 | A | A |
| A-97 | B | D |
| A-98 | A | C |
| A-99 | A | C |
| A-100 | A | A |
| A-101 | A | F |
| A-102 | A | A |
| A-103 | B | F |
| A-104 | A | B |
| A-105 | B | B |
| A-106 | A | C |
| A-107 | A | A |
| A-108 | A | C |
| A-109 | A | A |
| A-110 | A | C |
| A-111 | A | B |
| A-112 | A | D |
| A-113 | B | D |
| A-114 | A | A |
| A-115 | A | B |
| A-116 | A | D |
| A-117 | A | B |
| A-118 | A | B |
| A-119 | A | C |
| A-120 | A | B |
| A-121 | A | B |
| A-122 | A | C |
| A-123 | | F |
| A-124 | | D |
| A-125 | A | F |
| A-126 | A | B |
| A-127 | A | C |
| A-128 | A | C |
| A-129 | A | A |
| A-130 | A | B |
| A-131 | A | A |

TABLE C-continued

| Cmpd No. | PD-1/ PD-L1 PPI IC50 | Jurkat NFAT $EC_{50}$ |
|---|---|---|
| A-132 | A | C |
| A-133 | B | C |
| A-134 | A | A |
| A-135 | A | C |
| A-136 | A | A |
| A-137 | A | D |
| A-138 | | A |
| A-139 | | A |
| B-2 | A | B |
| B-3 | A | C |
| B-4 | A | B |
| D-1 | A | A |
| D-2 | A | A |
| D-3 | A | A |
| D-4 | A | B |
| D-5 | A | B |
| D-6 | A | B |
| D-7 | A | B |
| D-8a | | B |
| D-8b | | B |
| D-9 | A | B |
| D-10 | A | B |
| D-11 | A | B |
| D-12 | | B |
| D-13 | | B |
| D-14 | | A |
| D-15 | A | B |
| D-16 | B | C |
| D-17 | A | B |
| D-18 | A | B |
| D-19 | A | C |
| E-1 | A | n.r |
| E-2 | A | E |
| E-3 | A | E |
| F-1 | A | |
| G-1 | A | B |
| H-1 | A | A |
| I-1 | | A |
| J-1 | A | A |
| J-2 | A | A |
| J-3 | A | A |
| J-4 | A | C |
| K-1a | A | B |
| K-1b | A | C |
| L-1a | | C |
| L-1b | | A |
| M-1a | | C |
| M-1b | | A |
| M-2a | | C |
| M-2b | | A |
| M-3a | | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

(I)

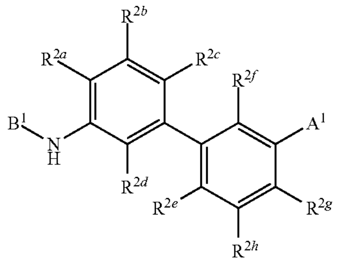

wherein:

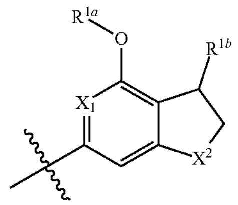

or

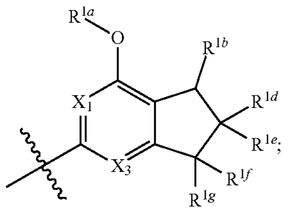

$A^1$ is

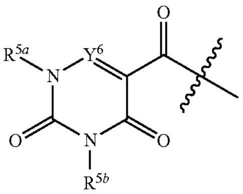

or

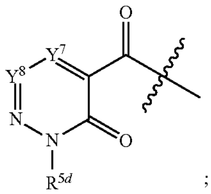

;

$B^1$ is each $X^1$ is N;

$X^2$ is O;

$X^3$ is CH;

$Y^6$ is selected from the group consisting of N and $CR^{5c}$;

$Y^7$ is $CR^{5e}$;

$Y^8$ is $CR^{5f}$;

each $R^{1a}$ is —$C_{1-4}$ alkyl;

each $R^{1b}$ is selected from the group consisting of —$N(R^{m1})R^{n1}$ and —$R^{x1}$;

wherein $R^{x1}$ is selected from the group consisting of:

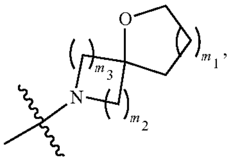,
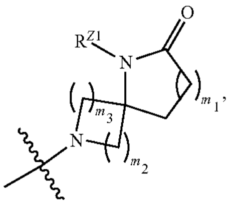,
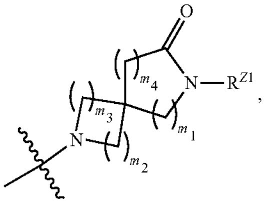,
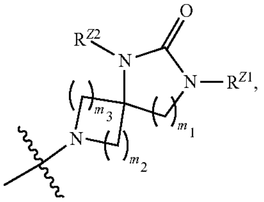,
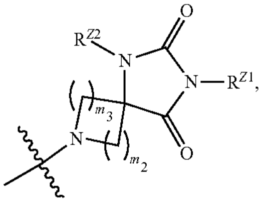,
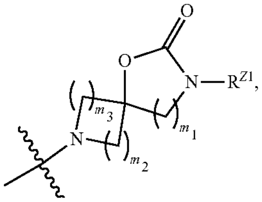,
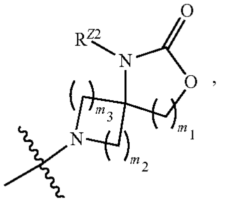,
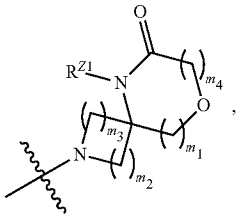,
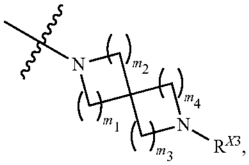,
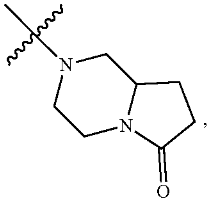,
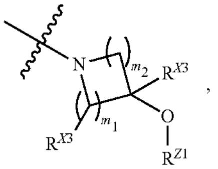,
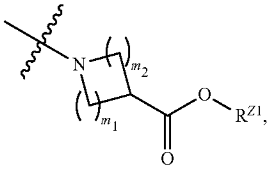,
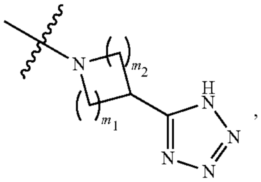, -continued

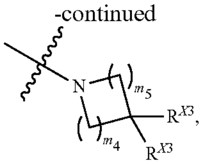,
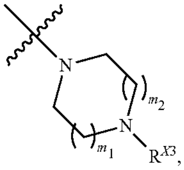,
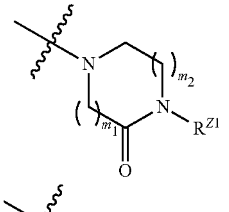
and
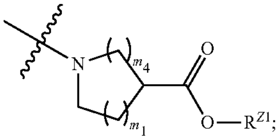;

$R^{1d}$, $R^{1e}$, $R^{1f}$ and $R^{1g}$ are each hydrogen;

$R^{2a}$, $R^{2b}$, $R^{2g}$ and $R^{2h}$ are each hydrogen;

$R^{2c}$ and $R^{2e}$ are independently selected from the group consisting of hydrogen and halogen;

$R^{2d}$ and $R^{2f}$ are independently selected from the group consisting of hydrogen, halogen, cyano, —$CH_3$ and —$OCH_3$;

$R^{5a}$ is selected from the group consisting of hydrogen and —$CH_3$;

$R^{5b}$ is selected from the group consisting of hydrogen and —$CH_3$;

$R^{5c}$ is selected from the group consisting of hydrogen and —$CH_3$;

$R^{5d}$ is selected from the group consisting of hydrogen and —$CH_3$;

$R^{5e}$ is selected from the group consisting of hydrogen, halogen and —$CH_3$;

$R^{5f}$ is selected from the group consisting of hydrogen, halogen and —$CH_3$;

$R^{m1}$ is selected from the group consisting of 4-7 membered monocyclic heterocyclyl and —$R^{x2}$; wherein the 4-7 membered monocyclic heterocyclyl is optionally substituted with hydroxy; and $R^{n1}$ is hydrogen; and wherein $R^{x2}$ is selected from the group consisting of:

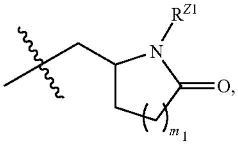,
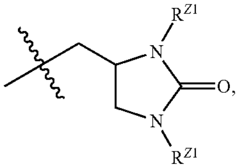,
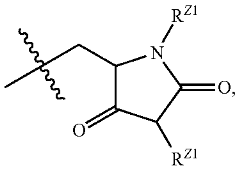,
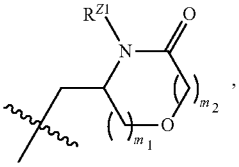,

-continued

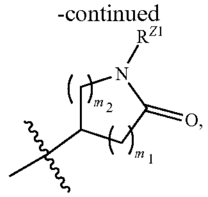

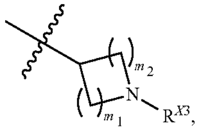

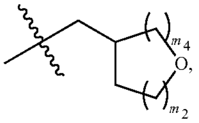

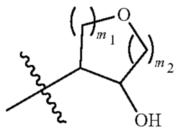

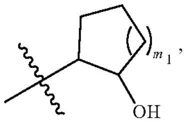

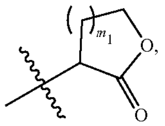

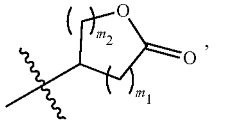

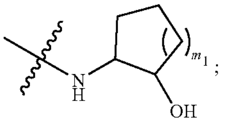

$m_1$, $m_2$ and $m_3$ are independently 1 or 2;

$m_4$ is 0, 1 or 2;

$m_5$ is 1, 2, 3 or 4;

each $R^{X3}$ is independently selected from the group consisting of hydrogen, —$C_{1-4}$ alkyl, —C(═O) $R^{Z3}$ and —C(═O) $OR^{Z1}$, $R^{Z1}$ and $R^{Z2}$ are independently selected from the group consisting of hydrogen and —$C_{1-4}$ alkyl; and each $R^{Z3}$ is independently selected from the group consisting of hydrogen and —$C_{1-4}$ alkyl.

2. A pharmaceutical composition comprising an effective amount of a compound of claim 1, or a pharmaceutically acceptable salt thereof, and excipient.

3. The compound of claim 1, or a pharmaceutically acceptable salt thereof, wherein $R^{1b}$ is —N($R^{m1}$)H, wherein $R^{m1}$ is the 4-7 membered monocyclic heterocyclyl optionally substituted with hydroxy, and wherein the 4-7 membered monocyclic heterocyclyl contains at least one O (oxygen) atom.

4. The compound of claim 3, or a pharmaceutically acceptable salt thereof, wherein $R^{m1}$ is selected from the group consisting of

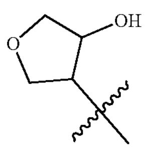

and

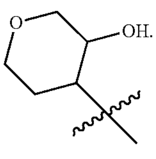

5. The compound of claim 3, or a pharmaceutically acceptable salt thereof, wherein $R^{2d}$ and $R^{2f}$ are independently selected from the group consisting of halogen and —$CH_3$; and $R^{2c}$ and $R^{2e}$ are each hydrogen.

6. The compound of claim 5, or a pharmaceutically acceptable salt thereof, wherein $B^1$ is selected from the group consisting of

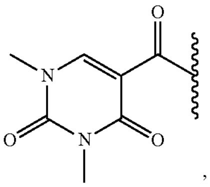

,

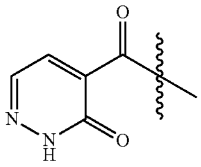

and

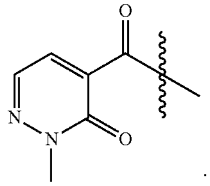

.

7. The compound of claim 1, or a pharmaceutically acceptable salt thereof, wherein $R^{1b}$ is —N($R^{m1}$)H, wherein $R^{m1}$ is —$R^{x2}$, wherein $R^{x2}$ is selected from the group consisting of

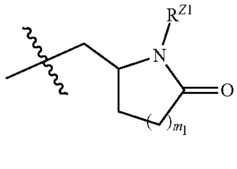

and

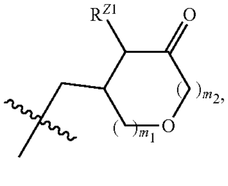

and wherein each $R^{Z1}$ is hydrogen.

8. The compound of claim 7, or a pharmaceutically acceptable salt thereof, wherein the N($R^{X2}$)H, is selected from the group consisting of

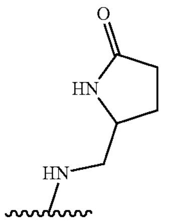

and

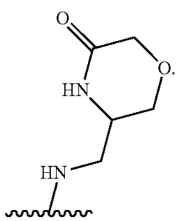

9. The compound of claim 7, or a pharmaceutically acceptable salt thereof, wherein $R^{2d}$ and $R^{2f}$ are independently selected from the group consisting of halogen and —$CH_3$; and $R^{2c}$ and $R^{2e}$ are each halogen.

10. The compound of claim 9, or a pharmaceutically acceptable salt thereof, wherein $B^1$ is selected from the group consisting of

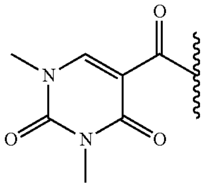
,
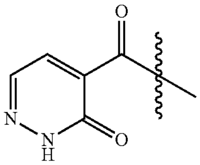
and
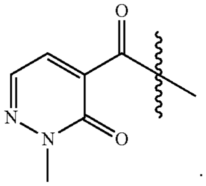
.

11. The compound of claim 1, or a pharmaceutically acceptable salt thereof, wherein $R^{1b}$ is $—R^{x1}$, wherein $R^{x1}$ is selected from the group consisting of:

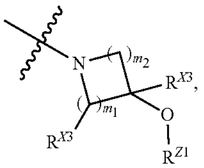
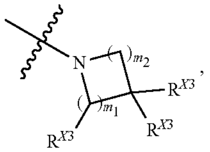
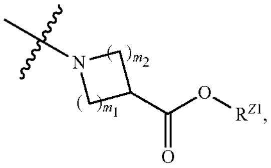
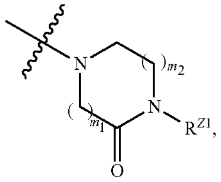
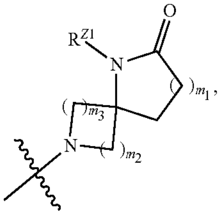
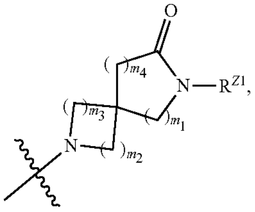
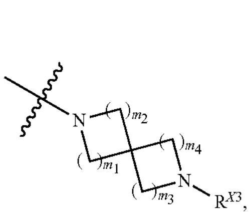
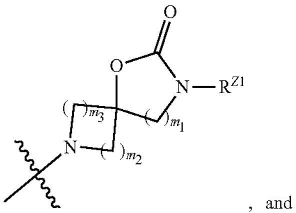
, and
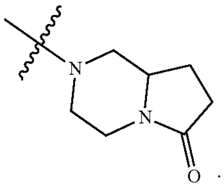
.

12. The compound of claim 11, or a pharmaceutically acceptable salt thereof, wherein $—R^{x1}$ is selected from the group consisting of:

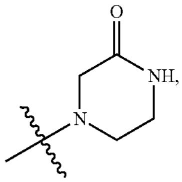
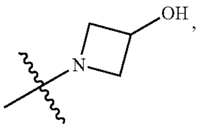
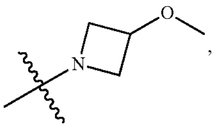
,
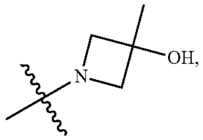
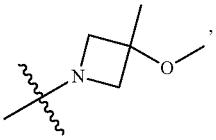
,
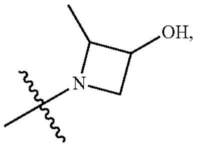
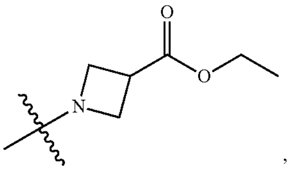
,
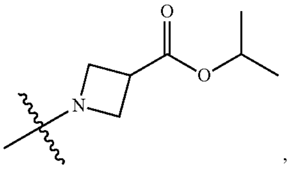
,
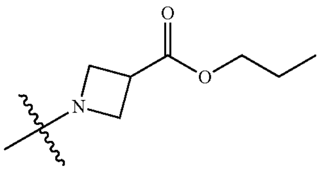
,
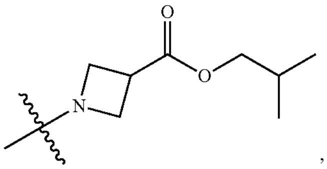
,
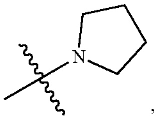
,
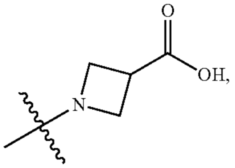
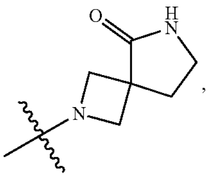
,
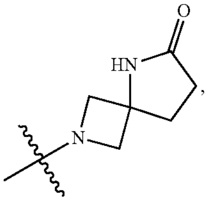
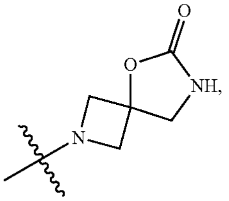
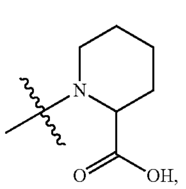
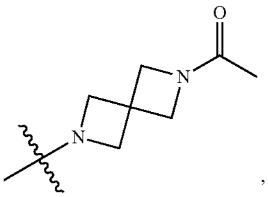
, -continued

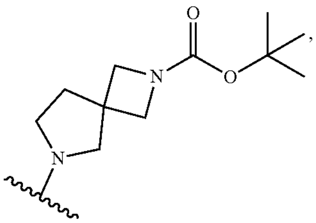

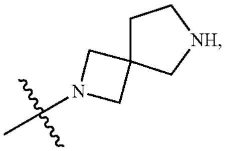

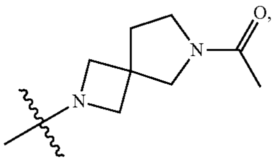

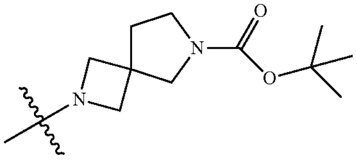

and

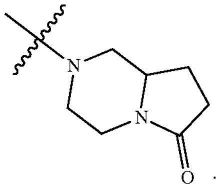

13. The compound of claim 11, or a pharmaceutically acceptable salt thereof, wherein —$R^{x1}$ is selected from the group consisting of:

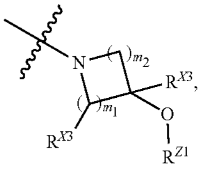

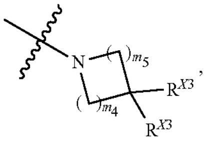

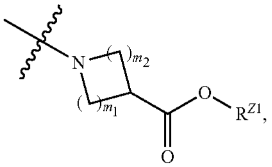

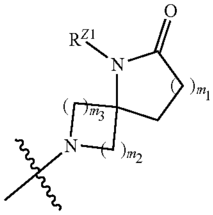

,

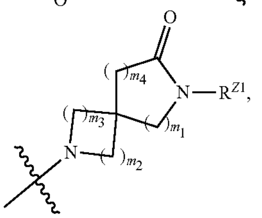

and

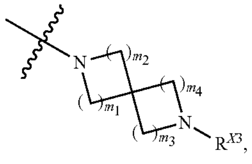

wherein $m_1$, $m_2$, $m_3$, $m_4$ and $m_5$, are each 1.

14. The compound of claim 11, or a pharmaceutically acceptable salt thereof, wherein —$R^{x1}$ is selected from the group consisting of:

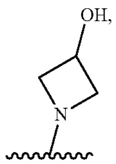

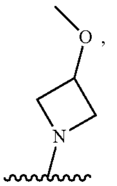

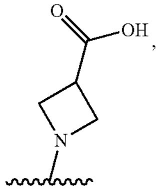

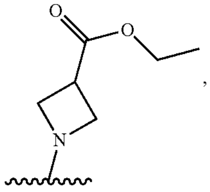

,

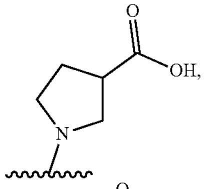

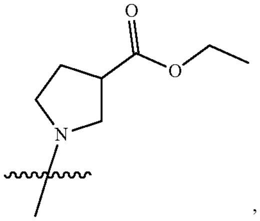

,

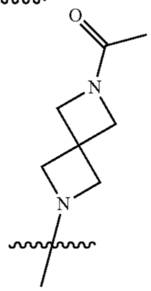

,

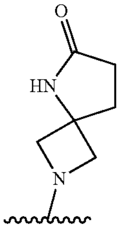

and

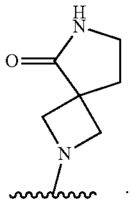

.

15. The compound of claim 11, or a pharmaceutically acceptable salt thereof, wherein $R^{2d}$ and $R^{2f}$ are independently selected from the group consisting of halogen and —$CH_3$; and $R^{2c}$ and $R^{2e}$ are each hydrogen.

16. The compound of claim 15, or a pharmaceutically acceptable salt thereof, wherein $B^1$ is selected from the group consisting of

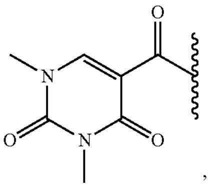

,

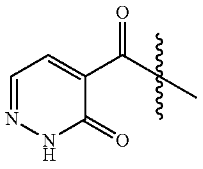

and

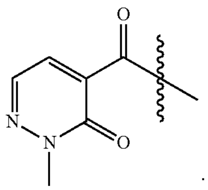

.

17. A method for treating hepatitis B in a subject comprising administering to the subject in need thereof an effective amount of a compound of claim 1, or a pharmaceutically acceptable salt thereof.

18. A method for treating hepatocellular carcinoma (HCC) in a subject comprising administering to the subject in need thereof an effective amount of a compound of claim 1, or a pharmaceutically acceptable salt thereof.

19. The method of claim 18, further comprising administering surgery, radiation therapy, chemotherapy, targeted therapy, immunotherapy, hormonal therapy, or antiviral therapy.

* * * * *